(12) United States Patent
Takahashi et al.

(10) Patent No.: US 8,618,094 B2
(45) Date of Patent: Dec. 31, 2013

(54) FUSED SUBSTITUTED AMINOPYRROLIDINE DERIVATIVE

(75) Inventors: Hisashi Takahashi, Tokyo (JP); Satoshi Komoriya, Tokyo (JP); Takahiro Kitamura, Tokyo (JP); Takashi Odagiri, Tokyo (JP); Hiroaki Inagaki, Tokyo (JP); Toshifumi Tsuda, Tokyo (JP); Kiyoshi Nakayama, Tokyo (JP); Makoto Takemura, Tokyo (JP); Kenichi Yoshida, Tokyo (JP); Rie Miyauchi, Tokyo (JP); Masatoshi Nagamochi, Tokyo (JP)

(73) Assignee: Daiichi Sankyo Company, Limited, Tokyo (JP)

(*) Notice: Subject to any disclaimer, the term of this patent is extended or adjusted under 35 U.S.C. 154(b) by 947 days.

(21) Appl. No.: 12/459,612

(22) Filed: Jul. 2, 2009

(65) Prior Publication Data

US 2012/0108582 A1 May 3, 2012
US 2013/0029977 A9 Jan. 31, 2013

Related U.S. Application Data

(63) Continuation of application No. PCT/JP2007/075434, filed on Dec. 28, 2007.

(30) Foreign Application Priority Data

Jan. 5, 2007 (JP) ................................. 2007-000667
Mar. 22, 2007 (JP) ................................. 2007-074991

(51) Int. Cl.
*C07D 401/10* (2006.01)
*C07D 498/06* (2006.01)
*A61K 31/4709* (2006.01)
*A61K 31/5383* (2006.01)

(52) U.S. Cl.
USPC ......... 514/230.2; 514/312; 544/101; 546/156

(58) Field of Classification Search
USPC ................. 514/230.2, 312; 544/101; 546/156
See application file for complete search history.

(56) References Cited

FOREIGN PATENT DOCUMENTS

| EP | 0 343 524 A | 11/1989 |
|---|---|---|
| EP | 0 812 838 A | 12/1997 |
| JP | 61-282382 A | 12/1986 |
| JP | 01 056673 A | 3/1989 |
| JP | 2231475 A | 9/1990 |
| JP | 3-095176 A | 4/1991 |
| JP | 6-345261 A | 12/1994 |
| JP | 8-225567 A | 9/1996 |
| WO | WO 95/21163 A1 | 8/1995 |
| WO | WO 96/23782 A | 8/1996 |
| WO | WO 96/23782 A1 | 8/1996 |
| WO | WO 96/39407 A | 12/1996 |
| WO | WO 2005/049602 A | 6/2005 |

OTHER PUBLICATIONS

Cianchetta et al. Journal of Medicinal Chemistry (2004), 47(12), 3193-3201.*
Ogata et al. European Journal of Medicinal Chemistry (1991), 26(9), 889-906.*
Bridges, Alexander J. et al., "Enantiomers of 1-Ethyl-7[3-[ethylamino)methyl]-1-pyrrolidinyl]-6,8-difluoro-1,4-dihydro-4-oxo-3-quinoline-carboxylic Acid: Preparation and Biological Activity", *J. Med. Chem.* 30 pp. 1711-1715 (1987).
Kobayashi, Hiroyuki, "Clinical Application of New Quinolone Agents," Table of Contents, *Iyaku (Medicine and Drug Journal Co., Ltd.)*, (Oct. 2001).
Alvarez-Lerma, Francisco et al. "Gram-Positive Cocci Infections in Intensive Care: Guide to Antibacterial Selection," *Drugs*, 66(6): 751-768 (2006).
Ball, P. et al. "A New Respiratory Gluoroquinolone, Oral Gemifloxacin: A Safety Profile in Context," *Int'l Jour. of Antimicrobial Agents*, 23: 421-429 (2004).
Cianchetta, G. et al. "Chemometric Studies on the Bacterial Activity of Quinolones Via an Extended Volsurf Approach," *Journal of Medicinal Chemistry*, 47: 3193-3201 (2004).
Domagala, John M. "Structure-Activity and Structure-Side-Effect Relationships for the Quinolone Antibacterials," *Jour. of Antimicrobial Chemotherapy*, 33: 685-706 (1994).
Frothingham, Richard. "Glucose Hemeostasis Abnormalities Associated with Use of Gatifloxacin," *Clinical Infectious Diseases*, 41(5): 1269-1276 (2005).
Galeazzi, Roberta et a. "Chiral 3-hydroxypyrrolidin-2-ones fro ma Baylis-Hillman adduct: convergent, stereoselective synthesis of a glycosidase inhibitor," *Tetrahedron: Asymmetry*, 15: 3249-3256 (2004).
Galeazzi, Roberta et al. "Conformationally restricted analogues of both (S)-β-homoserine and (S)-aspartic acid from chiral 3-acylamino pyrrolidin-2-ones", *Tetrahedron*, 61: 5465-5473 (2005).
Inagaki, Hiroaki et al. "Synthesis and Structure—Activity Relationships of 5-Amino-6-fluoro-1-[(1R,2S)-2-fluorocyclopropan-1-yl]-8-methylquinolonecarboxylic Acid Antibacterials Having Fluorinated 7-[(3R)-3-(1-Aminocyclopropan-1-yl)pyrrolidin-1-yl] Substituents," *J. Med. Chem.* 46:1005-1015 (2003).
Karlsson, Staffan et al. "Diastereoselective addition of chiral azomethine ylides to cyclic α,β-unsaturated N-enoylbornanesultams", *J. Chem. Soc., Perkin Trans.* 1: 1076-1082 (2002).

(Continued)

Primary Examiner — Kahsay Habte
(74) Attorney, Agent, or Firm — Dorsey and Whitney LLP

(57) ABSTRACT

A quinolone synthetic antibacterial agent having excellent properties as a medicine is provided, which has strong antibacterial activity not only to Gram-negative bacteria but also to Gram-positive cocci that have low sensitivity to quinolone antibacterial agents, and which exhibits high safety and excellent pharmacokinetics. A compound represented by the formula (I) or a salt thereof, or a hydrate thereof. Specifically, a quinolone derivative of the formula (I) wherein substituents R6 and R7 taken together with the carbon atoms to which they are bonded form a cyclic structure which may contain an oxygen atom as a ring constituent atom, the cyclic structure forming a 5-4, 5-5, or 5-6 fused bicyclic pyrrolidinyl substituent, the substituent being bonded to a quinolone mother skeleton Q containing a pyridobenzoxazine structure.

(I)

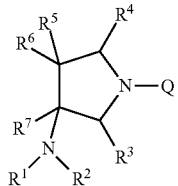

36 Claims, 1 Drawing Sheet

(56) References Cited

OTHER PUBLICATIONS

Kawabata, Takeo, et al. "Asymmetric Cycclization via Memory of Chirality: A Concise Access to Cyclic Amino Acids wit ha Quaternary Stereocenter," *J. Am. Chem. Soc.*, 125: 13012-13013 (2003).

Kobayashi, Hiroyuki (ed.), "Clinical Application of New Quinolone Agents," Iyaku (Medicine and Drug) Journal Co., Ltd., 62(1): 13 (2002).

Ma, X. et al. "Synthesis and Antimicrobial Activity of 4H-4-Oxoquinolizine Derivatives: Consequences of Structural Modification at the C-8 Position," *Journal of Medicinal Chemistry*, 42: 4202-4213 (Jan. 1, 1999).

Meyers, A. I. et al. "Asymmetric Synthesis of L-Deoxymannojirimycin," *Synlett*, 5:533-544 (May 1997).

Najera, Carmen et al. "Catalytic Enantioselective 1,3-Dipolar Cycloaddition Reaction of Azomethine Ylides and Alkenes: The Direct Strategy to Prepare Enantioenriched Highly Substituted Proline Derivatives," *Angew, Chem. Int.* 44: 6272-6276 (2005).

Ogata, M. et al. "Synthesis and Antibacterial Activity of New 7-(Aminoazabicycloalkanyl)quinolonecarboxylic Acids," *Eur. J. Med. Chem.* 26(9): 889-906 (1991).

Owens, Robert C., Jr. et al. "Antimicrobial Safety: Focus on Fluoroquinolones," *Clinical Infectious Diseases*, 41: S144-S157 (2005).

Padwa, Albert et al. "On the Use of N[(Trimethylsilyl)methyl]amino Ethers as Capped Azomethine Ylide Equivalents", *J. Org. Chem.* 52: 235-244 (1987).

Stahlmann, Ralf. "Clinical Toxicological Aspects of Fluoroquinolones," *Toxicology Letters*, 127: 269-277 (2002).

Takahashi, Hisashi et al. "The History of the Development and Changes of Quinolone Antibacterial Agents," *The Japanese Journal for History and Pharmacy*, 38(2): 161-179 (2003).

Van Bambeke, F. et al. "Quinolones in 2005: an update," *Clinical Microbiology and Infection*, 11(4): 256-280 (2005).

Zhanel, George G. et al. "A Critical Review of the Fluoroquinolones: Focus on Respiratory Tract Infections," *Drugs* 62(1): 13-69 (2002).

Avelox® Product Data Sheet, Merck & Co., Inc., Whitehouse Station, New Jersey, USA, 2011, 34 pages.

Cipro® XR (ciprofloxacin* extended-release tablets) Product Data Sheet, Merck & Co., Inc., Whitehouse Station, New Jersey, USA, 2011, 28 pages.

Rocephin® (ceftriaxone sodium) for Injection Product Data Sheet, Genentech USA, Inc., South San Francisco, California, USA, 2010, 23 pages.

Zithromax® (azithromycin tablets) and (azithromycin for oral suspension) Product Data Sheet, Pfizer Inc., New York, New York, USA, 2010, 27 pages.

* cited by examiner

FUSED SUBSTITUTED AMINOPYRROLIDINE DERIVATIVE

CROSS-REFERENCE TO RELATED APPLICATIONS

This application is a continuation of PCT/JP2007/075434 filed on Dec. 28, 2007, which claims priority to Japanese patent application number 2007-000667 filed on Jan. 5, 2007 and Japanese patent application number 2007-074991 filed on Mar. 22, 2007, the contents of all of which are herein incorporated by reference in their entirety.

BACKGROUND OF THE INVENTION

1. Field of the Invention

The present invention relates to quinolone compounds useful as medicines, veterinary medicines, fishery medicines, or antibacterial preservatives.

2. Description of the Related Art

Since the discovery of norfloxacin, quinolone synthetic antibacterial agents (including those having a pyridobenzoxazine skeleton) with improved antibacterial activity and pharmacokinetics have been developed into chemotherapeutic agents effective for almost all systemic infections, and many of them are now clinically used (see Japanese Patent Laid-Open No. 61-282382 or Japanese Patent Laid-Open No. 63-45261 and Clinical Microbiology and Infection, Vol. 11, No. 4, p. 256 (2005)).

However, the number of types of bacteria having low sensitivity to quinolone synthetic antibacterial agents has tended to increase in the clinical field in recent years. For example, the number of types of bacteria resistant to drugs other than quinolone synthetic antibacterial agents, which are so-called multidrug-resistant bacteria, such as Gram-positive cocci including *Staphylococcus aureus* (methicillin-resistant *Staphylococcus aureus*: MRSA) and pneumococcus (penicillin-resistant *Streptococcus pneumonia*: PRSP) having low sensitivity to β-lactam antibiotics; and enterococci having low sensitivity to aminoglycoside antibacterial agents (vancomycin-resistant *enterococcus*: VRE) and having also low sensitivity to quinolone synthetic antibacterial agents has increased. Bacterial infections caused by such resistant Gram-positive bacteria are known to be generally severe (fatal) and intractable. Accordingly, drugs more effective to Gram-positive cocci are particularly desired in the clinical field (see Drugs, Vol. 66, No. 6, p. 751 (2005)).

On the other hand, quinolone synthetic antibacterial compounds created in recent years have antibacterial activities that are much higher than those of previous ones (see Japanese Patent Laid-Open No. 2-231475 or Japanese Patent Laid-Open No. 3-95176). However, many of such quinolone compounds having high antibacterial activity cause side effects based on their physiological and pharmacological effects not observed for previous quinolone synthetic antibacterial agents.

Examples of the side effects of quinolone synthetic antibacterial agents include conventionally reported side effects such as induction of convulsion by use in combination with non-steroidal anti-inflammatory drugs (NSAIDs), central actions (mild central nervous system disorders such as sway, headache, and insomnia, and serious side effects such as the onset of fatal convulsion), and phototoxicity (photosensitivity); as well as recently disclosed side effects such as hepatotoxicity (serious allergic hepatitis), cardiotoxicity (electrocardiographic abnormality inducing fatal arrhythmia, observed as QT or QTc prolongation), delayed drug eruption (skin rash), and blood glucose level abnormality (see Hiroyuki Kobayashi (ed.), Clinical Application of New Quinolone Agents, Iyaku (Medicine and Drug) Journal Co., Ltd.; Drugs, Vol. 62, No. 1, p. 13 (2002); Toxicology Letters, Vol. 127, p. 269 (2002); Clinical Infectious Diseases, Vol. 41, p. 1269 (2005)); and International Journal of Antimicrobial Agents, Vol. 23, No. 5, p. 421 (2004)).

The clinical onset of cardiotoxicity among such side effects is a particular problem in recent years. Distinct QT or QTc prolongation is reported and some serious conditions (electrocardiographic abnormality inducing fatal arrhythmia) are also reported for some commercially available quinolone synthetic antibacterial agents (such as grepafloxacin, sparfloxacin, moxifloxacin, gatifloxacin, and gemifloxacin). Serious side effects such as the onset of serious allergic hepatitis accompanying liver transplantation (trovafloxacin: see Clinical Infectious Diseases, Vol. 41, p. 1269 (2005)) and blood glucose level abnormality including fatal hypoglycemia (gatifloxacin: see International Journal of Antimicrobial Agents, Vol. 23, No. 5, p. 421 (2004)) are also clinical problems. Further, delayed drug eruption (skin rash) caused by repeated administration of a quinolone agent in a clinical test (gatifloxacin: see Clinical Infectious Diseases, Vol. 41, p. 1269 (2005)) is reported. In such circumstances, the administration of some quinolone synthetic antibacterial agents has been limited, and the development and use as human medicines of some quinolone synthetic antibacterial agents has been abandoned. That is, some quinolone synthetic antibacterial agents have been observed which have strong antibacterial activity but which in terms of side effects are not sufficiently suitable as medicines.

Accordingly, there is a need for safer quinolone synthetic antibacterial agents for use as human medicines, having only low side effects such as induction of convulsion by use in combination with non-steroidal anti-inflammatory drugs, central actions, and phototoxicity (photosensitivity) which are conventionally known as side effects; as well as cardiotoxicity, hepatotoxicity, delayed drug eruption (skin rash), and blood glucose level abnormality which are clinical problems in recent years. Therefore, there is a need for the development of compounds conceptually different from conventional compounds that have high antibacterial activity but cause side effects and thus cannot be used as medicines. That is, there is a need for quinolone compounds having both strong antibacterial activity and high safety (see The Japanese Journal for History of Pharmacy, Vol. 38, No. 2, p. 161 (2003)).

Antibacterial activity, pharmacokinetics, and safety of a quinolone synthetic antibacterial agent are known to be influenced by the structure of the substituents at each position of the quinolone skeleton, in particular, the structure of the substituent at the 7-position (corresponding to the 10-position of the pyridobenzoxazine skeleton) (see Clinical Microbiology and Infection, Vol. 11, No. 4, p. 256 (2005), for example).

The characteristic feature of the compounds of the present invention is that they have, at the 7-position of the quinolone mother skeleton, a substituent represented by the following formula 1:

[Formula 1]

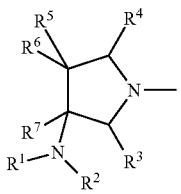

wherein $R^1$, $R^2$, $R^3$, $R^4$, $R^5$, $R^6$, and $R^7$ are as defined in claim 1. That is, the 7-position substituent in the compounds of the present invention has a fused bicyclic amine structure that is formed by fusion of the pyrrolidine ring with a cyclic structure formed by taking $R^6$ and $R^7$ together with the carbon atoms to which they are bonded, and further the fused bicyclic amine structure has an amino group at the bridgehead position. In relation to quinolone derivatives substituted with a 7-position substituent having such a structure, the following compounds are known.

For example, Japanese Patent Laid-Open No. 64-56673 describes a pyridonecarboxylic acid derivative represented by the general formula 2:

[Formula 2]

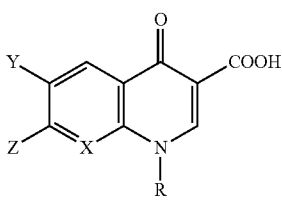

wherein R represents a lower alkyl group, a halogeno lower alkyl group, a lower alkenyl group, a cycloalkyl group, or a phenyl group which may have a substituent; X represents a nitrogen atom or C-A, wherein A represents a hydrogen atom or a halogen atom; Y represents a hydrogen atom or a halogen atom; and Z represents a group represented by the following formula 3:

[Formula 3]

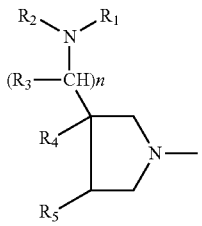

wherein $R_1$ represents a hydrogen atom, a lower alkyloxycarbonyl group, or an acyl group which may be substituted with a halogen atom; two of $R_2$, $R_3$, $R_4$, and $R_5$ are bonded directly or through a lower alkyl chain to form a ring and the remaining two of $R_2$, $R_3$, $R_4$, and $R_5$ each represents a hydrogen atom; and n represents 0 or 1, provided that $R_2$ and $R_3$ are a bond when these are bonded to each other. The definitions of substituents and the like in the compound represented by the formula 2 do not apply to the compounds of the present invention although the same symbols are used. However, Japanese Patent Laid-Open No. 64-56673 does not specifically disclose a quinolone compound in accordance with the present invention wherein $R_4$ and $R_5$ in the formula 3 are taken together to form a four- to seven-membered ring and n=0.

EP-A-343524 discloses a pyridonecarboxylic acid antibacterial agent represented by the general formula 4:

[Formula 4]

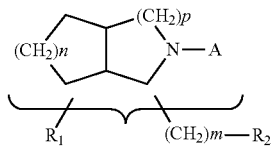

wherein $R_1$ is hydrogen, hydroxy, $C_1$-$C_4$ alkyl, $C_1$-$C_4$ alkoxy, oxo, halogen, or amino which may optionally be substituted with $C_1$-$C_4$ alkyl and/or $C_1$-$C_4$ alkanoyl; $R_2$ is azide, hydroxy, $C_1$-$C_4$ alkoxy, $C_1$-$C_4$ alkoxycarbonyl, $C_1$-$C_4$ alkanoyl, or amino which may optionally be substituted with $C_1$-$C_4$ alkyl and/or $C_1$-$C_4$ alkanoyl; A is a quinolone structure represented by the following formula 5:

[Formula 5]

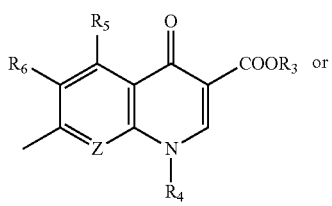 or

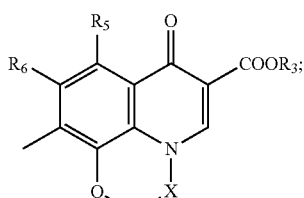

$R_3$ is hydrogen or a carboxy protecting group; $R_4$ is $C_1$-$C_4$ alkyl, $C_2$-$C_5$ alkenyl, $C_3$-$C_5$ cycloalkyl, mono- or di-fluorophenyl, or a five- or six-membered heterocycle which may optionally be substituted with halogen and/or $C_1$-$C_4$ alkyl; $R_5$ is hydrogen, amino, hydroxy, or $C_1$-$C_4$ alkoxy; $R_6$ is halogen; X is CH—($C_1$-$C_4$ alkyl), C=$CH_2$, N—H, or N—($C_1$-$C_4$ alkyl); Z is CQ or N; Q is hydrogen, $C_1$-$C_4$ alkoxy, halogen, $C_1$-$C_4$ alkyl, or cyano; m is an integer of 0 or 1; and n and p are each an integer of 1 to 3. However, as a specific compound related to the compounds of the present invention, EP-A-343524 discloses only a quinolonecarboxylic acid derivative represented by the following formula 6, that is, a derivative in which m is 0, p is 1, and the substituent $R_2$ is an amino group at the bridgehead position of the bicyclic amine:

[Formula 6]

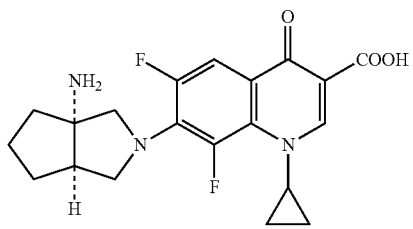

Moreover, EP-A-343524 does not disclose a compound having a halogenocyclopropyl group at the 1-position which is a typical example of the compounds of the present invention. The structure of the 7-position substituent is a (1R*, 5S*)-configuration in the compound represented as the formula 6 as disclosed in EP-A-343524. This compound is a so-called cis-racemate, and EP-A-343524 does not describe the antibacterial activity of an optical isomer. Further, EP-A-343524 does not describe the safety of the disclosed compound. A stereochemically single compound is preferable as a human medicine in terms of effectiveness and safety. In addition, the compound represented by the formula 6 has a fluorine atom at the 8-position of the quinolone skeleton and is thus presumed to cause phototoxicity (photosensitivity) with high probability (see Journal of Antimicrobial Chemotherapy, Vol. 33, p. 683 (1994), for example). That is, the compound represented by the formula 6 is not thought to be necessarily sufficient as a medicine for effective use in humans with safety. European Journal of Medicinal Chemistry, Vol. 26, p. 889 (1991) only describes the content in accordance with EP-A-343524.

WO 95/21163 discloses a pyridonecarboxylic acid antibacterial agent substituted with a bicyclic amino group, which is represented by the following general formula 7:

[Formula 7]

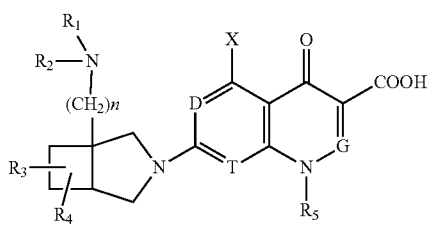

wherein $R_1$ and $R_2$ are the same or different and each represents a hydrogen atom, a lower alkyl group, or an amino-protecting group; $R_3$ and $R_4$ are the same or different and each represents a hydrogen atom, a halogen atom, a cyano group, a hydroxy group, an oxo group, a lower alkoxy group, or a lower alkyl group; n represents an integer of 0 or 1; $R_5$ represents a lower alkyl group, a lower alkenyl group, a lower cycloalkyl group, a phenyl group, or a heterocyclic group (these may be further substituted); G represents C-E, wherein E represents a hydrogen atom or together with $R_5$ forms a crosslinkage represented by —S—SE(CH$_3$)—; T represents C—Z or a nitrogen atom, wherein Z represents a hydrogen atom, a halogen atom, a cyano group, a lower alkoxy group, a halogeno lower alkoxy group, a lower alkyl group, or a halogeno lower alkyl group or together with $R_5$ forms a crosslinkage represented by —O—CH$_2$—CH(CH$_3$)—; X represents a hydrogen atom, a halogen atom, a hydroxy group, a lower alkyl group, or an amino group which may be protected; and D represents C—Y, wherein Y represents a hydrogen atom or a halogen atom. However, in relation to the compounds of the present invention, as a bicyclic amino group in the 7-position substituent of the quinolone derivative, only the substituent represented by the following formula 8, that is where $R_3$ and $R_4$ are each a hydrogen atom in the formula 7 and n is 0, is specifically disclosed:

[Formula 8]

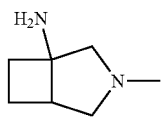

Further, WO 95/21163 does not specifically disclose a fused substituted aminopyrrolidine derivative (bicyclic amine) which is a feature of the present invention, that is where in the compound represented by the formula 7 one or both of the substituents $R_3$ and $R_4$ on the bicyclic amine has a substituent other than a hydrogen atom.

WO 96/23782 discloses a $N_1$-(halogenocyclopropyl) substituted pyridonecarboxylic acid derivative represented by the general formula 9:

[Formula 9]

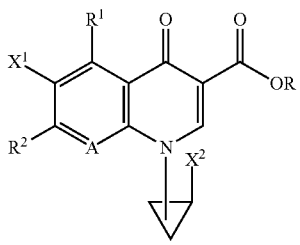

wherein $X^1$ represents a halogen atom or a hydrogen atom; $X^2$ represents a halogen atom; $R^1$ represents a hydrogen atom, a hydroxy group, a thiol group, a halogenomethyl group, an amino group, an alkyl group, or an alkoxy group; $R^2$ represents a substituent of formula 10:

[Formula 10]

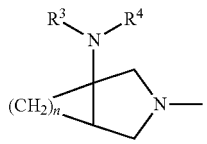

wherein $R^3$ and $R^4$ each represents a hydrogen atom or an alkyl group and n represents an integer of 1 or 2; A represents a group of formula 11:

[Formula 11]

wherein X³ represents a hydrogen atom, a halogen atom, a cyano group, an amino group, an alkyl group, a halogenomethyl group, an alkoxy group, or a halogenomethoxy group; and R represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group, an alkoxymethyl group, or a phenyl group. The definitions of substituents and the like in the compound represented by the formula 9 do not apply to the compounds of the present invention although the same symbols are used. However, in relation to the compounds of the present invention, as a bicyclic amino group in the 7-position substituent of the quinolone derivative, only the substituent represented by the following formula 12, that is where n is 2 in the formula 10, is specifically disclosed:

[Formula 12]

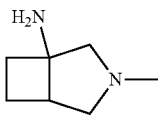

Further, WO 96/23782 does not disclose a 1-amino-3-azabicyclo[3.2.0]heptane derivative having a substituent other than a hydrogen atom on the bicyclic ring, which is a feature of the compounds of the present invention.

Japanese Patent Laid-Open No. 8-225567 discloses a quinolone- or naphthylidone-carboxylic acid derivative represented by the general formula 13:

T-Q  [Formula 13]

wherein Q represents a quinolone structure of formula 14:

[Formula 14]

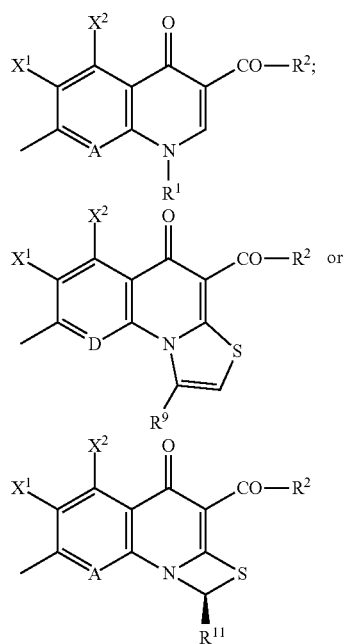

wherein X¹ represents halogen or nitro; X² represents hydrogen, halogen, amino, hydroxy, methoxy, or the like; A and D each represent N or C—R⁷ (wherein R⁷=H, F, OCH₃, or the like); R¹ represents $C_1$-$C_4$ alkyl, $C_3$-$C_6$ cycloalkyl, or the like; R² represents hydroxy, methoxy, benzyloxy, or the like; R⁹ represents hydrogen or $C_1$-$C_3$ alkyl; and R¹¹ represents hydrogen, methyl, or $CH_2F$; and T represents the following formula 15:

[Formula 15]

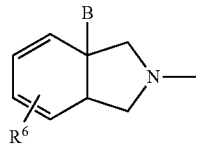

wherein B represents amino, hydroxy, or the like; and R⁶ represents hydrogen or methyl. The definitions of substituents and the like in the compound represented by the formula 13 do not apply to the compounds of the present invention although the same symbols are used. However, Japanese Patent Laid-Open No. 8-225567 only discloses a compound represented by the following formula 16 as such a derivative where B is an amino group.

[Formula 16]

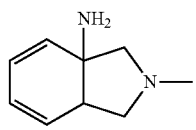

Further, Japanese Patent Laid-Open No. 8-225567 does not describe a specific compound related to the present invention.

SUMMARY OF THE INVENTION

Accordingly, an object of the present invention is to provide a quinolone synthetic antibacterial agent and a therapeutic agent for infections which has wide and strong antibacterial activity to Gram-positive bacteria, including those having low sensitivity to quinolone, and to Gram-negative bacteria, and which also has high safety.

The present inventors have conducted research on compounds having a 3-aminopyrrolidinyl group at the 7-position of quinolone compounds or its corresponding position (for example, the 10-position of pyridobenzoxazine compounds). The inventors have found that quinolone derivatives having a fused substituted aminopyrrolidinyl substituent represented by the following formula 17:

[Formula 17]

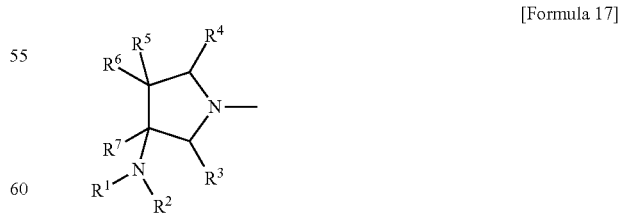

wherein substituents at 3- and 4-positions in the 3-aminopyrrolidinyl group taken together with the carbon atoms to which they are bonded form a four- to seven-membered cyclic structure which may contain a double bond and may contain an oxygen atom or a sulfur atom, the cyclic structure together with the pyrrolidine ring forming a fused cyclic (bicyclic) structure, have wide and strong antibacterial activity to Gram-positive bacteria, notably to resistant Gram-positive cocci such as pneumococcus resistant to multiple drugs including quinolone, and to Gram-negative bacteria. Various preclinical evaluations have revealed that the quinolone compounds not only have such high antibacterial activity but also cause only with low probability conventionally known side effects of quinolone antibacterial agents such as convulsion induction and phototoxicity (photosensitivity) and recently clinically reported side effects such as cardiotoxicity (QT prolongation), blood glucose level abnormality, and delayed drug eruption. It has also become clear that the quinolone compounds show excellent oral absorbability and permeability to organs. These results are quite unexpected from the contents disclosed in the aforementioned patent documents.

Finally, the inventors have found that quinolone compounds represented by the later-described formula (I) and their corresponding salts and hydrates are quinolone synthetic antibacterial agents having excellent properties as medicines, which have high antibacterial activity and safety and which also exhibit excellent pharmacokinetics. These findings have led to the completion of the present invention.

Specifically, the present invention provides a compound represented by the following formula (I), a salt, or a hydrate thereof:

[Formula 18]

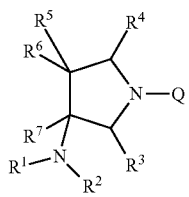

I wherein $R^1$ represents a hydrogen atom, an alkyl group having 1 to 6 carbon atoms, a cycloalkyl group having 3 to 6 carbon atoms, or a substituted carbonyl group derived from an amino acid, a dipeptide, or a tripeptide, said alkyl group may have one or more substituents selected from the group consisting of a hydroxy group, an amino group, a cyano group, a halogen atom, an alkylthio group having 1 to 6 carbon atoms, and an alkoxy group having 1 to 6 carbon atoms, and said cycloalkyl group may have one or more substituents selected from the group consisting of an alkyl group having 1 to 6 carbon atoms, an amino group, a hydroxy group, and a halogen atom;

$R^2$ represents a hydrogen atom, an alkyl group having 1 to 6 carbon atoms, or a cycloalkyl group having 3 to 6 carbon atoms, said alkyl group may have one or more substituents selected from the group consisting of a hydroxy group, an amino group, a halogen atom, an alkylthio group having 1 to 6 carbon atoms, and an alkoxy group having 1 to 6 carbon atoms, and said cycloalkyl group may have one or more substituents selected from the group consisting of an alkyl group having 1 to 6 carbon atoms, an amino group, a hydroxy group, and a halogen atom;

$R^3$ and $R^4$ each independently represents a hydrogen atom or an alkyl group having 1 to 6 carbon atoms, and said alkyl group may have one or more substituents selected from the group consisting a halogen atom and an alkoxy group having 1 to 6 carbon atoms;

$R^5$ represents a hydrogen atom, a halogen atom, an alkyl group having 1 to 6 carbon atoms, an alkoxy group having 1 to 6 carbon atoms, an alkenyl group having 2 to 6 carbon atoms, an alkynyl group having 2 to 6 carbon atoms, a cycloalkyl group having 3 to 6 carbon atoms which may have a substituent, an aryl group having 6 to 10 carbon atoms which may have a substituent, or a heteroaryl group which may have a substituent, said alkyl group, alkenyl group, and alkynyl group may be linear or branched, the alkyl group may have one or more substituents selected from the group consisting of a hydroxy group, an amino group, a halogen atom, an alkylthio group having 1 to 6 carbon atoms, and an alkoxy group having 1 to 6 carbon atoms, and the alkenyl group may have one or more substituents selected from the group consisting of a halogen atom and an alkoxy group having 1 to 6 carbon atoms;

$R^6$ and $R^7$ taken together with the carbon atoms to which they are bonded form a four- to seven-membered cyclic structure, the cyclic structure representing a partial structure that together with the pyrrolidine ring forms a fused cyclic (bicyclic) structure, the four- to seven-membered cyclic structure may contain a double bond and may contain an oxygen atom or a sulfur atom as a ring constituent atom, $R^5$ may be a methylene group taken together with $R^6$ to form a three-membered fused cyclic structure moiety, and the ring formed as described above may be located in other part of the fused cyclic (bicyclic) structure, and said four- to seven-membered cyclic structure may have one or more substituents selected from the group consisting of an alkyl group having 1 to 6 carbon atoms which may have a substituent, an alkoxy group having 1 to 6 carbon atoms which may have a substituent, an alkenyl group having 2 to 6 carbon atoms which may have a substituent, an alkynyl group having 2 to 6 carbon atoms which may have a substituent, a cycloalkyl group having 3 to 6 carbon atoms which may have a substituent, an exomethylene group which may have a substituent, a spiroalkyl group which may have a substituent, an aryl group having 6 to 10 carbon atoms which may have a substituent, a heteroaryl group which may have a substituent, an alkoxyimino group having 1 to 6 carbon atoms which may have a substituent, a halogen atom, a hydroxy group, a cyano group, and a hydroxyimino group; or a polymethylene chain of 2 to 5 carbon atoms may bind so as to form a spirocyclic ring system; and Q represents a partial structure represented by the following formula (II):

[Formula 19]

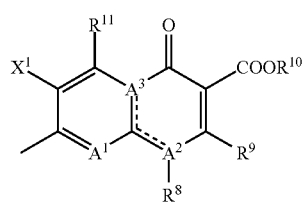

II wherein $R^8$ represents an alkyl group having 1 to 6 carbon atoms, an alkenyl group having 2 to 6 carbon atoms, a halogen-substituted alkyl group having 1 to 6 carbon atoms, a cycloalkyl group having 3 to 6 carbon atoms which may have a substituent, a halogen-substituted phenyl group which may have a substituent, a halogen-substituted heteroaryl group which may have a substituent, an alkoxy group having 1 to 6 carbon atoms, or an alkylamino group having 1 to 6 carbon atoms;

$R^9$ represents a hydrogen atom or an alkylthio group having 1 to 6 carbon atoms, or $R^9$ and $R^8$ taken together with the atoms to which they are bonded form a cyclic structure, said cyclic structure may contain a sulfur atom as a ring constituent atom and may have an alkyl group having 1 to 6 carbon atoms or a halogen-substituted alkyl group having 1 to 6 carbon atoms as a substituent;

$R^{10}$ represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxobutyl group, an alkyl group having 1 to 6 carbon atoms, an alkoxymethyl group having 2 to 7 carbon atoms, or a phenylalkyl group formed by an alkylene group having 1 to 6 carbon atoms and a phenyl group;

$R^{11}$ represents a hydrogen atom, an amino group, a hydroxy group, a thiol group, a halogenomethyl group, or an alkyl group having 1 to 6 carbon atoms, and the amino group may have one or two substituents selected from the group consisting of a formyl group, an alkyl group having 1 to 6 carbon atoms, and an acyl group having 2 to 5 carbon atoms;

$X^1$ represents a halogen atom or a hydrogen atom;

$A^1$ represents a nitrogen atom or a partial structure represented by the formula (III):

[Formula 20]

III wherein $X^2$ represents a hydrogen atom, an alkyl group having 1 to 6 carbon atoms, an alkoxy group having 1 to 6 carbon atoms, a cyano group, a halogen atom, a halogen-substituted methyl group, or a halogenomethoxy group, or $X^2$ and $R^8$ taken together with their connecting part of the mother skeleton form a cyclic structure, said cyclic structure may contain an oxygen atom, a nitrogen atom, or a sulfur atom as a ring constituent atom, and may be substituted with an alkyl group having 1 to 6 carbon atoms which may have a substituent; and $A^2$ and $A^3$ each represents a nitrogen atom or a carbon atom, and $A^1, A^2, A^3, R^8$ and the carbon atom to which $A^2$ and $A^3$ are bonded together represent a partial structure:

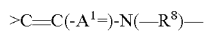

or a partial structure:

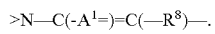

The present invention also provides a medicine comprising a compound represented by the formula (I), a salt, or a hydrate thereof as an active ingredient.

The present invention further provides a method for treating diseases comprising administering a compound represented by the formula (I), a salt, or a hydrate thereof. The present invention still further provides use of a compound represented by the formula (I), a salt or a hydrate thereof for production of a medicine.

The present invention can provide a quinolone synthetic antibacterial agent having excellent properties as a medicine, which has strong antibacterial activity not only to Gram-negative bacteria but also to Gram-positive cocci that have low sensitivity to quinolone antibacterial agents, and exhibits high safety and excellent pharmacokinetics.

Figure 1:
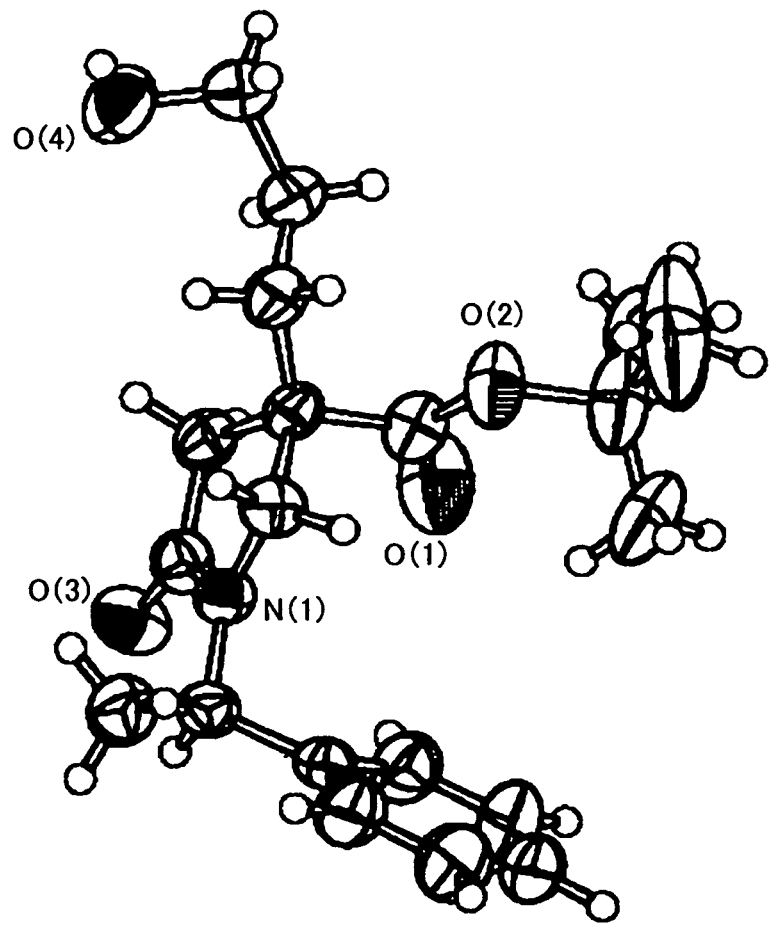
FIG. 1 shows the ORTEP diagram obtained by the x-ray crystallography for (3S)-3-(3-hydroxy-1-propyl)-5-oxo-1-[(1R)-1-phenylethyl]pyrrolidine-3-carboxylic acid tertbutyl ester obtained in Reference Example 24.

DETAILED DESCRIPTION OF THE PREFERRED EMBODIMENTS $R^1$ represents a hydrogen atom, an alkyl group having 1 to 6 carbon atoms, a cycloalkyl group having 3 to 6 carbon atoms, or a substituted carbonyl group derived from an amino acid, a dipeptide, or a tripeptide. The alkyl group may have one or more substituents selected from the group consisting of a hydroxy group, an amino group, a cyano group, a halogen atom, an alkylthio group having 1 to 6 carbon atoms, and an alkoxy group having 1 to 6 carbon atoms, and the cycloalkyl group may have one or more substituents selected from the group consisting of an alkyl group having 1 to 6 carbon atoms, an amino group, a hydroxy group, and a halogen atom.

$R^2$ represents a hydrogen atom, an alkyl group having 1 to 6 carbon atoms, or a cycloalkyl group having 3 to 6 carbon atoms. The alkyl group may have one or more substituents selected from the group consisting of a hydroxy group, an amino group, a halogen atom, an alkylthio group having 1 to 6 carbon atoms, and an alkoxy group having 1 to 6 carbon atoms. The cycloalkyl group may have one or more substituents selected from the group consisting of an alkyl group having 1 to 6 carbon atoms, an amino group, a hydroxy group, and a halogen atom.

When $R^1$ or $R^2$ is an alkyl group, the alkyl group may be linear or branched, and is preferably a methyl group, an ethyl group, a propyl group, or an isopropyl group, more preferably a methyl group or an ethyl group, and still more preferably a methyl group.

When $R^1$ or $R^2$ is an alkyl group having a hydroxy group, an amino group, or a cyano group as a substituent, the alkyl group may be a linear or branched alkyl group having 1 to 6 carbon atoms and is preferably substituted with the substituent on the terminal carbon atom of the alkyl group. The alkyl group having a hydroxy group is suitably an alkyl group having up to 3 carbon atoms and is preferably a 2-hydroxyethyl group, a 2-hydroxypropyl group, or a 3-hydroxypropyl group. The alkyl group having an amino group is suitably an alkyl group having up to 3 carbon atoms and is preferably a 2-aminoethyl group, a 2-aminopropyl group, or a 3-aminopropyl group. The alkyl group having a cyano group is suitably an alkyl group having 2 to 4 carbon atoms and is preferably a 2-cyanoethyl group or a 2-cyano-2,2-dimethylethyl group.

When $R^1$ or $R^2$ is an alkyl group having a halogen atom as a substituent, the alkyl group may be a linear or branched alkyl group having 1 to 6 carbon atoms and the halogen atom is preferably a fluorine atom. The alkyl group may be monofluoro-substituted to perfluoro-substituted. Suitable examples of the halogen-substituted alkyl group include a monofluoromethyl group, a difluoromethyl group, a trifluoromethyl group, and a 2,2,2-trifluoroethyl group.

When $R^1$ or $R^2$ is an alkyl group having an alkylthio group or an alkoxy group as a substituent, the alkyl group may be linear or branched and the alkyl moiety in the alkylthio group or alkoxy group may also be linear or branched. The alkyl group having an alkylthio group is preferably an alkylthiomethyl group, an alkylthioethyl group, or an alkylthiopropyl group, and the alkylthio group preferably has 1 to 3 carbon atoms. More preferred examples of the alkyl group having an alkylthio group include a methylthiomethyl group, an ethylthiomethyl group, and a methylthioethyl group. The alkyl group having an alkoxy group is preferably an alkoxymethyl group, an alkoxyethyl group, or an alkoxypropyl group, and the alkoxy group preferably has 1 to 3 carbon atoms. More preferred examples of the alkyl group having an alkoxy group include a methoxymethyl group, an ethoxymethyl group, and a methoxyethyl group.

When $R^1$ or $R^2$ is a cycloalkyl group, the cycloalkyl group is preferably a cyclopropyl group or a cyclobutyl group, and more preferably a cyclopropyl group. The cycloalkyl group may have one or more substituents selected from the group consisting of an alkyl group having 1 to 6 carbon atoms, an amino group, a hydroxy group, and a halogen atom. Specifically, the substituent is preferably a methyl group, an ethyl group, an amino group, a hydroxy group, a fluorine atom, or a chlorine atom.

A preferred combination of $R^1$ and $R^2$ is that wherein $R^1$ is selected from a hydrogen atom, an alkyl group, a cycloalkyl group and a substituted carbonyl group derived from an amino acid, a dipeptide, or a tripeptide, and $R^2$ is a hydrogen. A more preferred combination of $R^1$ and $R^2$ is that wherein $R^1$ is selected from a hydrogen atom, an alkyl group and a cycloalkyl group and $R^2$ is a hydrogen. The alkyl group is preferably a methyl group or an ethyl group, and particularly preferably a methyl group. The cycloalkyl group is preferably a cyclopropyl group or a cyclobutyl group, and particularly preferably a cyclopropyl group. A still more preferred combination that wherein both of $R^1$ and $R^2$ are hydrogen atoms or that wherein one of $R^1$ and $R^2$ is a hydrogen atom and the other is a methyl group, an ethyl group, a fluoroethyl group, or a cyclopropyl group.

A quinolone derivative, wherein $R^1$ is a substituted carbonyl group derived from an amino acid, a dipeptide, or a tripeptide and $R^2$ is a hydrogen atom, is useful as a prodrug. Amino acids, dipeptides, or tripeptides used for providing such a prodrug are those forming a peptide bond between a carboxyl group and the amino group to which $R^1$ and $R^2$ bonded and forming a free amine compound after being cleaved in vivo. Examples of substituted carbonyl groups for providing such a prodrug include substituted carbonyl groups derived from amino acids such as glycine, alanine, and aspartic acid; dipeptides formed by glycine, alanine, or asparagine such as glycine-glycine, glycine-alanine, and alanine-alanine; and tripeptides formed by glycine, alanine, or asparagine such as glycine-glycine-alanine and glycine-alanine-alanine.

$R^3$ and $R^4$ independently represent a hydrogen atom or an alkyl group having 1 to 6 carbon atoms. The alkyl group may have one or more substituents selected from the group consisting a halogen atom and an alkoxy group having 1 to 6 carbon atoms.

When $R^3$ and $R^4$ are independently an alkyl group, the alkyl group may be linear or branched, and is preferably a methyl group, an ethyl group, a propyl group, or an isopropyl group, more preferably a methyl group or an ethyl group, and still more preferably a methyl group.

When $R^3$ and $R^4$ are independently an alkyl group, the substituent may be a group selected from the group consisting of a halogen atom and an alkoxy group having 1 to 6 carbon atoms. The halogen atom is preferably a fluorine atom. The alkyl group may be monofluoro-substituted to perfluoro-substituted. Suitable examples of the halogen-substituted alkyl group include a monofluoromethyl group, a difluoromethyl group, and a trifluoromethyl group. Preferred examples of the alkoxy group having 1 to 6 carbon atoms include a methoxymethyl group, an ethoxymethyl group, and a methoxyethyl group. When $R^3$ and $R^4$ are independently a substituted alkyl group, the group is particularly preferably a fluoromethyl group.

A preferred combination of $R^3$ and $R^4$ is that wherein one of $R^3$ and $R^4$ is a hydrogen atom and the other is a methyl group or a fluoromethyl group. A more preferred combination of $R^3$ and $R^4$ is that wherein both of $R^3$ and $R^4$ are hydrogen atoms.

$R^5$ represents a hydrogen atom, a halogen atom, an alkyl group having 1 to 6 carbon atoms, an alkoxy group having 1 to 6 carbon atoms, an alkenyl group having 2 to 6 carbon atoms, an alkynyl group having 2 to 6 carbon atoms, a cycloalkyl group having 3 to 6 carbon atoms which may have a substituent, an aryl group having 6 to 10 carbon atoms which may have a substituent, or a heteroaryl group which may have a substituent.

When $R^5$ is an alkyl group, an alkenyl group, or an alkynyl group, the group may be linear or branched. The alkyl group may have one or more substituents selected from the group consisting of a hydroxy group, an amino group, a halogen atom, an alkylthio group having 1 to 6 carbon atoms, and an alkoxy group having 1 to 6 carbon atoms. The alkenyl group may have one or more substituents selected from the group consisting of a halogen atom and an alkoxy group having 1 to 6 carbon atoms.

When $R^5$ is a halogen atom, the halogen atom is preferably a fluorine atom or a chlorine atom, and particularly preferably a fluorine atom.

When $R^5$ is an alkyl group having 1 to 6 carbon atoms, the alkyl group is preferably a methyl group, an ethyl group, a propyl group, or an isopropyl group. The alkyl group is more preferably a methyl group or an ethyl group, and particularly preferably a methyl group.

The alkyl group may have one or more substituents selected from the group consisting of a hydroxy group, an amino group, a halogen atom, an alkylthio group having 1 to 6 carbon atoms, and an alkoxy group having 1 to 6 carbon atoms.

When a hydroxy group or an amino group is a substituent on the alkyl group, the substituent is preferably on the terminal carbon atom of the alkyl group. The alkyl group having a hydroxy group is preferably a hydroxymethyl group, a 2-hydroxyethyl group, a 2-hydroxypropyl group, or a 3-hydroxypropyl group. The alkyl group having an amino group is preferably an aminomethyl group, a 2-aminoethyl group, a 2-aminopropyl group, or a 3-aminopropyl group. The alkyl group having a hydroxy group or an amino group is preferably a methyl group or an ethyl group, and more preferably a hydroxymethyl group or an aminomethyl group having a hydroxy group or an amino group on the methyl group.

When the alkyl group has a halogen atom as a substituent, the alkyl group may be a linear or branched alkyl group having 1 to 6 carbon atoms, and is more preferably a methyl group or an ethyl group, and particularly preferably a methyl group. The halogen atom is preferably a fluorine atom. The alkyl group may be monofluoro-substituted to perfluoro-substituted. Examples of the halogen-substituted alkyl group include a monofluoromethyl group, a difluoromethyl group, a trifluoromethyl group, and a 2,2,2-trifluoroethyl group. A monofluoromethyl group, a difluoromethyl group, or a trifluoromethyl group are particularly preferred.

When the alkyl group has an alkylthio group or an alkoxy group as a substituent, the alkyl group may be linear or branched and the alkyl moiety in the alkylthio group or alkoxy group may also be linear or branched. The alkyl group having an alkylthio group is preferably an alkylthiomethyl group or an alkylthioethyl group, and the alkylthio group preferably has 1 or 2 carbon atoms. More preferred examples of the alkyl group having an alkylthio group include a methylthiomethyl group, an ethylthiomethyl group, and a methylthioethyl group. The alkyl group having an alkoxy group is preferably an alkoxymethyl group or an alkoxyethyl group, and the alkoxy group preferably has 1 or 2 carbon atoms. More preferred examples of the alkyl group having an alkoxy group include a methoxymethyl group, an ethoxymethyl group, and a methoxyethyl group. Among these, a methylthio group and a methoxymethyl group are still more preferred.

When $R^5$ is an alkoxy group having 1 to 6 carbon atoms, the alkoxy group is preferably an alkoxy group having 1 to 3 carbon atoms, specifically, a methoxy group or an ethoxy group.

When $R^5$ is an alkenyl group having 2 to 6 carbon atoms, the alkenyl group preferably contains one double bond and there are no specific limitations to the position of the double bond. The alkenyl group is preferably a vinyl group, a propenyl group, or a butenyl group, and particularly preferably a vinyl group, for example.

The alkenyl group may have one or more substituents selected from the group consisting of a halogen atom and an alkoxy group having 1 to 6 carbon atoms.

The halogen atom is preferably a fluorine atom. When the alkenyl group has a halogen atom as a substituent, the alkenyl group is preferably an alkenyl group having 2 or 3 carbon atoms, more preferably a vinyl group having a fluorine atom, and particularly preferably a fluorovinyl group.

When the alkenyl group has an alkoxy group as a substituent, the alkenyl group preferably has 2 or 3 carbon atoms. Examples of the alkenyl group having an alkoxy group include an alkoxyvinyl group and an alkoxypropenyl group, specifically, a methoxyvinyl group and an ethoxyvinyl group. A methoxyvinyl group is particularly preferred.

When $R^5$ is an alkynyl group having 2 to 6 carbon atoms, the alkynyl group preferably contains one triple bond and the triple bond may be at any position. The alkynyl group is preferably an ethynyl group, a propynyl group, or a butynyl group, and particularly preferably an ethynyl group.

When $R^5$ is a cycloalkyl group having 3 to 6 carbon atoms which may have a substituent, the cycloalkyl group is preferably a cyclopropyl group or a cyclobutyl group, and more preferably a cyclopropyl group.

The cycloalkyl group may have one or more substituents selected from the group consisting of an alkyl group having 1 to 6 carbon atoms, a phenyl group, a halogen atom, an amino group, and a hydroxy group. Specifically, the substituent is preferably a methyl group, an ethyl group, a phenyl group, a fluorine atom, or a chlorine atom, and more preferably a methyl group or a fluorine atom.

When $R^5$ is an aryl group having 6 to 10 carbon atoms which may have a substituent or is a heteroaryl group which may have a substituent, the heteroaryl group is a five-membered ring or a six-membered ring and may contain 1 to 4 heteroatoms arbitrarily selected from a nitrogen atom, an oxygen atom, and a sulfur atom, and the aryl group or heteroaryl group may have one or more substituents selected from the group consisting of a halogen atom, an amino group, a hydroxy group, a cyano group, a nitro group, a carboxyl group, a carbamoyl group, an alkyl group having 1 to 6 carbon atoms, an alkoxy group having 1 to 6 carbon atoms, an alkoxycarbonyl group having 2 to 6 carbon atoms, and an acyl group having 2 to 5 carbon atoms. The alkyl group, alkoxy group, alkoxycarbonyl group, or acyl group may have one or more substituents selected from the group consisting of a halogen atom, a hydroxy group, and an alkoxy group having 1 to 6 carbon atoms.

The substituent on the aryl group or heteroaryl group is preferably a halogen atom, an amino group, a hydroxy group, a cyano group, a carboxyl group, an alkyl group having 1 to 6 carbon atoms, an alkoxy group having 1 to 6 carbon atoms, or an alkoxycarbonyl group having 2 to 6 carbon atoms.

The halogen atom as a preferred substituent is preferably a fluorine atom or a chlorine atom, and more preferably a fluorine atom.

The alkyl group as a preferred substituent may be a linear or branched alkyl group having 1 to 6 carbon atoms and is for example, a methyl group, an ethyl group, a propyl group, an isopropyl group, or a tert-butyl group, and preferably a methyl group or an ethyl group. The substituent on the alkyl group is preferably a halogen atom, and more preferably a fluorine atom. Examples of the halogen-substituted alkyl group include a fluoromethyl group and a trifluoromethyl group.

The alkoxy group as a preferred substituent is preferably an alkoxy group having 1 to 3 carbon atoms, specifically, a methoxy group or an ethoxy group, and particularly preferably a methoxy group. The substituent on the alkoxy group is preferably a halogen atom, and more preferably a fluorine atom. Examples of the halogen-substituted alkoxy group include a trifluoromethoxy group.

The alkoxycarbonyl group as a preferred substituent is preferably an alkoxycarbonyl group having up to 3 carbon atoms. Preferred examples of the alkoxycarbonyl group include a methoxycarbonyl group and an ethoxycarbonyl group. The substituent on the alkoxycarbonyl group is preferably a halogen atom, and more preferably a fluorine atom. Examples of the halogen-substituted alkoxycarbonyl group include a trifluoromethoxycarbonyl group.

$R^6$ and $R^7$ taken together with the carbon atoms to which they are bonded form a four- to seven-membered cyclic structure, the cyclic structure representing a partial structure that together with the pyrrolidine ring forms a fused cyclic (bicyclic) structure. The four- to seven-membered cyclic structure moiety formed in this manner may contain an oxygen atom or a sulfur atom as a ring constituent atom. Such fused cyclic amines are represented by the following formulas:

[Formula 21]

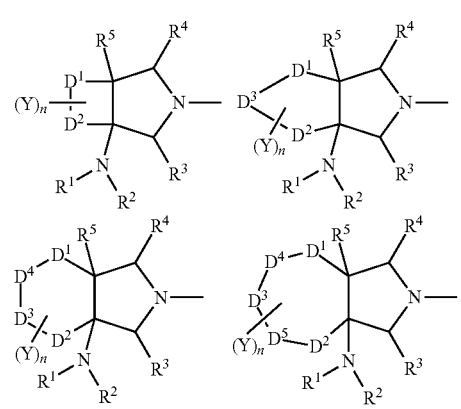

wherein $R^1$, $R^2$, $R^3$, $R^4$ and $R^5$ are as defined in claim 1; $D^1$, $D^2$, $D^3$, $D^4$, and $D^5$ each represents a carbon atom which may have a substituent, an oxygen atom, or a sulfur atom, provided that when two or more of $D^1$, $D^2$, $D^3$, $D^4$ and $D^5$ are each an oxygen atom or a sulfur atom, no adjacent two of them are simultaneously oxygen atoms or sulfur atoms, and the sulfur atom may be an oxidized sulfur atom such as S=O or S(=O)$_2$; Y represents a substituent on the ring (described later); and n represents an integer of 0 to 3.

$R^6$ and $R^7$ form a four- to seven-membered cyclic structure when taken together with the carbon atoms to which they are bonded. Preferred examples of the fused cyclic amine are listed as follows:

[Formula 22]

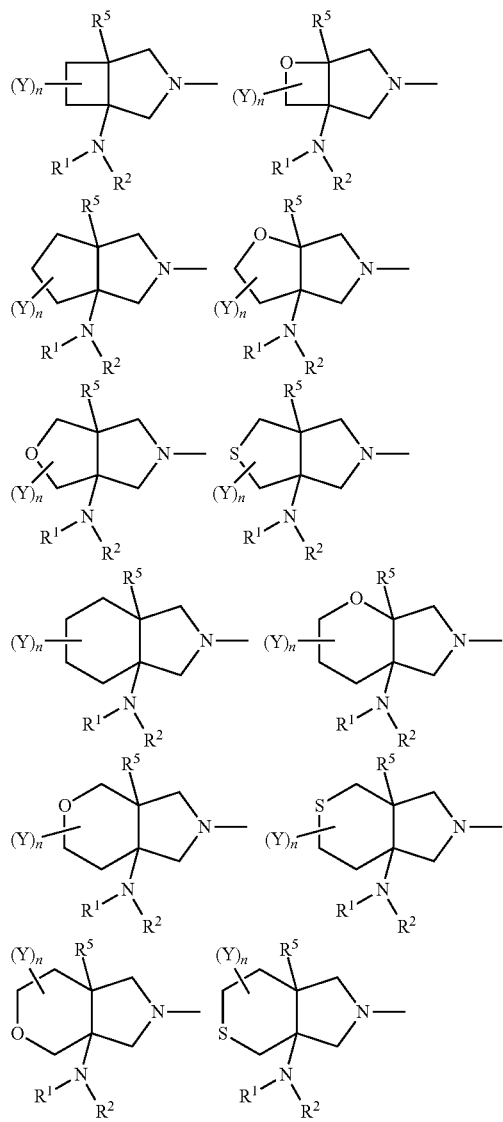

The four- to seven-membered cyclic structure formed by taking $R^6$ and $R^7$ together with the carbon atoms to which they are bonded may contain a ring double bond formed as a constituent structure. When the cyclic structure contains the double bond as a constituent structure, part of $R^6$ (the carbon atom substituted on the pyrrolidine ring) and $R^5$ may be taken together to form a double bond partial structure that together with $R^7$ forms a five- to seven-membered cyclic structure represented by the following formula:

[Formula 23]

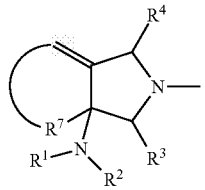

However, the double bond partial structure and $R^7$ preferably form a five- or six-membered cyclic structure. Preferred examples of the bicyclic amine are listed as follows:

[Formula 24]

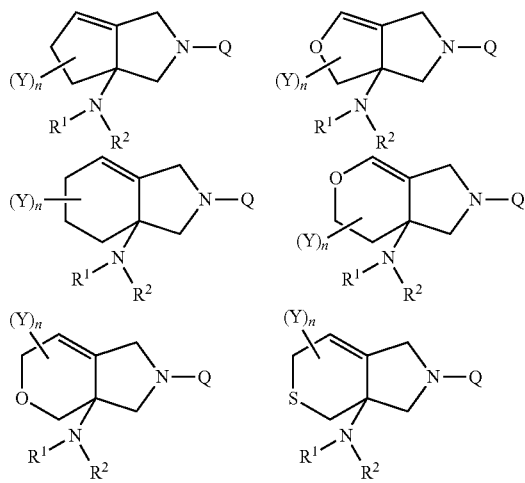

The four- to seven-membered cyclic structure may have a substituent selected from the group consisting of an alkyl group having 1 to 6 carbon atoms which may have a substituent, an alkoxy group having 1 to 6 carbon atoms which may have a substituent, an alkenyl group having 2 to 6 carbon atoms which may have a substituent, an alkynyl group having 2 to 6 carbon atoms which may have a substituent, a cycloalkyl group having 3 to 6 carbon atoms which may have a substituent, a heterocycloalkyl group having 3 to 6 carbon atoms which may have a substituent, an exomethylene group which may have a substituent, a spiroalkyl group which may have a substituent, an aryl group having 6 to 10 carbon atoms which may have a substituent, a heteroaryl group which may have a substituent, a halogen atom, a hydroxy group, a cyano group, a hydroxyimino group, and an alkoxyimino group having 1 to 6 carbon atoms which may have a substituent.

The alkyl group having 1 to 6 carbon atoms which may have a substituent may be linear or branched. Specific examples of the alkyl group include a methyl group, an ethyl group, a propyl group, an isopropyl group, a tert-butyl group, a fluoromethyl group, a trifluoromethyl group, a 2-fluoroethyl group, a 2,2,2-trifluoroethyl group, a fluorine-substituted tert-butyl group, a hydroxymethyl group, a 2-hydroxyethyl group, a 2-cyanoethyl group, a methoxymethyl group, and a 2-methoxyethyl group. The alkyl group is preferably a methyl group, an ethyl group, an isopropyl group, a fluoromethyl group, a 2-cyanoethyl group, or a methoxymethyl group.

The alkoxy group having 1 to 6 carbon atoms which may have a substituent may be an alkoxy group derived from the aforementioned alkyl group, and is preferably an alkoxy group having 1 to 3 carbon atoms, specifically, a methoxy group or an ethoxy group.

The alkenyl group having 2 to 6 carbon atoms which may have a substituent preferably contains one double bond and the position of the double bond is not limited. The alkenyl group is preferably a vinyl group, a propenyl group, or a butenyl group. The substituent on the alkenyl group is preferably a halogen atom or an alkoxy group, and the halogen atom is preferably a fluorine atom. Examples of the substituted alkenyl group include a fluorovinyl group and a methoxyvinyl group.

The alkynyl group having 2 to 6 carbon atoms which may have a substituent preferably contains one triple bond and the triple bond may be at any position. The alkynyl group is preferably an ethynyl group, a propynyl group, or a butynyl group. Preferably, the alkynyl group does not have a substituent other than a hydrogen atom.

The cycloalkyl group having 3 to 6 carbon atoms which may have a substituent is preferably a cyclopropyl group or a cyclobutyl group. The cycloalkyl group may be substituted with one or more substituents selected from the group consisting of an alkyl group having 1 to 6 carbon atoms, a halogen atom, an amino group, and a hydroxy group. Specifically, the substituent is preferably a methyl group, an ethyl group, a fluorine atom, or a chlorine atom.

The heterocycloalkyl group having 3 to 6 carbon atoms which may have a substituent is preferably an oxetan-3-yl group, a thioxetan-3-yl group, a tetrahydrofuranyl group, a tetrahydropyranyl group, or a 2,2-dimethyl-1,3-dioxan-4-yl group.

The exomethylene group which may have a substituent is preferably one that does not have a substituent other than a hydrogen atom. The substituent other than a hydrogen atom is preferably an amino group, a fluorine atom, a chlorine atom, a methylthio group, or a methoxy group.

The spiroalkyl group which may have a substituent is preferably a spirocyclopropyl group or a spirocyclobutyl group. The spiroalkyl group is composed of an alicyclic component and forms a spiro cyclic ring system. The spirocycloalkyl group may be substituted with one or more substituents selected from the group consisting of an alkyl group having 1 to 6 carbon atoms, a halogen atom, an amino group, and a hydroxy group. Specifically, the substituent is preferably a methyl group, an ethyl group, a fluorine atom, or a chlorine atom.

When the substituent on the four- to seven-membered cyclic structure is an aryl group having 6 to 10 carbon atoms which may have a substituent or is a heteroaryl group which may have a substituent, the heteroaryl group is a five- or six-membered ring and may contain 1 to 4 heteroatoms arbitrarily selected from a nitrogen atom, an oxygen atom, and a sulfur atom. The aryl group or heteroaryl group may have one or more substituents selected from the group consisting of a halogen atom, an amino group, a hydroxy group, a cyano group, a nitro group, a carboxyl group, a carbamoyl group, an alkyl group having 1 to 6 carbon atoms, an alkoxy group having 1 to 6 carbon atoms, an alkoxycarbonyl group having 2 to 6 carbon atoms, and an acyl group having 2 to 5 carbon atoms (i.e. alkyl carbonyl group of 2 to 5 carbon atoms). The alkyl group, alkoxy group, alkoxycarbonyl group, or acyl group may have one or more substituents selected from the group consisting of a halogen atom, a hydroxy group, and an alkoxy group having 1 to 6 carbon atoms. The substituent on the aryl group or heteroaryl group is preferably a halogen atom, an amino group, a hydroxy group, a cyano group, a carboxyl group, an alkyl group having 1 to 6 carbon atoms, an alkoxy group having 1 to 6 carbon atoms, or an alkoxycarbonyl group having 2 to 6 carbon atoms. Particularly preferred substituents on the aryl group or heteroaryl group include a fluorine atom, a chlorine atom, a methyl group, a fluoromethyl group, a methoxy group, an ethoxy group, a methoxycarbonyl group, and an ethoxycarbonyl group.

When the substituent is a halogen atom, the halogen atom is preferably a fluorine atom or a chlorine atom, and particularly preferably a fluorine atom.

Preferred examples of the alkoxyimino group having 1 to 6 carbon atoms which may have a substituent include a methoxyimino group and an ethoxyimino group.

Preferred examples of the aforementioned substituent include a methyl group, an ethyl group, a fluoromethyl group, a 2-fluoroethyl group, a methoxymethyl group, a cyanoethyl group, a methoxy group, a cyclopropyl group, a spirocyclopropyl group, a phenyl group, an oxazole group, a fluorine atom, a hydroxy group, a hydroxyimino group, and a methoxyimino group. Among these, a methyl group, a fluoromethyl group, a methoxymethyl group, a methoxy group, a fluorine atom, a cyanoethyl group, and a methoxyimino group are particularly preferred.

The polymethylene chain which binds to form a spirocyclic ring system is preferably one of 2 or 3 carbon atoms, and still preferably one having 2 carbon atoms.

$R^5$ may be a methylene group taken together with $R^6$ to form a three-membered fused cyclic structure, and this cyclic structure makes the fused bicyclic structure formed by combining $R^6$ and $R^7$ into a tri-cyclic ring system. Moreover, the third ring system derived from $R^5$ and $R^6$ may locate in another part of the fused bicyclic ring system derived from $R^6$ and $R^7$. In other words, the fused bicyclic substituent at 7-position may become a tri-cyclic ring system by incorporating a cyclopropan ring on any part of the bicyclic ring structure.

Q represents a partial structure represented by the following formula:

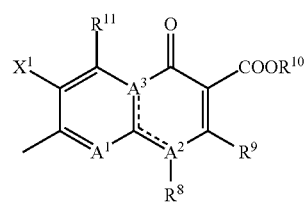

[Formula 25]

wherein $A^2$ and $A^3$ each represents a nitrogen atom or a carbon atom, and $A^1$, $A^2$, $A^3$, $R^8$ and the carbon atom to which $A^2$ and $A^3$ are bonded together form a partial structure:

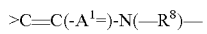

or a partial structure:

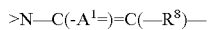

wherein ">" means that there are two bonds to a nitrogen atom or a carbon atom (hereinafter the same).

Q preferably represents a fused heterocyclic system partial structure represented by the formula:

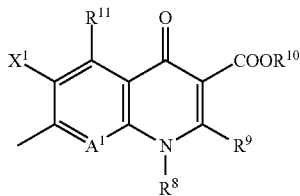

[Formula 26]

or the formula:

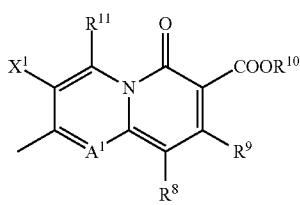

[Formula 27]

wherein $R^8$ represents an alkyl group having 1 to 6 carbon atoms, an alkenyl group having 2 to 6 carbon atoms, a halogen-substituted alkyl group having 1 to 6 carbon atoms, a cycloalkyl group having 3 to 6 carbon atoms which may have a substituent, a halogen-substituted phenyl group which may have a substituent, a halogen-substituted heteroaryl group which may have a substituent, an alkoxy group having 1 to 6 carbon atoms, or an alkylamino group having 1 to 6 carbon atoms.

When $R^8$ is an alkyl group having 1 to 6 carbon atoms, the alkyl group may be linear or branched. Specific examples of the alkyl group include a methyl group, an ethyl group, an isopropyl group, a sec-butyl group, and a tert-butyl group. Among these, an ethyl group and a tert-butyl group are preferred.

When $R^8$ is an alkenyl group having 2 to 6 carbon atoms, the alkenyl group may be linear or branched. Preferred specific examples of the alkenyl group include a vinyl group and an isopropenyl group.

When $R^8$ is a halogen-substituted alkyl group having 1 to 6 carbon atoms, the alkyl moiety may be linear or branched. Specific examples of the alkyl moiety include a methyl group, an ethyl group, a propyl group, an isopropyl group, a butyl group, an isobutyl group, a sec-butyl group, and a tert-butyl group. Among these, an ethyl group and a tert-butyl group are preferred. The halogen atom substituent on the alkyl group is preferably a fluorine atom or a chlorine atom, and more preferably a fluorine atom. Examples of the halogen-substituted alkyl group include a fluoromethyl group, a trifluoromethyl group, a 1-fluoroethyl group, a 2-fluoroethyl group, a 2,2,2-trifluoroethyl group, a 1,1-dimethyl-2-fluoroethyl group, a 1-methyl-1-(fluoromethyl)-2-fluoroethyl group, and a 1,1-(difluoromethyl)-2-fluoroethyl group. Among these, a 2-fluoroethyl group and a 1,1-dimethyl-2-fluoroethyl group are preferred.

When $R^8$ is a cycloalkyl group having 3 to 6 carbon atoms which may have a substituent, examples of the cycloalkyl group include a cyclopropyl group, a cyclobutyl group, and a cyclopentyl group. Among these, a cyclopropyl group is preferred. The substituent on the cycloalkyl group is preferably a halogen atom, a methyl group, or a phenyl group, and more preferably a halogen atom. The halogen atom is preferably a fluorine atom or a chlorine atom, and particularly preferably a fluorine atom. The number of substituents may be 1 or 2 but is preferably 1. Specifically, the cycloalkyl group which may have a substituent is preferably a monofluorocyclopropyl group, more preferably a 1,2-cis-2-fluorocyclopropyl group, and particularly preferably a (1R,2S)-2-fluorocyclopropyl group.

When $R^8$ is a halogen-substituted phenyl group which may have a substituent, the halogen atom is preferably a fluorine atom or a chlorine atom, and more preferably a fluorine atom. The number of halogen atom substituents is preferably 1 or 2. The substituent on the halogen-substituted phenyl group is preferably an amino group, a hydroxy group, or a methyl group. Examples of the halogen-substituted phenyl group which may have a substituent include a 2-fluorophenyl group, a 4-fluorophenyl group, a 2,4-fluorophenyl group, and a 5-amino-2,4-difluorophenyl group. Among these, a 2,4-difluorophenyl group and a 5-amino-2,4-difluorophenyl group are preferred.

When $R^8$ is a halogen-substituted heteroaryl group which may have a substituent, the heteroaryl group may be a five- or six-membered aromatic heterocyclic group containing one or more heteroatoms selected from a nitrogen atom, a sulfur atom, and an oxygen atom. Such a heteroaryl group is preferably a five- or six-membered nitrogen-containing aromatic heterocyclic group containing 1 or 2 nitrogen atoms. Specific examples of the heteroaryl group include a pyridyl group, a pyrimidyl group, a pyridazinyl group, an imidazolyl group, a thiazolyl group, and an oxazolyl group. Among these, a pyridyl group is preferred. The halogen atom is preferably a fluorine atom or a chlorine atom, and more preferably a fluorine atom. The number of halogen atoms is preferably 1 or 2. Preferred examples of the substituent on the halogen-substituted heteroaryl group include an amino group, a hydroxy group, and a methyl group. Such a halogen-substituted heteroaryl group which may have a substituent is preferably a 6-amino-3,5-difluoropyridin-2-yl group.

When $R^8$ is an alkoxy group having 1 to 6 carbon atoms, the alkoxy group is preferably a methoxy group.

When $R^8$ is an alkylamino group having 1 to 6 carbon atoms, the alkylamino group is preferably a methylamino group.

The aforementioned $R^8$ is preferably a cyclopropyl group or a 1,2-cis-2-fluorocyclopropyl group, and more preferably a (1R,2S)-2-fluorocyclopropyl group.

$R^9$ represents a hydrogen atom or an alkylthio group having 1 to 6 carbon atoms. $R^9$ and the aforementioned $R^8$ may be taken together with part of the mother skeleton (including the carbon atom to which $R^9$ is bonded and $A^2$; hereinafter the same) to form a cyclic structure. The ring formed in this manner may contain a sulfur atom as a ring constituent atom, and may have an alkyl group having 1 to 6 carbon atoms or a halogen-substituted alkyl group having 1 to 6 carbon atoms as a substituent. The ring formed here may be a four- to six-membered ring and may be saturated, partially saturated, or unsaturated. The fused ring structure formed in this manner may be represented by the following formulas:

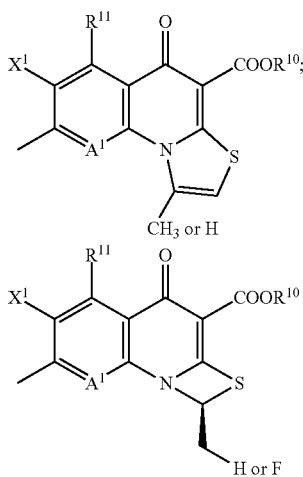

[Formula 28]

$R^{10}$ represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxobutyl group, an alkyl group having 1 to 6 carbon atoms, an alkoxymethyl group having 2 to 7 carbon atoms, or a phenylalkyl group formed by an alkylene group having 1 to 6 carbon atoms and a phenyl group.

$R^{10}$ is preferably a hydrogen atom.

$R^{11}$ represents a hydrogen atom, an amino group, a hydroxy group, a thiol group, a halogenomethyl group, or an alkyl group having 1 to 6 carbon atoms. The amino group may have one or two substituents selected from the group consisting of a formyl group, an alkyl group having 1 to 6 carbon atoms, and an acyl group having 2 to 5 carbon atoms.

When $R^{11}$ is an alkyl group having 1 to 6 carbon atoms, the alkyl group may be linear or branched and is preferably a methyl group, an ethyl group, a propyl group, or an isopropyl group, and particularly preferably a methyl group.

When $R^{11}$ is a halogenomethyl group, the halogen atom is preferably a fluorine atom and the number of halogen atoms may be 1 to 3.

When $R^{11}$ is an amino group, a hydroxy group, or a thiol group, the group may be protected by a protecting group ordinarily used.

Examples of such a protecting group include (substituted) alkoxycarbonyl groups such as a tert-butoxycarbonyl group and a 2,2,2-trichloroethoxycarbonyl group; (substituted) aralkyloxycarbonyl groups such as a benzyloxycarbonyl group, a p-methoxybenzyloxycarbonyl group, and a p-nitrobenzyloxycarbonyl group; (substituted) acyl groups such as an acetyl group, a methoxyacetyl group, a trifluoroacetyl group, a chloroacetyl group, a pivaloyl group, a formyl group, and a benzoyl group; (substituted) alkyl groups or (substituted) aralkyl groups such as a tert-butyl group, a benzyl group, a p-nitrobenzyl group, a p-methoxybenzyl group, and a triphenylmethyl group; (substituted) ethers such as a methoxymethyl group, a tert-butoxymethyl group, a tetrahydropyranyl group, and a 2,2,2-trichloroethoxymethyl group; and (alkyl- and/or aralkyl-) substituted silyl groups such as a trimethylsilyl group, an isopropyldimethylsilyl group, and a tert-butyldiphenylsilyl group. A compound having a substituent protected by such a protecting group is particularly preferable as a production intermediate.

Among the aforementioned examples, $R^{11}$ is preferably a hydrogen atom, an amino group, a hydroxy group, or a methyl group, and particularly preferably a hydrogen atom or an amino group.

$X^1$ represents a halogen atom or a hydrogen atom. The halogen atom is preferably a fluorine atom or a chlorine atom, and more preferably a fluorine atom. $X^1$ is preferably a fluorine atom or a hydrogen atom.

$A^1$ represents a nitrogen atom or a partial structure represented by the formula (III):

[Formula 29]

III wherein $X^2$ represents a hydrogen atom, an alkyl group having 1 to 6 carbon atoms, an alkoxy group having 1 to 6 carbon atoms, a cyano group, a halogen atom, a halogeno-substituted methyl group, or a halogenomethoxy group, the $X^2$ and the $R^8$ may be taken together with their connecting part of the mother skeleton (including the carbon atom to which $X^2$ is bonded and $A^2$) to form a cyclic structure, the ring formed in this manner may contain an oxygen atom, a nitrogen atom, or a sulfur atom as a ring constituent atom, and the ring may be substituted with an alkyl group having 1 to 6 carbon atoms which may have a substituent.

When $A^1$ is a partial structure represented by the formula (III) and $X^2$ is an alkyl group having 1 to 6 carbon atoms, the alkyl group may be linear or branched, and is preferably a methyl group, an ethyl group, a propyl group, or an isopropyl group, more preferably a methyl group or an ethyl group, and still more preferably a methyl group.

When $X^2$ is an alkoxy group having 1 to 6 carbon atoms, the alkoxy group may be an alkoxy group derived from the aforementioned alkyl group. The alkoxy group is preferably an alkoxy group having 1 to 3 carbon atoms, and particularly preferably a methoxy group.

When $X^2$ is a halogen atom, the halogen atom is preferably a fluorine atom or a chlorine atom. When the aforementioned $R^{11}$ is a hydrogen atom, $X^2$ is preferably a chlorine atom; when the $R^{11}$ is an amino group, a hydroxy group, or a methyl group, $X^2$ is preferably a fluorine atom.

When $X^2$ is a halogeno-substituted methyl group, the halogen atom is preferably a fluorine atom. Preferred examples of the halogeno-substituted methyl group include a fluoromethyl group, a difluoromethyl group, and a trifluoromethyl group.

When $X^2$ is a halogenomethoxy group, the halogen atom is preferably a fluorine atom as in the aforementioned case. Specific examples of the halogenomethoxy group include a fluoromethoxy group, a difluoromethoxy group, and a trifluoromethoxy group. Among these, a difluoromethoxy group is more preferred.

When $A^1$ is a partial structure represented by the formula (III), $X^2$ and $R^8$ may form a cyclic structure including part of the quinolone skeleton [the carbon atom to which $X^2$ is bonded, $A^2$ to which $R^8$ is bonded (where $A^2$ is a nitrogen atom or a carbon atom), and the skeleton ring carbon atom to which the carbon atom and the $A^2$ are bonded]. The ring formed here is preferably a five- to seven-membered ring and may be saturated or unsaturated. The cyclic structure may contain an oxygen atom, a nitrogen atom, or a sulfur atom and may be substituted with an alkyl group having 1 to 6 carbon atoms or a halogenomethyl group described for $X^2$. The fused ring structure formed in this manner may be represented by the following formulas:

[Formula 30]

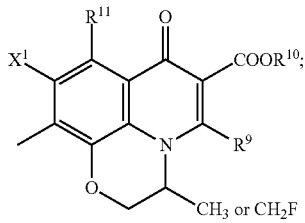

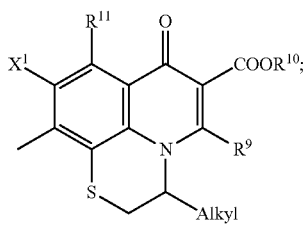

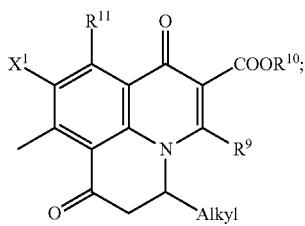

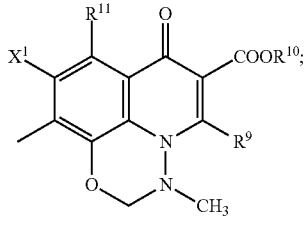

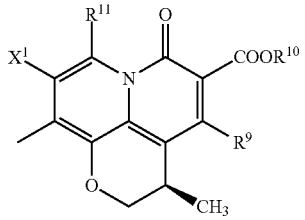

When $A^1$ is a partial structure represented by the formula (III) and the substituent $X^2$ does not form a cyclic structure, $X^2$ is preferably a methyl group, an ethyl group, a methoxy group, a difluoromethoxy group, a cyano group, or a chlorine atom, and particularly preferably a methyl group, a methoxy group, a difluoromethoxy group, or a cyano group. Such a substituent is particularly preferred when A is a partial structure represented by the following formula:

[Formula 31]

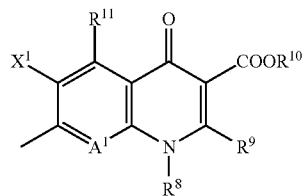

Moreover, such a substituent is more particularly preferred when Q is a partial structure 1-[(1R,2S)-2-fluorocyclopropyl]-1,4-dihydro-4-oxoquinoline-3-carboxylic acid skeleton represented by the following formula:

[Formula 32]

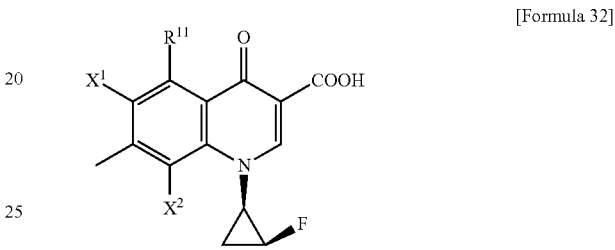

When $A^1$ is a partial structure represented by the formula (III) and the substituent $X^2$ forms a cyclic structure, a 2,3-dihydro-3-methyl (or fluoromethyl)-7-oxo-7H-pyrido[1,2,3-de][1,4]benzoxazine-6-carboxylic acid skeleton is preferably formed. A 3-(S)-methylpyridobenzoxazine skeleton represented by the following formula (the compound of $Y^0$ is methyl) is particularly preferred:

[Formula 33]

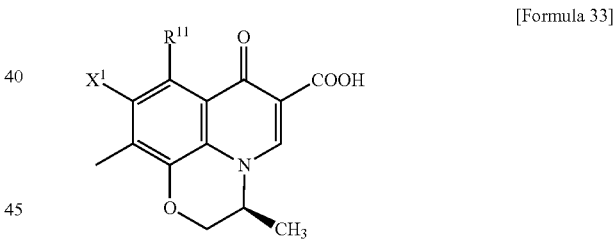

The compound of the present invention is characterized by having a substituent of a structure represented by the following formula at the 7-position of the quinolone skeleton (or its corresponding position):

[Formula 34]

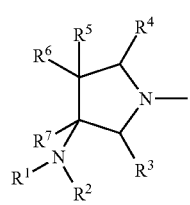

Specifically, the substituent of the compound of the present invention has an amino group at a position corresponding to the 3-position of the pyrrolidinyl group, and the substituent $R^7$ on the carbon atom substituted with the amino group and the substituent R⁶ at a position corresponding to the 4-position of the pyrrolidinyl group are taken together with the carbon atoms to which they are bonded to form a four- to seven-membered cyclic structure. That is, the substituent of the compound of the present invention is a fused substituted aminopyrrolidine structure, in which the cyclic structure together with the pyrrolidine ring forms a fused cyclic (bicyclic) structure represented by the following formula, in which the fused cyclic structure is substituted with an amino group at the bridgehead position as follows:

[Formula 35]

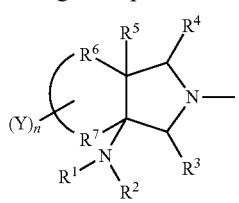

Further, the substituent of the compound of the present invention has a cyclic structure represented by the following formula, in which the cyclic structure formed by taking the substituents R⁶ and R⁷ together with the carbon atoms to which they are bonded is a five- or six-membered ring, and R⁵ and R⁶ are taken together to form a double bond partial structure as follows:

[Formula 36]

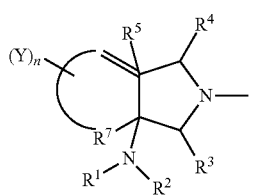

The bicyclic amino group contains an asymmetric carbon atom and stereoisomerism (optical isomerism) occurs. This stereoisomerism will now be described. Further, there are the following two kinds with regard to the bridgehead position substituted with an amino group:

[Formula 37]

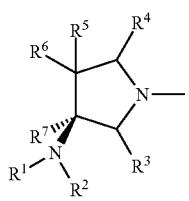

Here, the following structure where the amino group is in the β-configuration is preferred:

[Formula 38]

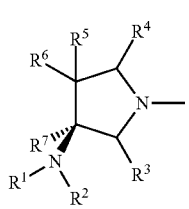

Further, when the substituents R⁵ and R⁶ are not taken together to form a double bond, there are the following four kinds with regard to the asymmetric carbon atom substituted with R⁵:

[Formula 39]

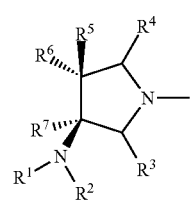

1

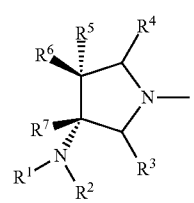

2

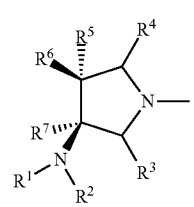

3

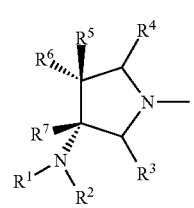

4

Typically, the structure 1 is more preferred than the structure 2 and the structure 3 is more preferred than the structure 4; however, which structure is preferred depends on the structure of the substituent R⁵. Typically, the structure 1 is more preferred than the structure 3 when the substituents R⁶ and R⁷ form a four-membered ring, and the structure 3 is more preferred than the structure 1 when the substituents R⁶ and R⁷ form a six-membered ring; however, which structure is preferred depends on the size of the ring formed by the substituents R⁶ and R⁷. The present invention includes all of the aforementioned types.

Preferred mother skeletons are listed below taking, as an example, a quinolonecarboxylic acid (or pyridobenzoxazinecarboxylic acid) basic skeleton having the aforementioned substituent at the 7-position (or its corresponding position):

[Formula 40]
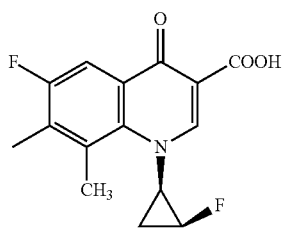
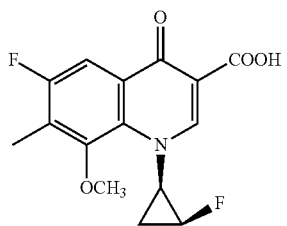
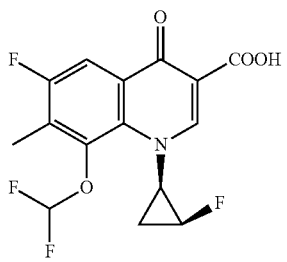
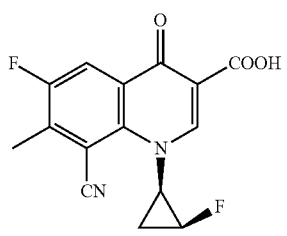
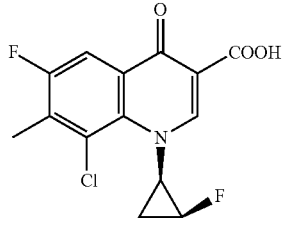
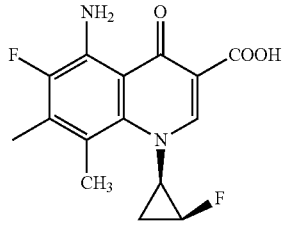
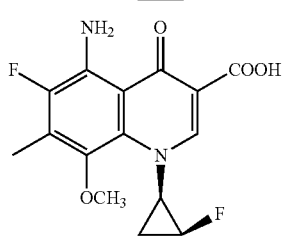
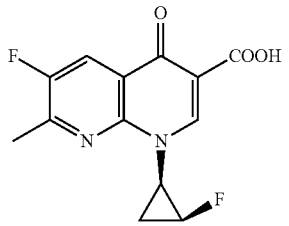
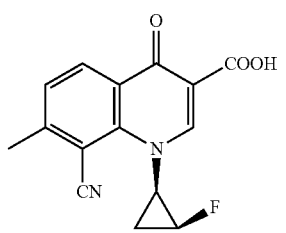
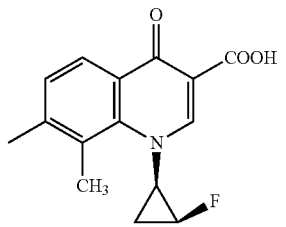
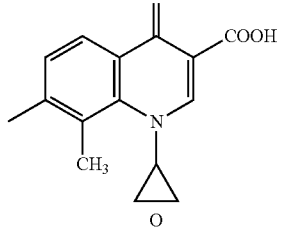
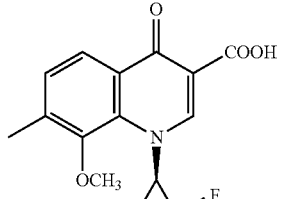
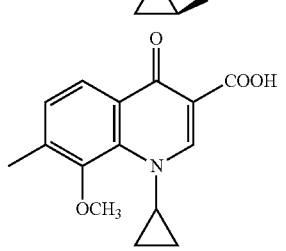
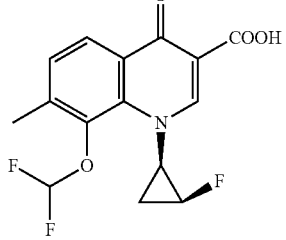

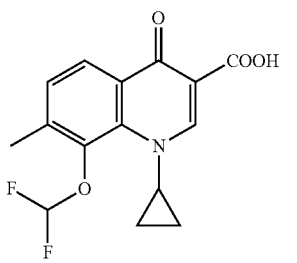
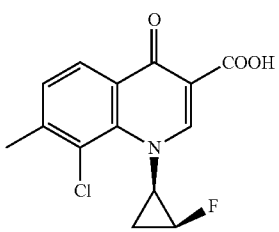
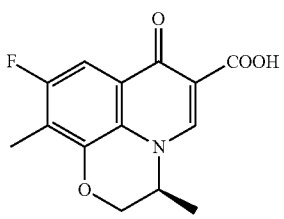
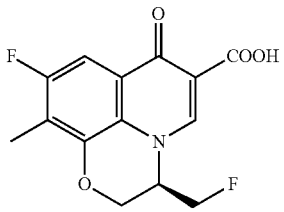
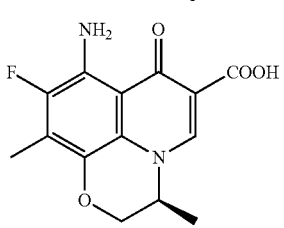
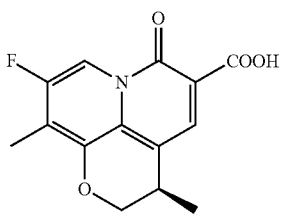
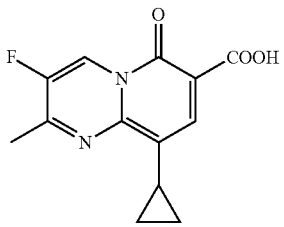

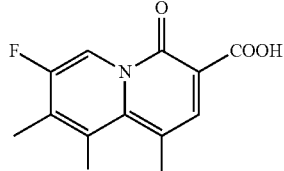
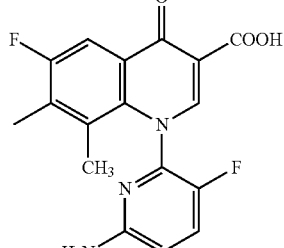
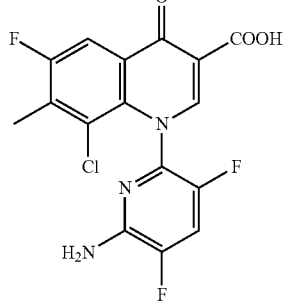

Preferred examples of the substituent at the 7-position (or its corresponding position) are listed below:

a (1R,5S)-1-amino-5-fluoro-3-azabicyclo[3.2.0]heptan-3-yl group;
a (1S,5S,6R)-1-amino-6-fluoro-3-azabicyclo[3.2.0]heptan-3-yl group;
a (1S,5S,6S)-1-amino-6-fluoro-3-azabicyclo[3.2.0]heptan-3-yl group;
a (1S,5S)-1-amino-6,6-difluoro-3-azabicyclo[3.2.0]heptan-3-yl group;
a (1S,5R,6R)-1-amino-6-methyl-3-azabicyclo[3.2.0]heptan-3-yl group;
a (1S,5R,6S)-1-amino-6-methyl-3-azabicyclo[3.2.0]heptan-3-yl group;
a (1S,5R,6R)-1-amino-6-fluoromethyl-3-azabicyclo[3.2.0]heptan-3-yl group;
a (1S,5R,6S)-1-amino-6-fluoromethyl-3-azabicyclo[3.2.0]heptan-3-yl group;
a spiro[(1S,5S)-1-amino-3-azabicyclo[3.2.0]heptane-6,1'-cyclopropan]-3-yl group;
a (1S,5R)-1-amino-3-azabicyclo[3.3.0]octan-3-yl group;
a (1S,5S)-1-amino-3-azabicyclo[3.3.0]octan-3-yl group;
a (1R,5S)-1-amino-5-fluoro-3-azabicyclo[3.3.0]octan-3-yl group;
a (1R,5R)-1-amino-5-fluoro-3-azabicyclo[3.3.0]octan-3-yl group;
a (1S,5R,6S)-1-amino-6-fluoro-3-azabicyclo[3.3.0]octan-3-yl group;
a (1S,5R)-1-amino-6,6-difluoro-3-azabicyclo[3.3.0]octan-3-yl group;
a (1S,5R,7S)-1-amino-7-fluoro-3-azabicyclo[3.3.0]octan-3-yl group;

a (1S,5R,7R)-1-amino-7-fluoro-3-azabicyclo[3.3.0]octan-3-yl group;
a (1S,5R)-1-amino-3-azabicyclo[3.3.0]oct-7-en-3-yl group;
a (1S,5R)-1-amino-7-methyl-3-azabicyclo[3.3.0]oct-7-en-3-yl group;
a (1S)-1-amino-3-azabicyclo[3.3.0]oct-5-en-3-yl group;
a (1S)-1-amino-6-methyl-3-azabicyclo[3.3.0]oct-5-en-3-yl group;
a (1R,5R)-1-amino-3-oxa-5-azabicyclo[3.3.0]octan-5-yl group;
a (1R,5S)-1-amino-3-oxa-5-azabicyclo[3.3.0]octan-5-yl group;
a (1R,5R)-1-amino-4-oxa-5-azabicyclo[3.3.0]octan-5-yl group;
a (1R,5S)-1-amino-4-oxa-5-azabicyclo[3.3.0]octan-5-yl group;
a 6-amino-8-azatricyclo[4.3.0.0$^{1,3}$]nonan-8-yl group;
a (1S,5R)-1-amino-3-azabicyclo[4.3.0]nonan-3-yl group;
a (1S,5S)-1-amino-3-azabicyclo[4.3.0]nonan-3-yl group;
a (1S,5S)-1-amino-3-azabicyclo[4.3.0]non-7-en-3-yl group;
a (1S,5S)-1-amino-3-azabicyclo[4.3.0]non-8-en-3-yl group;
a (1S)-1-amino-3-azabicyclo[4.3.0]non-5-en-3-yl group;
a (1R,6S)-1-amino-5-oxa-8-azabicyclo[4.3.0]nonan-8-yl group;
a (1S,6S)-1-amino-4-oxa-8-azabicyclo[4.3.0]nonan-8-yl group; and
a (1S,6S)-1-amino-3-oxa-8-azabicyclo[4.3.0]nonan-8-yl group.

[Formula 41]

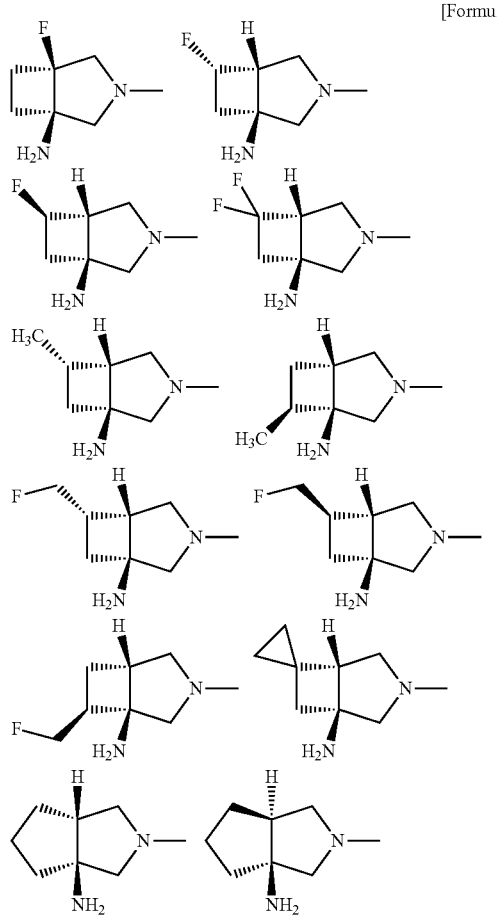

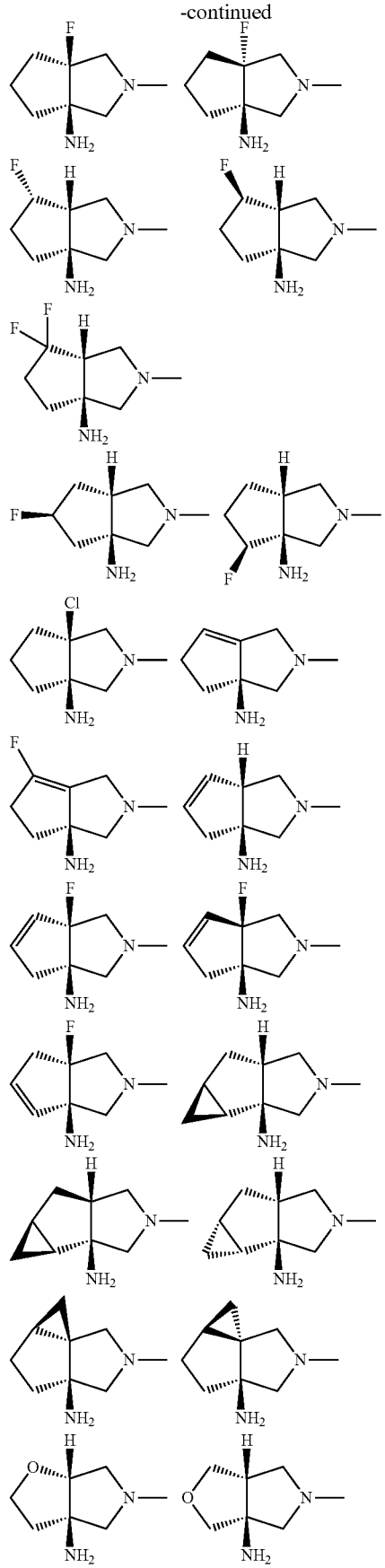

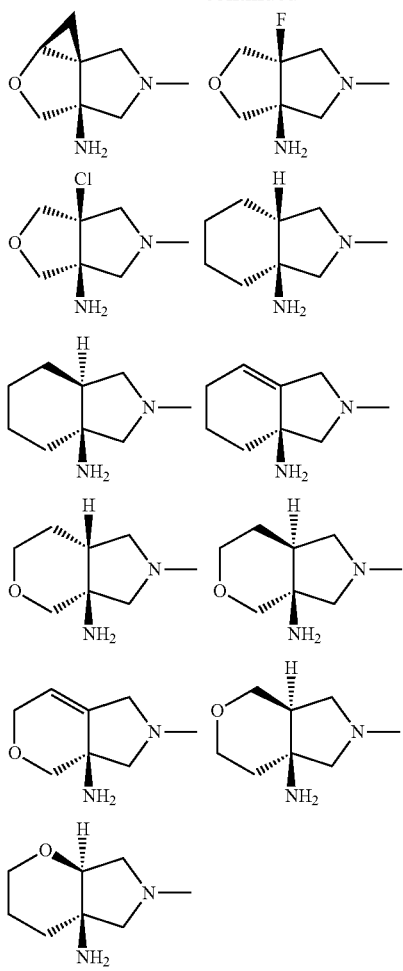
And still more preferred examples of the substituent at the 7-position (or its corresponding position) are listed below:
[Formula 42]
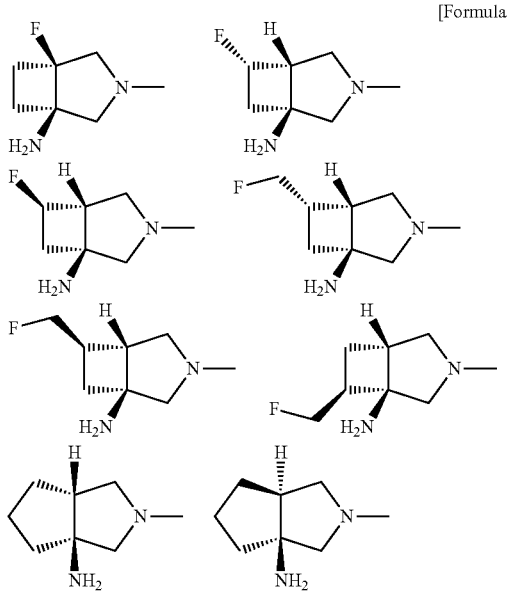
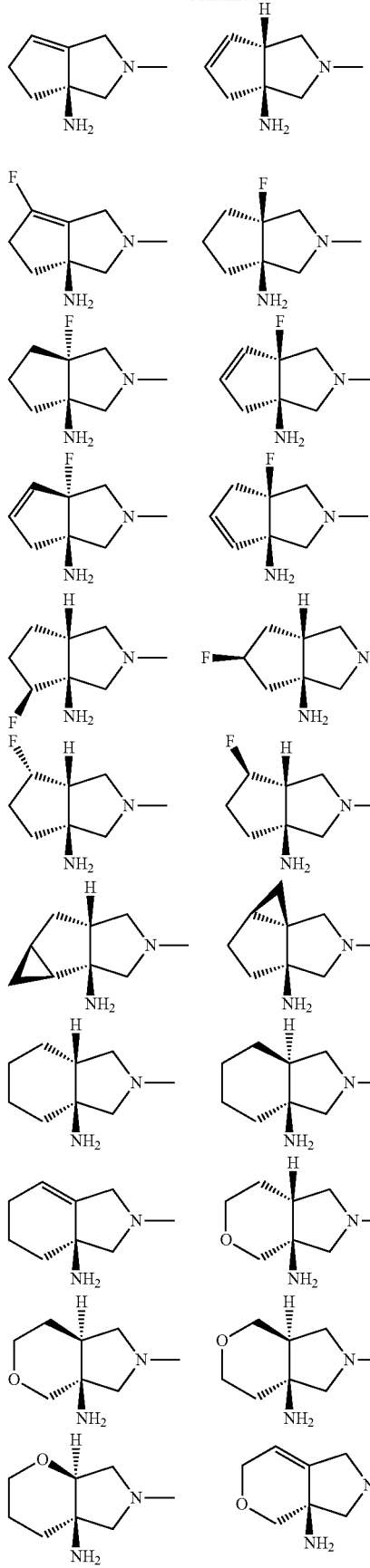

Accordingly, preferred compounds of the present invention are compounds each having the above-exemplified quinolonecarboxylic skeleton substituted with the above-exemplified 7-position substituent (a combination of the exemplified mother skeleton with the exemplified substituent). In the above formulas, the configuration of the 3-position (or its corresponding position) substituted with an amino group on the pyrrolidine ring is preferably the β-configuration. The absolute configuration of the 3-position (or its corresponding position) may be 3S or 3R according to the type of the 4-position substituent. The compounds of the present invention are preferably stereochemically single.

Preferred examples of the compounds of the present invention, which may be in a form of salts or hydrates are as follows:

7-[(1S,5R,6R)-1-amino-6-methyl-3-azabicyclo[3.2.0]heptan-3-yl]-6-fluoro-1-[(1R,2S)-2-fluorocyclopropyl]-1,4-dihydro-8-methoxy-4-oxoquinoline-3-carboxylic acid;

7-[(1S,5R,6S)-1-amino-6-methyl-3-azabicyclo[3.2.0]heptan-3-yl]-6-fluoro-1-[(1R,2S)-2-fluorocyclopropyl]-1,4-dihydro-8-methoxy-4-oxoquinoline-3-carboxylic acid;

7-[(1S,5R,6S)-1-amino-6-methyl-3-azabicyclo[3.2.0]heptan-3-yl]-6-fluoro-1-[(1R,2S)-2-fluorocyclopropyl]-1,4-dihydro-8-methyl-4-oxoquinoline-3-carboxylic acid;

10-[(1S,5R,6S)-1-amino-6-methyl-3-azabicyclo[3.2.0]heptan-3-yl]-9-fluoro-2,3-dihydro-3-(S)-methyl-7-oxo-7H-pyrido[1,2,3-de][1,4]benzoxazine-6-carboxylic acid;

7-[(1S,5R,6S)-1-amino-6-fluoromethyl-3-azabicyclo[3.2.0]heptan-3-yl]-6-fluoro-1-[(1R,2S)-2-fluorocyclopropyl]-1,4-dihydro-8-methoxy-4-oxoquinoline-3-carboxylic acid;

7-[(1S,5R,6S)-1-amino-3-azabicyclo-6-fluorobicyclo[3.2.0]heptan-3-yl]-6-fluoro-1-[(1R,2S)-2-fluorocyclopropyl]-1,4-dihydro-8-methyl-4-oxoquinoline-3-carboxylic acid;

10-[(1S,5R,6S)-1-amino-3-azabicyclo-6-fluorobicyclo[3.2.0]heptan-3-yl]-9-fluoro-2,3-dihydro-3-(S)-methyl-7-oxo-7H-pyrido[1,2,3-de][1,4]benzoxazine-6-carboxylic acid;

7-[(1S,5S,6R)-1-amino-3-azabicyclo-6-fluorobicyclo[3.2.0]heptan-3-yl]-6-fluoro-1-[(1R,2S)-2-fluorocyclopropyl]-1,4-dihydro-8-methoxy-4-oxoquinoline-3-carboxylic acid;

7-[(1S,5S,6R)-1-amino-3-azabicyclo-6-fluorobicyclo[3.2.0]heptan-3-yl]-6-fluoro-1-[(1R,2S)-2-fluorocyclopropyl]-1,4-dihydro-8-methyl-4-oxoquinoline-3-carboxylic acid;

10-[(1S,5S,6R)-1-amino-3-azabicyclo-6-fluorobicyclo[3.2.0]heptan-3-yl]-9-fluoro-2,3-dihydro-3-(S)-methyl-7-oxo-7H-pyrido[1,2,3-de][1,4]benzoxazine-6-carboxylic acid;

7-[(1S,5S,6S)-1-amino-3-azabicyclo-6-fluorobicyclo[3.2.0]heptan-3-yl]-6-fluoro-1-[(1R,2S)-2-fluorocyclopropyl]-1,4-dihydro-8-methoxy-4-oxoquinoline-3-carboxylic acid;

7-[(1S,5S,6S)-1-amino-3-azabicyclo-6-fluorobicyclo[3.2.0]heptan-3-yl]-6-fluoro-1-[(1R,2S)-2-fluorocyclopropyl]-1,4-dihydro-8-methyl-4-oxoquinoline-3-carboxylic acid;

10-[(1S,5S,6S)-1-amino-3-azabicyclo-6-fluorobicyclo[3.2.0]heptan-3-yl]-9-fluoro-2,3-dihydro-3-(S)-methyl-7-oxo-7H-pyrido[1,2,3-de][1,4]benzoxazine-6-carboxylic acid;

7-[(1S,5R)-1-amino-3-azabicyclo[3.3.0]octan-3-yl]-6-fluoro-1-[(1R,2S)-2-fluorocyclopropyl]-1,4-dihydro-8-methoxy-4-oxoquinoline-3-carboxylic acid;

10-[(1R,5S)-1-amino-3-aza-5-fluorobicyclo[3.3.0]octan-3-yl]-9-fluoro-2,3-dihydro-3-(S)-methyl-7-oxo-7H-pyrido[1,2,3-de][1,4]benzoxazine-6-carboxylic acid;

7-[(1R,5S)-1-amino-3-aza-5-fluorobicyclo[3.3.0]octan-3-yl]-8-chloro-6-fluoro-1-[(1R,2S)-2-fluorocyclopropyl]-1,4-dihydro-4-oxoquinoline-3-carboxylic acid;

7-[(1R,5S)-1-amino-3-aza-5-fluorobicyclo[3.3.0]octan-3-yl]-8-cyano-6-fluoro-1-[(1R,2S)-2-fluorocyclopropyl]-1,4-dihydro-4-oxoquinoline-3-carboxylic acid;

7-[(1R,5S)-1-amino-3-aza-5-fluorobicyclo[3.3.0]octan-3-yl]-6-fluoro-1-[(1R,2S)-2-fluorocyclopropyl]-1,4-dihydro-8-methoxy-4-oxoquinoline-3-carboxylic acid;

7-[(1R,5S)-1-amino-3-aza-5-fluorobicyclo[3.3.0]octan-3-yl]-6-fluoro-1-[(1R,2S)-2-fluorocyclopropyl]-1,4-dihydro-8-methyl-4-oxoquinoline-3-carboxylic acid;

7-[(1R,5S)-1-amino-3-aza-5-chlorobicyclo[3.3.0]octan-3-yl]-6-fluoro-1-[(1R,2S)-2-fluorocyclopropyl]-1,4-dihydro-8-methoxy-4-oxoquinoline-3-carboxylic acid;

7-[(1R,5S)-1-amino-3-aza-5-chlorobicyclo[3.3.0]octan-3-yl]-6-fluoro-1-[(1R,2S)-2-fluorocyclopropyl]-1,4-dihydro-8-methyl-4-oxoquinoline-3-carboxylic acid;

7-[(1S,5R)-1-amino-3-azabicyclo[3.3.0]oct-7-en-3-yl]-6-fluoro-1-[(1R,2S)-2-fluorocyclopropyl]-1,4-dihydro-8-methoxy-4-oxoquinoline-3-carboxylic acid;

7-[(1S,5R)-1-amino-3-azabicyclo[3.3.0]oct-7-en-3-yl]-6-fluoro-1-[(1R,2S)-2-fluorocyclopropyl]-1,4-dihydro-8-methyl-4-oxoquinoline-3-carboxylic acid;

7-[(1S)-1-amino-3-azabicyclo[3.3.0]oct-5-en-3-yl]-6-fluoro-1-[(1R,2S)-2-fluorocyclopropyl]-1,4-dihydro-8-methoxy-4-oxoquinoline-3-carboxylic acid;

7-[(1S)-1-amino-3-azabicyclo[3.3.0]oct-5-en-3-yl]-6-fluoro-1-[(1R,2S)-2-fluorocyclopropyl]-1,4-dihydro-8-methyl-4-oxoquinoline-3-carboxylic acid;

7-[(1S)-1-amino-5-methyl-3-azabicyclo[3.3.0]oct-5-en-3-yl]-6-fluoro-1-[(1R,2S)-2-fluorocyclopropyl]-1,4-dihydro-8-methoxy-4-oxoquinoline-3-carboxylic acid;

10-[6-amino-8-azatricyclo[4.3.0.0$^{1,3}$]nonan-8-yl]-9-fluoro-2,3-dihydro-3-(S)-methyl-7-oxo-7H-pyrido[1,2,3-de][1,4]benzoxazine-6-carboxylic acid;

7-[6-amino-8-azatricyclo[4.3.0.0$^{1,3}$]nonan-8-yl]-8-cyano-6-fluoro-1-[(1R,2S)-2-fluorocyclopropyl]-1,4-dihydro-4-oxoquinoline-3-carboxylic acid;

7-[6-amino-8-azatricyclo[4.3.0.0$^{1,3}$]nonan-8-yl]-6-fluoro-1-[(1R,2S)-2-fluorocyclopropyl]-1,4-dihydro-8-methoxy-4-oxoquinoline-3-carboxylic acid;

7-[6-amino-8-azatricyclo[4.3.0.0$^{1,3}$]nonan-8-yl]-fluoro-1-[(1R,2S)-2-fluorocyclopropyl]-1,4-dihydro-8-methyl-4-oxoquinoline-3-carboxylic acid;

7-[(1S,5S)-1-amino-3-azabicyclo[4.3.0]nonan-3-yl]-8-cyano-6-fluoro-1-[(1R,2S)-2-fluorocyclopropyl]-1,4-dihydro-4-oxoquinoline-3-carboxylic acid;

7-[(1S,5S)-1-amino-3-azabicyclo[4.3.0]nonan-3-yl]-6-fluoro-1-[(1R,2S)-2-fluorocyclopropyl]-1,4-dihydro-8-methoxy-4-oxoquinoline-3-carboxylic acid;

7-[(1S,5S)-1-amino-3-azabicyclo[4.3.0]nonan-3-yl]-1-[(1R,2S)-2-fluorocyclopropyl]-1,4-dihydro-8-methyl-4-oxoquinoline-3-carboxylic acid;

7-[(1S,5S)-1-amino-3-azabicyclo[4.3.0]nonan-3-yl]-6-fluoro-1-[(1R,2S)-2-fluorocyclopropyl]-1,4-dihydro-8-methyl-4-oxoquinoline-3-carboxylic acid;

10-[(1S,5S)-1-amino-3-azabicyclo[4.3.0]nonan-3-yl]-9-fluoro-2,3-dihydro-3-(S)-methyl-7-oxo-7H-pyrido[1,2,3-de][1,4]benzoxazine-6-carboxylic acid;

7-[(1S,6S)-1-amino-8-aza-3-oxabicyclo[4.3.0]nonan-8-yl]-8-chloro-6-fluoro-1-[(1R,2S)-2-fluorocyclopropyl]-1,4-dihydro-4-oxoquinoline-3-carboxylic;

7-[(1S,6S)-1-amino-8-aza-3-oxabicyclo[4.3.0]nonan-8-yl]-8-cyano-6-fluoro-1-[(1R,2S)-2-fluorocyclopropyl]-1,4-dihydro-4-oxoquinoline-3-carboxylic acid;

7-[(1S,6S)-1-amino-8-aza-3-oxabicyclo[4.3.0]nonan-8-yl]-6-fluoro-1-[(1R,2S)-2-fluorocyclopropyl]-1,4-dihydro-8-methoxy-4-oxoquinoline-3-carboxylic acid;

7-[(1S,6S)-1-amino-8-aza-3-oxabicyclo[4.3.0]nonan-8-yl]-6-fluoro-1-[(1R,2S)-2-fluorocyclopropyl]-1,4-dihydro-8-methyl-4-oxoquinoline-3-carboxylic acid;

10-[(1S,6S)-1-amino-8-aza-3-oxa-bicyclo[4.3.0]nonan-8-yl]-9-fluoro-2,3-dihydro-3-(S)-methyl-7-oxo-7H-pyrido[1,2,3-de][1,4]benzoxazine-6-carboxylic acid.

Next, the substituent at the 7-position of the quinolone skeleton (or its corresponding position) in relation to the compound of the present invention will be described. Specifically, the substituent has an amino group at a position corresponding to the 3-position of the pyrrolidinyl group, and the substituent $R^7$ on the carbon atom substituted with the amino group and the substituent $R^6$ at a position corresponding to the 4-position of the pyrrolidinyl group are taken together with the carbon atoms to which they are bonded to form a four- to seven-membered cyclic structure. More specifically, the substituent is a fused substituted aminopyrrolidine derivative, in which the cyclic structure together with the pyrrolidine ring forms a fused cyclic (bicyclic) structure represented by the following formula, in which the fused cyclic structure is substituted with an amino group at the bridgehead position:

[Formula 43]

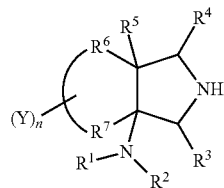

Further, the substituent is a fused substituted aminopyrrolidinyl substituent having a cyclic structure represented by the following formula, in which the cyclic structure formed by taking the substituents $R^6$ and $R^7$ together with the carbon atoms to which they are bonded is a five- or six-membered ring, and $R^5$ and $R^6$ are taken together to form a double bond partial structure:

[Formula 44]

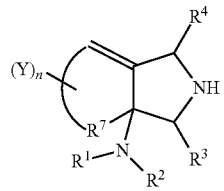

Preferred compounds of the present invention, which may be in the form of a salt or a hydrate are exemplified as follows:

[1] The compound represented by the formula (I) wherein it is a compound represented by the following formula:

[Formula 45]

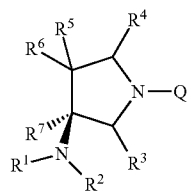

or the following formula:

[Formula 46]

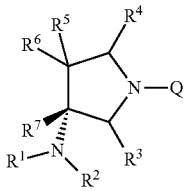

[2] The compound represented by the formula (I) wherein it is a compound represented by the following formula:

[Formula 47]

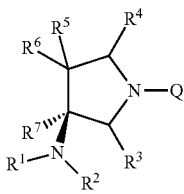

[3] The compound, wherein Q represented by the formula (II) in the compound represented by the formula (I) has a structure represented by the following formula:

[Formula 48]

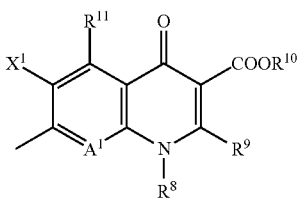

or the following formula:

[Formula 49]

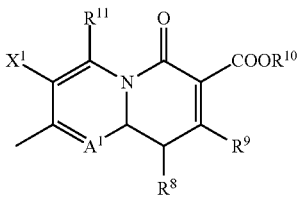

[4] The compound, wherein Q represented by the formula (II) in the compound represented by the formula (I) has a structure represented by the following formula:

[Formula 50]

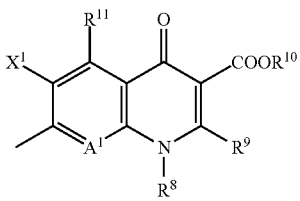

[5] The compound, wherein $R^1$ and $R^2$ in the formula (I) are each a hydrogen atom.
[6] The compound, wherein one of $R^1$ and $R^2$ in the formula (I) is a hydrogen atom and the other is a substituent selected from a methyl group, an ethyl group, an isopropyl group, a fluoroethyl group, a cyanoethyl group, a cyclopropyl group, and a cyclobutyl group.
[7] The compound, wherein $R^3$ and $R^4$ in the formula (I) are each a hydrogen atom.
[8] The compound, wherein $R^5$ in the formula (I) is a hydrogen atom, a fluorine atom, a chlorine atom, a methyl group, an ethyl group, an isopropyl group, a cyclopropyl group, a fluoromethyl group, a fluoroethyl group, a trifluoromethyl group, a methoxymethyl group, a vinyl group, an ethynyl group, a methoxy group, a phenyl group, or an oxazol-2-yl group.
[9] The compound, wherein the cyclic structure formed by taking $R^6$ and $R^7$ together with the carbon atoms to which they are bonded in the formula (I) is a four-membered ring which may be substituted by one or more substituents.
[10] The compound, wherein the cyclic structure formed by taking $R^6$ and $R^7$ together with the carbon atoms to which they are bonded in the formula (I) is a five- or six-membered ring which may be substituted by one or more substituents.
[11] The compound, wherein the cyclic structure formed by taking $R^6$ and $R^7$ together with the carbon atoms to which they are bonded in the formula (I) is a five- or six-membered ring containing a double bond as a constituent structure which may be substituted by one or more substituents.
[12] The compound, wherein the cyclic structure formed by taking $R^6$ and $R^7$ together with the carbon atoms to which they are bonded in the formula (I) is a five- or six-membered ring containing an oxygen atom as a constituent atom which may be substituted by one or more substituents.
[13] The compound, wherein the cyclic structure formed by taking $R^6$ and $R^7$ together with the carbon atoms to which they are bonded in the formula (I) is a five- or six-membered ring and is fused with the pyrrolidine ring to form a cis-fused bicyclic structure represented by the following formula:

[Formula 51]

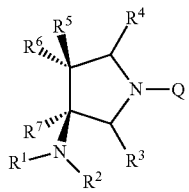

[14] The compound, wherein the cyclic structure formed by taking $R^6$ and $R^7$ together with the carbon atoms to which they are bonded in the formula (I) is a five- or six-membered ring and is fused with the pyrrolidine ring to form a trans-fused bicyclic structure represented by the following formula:

[Formula 52]

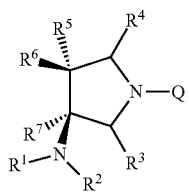

[15] The compound, wherein in the formula (I), the cyclic structure formed by taking $R^6$ and $R^7$ together with the carbon atoms to which they are bonded is a five- or six-membered ring, $R^5$ and $R^6$ are taken together to form a double bond partial structure, and the resulting cyclic structure is represented by the following formula:

[Formula 53]

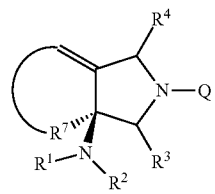

[16] The compound, wherein $X^1$ is a hydrogen atom or a fluorine atom in the partial structure Q in the formula (I) represented by the formula (II).
[17] The compound, wherein $X^1$ is a fluorine atom in the partial structure Q in the formula (I) represented by the formula (II).
[18] The compound, wherein $A^1$ is a nitrogen atom in the partial structure Q in the formula (I) represented by the formula (II).
[19] The compound, wherein $A^1$ is a partial structure represented by the formula (III) in the partial structure Q in the formula (I) represented by the formula (II).
[20] The compound, wherein $X^2$ in the formula (III) is a methyl group, an ethyl group, a methoxy group, a difluoromethoxy group, a cyano group, or a chlorine atom.
[21] The compound, wherein $X^2$ in the formula (III) is a methyl group or a methoxy group.
[22] The compound, wherein $R^8$ is a 1,2-cis-2-halogenocyclopropyl group in the partial structure Q in the formula (I) represented by the formula (II).
[23] The compound, wherein $R^8$ is a stereochemically single 1,2-cis-2-halogenocyclopropyl group in the partial structure Q in the formula (I) represented by the formula (II).
[24] The compound, wherein the 1,2-cis-2-halogenocyclopropyl group of $R^8$ is a (1R,2S)-2-halogenocyclopropyl group in the partial structure Q in the formula (I) represented by the formula (II).
[25] The compound, wherein the (1R,2S)-2-halogenocyclopropyl group of $R^8$ is a (1R,2S)-2-fluorocyclopropyl group in the partial structure Q in the formula (I) represented by the formula (II).
[26] The compound, wherein Q in the compound represented by the formula (I) is a compound represented by the following formula:

[Formula 54]

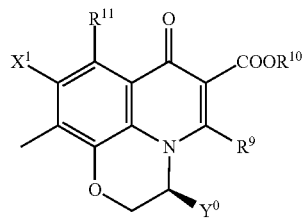

wherein $Y^0$ is a methyl group or a fluoromethyl group.

[27] The compound, wherein $R^9$ is a hydrogen atom in the partial structure Q in the formula (I) represented by the formula (II).

[28] The compound, wherein Q in the compound represented by the formula (I) is a compound represented by the following formula (IV):

[Formula 55]

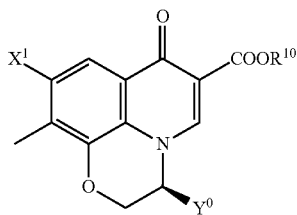

IV wherein $Y^0$ is a methyl group or a fluoromethyl group.

[29] The compound, wherein $Y^0$ in the formula (IV) is a methyl group.

[30] The compound, wherein $R^{10}$ is a hydrogen atom in the partial structure Q in the formula (I) represented by the formula (II).

[31] The compound, wherein the compound represented by the formula (I) is a stereochemically single compound.

Synthesis of a pyrrolidine compound necessary for introducing the substituent into the quinolone mother skeleton will be described below. There are several possible methods for synthesizing the fused substituted aminopyrrolidine derivative. Several examples of representative synthesis methods carried out by the present inventors will be summarized below (the details are described in reference examples in the section "Examples"). However, the method for synthesizing the fused substituted aminopyrrolidine derivative of the present invention is not limited thereto.

The present inventors have synthesized an important synthetic intermediate using the 1,3-dipolar cycloaddition reaction represented by the following scheme, with a β-electron-withdrawing group-substituted α,β-unsaturated cyclic or non-cyclic compound and an azomethine ylide as reactive elements, and synthesized fused substituted aminopyrrolidine derivatives through appropriate reaction steps:

[Formula 56]

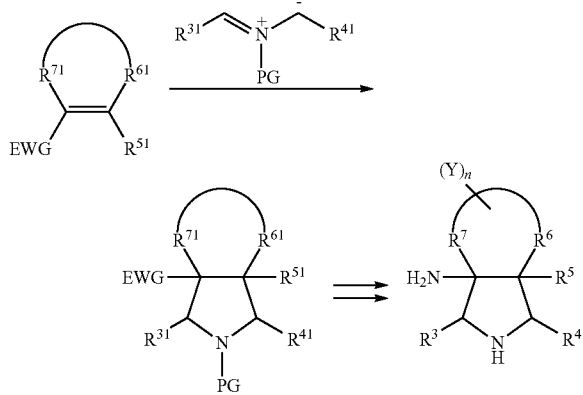

In this scheme, EWG is an electron-withdrawing group; PG is an amino-protecting group; $R^{31}$, $R^{41}$, $R^{51}$, $R^{61}$, and $R^{71}$ are each a hydrogen atom or a substituent appropriate for the intermediate; and $R^3$, $R^4$, $R^5$, $R^6$, $R^7$, Y, and n are as defined above.

The β-electron-withdrawing group-substituted α,β-unsaturated compound used in this reaction may be cyclic or non-cyclic. The bicyclic pyrrolidine derivatives can be synthesized from cyclic compounds in one step. Non-cyclic compounds can be converted to the bicyclic pyrrolidine derivatives by subjecting an appropriate synthetic intermediate to an appropriate cyclization or ring-closing reaction such as carbon-carbon bond formation reaction or carbon-oxygen (or sulfur) bond formation reaction by nucleophilic reaction of a carbanion; ether (or thioether) ring formation reaction by intramolecular Mitsunobu reaction; cyclic esterification or cyclic amidation which is called lactone or lactam formation reaction; intramolecular condensation ring-closing reaction such as aldol condensation, Dieckmann condensation, acyloin condensation, Wittig condensation, or Reformatsky reaction; ring-closing metathesis reaction (RCM); Diels-Alder reaction; deoxygenation coupling cyclization reaction such as McMurry reaction; radical cyclization reaction; coupling ring-closing reaction using a metal complex; or photocyclization reaction.

Further, the electron-withdrawing group (EWG) in the β-electron-withdrawing group-substituted α,β-unsaturated compound used in the above reaction may be converted into an amino group or an amino group protected by an appropriate protecting group in one or several steps. Examples of such a group include an ester group, a cyano group, an acyl group, a carbamoyl group, a carboxyl group, and a nitro group. The ester group or cyano group can be converted into an amine derivative by Curtius rearrangement reaction after conversion to a carboxylic group (carboxylic acid) by hydrolysis. The cyano group or carboxylic group can be converted into an amine derivative by Hofmann rearrangement reaction after conversion to a carbamoyl group. The acyl group can be converted into an amine derivative by Beckmann rearrangement reaction or the like after conversion to a hydroxyimino group. The nitro group can be converted to an amine derivative by reduction.

On the other hand, the azomethine ylide used as a reactive element in this reaction can be produced by adding a catalytic amount of trifluoroacetic acid or a catalytic amount of silver fluoride to N-benzyl-N-(methoxymethyl)trimethylsilylmethylamine as a reagent, for example [see Journal of Organic Chemistry, Vol. 52, No. 2, p. 235 (1987)]. PG in the azomethine ylide in the above reaction formula represents an appropriate amino-protecting group. The protecting group is a benzyl group in the aforementioned reagent for producing the azomethine ylide, but may be an optically active 1-phenylethyl group as a preferred example. The amino-protecting group (PG) and an amino-protecting group produced by converting the electron-withdrawing group in a later step may be the same or different; the protecting groups may be appropriately selected from generally used protecting groups for an amino group so long as they do not affect the reaction, for example, do not inhibit each reaction step, and can easily be later deprotected.

Next, synthesis of an optically active substance will be described. An optically active substance can be synthesized by optical resolution of an appropriate intermediate, for example. Specific examples of the optical resolution include HPLC resolution using a chiral column and diastereomer salt preferential crystallization for an appropriate intermediate; and a method of bonding a chiral element to an appropriate intermediate to convert the intermediate to diastereomers, then separating the diastereomers using an appropriate separation technique such as silica gel chromatography, and removing the chiral element to convert the diastereomer to an optically active substance. An optically active substance may also be synthesized from a chiral building block as a starting material. Specifically, an optically active cycloadduct can be obtained by enantioselective 1,3-dipolar cycloaddition reaction using a dipolarophile having an asymmetric element (for example, an asymmetric functional group such as a 1-menthyl group, a (2'S)-bornane-10,2-sultam group, or a (S)-4-benzyl-2-oxazolidinone group); enantioselective 1,3-dipolar cycloaddition reaction using an azomethine ylide having an asymmetric element (for example, a (1R)-1-phenylethyl group) in the molecule; or diastereoselective 1,3-dipolar cycloaddition reaction using both an asymmetric dipolarophile and an asymmetric azomethine ylide [see Journal of the Chemical Society Perkin Transactions 1, p. 1076 (2002)]. Further, an optically active cycloadduct can be obtained by asymmetric 1,3-dipolar cycloaddition reaction using an asymmetric metal complex or salt as a catalyst [see Angewandte Chemie International Edition, Vol. 44, p. 6272 (2005)].

The synthesis of fused substituted aminopyrrolidine derivatives carried out by the present inventors using, as a key reaction, 1,3-dipolar cycloaddition reaction with a β-electron-withdrawing group-substituted α,β-unsaturated compound and an azomethine ylide as reactive elements will be more specifically described taking the synthesis of a 1-amino-3-azabicyclo[3.3.0]octane derivative as an example:

[Formula 57]

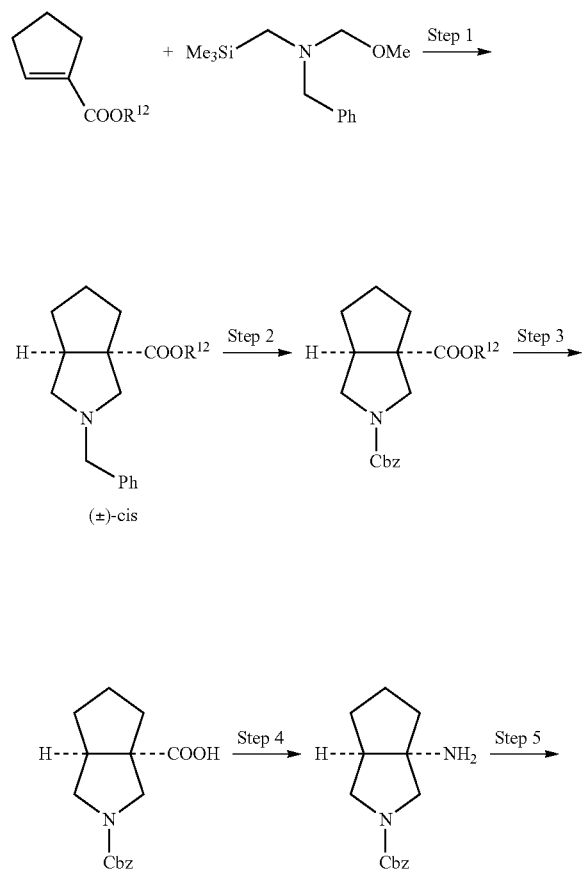

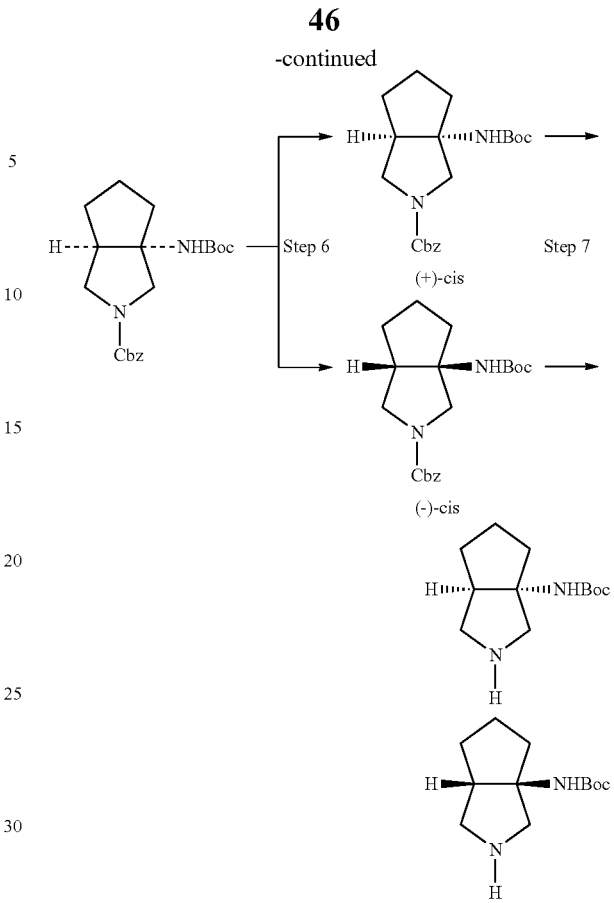

In the above scheme, Boc represents a tert-butoxycarbonyl group and Cbz represents a benzyloxycarbonyl group, provided that these substituents may be the same or different generally used protecting groups for an amino group; and $R^{12}$ represents an alkyl group having 1 to 6 carbon atoms.

Step 1 is a step of synthesizing a 1-alkoxycarbonyl-3-azabicyclo[3.3.0]octane derivative which is a fused substituted pyrrolidine derivative using 1,3-dipolar cycloaddition reaction with a 1-cyclopentene-1-ester and an azomethine ylide as reactive elements. The azomethine ylide reactive element is produced by adding a catalytic amount of trifluoroacetic acid or a catalytic amount of silver fluoride to N-benzyl-N-(methoxymethyl)trimethylsilylmethylamine as a reagent, for example, as described above. The reaction solvent may be any solvent that does not inhibit production of the azomethine ylide and 1,3-dipolar cycloaddition reaction, but is preferably dichloromethane or 1,2-dichloroethane. The reaction may be carried out at −20° C. to the solvent reflux temperature, but preferably at room temperature to the solvent reflux temperature.

Step 2 is a step of converting the benzyl group at the 3-position of the 3-azabicyclo[3.3.0]octane ring to a protecting group. This step is carried out in order to easily extract, isolate, and purify the carboxylic acid derivative produced after hydrolysis of the 1-position ester (without conversion of the benzyl group, an amino acid derivative is formed and isolation and purification may be difficult). The 3-position protecting group is preferably a protecting group that can generally be distinguished in the deprotection step from the protecting group for the 1-position amino group produced after conversion of the 1-position carboxylic acid, but may be the same as the protecting group for the 1-position amino group. The 3-position protecting group is preferably a benzyloxycarbonyl group or a tert-butoxycarbonyl group, and particularly preferably a benzyloxycarbonyl group. The benzyloxycarbonylation reaction is usually carried out by direct conversion by von Braun reaction using benzyl chloroformate in a solvent such as dichloromethane; or by reacting benzyl chloroformate in an appropriate solvent in the presence of a base after catalytic hydrogenolysis using a catalyst such as palladium-carbon.

Step 3 is a step of hydrolyzing the ester at the 1-position of the 3-azabicyclo[3.3.0]octane ring. The ester is an alkyl ester having 1 to 6 carbon atoms, and preferably a methyl ester, ethyl ester, or tert-butyl ester. The hydrolysis reaction may be carried out by a common method using a base or an acid that does not affect the 3-position protecting group. In the hydrolysis of a methyl ester or ethyl ester, the ester is reacted with an alkaline solution such as a sodium hydroxide solution, potassium hydroxide solution, or barium hydroxide solution in ethanol or water, then made acidic with an appropriate acid that does not affect the 3-position protecting group, and isolated and purified. The tert-butyl ester is hydrolyzed in an appropriate solvent in which the ester can be dissolved under acidic conditions or in the presence of an acid catalyst. Preferred acids include hydrochloric acid, formic acid, acetic acid, trifluoroacetic acid, and p-toluenesulfonic acid.

Step 4 is a step of converting the carboxylic acid at the 1-position of the 3-azabicyclo[3.3.0]octane ring to an amine. This step is usually carried out by rearrangement reaction from carboxylic acid to an amine. For example, when the rearrangement reaction is Curtius rearrangement reaction, the carboxylic acid is converted to an acid azide in an appropriate solvent such as toluene using a reagent such as sodium azide, trimethylsilyl azide, or diphenylphosphoryl azide (DPPA), the reaction solution is then heated to form an isocyanate, and the isocyanate is converted to an amine by hydrolysis using hydrochloric acid or the like.

Step 5 is a step of protecting the amino group at the 1-position of the 1-amino-3-azabicyclo[3.3.0]octane ring; however, the subsequent steps may be carried out without this protection. The protecting group for the 1-position amino group may be a commonly used amino-protecting group, but is preferably a protecting group that can be distinguished from the 3-position protecting group in the deprotection step. Specific examples of the protecting group include a tert-butoxycarbonyl group, an acetyl group, and a trifluoroacetyl group. The present inventors have selected a tert-butoxycarbonyl group.

Steps 4 and 5 can be carried out in one step by rearrangement reaction using an appropriate solvent. For example, a 1-(tert-butoxycarbonyl)amino-3-azabicyclo[3.3.0]octane derivative can be prepared by Curtius rearrangement reaction using diphenylphosphoryl azide (DPPA) in tert-butyl alcohol.

Step 6 is a step of optical resolution of the 1-amino-3-azabicyclo[3.3.0]octane derivative. This step can be carried out by HPLC resolution using an appropriate chiral column. As a result of this optical resolution, it has been found that a quinolonecarboxylic acid derivative derived from the resulting enantiomer of the 1-amino-3-azabicyclo[3.3.0]octane derivative having a positive optical rotation is superior in antibacterial activity to a quinolonecarboxylic acid derivative derived from the resulting enantiomer having a negative optical rotation (see the section "Examples"). The present inventors have selected a tert-butoxycarbonyl group as the protecting group for the 1-position amino group; however, it is possible to carry out optical resolution even when the 1-position amino group is not protected or is protected by a protecting group other than a tert-butoxycarbonyl group. For example, when the 1-position amino group is not protected or is protected by a protecting group such as a benzyl group or a tert-butyl group (the protected amino group is basic in this case), it is also possible to carry out a method of converting an appropriate optically active acid to a diastereomer salt and preferentially crystallizing the diastereomer salt, in addition to HPLC optical resolution using an appropriate chiral column. In this case, an optically active 1-amino-3-azabicyclo[3.3.0]octane derivative can be obtained by converting the preferentially crystallized diastereomer salt to a free base. Further, when the 1-position amino group is not protected, it is possible to use a method of bonding a chiral element to convert the derivative to diastereomers, then separating the diastereomers using an appropriate separation technique such as silica gel chromatography, and removing the chiral element to convert the diastereomer to an optically active substance.

The present inventors have described a specific optical resolution method in this step; however, when an appropriate synthetic intermediate can be optically resolved, the intermediate may be appropriately selected and optically resolved as described above.

Step 7 is a step of deprotecting the 3-position of the 1-amino-3-azabicyclo[3.3.0]octane derivative. The deprotection reaction may be carried out under any conditions that do not change other functional groups and the configuration. Accordingly, since the 1-position protecting group in relation to the compound of the present invention is a benzyloxycarbonyl group, the deprotection reaction is carried out under commonly used deprotection conditions, for example, under conditions using a catalyst such as palladium-carbon, or by catalytic hydrogenolysis reaction using ammonium formate in a protic polar solvent. When the 3-azabicyclo[3.3.0]octane derivative has a carbon-carbon unsaturated bond in the molecule, the deprotection must be carried out with the carbon-carbon unsaturated bond maintained. Accordingly, since the 3-position protecting group in relation to the compound of the present invention is a benzyloxycarbonyl group, the deprotection may be carried out with the carbon-carbon unsaturated bond maintained on the 3-azabicyclo[3.3.0]octane ring under strong acid conditions (for example, hydrobromic acid-acetic acid, trifluoroacetic acid, or trifluoromethanesulfonic acid-trifluoroacetic acid), by use of sodium-liquid ammonia (Birch reduction conditions), or by use of barium hydroxide, for example.

Further, the fused substituted aminopyrrolidine derivative which is the compound of the present invention can be synthesized from a chiral pyrrolidine derivative as a starting material. The following synthetic intermediates are used in synthesis using a so-called chiral building block, for example. The chiral pyrrolidine derivatives that can be used as intermediates are not limited to the following compounds.

[Formula 58]

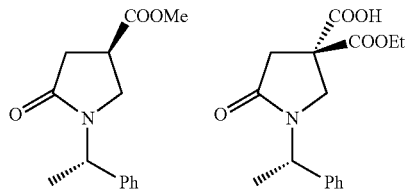

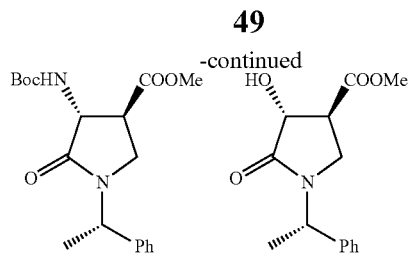

[Journal of Medicinal Chemistry, Vol. 30, No. 10, p. 1711 (1987); WO 94/14794; Tetrahedron, Vol. 61, No. 23, p. 5465 (2005); Tetrahedron Asymmetry, Vol. 15, No. 20, p. 3249 (2004)].

Such chiral pyrrolidine derivatives can be converted to the bicyclic pyrrolidine derivatives which are the compounds of the present invention in an appropriate number of steps. For example, the chiral pyrrolidine derivatives can be converted to the fused substituted aminopyrrolidine derivatives by introducing appropriate substituents into the 3- and 4-positions on the pyrrolidine ring, then carrying out appropriate homologation reaction or functional group conversion, and carrying out cyclization (ring-closing) reaction. Examples of cyclization (ring-closing) reactions for an appropriate synthetic intermediate which is an important step for this conversion include carbon-carbon bond formation reaction or carbon-oxygen (or sulfur) bond formation reaction by nucleophilic reaction of a carbanion; ether (or thioether) ring formation reaction by intramolecular Mitsunobu reaction; cyclic esterification or cyclic amidation which is called lactone or lactam formation reaction; intramolecular condensation ring-closing reaction such as aldol condensation, Dieckmann condensation, acyloin condensation, Wittig condensation, or Reformatsky reaction; deoxygenation coupling cyclization reaction such as McMurry reaction; ring-closing metathesis reaction (RCM); Diels-Alder reaction; radical cyclization reaction; coupling ring-closing reaction using a metal complex; and photocyclization reaction.

The synthesis of fused substituted aminopyrrolidine derivatives carried out by the present inventors using a chiral pyrrolidine derivative as an important intermediate will more specifically be described taking the synthesis of a (1S,5R)-1-amino-3-azabicyclo[3.3.0]octane derivative as an example. The present inventors have selected a tert-butoxycarbonyl group as the protecting group for the 1-position amine moiety; however, the protecting group for the 1-position amino group may be a protecting group other than a tert-butoxycarbonyl group which does not affect, for example, does not inhibit each reaction step and can easily be deprotected, and the protecting group may be the same as the 3-position protecting group. In the following case, the 1-position protecting group is a (1R)-1-phenylethyl group:

[Formula 59]

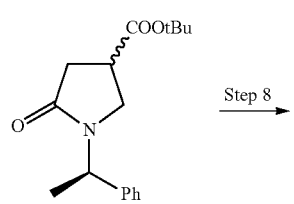

JP patent application
No. 2005-146386

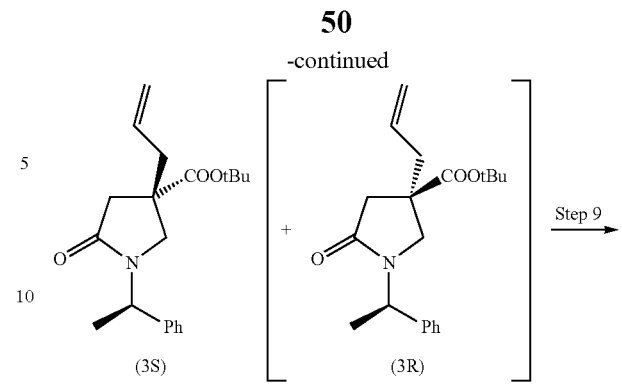

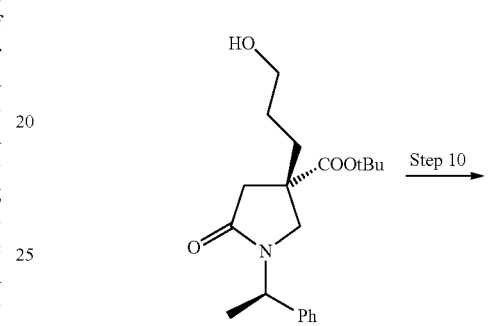

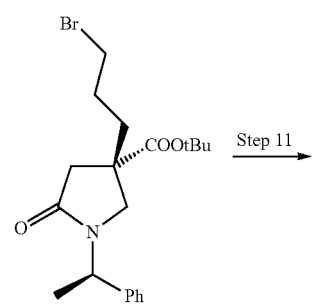

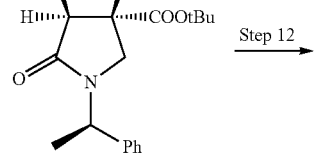

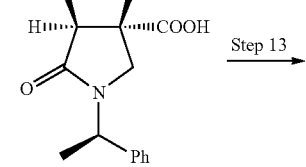

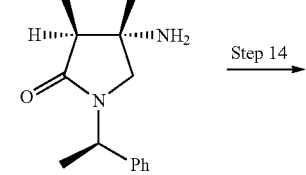

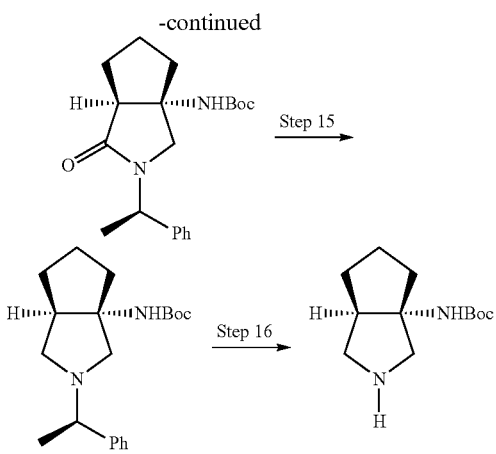

In the above scheme, Boc represents a tert-butoxycarbonyl group.

Step 8 is a step of allylating the 3-position of the pyrrolidine ring (the α-position of the ester). Step 8 is usually carried out using an allyl halide such as allyl bromide as an allylating agent in the presence of a base. Examples of the base include potassium carbonate, cesium carbonate, sodium hydride, metallic sodium, sodium ethoxide, potassium tert-butoxide, lithium diisopropylamide (LDA), and lithium bis(trimethylsilyl)amide. Examples of the reaction solvent include tetrahydrofuran, acetone, N,N-dimethylformamide, toluene, and mixed solvents thereof. After completion of the reaction, diastereomers of the allylated compound can be separated and purified by silica gel chromatography or the like. The present inventors have used a tert-butyl ester as the ester at the 3-position of the pyrrolidine ring; however, other ester derivatives can also be used. The above diastereomer separation operation is easily carried out when a bulky tert-butyl ester is used.

Step 9 is a step of converting the allyl group moiety to a primary alcohol, specifically, a 1-hydroxypropyl group by hydroboration-oxidation reaction of the terminal olefin of the allyl group moiety. The hydroboration reaction is usually carried out in anhydrous tetrahydrofuran using, as reagents, various borane complexes (such as a borane-tetrahydrofuran complex and a borane-dimethyl sulfide complex), monoalkylboranes (such as hexylborane), dialkylboranes (such as 9-borabicyclo[3.3.1]nonane (9-BBN), dicyclohexylborane, and disiamylborane), a chloroborane-dimethyl sulfide complex, a dichloroborane-dimethyl sulfide complex, catecholborane, and the like. Oxidation of the organoborane compound produced by the hydroboration reaction is usually carried out using aqueous hydrogen peroxide under alkaline conditions of a sodium hydroxide solution or the like in water or ethanol-containing water.

The present inventors have synthesized a compound in which a 1-hydroxypropyl group is introduced into the 3-position of the pyrrolidine ring in two steps shown as Steps 8 and 9; however, this product can be synthesized by another synthesis method. For example, the product can be synthesized by protecting a hydroxy group moiety of commercially available 3-iodopropanol using an appropriate protecting group (such as a tert-butyldimethylsilyl group), then 3-substitution oxypropylating in the presence of an appropriate base (such as a base described for Step 8), and subsequently deprotecting under appropriate conditions. Further, the 3-substitution oxypropylation reaction can be carried out after protecting one hydroxy group of 1,3-propanediol using an appropriate protecting group and then converting the other hydroxy group to a halogen atom or a commonly known leaving group. Examples of the leaving group in this case include a methanesulfonyloxy group, a trifluoromethanesulfonyloxy group, a benzenesulfonyloxy group, and a p-toluenesulfonyloxy group.

Step 10 is a step of brominating the hydroxy group. It is inappropriate to carry out the bromination reaction under typical strong acidic conditions of hydrobromic acid-concentrated concentrated sulfuric acid, sodium bromide-sulfuric acid, or the like, because there is a tert-butyl ester in the molecule. The bromination reaction is appropriately reaction using triphenylphosphine-tetrabromomethane in dichloromethane or tetrahydrofuran, reaction using triphenylphosphine dibromide in N,N-dimethylformamide, or the like [see Journal of American Chemical Society, Vol. 125, No. 43, p. 13012 (2003)]. Further, tetrabutylammonium bromide or a Vilsmeier reagent [(chloromethylene)dimethyliminium chloride] can be used as a reagent in N,N-dimethylformamide in this bromination reaction. The bromination reaction can be carried out using a brominating agent such as sodium bromide, lithium bromide, or calcium bromide in N,N-dimethylformamide or dimethyl sulfoxide after converting the hydroxy group moiety to an appropriate leaving group. Examples of the leaving group in this case include a methanesulfonyloxy group, a trifluoromethanesulfonyloxy group, a benzenesulfonyloxy group, and a p-toluenesulfonyloxy group.

The present inventors have synthesized a compound in which a 1-bromopropyl group is introduced into the 3-position of the pyrrolidine ring as a compound used in the next step. Examples of compounds that can be used in the next step other than this product include a 1-iodo compound and a compound into which a leaving group such as a methanesulfonyloxy group, a trifluoromethanesulfonyloxy group, a benzenesulfonyloxy group, or a p-toluenesulfonyloxy group is introduced.

Step 11 is a step of generating a carbanion at the 4-position of the pyrrolidine ring of the bromo compound synthesized in Step 10 (amide: α-position of pyrrolidone) using an appropriate base to cause a reaction of forming a carbon-carbon double bond by intramolecular nucleophilic substitution (intramolecular ring-closing reaction). Typical examples of the base include potassium carbonate, cesium carbonate, sodium hydride, metallic sodium, sodium ethoxide, potassium tert-butoxide, lithium diisopropylamide (LDA), lithium bis(trimethylsilyl)amide, potassium bis(trimethylsilyl)amide, and sodium bis(trimethylsilyl)amide. Examples of the reaction solvent include tetrahydrofuran, acetone, N,N-dimethylformamide, toluene, and mixed solvents thereof. The cyclopentane ring formed by the intramolecular ring-closing reaction usually forms a cis-fused ring (cis-3-azabicyclo[3.3.0]octane ring) together with the pyrrolidine ring moiety. This synthesis method can be applied to synthesis of a fused substituted aminopyrrolidine derivative such as a 3-azabicyclo[4.3.0]nonane derivative, but may produce a mixture of cis- and trans-isomers of the fused substituted aminopyrrolidine derivative. In this case, a necessary isomer may be separated by an appropriate separation and purification operation such as silica gel chromatography.

Step 12 is a step of converting the tert-butyl ester to carboxylic acid by hydrolysis or deprotection. The present inventors have selected tert-butyl ester as an ester; however, the ester is suitably an alkyl ester having 1 to 6 carbon atoms, and preferably a methyl ester, ethyl ester, or tert-butyl ester. The tert-butyl ester is hydrolyzed or deprotected in an appropriate solvent in which the ester can be dissolved under acidic conditions or in the presence of an acid catalyst. Preferred acids include hydrochloric acid, formic acid, acetic acid, trifluoroacetic acid, and p-toluenesulfonic acid. In the hydrolysis of a methyl ester or ethyl ester, the ester is reacted with an alkaline solution such as a sodium hydroxide solution, potassium hydroxide solution, or barium hydroxide solution in ethanol or water, then made acidic with an appropriate acid that does not affect the 3-position protecting group, and isolated and purified.

Step 13 is a step of converting the carboxylic acid at the 1-position of the 3-azabicyclo[3.3.0]octane ring to an amine. This step is usually carried out by rearrangement reaction from carboxylic acid to an amine. For example, when the rearrangement reaction is Curtius rearrangement reaction, the carboxylic acid is converted to an acid azide in an appropriate solvent such as toluene using a reagent such as sodium azide, trimethylsilyl azide, or diphenylphosphoryl azide (DPPA), the reaction solution is then heated to form an isocyanate, and the isocyanate is converted to an amine by hydrolysis using hydrochloric acid or the like.

Step 14 is a step of protecting the amino group at the 1-position of the 1-amino-3-azabicyclo[3.3.0]octane ring; however, the subsequent steps may be carried out without this protection. The protecting group for the 1-position amino group may be a commonly used amino-protecting group, but is preferably a protecting group that can be distinguished from the 3-position protecting group in the deprotection step. Specific examples of the protecting group include a tert-butoxycarbonyl group, an acetyl group, and a trifluoroacetyl group. The present inventors have selected a tert-butoxycarbonyl group.

Steps 13 and 14 can be carried out in one step by rearrangement reaction using an azide reagent in an appropriate solvent. For example, a 1-(tert-butoxycarbonyl)amino-3-azabicyclo[3.3.0]octane derivative can be prepared by Curtius rearrangement reaction using diphenylphosphoryl azide (DPPA) in tert-butyl alcohol.

Step 15 is a step of reducing the carbonyl group of the pyrrolidone (called amide). Step 15 is carried out using a metal hydride such as lithium aluminum hydride or sodium bis(2-methoxyethoxy)aluminum hydride, or a borohydride compound such as diborane or a borane-tetrahydrofuran complex, as a reduction reagent. An ether solvent represented by toluene or tetrahydrofuran is usually used as a solvent. The reaction is carried out usually at a temperature of −78° C. to 100° C.

Step 16 is a step of deprotecting the 1-position of the pyrrolidine ring. The deprotection reaction may be carried out under any conditions that do not change other functional groups and the configuration. Accordingly, since the 1-position protecting group in relation to the compound of the present invention is a (1R)-1-phenylethyl group, the deprotection reaction is carried out under commonly used deprotection conditions, for example, under conditions using a catalyst such as palladium-carbon, or by catalytic hydrogenolysis reaction using ammonium formate in a protic polar solvent. When there is a carbon-carbon unsaturated bond as a substituent in the molecule, the deprotection must be carried out with the carbon-carbon unsaturated bond maintained. Accordingly, since the 1-position protecting group in relation to the compound of the present invention is a (1R)-1-phenylethyl group, the deprotection may be carried out with the carbon-carbon unsaturated bond maintained in the molecule by use of sodium-liquid ammonia (Birch reduction conditions), for example. After the 1-position (1R)-1-phenylethyl group is converted to a benzyloxycarbonyl group by von Braun reaction using benzyl chloroformate typically in a solvent such as dichloromethane, the group can be deprotected by the method described above.

Further, the pyrrolidine ring of the fused substituted aminopyrrolidine derivatives which are the compounds of the present invention can be formed by a common synthesis method or the like after previously synthesizing a corresponding heterocyclic compound (important synthetic intermediate) appropriately, as shown in the following scheme:

[Formula 60]

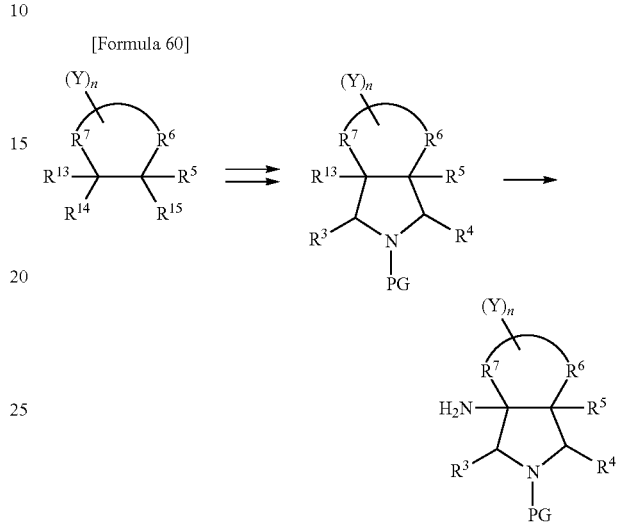

wherein $R^{13}$ is an ester group having 2 to 7 carbon atoms, a carbamoyl group, a nitro group, or a cyano group, which may be converted to an amino group, or an amino group which may have a substituent; PG is an amino-protecting group; $R^{14}$ and $R^{15}$ are generally known appropriate substituents that can be taken together and then optionally subjected to an appropriate reaction to form a pyrrolidine ring; and $R^3$, $R^4$, $R^5$, $R^6$, $R^7$, Y, and n are as defined above.

The substituent $R^{13}$ is preferably an ester group having 2 to 7 carbon atoms or an amino group which may have a substituent, and particularly preferably such a group stable in each reaction step listed below in the pyrrolidine ring formation reaction.

Here, there will be described the substituents $R^{14}$ and $R^{15}$ and the pyrrolidine ring formation method in which $R^{14}$ and $R^{15}$ are taken together and then optionally subjected to an appropriate reaction.

When the substituents $R^{14}$ and $R^{15}$ are each a hydroxymethyl group (—CH$_2$OH), the pyrrolidine ring can be formed by alkylating the primary amine directly or after converting the hydroxy group moiety to a halogen atom or an appropriate leaving group. Preferred examples of the halogen atom include chlorine, bromine, and iodine. Examples of the leaving group include a methanesulfonyloxy group, a trifluoromethanesulfonyloxy group, a benzenesulfonyloxy group, and a p-toluenesulfonyloxy group.

When the substituents $R^{14}$ and $R^{15}$ are each a carboxyl group, an ester group, or an acid halide, the synthetic intermediate can be converted to the pyrrolidine derivative by synthesizing an imide derivative directly or through an acid anhydride synthesized by an appropriate condensation reaction and then subjecting the imide to a reduction. The ester group preferably has 2 to 7 carbon atoms. The imide is reduced using a metal hydride such as lithium aluminum hydride or sodium bis(2-methoxyethoxy)aluminum hydride, or a borohydride compound such as diborane or a borane-tetrahydrofuran complex, as an imide reduction reagent. An ether solvent represented by tetrahydrofuran is usually used as a solvent. The reaction is carried out usually at a temperature of −78° C. to 100° C.

When one of the substituents $R^{14}$ and $R^{15}$ is an aminomethyl group (—$CH_2NH_2$) and the other is a carboxylic group or an ester group, the synthetic intermediate can be converted to the pyrrolidine derivative by synthesizing an amide derivative (lactam derivative) using an appropriate condensation reaction and then subjecting the amide to a reduction. The ester group preferably has 2 to 7 carbon atoms. The amide derivative (lactam derivative) is generally synthesized by heating in an alcohol solvent in the presence or absence of an appropriate base. The amide is reduced using a metal hydride such as lithium aluminum hydride or sodium bis(2-methoxyethoxy)aluminum hydride, or a borohydride compound such as diborane or a borane-tetrahydrofuran complex as an imide reduction reagent. An ether solvent represented by tetrahydrofuran is usually used as a solvent. The reaction is carried out usually at a temperature of −78° C. to 100° C. One of substituents $R^{14}$ and $R^{15}$ of a precursor useful for synthesizing the intermediate amide derivative (lactam derivative) may be a nitromethyl group (—$CH_2NO_2$), an azidomethyl group (—$CH_2N_3$), or a cyano group (—CN) (in this case, the other substituent is a carboxyl group or an ester group). The precursor can be converted to the amide derivative (lactam derivative) by converting the substituent into an aminomethyl group (—$CH_2NH_2$) in a reduction step and then performing a condensation reaction. The reduction step is carried out using catalytic hydrogen reduction; a metal hydride such as lithium borohydride, lithium aluminum hydride or sodium bis(2-methoxyethoxy)aluminum hydride; or a borohydride compound such as diborane or a borane-tetrahydrofuran complex. Further, when one of the substituents $R^{14}$ and $R^{15}$ is a hydroxymethyl group (—$CH_2OH$) or a halogenomethyl group and the other is a carboxylic group or an ester group, a lactone derivative synthesized by an appropriate condensation reaction can be converted to the lactam derivative.

When one of the substituents $R^{14}$ and $R^{15}$ is an aminomethyl group (—$CH_2NH_2$) and the other is a formyl group, the synthetic intermediate can be converted to the pyrrolidine derivative by synthesizing a cyclic imine derivative using an appropriate condensation reaction and then subjecting the imine to a reduction, specifically, a reductive amination reaction. The synthetic intermediate can be converted to the pyrrolidine derivative by subjecting the imine to catalytic hydrogen reduction and an appropriate condensation reaction to synthesize an amide derivative (lactam derivative) and then subjecting the amide to a reduction.

When one of the substituents $R^{14}$ and $R^{15}$ is a methyl group and the other is a N-halogenoaminomethyl group (such as —$CH_2NCl$—), the pyrrolidine ring can be formed by radical reaction (Hofmann-Loeffler-Freitag pyrrolidine synthesis reaction).

Several representative pyrrolidine ring formation methods are represented by the following scheme taking, as an example, the synthesis of a 3-benzyl-1-(tert-butoxycarbonyl)-3-azabicyclo[3.3.0]octane derivative which is a synthetic intermediate for a 1-amino-3-azabicyclo[3.3.0]octane derivative which is a representative compound of the present invention:

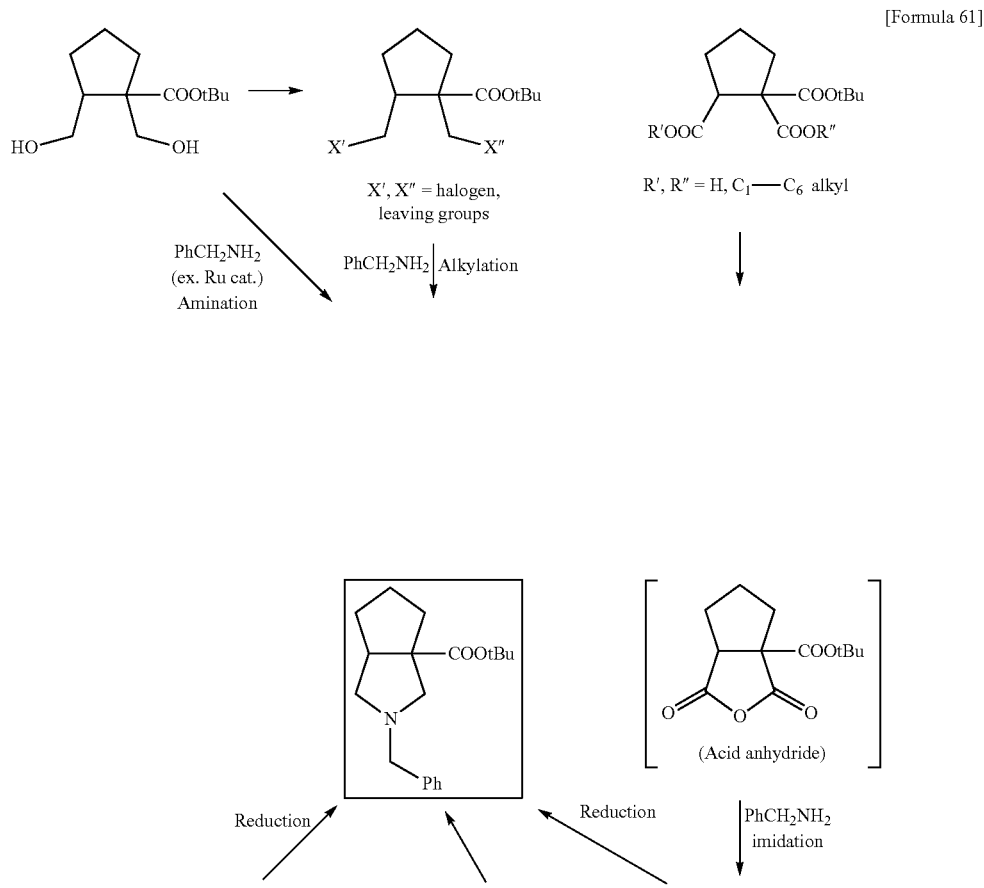

[Formula 61]

-continued

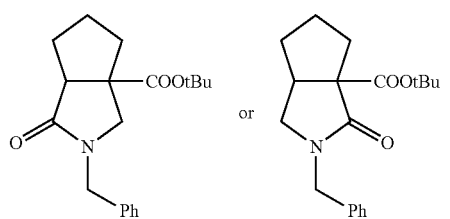
(Amide)

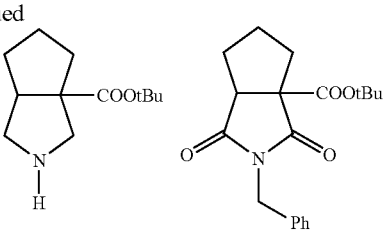
(Imide)

↑ Reduction

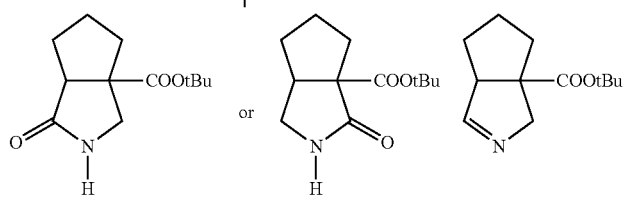

↑ Cyclic amidation

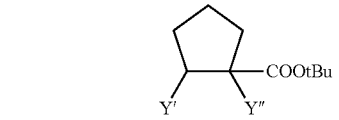

Y' = —CH₂NH₂, Y" = —COOR
Y' = —COOR, Y" = —CH₂NH₂

( —CH₂NH₂ ⇐ —CH₂NO₂, —CH₂N₃, —CN )

↑ Cyclic imination

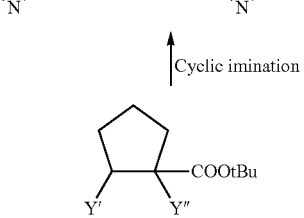

Y' = —CH₂NH₂, Y" = —CHO
Y' = —CHO, Y" = —CH₂NH₂

Reactions in the above-exemplified steps for synthesizing the fused substituted aminopyrrolidine derivatives can be appropriately modified by those skilled in the art based on the above description to find a new synthesis method, and the above description should not be construed as limiting.

In order to produce a compound included in the present invention by introduction of a 1-(tert-butoxycarbonyl)amino-3-azabicyclo[3.3.0]octane derivative which is a fused substituted aminopyrrolidine derivative obtained as described above as the 7-position (10-position) substituent of a quinolonecarboxylic acid mother skeleton (pyridobenzoxazinecarboxylic acid mother skeleton), a quinolonecarboxylic acid mother skeleton compound represented by the following formula:

[Formula 62]

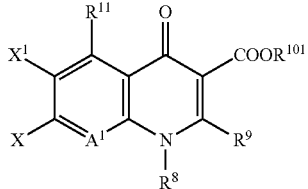

wherein $R^8$, $R^9$, $R^{11}$, $X^1$, and $A^1$ are as defined above; $R^{101}$ represents a hydrogen atom, an alkyl group having 1 to 6 carbon atoms, or a boron substituent that can form a boron chelate; and X represents a leaving group, can be reacted with 1-(tert-butoxycarbonyl)amino-3-azabicyclo[3.3.0]octane.

Preferred examples of the alkyl group having 1 to 6 carbon atoms include a methyl group, an ethyl group, an isopropyl group, and a tert-butyl group. The boron substituent may be dihalogenoboron or diacyloxyboron. The dihalogenoboron is preferably difluoroboron (—BF₂). The diacyloxyboron is preferably diacetyloxyboron [—B(OAc)₂]. Such boron substituents can be obtained according to known methods.

Production of such a compound included in the present invention will be described taking a compound of the later-described Example 11 as an example.

[Formula 63]

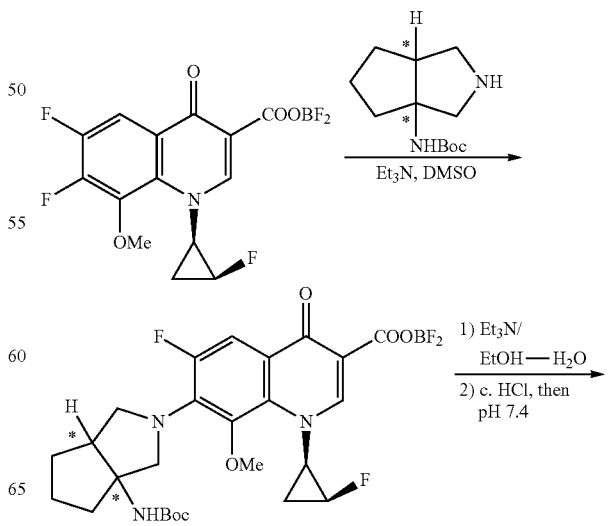

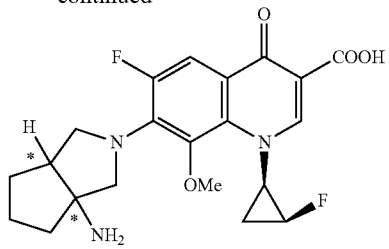
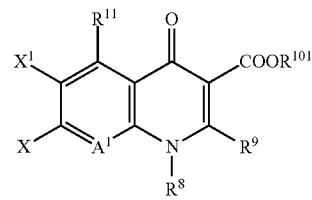

The target compound can be obtained by dissolving a quinolonecarboxylic acid mother skeleton compound in an appropriate solvent and reacting the compound with (−)-1-(tert-butoxycarbonyl)amino-3-azabicyclo[3.3.0]octane which is a compound for introduction as the 7-position substituent in the presence of a base. The amino group in the compound for introduction as the 7-position substituent may be protected by a protecting group. Examples of the protecting group include, in addition to a tert-butoxycarbonyl group (Boc group), a benzyloxycarbonyl group, a p-methoxybenzyloxycarbonyl group, an acetyl group, a methoxyacetyl group, a trifluoroacetyl group, a pivaloyl group, a formyl group, a benzoyl group, a tert-butyl group, a benzyl group, a trimethylsilyl group, and an isopropyldimethylsilyl group. Examples of bases that can be used include carbonates, bicarbonates, or hydroxide salts of alkali metals or alkali earth metals; trialkylamines such as triethylamine and N,N-diisopropylethylamine; and nitrogen-containing heterocyclic compounds such as pyridine, 1,8-diazabicycloundecene, and N-methylpiperidine. Trialkylamines, N-methylpiperidine, and triethylamine are preferred. There are no specific limitations to the solvent used so long as it does not inhibit the reaction. The solvent is preferably N,N-dimethylformamide, dimethyl sulfoxide, sulfolane, acetonitrile, dimethylacetamide, tetrahydrofuran, or N-methylpyrrolidone, and particularly preferably dimethyl sulfoxide, sulfolane, acetonitrile, or dimethylacetamide.

When the quinolonecarboxylic acid mother skeleton compound is a boron chelate compound, the target compound can be obtained by cleaving the boron substituent moiety by hydrolysis and then deprotecting the protecting group for the amino group. The boron substituent may be hydrolyzed under commonly used conditions. For example, the boron substituent can be hydrolyzed by reacting a base in the presence of an aqueous alcohol solvent such as methanol or ethanol. The base is preferably triethylamine. The reaction is preferably carried out in a temperature range between ice-cold and 90° C. The deprotection can be carried out under conditions suitable for the protecting group used by treating the hydrolysate with concentrated hydrochloric acid, for example. After completion of the reaction, the reaction solution is made basic with a sodium hydroxide solution, for example, and then neutralized with an appropriate acid such as hydrochloric acid; the precipitated crystals are subsequently collected by filtration or extracted with chloroform; and the resulting compound is appropriately purified by a recrystallization operation using an appropriate solvent, for example, to obtain the target compound.

The quinolone compounds of the present invention, especially those having a methyl group at the 8-position, are prepared by the reaction of fused substituted aminopyrrolidine derivatives and the quinolone skeleton compounds of the following formula:

[Formula 64]

in the presence of an appropriate solvent and a catalyst, optionally with the coexistence of a ligand, and in the presence of a base. This reaction may be carried out without ligand.

The substituent $R^{101}$ of the quinolone skeleton compound is a hydrogen atom or an alkyl group having 1 to 6 carbon atoms. Examples of the preferred alkyl groups are a methyl group, an ethyl group, an isopropyl group, and a tert-butyl group. In relation to the leaving group $X^1$, those ordinarily used in this field are also preferably applicable to this reaction. The preferred example of such leaving group is a halogen atom such as a bromine atom, or an iodine atom; a substituted sulfonyloxy group such as a trifluoromethansulfonyloxy group. As for the catalyst, those ordinarily used in this field are preferably applicable to this reaction. A Pd catalyst, Cu catalyst, or Ni catalyst is preferably used, and more preferably a Pd catalyst or a Cu catalyst. The catalyst may be applied to the reaction mixture in the from of tris(dibenzylideneacetone)dipalladium(0), palladium(II)acetate, tetrakis(triphenylphosphine)nickel(0), nickel(II) acetylacetonato, copper(I) iodide, or copper(I) bromide and the like. As for the ligand for the present reaction, monodentate ligands or bidentate ligands ordinarily used in this field are preferably applicable to this reaction. Examples of such ligand are 1,1-bis(diphenylphosphino)ferrocene, 4,5-bis(diphenylphospino)-9,9-dimethylxanthene, or BINAP. As for the base, those ordinarily used in this field are preferably applicable to this reaction. The carbonates of alkaline earth metal or alkali metal such as cesium carbonate, potassium carbonate, or sodium carbonate, and alkoxide of alkali metal such as sodium methoxide, sodium ethoxide, or potassium tert-butoxide are preferably used.

This reaction is explained in the following reaction scheme:

[Formula 65]

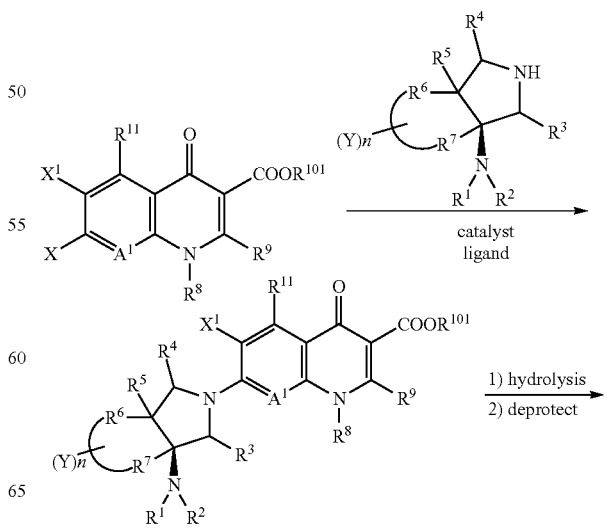

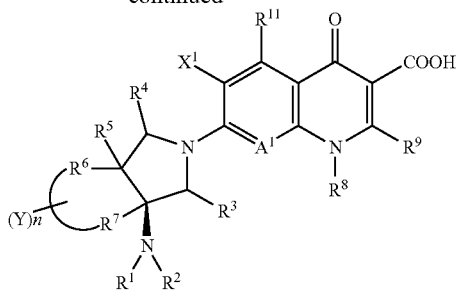

The quinolone compounds of the present invention are obtained by the reaction of the quinolone carboxylic acid skeleton compounds with fused substituted aminopyrrolidine compounds in an appropriate solvent, in the presence of a catalyst, optionally with the coexistence of a ligand, and in the presence of a base. The amino group of the fused substituted pyyrolidine compound used for the introduction of 7-positioned substituent may have a protective group. Examples of such protective groups are an alkyloxycarbonyl group such as a tert-butoxycarbonyl group; an aralkyloxycarbonyl group such as a benzyloxycarbonyl group, or a p-methoxy benzyloxycarbonyl group; an acyl or an alkyl carbonyl group such as an acetyl group, a methoxy acetyl group, a trifluoroacetyl group, a pivaloyl group, or a formyl group; an arylkylcarbonyl group such as a benzoyl group, or a p-nitrobenzoyl group; an alkyl group such as a tert-butyl group; an aralkyl group such as a benzyl group, a p-methoxybenzyl group, or a p-nitro benzyl group; a substituted silyl group such as a trimethylsilyl group, or an isopropyldimethylsilyl group. The example of the base for this reaction is a carbonate, a bicarbonate, a phosphate, a hydrate, or an alkoxide of an alkali metal atom or an alkaline earth metal atom; a trialkylamine such as a triethylamine, or an N,N-diisopropylethylamine; a nitrogen containing heterocyclic compound such as a pyridine, a 1,8-diazabicycloundecene, or an N-methylpiperidine. As for the solvent, any solvent that does not inhibit the reaction is preferably applied for this reaction. Examples of the solvent are an amide such as an N,N-dimethylformamide, an N,N-dimethylacetamide, or an N-methyl-2-pyrrolidone; an aryl hydrocarbon such as a toluene, or a xylene; an ether such as a tetrahydrofuran, a 1,4-dioxane, or a 1,2-dimethoxyethane; and an acetonitrile. More preferred solvents are an N,N-dimethylformamide, a xylene, a 1,4-dioxane, or a 1,2-dimethoxyethane.

The reaction may be conducted in the forms of both homogeneous and heterogeneous reactions. The reaction is also preferably carried out in a catalytic phase reaction. The reaction is completed in from 10 minutes to 7 days. The reaction can be conducted at a temperature between 0° C./to 300° C., preferably between 30° C. to the temperature of the boiling point of the solvent used. The catalyst compound and ligand compound may be mixed to form the catalyst complex prior to the addition of the other reacting compounds, or all of the reaction components may be mixed at once. The amount of the catalyst is in the range of a catalytic amount to the equimolar amount, and a catalytic amount is preferred.

In case that the quinolone skeleton compounds have an ester moiety, the carboxy compounds are obtained by cleavage of the ester group according to already known methods in this field. The quinolone compounds are obtained by cleavage of the protective group of the amino moiety on the fused substituted aminopyrrolidine moiety according to an already known method of the corresponding protective group. The quinolone compounds are isolated after cleavage of the protective group by an already known method in this field, such as recrystallization from appropriate solvents or the like.

Compounds represented by the following two formulas are useful as production intermediates for the compound (I) of the present invention, respectively:

[Formula 66]

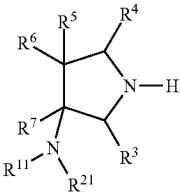

In the above formula, $R^{11}$ represents $R^1$ as already defined (a hydrogen atom, an alkyl group having 1 to 6 carbon atoms, a cycloalkyl group having 3 to 6 carbon atoms, or a substituted carbonyl group derived from an amino acid, a dipeptide, or a tripeptide; the alkyl group may have a substituent selected from the group consisting of a hydroxy group, an amino group, a cyano group, a halogen atom, an alkylthio group having 1 to 6 carbon atoms, and an alkoxy group having 1 to 6 carbon atoms, and the cycloalkyl group may have one or more substituents selected from the group consisting of an alkyl group having 1 to 6 carbon atoms, an amino group, a hydroxy group, and a halogen atom) or an amino-protecting group;

$R^{21}$ represents $R^2$ as already defined (a hydrogen atom, an alkyl group having 1 to 6 carbon atoms, or a cycloalkyl group having 3 to 6 carbon atoms; the alkyl group may have a substituent selected from the group consisting of a hydroxy group, an amino group, a halogen atom, an alkylthio group having 1 to 6 carbon atoms, and an alkoxy group having 1 to 6 carbon atoms, and the cycloalkyl group may have one or more substituents selected from the group consisting of an alkyl group having 1 to 6 carbon atoms, an amino group, a hydroxy group, and a halogen atom) or an amino-protecting group; and $R^3$, $R^4$, $R^5$, $R^6$, and $R^7$ are as already defined.

Here, the amino-protecting group represented by $R^{11}$ or $R^{21}$ will be described. The protecting group is not limited so long as it is generally used in the art. Examples of the protecting group include alkoxycarbonyl groups such as a tert-butoxycarbonyl group and a 2,2,2-trichloroethoxycarbonyl group; aralkyloxycarbonyl groups such as a benzyloxycarbonyl group, a p-methoxybenzyloxycarbonyl group, and a p-nitrobenzyloxycarbonyl group; acyl groups such as an acetyl group, a methoxyacetyl group, a trifluoroacetyl group, a chloroacetyl group, a pivaloyl group, a formyl group, and a benzoyl group; alkyl groups or aralkyl groups such as a tert-butyl group, a benzyl group, a p-nitrobenzyl group, a p-methoxybenzyl group, and a triphenylmethyl group; ethers such as a methoxymethyl group, a tert-butoxymethyl group, a tetrahydropyranyl group, and a 2,2,2-trichloroethoxymethyl group; (alkyl- and/or aralkyl-) substituted silyl groups such as a trimethylsilyl group, an isopropyldimethylsilyl group, a tert-butyldimethylsilyl group, a tribenzylsilyl group, and a tert-butyldiphenylsilyl group; and an allyl group.

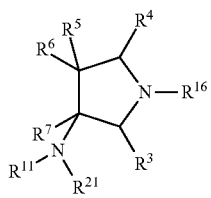

[Formula 67]

In the above formula, $R^{16}$ represents an amino-protecting group; and $R^{11}$, $R^{21}$, $R^3$, $R^4$, $R^5$, $R^6$, and $R^7$ are as already defined.

The protecting group represented by $R^{16}$ is not limited so long as it is generally used in the art. Examples of the protecting group include alkoxycarbonyl groups such as a tert-butoxycarbonyl group and a 2,2,2-trichloroethoxycarbonyl group; aralkyloxycarbonyl groups such as a benzyloxycarbonyl group, a p-methoxybenzyloxycarbonyl group, and a p-nitrobenzyloxycarbonyl group; acyl groups such as an acetyl group, a methoxyacetyl group, a trifluoroacetyl group, a chloroacetyl group, a pivaloyl group, a formyl group, and a benzoyl group; alkyl groups or aralkyl groups such as a tert-butyl group, a benzyl group, a p-nitrobenzyl group, a p-methoxybenzyl group, and a triphenylmethyl group; ethers such as a methoxymethyl group, a tert-butoxymethyl group, a tetrahydropyranyl group, and a 2,2,2-trichloroethoxymethyl group; (alkyl- and/or aralkyl-) substituted silyl groups such as a trimethylsilyl group, an isopropyldimethylsilyl group, a tert-butyldimethylsilyl group, a tribenzylsilyl group, and a tert-butyldiphenylsilyl group; and an allyl group.

When two or more of $R^{11}$, $R^{21}$, and $R^{16}$ are protecting groups, any protecting groups can be selected based on the common knowledge in the art so that the protecting groups can be selectively removed.

It has been found from the later-described test example that compounds obtained as described above having the 7-position of the quinolonecarboxylic acid mother skeleton (or its corresponding position) substituted with the fused bicyclic aminopyrrolidine derivative of the present invention, which are represented by a compound of Example X, have antibacterial activity, in particular, antibacterial activity to *Staphylococcus aureus* and Gram-positive bacteria such as pneumococcus stronger than that of levofloxacin or ciprofloxacin generally used in the art. It has been confirmed in this case that the site substituted with an amino group in the 7-position substituent is an asymmetric carbon, and that quinolonecarboxylic acid substituted with a 7-position substituent derived from one enantiomer has higher activity and exhibits more excellent properties, pharmacokinetics, and safety. As a result of X-ray crystallography of the highly active 7-position substituent or synthesis of each enantiomer by the chiral pool method and measurement of antibacterial activity, it has been confirmed that the 7-position amino group has a configuration represented by the following formula:

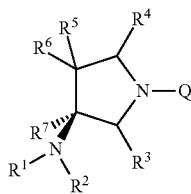

[Formula 68]

wherein $R^1$, $R^2$, $R^3$, $R^4$, $R^5$, $R^6$, $R^7$, and Q are as already defined.

The compound of the present invention may be of a free form. Alternatively, an acid addition salt or a salt with a carboxylic group may be formed. Examples of the acid addition salt include inorganic acid salts such as hydrochloride, sulfate, nitride, hydrobromide, hydriodate, and phosphate; and organic acid salts such as sulfonate (e.g., methanesulfonate, benzenesulfonate, p-toluenesulfonate), and carboxylate (e.g., acetate, citrate, maleate, fumarate, lactate). Examples of the salt with a carboxyl group include alkali metal salts such as lithium salt, sodium salt, and potassium salt; alkaline earth metal salts such as magnesium salt and calcium salt; ammonium salt, triethylamine salt, N-methylglucamine salt, and tris-(hydroxymethyl)aminomethane salt. The compound of the present invention in free form and an acid addition salt or a salt with a carboxyl group of the compound may be present as a hydrate.

The compound (I) of the present invention has strong antibacterial activity and therefore can be used as a medicine for humans, animals, and fish, an agricultural chemical, or a food preservative. The dose of the compound of the present invention used as a human medicine is 50 mg to 1 g, and more preferably 100 to 500 mg, per day for an adult. The dose for an animal varies depending on the purpose of administration, the size of the animal to be treated, the type of the pathogen with which the animal is infected, and the degree of the disease; the daily dose is generally 1 to 200 mg, and more preferably 5 to 100 mg, per kg body weight of the animal. The daily dose is administered once or in two to four divided doses. The daily dose may exceed the aforementioned dose if necessary.

The compound (I) of the present invention is active to a wide range of microorganisms causing various infections and can treat, prevent, or relieve diseases caused by these pathogens. Examples of bacteria or bacteria-like microorganisms for which the compound of the present invention is effective include *Staphylococcus, Streptococcus pyogenes*, hemolytic streptococcus, enterococcus, pneumococcus, *Peptostreptococcus*, gonococcus, *Escherichia coli, Citrobacter, Shigella, Klebsiella pneumoniae, Enterobacter, Serratia, Proteus, Pseudomonas aeruginosa, Haemophilus influenzae, Acinetobacter, Campylobacter*, and *Chlamydia trachomatis*.

Examples of diseases caused by these pathogens include folliculitis, furuncle, carbuncle, erysipelas, cellulitis, lymphangitis, whitlow, subcutaneous abscess, hidradenitis, acne conglobata, infectious atheroma, perirectal abscess, mastitis, superficial secondary infection such as traumatic infection, burn infection, or surgical wound infection, laryngopharyngitis, acute bronchitis, tonsillitis, chronic bronchitis, bronchiectasis, diffuse panbronchiolitis, infection secondary to a chronic breathing disease, pneumonia, pyelonephritis, cystitis, prostatitis, epididymitis, gonococcal urethritis, nongonococcal urethritis, cholecystitis, cholangitis, shigellosis, enteritis, adnexitis, intrauterine infection, bartholinitis, blepharitis, hordeolum, dacryocystitis, meibomianitis, corneal ulcer, otitis media, sinusitis, periodontitis, pericoronitis, jaw inflammation, peritonitis, endocarditis, sepsis, meningitis, and skin infection.

Examples of *Mycobacterium* spp. for which the compound (I) of the present invention is effective include tubercle bacilli (*Mycobacterium tuberculosis, M. bobis*, and *M. africanum*) and atypical mycobacteria (*M. cansasii, M. marinum, M. scrofulaceum, M. avium, M. intracellulare, M. xenopi, M. fortuitum*, and *M. chelonae*). Mycobacterial infections caused by these pathogens are broadly classified into tuberculosis, atypical mycobacterial infections, and leprosy. *Mycobacterium tuberculosis* infections are observed in the thoracic cavity, trachea and bronchus, lymph node, systemic dissemination, bone joints, meninges and brain, digestive organs (intestine and liver), skin, mammary gland, eyes, middle ear and pharynx, urinary tract, male genital organs, and female genital organs, in addition to lung. Atypical mycobacterial infections (nontuberculous mycobacterial infections) mainly affect the lung, and may also appear as local lymphadenitis, soft skin tissue infection, osteoarthritis, or systemic dissemination-type infection.

The compound of the present invention is also effective for various microorganisms causing animal infections such as *Escherichia, Salmonella, Pasteurella, Haemophilus, Bordetella, Staphylococcus*, and *Mycoplasma*. Specific examples of animal diseases include bird diseases such as *Escherichia coli* disease, pullorum disease, fowl paratyphoid, fowl cholera, infectious coryza, staphylococcal disease, and mycoplasma infection; pig diseases such as *Escherichia coli* disease, salmonellosis, pasteurellosis, hemophilus infection, atrophic rhinitis, exudative epidermitis, and mycoplasma infection; bovine diseases such as *Escherichia coli* disease, salmonellosis, hemorrhagic septicemia, mycoplasma infection, contagious bovine pleuropneumonia, and mastitis; dog diseases such as *Escherichia coli* sepsis, salmonella infection, hemorrhagic septicemia, pyometra, and cystitis; and cat diseases such as exudative pleuritis, cystitis, chronic rhinitis, hemophilus infection, kitten diarrhea, and mycoplasma infection.

An antibacterial agent containing the compound (I) of the present invention can be appropriately selected according to the administration method and prepared by a method for preparing various preparations commonly used. Examples of the antibacterial agent dosage form containing the compound of the present invention as a main agent include tablets, powders, granules, capsules, solutions, syrups, elixirs, and oily or aqueous suspensions. An injection preparation may contain an additive such as a stabilizer, a preservative, or a solution adjuvant, and may be prepared before use from a solid preparation formed by storing a solution that may contain such an additive in a container and then lyophilizing the solution, for example. One dose may be stored in a container, or multiple doses may be stored in a single container. Examples of external preparations include solutions, suspensions, emulsions, ointments, gels, creams, lotions, and sprays. A solid preparation may contain a pharmaceutically acceptable additive together with the active compound. Examples of the additive include fillers, binders, disintegrants, solution promoters, wetting agents, and lubricants. A liquid preparation may be a solution, a suspension, an emulsion, or the like, and may contain an additive such as a suspending agent or an emulsifier.

Next, preparation examples will be described.

Preparation Example 1

Capsules

| | |
|---|---|
| Compound of Example 11 | 100.0 mg |
| Corn starch | 23.0 mg |
| Calcium carboxymethylcellulose | 22.5 mg |
| Hydroxymethylcellulose | 3.0 mg |
| Magnesium stearate | 1.5 mg |
| Total | 150.0 mg |

Preparation Example 2

Solution Preparation

| | |
|---|---|
| Compound of Example 11 | 1 to 10 g |
| Acetic acid or sodium hydroxide | 0.5 to 2 g |
| Ethyl p-oxybenzoate | 0.1 g |
| Purified water | 87.9 to 98.4 g |
| Total | 100 g |

Preparation Example 3

Powder to be Mixed with Forage

| | |
|---|---|
| Compound of Example 17 | 1 to 10 g |
| Corn starch | 89.5 to 98.5 g |
| Light anhydrous silicic acid | 0.5 g |
| Total | 100 g |

EXAMPLES

The present invention will be specifically described below with reference to examples; however, the present invention is not limited to the examples, and the examples should not be construed as limitative in any sense.

Reference Example 1

(S)-3-(tert-Butyldimethylsilyloxy)-2-methylpropionic acid methyl ester

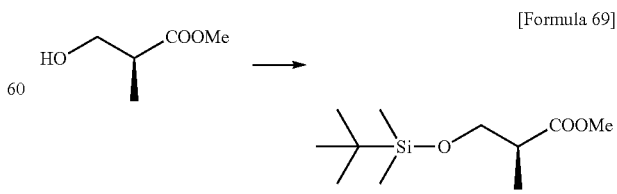

[Formula 69]

Imidazole (13.3 g, 196 mmol) and tert-butyldimethylsilyl chloride (14.2 g, 94.1 mmol) were added to a solution of (S)-3-hydroxy-2-methylpropionic acid methyl ester (11.0 g, 93.1 mmol) in dimethylformamide (100 mL), and the mixture was stirred at room temperature for four hours. Water was added to the reaction mixture, followed by extraction with hexane twice. The extract was then dried over magnesium sulfate. After filtration, the solvent was evaporated under reduced pressure to give 24 g (quantitative) of the title compound as a colorless oil.

$^1$H-NMR (400 MHz, CDCl$_3$) δ: 3.76-3.72 (1H, m), 3.64 (3H, s), 3.63-3.59 (1H, m), 2.65-2.57 (1H, m), 1.10 (3H, d, J=6.84 Hz), 0.84 (9H, s), 0.01 (3H, s), 0.00 (3H, s).

Reference Example 2

(E)-(R)-5-(tert-Butyldimethylsilyloxy)-4-methyl-pent-2-ene acid methyl ester

[Formula 70]

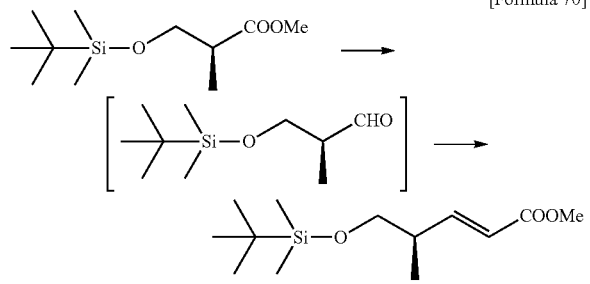

Diisobutylaluminum hydride (1 M solution in hexane, 86 mL) was added to a solution of (S)-3-(tert-butyldimethylsilyloxy)-2-methylpropionic acid methyl ester (20 g, 86.1 mmol) in dichloromethane (400 mL) at −78° C., and the mixture was stirred at the same temperature for two hours. A saturated potassium sodium tartrate solution was added to the reaction mixture which was then stirred while heating to room temperature. The organic layer was separated, and then the aqueous layer was extracted with ethyl acetate. The organic layers were combined, dried over magnesium sulfate, and filtered, and the solvent was evaporated under reduced pressure. The residue was dissolved in dichloromethane (200 mL). Triphenylphosphonylideneacetic acid methyl ester (32 g, 94.7 mmol) was added under ice-cooling, and the mixture was stirred at room temperature overnight. The reaction solution was filtered, and then the solvent was evaporated under reduced pressure. Hexane was added to the resulting residue, and the insoluble material was removed by filtration. The filtrate was concentrated under reduced pressure, and the resulting residue was purified by silica gel column chromatography (hexane:ethyl acetate=4:1) to give 25 g (quantitative) of the title compound as a colorless oil.

$^1$H-NMR (400 MHz, CDCl$_3$) δ: 6.94 (1H, dd, J=7.10, 15.90 Hz), 5.84 (1H, dd, J=1.20, 15.90 Hz), 3.73 (3H, s), 3.57-3.49 (2H, m), 2.53-2.46 (1H, m), 1.05 (3H, d, J=6.80 Hz), 0.89 (9H, s), 0.04 (6H, s).

Reference Example 3

1-Benzyl-4-[(R)-2-(tert-butyldimethylsilyloxy)-1-(methyl)ethyl]pyrrolidine-3-carboxylic acid methyl ester

[Formula 71]

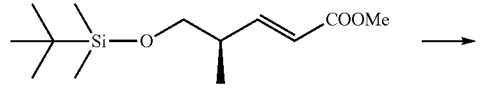

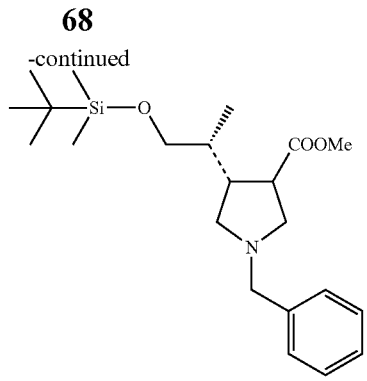

3,4-dl-trans

N-Benzyl-N-(methoxymethyl)-N-trimethylsilylmethylamine (16.6 mL, 65.0 mmol) was added to a solution of (E)-(R)-5-(tert-butyldimethylsilyloxy)-4-methylpent-2-ene acid methyl ester (14 g, 54.2 mmol) in methylene chloride (100 mL), and then a trace amount of trifluoroacetic acid was added. The mixture was stirred for 30 minutes and then saturated sodium bicarbonate water was added. The organic layer was separated and dried over magnesium sulfate. After filtration, the solvent was evaporated under reduced pressure, and the resulting residue was purified by silica gel column chromatography (hexane:ethyl acetate=4:1) to give 14.6 g (69%) of the diastereomer mixture title compound as a colorless oil. The diastereomers were used for the next step without separation.

Reference Example 4

4-[(R)-2-(tert-Butyldimethylsilyloxy)-1-(methyl)ethyl]pyrrolidine-1,3-dicarboxylic acid 1-benzyl ester 3-methyl ester

[Formula 72]

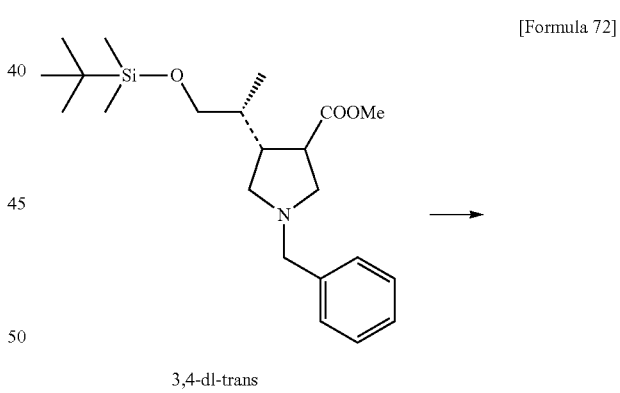

3,4-dl-trans

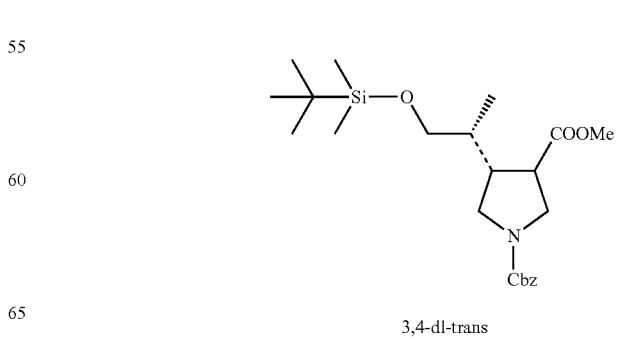

3,4-dl-trans

Benzyloxycarbonyl chloride (10.2 mL, 71.5 mmol) was added to a solution of 1-benzyl-4-[(R)-2-(tert-butyldimethylsilyloxy)-1-(methyl)ethyl]pyrrolidine-3-carboxylic acid methyl ester (14.0 g, 35.8 mmol) in dichloromethane (200 mL), and the mixture was stirred for one hour. Saturated sodium bicarbonate water was added to the reaction mixture. The organic layer was separated, dried over magnesium sulfate, and filtered. Then, the solvent was evaporated under reduced pressure. The residue was purified by silica gel column chromatography (hexane:ethyl acetate=4:1) to give 13.9 g (89%) of the diastereomer mixture title compound as a colorless oil. The diastereomers were used for the next step without separation.

Reference Example 5

4-[(R)-2-Hydroxy-1-(methyl)ethyl]pyrrolidine-1,3-dicarboxylic acid 1-benzyl ester 3-methyl ester

[Formula 73]

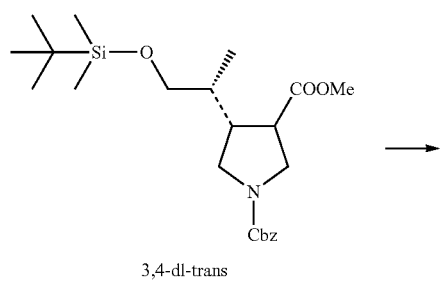

3,4-dl-trans

Hydrogen fluoride-pyridine (4 mL) was added to a solution of 4-[(R)-2-(tert-butyldimethylsilyloxy)-1-(methyl)ethyl]-pyrrolidine-1,3-dicarboxylic acid 1-benzyl ester 3-methyl ester (6.0 g, 7.1 mmol) in pyridine (20 mL) under ice-cooling, and the mixture was stirred at room temperature for 13 hours. The reaction mixture was poured into ice water, followed by extraction with ethyl acetate and washing with 1N hydrochloric acid and brine. After drying over magnesium sulfate and filtration, the solvent was evaporated under reduced pressure to give 4.1 g (93%) of the diastereomer mixture title compound as a colorless oil. The diastereomers were used for the next step without separation.

Reference Example 6

4-[(R)-2-Iodo-1-(methyl)ethyl]-pyrrolidine-1,3-dicarboxylic acid 1-benzyl ester 3-methyl ester

[Formula 74]

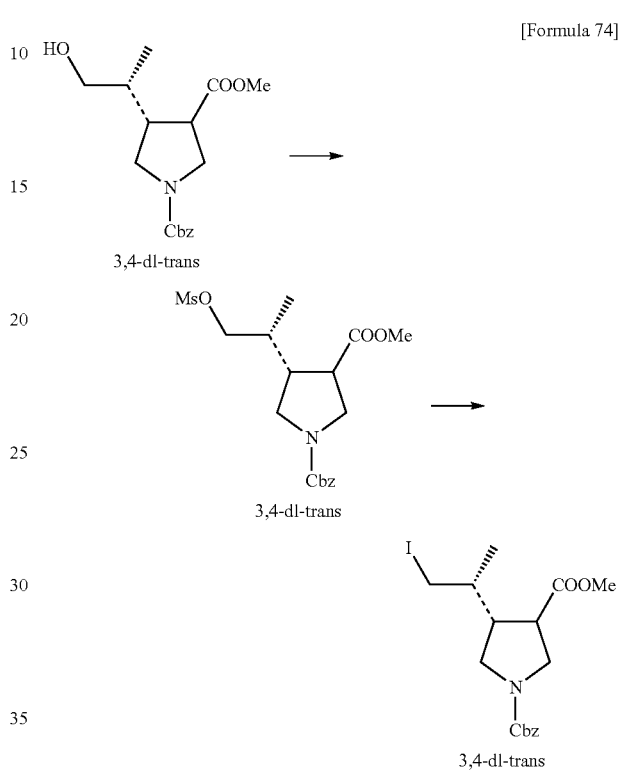

Triethylamine (2.7 mL, 19.1 mmol) and mesyl chloride (1.2 mL, 15.3 mmol) were added to a solution of 4-[(R)-2-hydroxy-1-(methyl)ethyl]pyrrolidine-1,3-dicarboxylic acid 1-benzyl ester 3-methyl ester (4.1 g, 12.8 mmol) in dichloromethane (100 mL) under ice-cooling, and then the mixture was stirred at room temperature for 30 minutes. After adding methanol to the reaction mixture, the mixture was blended with a mixture of ethyl acetate and a 10% citric acid solution. The organic layer was washed with brine and dried over magnesium sulfate. After filtration, the solvent was evaporated under reduced pressure, and the resulting residue was dissolved in acetone (100 mL). Sodium iodide (4.1 g, 27.4 mmol) was added, and the mixture was heated to reflux for 20 hours. The reaction mixture was cooled and then the solvent was evaporated under reduced pressure. The resulting residue was blended with a mixture of ethyl acetate and water. The organic layer was washed with a saturated sodium thiosulfate solution and brine, dried over magnesium sulfate, and then filtered, and the solvent was evaporated under reduced pressure. The residue was purified by silica gel column chromatography (hexane:ethyl acetate=10:0→7:3) to give 5.0 g (84%) of the diastereomer mixture title compound as a colorless oil. The diastereomers were used for the next step without separation.

$^{1}$H-NMR (400 MHz, CDCl$_3$) δ: 7.37-7.33 (5H, m), 5.13 (2H, s), 3.83-3.71 (4H, m), 3.58-3.51 (1H, m), 3.27-3.23 (1H, m), 3.18-3.09 (2H, m), 2.92-2.83 (1H, m), 2.64-2.55 (1H, m), 1.81-1.75 (1H, m), 1.53-1.48 (1H, m), 1.06-1.01 (3H, m).

Reference Example 7

(S)-6-Methyl-3-azabicyclo[3.2.0]heptane-1,3-dicarboxylic acid 3-benzyl ester 1-methyl ester

[Formula 75]

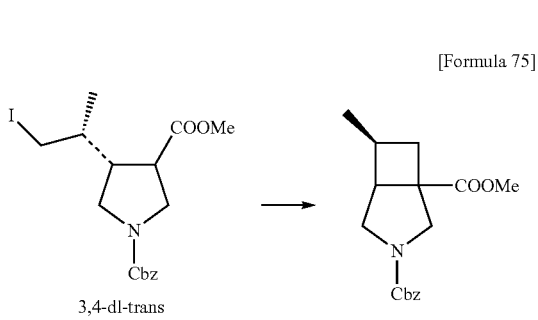 [SMILES: COC(=O)C1CN(C(=O)OCc2ccccc2)C[C@@H]1[C@@H](C)CI ; COC(=O)C12C[C@H](C)C1CN(C(=O)OCc1ccccc1)C2]

3,4-dl-trans

A 0.5 M solution of potassium hexamethyldisilazide in toluene (28 mL, 14.0 mmol) was added dropwise to a solution of 4-[(R)-2-iodo-1-(methyl)ethyl]pyrrolidine-1,3-dicarboxylic acid 1-benzyl ester 3-methyl ester (5.0 g, 11.5 mmol) in anhydrous tetrahydrofuran (100 mL) in an argon atmosphere at −78° C. After completion of dropwise addition, the mixture was stirred at the same temperature for 30 minutes. An ammonium chloride solution was added, and the mixture was heated to room temperature. After extraction with ethyl acetate, drying over magnesium sulfate, and filtration, the solvent was evaporated under reduced pressure. The residue was purified by silica gel column chromatography (hexane:ethyl acetate=10:0→7:3) to give 3.2 g (91%) of the diastereomer mixture title compound as a colorless oil. The diastereomers were used for the next step without separation.

$^1$H-NMR (400 MHz, CDCl$_3$) δ: 7.35-7.32 (5H, m), 5.17-5.14 (2H, m), 3.94 (0.5H, dd, J=10.86, 18.92 Hz), 3.76-3.69 (5H, m), 3.46 (0.5H, d, J=11.72 Hz), 3.36 (0.5H, dd, J=6.10, 11.47 Hz), 3.25 (0.5H, dd, J=8.06, 11.96 Hz), 3.06 (0.5H, t, J=8.30 Hz), 2.73-2.65 (1.5H, m), 2.13-2.09 (1.5H, m), 1.11 (1.5H, d, J=6.10 Hz), 0.94 (1.5H, brs).

Reference Example 8

(S)-6-Methyl-3-azabicyclo[3.2.0]heptane-1,3-dicarboxylic acid 3-benzyl ester

[Formula 76]

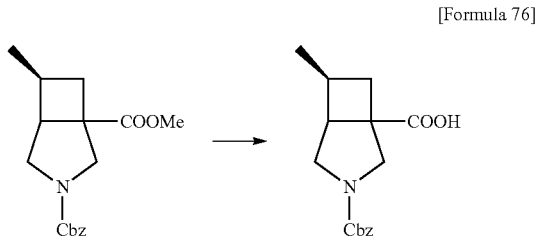 [SMILES: COC(=O)C12C[C@H](C)C1CN(C(=O)OCc1ccccc1)C2 ; C[C@H]1CC2(C(=O)O)CN(C(=O)OCc3ccccc3)CC12]

A 1N sodium hydroxide solution (21 ml) was added dropwise to a mixed solution of (S)-6-methyl-3-azabicyclo[3.2.0]heptane-1,3-dicarboxylic acid 3-benzyl ester 1-methyl ester (3.2 g, 10.4 mmol) in tetrahydrofuran (60 ml) and methanol (20 ml) under ice-cooling, and the mixture was stirred for 30 minutes. The reaction solution was neutralized with 1N hydrochloric acid, followed by extraction with ethyl acetate. The extract was dried over magnesium sulfate and filtered. The solvent was evaporated under reduced pressure to give 3.0 g (quantitative) of the diastereomer mixture title compound as a colorless oil. The diastereomers were used for the next step without separation.

Reference Example 9

(S)-1-tert-Butoxycarbonylamino-6-methyl-3-azabicyclo[3.2.0]heptane-3-carboxylic acid benzyl ester (Optical Isomer A, Optical Isomer B)

[Formula 77]

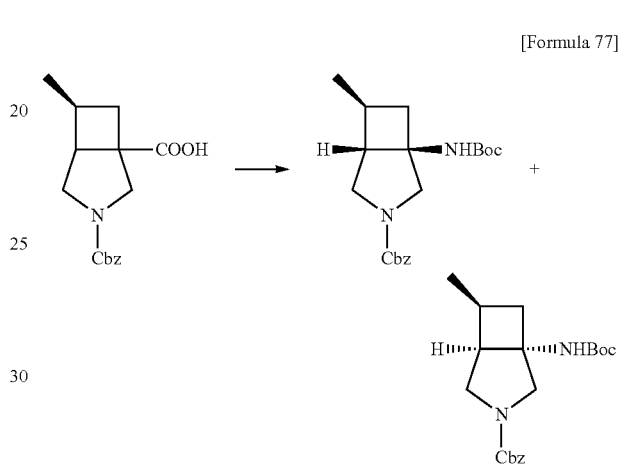

Triethylamine (2.9 mL, 20.7 mmol) and diphenyl phosphoazide (3.4 mL, 15.6 mmol) were added to a solution of (S)-6-methyl-3-azabicyclo[3.2.0]heptane-1,3-dicarboxylic acid 3-benzyl ester (3.0 g, 10.4 mmol) in toluene (60 mL) at room temperature, and then tert-butyl alcohol (60 mL) was added. The mixture was heated with stirring at 100° C. for 15 hours. The reaction mixture was cooled, and then the solvent was evaporated under reduced pressure. The residue was purified by silica gel column chromatography (hexane:ethyl acetate=10:0→8:2) to give the diastereomer mixture title compound (3.1 g) as a colorless oil. The diastereomers were separated by Chiralpak AD (2 cm, hexane:isopropyl alcohol=92.5:7.5, flow: 30 mL/min) to give 1.48 g (40%) of a first fraction colorless oil (optical isomer A) and 1.38 g (37%) of a second fraction colorless oil (optical isomer B).

Optical Isomer A:
$^1$H-NMR (400 MHz, CDCl$_3$) δ: 7.37-7.29 (5H, m), 5.14 (2H, s), 4.81-4.76 (1H, m), 3.84 (1H, d, J=10.70 Hz), 3.61-3.53 (3H, brm), 2.43-2.31 (2H, m), 1.92-1.86 (1H, m), 1.75-1.68 (1H, m), 1.43 (9H, s), 1.14 (3H, d, J=6.80 Hz).

Optical Isomer B:
$^1$H-NMR (400 MHz, CDCl$_3$) δ: 7.37-7.30 (5H, m), 5.16 (2H, s), 4.87-4.73 (1H, brm), 3.88-3.79 (1H, m), 3.72 (1H, d, J=11.00 Hz), 3.43-3.28 (2H, brm), 2.89-2.77 (1H, brm), 2.67-2.58 (1H, m), 2.32 (1H, t, J=11.70 Hz), 1.76-1.68 (1H, m), 1.44 (9H, s), 0.95-0.92 (3H, m).

Based on NMR comparison between the more polar isomer and the less polar isomer, the optical isomer A was identified as (1R,5S,6S)-1-tert-butoxycarbonylamino-6-methyl-3-azabicyclo[3.2.0]heptane-3-carboxylic acid benzyl ester, and the optical isomer B was identified as (1S,5R,6S)-1-tert-butoxycarbonylamino-6-methyl-3-azabicyclo[3.2.0]heptane-3-carboxylic acid benzyl ester.

Reference Example 10

(1R,5S,6S)-1-(tert-Butoxycarbonylamino)-6-methyl-3-azabicyclo[3.2.0]heptane

[Formula 78]

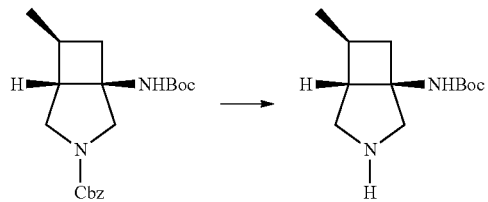

(1R,5S,6S)-1-tert-Butoxycarbonylamino-6-methyl-3-azabicyclo[3.2.0]heptane-3-carboxylic acid benzyl ester (1.4 g, 3.9 mmol) was dissolved in a mixed solvent of methanol (20 mL) and tetrahydrofuran (10 mL). A small amount of 10% palladium-carbon (50% wet) was added, and the mixture was stirred in a hydrogen atmosphere for three hours. After removing the catalyst by filtration, the filtrate was concentrated under reduced pressure to give 0.89 g (quantitative) of the title compound as a colorless oil.

$^1$H-NMR (400 MHz, CDCl$_3$) δ: 4.80 (1H, brs), 3.09 (1H, d, J=11.20 Hz), 3.02 (2H, dd, J=5.40, 11.20 Hz), 2.82 (2H, d, J=11.20 Hz), 2.27-2.22 (2H, m), 1.77-1.69 (2H, m), 1.44 (9H, s), 1.17 (3H, d, J=6.60 Hz).

Reference Example 11

(1S,5R,6S)-1-(tert-Butoxycarbonylamino)-6-methyl-3-azabicyclo[3.2.0]heptane

[Formula 79]

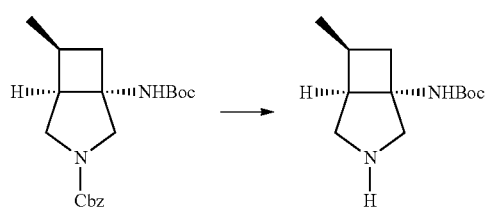

(1S,5R,6S)-1-tert-Butoxycarbonylamino-6-methyl-3-azabicyclo[3.2.0]heptane-3-carboxylic acid benzyl ester (1.4 g, 3.8 mmol) was dissolved in a mixed solvent of methanol (20 mL) and tetrahydrofuran (10 mL). A small amount of 10% palladium-carbon (50% wet) was added, and the mixture was stirred in a hydrogen atmosphere for three hours. After removing the catalyst by filtration, the filtrate was concentrated under reduced pressure to give 0.85 g (quantitative) of the title compound as a colorless oil.

$^1$H-NMR (400 MHz, CDCl$_3$) δ: 4.88 (1H, brs), 3.06 (1H, d, J=12.00 Hz), 2.96-2.89 (2H, m), 2.71-2.61 (3H, m), 2.39-2.33 (1H, m), 1.58 (1H, dd, J=7.40, 12.80 Hz), 1.45 (9H, s), 0.94 (3H, d, J=6.80 Hz).

Example 1

7-{(1R,5S,6S)-1-Amino-6-methyl-3-azabicyclo[3.2.0]hept-3-yl}-6-fluoro-1-[(1R,2S)-2-fluorocyclopropyl]-1,4-dihydro-8-methoxy-4-oxoquinoline-3-carboxylic acid

[Formula 80]

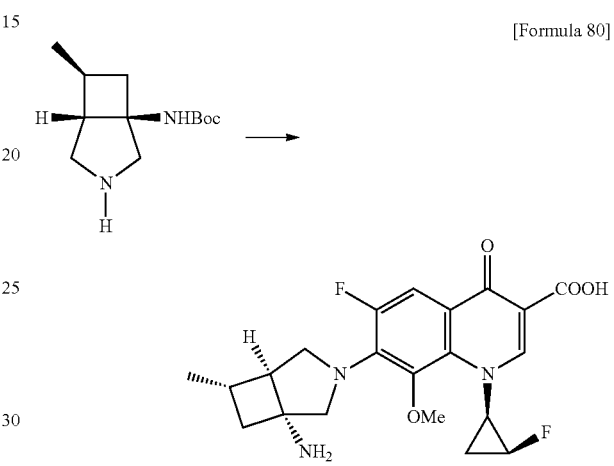

(1R,5S,6S)-1-(tert-Butoxycarbonylamino)-6-methyl-3-azabicyclo[3.2.0]heptane (870 mg, 3.84 mmol) and 6,7-difluoro-1-[(1R,2S)-2-fluorocyclopropyl]-1,4-dihydro-8-methoxy-4-oxoquinoline-3-carboxylic acid-BF$_2$ chelate (1.25 g, 3.46 mmol) were dissolved in dimethyl sulfoxide (15 mL). Triethylamine (0.64 mL) was added, and the mixture was stirred at 40° C. for 12 hours. After cooling the reaction solution with ice, water was added, and the precipitate was collected by filtration, washed with water, and dried. The precipitate was dissolved in ethanol (140 mL). Water (30 mL) and triethylamine (0.64 mL) were added, and the mixture was heated to reflux for five hours. The reaction mixture was diluted with ethyl acetate and washed with a 10% citric acid solution, water, and brine. The organic layer was dried over anhydrous sodium sulfate and filtered, and then the solvent was evaporated under reduced pressure. Concentrated hydrochloric acid (25 mL) was added to the residue, and the mixture was stirred at room temperature for one hour. Then, the reaction solution was washed with chloroform. The aqueous layer was adjusted to pH 12.0 with a 10 mol/L sodium hydroxide solution under ice-cooling and then adjusted to pH 7.4 with hydrochloric acid, followed by extraction with chloroform-methanol (9:1) eight times. The organic layer was dried over anhydrous sodium sulfate and then filtered, and the solvent was evaporated under reduced pressure. The resulting residue was dissolved in ethanol, and the insoluble material was removed by filtration. The solvent was evaporated under reduced pressure, and the resulting powder was dried under reduced pressure to give 562 mg (35%) of the title compound as a pale yellow solid.

$^1$H-NMR (400 MHz, 0.1N NaOD) δ: 8.49 (1H, brs), 7.70 (1H, d, J=13.70 Hz), 5.03-4.85 (1H, m), 4.09-4.03 (1H, m), 3.90 (1H, d, J=10.50 Hz), 3.67 (3H, s), 3.48 (1H, d, J=10.50 Hz), 3.03 (1H, d, J=10.50 Hz), 2.44 (1H, dd, J=12.00, 8.80

Hz), 2.15 (1H, t, J=5.10 Hz), 1.92-1.84 (1H, m), 1.69-1.62 (1H, m), 1.61-1.49 (1H, m), 1.14 (3H, d, J=7.10 Hz).

Anal; Calcd for $C_{21}H_{23}F_2N_3O_4 \cdot 0.7H_2O \cdot 0.2EtOH$: C, 58.25; H, 5.85; F, 8.61; N, 9.52. Found: C, 58.22; H, 5.84; F, 8.47; N, 9.37.

MS (ESI) m/z: 420 (M+H)+.

Example 2

7-{(1S,5R,6S)-1-Amino-6-methyl-3-azabicyclo[3.2.0]hept-3-yl}-6-fluoro-1-[(1R,2S)-2-fluorocyclopropyl]-1,4-dihydro-8-methoxy-4-oxoquinoline-3-carboxylic acid

[Formula 81]

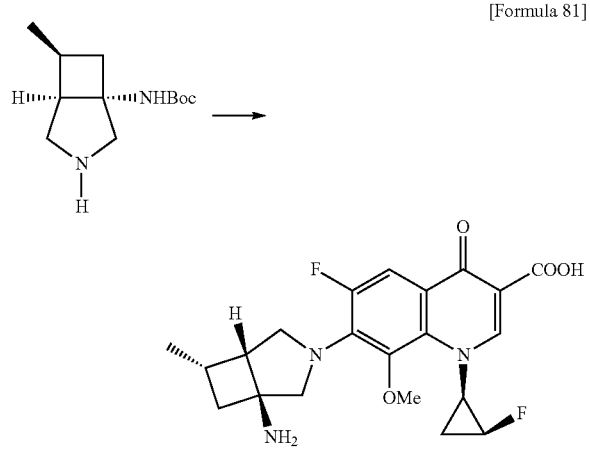

(1S,5R,6S)-1-(tert-Butoxycarbonylamino)-6-methyl-3-azabicyclo[3.2.0]heptane (820 mg, 3.62 mmol) and 6,7-difluoro-1-[(1R,2S)-2-fluorocyclopropyl]-1,4-dihydro-8-methoxy-4-oxoquinoline-3-carboxylic acid-BF$_2$ chelate (1.18 g, 3.26 mmol) were dissolved in dimethyl sulfoxide (15 mL). Triethylamine (0.61 mL) was added, and the mixture was stirred at 40° C. for 12 hours. After cooling the reaction solution with ice, water was added, and the precipitate was collected by filtration, washed with water, and dried. The precipitate was dissolved in ethanol (120 mL). Water (30 mL) and triethylamine (0.61 mL) were added, and the mixture was heated to reflux for five hours. The reaction mixture was diluted with ethyl acetate and washed with a 10% citric acid solution, water, and brine. The organic layer was dried over anhydrous sodium sulfate and filtered, and then the solvent was evaporated under reduced pressure. Concentrated hydrochloric acid (25 mL) was added to the residue, and the mixture was stirred at room temperature for one hour. Then, the reaction solution was washed with chloroform. The aqueous layer was adjusted to pH 12.0 with a 10 mol/L sodium hydroxide solution under ice-cooling and then adjusted to pH 7.4 with hydrochloric acid, followed by extraction with chloroform-methanol (9:1) six times. The organic layer was dried over anhydrous sodium sulfate, and the solvent was evaporated under reduced pressure. The resulting residue was dissolved in ethanol, and the insoluble material was removed by filtration. The solvent was evaporated under reduced pressure, and the resulting powder was dried under reduced pressure to give 1.1 g (72%) of the title compound as a pale yellow solid.

$^1$H-NMR (400 MHz, 0.1N NaOD) δ: 8.46 (1H, d, J=2.20 Hz), 7.72 (1H, d, J=13.70 Hz), 5.10-4.90 (1H, m), 4.07-4.02 (1H, m), 3.75 (1H, d, J=11.20 Hz), 3.64 (3H, s), 3.64-3.59 (1H, m), 3.49-3.47 (1H, m), 3.09 (1H, d, J=10.00 Hz), 2.68-2.60 (1H, m), 2.51 (1H, t, J=7.30 Hz), 2.20 (1H, t, 10.5 Hz), 1.85 (1H, dd, J=8.50, 12.70 Hz), 1.63-1.42 (2H, m), 0.96 (3H, d, J=7.30 Hz).

Anal; Calcd for $C_{21}H_{23}F_2N_3O_4 \cdot 0.7H_2O$: C, 58.38; H, 5.69; F, 8.79; N, 9.73. Found: C, 58.24; H, 5.69; F, 8.59; N, 9.52.

MS (ESI) m/z: 420 (M+H)+.

Example 3

10-{(1S,5R,6S)-1-Amino-6-methyl-3-azabicyclo[3.2.0]hept-3-yl}-9-fluoro-2,3-dihydro-3-(S)-methyl-7-oxo-7H-pyrido[1,2,3-de][1,4]benzoxazine-6-carboxylic acid

[Formula 82]

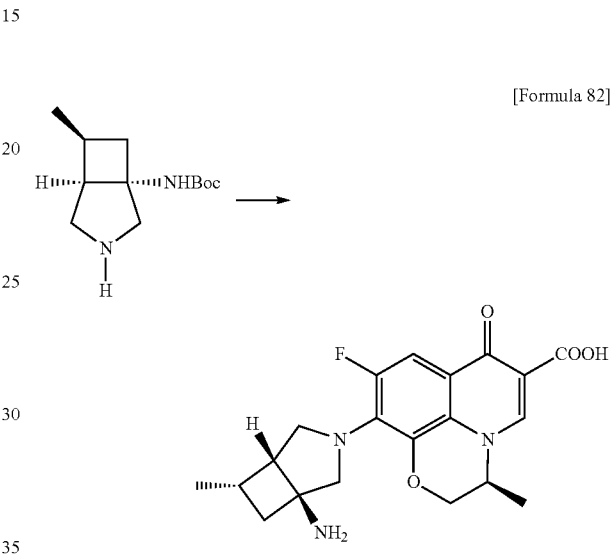

(1S,5R,6S)-1-(tert-Butoxycarbonylamino)-6-methyl-3-azabicyclo[3.2.0]heptane (546.3 mg, 2.41 mmol) was dissolved in dimethyl sulfoxide (12 mL). 9,10-Difluoro-2,3-dihydro-3-(S)-methyl-7-oxo-7H-pyrido[1,2,3-de][1,4]benzoxazine-6-carboxylic acid-BF$_2$ chelate (794.1 mg, 2.41 mmol) and triethylamine (1221 mg, 12.07 mmol) were added, and the mixture was stirred for five days. Then, 90% aqueous ethanol (135 mL) and triethylamine (15 mL) were added to the reaction mixture, which was stirred at 80° C. for 4.5 hours. The solvent was evaporated under reduced pressure and a 10% citric acid solution was added, followed by extraction with ethyl acetate. The organic layer was washed with water and brine and dried over anhydrous sodium sulfate. After filtration, the solvent was evaporated under reduced pressure, and the resulting residue was subjected to short silica gel column chromatography (3% methanol/chloroform). The resulting crude was dissolved in concentrated hydrochloric acid and washed with dichloromethane. The aqueous layer was adjusted to pH 12 with aqueous sodium hydroxide at 0° C. and then adjusted to pH 7.4 with hydrochloric acid, followed by extraction with chloroform. The organic layer was dried over anhydrous sodium sulfate and filtered, and then the solvent was evaporated under reduced pressure. The resulting solid was washed with ethanol and dried under reduced pressure to give the title compound (695 mg) as a pale yellow solid.

mp: 122-124° C.

$^1$H-NMR (400 MHz, 0.1N NaOD) δ: 8.31 (1H, s), 7.46 (1H, d, J=13.67 Hz), 4.55 (1H, d, J=6.84 Hz), 4.46 (1H, d, J=11.47 Hz), 4.30 (1H, d, J=11.47 Hz), 3.71 (1H, d, J=10.74 Hz), 3.45 (1H, d, J=9.77 Hz), 3.27 (1H, t, J=8.79 Hz), 3.09

(1H, d, J=9.77 Hz), 2.58-2.56 (1H, m), 2.37 (1H, t, J=7.81 Hz), 2.12 (1H, t, J=11.47 Hz), 1.78 (1H, dd, J=12.33, 8.42 Hz), 1.48 (3H, d, J=6.59 Hz), 0.94 (3H, d, J=7.08 Hz).

Anal; Calcd for $C_{20}H_{22}FN_3O_4 \cdot H_2O$: C, 59.25; H, 5.97; N, 10.36; F, 4.69. Found: C, 59.41; H, 5.65; N, 10.36; F, 4.97.

MS (EI) m/z: 388 (M+H)$^+$.

IR (ATR) ν: 2956, 2929, 2866, 1716, 1612, 1579, 1523, 1450, 1385, 1335, 1298, 1255 cm$^{-1}$.

Reference Example 12

(R)-3-(tert-Butyldimethylsilyloxy)-2-methylpropionic acid methyl ester

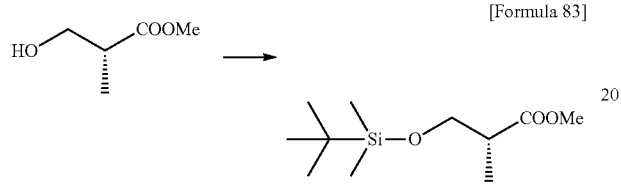

[Formula 83]

Imidazole (6.44 g, 42.8 mmol) and tert-butyldimethylsilyl chloride (6.05 g, 88.8 mmol) were added to a solution of (R)-3-hydroxy-2-methylpropionic acid methyl ester (5.0 g, 42.33 mmol) in dimethylformamide (50 mL), and the mixture was stirred at room temperature for 1.5 hours. Water was added to the reaction mixture, followed by extraction with hexane twice. The extract was then dried over magnesium sulfate. After filtration, the solvent was evaporated under reduced pressure to give 9.3 g (95%) of the title compound as a colorless oil.

$^1$H-NMR (400 MHz, CDCl$_3$) δ: 3.76-3.72 (1H, m), 3.64 (3H, s), 3.63-3.59 (1H, m), 2.65-2.57 (1H, m), 1.10 (3H, d, J=6.84 Hz), 0.84 (9H, s), 0.01 (3H, s), 0.00 (3H, s).

Reference Example 13

(E)-(S)-5-(tert-Butyldimethylsilyloxy)-4-methylpent-2-ene acid methyl ester

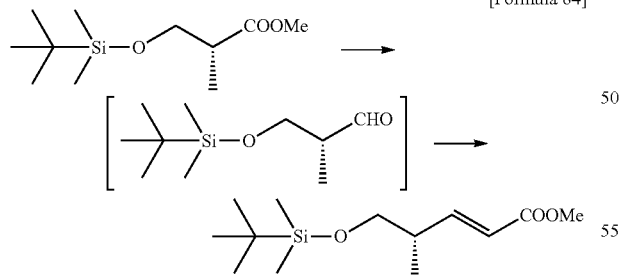

[Formula 84]

Diisobutylaluminum hydride (1 M solution in hexane, 17.2 mL) was added to a solution of (R)-3-(tert-butyldimethylsilyloxy)-2-methylpropionic acid methyl ester (4.0 g, 17.2 mmol) in dichloromethane (100 mL) at −78° C., and the mixture was stirred at the same temperature for four hours. A saturated potassium sodium tartrate solution was added to the reaction mixture which was then stirred while heating to room temperature. The organic layer was separated, and then the aqueous layer was extracted with ethyl acetate. The organic layers were combined, dried over magnesium sulfate, and filtered. Then, the solvent was evaporated under reduced pressure to give aldehyde (3.5 g) as a colorless oil. The aldehyde was dissolved in dichloromethane (50 mL). Triphenylphosphonylideneacetic acid methyl ester (7.08 g, 20.75 mmol) was added under ice-cooling, and the mixture was stirred at room temperature overnight. The solvent was evaporated under reduced pressure, and the resulting residue was purified by silica gel column chromatography (hexane:ethyl acetate=4:1) to give 3.8 g (85%) of the title compound as a colorless oil.

$^1$H-NMR (400 MHz, CDCl$_3$) δ: 6.94 (1H, dd, J=7.10, 15.90 Hz), 5.84 (1H, dd, J=1.20, 15.90 Hz), 3.73 (3H, s), 3.57-3.49 (2H, m), 2.53-2.46 (1H, m), 1.05 (3H, d, J=6.80 Hz), 0.89 (9H, s), 0.04 (6H, s).

Reference Example 14

1-Benzyl-4-[(S)-2-(tert-butyldimethylsilyloxy)-1-(methyl)ethyl]pyrrolidine-3-carboxylic acid methyl ester

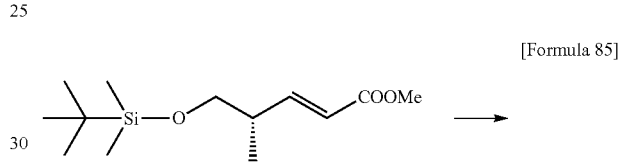

[Formula 85]

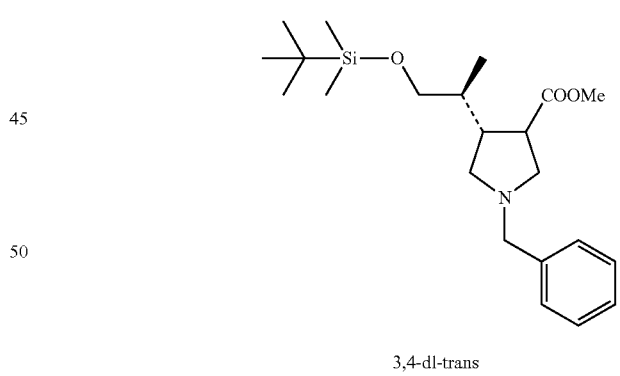

3,4-dl-trans

N-Benzyl-N-(methoxymethyl)-N-trimethylsilylmethylamine (2.97 mL, 11.6 mmol) was added to a solution of (E)-(S)-5-(tert-butyldimethylsilyloxy)-4-methylpent-2-ene acid methyl ester (2.5 g, 9.67 mmol) in dichloromethane (20 mL), and then a trace amount of trifluoroacetic acid was added. The mixture was stirred for 30 minutes and then saturated sodium bicarbonate water was added. The organic layer was separated and dried over magnesium sulfate. After filtration, the solvent was evaporated under reduced pressure, and the resulting residue was purified by silica gel column chromatography (hexane:ethyl acetate=4:1) to give 3.0 g (78%) of the diastereomer mixture title compound as a colorless oil. The diastereomers were used for the next step without separation.

Reference Example 15

4-[(S)-2-(tert-Butyldimethylsilyloxy)-1-(methyl)ethyl]pyrrolidine-1,3-dicarboxylic acid 1-benzyl ester 3-methyl ester

[Formula 86]

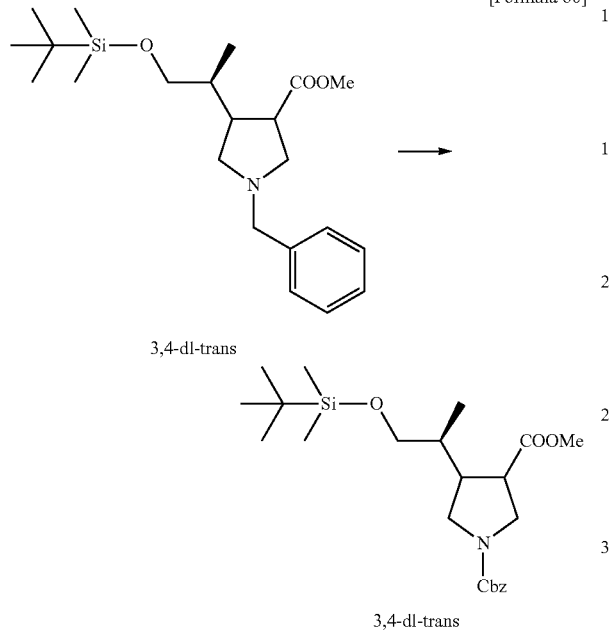

3,4-dl-trans

Benzyloxycarbonyl chloride (3.25 mL, 22.8 mmol) was added to a solution of 1-benzyl-4-[(S)-2-(tert-butyldimethylsilyloxy)-1-(methyl)ethyl]pyrrolidine-3-carboxylic acid methyl ester (2.97 g, 7.58 mmol) in dichloromethane (20 mL), and the mixture was stirred for one hour. Saturated sodium bicarbonate water was added to the reaction mixture. The organic layer was separated, dried over magnesium sulfate, and filtered. Then, the solvent was evaporated under reduced pressure. The residue was purified by silica gel column chromatography (hexane:ethyl acetate=4:1) to give 3.1 g (96%) of the diastereomer mixture title compound as a colorless oil. The diastereomers were used for the next step without separation.

Reference Example 16

4-[(S)-2-Hydroxy-1-(methyl)ethyl]pyrrolidine-1,3-dicarboxylic acid 1-benzyl ester 3-methyl ester

[Formula 87]

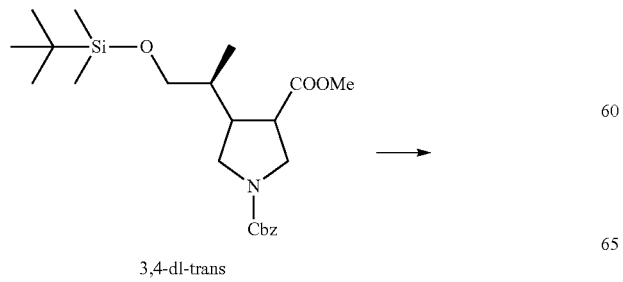

3,4-dl-trans

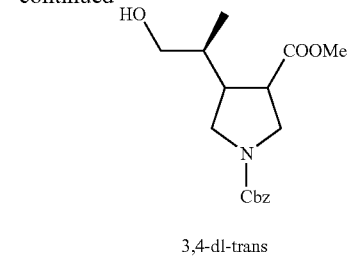

3,4-dl-trans

Hydrogen fluoride-pyridine (2 mL) was added to a solution of 4-[(S)-2-(tert-butyldimethylsilyloxy)-1-(methyl)ethyl]pyrrolidine-1,3-dicarboxylic acid 1-benzyl ester 3-methyl ester (6.0 g, 7.1 mmol) in pyridine (20 mL) under ice-cooling, and the mixture was stirred at room temperature for 13 hours. Further 2 mL of hydrogen fluoride-pyridine was added, and the mixture was stirred for 23 hours. The reaction mixture was poured into ice water, followed by extraction with ethyl acetate and washing with 1N hydrochloric acid and brine. After drying over magnesium sulfate and filtration, the solvent was evaporated under reduced pressure to give 4.5 g (quantitative) of the diastereomer mixture title compound as a colorless oil. The diastereomers were used for the next step without separation.

$^1$H-NMR (400 MHz, CDCl$_3$) δ: 7.37-7.31 (5H, m), 5.13 (2H, brs), 3.87-3.75 (2H, brm), 3.72 (3H, s), 3.52-3.47 (3H, m), 3.27-3.11 (1H, m), 2.98-2.90 (1H, m), 2.69-2.58 (1H, m), 1.82-1.66 (2H, m), 0.95 (3H, d, J=19.80 Hz).

Reference Example 17

4-[(S)-2-Iodo-1-(methyl)ethyl]pyrrolidine-1,3-dicarboxylic acid 1-benzyl ester 3-methyl ester

[Formula 88]

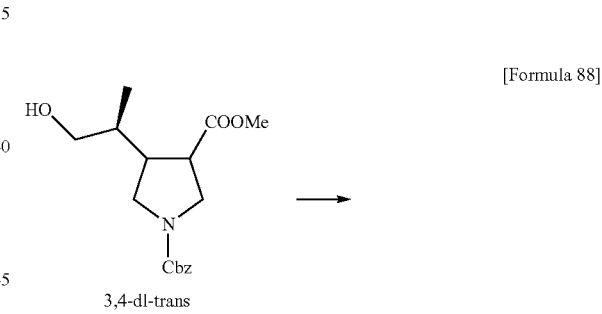

3,4-dl-trans

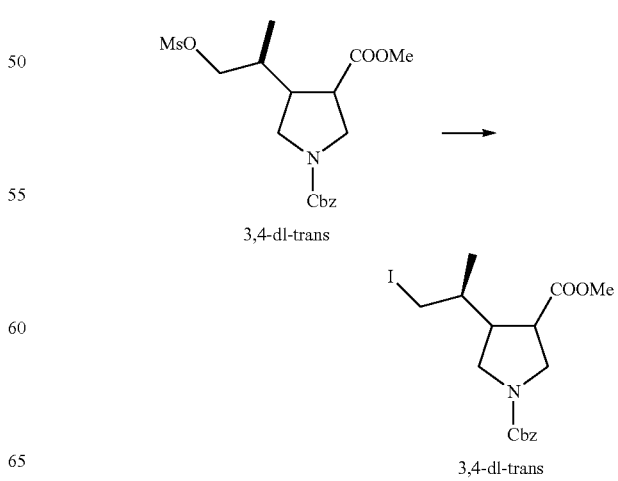

3,4-dl-trans

Triethylamine (3.4 mL, 24 mmol) and mesyl chloride (1.5 mL, 19.2 mmol) were added to a solution of 4-[(S)-2-hydroxy-1-(methyl)ethyl]pyrrolidine-1,3-dicarboxylic acid 1-benzyl ester 3-methyl ester (5.1 g, 16 mmol) in dichloromethane (50 mL) under ice-cooling, and then the mixture was stirred at room temperature for 30 minutes. After adding methanol to the reaction mixture, the mixture was blended with a mixture of ethyl acetate and a 10% citric acid solution. The organic layer was washed with brine and dried over magnesium sulfate. After filtration, the solvent was evaporated under reduced pressure, and then the residue was dissolved in acetone (100 mL). Sodium iodide (4.8 g, 32 mmol) was added, and the mixture was heated to reflux for 20 hours. The reaction mixture was cooled and then the solvent was evaporated under reduced pressure. The resulting residue was blended with a mixture of ethyl acetate and water. The organic layer was washed with a saturated sodium thiosulfate solution and brine, dried over magnesium sulfate, and then filtered. Then, the solvent was evaporated under reduced pressure. The residue was purified by silica gel column chromatography (hexane:ethyl acetate=10:0→7:3) to give 6.5 g (94%) of the diastereomer mixture title compound as a colorless oil. The diastereomers were used for the next step without separation.

$^1$H-NMR (400 MHz, CDCl$_3$) δ: 7.37-7.35 (5H, m), 5.13 (2H, s), 3.83-3.71 (4H, m), 3.58-3.51 (1H, m), 3.27-3.23 (1H, m), 3.18-3.09 (2H, m), 2.92-2.83 (1H, m), 2.64-2.55 (1H, m), 1.59-1.48 (2H, m), 1.02 (3H, d, J=6.60 Hz).

Reference Example 18

(R)-6-Methyl-3-azabicyclo[3.2.0]heptane-1,3-dicarboxylic acid 3-benzyl ester 1-methyl ester

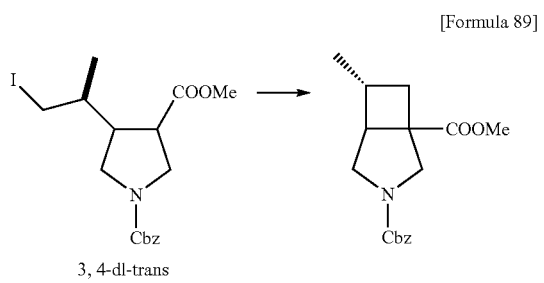 [SMILES: COC(=O)C1CN(C(=O)OCc2ccccc2)CC1[C@H](C)CI ; COC(=O)C12C[C@@H](C)C1CN(C(=O)OCc1ccccc1)C2]

[Formula 89]

3, 4-dl-trans

A 0.5 M solution of potassium hexamethyldisilazide in toluene (33 mL, 16.5 mmol) was added dropwise to a solution of 4-[(S)-2-iodo-1-(methyl)ethyl]pyrrolidine-1,3-dicarboxylic acid 1-benzyl ester 3-methyl ester (6.4 g, 14.8 mmol) in anhydrous tetrahydrofuran (100 mL) in an argon atmosphere at −78° C. After completion of dropwise addition, the mixture was stirred at the same temperature for 30 minutes. An ammonium chloride solution was added, and the mixture was heated to room temperature. After extraction with ethyl acetate, drying over magnesium sulfate, and filtration, the solvent was evaporated under reduced pressure. The residue was purified by silica gel column chromatography (hexane:ethyl acetate=10:0→7:3) to give 3.5 g (78%) of the diastereomer mixture title compound as a colorless oil. The diastereomers were used for the next step without separation.

$^1$H-NMR (400 MHz, CDCl$_3$) δ: 7.39-7.29 (5H, m), 5.18 (2H, brs), 3.97-3.89 (1H, m), 3.77-3.69 (4H, m), 3.46 (1H, d, J=11.70 Hz), 3.25 (1H, dd, J=12.10, 7.90 Hz), 3.08-3.03 (1H, m), 2.60-2.75 (2H, m), 1.51-1.57 (1H, m), 0.94 (3H, brs).

Reference Example 19

(R)-6-Methyl-3-azabicyclo[3.2.0]heptane-1,3-dicarboxylic acid 3-benzyl ester

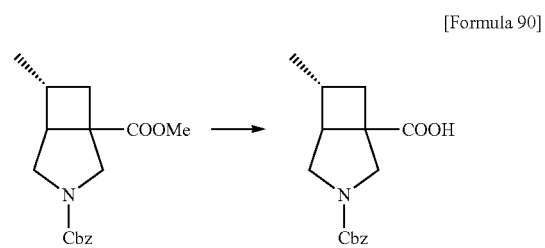 [SMILES: COC(=O)C12C[C@@H](C)C1CN(C(=O)OCc1ccccc1)C2 ; C[C@@H]1CC2(C(=O)O)CN(C(=O)OCc3ccccc3)CC12]

[Formula 90]

A 1N sodium hydroxide solution (23 mL) was added dropwise to a mixed solution of (R)-6-methyl-3-azabicyclo[3.2.0]heptane-1,3-dicarboxylic acid 3-benzyl ester 1-methyl ester (3.5 g, 11.5 mmol) in tetrahydrofuran (60 mL) and methanol (20 mL) under ice-cooling, and the mixture was stirred for 30 minutes. The reaction solution was neutralized with 1N hydrochloric acid, followed by extraction with ethyl acetate. The extract was dried over magnesium sulfate and filtered. The solvent was evaporated under reduced pressure to give 3.4 g (quantitative) of the diastereomer mixture title compound as a colorless oil. The diastereomers were used for the next step without separation.

$^1$H-NMR (400 MHz, CDCl$_3$) δ: 7.38-7.30 (5H, m), 5.19 (2H, brs), 4.00-3.91 (1H, m), 3.81-3.70 (1H, m), 3.50 (1H, d, J=11.70 Hz), 3.27 (1H, dd, J=11.70, 7.80 Hz), 3.11 (1H, t, J=7.70 Hz), 2.80-2.66 (2H, m), 0.95 (3H, s).

Reference Example 20

(R)-1-tert-Butoxycarbonylamino-6-methyl-3-azabicyclo[3.2.0]heptane-3-carboxylic acid benzyl ester (Optical Isomer C, Optical Isomer D)

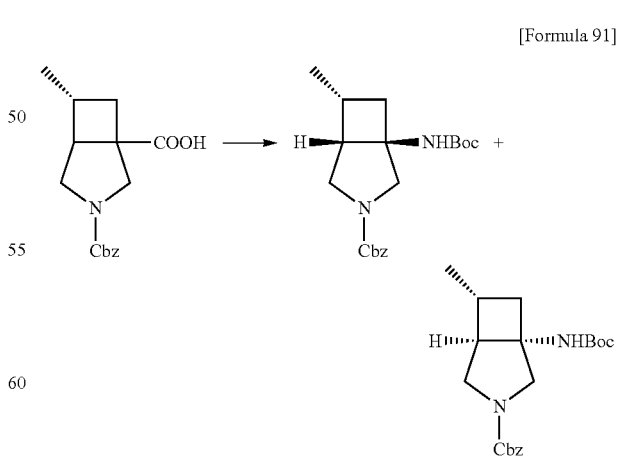

[Formula 91]

Triethylamine (3.2 mL, 22.8 mmol) and diphenyl phosphoazide (3.7 mL, 17.1 mmol) were added to a solution of (R)-6-methyl-3-azabicyclo[3.2.0]heptane-1,3-dicarboxylic acid 3-benzyl ester (3.3 g, 11.4 mmol) in toluene (70 mL) at room temperature, and then tert-butyl alcohol (70 mL) was added. The mixture was heated with stirring at 100° C. for 15 hours. The reaction mixture was cooled, and then the solvent was evaporated under reduced pressure. The residue was purified by silica gel column chromatography (hexane:ethyl acetate=10:0→8:2) to give 3.5 g of the diastereomer mixture title compound as a colorless oil. The diastereomers were separated by Chiralpak AD (2 cm, hexane:isopropyl alcohol=92.5:7.5, flow: 30 mL/min) to give 1.72 g (42%) of a first fraction colorless oil (optical isomer C) and 1.68 g (41%) of a second fraction colorless oil (optical isomer D).

Optical Isomer C:

$^1$H-NMR (400 MHz, CDCl$_3$) δ: 7.37-7.30 (5H, m), 5.16 (2H, s), 4.87-4.73 (1H, brm), 3.88-3.79 (1H, m), 3.72 (1H, d, J=11.00 Hz), 3.43-3.28 (2H, brm), 2.89-2.77 (1H, brm), 2.67-2.58 (1H, m), 2.32 (1H, t, J=11.70 Hz), 1.76-1.68 (1H, m), 1.44 (9H, s), 0.95-0.92 (3H, m).

Optical Isomer D:

$^1$H-NMR (400 MHz, CDCl$_3$) δ: 7.37-7.29 (5H, m), 5.14 (2H, s), 4.81-4.76 (1H, m), 3.84 (1H, d, J=10.70 Hz), 3.61-3.53 (3H, brm), 2.43-2.31 (2H, m), 1.92-1.86 (1H, m), 1.75-1.68 (1H, m), 1.43 (9H, s), 1.14 (3H, d, J=6.80 Hz).

Based on the results of NOE test, the optical isomer C was identified as (1R,5S,6R)-1-tert-butoxycarbonylamino-6-methyl-3-azabicyclo[3.2.0]heptane-3-carboxylic acid benzyl ester, and the optical isomer D was identified as (1S,5R,6R)-1-tert-butoxycarbonylamino-6-methyl-3-azabicyclo[3.2.0]heptane-3-carboxylic acid benzyl ester.

Reference Example 21

(1R,5S,6R)-1-(tert-Butoxycarbonylamino)-6-methyl-3-azabicyclo[3.2.0]heptane

[Formula 92]

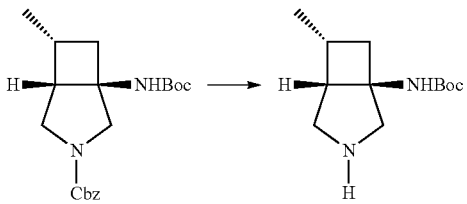

(1R,5S,6R)-1-tert-Butoxycarbonylamino-6-methyl-3-azabicyclo[3.2.0]heptane-3-carboxylic acid benzyl ester (180 mg, 0.59 mmol) was dissolved in a methanol (5 mL). A small amount of 10% palladium-carbon (50% wet) was added, and the mixture was stirred in a hydrogen atmosphere for one hour. After removing the catalyst by filtration, the filtrate was concentrated under reduced pressure to give 114 mg (85%) of the title compound as a colorless oil.

$^1$H-NMR (400 MHz, CDCl$_3$) δ: 4.88 (1H, brs), 3.06 (1H, d, J=12.00 Hz), 2.96-2.89 (2H, m), 2.71-2.61 (3H, m), 2.39-2.33 (1H, m), 1.58 (1H, dd, J=12.80, 7.40 Hz), 1.45 (9H, s), 0.94 (3H, d, J=6.80 Hz).

Reference Example 22

(1S,5R,6R)-1-(tert-Butoxycarbonylamino)-6-methyl-3-azabicyclo[3.2.0]heptane

[Formula 93]

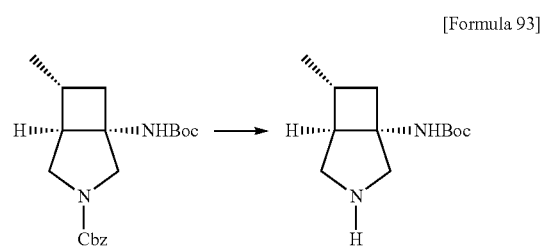 [SMILES: C[C@@H]1C[C@@]2(NC(=O)OC(C)(C)C)CN(C(=O)OCc3ccccc3)C[C@@H]12 ; C[C@@H]1C[C@@]2(NC(=O)OC(C)(C)C)CNC[C@@H]12]

(1S,5R,6R)-1-tert-Butoxycarbonylamino-6-methyl-3-azabicyclo[3.2.0]heptane-3-carboxylic acid benzyl ester (1.1 g, 3.1 mmol) was dissolved in a mixed solvent of methanol (20 mL) and tetrahydrofuran (10 mL). A small amount of 10% palladium-carbon (50% wet) was added, and the mixture was stirred in a hydrogen atmosphere for three hours. After removing the catalyst by filtration, the filtrate was concentrated under reduced pressure to give 0.70 g (quantitative) of the title compound as a colorless oil.

$^1$H-NMR (400 MHz, CDCl$_3$) δ: 4.80 (1H, brs), 3.09 (1H, d, J=11.20 Hz), 3.02 (2H, dd, J=11.20, 5.40 Hz), 2.82 (2H, d, J=11.20 Hz), 2.27-2.22 (2H, m), 1.77-1.69 (2H, m), 1.44 (9H, s), 1.17 (3H, d, J=6.60 Hz).

Example 4

7-{(1R,5S,6R)-1-Amino-6-methyl-3-azabicyclo[3.2.0]hept-3-yl}-6-fluoro-1-[(1R,2S)-2-fluorocyclopropyl]-1,4-dihydro-8-methoxy-4-oxoquinoline-3-carboxylic acid

[Formula 94]

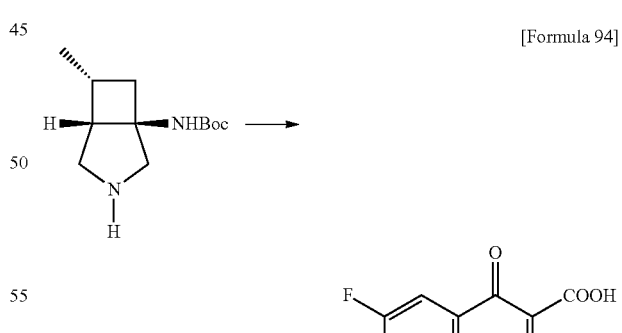

(1R,5S,6R)-1-(tert-Butoxycarbonylamino)-6-methyl-3-azabicyclo[3.2.0]heptane (114 mg, 0.50 mmol) and 6,7-difluoro-1-[(1R,2S)-2-fluorocyclopropyl]-1,4-dihydro-8-methoxy-4-oxoquinoline-3-carboxylic acid-BF₂ chelate (155 mg, 0.43 mmol) were dissolved in dimethyl sulfoxide (2 mL). Triethylamine (0.084 mL) was added, and the mixture was stirred at 40° C. for 12 hours. After cooling the reaction solution with ice, water was added, and the precipitate was collected by filtration, washed with water, and dried. The precipitate was dissolved in ethanol (20 mL). Water (5 mL) and triethylamine (0.084 mL) were added, and the mixture was heated to reflux for three hours. The reaction mixture was dissolved in ethyl acetate and washed with a 10% citric acid solution, water, and brine. The organic layer was dried over anhydrous sodium sulfate and then filtered, and the solvent was evaporated under reduced pressure. Concentrated hydrochloric acid (5 mL) was added to the residue, and the mixture was stirred at room temperature for one hour. Then, the reaction solution was washed with chloroform. The aqueous layer was adjusted to pH 12.0 with a 10 mol/L sodium hydroxide solution under ice-cooling and then adjusted to pH 7.4 with hydrochloric acid, followed by extraction with chloroform-methanol (9:1) eight times. The organic layer was dried over anhydrous sodium sulfate and then filtered, and the solvent was evaporated under reduced pressure. The resulting residue was dissolved in ethanol, and the insoluble material was removed by filtration. The solvent was evaporated under reduced pressure, and the resulting powder was dried under reduced pressure to give 70 mg (39%) of the title compound as a pale yellow solid.

¹H-NMR (400 MHz, 0.1N NaOD) δ: 8.50 (1H, s), 7.70 (1H, d, J=13.67 Hz), 5.02-4.84 (1H, m), 4.07-4.03 (1H, m), 3.74 (1H, d, J=10.25 Hz), 3.62 (3H, s), 3.60-3.56 (2H, m), 2.94 (1H, d, J=10.25 Hz), 2.63-2.55 (1H, m), 2.51-2.47 (1H, m), 2.24-2.18 (1H, m), 1.85 (1H, dd, J=12.57, 7.93 Hz), 1.69-1.48 (2H, m), 0.87 (3H, d, J=6.84 Hz).

Anal; Calcd for C₂₁H₂₃F₂N₃O₄·0.4H₂O·0.3EtOH: C, 58.90; H, 5.86; F, 8.63; N, 9.54. Found: C, 58.84; H, 5.78; F, 8.66; N, 9.51.

MS (ESI) m/z: 420 (M+H)⁺.

Example 5

7-{(1S,5R,6R)-1-Amino-6-methyl-3-azabicyclo[3.2.0]hept-3-yl}-6-fluoro-1-[(1R,2S)-2-fluorocyclopropyl]-1,4-dihydro-8-methoxy-4-oxoquinoline-3-carboxylic acid

[Formula 95]

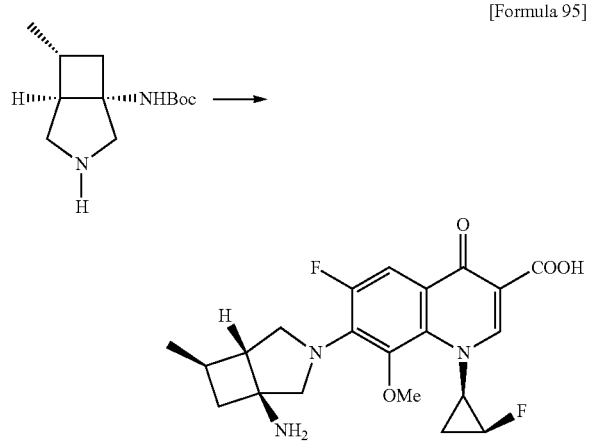

(1S,5R,6R)-1-(tert-Butoxycarbonylamino)-6-methyl-3-azabicyclo[3.2.0]heptane (705 mg, 3.12 mmol) and 6,7-difluoro-1-[(1R,2S)-2-fluorocyclopropyl]-1,4-dihydro-8-methoxy-4-oxoquinoline-3-carboxylic acid-BF₂ chelate (1.07 g, 2.96 mmol) were dissolved in dimethyl sulfoxide (12 mL). Triethylamine (0.52 mL) was added, and the mixture was stirred at 40° C. for 12 hours. After cooling the reaction solution with ice, water was added, and the precipitate was collected by filtration, washed with water, and dried. The precipitate was dissolved in ethanol (120 mL). Water (30 mL) and triethylamine (0.52 mL) were added, and the mixture was heated to reflux for three hours. The reaction mixture was dissolved in ethyl acetate and washed with a 10% citric acid solution, water, and brine. The organic layer was dried over anhydrous sodium sulfate and then filtered, and the solvent was evaporated under reduced pressure. Concentrated hydrochloric acid (25 mL) was added to the residue, and the mixture was stirred at room temperature for one hour. Then, the reaction solution was washed with chloroform. The aqueous layer was adjusted to pH 12.0 with a 10 mol/L sodium hydroxide solution under ice-cooling and then adjusted to pH 7.4 with hydrochloric acid, followed by extraction with chloroform-methanol (9:1) eight times. The organic layer was dried over anhydrous sodium sulfate and then filtered, and the solvent was evaporated under reduced pressure. The resulting residue was dissolved in ethanol, and the insoluble material was removed by filtration. The solvent was evaporated under reduced pressure, and the resulting powder was dried under reduced pressure to give 740 mg (57%) of the title compound as a pale yellow solid.

¹H-NMR (400 MHz, 0.1N NaOD) δ: 8.47 (1H, d, J=1.71 Hz), 7.70 (1H, d, J=13.67 Hz), 5.07-4.88 (1H, m), 4.08-4.03 (1H, m), 3.73-3.63 (2H, m), 3.67 (3H, s), 3.55-3.51 (1H, m), 3.18 (1H, d, J=10.50 Hz), 2.40 (1H, dd, J=12.21, 8.79 Hz), 2.13 (1H, t, J=5.13 Hz), 1.95-1.89 (1H, m), 1.16 (3H, d, J=7.08 Hz), 1.66-1.57 (2H, m), 1.56-1.44 (1H, m).

Anal; Calcd for C₂₁H₂₃F₂N₃O₄·HCl·1.3H₂O·0.6EtOH: C, 52.60; H, 6.00; Cl, 6.99; F, 7.50; N, 8.29. Found: C, 52.35; H, 5.74; Cl, 6.84; F, 7.54; N, 8.01.

MS (ESI); m/z: 420 (M+H)⁺.

Reference Example 23

(3R)-3-Allyl-5-oxo-1-[(1R)-1-phenylethyl]pyrrolidine-3-carboxylic acid tert-butyl ester (Less Polar Isomer)

(3S)-3-Allyl-5-oxo-1-[(1R)-1-phenylethyl]pyrrolidine-3-carboxylic acid tert-butyl ester (More Polar Isomer)

[Formula 96]

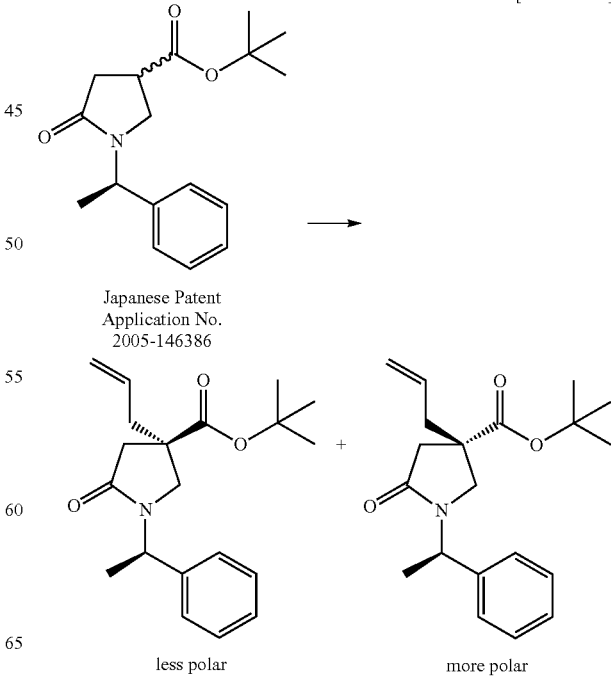

less polar                more polar

5-Oxo-1-[(1R)-1-phenylethyl]pyrrolidine-3-carboxylic acid tert-butyl ester (30 g, 104 mmol) and allyl bromide (62.71 g, 518 mmol.) were dissolved in dimethylformamide (300 mL), and the atmosphere was replaced with argon. Sodium hydride (55% oil dispersion, 11.3 g, 259 mmol) was added under ice-cooling, and the mixture was stirred at room temperature for five hours. A 10% tartaric acid solution was added, followed by extraction with ethyl acetate. The organic layer was washed with brine and dried over magnesium sulfate. After filtration, the solvent was evaporated under reduced pressure. Then, the residue was separated and purified by silica gel chromatography (hexane:ethyl acetate=100:0→80:20→65:35) to give 15.8 g (46%) of a colorless oil as a first fraction (less polar isomer) and 15.1 g (44%) of a colorless oil as a second fraction (more polar isomer). The resulting more polar isomer was left to stand at room temperature and crystallized.

The absolute configuration at the 3-position of each isomer was determined based on X-ray crystallography of the product described in Reference Example 24 after converting the more polar isomer to the product.

Less Polar Isomer:
$^1$H-NMR (400 MHz, CDCl$_3$) δ: 7.37-7.26 (5H, m), 5.52-5.42 (2H, m), 4.95 (1H, dd, J=10.30, 1.00 Hz), 4.78 (1H, dd, J=17.10, 1.20 Hz), 3.60 (1H, d, J=10.30 Hz), 2.86 (1H, d, J=17.10 Hz), 2.80 (1H, d, J=10.30 Hz), 2.35 (1H, d, J=17.10 Hz), 2.27 (1H, dd, J=13.70, 6.80 Hz), 2.16 (1H, dd, J=13.70, 7.80 Hz), 1.52 (3H, d, J=7.30 Hz), 1.44 (9H, s).

More Polar Isomer:
$^1$H-NMR (400 MHz, CDCl$_3$) δ: 7.35-7.24 (5H, m), 5.72-5.62 (1H, m), 5.49 (1H, q, J=7.20 Hz), 5.15 (1H, s), 5.13-5.10 (1H, m), 3.28 (1H, d, J=10.30 Hz), 3.16 (1H, d, J=10.30 Hz), 2.88 (1H, d, J=17.10 Hz), 2.48-2.35 (3H, m), 1.51 (3H, d, J=7.10 Hz), 1.35 (9H, s).

Reference Example 24

(3S)-3-(3-hydroxy-1-propyl)-5-oxo-1-[(1R)-1-phenylethyl]pyrrolidine-3-carboxylic acid tert-butyl ester (Derived from More Polar Isomer)

[Formula 97]

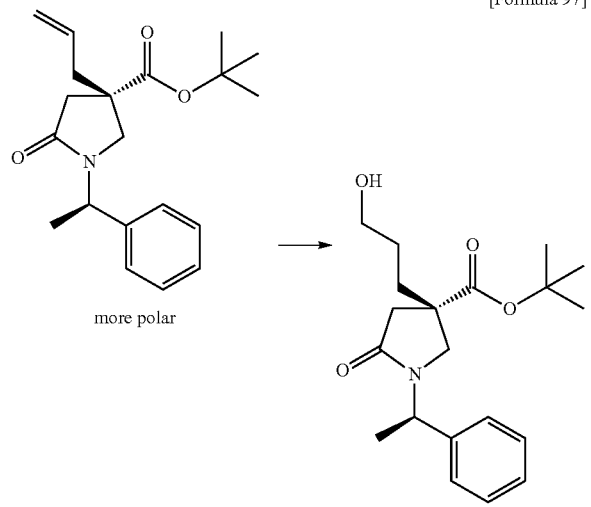

more polar (3S)-3-Allyl-5-oxo-1-[(1R)-1-phenylethyl]pyrrolidine-3-carboxylic acid tert-butyl ester (more polar isomer) (51.5 g, 0.156 mol) was dissolved in tetrahydrofuran (780 mL). Then, a 0.5 M solution of 9-BBN in tetrahydrofuran (345 mL, 0.173 mol) was added dropwise from a dropping funnel in a nitrogen stream under cooling and stirring in an ice salt bath at an internal temperature of 0° C. After completion of the dropwise addition, the mixture was stirred at the same temperature for 30 minutes and subsequently at room temperature for 1.5 hours. The mixture was cooled again in an ice salt bath, and a 0.5 M solution of 9-BBN in tetrahydrofuran (156 mL, 78 mmol) was added dropwise from a dropping funnel at an internal temperature of 2° C. After completion of the dropwise addition, the mixture was stirred at the same temperature for 30 minutes and then at room temperature for 1.5 hours. The mixture was cooled again in an ice salt bath, and a 0.5 M solution of 9-BBN in tetrahydrofuran (120 mL, 60 mmol) was added dropwise from a dropping funnel at an internal temperature of 2° C. After completion of the dropwise addition, the mixture was stirred at the same temperature for 30 minutes and then at room temperature for one hour. The mixture was cooled again in an ice salt bath, and 780 mL of a 1N sodium hydroxide solution was added dropwise at an internal temperature of 0° C. over 15 minutes (internal temperature: 2° C. or less). The mixture was stirred for 10 minutes, and then 78 mL of a 30% hydrogen peroxide solution was added dropwise at an internal temperature of 4° C. or less over 30 minutes. After vigorously stirring at the same temperature for 30 minutes, 1.6 L of diethyl ether was added. After addition of 1.6 L of a saturated sodium bicarbonate solution, the layers are separated, and the aqueous layer was extracted with diethyl ether. The combined organic layers were washed with brine, a 10% citric acid solution, a 10% sodium thiosulfate solution, and then brine, and dried over anhydrous sodium sulfate. After filtration, the filtrate was concentrated, and the resulting residue was subjected to flash silica gel column chromatography and eluted with a mixed solvent of methanol-chloroform (1:50, v/v). The fractions containing the target substance were combined and concentrated and dried under reduced pressure to give 40.61 g (74.9%) of the title compound as a colorless oil. Further, part of the title compound was purified by recrystallization from diethyl ether to provide needle-like crystals which were used for X-ray crystallography. As a result, the absolute configuration at the 3-position of this product was determined as a (3S)-configuration.

$^1$H-NMR (400 MHz, CDCl$_3$) δ: 7.35-7.24 (5H, m), 5.48 (1H, q, J=7.3 Hz), 3.62 (2H, t, J=6.2 Hz), 3.34 (1H, d, J=10.3 Hz), 3.14 (1H, d, J=10.3 Hz), 2.95 (1H, d, J=17.1 Hz), 2.33 (1H, d, J=16.8 Hz), 1.88-1.67 (3H, m), 1.51 (3H, d, J=7.1 Hz), 1.54-1.47 (1H, m), 1.33 (9H, s).

TABLE 1

| X-ray crystallography conditions: | |
|---|---|
| Crystal size | 0.36 mm × 0.18 mm × 0.08 mm |
| Radiation | CuKα (1.54178 Å) |
| Tube current | 50 kV |
| Tube Voltage | 80 mA |
| Diffractometer | AFC7R |
| Temperature | 25° C. |
| Formula | C20H29NO4 |
| Formula weight | 347.45 |
| Crystal system | orthorhombic |
| Space group | P2$_1$2$_1$2 |
| Z value | 4 |
| Cell parameters | a = 13.2806(14) Å |
| | b = 26.6894(16) Å |
| | c = 5.8585(11) Å |
| | α = 90.0000° β = 90.0000° γ = 90.0000° |
| d$_{calc}$ | 1.11 g/cm$^3$ |
| No. of reflection measured | 1828 (unique) |
| μ | 6.19 cm$^{-1}$ |
| Phase determination | Direct method (software; SIR92) |
| Phase refinement | Full matrix least-square |

TABLE 1-continued

| | | |
|---|---|---|
| R1 | 5.3% = | $\Sigma||Fo| - |Fc||/\Sigma|Fo|$ for $I>2.0\sigma$ data |
| R | 7.0% = | $\Sigma(Fo^2 - Fc^2)/\Sigma Fo^2$ |
| Rw | 14.0% = | $[\Sigma w (Fo^2 - Fc^2)^2/\Sigma w(Fo^2)^2]^{1/2}$ |

Figure 2:
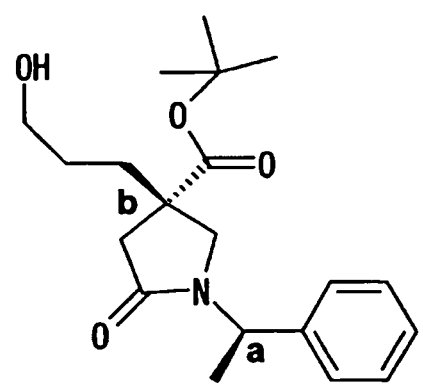
FIG. 2 shows the absolute configuration of (3S)-3-(3-hydroxy-1-propyl)-5-oxo-1-[(1R)-1-phenylethyl]pyrrolidine-3-carboxylic acid tert-butyl ester obtained in Reference Example 24.

Data were collected under the measurement conditions shown in the above table, and then the initial phase was determined by the direct method, and the phase was refined by full matrix least-squares method. For refinement, an anisotropic temperature factor was applied to a non-hydrogen atom and the position of a hydrogen atom was determined by calculation to fix the coordinates. As a result of the analysis, the relative configuration of this compound is as shown in the ORTEP diagram of FIG. 1. The absolute configuration of the asymmetric carbon b was determined from the asymmetric carbon a having a known absolute configuration. The results are shown in FIG. 2.

Reference Example 25

(3S)-5-Oxo-3-(2-oxoethyl)-1-[(1R)-1-phenylethyl]pyrrolidine-3-carboxylic acid tert-butyl ester

[Formula 98]

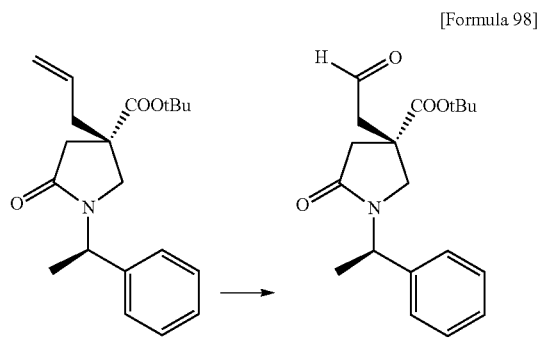

A solution of (3S)-3-allyl-5-oxo-1-[(1R)-1-phenylethyl]pyrrolidine-3-carboxylic acid tert-butyl ester (3.29 g, 10.0 mmol) in methanol (100 mL) was bubbled with ozone at −74° C. When the reaction solution turned blue, ozone bubbling was stopped and then the solution was bubbled with nitrogen at the same temperature. Sodium borohydride (568 mg) was added at the same temperature, and the mixture was stirred for 1.5 hours while heating to −40° C. The reaction solution was poured into a 10% citric acid solution (50 mL), and then the mixture was stirred sufficiently. The methanol component was evaporated, and then the aqueous layer was extracted with ethyl acetate (200 mL, 100 mL). The organic layer was washed with brine (50 mL×2), and then dried over anhydrous sodium sulfate. After filtration, the filtrate was concentrated under reduced pressure into a slurry. Hexane was added to the resulting residue, and the slurry was stirred. The solid was collected by filtration and dried to give 1.70 g of the title compound as a white solid. The filtrate was concentrated, hexane was added to the resulting residue, and the slurry was stirred. The solid was collected by filtration to give 0.66 g of the title compound as a white solid. The same operation was repeated to give 0.35 g of the title compound as a white solid (total yield: 2.71 g, 82%).

$^1$H-NMR (400 MHz, CDCl$_3$) δ: 9.71 (1H, s), 7.35-7.24 (5H, m), 5.50 (1H, q, J=7.3 Hz), 3.41 (1H, d, J=10.5 Hz), 3.20 (1H, d, J=10.5 Hz), 2.98 (1H, d, J=17.1 Hz), 2.92 (1H, d, J=17.8 Hz), 2.87 (1H, d, J=17.8 Hz), 2.37 (1H, d, J=17.1 Hz), 1.51 (3H, d, J=7.3 Hz), 1.31 (9H, s).

MS (ESI) m/z: 332 (M+H)$^+$.

Reference Example 26

(3S)-3-(2-Hydroxyethyl)-5-oxo-1-[(1R)-1-phenylethyl]pyrrolidine-3-carboxylic acid tert-butyl ester

[Formula 99]

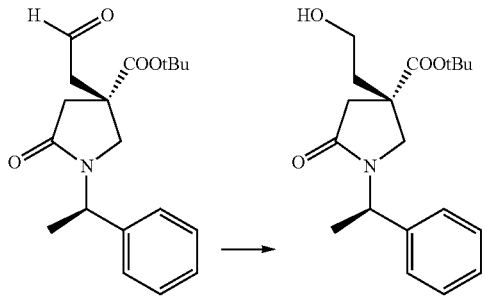

Sodium borohydride (465 mg) was added to a solution of (3S)-5-oxo-3-(2-oxoethyl)-1-[(1R)-1-phenylethyl]pyrrolidine-3-carboxylic acid tert-butyl ester (2.71 g, 8.19 mmol) in methanol at −40° C. After heating to room temperature, a 10% citric acid solution was added to the reaction solution, and the mixture was stirred. The reaction solution was poured into a mixture of ethyl acetate (50 mL) and a 10% citric acid solution (10 mL), followed by extraction with ethyl acetate (100 mL). The aqueous layer was extracted with ethyl acetate (100 mL), and then the organic layers were combined and washed with brine (50 mL×2). The resulting organic layer was dried over anhydrous sodium sulfate and filtered, and then the filtrate was concentrated under reduced pressure. The resulting residue was purified by silica gel column chromatography (hexane:ethyl acetate=2:1→1:1→0:1→ethyl acetate-methanol=10:1) to give 2.20 g (81%) of the title compound as a white solid.

$^1$H-NMR (400 MHz, CDCl$_3$) δ: 7.34-7.24 (5H, m), 5.48 (1H, q, J=7.1 Hz), 3.73-3.64 (2H, m), 3.38 (1H, d, J=10.2 Hz), 3.23 (1H, d, J=10.2 Hz), 2.97 (1H, d, J=17.0 Hz), 2.41 (1H, d, J=17.0 Hz), 2.05 (1H, dt, J=14.0, 6.8 Hz), 1.91 (1H, dt, J=14.0, 6.6 Hz), 1.51 (3H, d, J=7.1 Hz), 1.32 (9H, s).

MS (ESI) m/z: 334 (M+H)$^+$.

Reference Example 27

(3S)-3-[2-(tert-Butyldimethylsilyloxy)ethyl]-5-oxo-1-[(1R)-1-phenylethyl]pyrrolidine-3-carboxylic acid tert-butyl ester

[Formula 100]

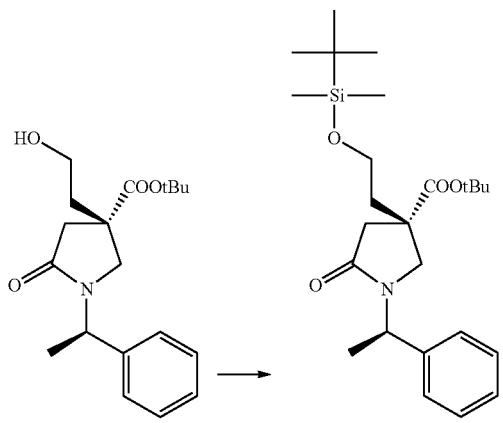

Triethylamine (3.0 mL, 21.8 mmol) was added to a solution of (3S)-3-(2-hydroxyethyl)-5-oxo-1-[(1R)-1-phenylethyl]pyrrolidine-3-carboxylic acid tert-butyl ester (2.42 g, 7.25 mmol) in dichloromethane (70 mL), and the mixture was cooled to 0° C. tert-Butyldimethylsilyl trifluoromethanesulfonate (2.50 mL, 10.9 mmol) was added dropwise, and the mixture was stirred at the same temperature for 1.5 hours. After addition of an ice piece and stirring, the reaction solution was poured into a mixture of ethyl acetate (50 mL) and saturated sodium bicarbonate (50 mL), followed by extraction with ethyl acetate (200 mL, 100 mL). The organic layers were combined and washed with brine (50 mL). After drying over anhydrous sodium sulfate and filtration, the solvent was concentrated under reduced pressure. The resulting residue was purified by silica gel chromatography (hexane:ethyl acetate=4:1→2:1) to give 2.84 g (88%) of the title compound as a white solid.

¹H-NMR (400 MHz, CDCl₃) δ: 7.32-7.22 (5H, m), 5.45 (1H, q, J=7.1 Hz), 3.62-3.57 (2H, m), 3.38 (1H, d, J=10.3 Hz), 3.26 (1H, d, J=10.3 Hz), 2.93 (1H, d, J=17.0 Hz), 2.42 (1H, d, J=17.0 Hz), 1.98 (1H, dt, J=13.7, 6.8 Hz), 1.88 (1H, dt, J=13.7, 6.7 Hz), 1.50 (3H, d, J=7.1 Hz), 1.31 (9H, s)

Reference Example 28

(3S)-3-[2-(tert-Butyldimethylsilyloxy)ethyl]-4-fluoro-5-oxo-1-[(1R)-1-phenylethyl]pyrrolidine-3-carboxylic acid tert-butyl ester

[Formula 101]

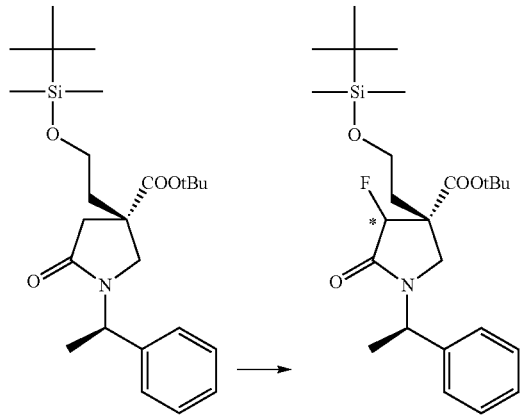

A 1.8 M solution of lithium diisopropylamide in tetrahydrofuran (4.10 mL) was added dropwise to a solution of (3S)-3-[2-(tert-butyldimethylsilyloxy)ethyl]-5-oxo-1-[(1R)-1-phenylethyl]pyrrolidine-3-carboxylic acid tert-butyl ester in tetrahydrofuran in a nitrogen atmosphere at −73° C. over 10 minutes. After stirring at the same temperature for 15 minutes, a solution of N-fluorobenzenesulfonimide (2.63 g, 8.33 mmol) in tetrahydrofuran (18 mL) was added dropwise over 15 minutes. After stirring at the same temperature for 30 minutes, a saturated ammonium chloride solution (20 mL) was added, and the mixture was heated to 0° C. The reaction solution was poured into a mixture of ethyl acetate (100 mL) and 1 mol/mL hydrochloric acid (50 mL), followed by extraction with ethyl acetate (200 mL). The organic layer was sequentially washed with a saturated sodium bicarbonate solution (50 mL) and brine (50 mL×2) and dried over anhydrous sodium sulfate. After filtration, the filtrate was concentrated under reduced pressure. Dichloromethane was added to the resulting residue to prepare a slurry, and the solid was removed by filtration. The filtrate was concentrated, and the resulting solid was removed by filtration. The filtrate was further concentrated to give 3.44 g of the crude title compound as a pale yellow oil. The resulting crude was used for the next reaction without further purification.

Reference Example 29

(3S)-4-Fluoro-3-(2-hydroxyethyl)-5-oxo-1-[(1R)-1-phenylethyl]pyrrolidine-3-carboxylic acid tert-butyl ester

[Formula 102]

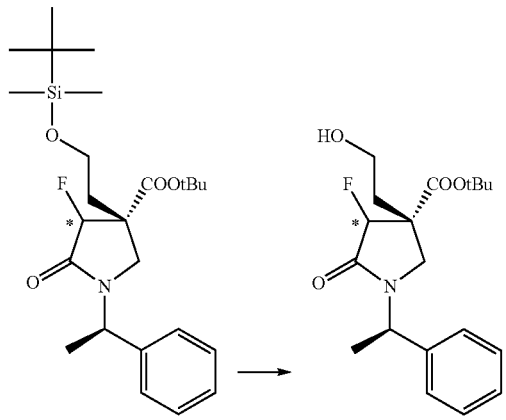

Acetic acid (0.66 mL, 11.54 mmol) and a 1 M solution of tetrabutylammonium fluoride in tetrahydrofuran (8.3 mL, 8.3 mmol) were sequentially added to a solution of the crude (3S)-3-[2-(tert-butyldimethylsilyloxy)ethyl]-4-fluoro-5-oxo-1-[(1R)-1-phenylethyl]pyrrolidine-3-carboxylic acid tert-butyl ester (3.44 g) in tetrahydrofuran in a nitrogen atmosphere at 0° C. After stirring at room temperature for 20 hours, the reaction solution was poured into a mixture of ethyl acetate (100 mL) and a saturated sodium bicarbonate solution (50 mL), followed by extraction with ethyl acetate (200 mL). The organic layer was washed with brine (50 mL×2), and then dried over anhydrous sodium sulfate and filtered. The filtrate was then concentrated under reduced pressure. The resulting residue was purified by silica gel column chromatography (hexane:ethyl acetate=1:1) to give 2.06 g (91%, two steps) of the title compound as colorless crystals.

¹H-NMR (400 MHz, CDCl₃) δ: 7.35-7.26 (5H, m), 5.48 (1H, q, J=7.1 Hz), 5.21 (1H, d, J=51.7 Hz), 3.78-3.69 (2H, m), 3.38 (1H, dd, J=1.1, 10.5 Hz), 3.30 (1H, d, J=10.5 Hz), 2.10 (1H, m), 2.01 (1H, m), 1.56 (3H, d, J=7.1 Hz), 1.32 (9H, s).

Reference Example 30

(3S)-3-(2-Bromoethyl)-4-fluoro-5-oxo-1-[(1R)-1-phenylethyl]pyrrolidine-3-carboxylic acid tert-butyl ester

[Formula 103]

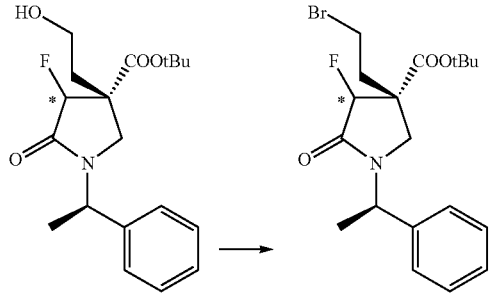

Carbon tetrabromide (1.88 g, 5.68 mmol) and triphenylphosphine (1.49 g, 5.68 mmol) were sequentially added to a solution of (3S)-4-fluoro-3-(2-hydroxyethyl)-5-oxo-1-[(1R)-1-phenylethyl]pyrrolidine-3-carboxylic acid tert-butyl ester (1.66 g, 4.74 mmol) in dichloromethane (20 mL) in a nitrogen atmosphere at 0° C. After heating to room temperature, the reaction solution was stirred for one hour and concentrated to about 5 mL. The residue was purified by silica gel column chromatography (dichloromethane→hexane:ethyl acetate=2:1) to give 2.17 g (91%) of the title compound as a white solid.

$^1$H-NMR (400 MHz, CDCl$_3$) δ: 7.36-7.25 (5H, m), 5.48 (1H, q, J=7.1 Hz), 5.22 (1H, d, J=51.5 Hz), 3.39 (1H, ddd, J=5.5, 10.7, 11.0 Hz), 3.30-3.23 (3H, m), 2.42 (1H, dddd, J=1.2, 5.5, 11.0, 14.2 Hz), 2.32 (1H, dddd, J=2.4, 5.5, 10.7, 14.2 Hz), 1.57 (3H, d, J=7.1 Hz), 1.33 (9H, s).

Reference Example 31

(1S,5R)-5-Fluoro-4-oxo-3-[(1R)-1-phenylethyl]-3-azabicyclo[3.2.0]heptane-1-carboxylic acid tert-butyl ester

[Formula 104]

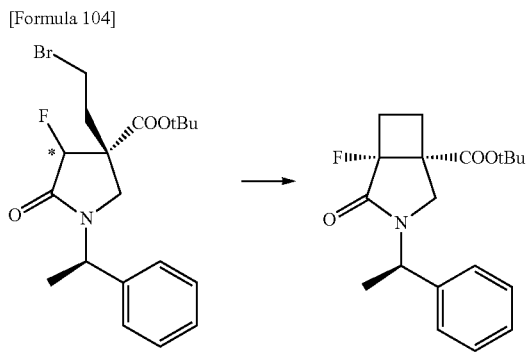

A 1.0 M solution of lithium hexamethyldisilazide in tetrahydrofuran (5.02 mL) was added dropwise to a solution of (3S)-3-(2-bromoethyl)-4-fluoro-5-oxo-1-[(1R)-1-phenylethyl]pyrrolidine-3-carboxylic acid tert-butyl ester (2.04 g, 4.92 mmol) in tetrahydrofuran (40 mL) in a nitrogen atmosphere at −72° C. over 10 minutes. The mixture was stirred at the same temperature for 15 minutes and then at 0° C. for 30 minutes. The reaction was quenched with a 10% citric acid solution (2 mL) and then poured into a mixture of ethyl acetate (100 mL) and a 10% citric acid solution (20 mL). After extraction with ethyl acetate (150 mL), the organic layer was washed with brine (20 mL×2), dried over anhydrous sodium sulfate, and filtered. The filtrate was then concentrated under reduced pressure. The residue was purified by silica gel column chromatography (hexane:ethyl acetate=2:1) to give 1.41 g (86%) of the title compound as a white solid.

$^1$H-NMR (400 MHz, CDCl$_3$) δ: 7.37-7.26 (5H, m), 5.57 (1H, q, J=7.3 Hz), 3.53 (1H, d, J=10.7 Hz), 3.09 (1H, dd, J=4.9, 10.7 Hz), 2.76-2.51 (3H, m), 1.57 (3H, d, J=7.3 Hz), 1.45 (9H, s), 1.42 (1H, m).

MS (ESI) m/z: 334 (M+H)$^+$.

Reference Example 32

(1R,5R)-1-(tert-Butoxycarbonylamino)-5-fluoro-4-oxo-3-[(1R)-1-phenylethyl]-3-azabicyclo[3.2.0]heptane

[Formula 105]

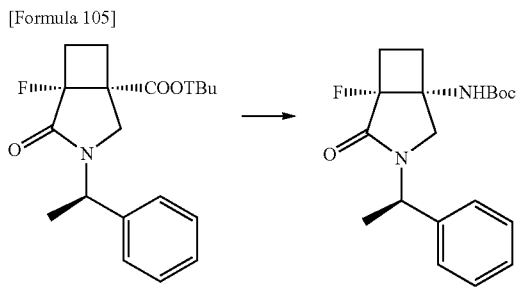

Trifluoroacetic acid (10 mL) was added to a solution of (1S,5R)-1-5-fluoro-4-oxo-3-[(1R)-1-phenylethyl]-3-azabicyclo[3.2.0]heptane-1-carboxylic acid tert-butyl ester (1.06 g, 3.18 mmol) in dichloromethane (10 mL). The mixture was stirred for four hours, and then the solvent was concentrated under reduced pressure. Toluene (40 mL) was added to the residue, and trifluoroacetic acid was removed by evaporation. The residue was dried under reduced pressure to give crude carboxylic acid as a pale yellow solid.

Triethylamine (0.89 mL) and diphenylphosphoryl azide (0.75 mL) were sequentially added to a solution of the crude carboxylic acid obtained above in toluene (10 mL) and tert-butyl alcohol (10 mL). The mixture was stirred at room temperature for 20 minutes, at 40° C. for one hour, and further at 90° C. for one hour. The reaction solution was concentrated under reduced pressure, and the resulting residue was purified by silica gel column chromatography (hexane:ethyl acetate=4:1→3:2) to give 811 mg (73%) of the title compound as a white amorphous.

$^1$H-NMR (400 MHz, CDCl$_3$) δ: 7.37-7.27 (5H, m), 5.59 (1H, q, J=7.3 Hz), 5.36 (1H, br), 3.68 (1H, br), 2.96 (1H, brd, J=10.0 Hz), 2.66-2.45 (2H, m), 2.39 (1H, br), 1.72 (1H, dt, J=12.9, 9.0 Hz), 1.56 (3H, d, J=7.3 Hz), 1.40 (9H, s).

MS (ESI) m/z: 349 (M+H)$^+$.

Reference Example 33

(1R,5R)-1-(tert-Butoxycarbonylamino)-5-fluoro-3-[(1R)-1-phenylethyl]-3-azabicyclo[3.2.0]heptane

[Formula 106]

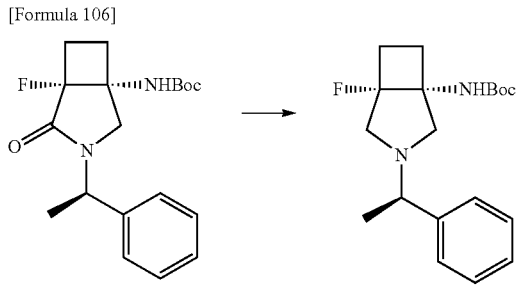

A 1.16 M solution of a borane-tetrahydrofuran complex in tetrahydrofuran (6.0 mL) was added dropwise to a solution of (1R,5R)-1-(tert-butoxycarbonylamino)-5-fluoro-4-oxo-3-[(1R)-1-phenylethyl]-3-azabicyclo[3.2.0]heptane (811 mg, 2.33 mmol) in tetrahydrofuran (6.0 mL) at 0° C. over five minutes. The mixture was heated to room temperature, stirred for five hours, and then cooled to −10° C. A mixture of ethanol (9.0 mL)-water (1.0 mL) was carefully added dropwise. After addition of triethylamine (3.0 mL) dropwise, the mixture was heated to reflux for one hour. The reaction solution was concentrated, and the precipitated white solid was removed by filtration through Celite. The filtrate was concentrated, and the resulting residue was purified by silica gel column chromatography (hexane:ethyl acetate=9:1→4:1) to give 530 mg (68%) of the title compound as a white solid.

$^1$H-NMR (400 MHz, CDCl$_3$) δ: 7.32-7.18 (5H, m), 5.19 (1H, br), 3.37 (1H, q, J=6.8 Hz), 3.27 (1H, dd, J=1.7, 9.0 Hz), 3.13 (1H, brd, J=8.3 Hz), 2.49-2.38 (2H, m), 2.23 (1H, m), 2.13-2.08 (2H, m), 2.00 (1H, m), 1.39 (9H, brs), 1.36 (3H, d, J=6.8 Hz).

Reference Example 34

(1R,5R)-1-(tert-Butoxycarbonylamino)-5-fluoro-3-azabicyclo[3.2.0]heptane

[Formula 107]

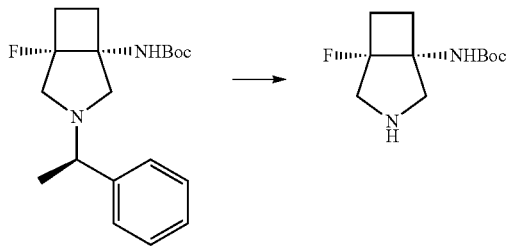

A 10% palladium-carbon catalyst (50% wet, 50 mg) was added to a solution of (1R,5R)-1-(tert-butoxycarbonylamino)-5-fluoro-3-[(1R)-1-phenylethyl]-3-azabicyclo[3.2.0]heptane (530 mg, 1.58 mmol) in ethanol, and the mixture was stirred in a hydrogen atmosphere at 50° C. for five hours. After removing the catalyst by filtration, the filtrate was concentrated under reduced pressure to give 321 mg of crude amine as a white solid.

$^1$H-NMR (400 MHz, CD$_3$OD) δ: 3.07-3.00 (2H, m), 2.87-2.80 (2H, m), 2.35 (1H, m), 2.03-1.95 (2H, m), 1.67 (1H, dt, J=12.0, 9.0 Hz), 1.34 (9H, s), 1.00 (1H, dd, J=2.1, 6.2 Hz).

Example 6

7-[(1R,5S)-1-Amino-5-fluoro-3-azabicyclo[3.2.0]hept-3-yl]-6-fluoro-1-[(1R,2S)-2-fluorocyclopropyl]-1,4-dihydro-8-methoxy-4-oxoquinoline-3-carboxylic acid

[Formula 108]

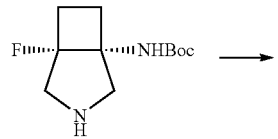

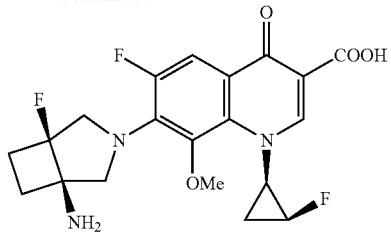

6,7-Difluoro-1-[(1R,2S)-2-fluorocyclopropyl]-1,4-dihydro-8-methoxy-4-oxoquinoline-3-carboxylic acid-BF$_2$ chelate (577 mg, 1.60 mmol) and triethylamine (0.699 mL, 5.02 mmol) were sequentially added to a solution of (1R,5R)-1-(tert-butoxycarbonylamino)-5-fluoro-3-azabicyclo[3.2.0]heptane (crude; 321 mg) in dimethyl sulfoxide (5.0 mL). The mixture was heated with stirring at 40° C. for 24 hours. Triethylamine (0.35 mL) was added, and the mixture was further stirred at the same temperature for 17 hours. Then, 6,7-difluoro-1-[(1R,2S)-2-fluorocyclopropyl]-1,4-dihydro-8-methoxy-4-oxoquinoline-3-carboxylic acid-BF$_2$ chelate (58 mg) and triethylamine (0.125 mL) were added. Further, 6,7-difluoro-1-[(1R,2S)-2-fluorocyclopropyl]-1,4-dihydro-8-methoxy-4-oxoquinoline-3-carboxylic acid-BF$_2$ chelate (480 mg, 240 mg) and triethylamine (0.389 mL, 0.195 mL) were added after 6 hours and 24 hours, respectively. After the final reagent addition, the mixture was stirred for 5.5 hours. Then, a mixture of ethanol:water=4:1 (30 mL) and triethylamine (4.5 mL) were added to the reaction solution, and the mixture was heated to reflux for two hours. The reaction solution was concentrated under reduced pressure. The residue was dissolved in ethyl acetate (150 mL) and sequentially washed with a 10% citric acid solution (30 mL), water (30 mL×2), and brine (30 mL). The organic layer was dried over anhydrous sodium sulfate and filtered, and then the filtrate was concentrated under reduced pressure. The resulting residue (890 mg) was dissolved in concentrated hydrochloric acid (4.0 mL), and the solution was stirred at room temperature for 10 minutes. The reaction solution was diluted with 6 M hydrochloric acid and washed with chloroform (5 mL×15). The aqueous layer was adjusted to pH 13.2 with a saturated sodium hydroxide solution under ice-cooling and then adjusted to pH 7.4 with hydrochloric acid, followed by extraction with chloroform (80 mL×3). The organic layer was dried over anhydrous sodium sulfate, and the drying agent was removed by filtration. Then, the filtrate was concentrated under reduced pressure. The residue was sufficiently dried under vacuum and then dissolved in a mixed solvent of chloroform:methanol=10:1 and filtered through a membrane filter. The filtrate was concentrated under reduced pressure to give a yellow brown solid. The resulting solid was purified by recrystallization from ethanol-aqueous ammonia to give 193 mg (33%) of the title compound as pale yellow needle-like crystals.

mp: 235° C. (dec.).

¹H-NMR (400 MHz, 0.1N NaOD) δ: 8.48 (1H, d, J=1.2 Hz), 7.73 (1H, d, J=13.4 Hz), 4.96 (1H, m), 4.13 (1H, m), 4.07 (1H, m), 3.72 (3H, s), 3.60 (1H, brd, J=10.4 Hz), 3.52 (1H, m), 3.42 (1H, brd, J=10.4 Hz), 2.51 (1H, m), 2.32 (1H, m), 1.99-1.92 (2H, m), 1.70-1.52 (2H, m).

Anal; Calcd for $C_{20}H_{21}F_3N_3O_4$: C, 56.74; H, 4.76; F, 13.46; N, 9.92. Found: C, 56.68; H, 4.71; F, 13.15; N, 9.86.

HRMS (FAB); m/z Calcd for $C_{20}H_{21}F_3N_3O_4$ (M+H)+: 424.1484.

Found: 424.1475.

IR (ATR) ν: 2938, 2842, 1720, 1616, 1544, 1511, 1450, 1436, 1365, 1324, 1276, 1222, 1180, 1159, 1135, 1052, 1010, 931 cm⁻¹.

Reference Example 35

(3S)-3-[2-(tert-Butyldimethylsilyloxy)ethyl]-4-methyl-5-oxo-1-[(1R)-1-phenylethyl]pyrrolidine-3-carboxylic acid tert-butyl ester

[Formula 109]

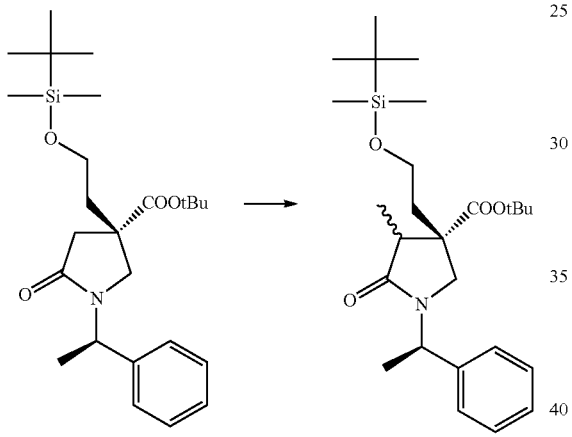

A 1.8 M solution of lithium diisopropylamide in tetrahydrofuran (3.10 mL) was added dropwise to a solution of (3S)-3-[2-(tert-butyldimethylsilyloxy)ethyl]-5-oxo-1-[(1R)-1-phenylethyl]pyrrolidine-3-carboxylic acid tert-butyl ester (2.24 g, 5.00 mmol) in tetrahydrofuran (20 mL) in a nitrogen atmosphere at −72° C. over five minutes. After stirring at the same temperature for 10 minutes, methyl iodide (0.34 mL, 5.50 mmol) was added. The mixture was stirred at the same temperature for 15 minutes and then heated to −10° C. over 10 minutes. Thereafter, a 10% citric acid aqueous solution (5 mL) was added. The reaction solution was poured into a mixture of ethyl acetate (100 mL) and 10% citric acid solution (50 mL), followed by extraction with ethyl acetate (200 mL). The organic layer was washed with brine (50 mL×2), dried over anhydrous sodium sulfate, and filtered. The filtrate was then concentrated under reduced pressure. The resulting dark brown residue was used for the next reaction without further purification.

¹H-NMR (400 MHz, CDCl₃) δ: 7.34-7.23 (5H, m), 5.46 (0.5H, q, J=7.1 Hz), 5.45 (0.5H, q, J=7.1 Hz), 3.73-3.54 (2H, m), 3.37 (0.5H, d, J=10.5 Hz), 3.36-3.31 (1H, m), 3.28 (0.5H, d, J=10.2 Hz), 2.75 (0.5H, q, J=7.3 Hz), 2.40 (0.5H, q, J=7.3 Hz), 2.03 (0.5H, m), 1.92 (0.5H, ddd, J=5.4, 7.2, 13.8 Hz), 1.83 (0.5H, m), 1.71 (0.5H, m), 1.51 (1.5H, d, J=7.1 Hz), 1.50 (1.5H, d, J=7.1 Hz), 1.35 (4.5H, s), 1.34 (4.5H, s), 1.21 (1.5H, d, J=7.3 Hz), 1.12 (1.5H, d, J=7.3 Hz), 0.88 (2×4.5H, s), 0.03 (2×1.5H, s), 0.02 (1.5H, s), 0.01 (1.5H, s).

Reference Example 36

(3S)-3-(2-Hydroxyethyl)-4-methyl-5-oxo-1-[(1R)-1-phenylethyl]pyrrolidine-3-carboxylic acid tert-butyl ester

[Formula 110]

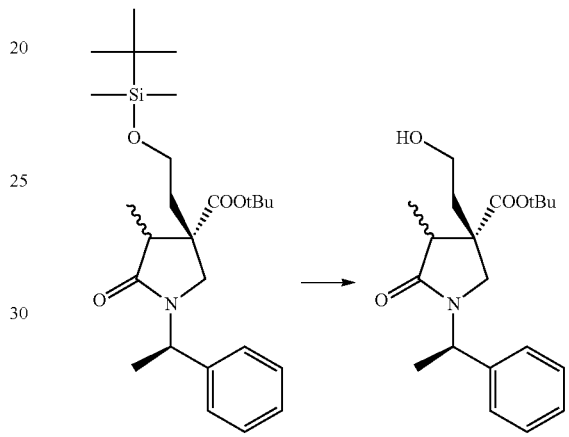

The aforementioned crude (3S)-3-[2-(tert-butyldimethylsilyloxy)ethyl]-4-methyl-5-oxo-1-[(1R)-1-phenylethyl]pyrrolidine-3-carboxylic acid tert-butyl ester was dissolved in tetrahydrofuran (10 mL). Then, acetic acid (0.572 mL, 10.0 mmol) and a 1 M solution of tetrabutylammonium fluoride in tetrahydrofuran (10.0 mL, 10.0 mmol) were sequentially added in a nitrogen atmosphere. After stirring at room temperature for 12 hours, the reaction solution was poured into a mixture of ethyl acetate (100 mL) and brine (50 mL), followed by extraction with ethyl acetate (200 mL). The organic layer was washed with brine (50 mL), and then dried over anhydrous sodium sulfate and filtered. The filtrate was then concentrated under reduced pressure. The resulting residue was purified by silica gel column chromatography (hexane:ethyl acetate=1:1→1:2) to give 1.56 g (90%, two steps) of the diastereomer mixture title compound as a colorless oil.

¹H-NMR (400 MHz, CDCl₃) δ: 7.34-7.25 (5H, m), 5.46 (0.5H, q, J=7.1 Hz), 5.45 (0.5H, q, J=7.1 Hz), 3.73-3.62 (2H, m), 3.35 (0.5H, d, J=10.5 Hz), 3.33 (0.5H, d, J=10.5 Hz), 3.26 (0.5H, d, J=10.5 Hz), 3.25 (0.5H, d, J=10.5 Hz), 2.78 (0.5H, q, J=7.3 Hz), 2.42 (0.5H, q, J=7.3 Hz), 2.13 (0.5H, dt, J=14.2, 6.6 Hz), 2.00 (0.5H, dt, J=14.2, 6.8 Hz), 1.84 (0.5H, dt, J=14.2, 6.4 Hz), 1.71 (0.5H, dt, J=14.2, 6.4 Hz), 1.52 (1.5H, d, J=7.1 Hz), 1.50 (1.5H, d, J=7.1 Hz), 1.37 (4.5H, s), 1.35 (4.5H, s), 1.22 (1.5H, d, J=7.3 Hz), 1.14 (1.5H, d, J=7.3 Hz).

Reference Example 37

(3S)-3-(2-Bromoethyl)-4-methyl-5-oxo-1-[(1R)-1-phenylethyl]pyrrolidine-3-carboxylic acid tert-butyl ester

[Formula 111]

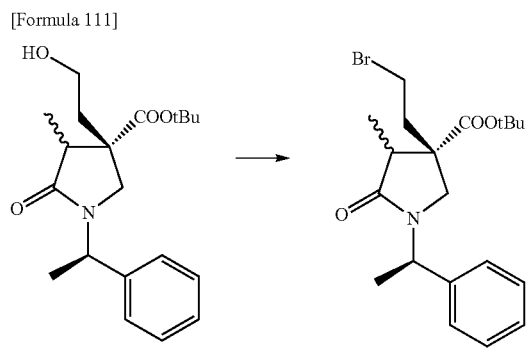

Carbon tetrabromide (1.64 g, 4.95 mmol) and triphenylphosphine (1.30 g, 4.95 mmol) were sequentially added to a solution of (3S)-3-(2-hydroxyethyl)-4-methyl-5-oxo-1-[(1R)-1-phenylethyl]pyrrolidine-3-carboxylic acid tert-butyl ester (1.56 g, 4.50 mmol) in dichloromethane (20 mL) in a nitrogen atmosphere at 0° C. After heating to room temperature, the reaction solution was stirred for 10 minutes and concentrated to about 5 mL. The residue was purified by silica gel column chromatography (dichloromethane→hexane: ethyl acetate=4:1→2:1→1.5:1) to give 1.30 g (70%) of the diastereomer mixture title compound as a white solid.

$^1$H-NMR (400 MHz, CDCl$_3$) δ: 7.36-7.26 (5H, m), 5.47 (0.5H, q, J=7.1 Hz), 5.46 (0.5H, q, J=7.1 Hz), 3.35-3.19 (3H, m), 3.14 (0.5H, d, J=10.5 Hz), 3.13 (0.5H, d, J=10.5 Hz), 2.80 (0.5H, q, J=7.4 Hz), 2.48-2.39 (1H, m), 2.30 (0.5H, ddd, J=6.2, 10.4, 13.9 Hz), 2.19-2.02 (1H, m), 1.54 (1.5H, d, J=7.1 Hz), 1.52 (1.5H, d, J=7.1 Hz), 1.37 (4.5H, s), 1.36 (4.5H, s), 1.22 (1.5H, d, J=7.4 Hz), 1.14 (1.5H, d, J=7.4 Hz).

MS (ESI) m/z: 410 (M+H)$^+$.

Reference Example 38

(1S,5S)-5-Methyl-4-oxo-3-[(1R)-1-phenylethyl]-3-azabicyclo[3.2.0]heptane-1-carboxylic acid tert-butyl ester

[Formula 112]

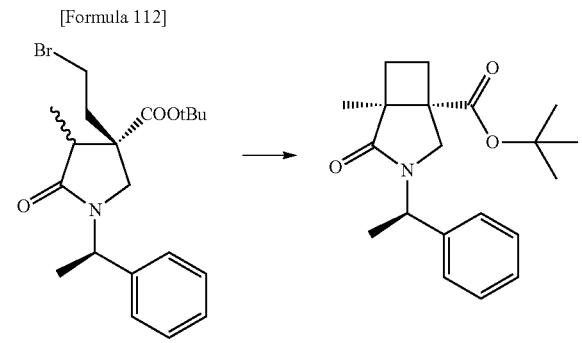

A 1.0 M solution of lithium hexamethyldisilazide in tetrahydrofuran (3.8 mL, 3.80 mmol) was added dropwise to a solution of (3S)-3-(2-bromoethyl)-4-methyl-5-oxo-1-[(1R)-1-phenylethyl]pyrrolidine-3-carboxylic acid tert-butyl ester (1.30 g, 3.17 mmol) in tetrahydrofuran (20 mL) in a nitrogen atmosphere at −72° C. over seven minutes. The mixture was stirred at the same temperature for 30 minutes. After heating to −10° C. and stirring for 1.5 hours, a 1.0 M solution of lithium hexamethyldisilazide in tetrahydrofuran (4.0 mL, 4.0 mmol) was added over two minutes, and the mixture was stirred at 0° C. for 20 hours. A 10% citric acid solution (20 mL) was added at the same temperature. The reaction solution was poured into a mixture of ethyl acetate (100 mL) and a 10% citric acid solution (10 mL). After extraction with ethyl acetate (150 mL), the organic layer was washed with brine (30 mL), dried over anhydrous sodium sulfate, and filtered. The filtrate was then concentrated under reduced pressure. The residue was purified by silica gel column chromatography (hexane:ethyl acetate=2:1→1:1) to give 0.845 g (81%) of the title compound as a white solid.

$^1$H-NMR (400 MHz, CDCl$_3$) δ: 7.35-7.26 (5H, m), 5.56 (1H, q, J=7.1 Hz), 3.42 (1H, d, J=10.2 Hz), 3.13 (1H, d, J=10.2 Hz), 2.65 (1H, ddd, J=4.7, 10.3, 11.9 Hz), 2.25 (1H, ddd, J=4.7, 9.5, 11.9 Hz), 2.09 (1H, m), 1.86 (1H, dt, J=11.9, 9.5 Hz), 1.57 (3H, d, J=7.1 Hz), 0.71 (9H, s), 1.25 (3H, s).

MS (ESI) m/z: 330 (M+H)$^+$.

Reference Example 39

(1S,5S)-1-(tert-Butoxycarbonylamino)-5-methyl-4-oxo-3-[(1R)-1-phenylethyl]-3-azabicyclo[3.2.0]heptane

[Formula 113]

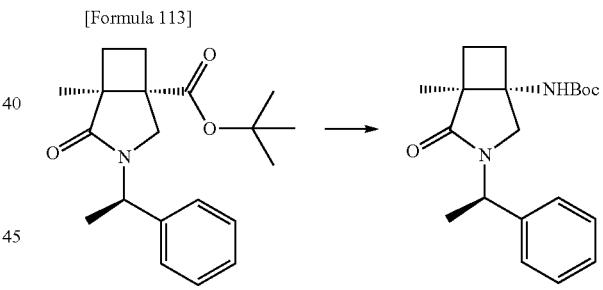

Trifluoroacetic acid (5 mL) was added to a solution of (1S,5S)-5-methyl-4-oxo-3-[(1R)-1-phenylethyl]-3-azabicyclo[3.2.0]heptane-1-carboxylic acid tert-butyl ester (0.845 g, 2.56 mmol) in dichloromethane (10 mL). The mixture was stirred for 15 hours, and then the reaction solution was concentrated under reduced pressure. Toluene (3×40 mL) was added to the residue, and trifluoroacetic acid was removed by evaporation. The residue was dried under reduced pressure to give crude carboxylic acid as a white solid.

Triethylamine (0.786 mL) and diphenylphosphoryl azide (0.608 mL) were sequentially added to a solution of the crude carboxylic acid obtained above in toluene (10 mL) and tert-butyl alcohol (10 mL). The mixture was stirred at room temperature for one hour and at 80° C. for 10 hours. The reaction solution was concentrated under reduced pressure, and the resulting residue was purified by silica gel column chromatography (hexane:ethyl acetate=7:3→3:2) to give 548 mg (62%, two steps) of the title compound as a colorless viscous oil.

¹H-NMR (400 MHz, CDCl₃) δ: 7.34-7.23 (5H, m), 5.55 (1H, q, J=7.1 Hz), 4.81 (1H, br), 3.60 (1H, br), 3.02 (1H, d, J=11.3 Hz), 2.30-2.10 (3H, m), 2.02 (1H, m), 1.56 (3H, d, J=7.1 Hz), 1.38 (9H, s), 1.27 (3H, s).
MS (ESI) m/z: 345 (M+H)⁺.

Reference Example 40

(1S,5S)-1-(tert-Butoxycarbonylamino)-5-methyl-3-[(1R)-1-phenylethyl]-3-azabicyclo[3.2.0]heptane

[Formula 114]

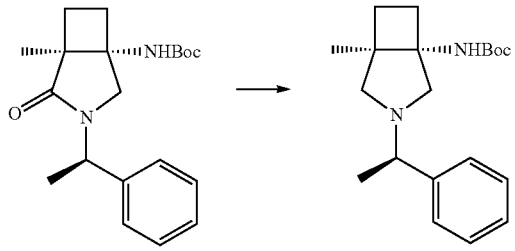

A 1.09 M solution of a borane/tetrahydrofuran complex in tetrahydrofuran (3.6 mL, 3.98 mmol) was added dropwise to a solution of (1S,5S)-1-(tert-butoxycarbonylamino)-5-methyl-4-oxo-3-[(1R)-1-phenylethyl]-3-azabicyclo[3.2.0]heptane (548 mg, 1.59 mmol) in tetrahydrofuran (10 mL) at 0° C. over five minutes. After heating to room temperature and stirring for three hours, a 1.09 M solution of a borane/tetrahydrofuran complex in tetrahydrofuran (3.6 mL, 3.98 mmol) was added at the same temperature. The mixture was stirred at room temperature for 15 hours and then cooled to 0° C. A mixture of ethanol (9.0 mL)-water (1.0 mL) was carefully added dropwise. After addition of triethylamine (3.0 mL) dropwise, the mixture was heated to reflux for one hour. The reaction solution was concentrated, and the precipitated white solid was removed by filtration through Celite. The filtrate was concentrated, and the resulting residue was purified by silica gel column chromatography (hexane:ethyl acetate=10:1→5:1) to give 184 mg (35%) of the title compound as a colorless oil.
¹H-NMR (400 MHz, CDCl₃) δ: 7.37-7.17 (5H, m), 4.58 (1H, br), 3.28 (1H, q, J=6.6 Hz), 2.95 (1H, d, J=8.5 Hz), 2.91 (1H, brd, J=9.0 Hz), 2.14-2.05 (4H, m), 1.68 (1H, m), 1.38 (9H, brs), 1.34 (3H, d, J=6.6 Hz), 1.14 (3H, s).

Reference Example 41

(1S,5S)-1-(tert-Butoxycarbonylamino)-5-methyl-3-azabicyclo[3.2.0]heptane

[Formula 115]

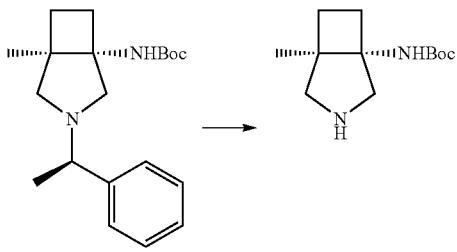

A 10% palladium-carbon catalyst (50% wet, 200 mg) was added to a solution of (1S,5S)-1-(tert-butoxycarbonylamino)-5-methyl-3-[(1R)-1-phenylethyl]-3-azabicyclo[3.2.0]heptane (184 mg, 0.057 mmol) in ethanol, and the mixture was stirred in a hydrogen atmosphere at 40° C. for five hours. After removing the catalyst by filtration, the filtrate was concentrated under reduced pressure to give crude amine as a white solid.
¹H-NMR (400 MHz, CDCl₃) δ: 4.69 (1H, br), 3.27 (1H, d, J=11.5 Hz), 2.92 (1H, br), 2.82 (1H, d, J=11.2 Hz), 2.62 (1H, brd, J=11.2 Hz), 2.13 (1H, brm), 1.98 (1H, ddd, J=5.6, 9.8, 12.7 Hz), 1.71 (1H, m), 1.59 (1H, m), 1.44 (9H, s), 1.16 (3H, s).

Example 7

7-[(1R,5S)-1-Amino-5-methyl-3-azabicyclo[3.2.0]hept-3-yl]-6-fluoro-1-[(1R,2S)-2-fluorocyclopropyl]-1,4-dihydro-8-methoxy-4-oxoquinoline-3-carboxylic acid

[Formula 116]

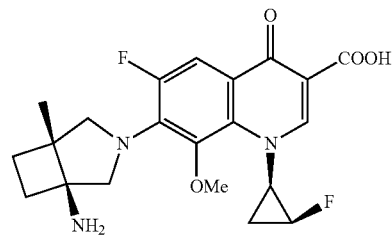

6,7-Difluoro-1-[(1R,2S)-2-fluorocyclopropyl]-1,4-dihydro-8-methoxy-4-oxoquinoline-3-carboxylic acid-BF₂ chelate (231 mg, 0.668 mmol) and triethylamine (0.279 mL, 2.01 mmol) were sequentially added to a solution of the aforementioned crude (1S,5S)-1-(tert-butoxycarbonylamino)-5-methyl-3-azabicyclo[3.2.0]heptane in dimethyl sulfoxide (2.0 mL). The mixture was heated with stirring at 40° C. for five hours. Then, a mixture of ethanol:water=4:1 (7.5 mL) and triethylamine (1.0 mL) was added to the reaction solution, and the mixture was heated to reflux for 1.5 hours. The reaction solution was concentrated under reduced pressure. The residue was dissolved in ethyl acetate (100 mL) and sequentially washed with a 10% citric acid solution (20 mL), water (20 mL×2), and brine (20 mL). The organic layer was dried over anhydrous sodium sulfate and filtered, and then the filtrate was concentrated under reduced pressure. The resulting residue was purified by reverse phase preparative HPLC (0.1% formic acid solution-acetonitrile system) to give a pale yellow solid. The resulting pale yellow solid was dissolved in concentrated hydrochloric acid (1.0 mL), and then the solution was stirred at room temperature for 10 minutes. The reaction solution was diluted with 6 M hydrochloric acid (8 mL) and washed with chloroform (5 mL). The aqueous layer was adjusted to pH 12.4 with a saturated sodium hydroxide solution under ice-cooling and then adjusted to pH 7.3 with hydrochloric acid, and then diluted with water (10 mL), followed by extraction with chloroform (50 mL×3). The organic layer was dried over anhydrous sodium sulfate and filtered, and then the filtrate was concentrated under reduced pressure. The residue was sufficiently dried under vacuum and then dissolved in a mixed solvent of chloroform:methanol=10:1 and filtered through a membrane filter. The filtrate was concentrated under reduced pressure to give 60 mg (26%) of the title compound as a pale yellow solid.
mp: 123-125° C.
¹H-NMR (400 MHz, 0.1N NaOD) δ: 8.46 (1H, d, J=1.7 Hz), 7.70 (1H, d, J=13.7 Hz), 4.97 (1H, m), 4.05 (1H, m), 3.74 (1H, d, J=11.5 Hz), 3.68 (3H, s), 3.65 (1H, m), 3.20 (1H, brd, J=9.8 Hz), 3.11 (1H, brd, J=10.3 Hz), 2.11 (1H, m), 1.95 (1H, m), 1.83 (1H, m), 1.72-1.46 (3H, m), 1.14 (3H, s).

Anal; Calcd for $C_{21}H_{23}F_2N_3O_4 \cdot H_2O \cdot 0.25EtOH$: C, 57.52; H, 5.95; F, 8.46; N, 9.36. Found: C, 57.80; H, 5.77; F, 8.41; N, 9.40. HRMS (FAB); m/z Calcd for $C_{21}H_{24}F_2N_3O_4$ (M+H)$^+$: 420.1735.
Found: 420.1739.
IR (ATR) ν: 2931, 2842, 1727, 1616, 1540, 1508, 1436, 1346, 1315, 1270, 1226, 1187, 1133, 1097, 1051 cm$^{-1}$.

Reference Example 42

(4R)-4-Allyl-4-hydroxymethyl-1-[(1R)-1-phenylethyl]pyrrolidin-2-one

[Formula 117]

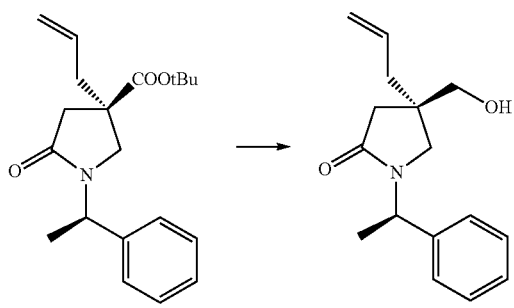

Lithium borohydride (4.96 g, 0.228 mol) was suspended in tetrahydrofuran (500 mL). A solution of (3R)-3-allyl-5-oxo-1-[(1R)-1-phenylethyl]pyrrolidine-3-carboxylic acid tert-butyl ester (50.0 g, 0.152 mol) in tetrahydrofuran (100 mL)-ethanol (17.7 mL) was added to the suspension using a dropping funnel over 10 minutes. The mixture was heated to 40° C., stirred for 12 hours, and then heated to reflux for 20 hours. After cooling to 0° C., a saturated ammonium chloride solution (100 mL) was carefully added. After the tetrahydrofuran component was evaporated under reduced pressure, the reaction solution was poured into a mixture of ethyl acetate (100 mL) and a saturated ammonium chloride solution (100 mL), followed by extraction with ethyl acetate (1000 mL, 750 mL). The organic layers were combined and washed with brine (200 mL). After drying over anhydrous sodium sulfate and filtration, the filtrate was concentrated under reduced pressure. The residue was purified by silica gel column chromatography (hexane:ethyl acetate=1:4) to give 29.9 g (76%) of the title compound as a colorless viscous oil.
$^1$H-NMR (400 MHz, CDCl$_3$) δ: 7.35-7.25 (5H, m), 5.59-5.47 (2H, m), 4.97 (1H, m), 4.90 (1H, m), 3.50 (2H, d, J=5.1 Hz), 3.23 (1H, d, J=10.1 Hz), 2.71 (1H, d, J=10.1 Hz), 2.37 (1H, d, J=16.8 Hz), 2.26 (1H, d, J=16.8 Hz), 2.08 (2H, d, J=7.3 Hz), 1.84 (1H, m), 1.51 (3H, d, J=7.1 Hz).
MS (ESI) m/z: 260 (M+H)$^+$.

Reference Example 43

(4R)-4-Allyl-4-benzyloxymethyl-1-[(1R)-1-phenylethyl]pyrrolidin-2-one

[Formula 118]

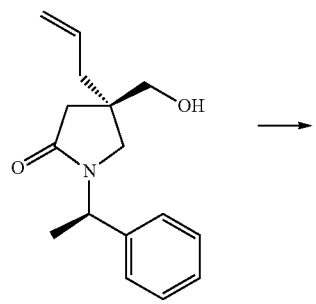

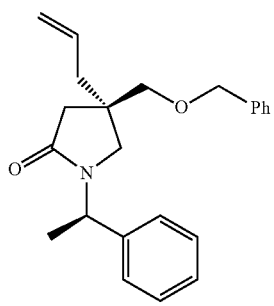

Benzyl bromide (17.1 mL, 0.144 mol) and sodium hydride (55% in liquid paraffin, 6.27 g, 0.144 mol) were sequentially added to a solution of (4R)-4-allyl-4-hydroxymethyl-1-[(1R)-1-phenylethyl]pyrrolidin-2-one (31.1 g, 0.120 mol) in tetrahydrofuran (300 mL)-dimethylformamide (75 mL) in a nitrogen atmosphere at 0° C. The mixture was stirred at the same temperature for 30 minutes. Methanol (5 mL) was carefully added and stirred until gas was not generated. Then, the reaction was quenched with a saturated ammonium chloride solution (50 mL). The reaction solution was poured into a mixture of ethyl acetate (1000 mL) and water (150 mL), followed by extraction with ethyl acetate (1500 mL). The organic layer was sequentially washed with water (200 mL) and brine (200 mL×2), dried over anhydrous sodium sulfate, and filtered. The filtrate was then concentrated under reduced pressure. The resulting residue was purified by silica gel column chromatography (hexane:ethyl acetate=3:1→2:1→1:1) to give 41.3 g (99%) of the title compound as a pale yellow oil.

$^1$H-NMR (400 MHz, CDCl$_3$) δ: 7.36-7.23 (10H, m), 5.52-5.42 (2H, m), 4.93 (1H, m), 4.84 (1H, m), 4.51 (1H, d, J=12.2 Hz), 4.47 (1H, d, J=12.2 Hz), 3.27 (2H, s), 3.21 (1H, d, J=10.0 Hz), 2.69 (1H, d, J=10.0 Hz), 2.37 (1H, d, J=16.9 Hz), 2.26 (1H, d, J=16.9 Hz), 2.11 (1H, m), 2.05 (1H, m), 1.46 (3H, d, J=7.3 Hz).

Reference Example 44

(4R)-4-Benzyloxymethyl-4-(2-hydroxyethyl)-1-[(1R)-1-phenylethyl]pyrrolidin-2-one

[Formula 119]

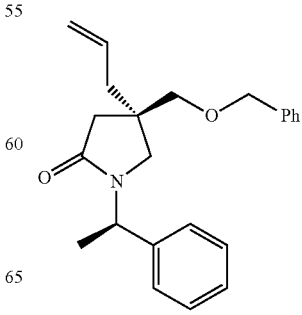

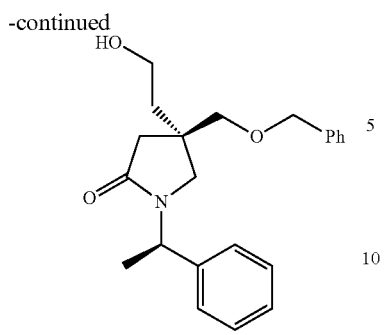

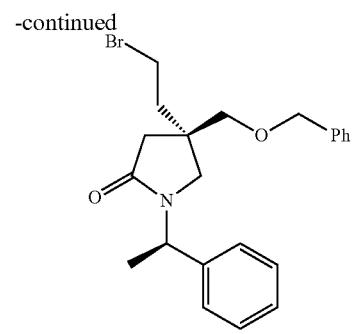

A solution of (4R)-4-allyl-4-benzyloxymethyl-1-[(1R)-1-phenylethyl]pyrrolidin-2-one (4.00 g, 11.45 mmol) in dichloromethane (100 mL) was bubbled with ozone gas at −70° C. and stirred at the same temperature for 15 minutes. Ozone bubbling was stopped when the reaction solution was turned dark blue, and then the reaction solution was bubbled with nitrogen gas until the solution turned colorless. Sodium borohydride (434 mg, 11.45 mmol) and methanol (40 mL) were added at the same temperature, and the mixture was heated to room temperature over three hours. Sodium borohydride (325 mg, 8.58 mmol) was added, and the mixture was stirred at room temperature for further 24 hours. A saturated ammonium chloride solution was added, and the mixture was stirred for 10 minutes. Then, the reaction solution was poured into a mixture of ethyl acetate (200 mL) and water (200 mL), followed by extraction with ethyl acetate (500 mL). The organic layer was washed with brine (200 mL), and then dried over anhydrous sodium sulfate and filtered. The filtrate was then concentrated under reduced pressure. The residue was purified by silica gel column chromatography (hexane:ethyl acetate=1:2→1:9→0:1) to give 3.22 g (79%) of the title compound as a colorless viscous oil.

$^1$H-NMR (400 MHz, CDCl$_3$) δ: 7.37-7.23 (10H, m), 5.46 (1H, q, J=7.1 Hz), 4.55 (1H, d, J=11.8 Hz), 4.48 (1H, d, J=11.8 Hz), 3.54-3.45 (2H, brm), 3.36 (2H, s), 3.24 (1H, d, J=10.2 Hz), 2.72 (1H, d, J=10.2 Hz), 2.38 (1H, d, J=17.0 Hz), 2.28 (1H, d, J=17.0 Hz), 2.15 (1H, br), 1.69-1.58 (2H, m), 1.44 (3H, d, J=7.1 Hz).

Reference Example 45

(4S)-4-Benzyloxymethyl-4-(2-bromoethyl)-1-[(1R)-1-phenylethyl]pyrrolidin-2-one

[Formula 120]

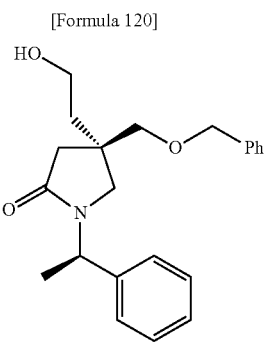

Carbon tetrabromide (3.17 g, 9.56 mmol) and triphenylphosphine (2.51 g, 9.56 mmol) were sequentially added to a solution of (4R)-4-benzyloxymethyl-4-(2-hydroxyethyl)-1-[(1R)-1-phenylethyl]pyrrolidin-2-one (3.22 g, 9.10 mmol) in dichloromethane (20 mL) in a nitrogen atmosphere, and the mixture was stirred for 15 minutes. The reaction solution was concentrated under reduced pressure, and the resulting residue was purified by silica gel column chromatography (hexane:ethyl acetate=2:1→1:1→1:2) to give 3.18 g (84%) of the title compound as a pale yellow oil.

$^1$H-NMR (400 MHz, CDCl$_3$) δ: 7.37-7.25 (10H, m), 5.46 (1H, q, J=7.1 Hz), 4.52 (1H, d, J=12.2 Hz), 4.46 (1H, d, J=12.2 Hz), 3.28 (2H, s), 3.25 (1H, d, J=10.1 Hz), 3.17-3.04 (2H, m), 2.67 (1H, d, J=10.1 Hz), 2.37 (1H, d, J=17.1 Hz), 2.26 (1H, d, J=17.1 Hz), 2.05 (1H, ddd, J=5.9, 10.4, 14.0 Hz), 1.96 (1H, ddd, J=6.1, 10.6, 14.0 Hz), 1.44 (3H, d, J=7.1 Hz).

Reference Example 46

(1S,5R)-5-Benzyloxymethyl-2-oxo-3-[(1R)-1-phenylethyl]-3-azabicyclo[3.2.0]heptane-1-carboxylic acid methyl ester

[Formula 121]

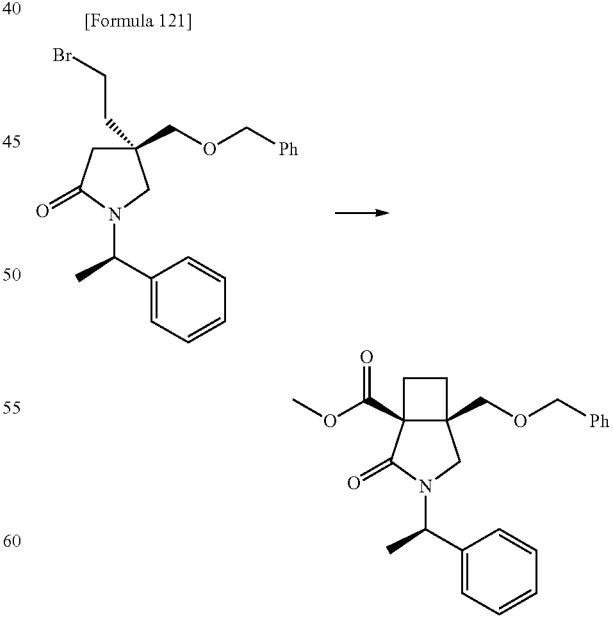

A 1.0 M solution of lithium hexamethyldisilazide in tetrahydrofuran (14.5 mL, 14.5 mmol) was added to a solution of (4S)-4-benzyloxymethyl-4-(2-bromoethyl)-1-[(1R)-1- phenylethyl]pyrrolidin-2-one (2.75 g, 6.60 mmol) and methyl chloroformate (0.54 mL, 6.93 mmol) in tetrahydrofuran (20 mL) in a nitrogen atmosphere at 0° C. The mixture was stirred for 12 hours while gradually heating to room temperature. The reaction solution was cooled to 0° C. A saturated ammonium chloride solution (5 mL) was added, and the mixture was stirred for 10 minutes. Then, the reaction solution was poured into a mixture of ethyl acetate (100 mL) and water (50 mL), followed by extraction with ethyl acetate (200 mL). The organic layer was washed with brine (50 mL) and then dried over anhydrous sodium sulfate. The drying agent was removed by filtration, and then the filtrate was concentrated under reduced pressure. The residue was purified by silica gel column chromatography (hexane:ethyl acetate=3:1→2:1→1:1) to give 2.12 g (82%) of the title compound as a pale yellow oil.

$^1$H-NMR (400 MHz, CDCl$_3$) δ: 7.36-7.24 (10H, m), 5.59 (1H, q, J=7.1 Hz), 4.47 (1H, d, J=12.0 Hz), 4.43 (1H, d, J=12.0 Hz), 3.63 (3H, s), 3.53 (1H, d, J=9.3 Hz), 3.49 (1H, d, J=9.3 Hz), 3.37 (1H, d, J=10.0 Hz), 2.78 (1H, ddd, J=9.3, 9.5, 12.2 Hz), 2.73 (1H, d, J=10.0 Hz), 2.22 (1H, ddd, J=3.4, 9.3, 12.2 Hz), 1.91 (1H, ddd, J=3.4, 10.5, 12.2 Hz), 1.63 (1H, ddd, J=9.5, 10.5, 12.2 Hz), 1.58 (3H, d, J=7.1 Hz).

MS (ESI) m/z: 394 (M+H)$^+$.

Reference Example 47

(1S,5R)-5-Hydroxymethyl-2-oxo-3-[(1R)-1-phenylethyl]-3-azabicyclo[3.2.0]heptane-1-carboxylic acid methyl ester

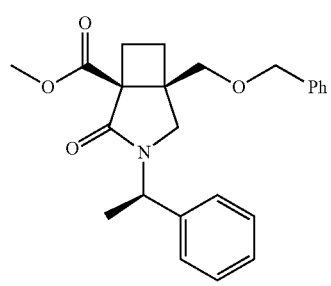

[Formula 122]

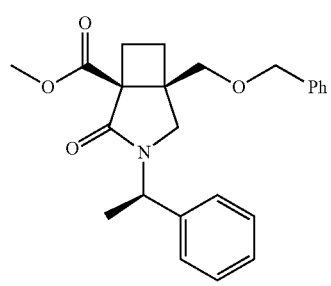

A 10% palladium-carbon catalyst (50% wet, 200 mg) was added to a solution of (1S,5R)-5-benzyloxymethyl-2-oxo-3-[(1R)-1-phenylethyl]-3-azabicyclo[3.2.0]heptane-1-carboxylic acid methyl ester (1.82 g, 4.62 mmol) in ethanol (20 mL)-tetrahydrofuran (20 mL), and the mixture was stirred in a hydrogen atmosphere at 40° C. for 2.5 hours. After removing the catalyst by filtration, the filtrate was concentrated to give the title compound as colorless crystals.

$^1$H-NMR (400 MHz, CDCl$_3$) δ: 7.37-7.27 (5H, m), 5.60 (1H, q, J=7.1 Hz), 3.79 (1H, dd, J=4.2, 11.8 Hz), 3.78 (3H, s), 3.58 (1H, dd, J=7.1, 11.8 Hz), 3.56 (1H, d, J=10.0 Hz), 2.73-2.65 (2H, m), 2.57 (1H, dd, J=4.2, 7.1 Hz), 2.30 (1H, m), 1.83 (1H, m), 1.62 (1H, m), 1.59 (3H, d, J=7.1 Hz).

MS (ESI) m/z: 304 (M+H)$^+$.

Reference Example 48

(1S,5R)-5-Fluoromethyl-2-oxo-3-[(1R)-1-phenylethyl]-3-azabicyclo[3.2.0]heptane-1-carboxylic acid methyl ester

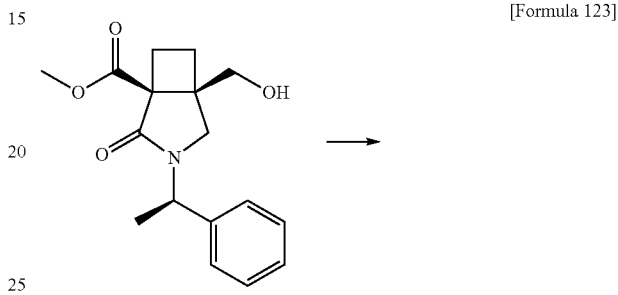

[Formula 123]

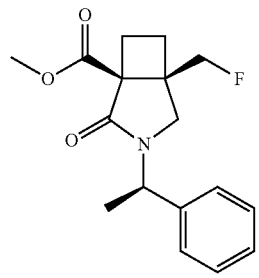

Bis(2-methoxyethyl)aminosulfur trifluoride (1.98 mL, 10.7 mmol) was added to a solution of (1S,5R)-5-hydroxymethyl-2-oxo-3-[(1R)-1-phenylethyl]-3-azabicyclo[3.2.0]heptane-1-carboxylic acid methyl ester (1.30 g, 4.30 mmol) in dichloromethane in a nitrogen atmosphere at room temperature. The mixture was heated to 50° C. and stirred for 12 hours. Then, a saturated sodium bicarbonate solution (10 mL) was added, and the mixture was stirred for 10 minutes. The reaction solution was poured into a mixture of ethyl acetate (50 mL) and water (30 mL), followed by extraction with ethyl acetate (200 mL). After filtration, the filtrate was concentrated under reduced pressure. The residue was purified by silica gel column chromatography (hexane:ethyl acetate=3:1→2:1→1.5:1) to give 1.26 g (96%) of the title compound as a pale yellow oil.

$^1$H-NMR (400 MHz, CDCl$_3$) δ: 7.40-7.29 (5H, m), 5.63 (1H, q, J=7.2 Hz), 4.51 (1H, dd, J=9.8, 47.1 Hz), 4.47 (1H, dd, J=9.8, 47.0 Hz), 3.76 (3H, s), 3.41 (1H, d, J=10.0 Hz), 2.78 (1H, m), 2.76 (1H, d, J=10.0 Hz), 2.27 (1H, ddd, J=3.6, 9.3, 12.5 Hz), 1.93 (1H, ddd, J=3.6, 10.5, 12.4 Hz), 1.68 (1H, m), 1.62 (3H, d, J=7.2 Hz).

MS (ESI) m/z: 306 (M+H)$^+$.

Reference Example 49
(1S,5S)-1-(tert-Butoxycarbonylamino)-5-fluoromethyl-2-oxo-3-[(1R)-1-phenylethyl]-3-azabicyclo[3.2.0]heptane

[Formula 124]

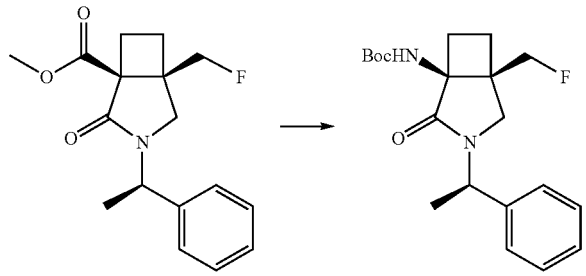

A 1 M sodium hydroxide solution was added to a solution of (1S,5R)-5-fluoromethyl-2-oxo-3-[(1R)-1-phenylethyl]-3-azabicyclo[3.2.0]heptane-1-carboxylic acid methyl ester (1.26 g, 4.13 mmol) in tetrahydrofuran (10 mL)-methanol (5.0 mL). The mixture was stirred for 12 hours. The reaction solution was adjusted to pH 2 or less with 6 M hydrochloric acid, and the tetrahydrofuran and methanol components were removed by filtration under reduced pressure. The residue was poured into a mixture of ethyl acetate and 1 M hydrochloric acid, followed by extraction with ethyl acetate. The organic layer was washed with a saturated sodium chloride solution and then dried over anhydrous sodium sulfate. After removing the drying agent by filtration, the filtrate was concentrated under reduced pressure to give 1.17 g (97%) of crude carboxylic acid as a white solid.

The crude carboxylic acid (1.02 g, 3.51 mmol) was dissolved in a mixture of toluene (20 mL), tert-butyl alcohol (20 mL), and triethylamine (0.98 mL, 7.03 mmol), and diphenylphosphoryl azide (0.833 mL, 3.87 mmol) was added in a nitrogen atmosphere. The mixture was stirred at 40° C. for one hour and then at 80° C. for 12 hours. The reaction solution was poured into a mixture of ethyl acetate (50 mL) and a saturated sodium bicarbonate solution (30 mL), followed by extraction with ethyl acetate (150 mL). The organic layer was washed with brine (30 mL), dried over anhydrous sodium sulfate, and filtered. The filtrate was then concentrated under reduced pressure. The resulting residue was purified by silica gel column chromatography (hexane:ethyl acetate=3:1→2:1→1:1) to give 746 mg (59%) of the title compound as colorless crystals.

$^1$H-NMR (400 MHz, CDCl$_3$) δ: 7.39-7.29 (5H, m), 5.60 (1H, q, J=7.1 Hz), 4.95 (1H, br), 4.61 (1H, dd, J=9.6, 47.3 Hz), 4.47 (1H, dd, J=9.6, 47.3 Hz), 2.15 (1H, d, J=9.5 Hz), 2.70 (1H, d, J=9.5 Hz), 2.36 (1H, m), 2.17-2.08 (2H, m), 1.60 (3H, d, J=7.1 Hz), 1.42 (9H, s).
MS (ESI) m/z: 363 (M+H)$^+$.

Reference Example 50
(1S,5S)-1-(tert-Butoxycarbonylamino)-5-fluoromethyl-3-[(1R)-1-phenylethyl]-3-azabicyclo[3.2.0]heptane

[Formula 125]

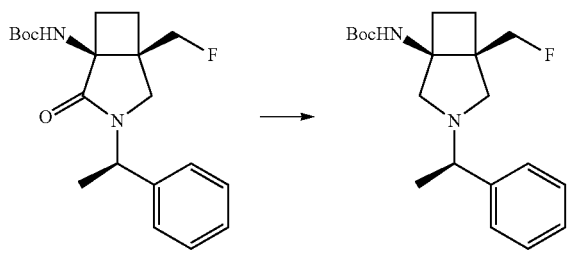

A 65% solution of Red-Al™ in toluene (1.76 mL, 5.85 mmol) was added dropwise to a solution of (1S,5S)-1-(tert-butoxycarbonylamino)-5-fluoromethyl-2-oxo-3-[(1R)-1-phenylethyl]-3-azabicyclo[3.2.0]heptane (707 mg, 1.95 mmol) in toluene in a nitrogen atmosphere at −15° C. over 10 minutes. The mixture was heated to room temperature, stirred for 1.5 hours, and cooled to 0° C. A 25% potassium sodium tartrate tetrahydrate solution (10 mL) was carefully added while maintaining the internal temperature of the reaction solution at 10° C. or less. The reaction solution was poured into a mixture of ethyl acetate (10 mL) and brine (10 mL), followed by extraction with ethyl acetate (150 mL). The organic layer was washed with brine (30 mL) and then dried over anhydrous sodium sulfate. The drying agent was removed by filtration, and then the filtrate was concentrated under reduced pressure. The resulting residue was purified by silica gel column chromatography (hexane:ethyl acetate=9:1→5:1→2:1) to give 567 mg (83%) of the title compound as a pale yellow oil.

$^1$H-NMR (400 MHz, CDCl$_3$) δ: 7.37-7.18 (5H, m), 4.89 (1H, br), 4.63 (1H, dd, J=9.8, 47.9 Hz), 4.53 (1H, J=9.8, 47.6 Hz), 3.33 (1H, q, J=6.4 Hz), 2.95 (2H, d, J=8.8 Hz), 2.40 (1H, d, J=8.8 Hz), 2.18-2.14 (3H, m), 1.93-1.87 (2H, m), 1.37 (9H, s), 1.36 (3H, d, J=6.4 Hz).
MS (ESI) m/z: 349 (M+H)$^+$.

Example 8
7-[(1S,5S)-1-Amino-5-fluoromethyl-3-bicyclo[3.2.0]hept-3-yl]-6-fluoro-1-[(1R,2S)-2-fluorocyclopropyl-1-yl]-1,4-dihydro-8-methoxy-4-oxoquinoline-3-carboxylic acid

[Formula 126]

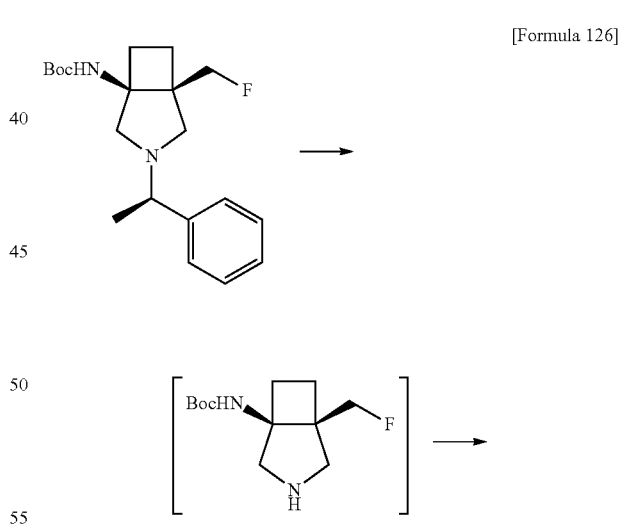

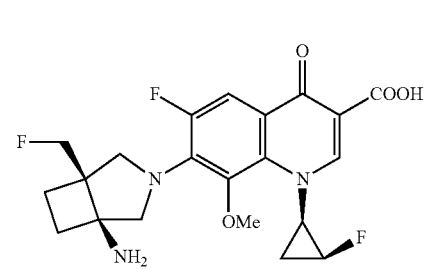

A 10% palladium-carbon catalyst (M, about 50% wet, 50 mg) was added to a solution of (1S,5S)-1-(tert-butoxycarbonylamino)-5-fluoromethyl-3-[(1R)-1-phenylethyl]-3-azabicyclo[3.2.0]heptane (567 mg, 1.63 mmol) in ethanol (10 mL), and the mixture was stirred in a hydrogen atmosphere at 50° C. for 2.5 hours. After removing the catalyst by filtration, the filtrate was concentrated under reduced pressure to give crude amine (364 mg) as colorless crystals.

The crude amine was dissolved in dimethyl sulfoxide (4.0 mL), and triethylamine (0.62 mL, 4.45 mmol) and 6,7-difluoro-1-[(1R,2S)-2-fluorocyclopropyl]-1,4-dihydro-8-methoxy-4-oxoquinoline-3-carboxylic acid-$BF_2$ chelate (642 mg, 1.78 mmol) were sequentially added. The mixture was heated with stirring at 40° C. for 24 hours. Then, a mixture of ethanol:water=3:1 (20.0 mL) and triethylamine (3.0 mL) were added to the reaction solution, and the mixture was heated to reflux for 1.5 hours. The reaction solution was poured into a mixture of ethyl acetate (20 mL) and a 10% citric acid solution (10 mL), followed by extraction with ethyl acetate (50 mL×3). The organic layers were combined and washed with brine (50 mL). Thereafter, the organic layers were dried over anhydrous sodium sulfate and filtered, and then the filtrate was concentrated under reduced pressure. The resulting residue was purified by reverse phase preparative HPLC (0.1% formic acid solution-acetonitrile system) to give a pale yellow solid. The resulting pale yellow solid was dissolved in concentrated hydrochloric acid (1.5 mL), and the solution was stirred at room temperature for 10 minutes. The reaction solution was diluted with 6 M hydrochloric acid (20 mL) and washed with chloroform (7 mL). The aqueous layer was adjusted to pH 12.4 with a saturated sodium hydroxide solution under ice-cooling and then adjusted to pH 7.3 with hydrochloric acid, followed by extraction with chloroform (50 mL×2). The aqueous layer was readjusted to pH 7.4, followed by extraction with chloroform (50 mL×2). The organic layers were combined, dried over anhydrous sodium sulfate, and filtered. Then, the filtrate was concentrated under reduced pressure. The residue was sufficiently dried under vacuum and then dissolved in chloroform. The solution was filtered through a membrane filter, and the filtrate was concentrated under reduced pressure. The resulting residue was dissolved in ethanol and then reprecipitated with hexane. The resulting solid was collected by filtration and dried to give 219 mg (31%) of the title compound as a pale yellow solid.

mp: 186-188° C.
$^1$H-NMR (400 MHz, 0.1N NaOD) δ: 8.47 (1H, s), 4.34 (1H, d, J=7.9 Hz), 4.96 (1H, m), 4.70 (1H, dd, J=10.0, 47.4 Hz), 4.64 (1H, dd, J=10.0, 47.1 Hz), 4.02 (1H, m), 3.67-3.61 (5H, m), 3.33 (1H, brd, J=10.5 Hz), 3.22 (1H, brd, J=9.8 Hz), 2.11 (1H, m), 2.00-1.88 (2H, m), 1.73 (1H, m), 1.60 (1H, m), 1.47 (1H, m).

Anal; Calcd for $C_{21}H_{22}F_3N_3O_4$·0.25$H_2O$·0.25EtOH: C, 56.95; H, 5.33; F, 12.57; N, 9.27. Found: C, 56.94; H, 5.11; F, 12.74; N, 9.23.

HRMS (FAB); m/z Calcd for $C_{21}H_{23}F_3N_3O_4$ $(M+H)^+$: 438.16406.
Found: 438.16743.

IR (ATR) ν: 3386, 2935, 1716, 1616, 1540, 1508, 1442, 1436, 1351, 1319, 1274, 1228, 1184, 1122, 1051 $cm^{-1}$.

Reference Example 51

(4R)-4-Allyl-4-methoxymethyl-1-[(1R)-1-phenylethyl]pyrrolidin-2-one

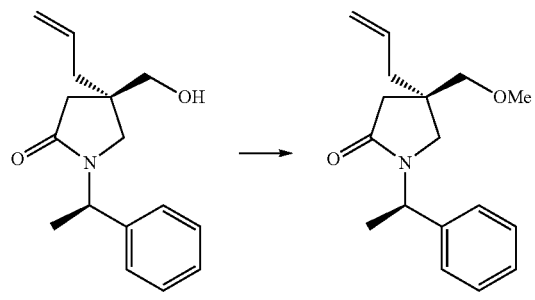

[Formula 127]

Methyl iodide (1.87 mL, 30.1 mmol) and sodium hydride (55% in liquid paraffin, 1.31 g, 30.1 mol) were sequentially added to a solution of (4R)-4-allyl-4-hydroxymethyl-1-[(1R)-1-phenylethyl]pyrrolidin-2-one (7.09 g, 27.3 mmol) in tetrahydrofuran (80 mL)-dimethylformamide (20 mL) in a nitrogen atmosphere at 0° C. The mixture was heated to room temperature and stirred for one hour. Methanol (2 mL) was carefully added and stirred until gas was not generated. Then, the reaction was quenched with a saturated ammonium chloride solution (10 mL). The reaction solution was poured into a mixture of ethyl acetate (100 mL) and water (100 mL), followed by extraction with ethyl acetate (800 mL). The organic layer was sequentially washed with water (200 mL) and brine (200 mL×2), dried over anhydrous sodium sulfate, and filtered. The filtrate was then concentrated under reduced pressure. The resulting residue was purified by silica gel column chromatography (hexane:ethyl acetate=4:1→2:1→1:1) to give 7.42 g (99%) of the title compound as a colorless oil.

$^1$H-NMR (400 MHz, $CDCl_3$) δ: 7.35-7.24 (5H, m), 5.54-5.43 (2H, m), 4.94 (1H, m), 4.84 (1H, m), 3.33 (3H, s), 3.20 (2H, s), 3.19 (1H, d, J=10.0 Hz), 2.69 (1H, d, J=10.0 Hz), 2.36 (1H, d, J=17.1 Hz), 2.24 (1H, d, J=17.1 Hz), 2.05-2.03 (2H, m), 1.50 (3H, d, J=7.3 Hz).

Reference Example 52

(4R)-4-(2-Hydroxyethyl)-4-methoxymethyl-1-[(1R)-1-phenylethyl]pyrrolidin-2-one

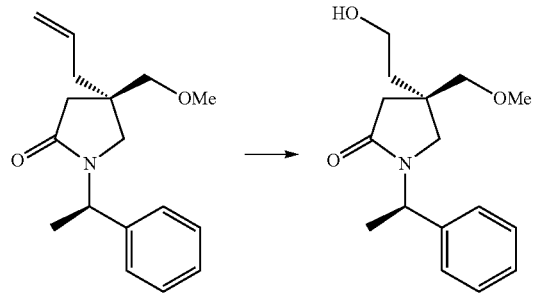

[Formula 128]

A solution of (4R)-4-allyl-4-methoxymethyl-1-[(1R)-1-phenylethyl]pyrrolidin-2-one (3.28 g, 12.0 mmol) in methanol (20 mL)-dichloromethane (20 mL) was bubbled with ozone gas at −70° C. and stirred at the same temperature for 30 minutes. Ozone bubbling was stopped when the reaction solution was turned dark blue, and then the reaction solution was bubbled with nitrogen gas until the solution turned colorless. Sodium borohydride (454 mg, 12.0 mmol) was added at the same temperature, and the mixture was heated to room temperature over two hours. After heating, sodium borohydride (227 mg, 6.0 mmol) was added and the mixture was stirred for 24 hours. Then, sodium borohydride (113 mg, 3.0 mmol) was further added and the mixture was stirred for 0.5 hour. A saturated ammonium chloride solution (10 mL) was added, and the mixture was stirred for 10 minutes. Then, the reaction solution was poured into a mixture of ethyl acetate (50 mL) and water (50 mL), followed by extraction with ethyl acetate (200 mL). The organic layer was washed with brine (50 mL), and then dried over anhydrous sodium sulfate and filtered. The filtrate was then concentrated under reduced pressure. The residue was purified by silica gel column chromatography (ethyl acetate:methanol=10:0→10:1) to give 2.85 g (86%) of the title compound as a colorless viscous oil.

$^1$H-NMR (400 MHz, CDCl$_3$) δ: 7.35-7.25 (5H, m), 5.49 (1H, q, J=7.1 Hz), 3.55-3.44 (2H, m), 3.37 (3H, s), 3.30 (1H, d, J=9.5 Hz), 3.28 (1H, d, J=9.5 Hz), 3.22 (1H, d, J=10.0 Hz), 2.72 (1H, d, J=10.0 Hz), 2.38 (1H, d, J=16.8 Hz), 2.26 (1H, d, J=16.8 Hz), 1.64 (2H, t, J=6.0 Hz), 1.50 (3H, d, J=7.1 Hz).

Reference Example 53

(4S)-4-(2-Bromoethyl)-4-methoxymethyl-1-[(1R)-1-phenylethyl]pyrrolidin-2-one

[Formula 129]

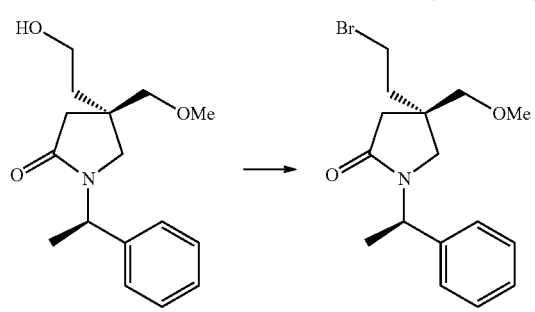

Carbon tetrabromide (3.58 g, 10.8 mmol) and triphenylphosphine (2.83 g, 10.8 mmol) were sequentially added to a solution of (4R)-4-(2-hydroxyethyl)-4-methoxymethyl-1-[(1R)-1-phenylethyl]pyrrolidin-2-one (2.85 g, 10.3 mmol) in dichloromethane (30 mL) in a nitrogen atmosphere at 0° C., and the mixture was stirred for 10 minutes. The mixture was heated to room temperature and stirred for 24 hours, and then the reaction solution was concentrated under reduced pressure. The residue was purified by silica gel column chromatography (dichloromethane→hexane:ethyl acetate=2:1→1:1→1:2) to give 2.07 g (59%) of the title compound as a colorless oil.

$^1$H-NMR (400 MHz, CDCl$_3$) δ: 7.36-7.25 (5H, m), 5.49 (1H, q, J=7.3 Hz), 3.32 (3H, s), 3.24 (1H, d, J=10.3 Hz), 3.23 (2H, s), 3.20-3.07 (2H, m), 2.67 (1H, d, J=10.3 Hz), 2.38 (1H, d, J=16.8 Hz), 2.25 (1H, d, J=16.8 Hz), 2.03-1.90 (2H, m), 1.50 (3H, d, J=7.3 Hz).

Reference Example 54

(1S,5R)-5-Methoxymethyl-2-oxo-3-[(1R)-1-phenylethyl]-3-azabicyclo[3.2.0]heptane-1-carboxylic acid methyl ester

[Formula 130]

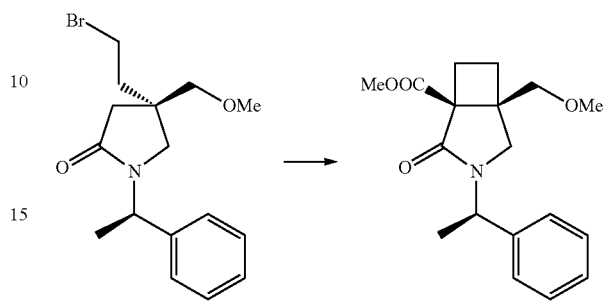

A 1.0 M solution of lithium hexamethyldisilazide in tetrahydrofuran (13.4 mL, 13.4 mmol) was added to a solution of (4S)-4-(2-bromoethyl)-4-methoxymethyl-1-[(1R)-1-phenylethyl]pyrrolidin-2-one (2.07 g, 6.08 mmol) and methyl chloroformate (0.493 mL, 6.38 mmol) in tetrahydrofuran (20 mL) in a nitrogen atmosphere at −70° C. The mixture was stirred for 14 hours while gradually heating to room temperature. The reaction solution was cooled to 0° C. A 10% citric acid solution (20 mL) was added, and the mixture was stirred for 10 minutes. Then, the reaction solution was poured into a mixture of ethyl acetate (100 mL) and water (50 mL), followed by extraction with ethyl acetate (200 mL). The organic layer was washed with brine (50 mL), and then dried over anhydrous sodium sulfate and filtered. The filtrate was then concentrated under reduced pressure. The residue was purified by silica gel column chromatography (hexane:ethyl acetate=2:1→1:1→2:1) to give 1.53 g (79%) of the title compound as a pale brown oil.

$^1$H-NMR (400 MHz, CDCl$_3$) δ: 7.35-7.26 (5H, m), 5.60 (1H, q, J=7.1), 3.72 (3H, s), 3.43 (1H, d, J=9.5 Hz), 3.40 (1H, d, J=9.5 Hz), 3.36 (1H, d, J=9.8 Hz), 3.28 (3H, s), 2.75 (1H, dt, J=12.2, 10.5 Hz), 2.72 (1H, d, J=9.5 Hz), 2.21 (1H, ddd, J=3.4, 9.3, 12.2 Hz), 1.86 (1H, ddd, J=3.4, 10.5, 12.2 Hz), 1.62 (1H, dt, J=12.2, 9.3 Hz), 1.58 (3H, d, J=7.1 Hz).

MS (ESI) m/z: 318 (M+H)$^+$.

Reference Example 55

(1S,5S)-1-(tert-Butoxycarbonylamino)-5-methoxymethyl-2-oxo-3-[(1R)-1-phenylethyl]-3-azabicyclo[3.2.0]heptane

[Formula 131]

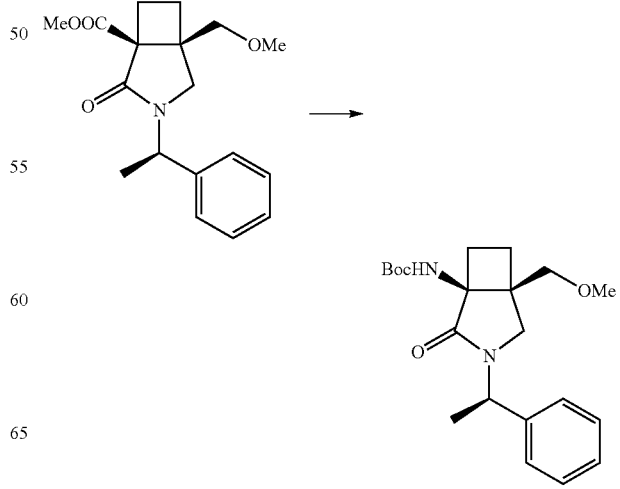

A 1 M sodium hydroxide solution (5.0 mL) was added to a solution of (1S,5R)-5-methoxymethyl-2-oxo-3-[(1R)-1-phenylethyl]-3-azabicyclo[3.2.0]heptane-1-carboxylic acid methyl ester (1.53 g, 4.82 mmol) in tetrahydrofuran (10 mL)-methanol (5.0 mL). The mixture was stirred for nine hours. The reaction solution was adjusted to pH 2 or less with 6 M hydrochloric acid, and the tetrahydrofuran and methanol components were removed by filtration under reduced pressure. The residue was poured into a mixture of ethyl acetate (30 mL) and 1 M hydrochloric acid (30 mL), followed by extraction with ethyl acetate (150 mL). The organic layer was washed with a saturated sodium chloride solution (30 mL), and then dried over anhydrous sodium sulfate and filtered. The filtrate was then concentrated under reduced pressure to give crude carboxylic acid as a pale yellow oil.

The crude carboxylic acid was dissolved in a mixture of tert-butyl alcohol (30 mL) and triethylamine (1.34 mL, 9.64 mmol), and diphenylphosphoryl azide (1.14 mL, 5.30 mmol) was added in a nitrogen atmosphere. The mixture was stirred at 40° C. for two hours and then at 80° C. for 20 hours. The reaction solution was concentrated under reduced pressure, and the resulting residue was purified by silica gel column chromatography (hexane:ethyl acetate=2:1→1:1) to give 595 mg (33%, two steps) of the title compound as a white solid.
$^1$H-NMR (400 MHz, CDCl$_3$) δ: 7.34-7.23 (5H, m), 2.25 (1H, q, J=7.1H), 4.87 (1H, brs), 3.55 (1H, d, J=9.2 Hz), 3.42 (1H, brd, J=9.2 Hz), 3.35 (1H, d, J=9.6 Hz), 3.33 (3H, s), 2.71 (1H, d, J=9.6 Hz), 2.33 (1H, m), 2.12-2.00 (2H, m), 1.60 (3H, d, J=7.1 Hz), 1.43 (9H, s).

Reference Example 56

(1S,5S)-1-(tert-Butoxycarbonylamino)-5-methoxymethyl-3-[(1R)-1-phenylethyl]-3-azabicyclo[3.2.0]heptane

[Formula 132]

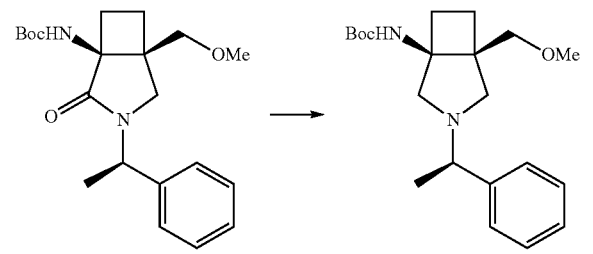

A 65% solution of Red-Al™ in toluene (1.43 mL, 4.75 mmol) was added dropwise to a solution of (1S,5S)-1-(tert-butoxycarbonylamino)-5-methoxymethyl-2-oxo-3-[(1R)-1-phenylethyl]-3-azabicyclo[3.2.0]heptane (593 mg, 1.58 mmol) in toluene in a nitrogen atmosphere at 0° C. over two minutes. The mixture was heated to room temperature, stirred for two hours, and cooled to 0° C. A 20% potassium sodium tartrate tetrahydrate solution (10 mL) was carefully added while maintaining the internal temperature of the reaction solution at 10° C. or less. The reaction solution was poured into a mixture of ethyl acetate (10 mL) and brine (10 mL), followed by extraction with ethyl acetate (100 mL). The organic layer was washed with brine (20 mL), and then dried over anhydrous sodium sulfate and filtered. The filtrate was then concentrated under reduced pressure. The resulting residue was purified by silica gel column chromatography (hex-ane:ethyl acetate=19:1→9:1) to give 244 mg (43%) of the title compound as colorless crystals.
$^1$H-NMR (400 MHz, CDCl$_3$) δ: 7.37-7.17 (5H, m), 5.56 (1H, brs), 3.58 (1H, d, J=10.0 Hz), 3.43 (1H, d, J=10.0 Hz), 3.37 (3H, s), 3.28 (1H, q, J=6.5 Hz), 3.10 (1H, br), 2.86 (1H, d, J=8.7 Hz), 2.34 (1H, d, J=8.7 Hz), 2.23-2.01 (3H, brm), 1.84 (2H, brt, J=8.1 Hz), 1.35 (9H, brs), 1.34 (3H, d, J=6.5 Hz).
MS (ESI) m/z: 361 (M+H)$^+$.

Example 9

7-[(1S,5S)-1-Amino-5-methoxymethyl-3-azabicyclo[3.2.0]hept-3-yl]-6-fluoro-1-[(1R,2S)-2-fluorocyclopropyl-1-yl]-1,4-dihydro-8-methoxy-4-oxoquinoline-3-carboxylic acid

[Formula 133]

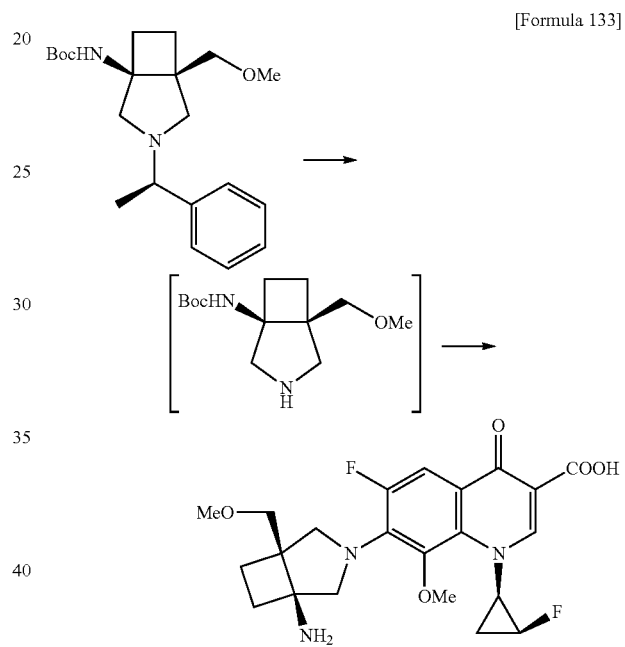

A 10% palladium-carbon catalyst (50% wet, 50 mg) was added to a solution of (1S,5S)-1-(tert-butoxycarbonylamino)-5-methoxymethyl-3-[(1R)-1-phenylethyl]-3-azabicyclo[3.2.0]heptane (242 mg, 0.67 mmol) in ethanol (20 mL), and the mixture was stirred in a hydrogen atmosphere at 50° C. for seven hours. After removing the catalyst by filtration, the filtrate was concentrated under reduced pressure to give crude amine (164 mg) as a colorless viscous oil.

The crude amine (164 mg) was dissolved in dimethyl sulfoxide (2.0 mL), and triethylamine (0.178 mL, 1.28 mmol) and 6,7-difluoro-1-[(1R,2S)-2-fluorocyclopropyl]-8-methoxy-4-oxo-1,4-dihydroquinoline-3-carboxylic acid-BF$_2$ chelate (254 mg, 0.704 mmol) were sequentially added. The mixture was heated with stirring at 40° C. for 23 hours. Then, a mixture of ethanol:water=5:1 (6.0 mL) and triethylamine (1.0 mL) were added to the reaction solution, and the mixture was heated to reflux for two hours. After the ethanol and triethylamine components in the reaction solution were evaporated under reduced pressure, the residue was poured into a mixture of ethyl acetate (20 mL) and a 10% citric acid solution (10 mL), followed by extraction with ethyl acetate (80 mL). The organic layer was washed with brine (20 mL), and then dried over anhydrous sodium sulfate and filtered.

The filtrate was then concentrated under reduced pressure. The resulting residue was purified by reverse phase preparative HPLC (0.1% formic acid solution-acetonitrile system) to give a pale yellow amorphous. The resulting pale yellow amorphous was dissolved in concentrated hydrochloric acid (2.0 mL), and the solution was stirred at room temperature for 10 minutes. The reaction solution was diluted with 6 M hydrochloric acid (15 mL) and washed with chloroform (10 mL). The aqueous layer was adjusted to pH 12 with a saturated sodium hydroxide solution under ice-cooling and then adjusted to pH 7.4 with hydrochloric acid, followed by extraction with chloroform (50 mL×2, 30 mL). The organic layers were combined, dried over anhydrous sodium sulfate, and filtered. Then, the filtrate was concentrated under reduced pressure. The residue was sufficiently dried under vacuum and then dissolved in chloroform. The solution was filtered through a membrane filter, and the filtrate was concentrated under reduced pressure. The resulting residue was crystallized from hexane, and the crystals were collected by filtration and dried to give 184 mg (61%) of the title compound as a pale yellow solid.

mp: 86-88° C.

$^1$H-NMR (400 MHz, 0.1N NaOD) δ: 8.47 (1H, d, J=1.5 Hz), 7.69 (1H, d, J=13.4 Hz), 4.95 (1H, m), 4.02 (1H, m), 3.70-3.58 (7H, m), 3.39 (3H, s), 3.23 (1H, d, J=10.5 Hz), 3.19 (1H, d, J=10.3 Hz), 2.09 (1H, m), 1.99-1.87 (2H, m), 1.74 (1H, m), 1.61 (1H, m), 1.48 (1H, m).

Anal; Calcd for $C_{22}H_{25}F_2N_3O_5 \cdot 0.25H_2O \cdot 0.25EtOH$: C, 58.06; H, 5.85; F, 8.16; N, 9.03. Found: C, 57.92; H, 5.86; F, 8.16; N, 9.09.

HRMS (FAB); m/z Calcd for $C_{22}H_{26}F_2N_3O_5$ (M+H)$^+$: 450.18405.

Found: 450.18358.

IR (ATR) ν: 2931, 2827, 1724, 1616, 1546, 1504, 1434, 1392, 1348, 1313, 1274, 1228, 1184, 1101, 1051 cm$^{-1}$.

Reference Example 57

(3R)-3-[1-(Hydroxymethyl)cyclopropan-1-yl]-5-oxo-1-[(1S)-1-phenylethyl]pyrrolidine

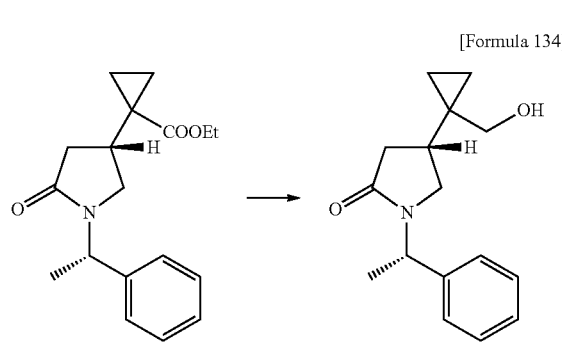 [SMILES: CCOC(=O)C1([C@H]2CC(=O)N([C@@H](C)c3ccccc3)C2)CC1 ; C[C@@H](c1ccccc1)N1C[C@@H](C2(CO)CC2)CC1=O]

[Formula 134]

Lithium borohydride (1.174 g, 53.90 mmol) was added to a solution of 1-[(3R)-5-oxo-1-[(1S)-1-phenylethyl]pyrrolidin-3-yl]cyclopropanecarboxylic acid ethyl ester [see Journal of Medicinal Chemistry, Vol. 46, No. 6, p. 1005 (2003)] (2.03 g, 6.74 mmol) in tetrahydrofuran (20 mL). The mixture was heated with stirring on an oil bath at 70° C. for 30 hours. After cooling to room temperature, the reaction solution was poured into an ice-cooled 10% citric acid solution (80 mL), followed by extraction with ethyl acetate (200 mL). The organic layer was washed with water (80 mL) and brine (80 mL), dried over anhydrous sodium sulfate, and then filtered, and the solvent was evaporated under reduced pressure. The resulting residue was purified by silica gel column chromatography (ethyl acetate:hexane=1:2→1:1→2:1→1:0→chloroform:methanol=9:1) to give 1.30 g (74%) of the title compound as a colorless transparent gummy solid.

$^1$H-NMR (400 MHz, CDCl$_3$) δ: 7.26-7.35 (5H, m), 5.48 (1H, q, J=6.9 Hz), 3.45 (2H, s), 3.04-3.12 (1H, m), 2.37-2.50 (2H, m), 2.19 (1H, dd, J=16.0, 8.9 Hz), 1.51 (2H, d, J=7.1 Hz), 0.43 (4H, s).

MS (ESI) m/z: 260 (M+H)$^+$.

Reference Example 58

(3R)-3-[1-(tert-Butyldiphenylsiloxymethyl)cyclopropan-1-yl]-5-oxo-1-[(1S)-1-phenylethyl]pyrrolidine

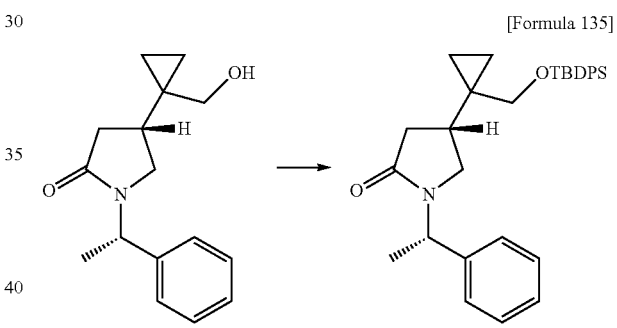

[Formula 135]

tert-Butyldiphenylsilyl chloride (2.83 ml, 10.88 mmol) was added to a solution of (3R)-3-[1-(hydroxymethyl)cyclopropan-1-yl]-5-oxo-1-[(1S)-1-phenylethyl]pyrrolidine (2.35 g, 9.06 mmol) and imidazole (925 mg, 13.59 mmol) in N,N-dimethylformamide (30 mL), and the mixture was stirred at room temperature for 20 hours. The reaction solution was diluted with ethyl acetate (150 mL), washed with water (50 mL×2) and brine (50 mL×2), dried over anhydrous sodium sulfate, and then filtered. The solvent was evaporated under reduced pressure. The resulting residue was purified by silica gel column chromatography (ethyl acetate:hexane=1:19→1:9→1:4→1:1) to give 3.88 g (86%) of the title compound as a colorless transparent gummy solid.

$^1$H-NMR (400 MHz, CDCl$_3$) δ: 7.56-7.59 (4H, m), 7.26-7.46 (11H, m), 5.48 (1H, q, J=7.0 Hz), 3.46 (1H, d, J=10.7 Hz), 3.39 (1H, d, J=10.7 Hz), 3.10 (2H, td, J=18.4, 9.6 Hz), 2.51 (1H, m), 2.32 (1H, dd, J=16.5, 8.9 Hz), 2.14 (1H, dd, J=16.5, 10.4 Hz), 1.46 (3H, d, J=7.1 Hz), 1.01 (9H, s), 0.33-0.39 (4H, m).

MS (ESI) m/z: 498 (M+H)$^+$.

Reference Example 59

(3R)-3-[1-(tert-Butyldiphenylsiloxymethyl)cyclopropan-1-yl]-5-oxo-1-[(1S)-1-phenylethyl]pyrrolidin-4-ylcarboxylic acid ethyl ester

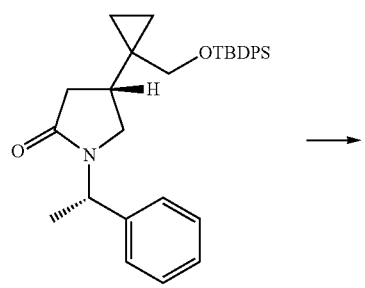

[Formula 136]

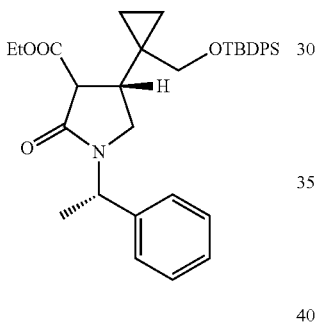

Ethyl chloroformate (0.059 mL, 0.617 mmol) and a solution of lithium hexamethyldisilazide in tetrahydrofuran (1.0 M, 0.57 mL, 0.570 mmol) were sequentially added dropwise to a solution of (3R)-3-[1-(tert-butyldiphenylsiloxymethyl)cyclopropan-1-yl]-5-oxo-1-[(1S)-1-phenylethyl]pyrrolidine (258 mg, 0.518 mmol) in tetrahydrofuran (2 mL) at 0° C. over two minutes. The mixture was stirred at 0° C. for 30 minutes and at room temperature for 30 minutes, and a solution of lithium hexamethyldisilazide in tetrahydrofuran (1.0 M, 0.57 mL, 0.570 mmol) was further added. The mixture was stirred at room temperature for 2.5 hours and then ice-cooled. The reaction was quenched with a 10% citric acid solution (20 mL). The resulting mixture was extracted with ethyl acetate (50 mL). The organic layer was washed with water (20 mL) and brine (20 mL) and then dried over anhydrous sodium sulfate. After filtration, the solvent was evaporated under reduced pressure. Then, the resulting residue was purified by silica gel column chromatography (ethyl acetate:hexane=1:9→1:4→1:2) to give 227 mg (77%) of the title compound as a colorless transparent gummy solid.

$^1$H-NMR (400 MHz, CDCl$_3$) δ: 7.54-7.64 (4H, m), 7.26-7.45 (11H, m), 5.46 (1H, q, J=6.9 Hz), 4.23 (1H, ddd, J=14.3, 7.1, 1.8 Hz), 3.29-3.52 (4H, m), 3.12 (1H, t, J=9.0 Hz), 2.65 (1H, dd, J=18.6, 8.5 Hz), 1.48 (2H, d, J=7.1 Hz), 1.29 (3H, t, J=7.1 Hz), 1.02 (9H, s), 0.33 (4H, m).

MS (ESI) m/z: 570 (M+H)$^+$.

Reference Example 60

(3R)-3-[1-(Hydroxymethyl)cyclopropan-1-yl]-5-oxo-1-[(1S)-1-phenylethyl]pyrrolidin-4-ylcarboxylic acid ethyl ester

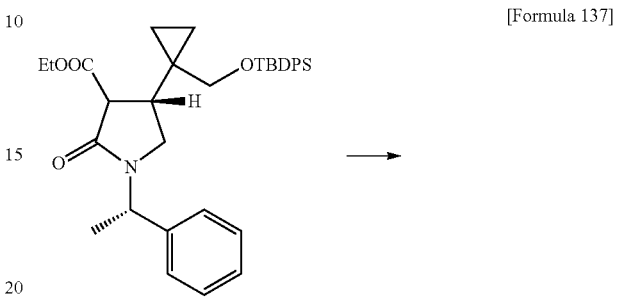

[Formula 137]

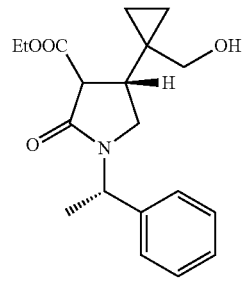

A hydrogen fluoride-pyridine complex (10 mL) was added dropwise to a solution of (3R)-3-[1-(tert-butyldiphenylsiloxymethyl)cyclopropan-1-yl]-5-oxo-1-[(1S)-1-phenylethyl]pyrrolidin-4-ylcarboxylic acid ethyl ester (2.81 g, 4.93 mmol) in pyridine (20 mL) at 0° C. over five minutes. The mixture was stirred at room temperature for 2.5 hours and then poured into ice water (150 mL), followed by extraction with ethyl acetate (300 mL). The resulting organic layer was washed with a 10% citric acid solution (100 mL), water (100 mL), and brine (100 mL) and then dried over anhydrous sodium sulfate. The solvent was evaporated under reduced pressure, and then the resulting residue was purified by silica gel column chromatography (ethyl acetate:hexane=1:2→1:1→2:1) to give 1.378 g (84%) of the title compound as a pale yellow gummy solid.

$^1$H-NMR (400 MHz, CDCl$_3$) δ: 7.26-7.36 (5H, m), 5.46 (1H, q, J=7.1 Hz), 4.25 (2H, q, J=7.2 Hz), 3.49 (2H, dd, J=23.2, 10.5 Hz), 3.36 (1H, d, J=11.7 Hz), 3.09 (2H, dt, J=20.8, 8.9 Hz), 2.67 (1H, q, J=8.5 Hz), 1.54 (3H, d, J=7.1 Hz), 1.31 (3H, t, J=7.1 Hz), 0.35-0.50 (4H, m).

MS (ESI) m/z: 332 (M+H)$^+$.

Reference Example 61

(3R)-3-[1-(Iodomethyl)cyclopropan-1-yl]-5-oxo-1-[(1S)-1-phenylethyl]pyrrolidin-4-ylcarboxylic acid ethyl ester

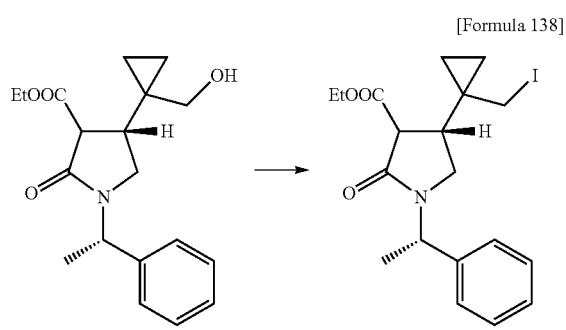 [SMILES: CCOC(=O)C1C(=O)N([C@@H](C)c2ccccc2)C[C@H]1C1(CO)CC1 ; CCOC(=O)C1C(=O)N([C@@H](C)c2ccccc2)C[C@H]1C1(CI)CC1]

[Formula 138]

Imidazole (708 mg, 10.40 mmol), triphenylphosphine (2.727 g, 10.40 mmol), and iodine (2.111 g, 8.32 mmol) were sequentially added to a solution of (3R)-3-[1-(hydroxymethyl)cyclopropan-1-yl]-5-oxo-1-[(1S)-1-phenylethyl]pyrrolidin-4-ylcarboxylic acid ethyl ester (1.378 g, 4.16 mmol) in dichloromethane (50 mL) at room temperature. The mixture was stirred at room temperature for 15 hours. The solvent was evaporated under reduced pressure. Then, the residue was dissolved in ethyl acetate (200 mL) and washed with water (50 mL×2) and brine (50 mL). After drying over anhydrous sodium sulfate and filtration, the solvent was evaporated under reduced pressure. The resulting residue was purified by silica gel column chromatography (ethyl acetate:hexane=1:9→1:4→1:2) to give 1.606 g (88%) of the title compound as a pale yellow gummy solid.

$^1$H-NMR (400 MHz, CDCl$_3$) δ: 7.26-7.39 (5H, m), 5.47 (1H, q, J=7.2 Hz), 4.28 (2H, q, J=7.2 Hz), 3.19-3.23 (2H, m), 3.03-3.12 (3H, m), 2.94 (1H, m), 1.54 (3H, d, J=7.1 Hz), 1.33 (3H, t, J=7.1 Hz), 0.80-0.87 (2H, m), 0.63 (2H, m).

MS (ESI) m/z: 442 (M+H)$^+$.

Reference Example 62

(1S,5S)-2-Oxo-3-[(1S)-1-phenylethyl]-6-spirocyclopropane-3-azabicyclo[3.2.0]heptan-1-ylcarboxylic acid ethyl ester

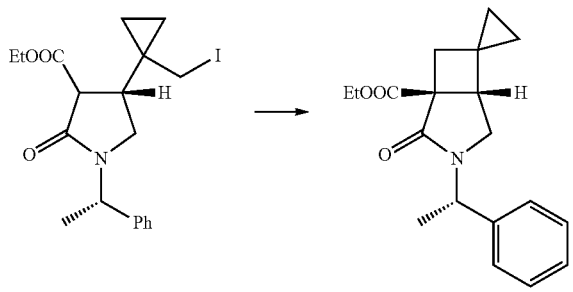

[Formula 139]

A solution of potassium hexamethyldisilazide in toluene (0.5 M, 8.94 mL, 4.47 mmol) was added dropwise to a solution of (3R)-3-[1-(iodomethyl)cyclopropan-1-yl]-5-oxo-1-[(1S)-1-phenylethyl]pyrrolidin-4-ylcarboxylic acid ethyl ester (1.517 g, 3.44 mmol) in toluene (30 mL) under salt-ice cooling over five minutes. The mixture was stirred at the same temperature for one hour and 20 minutes and then at room temperature for 5.5 hours. The reaction solution was ice-cooled and the reaction was quenched with a 10% citric acid solution (20 mL), followed by extraction with ethyl acetate (200 mL). The organic layer was washed with water (50 mL×2) and brine (50 mL). After drying over anhydrous sodium sulfate and filtration, the solvent was evaporated under reduced pressure. The resulting residue was purified by silica gel column chromatography (ethyl acetate:hexane=1:9→1:4→1:2) to give 717 mg (67%) of the title compound as a white solid.

$^1$H-NMR (400 MHz, CDCl$_3$) δ: 7.27-7.38 (5H, m), 5.61 (1H, q, J=7.1 Hz), 4.14-4.28 (2H, m), 3.02-3.07 (3H, m), 2.91 (1H, dt, J=9.8, 3.8 Hz), 2.29 (1H, d, J=12.2 Hz), 1.61 (3H, d, J=7.1 Hz), 1.28 (3H, t, J=7.2 Hz), 0.62 (2H, m), 0.44 (2H, m).

MS (ESI) m/z: 314 (M+H)$^+$.

Reference Example 63

(1R,5S)-3-[(1S)-1-Phenylethyl]-6-spirocyclopropane-2-thioxo-3-azabicyclo[3.2.0]heptan-1-ylcarboxylic acid ethyl ester

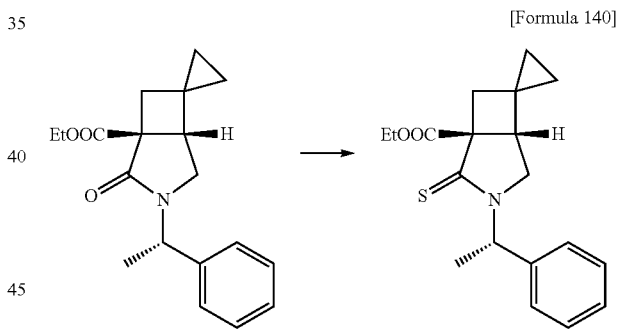

[Formula 140]

Lawesson's reagent (1.146 g, 2.83 mmol) was added to a solution of (1S,5S)-2-oxo-3-[(1S)-1-phenylethyl]-6-spirocyclopropane-3-azabicyclo[3.2.0]heptan-1-ylcarboxylic acid ethyl ester (592 mg, 1.89 mmol) in toluene (20 mL). The mixture was heated with stirring in a nitrogen atmosphere on an oil bath at 90° C. for 6.5 hours. The solvent was evaporated under reduced pressure, and then the residue was purified by silica gel column chromatography (ethyl acetate:hexane=1:19→1:9→1:4) to give 0.57 g (92%) of the title compound as a white solid.

$^1$H-NMR (400 MHz, CDCl$_3$) δ: 7.30-7.36 (5H, m), 6.40 (1H, q, J=7.1 Hz), 4.11-4.32 (2H, m), 3.33 (1H, dd, J=12.0, 6.8 Hz), 3.22 (2H, t, J=11.7 Hz), 3.09 (1H, d, J=6.3 Hz), 2.37 (1H, d, J=12.2 Hz), 1.68 (3H, d, J=7.1 Hz), 1.28 (3H, t, J=7.2 Hz), 0.58 (1H, m), 0.42 (2H, m).

MS (ESI) m/z: 330 (M+H)$^+$.

Reference Example 64

(1S,5S)-3-[(1S)-1-Phenylethyl]-6-spirocyclopropane-3-azabicyclo[3.2.0]heptan-1-ylcarboxylic acid ethyl ester

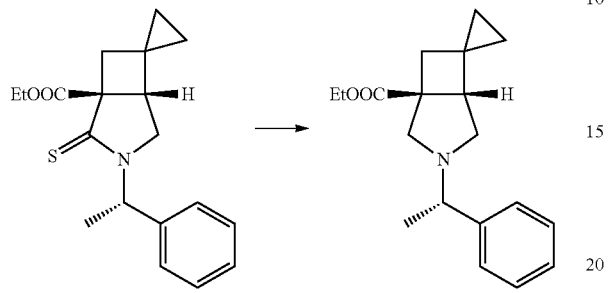

[Formula 141]

Raney nickel (4 mL) was added to a solution of (1R,5S)-3-[(1S)-1-phenylethyl]-6-spirocyclopropane-2-thioxo-3-azabicyclo[3.2.0]heptan-1-ylcarboxylic acid ethyl ester (0.57 g, 1.73 mmol) in ethanol (40 mL). The mixture was stirred in a nitrogen atmosphere at room temperature for 30 minutes. After filtration through Celite, the filtrate was concentrated under reduced pressure. The residue was dissolved in ethyl acetate and then filtered through a short silica gel column. The filtrate was evaporated under reduced pressure to give 503 mg (97%) of the title compound as a colorless oil.

$^1$H-NMR (400 MHz, CDCl$_3$) δ: 7.22-7.44 (5H, m), 4.20 (2H, q, J=7.0 Hz), 3.30 (1H, m), 3.24 (1H, d, J=8.8 Hz), 2.72 (1H, d, J=5.1 Hz), 2.59 (1H, d, J=11.5 Hz), 2.52 (1H, d, J=9.8 Hz), 2.45 (1H, d, J=8.8 Hz), 2.26 (1H, d, J=11.5 Hz), 1.95 (1H, dd, J=9.3, 5.6 Hz), 1.39 (3H, d, J=6.3 Hz), 1.29 (3H, t, J=7.1 Hz), 0.51 (1H, m), 0.31-0.40 (3H, m).

MS (ESI); m/z: 300 (M+H)$^+$.

Reference Example 65

(1S,5S)-3-Benzyloxycarbonyl-6-spirocyclopropane-3-azabicyclo[3.2.0]heptan-1-ylcarboxylic acid ethyl ester

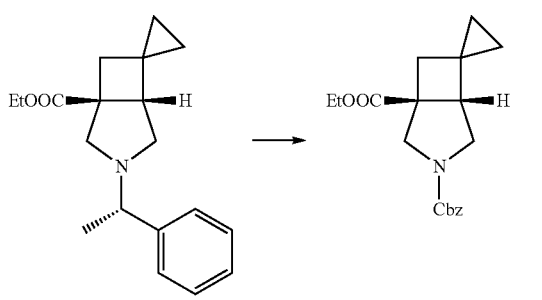

[Formula 142]

Benzyl chloroformate (0.72 mL, 5.04 mmol) was added to a solution of (1S,5S)-3-[(1S)-1-phenylethyl]-6-spirocyclopropane-3-azabicyclo[3.2.0]heptan-1-ylcarboxylic acid ethyl ester (503 mg, 1.68 mmol) in dichloromethane (10 mL). The mixture was stirred in a nitrogen atmosphere at room temperature for 16 hours. The solvent was evaporated under reduced pressure, and then the residue was purified by silica gel column chromatography (ethyl acetate:hexane=1:9→1:4→1:2) to give 505 mg (91%) of the title compound as a colorless oil.

$^1$H-NMR (400 MHz, CDCl$_3$) δ: 7.27-7.40 (5H, m), 5.18 (2H, m), 4.21 (2H, q, J=7.2 Hz), 3.92 (1H, dd, J=36.6, 12.0 Hz), 3.64 (2H, dd, J=23.3, 11.6 Hz), 3.27 (1H, m), 3.02 (1H, d, J=6.1 Hz), 2.73 (1H, m), 2.02 (1H, t, J=10.4 Hz), 1.29 (3H, t, J=7.1 Hz), 0.47-0.58 (3H, m), 0.32 (1H, m).

MS (ESI); m/z: 330 (M+H)$^+$.

Reference Example 66

(1S,5R)-3-Benzyloxycarbonyl-1-(tert-butoxycarbonylamino)-6-spirocyclopropane-3-azabicyclo[3.2.0]heptane

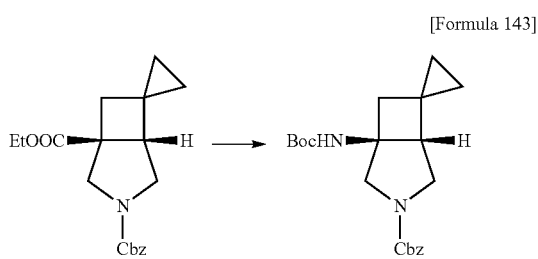 [SMILES: CCOC(=O)[C@]12CN(C(=O)OCc3ccccc3)C[C@H]1C1(CC1)C2 ; CC(C)(C)OC(=O)N[C@]12CN(C(=O)OCc3ccccc3)C[C@H]1C1(CC1)C2]

[Formula 143]

A 1N sodium hydroxide solution (4.60 mL, 4.60 mmol) was added to a solution of (1S,5S)-3-benzyloxycarbonyl-6-spirocyclopropane-3-azabicyclo[3.2.0]heptan-1-ylcarboxylic acid ethyl ester (500 mg, 1.52 mmol) in ethanol/tetrahydrofuran (4.6 mL/2.3 mL) at room temperature. The mixture was stirred at the same temperature for one hour. The solvent was evaporated under reduced pressure, and the residue was made acidic with 1N hydrochloric acid, followed by extraction with ethyl acetate (100 mL). The organic layer was dried over anhydrous sodium sulfate and then filtered. The solvent was evaporated under reduced pressure to give crude (1S,5S)-3-benzyloxycarbonyl-6-spirocyclopropane-3-azabicyclo[3.2.0]heptan-1-ylcarboxylic acid (501 mg) as a colorless transparent gummy solid.

Diphenylphosphoryl azide (0.393 mL, 1.82 mmol) was added to a solution of the resulting crude (1S,5S)-3-benzyloxycarbonyl-6-spirocyclopropane-3-azabicyclo[3.2.0]heptan-1-ylcarboxylic acid (501 mg) and triethylamine (0.381 mL, 2.73 mmol) in toluene (7.5 mL) at room temperature. The mixture was stirred in a nitrogen atmosphere at room temperature for five minutes and subsequently on an oil bath at 90° C. for 40 minutes. Next, tert-butyl alcohol (15 mL) was added to the reaction solution, and the mixture was heated with stirring on an oil bath at 120° C. for six hours. The reaction solvent was evaporated under reduced pressure, and then the resulting residue was purified by silica gel column chromatography (ethyl acetate:hexane=1:9→1:4→1:2) to give 347 mg (two steps, 61%) of the title compound as a colorless transparent gummy solid.

$^1$H-NMR (400 MHz, CDCl$_3$) δ: 7.28-7.39 (5H, m), 5.16 (2H, m), 4.90 (1H, m), 3.95 (1H, t, J=11.6 Hz), 3.41-3.58 (3H, m), 2.80 (1H, m), 2.34 (1H, t, J=10.3 Hz), 2.20 (1H, d, J=12.0 Hz), 1.45 (9H, s), 0.46-0.56 (3H, m), 0.28 (1H, m).

MS (ESI) m/z: 317 (M-tBu+H)$^+$.

Example 10

7-[(1S,5R)-1-Amino-6-spirocyclopropane-3-azabicyclo[3.2.0]heptan-3-yl]-1-[(1R,2S)-2-fluorocyclopropyl]-6-fluoro-1,4-dihydro-8-methoxy-4-oxoquinoline-3-carboxylic acid

[Formula 144]

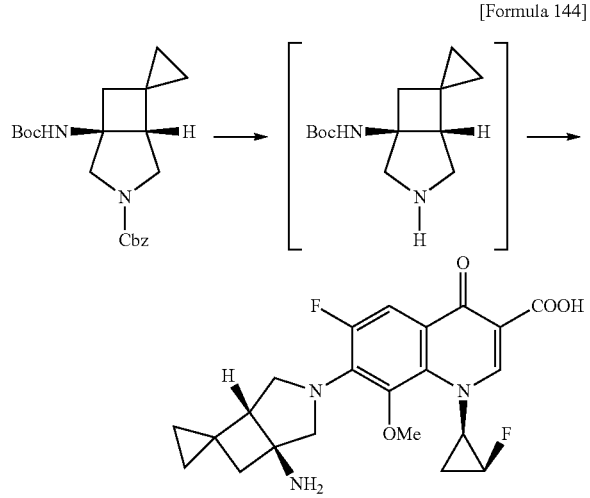

A 10% palladium-carbon catalyst (about 50% wet, 103 mg) was added to a solution of (1S,5R)-3-benzyloxycarbonyl-1-(tert-butoxycarbonylamino)-6-spirocyclopropane-3-azabicyclo[3.2.0]heptane (342 mg, 0.918 mmol) in methanol (30 mL), and the mixture was stirred in a hydrogen atmosphere at room temperature for 1.5 hours. The catalyst was removed by filtration, and then the solvent was evaporated under reduced pressure to give crude (1S,5R)-1-(tert-butoxycarbonylamino)-6-spirocyclopropane-3-azabicyclo[3.2.0]heptane (230 mg) as a colorless transparent gummy solid.

A mixture of the resulting crude (1S,5R)-1-(tert-butoxycarbonylamino)-6-spirocyclopropane-3-azabicyclo[3.2.0]heptane (230 mg), 6,7-difluoro-1-[(1R,2S)-2-fluorocyclopropyl]-1,4-dihydro-8-methoxy-4-oxoquinoline-3-carboxylic acid-$BF_2$ chelate (331 mg, 0.918 mmol), triethylamine (0.384 mL, 2.76 mmol), and dimethyl sulfoxide (3 mL) was stirred in a nitrogen atmosphere at room temperature for 17 hours. Next, ethanol (20 mL), water (5 mL), and triethylamine (2.5 mL) were added to the reaction solution, and the mixture was heated to reflux on an oil bath at 110° C. for three hours. The solvent was evaporated under reduced pressure, and then a 10% citric acid solution (50 mL) was added to the residue, followed by extraction with ethyl acetate (200 mL). The organic layer was washed with water (50 mL×2) and brine (50 mL) and dried over anhydrous sodium sulfate, and then the solvent was evaporated under reduced pressure. The resulting residue was dissolved in concentrated hydrochloric acid (20 mL). The resulting acidic solution was transferred to a separatory funnel and then washed with chloroform (20 mL×8). The aqueous layer was adjusted to pH 12.0 with a 10 mol/L sodium hydroxide solution under ice-cooling and then adjusted to pH 7.4 with hydrochloric acid, followed by extraction with a mixed solvent of chloroform:methanol=9:1 (200 mL×2). The organic layers were combined and dried over anhydrous sodium sulfate and filtered, and then the solvent was evaporated under reduced pressure. The resulting residue was purified by recrystallization from ethanol and dried under reduced pressure to give 125 mg (32%) of the title compound as a light pink powder.

mp: 182-203° C. (dec.).

$[\alpha]_D^{23.5}$=−14.4° (c=0.104, 0.1N NaOH).

$^1$H-NMR (400 MHz, 0.1N NaOD) δ: 8.48 (1H, d, J=1.2 Hz), 7.71 (1H, d, J=13.9 Hz), 4.98 (1H, dm, J=47.4 Hz), 4.03-4.08 (1H, m), 3.70-3.73 (1H, m), 3.70 (3H, s), 3.61 (1H, d, J=10.7 Hz), 3.37 (1H, m), 3.23 (1H, d, J=10.0 Hz), 2.42 (1H, d, J=5.9 Hz), 2.29 (1H, d, J=12.2 Hz), 2.16 (1H, d, J=12.5 Hz), 1.44-1.66 (2H, m), 0.48-0.57 (3H, m), 0.29-0.33 (1H, m).

Anal; Calcd for $C_{22}H_{23}F_2N_3O_4 \cdot 0.75H_2O \cdot 0.25HCl$: C, 58.19; H, 5.49; N, 9.25; F, 8.37; Cl, 1.95. Found: C, 57.93; H, 5.41; N, 9.15; F, 8.43; Cl, 2.44.

MS (FAB) m/z: 432 (M+H)$^+$.

HRMS (FAB) Calcd for $C_{22}H_{23}F_2N_3O_4$+H, 432.1735. Found: 432.1714.

IR (ATR) ν: 2871, 2763, 2721, 2575, 2517, 1720, 1612, 1568, 1535, 1493, 1456, 1365, 1350, 1321, 1267, 1205, 1157 cm$^{-1}$.

Reference Example 67

(1R*,5R*)-3-Benzyl-3-azabicyclo[3.3.0]octan-1-ylcarboxylic acid methyl ester

[Formula 145]

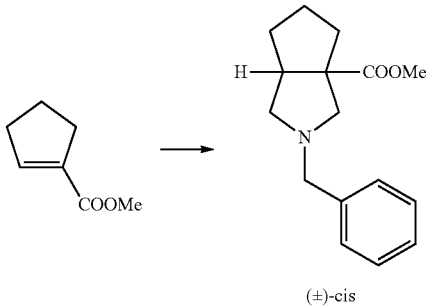

(±)-cis

A catalytic amount of trifluoroacetic acid was added to a solution of 1-cyclopentene-1-carboxylic acid methyl ester (2.52 g, 20.0 mmol) and N-benzyl-N-(methoxymethyl)-N-trimethylsilylmethylamine (5.00 g, 21.1 mmol) in dichloromethane (40 mL) at room temperature, and the mixture was heated with stirring at room temperature for 15.5 hours. The reaction solution was diluted with dichloromethane (100 mL) and washed with a saturated sodium bicarbonate solution (80 mL). The washed aqueous layer was further extracted with dichloromethane (50 mL). The organic layers were combined and dried over anhydrous sodium sulfate. After filtration, the solvent was evaporated under reduced pressure. The resulting residue was purified by silica gel column chromatography (hexane:ethyl acetate=95:5→90:10→80:20) to give 4.28 g (83%) of the title compound as a colorless transparent oil.

$^1$H-NMR (400 MHz, CDCl$_3$) δ: 7.33-7.21 (5H, m), 3.67 (3H, s), 3.58 (1H, d, J=13.2 Hz), 3.52 (1H, d, J=13.2 Hz), 2.92 (1H, d, J=9.3 Hz), 2.88 (1H, m), 2.67 (1H, t, J=8.2 Hz), 2.44 (1H, d, J=9.3 Hz), 2.31 (1H, dd, J=8.8, 4.4 Hz), 2.06-1.60 (5H, m), 1.54-1.47 (1H, m).

MS (ESI); m/z: 260 (M+H)$^+$.

Reference Example 68

(1R*,5R*)-3-Benzyloxycarbonyl-3-azabicyclo[3.3.0]octan-1-ylcarboxylic acid methyl ester

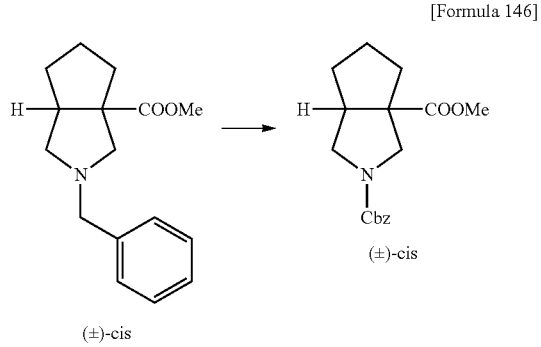 [SMILES: COC(=O)C12CCCC1CN(Cc1ccccc1)C2 ; COC(=O)C12CCCC1CN(C(=O)OCc1ccccc1)C2]

[Formula 146]

Benzyl chloroformate (3.53 mL, 24.6 mmol) was added to a solution of (1R*,5R*)-3-benzyl-3-azabicyclo[3.3.0]octan-1-ylcarboxylic acid methyl ester (4.27 g, 16.46 mmol) in dichloromethane (50 mL) at room temperature, and the mixture was stirred on an oil bath at 40° C. for 23 hours. The solvent was evaporated under reduced pressure, and then the residue was purified by silica gel column chromatography (hexane:ethyl acetate=90:10→80:20→67:33) to give 2.24 g (45%) of the title compound as a colorless transparent oil.

$^1$H-NMR (400 MHz, CDCl$_3$) δ: 7.38-7.28 (5H, m), 5.12 (2H, s), 3.97 (1H, d, J=11.7 Hz), 3.71-3.64 (4H, m), 3.45-3.28 (2H, m), 2.94-2.87 (1H, m), 2.23-2.15 (1H, m), 2.03-1.94 (1H, m), 1.85-1.71 (3H, m), 1.52 (1H, m).

MS (ESI) m/z: 304 (M+H)$^+$.

Reference Example 69

(1R*,5R*)-3-Benzyloxycarbonyl-1-(tert-butoxycarbonylamino)-3-azabicyclo[3.3.0]octane

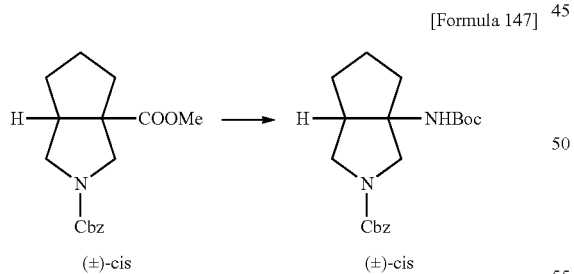

[Formula 147]

A 1N sodium hydroxide solution (22.0 mL, 22.0 mmol) was added to a solution of (1R*,5R*)-3-benzyloxycarbonyl-3-azabicyclo[3.3.0]octan-1-ylcarboxylic acid methyl ester (2.21 g, 7.29 mmol) in methanol (22 mL)-tetrahydrofuran (44 mL) at room temperature, and the mixture was stirred at room temperature for two hours. The solvent was concentrated under reduced pressure, and then the residue was made acidic with 3N hydrochloric acid, followed by extraction with ethyl acetate (200 mL). The resulting organic layer was dried over anhydrous sodium sulfate and filtered. Then, the solvent was evaporated under reduced pressure to give crude carboxylic acid. The resulting crude carboxylic acid was used for the next reaction without further purification.

Diphenylphosphoryl azide (2.03 mL, 9.42 mmol) was added to a solution of the crude carboxylic acid obtained above and triethylamine (2.02 mL, 14.5 mmol) in toluene (40 mL) under ice-cooling. The mixture was heated with stirring at room temperature for 30 minutes and then on an oil bath at 90° C. for 3.5 hours. The reaction solution was diluted with ethyl acetate (200 mL) and sequentially washed with a saturated sodium bicarbonate solution (80 mL), water (80 mL), and brine (80 mL). The resulting organic layer was dried over anhydrous sodium sulfate and filtered. Then, the solvent was evaporated under reduced pressure to give crude isocyanate. The resulting crude isocyanate was dissolved in 1,4-dioxane (20 mL), and 6N hydrochloric acid (20 mL) was added. Then, the mixture was heated with stirring on an oil bath at 50° C. for 0.5 hour. The reaction solution was diluted with water and ethanol, concentrated under reduced pressure, and then azeotropically distilled with ethanol (twice). The residue was dissolved in dichloromethane (40 mL), and triethylamine (5.05 mL, 36.3 mmol) and di-tert-butyl dicarbonate (3.17 g, 14.5 mmol) were sequentially added at room temperature. The reaction solution was stirred at room temperature for five hours, and then diluted with ethyl acetate (200 mL) and washed with water (80 mL) and brine (80 mL). The resulting organic layer was dried over anhydrous sodium sulfate and filtered. Then, the solvent was evaporated under reduced pressure. The resulting residue was purified by silica gel column chromatography (hexane:ethyl acetate=90:10→80:20→67:33) to give 1.32 g (3.66 mmol, 51%) of the title compound as a colorless transparent gummy solid.

$^1$H-NMR (400 MHz, CDCl$_3$) δ: 7.36-7.27 (5H, m), 5.12 (2H, s), 4.75 (1H, brs), 3.74-3.59 (3H, m), 3.31-3.23 (1H, m), 2.74-2.48 (1H, m), 2.04-1.88 (3H, m), 1.80-1.71 (2H, m), 1.43 (10H, m).

MS (ESI) m/z: 305 (M-tBu+H)$^+$.

Reference Example 70

(+)-(1R*,5S*)-3-Benzyloxycarbonyl-1-(tert-butoxycarbonylamino)-3-azabicyclo[3.3.0]octane and (−)-(1R*,5S*)-3-benzyloxycarbonyl-1-(tert-butoxycarbonylamino)-3-azabicyclo[3.3.0]octane

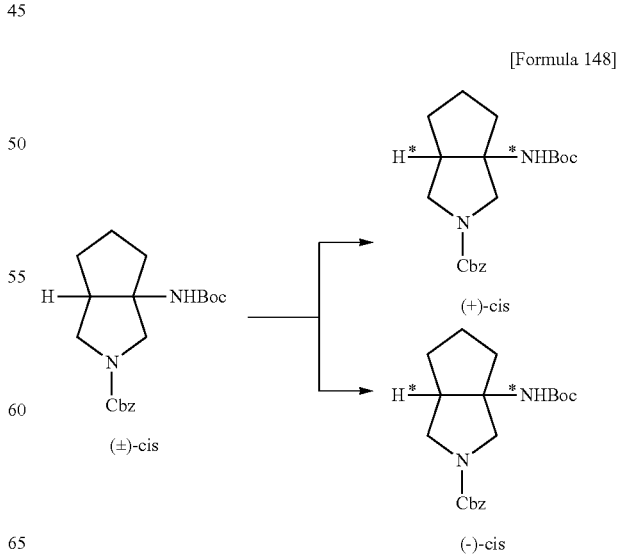

[Formula 148]

The racemate (1R*,5S*)-3-benzyloxycarbonyl-1-(tert-butoxycarbonylamino)-3-azabicyclo[3.3.0]octane (1.32 g, 3.66 mmol) obtained as described above was optically resolved by an optically active column (CHIRALCEL OJ, 20 mm diameter×250 mm, hexane:isopropyl alcohol=90:10, flow rate=20 mL/min, resolving 50 mg each time) to give (+)-(1R*,5S*)-3-benzyloxycarbonyl-1-(tert-butoxycarbonylamino)-3-azabicyclo[3.3.0]octane (586 mg, 1.626 mmol, retention time=5.5 min, $[\alpha]_D^{25.1}$=+19.3° (c=0.145, chloroform)) and (−)-(1R*,5S*)-3-benzyloxycarbonyl-1-(tert-butoxycarbonylamino)-3-azabicyclo[3.3.0]octane (590 mg, 1.637 mmol, retention time=6.9 min, $[\alpha]_D^{25.1}$=−20.0° (c=0.155, chloroform).

Example 11

7-{(1R*,5S*)-1-Amino-3-azabicyclo[3.3.0]octan-3-yl}-6-fluoro-1-[(1R,2S)-2-fluorocyclopropyl]-8-methoxy-1,4-dihydro-4-oxoquinoline-3-carboxylic acid [7-position substituent derived from (+)-optical isomer]

[Formula 149]

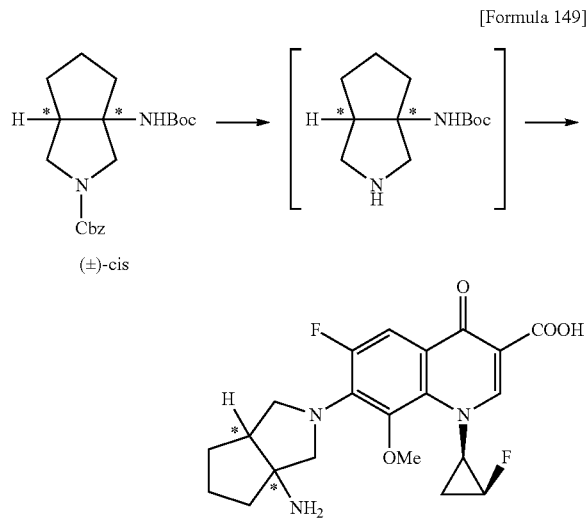

A 10% palladium-carbon catalyst (about 50% wet, 115 mg) was added to a solution of (+)-(1R*,5S*)-3-benzyloxycarbonyl-1-(tert-butoxycarbonylamino)-3-azabicyclo[3.3.0]octane (575 mg, 1.595 mmol) in methanol (20 mL), and the mixture was stirred in a hydrogen atmosphere at room temperature for two hours. The catalyst was removed by filtration, and then the solvent was evaporated under reduced pressure to give crude 1-(tert-butoxycarbonylamino)-3-azabicyclo[3.3.0]octane (388 mg) as a colorless transparent gummy solid.

The crude 1-(tert-butoxycarbonylamino)-3-azabicyclo[3.3.0]octane obtained above (388 mg), 6,7-difluoro-1-[(1R,2S)-2-fluorocyclopropyl]-1,4-dihydro-8-methoxy-4-oxoquinoline-3-carboxylic acid-BF₂ chelate (576 mg, 1.595 mmol), and triethylamine (0.667 mL, 4.79 mmol) were dissolved in dimethyl sulfoxide (4 mL), and the solution was heated with stirring on an oil bath at 35 to 40° C. for 16 hours. A mixed solution of ethanol:water=4:1 (50 mL) and triethylamine (5 mL) was added to the reaction solution, and the mixture was heated to reflux on an oil bath at 90° C. for three hours. The reaction solution was concentrated under reduced pressure. The residue was dissolved in ethyl acetate (200 mL) and washed with a 10% citric acid solution (80 mL), water (50 mL×2), and brine (50 mL). The organic layer was dried over anhydrous sodium sulfate and filtered, and then the solvent was evaporated under reduced pressure. The resulting residue was dissolved in concentrated hydrochloric acid (10 mL) under ice-cooling. After stirring at room temperature for 20 minutes, the reaction solution was washed with chloroform (30 mL×3). The aqueous layer was adjusted to pH 12.0 with a 10 mol/L sodium hydroxide solution under ice-cooling and then adjusted to pH 7.4 with hydrochloric acid. Thereafter, the solvent was evaporated under reduced pressure. The residue was suspended in methanol and filtered. Then, the filtrate was concentrated under reduced pressure (twice), suspended in a mixed solvent of chloroform:methanol=9:1 subsequently, and filtered. The mother liquor was concentrated under reduced pressure to remove sodium chloride. The resulting residue was purified by PTLC (preparative TLC; lower layer solvent of chloroform:methanol:water=7:3:1) and subsequently purified by recrystallization from ethanol-aqueous ammonia to give 111 mg (17%) of the title compound as a pale yellow powder.

mp: 169-172° C.

$[\alpha]_D^{25.1}$=+103.5° (c=0.228, 0.1N NaOH).

¹H-NMR (400 MHz, 0.1N NaOD) δ: 8.47 (1H, s), 7.68 (1H, d, J=13.9 Hz), 5.05-4.80 (1H, m), 4.04 (1H, m), 3.77 (1H, t, J=9.0 Hz), 3.63 (3H, s), 3.52 (2H, s), 3.35 (1H, dd, J=9.8, 4.9 Hz), 2.30 (1H, m), 2.04 (1H, m), 1.89-1.47 (7H, m).

Anal; Calcd for $C_{21}H_{23}F_2N_3O_4 \cdot 0.25EtOH \cdot 0.75H_2O$: C, 58.10; H, 5.90; F, 8.55; N, 9.45. Found: C, 57.87; H, 5.51; F, 8.60; N, 9.11.

MS (EI); m/z: 419 (M⁺).

IR (ATR) ν: 2952, 2873, 2831, 2177, 1712, 1614, 1577, 1535, 1498, 1460, 1389, 1360, 1323, 1271, 1205 cm⁻¹.

Example 12

7-[(1R*,5S*)-1-Amino-3-azabicyclo[3.3.0]octan-3-yl]-6-fluoro-1-[(1R,2S)-2-fluorocyclopropyl]-8-methoxy-1,4-dihydro-4-oxoquinoline-3-carboxylic acid [7-Position Substituent Derived from (−)-Optical Isomer]

[Formula 150]

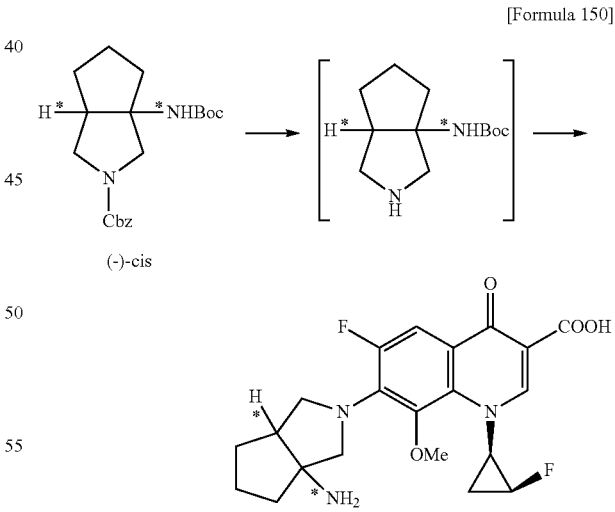

A 10% palladium-carbon catalyst (about 50% wet, 114 mg) was added to a solution of (−)-(1R*,5S*)-3-benzyloxycarbonyl-1-(tert-butoxycarbonylamino)-3-azabicyclo[3.3.0]octane (569 mg, 1.579 mmol) in methanol (30 mL), and the mixture was stirred in a hydrogen atmosphere at room temperature for two hours. The catalyst was removed by filtration, and then the solvent was evaporated under reduced pressure to give crude 1-(tert-butoxycarbonylamino)-3-azabicyclo[3.3.0]octane (373 mg) as a colorless transparent gummy solid.

The crude 1-(tert-butoxycarbonylamino)-3-azabicyclo[3.3.0]octane obtained above (373 mg), 6,7-difluoro-1-[(1R,2S)-2-fluorocyclopropyl]-1,4-dihydro-8-methoxy-4-oxoquinoline-3-carboxylic acid-BF$_2$ chelate (570 mg, 1.579 mmol), and triethylamine (0.660 mL, 4.74 mmol) were dissolved in dimethyl sulfoxide (4 mL), and the solution was heated with stirring on an oil bath at 35 to 40° C. for 16 hours. A mixed solution of ethanol:water=4:1 (50 mL) and triethylamine (5 mL) was added to the reaction solution, and the mixture was heated to reflux on an oil bath at 90° C. for three hours. The reaction solution was concentrated under reduced pressure. The residue was dissolved in ethyl acetate (200 mL) and washed with a 10% citric acid solution (80 mL), water (50 mL×2), and brine (50 mL). The organic layer was dried over anhydrous sodium sulfate and filtered, and then the solvent was evaporated under reduced pressure. The resulting residue was dissolved in concentrated hydrochloric acid (10 mL) under ice-cooling. After stirring at room temperature for 20 minutes, the reaction solution was washed with chloroform (30 mL×3). The aqueous layer was adjusted to pH 12.0 with a 10 mol/L sodium hydroxide solution under ice-cooling and then adjusted to pH 7.4 with hydrochloric acid. Thereafter, the solvent was evaporated under reduced pressure. The residue was suspended in methanol:aqueous ammonia=20:1 and filtered. Then, the filtrate was concentrated under reduced pressure (twice), and subsequently suspended in a mixed solvent of chloroform:methanol=9:1 and filtered. The mother liquor was concentrated under reduced pressure to remove sodium chloride. The resulting residue was purified by PTLC (lower layer solvent of chloroform:methanol:water=7:3:1) and crystallized in ethanol-diethyl ether to give 32 mg (5%) of the title compound as a yellow brown powder.

mp: 171-174° C.

$[\alpha]_D^{25.1}$=+52.1° (c=0.073, 0.1NNaOH).

$^1$H-NMR (400 MHz, 0.1N NaOD) δ: 8.47 (1H, s), 7.65 (1H, d, J=13.9 Hz), 5.02-4.82 (1H, m), 4.00 (1H, m), 3.86-3.80 (1H, m), 3.62-3.55 (4H, m), 3.36-3.31 (1H, m), 3.15-3.10 (1H, m), 2.24 (1H, m), 2.05-1.30 (8H, m).

Anal; Calcd for C$_{21}$H$_{23}$F$_2$N$_3$O$_4$·0.5EtOH·1.25H$_2$O: C, 56.83; H, 6.18; F, 8.17; N, 9.04. Found: C, 56.41; H, 5.68; F, 8.76; N, 8.64.

MS (EI); m/z: 419 (M$^+$).

IR (ATR) ν: 2948, 2871, 2576, 2162, 1712, 1616, 1566, 1495, 1456, 1390, 1363, 1319, 1269 cm$^{-1}$.

Reference Example 71

(3S)-3-[3-(tert-Butyldimethylsilyloxy)-1-propyl]-5-oxo-1-[(1R)-1-phenylethyl]pyrrolidine-3-carboxylic acid tert-butyl ester

[Formula 151]

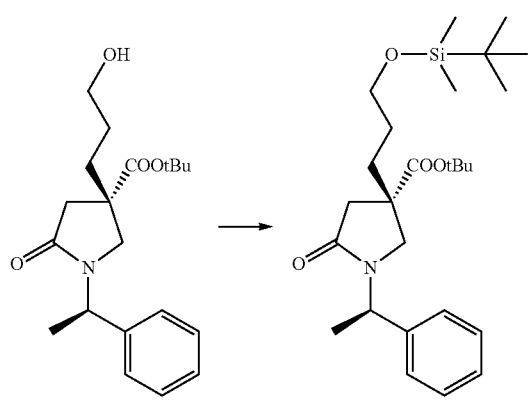

(3S)-3-(3-Hydroxy-1-propyl)-5-oxo-1-[(1R)-1-phenylethyl]pyrrolidine-3-carboxylic acid tert-butyl ester (46 g) and imidazole (11.9 g) were dissolved in dimethylformamide (600 mL). After addition of tert-butyldimethylsilyl chloride (23.2 g) under ice-cooling, the mixture was stirred at room temperature for 59.5 hours. The reaction solution was extracted with a 10% citric acid solution and ethyl acetate. Then, the organic layer was sequentially washed with saturated sodium bicarbonate water and brine, dried over anhydrous sodium sulfate, and filtered. Thereafter, the solvent was evaporated under reduced pressure. The residue was subjected to silica gel column chromatography (hexane:ethyl acetate=9:1→8:2→2:1) to give 29.7 g of the title compound as a pale yellow oil.

$^1$H-NMR (400 MHz, CDCl$_3$) δ: 7.37-7.22 (5H, m), 5.48 (1H, q, J=7.11 Hz), 3.58 (2H, t, J=6.13 Hz), 3.34 (1H, d, J=10.05 Hz), 3.12 (1H, d, J=10.05 Hz), 2.94 (1H, d, J=16.91 Hz), 2.31 (1H, d, J=17.16 Hz), 1.86-1.74 (1H, m), 1.72-1.62 (1H, m), 1.51 (3H, d, J=7.11 Hz), 1.49-1.24 (2H, m), 1.33 (9H, s), 0.88 (9H, s), 0.03 (6H, s).

Reference Example 72

(3S)-3-[3-(tert-Butyldimethylsilyloxy)-1-propyl]-4-fluoro-5-oxo-1-[(1R)-1-phenylethyl]pyrrolidine-3-carboxylic acid tert-butyl ester

[Formula 152]

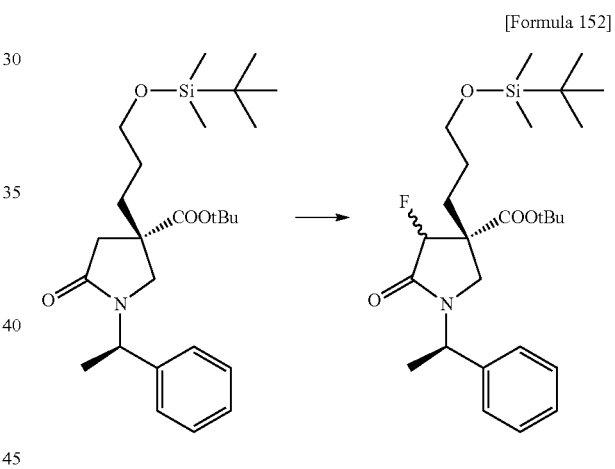

(3S)-3-[3-(tert-Butyldimethylsilyloxy)-1-propyl]-5-oxo-1-[(1R)-1-phenylethyl]pyrrolidine-3-carboxylic acid tert-butyl ester (30 g) was dissolved in tetrahydrofuran (280 mL), and the atmosphere was replaced with argon. Then, lithium hexamethyldisilazide (1.0 M solution in tetrahydrofuran) (78.0 mL) was added dropwise at −15° C., and the mixture was stirred at −5° C. for 30 minutes. After cooling to −15° C. again, a solution of N-fluorobenzenesulfonimide (26.6 g) in tetrahydrofuran (220 mL) was added dropwise, and the mixture was stirred at room temperature for 17 hours. The reaction solution was extracted with a 10% citric acid solution and ethyl acetate. Then, the organic layer was washed with brine, dried over anhydrous sodium sulfate, and filtered. Thereafter, the solvent was evaporated under reduced pressure. The residue was subjected to silica gel column chromatography (hexane:ethyl acetate=9:1→8:2) to give 8.15 g of the title compound as a pale yellow solid.

$^1$H-NMR (400 MHz, CDCl$_3$) δ: 7.37-7.23 (5H, m), 5.53-5.44 (1H, m), 5.18 (1H, d, J=51.72 Hz), 3.64-3.52 (2H, m), 3.32-3.19 (2H, m), 1.92-1.65 (2H, m), 1.55 (3H, d, J=4.66 Hz), 1.33 (9H, s), 0.88 (9H, s), 0.03 (6H, s). MS (FAB) m/z: 480 (M+H)$^+$.

IR (ATR) ν: 3421, 2977, 2935, 2877, 1698, 1454, 1369, 1309, 1249, 1153, 1058, 1035, 1006, 842 cm$^{-1}$.

Reference Example 73

(3S)-4-Fluoro-3-(3-hydroxy-1-propyl)-5-oxo-1-[(1R)-1-phenylethyl]pyrrolidine-3-carboxylic acid tert-butyl ester

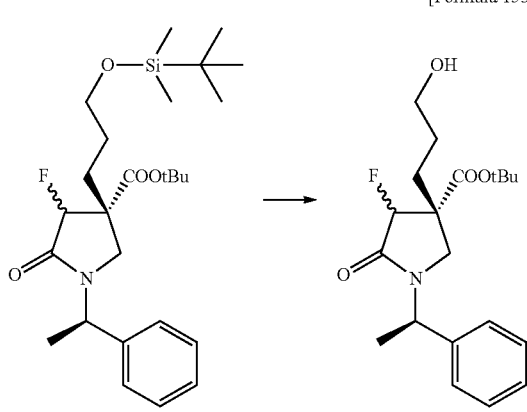

[Formula 153]

(3S)-3-[3-(tert-Butyldimethylsilyloxy)-1-propyl]-4-fluoro-5-oxo-1-[(1R)-1-phenylethyl]pyrrolidine-3-carboxylic acid tert-butyl ester (8.15 g) was dissolved in tetrahydrofuran (25.0 mL). Acetic acid (22.0 mL) and tetrabutylammonium fluoride (1.0 M solution in tetrahydrofuran) (25.0 mL) were added under ice-cooling, and the mixture was stirred at room temperature for 21.5 hours. The reaction solution was extracted with a 10% citric acid solution and ethyl acetate. Then, the organic layer was sequentially washed with saturated sodium bicarbonate water and brine, dried over anhydrous sodium sulfate, and filtered. Thereafter, the solvent was evaporated under reduced pressure. The residue was subjected to silica gel column chromatography (hexane:ethyl acetate=9:1→8:2→1:1) to give 5.77 g of the title compound as a pale yellow oil.

$^1$H-NMR (400 MHz, CDCl$_3$) δ: 7.37-7.22 (5H, m), 5.48 (1H, q, J=7.03 Hz), 5.20 (1H, d, J=51.48 Hz), 3.69-3.59 (2H, m), 3.31-3.21 (2H, m), 1.95-1.72 (2H, m), 1.68-1.43 (2H, m), 1.56 (3H, d, J=7.11 Hz), 1.33 (9H, s).

Reference Example 74

(3S)-3-(3-benzenesulfonyloxy-1-propyl)-4-Fluoro-5-oxo-1-[(1R)-1-phenylethyl]pyrrolidine-3-carboxylic acid tert-butyl ester

[Formula 154]

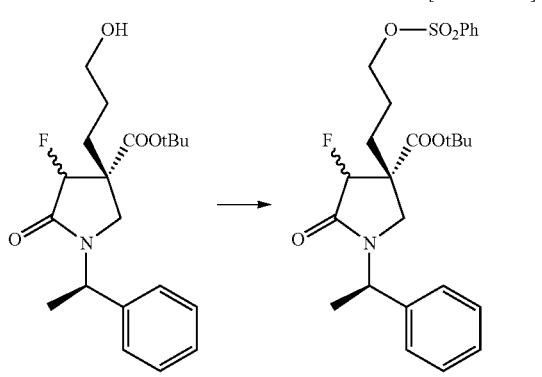

(3S)-4-Fluoro-3-(3-hydroxy-1-propyl)-5-oxo-1-[(1R)-1-phenylethyl]pyrrolidine-3-carboxylic acid tert-butyl ester (12.20 g) was dissolved in dichloromethane (400 mL). Benzenesulfonyl chloride (9.06 mL), triethylamine (10.7 mL), and 4-dimethylaminopyridine (2.04 g) were added under ice-cooling, and the mixture was stirred at room temperature for 12.5 hours. Saturated sodium bicarbonate water was added to the reaction solution, and the mixture was stirred for 30 minutes, followed by extraction with dichloromethane. The organic layer was sequentially washed with a 10% citric acid solution and brine, dried over anhydrous sodium sulfate, and filtered. Thereafter, the solvent was evaporated under reduced pressure. The residue was subjected to silica gel column chromatography (hexane:ethyl acetate=8:2→1:1) to give 11.7 g of the title compound as a pale yellow oil.

$^1$H-NMR (400 MHz, CDCl$_3$) δ: 7.94-7.87 (2H, m), 7.71-7.63 (1H, m), 7.60-7.53 (2H, m), 7.37-7.23 (5H, m), 5.46 (1H, q, J=7.11 Hz), 5.15 (1H, d, J=51.48 Hz), 4.10-3.98 (2H, m), 3.26-3.15 (2H, m), 1.88-1.50 (4H, m), 1.55 (3H, s), 1.30 (9H, s).

Reference Example 75

(1S,5R)-5-Fluoro-4-oxo-3-[(1R)-1-phenylethyl]-3-azabicyclo[3.3.0]octan-1-ylcarboxylic acid tert-butyl ester

[Formula 155]

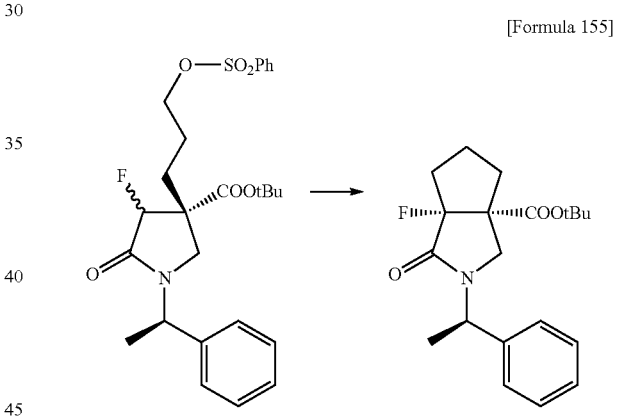

(3S)-3-(3-benzenesulfonyloxy-1-propyl)-4-Fluoro-5-oxo-1-[(1R)-1-phenylethyl]pyrrolidine-3-carboxylic acid tert-butyl ester (10.9 g) was dissolved in tetrahydrofuran (350 mL), and the atmosphere was replaced with argon. Then, potassium hexamethyldisilazide (0.5 M solution in toluene) (86.5 mL) was added dropwise at −15° C., and the mixture was stirred at 0° C. for 1.5 hours. After cooling to −10° C., saturated aqueous ammonium chloride (100 mL) was added dropwise, and the mixture was stirred at room temperature for 30 minutes. The reaction solution was extracted with a 10% citric acid solution and ethyl acetate. Then, the organic layer was washed with brine, dried over anhydrous sodium sulfate, and filtered. Thereafter, the solvent was evaporated under reduced pressure. The residue was subjected to silica gel column chromatography (hexane:ethyl acetate=9:1→7:1) to give 4.36 g of the title compound as a pale yellow solid.

$^1$H-NMR (400 MHz, CDCl$_3$) δ: 7.38-7.25 (5H, m), 5.58-5.49 (1H, m), 3.63 (1H, d, J=10.3 Hz), 2.91 (1H, dd, J=10.3, 3.2 Hz), 2.67-2.56 (1H, m), 2.50-2.38 (1H, m), 2.26-2.09 (1H, m), 2.06-1.94 (1H, m), 1.74-1.66 (1H, m), 1.54 (3H, d, J=7.1 Hz), 1.50-1.40 (1H, m), 1.34 (9H, s).

Reference Example 76

(1R,5R)-1-(tert-Butoxycarbonylamino)-5-fluoro-4-oxo-3-[(1R)-1-phenylethyl]-3-azabicyclo[3.3.0]octane

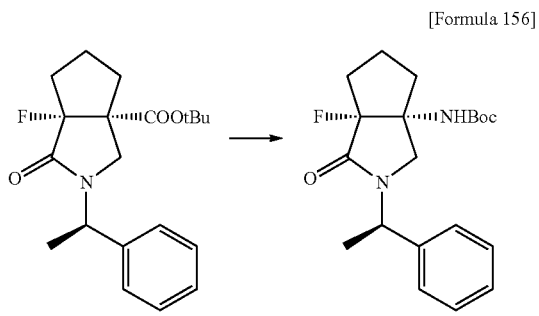

[Formula 156]

(1S,5R)-5-Fluoro-4-oxo-3-[(1R)-1-phenylethyl]-3-azabicyclo[3.3.0]octan-1-ylcarboxylic acid tert-butyl ester (4.36 g, 12.5 mmol) was dissolved in dichloromethane (70 mL). Trifluoroacetic acid (70 mL) was added dropwise, and the mixture was stirred at room temperature for six hours. The solvent was evaporated under reduced pressure, and then the residue was azeotropically distilled with toluene to give carboxylic acid (3.70 g).

The resulting carboxylic acid was dissolved in toluene. Triethylamine (3.51 mL, 25.2 mmol) and diphenylphosphoryl azide (2.98 ml, 13.8 mmol) were added, and the mixture was heated to reflux for five hours. The solvent was evaporated under reduced pressure. Then, 1,4-dioxane (110 ml) and 6N hydrochloric acid (110 mL) were added to the residue, and the mixture was stirred at 60° C. for 2.5 hours. After extraction with water and ethyl acetate, the aqueous layer was made alkaline with a saturated sodium hydroxide solution and extracted with chloroform twice. The organic layers were combined, dried over anhydrous sodium sulfate, and filtered, and then the solvent was evaporated under reduced pressure. Di-tert-butyl dicarbonate (11.05 g) was added to the residue, and the mixture was stirred at 75° C. for six hours. The reaction solution was concentrated under reduced pressure, and then the residue was subjected to silica gel column chromatography (hexane:ethyl acetate=9:1→1:1) to give 3.69 g of the title compound as a pale yellow oil.

$^1$H-NMR (400 MHz, CDCl$_3$) δ: 7.37-7.23 (5H, m), 5.50 (1H, q, J=7.1 Hz), 5.22 (1H, brs), 3.34 (2H, s), 2.49-2.37 (1H, m), 2.32-2.03 (3H, m), 2.02-1.90 (1H, m), 1.51 (3H, d, J=7.1 Hz), 1.55-1.48 (1H, m), 1.35 (9H, s).

Reference Example 77

(1R,5S)-1-(tert-Butoxycarbonylamino)-5-fluoro-3-[(1R)-1-phenylethyl]-3-azabicyclo[3.3.0]octane

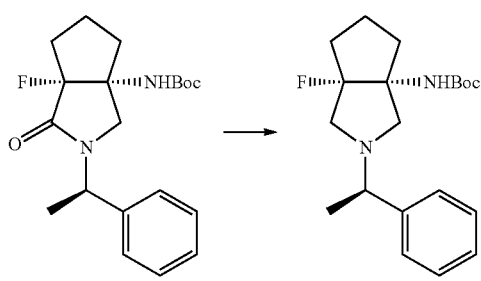

[Formula 157]

(1R,5R)-1-(tert-Butoxycarbonylamino)-5-fluoro-4-oxo-3-[(1R)-1-phenylethyl]-3-azabicyclo[3.3.0]octane (3.69 g, 10.2 mmol) was dissolved in tetrahydrofuran (200 mL). A 1.20 M solution of a borane-tetrahydrofuran complex in tetrahydrofuran (42.4 mL, 50.9 mmol) was added dropwise under ice-cooling, and the mixture was stirred for two hours while gradually heating to room temperature. The solvent was evaporated under reduced pressure. Under ice-cooling, 90% aqueous ethanol (100 mL) and triethylamine (100 mL) were added to the residue, and the mixture was heated to reflux for two hours. The solvent was evaporated under reduced pressure, and then the residue was extracted with saturated sodium bicarbonate water and dichloromethane. Thereafter, the target substance was extracted from the aqueous layer with dichloromethane. The organic layers were combined, washed with brine, and dried over anhydrous sodium sulfate. After filtration, the solvent was evaporated under reduced pressure, and the resulting residue was subjected to silica gel column chromatography (hexane:ethyl acetate=95:5→90:10) to give 3.33 g of the title compound as a pale yellow oil.

$^1$H-NMR (400 MHz, CDCl$_3$) δ: 7.32-7.18 (5H, m), 5.38 (1H, brs), 3.22 (1H, q, J=6.37 Hz), 2.92-2.57 (4H, m), 2.12-1.86 (4H, m), 1.80-1.67 (1H, m), 1.63-1.52 (3H, m), 1.42 (9H, s), 1.32 (3H, d, J=6.37 Hz).

Reference Example 78

(1R,5S)-1-(tert-Butoxycarbonylamino)-5-fluoro-3-azabicyclo[3.3.0]octane

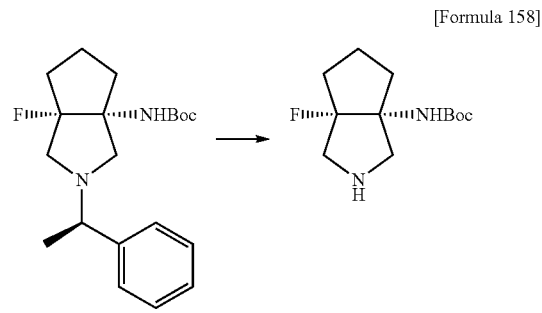 [SMILES: C[C@H](c1ccccc1)N1C[C@@]2(F)CCC[C@@]2(NC(=O)OC(C)(C)C)C1 ; CC(C)(C)OC(=O)N[C@@]12CCC[C@]1(F)CNC2]

[Formula 158]

(1R,5S)-1-(tert-Butoxycarbonylamino)-5-fluoro-3-[(1R)-1-phenylethyl]-3-azabicyclo[3.3.0]octane (700 mg, 2.0 mmol) was dissolved in ethanol (30 mL). 10% palladium-carbon (50% wet) (1.01 g) was added, and the mixture was stirred in a hydrogen atmosphere at 50° C. for 15 hours. The catalyst was removed by filtration, and then the filtrate was concentrated under reduced pressure. The resulting residue was subjected to silica gel column chromatography (dichloromethane:methanol=98:2→95:5) to give 446 mg of the title compound as a pale yellow solid.

$[α]_D^{23}$ −15° (c=0.100, MeOH).

$^1$H-NMR (400 MHz, CDCl$_3$) δ: 5.29 (1H, brs), 3.47-3.18 (2H, m), 2.93-2.79 (2H, m), 2.15-1.71 (6H, m), 1.45 (9H, s).

Example 13

10-[(1R,5S)-1-Amino-5-fluoro-3-azabicyclo[3.3.0]octan-3-yl]-9-fluoro-2,3-dihydro-3-(S)-methyl-7-oxo-7H-pyrido[1,2,3-de][1,4]benzoxazine-6-carboxylic acid

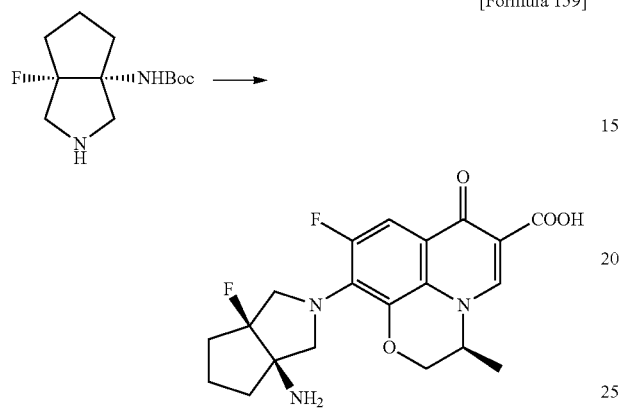

[Formula 159]

Triethylamine (0.222 mL, 1.59 mmol) and 9,10-difluoro-2,3-dihydro-3-(S)-methyl-7-oxo-7H-pyrido[1,2,3-de][1,4]benzoxazine-6-carboxylic acid-$BF_2$ chelate (209 mg, 0.64 mmol) were added to a solution of (1R,5S)-1-(tert-butoxycarbonylamino)-5-fluoro-3-azabicyclo[3.3.0]octane (129 mg, 0.53 mmol) in dimethyl sulfoxide (4.0 mL). The mixture was stirred at 40° C. for 18.5 hours. Triethylamine (0.111 mL, 0.80 mmol) was further added to the reaction solution, and the mixture was stirred at 40° C. for 6.5 hours. Ethanol (6.0 mL), water (2.0 mL), and triethylamine (2.0 mL) were added to the reaction solution, and the mixture was heated to reflux for 1.5 hours. The solvent was evaporated under reduced pressure, and then the residue was extracted with a 10% citric acid solution and ethyl acetate. Then, the organic layer was washed with water twice and brine, dried over anhydrous sodium sulfate, and filtered. Thereafter, the solvent was evaporated under reduced pressure. The residue was subjected to silica gel column chromatography (dichloromethane:methanol=99:1→98:2) to give an oil (261 mg). The resulting oil (261 mg) was dissolved in concentrated hydrochloric acid (2.4 ml) under ice-cooling, and the solution was stirred at room temperature for three hours. The reaction solution was washed with chloroform twice, and then the aqueous layer was adjusted to pH 12 with a saturated sodium hydroxide solution. The basic solution was adjusted to pH 7.4 with hydrochloric acid, followed by extraction with chloroform. The organic layer was dried over anhydrous sodium sulfate and filtered, and then the solvent was evaporated under reduced pressure. 10% methanol-chloroform was added to the residue. After filtration, the filtrate was concentrated under reduced pressure. The residue was purified by recrystallization from ethanol-aqueous ammonia to give 145 mg of the title compound as a pale yellow solid.

mp: 285-293° C. (dec.).
$[\alpha]_D^{24}$ −40.3° (c=0.100, 0.1NNaOH).
$^1$H-NMR (400 MHz, 0.1N NaOD) δ: 8.48 (1H, d, J=1.23 Hz), 7.70 (1H, d, J=13.7 Hz), 5.07-4.85 (1H, m), 4.10-4.02 (1H, m), 3.93-3.78 (2H, m), 3.70-3.53 (2H, m), 3.66 (3H, s), 2.21-2.04 (2H, m), 2.01-1.83 (2H, m), 1.83-1.46 (4H, m).

MS (FAB) m/z: 406 (M+H)$^+$. Anal. Calcd $C_{20}H_{21}F_2N_3O_4$: C, 59.25; H, 5.22; F, 9.37; N, 10.37.
Found: C, 59.22; H, 5.16; F, 9.16; N, 10.27.
IR (ATR) ν: 3365, 2931, 2861, 1706, 1619, 1521, 1461, 1442, 1415, 1396, 1278, 1230, 1141, 1130, 1093, 1047, 983, 964, 900, 879, 863, 800 cm$^{-1}$.

Example 14

7-[(1R,5S)-1-Amino-5-fluoro-3-azabicyclo[3.3.0]octan-3-yl]-8-cyano-6-fluoro-1-[(1R,2S)-2-fluorocyclopropan-1-yl]-1,4-dihydro-4-oxoquinoline-3-carboxylic acid

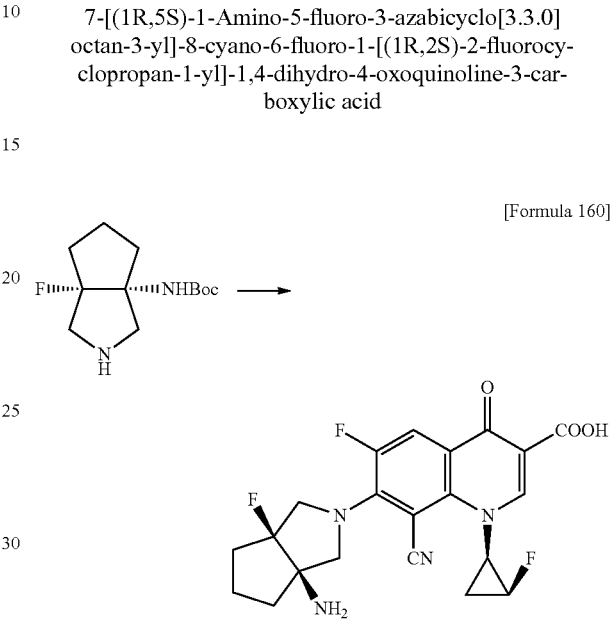

[Formula 160]

Triethylamine (0.272 mL, 1.95 mmol) and 8-cyano-6,7-difluoro-1-[(1R,2S)-2-fluorocyclopropane]-6,7-difluoro-1,4-dihydro-4-oxoquinoline-3-carboxylic acid ethyl ester (240 mg, 0.71 mmol) were added to a solution of (1R,5R)-1-(tert-butoxycarbonylamino)-5-fluoro-3-azabicyclo[3.3.0]octane (148 mg, 0.61 mmol) in acetonitrile (10 ml), and the mixture was stirred at room temperature for three days. The solvent was evaporated under reduced pressure, and then the residue was extracted with a 10% citric acid solution and ethyl acetate. Then, the organic layer was washed with brine, dried over anhydrous sodium sulfate, and filtered. Thereafter, the solvent was evaporated under reduced pressure. The residue was subjected to silica gel column chromatography (hexane:ethyl acetate=1:1→3:7) to give ethyl ester substituted with a 7-position substituent (231 mg). The resulting ethyl ester (231 mg) was dissolved in tetrahydrofuran (3.0 mL) and ethanol (6.0 mL). A 1N sodium hydroxide solution (0.82 mL) was added, and the mixture was stirred at room temperature for 3.5 hours. The solvent was evaporated under reduced pressure, and then the residue was extracted with a 10% citric acid solution and ethyl acetate. Then, the organic layer was washed with brine, dried over anhydrous sodium sulfate, and filtered. Thereafter, the solvent was evaporated under reduced pressure. Concentrated hydrochloric acid (2.0 ml) was added to the residue, and the mixture was stirred at room temperature for one hour. Thereafter, the reaction solution was washed with chloroform twice, and then the aqueous layer was adjusted to pH 12 with a saturated sodium hydroxide solution. The basic solution was adjusted to pH 7.4 with hydrochloric acid, followed by extraction with chloroform. The organic layer was dried over anhydrous sodium sulfate and filtered, and then the solvent was evaporated under reduced pressure. 10% methanol-chloroform was added to the residue, and the insoluble material was removed by filtration. Then, the filtrate was concentrated under reduced pressure. The residue was purified by recrystallization from ethanol-aqueous ammonia to give 128 mg of the title compound as a pale yellow solid.

mp: 268-280° C. (dec.).

$[\alpha]_D^{24}$ −1.8° (c=0.100, 0.1NNaOH).

$^1$H-NMR (400 MHz, 0.1N NaOD) δ: 8.40 (1H, d, J=1.96 Hz), 7.96 (1H, d, J=14.46 Hz), 5.29-5.05 (1H, m), 4.28-4.00 (3H, m), 3.94-3.80 (2H, m), 2.23-2.10 (2H, m), 2.04-1.56 (6H, m).

MS (FAB); m/z: 433 (M+H)$^+$.

Anal. Calcd C$_{21}$H$_{19}$F$_3$N$_4$O$_3$: C, 58.33; H, 4.43; F, 13.18; N, 12.96. Found: C, 58.24; H, 4.36; F, 13.10; N, 12.84.

IR (ATR) ν: 3359, 3039, 2213, 1720, 1623, 1552, 1477, 1452, 1405, 1375, 1311, 1259, 1226, 1172, 1137, 1112, 1074, 1054, 991, 931, 887, 806 cm$^{-1}$.

Example 15

7-[(1R,5S)-1-Amino-5-fluoro-3-azabicyclo[3.3.0]octan-3-yl]-6-fluoro-1-[(1R,2S)-2-fluorocyclopropan-1-yl]-1,4-dihydro-8-methoxy-4-oxoquinoline-3-carboxylic acid

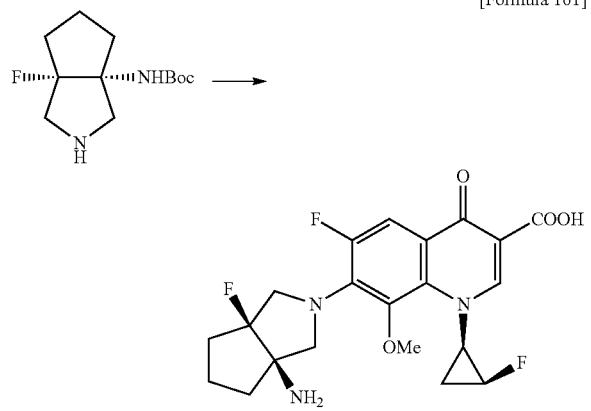

[Formula 161]

Triethylamine (3.30 mL, 23.7 mmol) and 6,7-difluoro-1-[(1R,2S)-2-fluorocyclopropane]-1,4-dihydro-8-methoxy-4-oxoquinoline-3-carboxylic acid-BF$_2$ chelate (2.93 g, 8.12 mmol) were added to a solution of (1R,5S)-1-(tert-butoxycarbonylamino)-5-fluoro-3-azabicyclo[3.3.0]octane (1.32 g, 5.40 mmol) in dimethyl sulfoxide (30 mL). The mixture was stirred at 40° C. for 19 hours. Triethylamine (1.70 mL, 12.3 mmol) and 6,7-difluoro-1-[(1R,2S)-2-fluorocyclopropane]-1,4-dihydro-8-methoxy-4-oxoquinoline-3-carboxylic acid-BF$_2$ chelate (1.00 g, 2.77 mmol) were further added to the reaction solution, and the mixture was stirred at 40° C. for 16 hours. Ethanol (45 mL), water (15 mL), and triethylamine (15 mL) were added to the reaction solution, and the mixture was heated to reflux for 1.5 hours. The solvent was evaporated under reduced pressure, and then the resulting residue was extracted with a 10% citric acid solution and ethyl acetate. Then, the organic layer was washed with water three times and brine, dried over anhydrous sodium sulfate, and filtered. Thereafter, the solvent was evaporated under reduced pressure. The residue was subjected to silica gel column chromatography (dichloromethane:methanol=99:1). The resulting oil (3.30 g) was dissolved in concentrated hydrochloric acid (20 mL) under ice-cooling, and the solution was stirred at room temperature for one hour. The reaction solution was washed with chloroform twice, and then the aqueous layer was adjusted to pH 12 with a saturated sodium hydroxide solution. The basic solution was adjusted to pH 7.4 with hydrochloric acid, followed by extraction with chloroform. The organic layer was dried over anhydrous sodium sulfate and filtered, and then the solvent was evaporated under reduced pressure. Chloroform was added to the residue. After filtration, the filtrate was concentrated under reduced pressure. The residue was purified by recrystallization from ethanol to give 769 mg of the title compound as a pale yellow solid.

mp: 191-195° C. (dec.).

$[\alpha]_D^{24}$ +97° (c=0.100, 0.1NNaOH).

$^1$H-NMR (400 MHz, 0.1N NaOD) δ: 8.48 (1H, d, J=1.23 Hz), 7.70 (1H, d, J=13.73 Hz), 5.07-4.85 (1H, m), 4.10-4.02 (1H, m), 3.93-3.78 (2H, m), 3.70-3.53 (2H, m), 3.66 (3H, s), 2.21-2.04 (2H, m), 2.01-1.83 (2H, m), 1.83-1.46 (4H, m). MS (FAB); m/z: 438 (M+H)$^+$.

Anal. Calcd C$_{21}$H$_{22}$F$_3$N$_3$O$_4$·0.75H$_2$O: C, 55.94; H, 5.25; F, 12.64; N, 9.32. Found: C, 56.03; H, 5.51; F, 12.79; N, 9.66.

IR (ATR) ν: 2958, 2871, 1724, 1621, 1513, 1452, 1319, 1056, 929, 804 cm$^{-1}$.

Example 16

7-[(1R,5S)-1-Amino-5-fluoro-3-azabicyclo[3.3.0]octan-3-yl]-1-[(1R,2S)-2-fluorocyclopropane]-1,4-dihydro-8-methyl-4-oxoquinoline-3-carboxylic acid

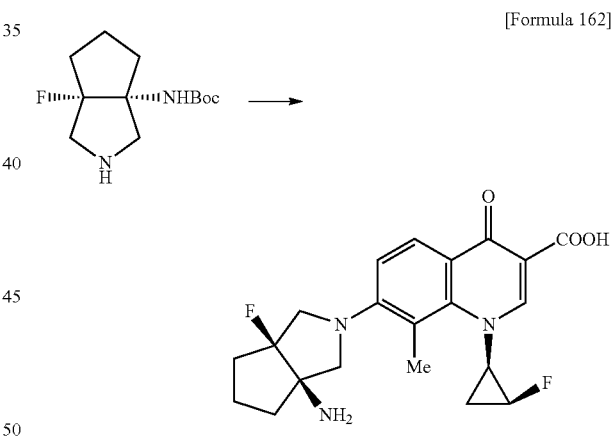

[Formula 162]

Triethylamine (0.447 mL, 3.21 mmol) and 7-fluoro-1-[(1R,2S)-2-fluorocyclopropan-1-yl]-1,4-dihydro-8-methyl-4-oxoquinoline-3-carboxylic acid (450 mg, 1.61 mmol) were added to a solution of (1R,5S)-1-(tert-butoxycarbonylamino)-5-fluoro-3-azabicyclo[3.3.0]octane (260 mg, 1.07 mmol) in dimethyl sulfoxide (6.0 mL), and the mixture was stirred at 70 to 80° C. for 18.5 hours. Triethylamine (0.224 mL, 1.61 mmol) was added again to the reaction solution, and the mixture was stirred at 70 to 80° C. for six days. Triethylamine (0.447 mL, 3.21 mmol) was further added, the mixture was stirred at 70 to 80° C. for 10 days. The reaction solution was extracted with a 10% citric acid solution and ethyl acetate. Then, the organic layer was washed with water twice and brine, dried over anhydrous sodium sulfate, and filtered. Thereafter, the solvent was evaporated under reduced pressure. The residue was subjected to silica gel column chromatography (dichloromethane:methanol=98:2) to give an oil (369 mg). The resulting oil (369 mg) was dissolved in concentrated hydrochloric acid (3.0 mL) under ice-cooling, and the solution was stirred at room temperature for one hour. The reaction solution was washed with chloroform twice, and then the aqueous layer was adjusted to pH 12 with a saturated sodium hydroxide solution. The basic solution was adjusted to pH 7.4 with hydrochloric acid, followed by extraction with chloroform. The organic layer was dried over anhydrous sodium sulfate and filtered, and then the solvent was evaporated under reduced pressure. The resulting residue was purified by PTLC (developed with the lower layer of chloroform:methanol:water=7:3:1). Then, the resulting fraction was concentrated under reduced pressure to give a residue, which was solidified with isopropanol to give 21 mg of the title compound as a pale yellow solid.

$^1$H-NMR (400 MHz, 0.1N NaOD) δ: 8.50 (1H, d, J=2.94 Hz), 8.06 (1H, d, J=8.58 Hz), 7.13 (1H, d, J=8.82 Hz), 5.13-4.90 (1H, m), 4.18-4.10 (1H, m), 3.89-3.77 (1H, m), 3.45-3.25 (3H, m), 2.58 (3H, s), 2.20-1.98 (3H, m), 1.93-1.82 (1H, m), 1.81-1.57 (3H, m), 1.37-1.22 (1H, m).

MS (FAB); m/z: 404 (M+H)$^+$.

Anal. Calcd $C_{21}H_{23}F_2N_3O_3 \cdot 0.5H_2O \cdot 0.25$IPA: C, 61.11; H, 6.13; N, 9.83. Found: C, 61.11; H, 5.72; N, 9.74.

IR (ATR) ν: 2956, 2873, 2823, 1708, 1610, 1508, 1432, 1355, 1313, 1255, 1133, 929 cm$^{-1}$.

Example 17

7-[(1R,5S)-1-Amino-5-fluoro-3-azabicyclo[3.3.0]octan-3-yl]-6-fluoro-1-[(1R,2S)-2-fluorocyclopropane]-1,4-dihydro-8-methyl-4-oxoquinoline-3-carboxylic acid

[Formula 163]

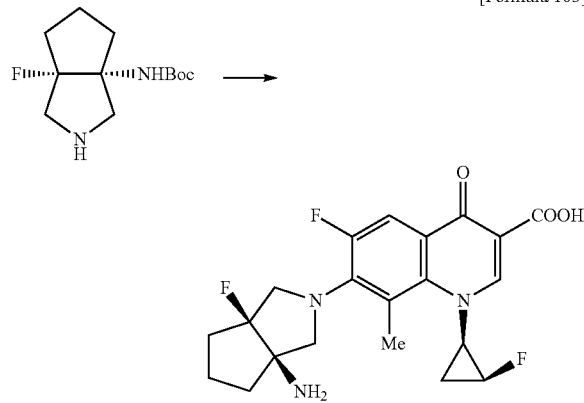

Triethylamine (0.215 mL, 1.54 mmol) and 6,7-difluoro-1-[(1R,2S)-2-fluorocyclopropane]-1,4-dihydro-8-methyl-4-oxoquinoline-3-carboxylic acid-BF$_2$ chelate (530 mg, 1.53 mmol) were added to a solution of (1R,5S)-1-(tert-butoxycarbonylamino)-5-fluoro-3-azabicyclo[3.3.0]octane (250 mg, 1.02 mmol) in dimethyl sulfoxide (5.0 mL). The mixture was stirred at room temperature for seven days. Triethylamine (0.215 mL, 1.54 mmol) and 6,7-difluoro-1-[(1R,2S)-2-fluorocyclopropane]-1,4-dihydro-8-methyl-4-oxoquinoline-3-carboxylic acid-BF$_2$ chelate (530 mg, 1.53 mmol) were further added to the reaction solution, and the mixture was stirred at room temperature for seven days. Triethylamine (0.215 mL, 1.54 mmol) and 6,7-difluoro-1-[(1R,2S)-2-fluorocyclopropane]-1,4-dihydro-8-methyl-4-oxoquinoline-3-carboxylic acid-BF$_2$ chelate (530 mg, 1.53 mmol) were further added to the reaction solution, and the mixture was stirred at room temperature for ten days. Ethanol (6.0 mL), water (2.0 mL), and triethylamine (2.0 mL) were added to the reaction solution, and the mixture was stirred at 80° C. for one hour. The solvent was evaporated under reduced pressure, and then the residue was extracted with a 10% citric acid solution and ethyl acetate. Then, the organic layer was washed with water twice and brine, dried over anhydrous sodium sulfate, and filtered. Thereafter, the solvent was evaporated under reduced pressure. The residue was subjected to silica gel column chromatography (dichloromethane:methanol=98:2), and the resulting fraction was concentrated under reduced pressure. Then, the residue was dissolved in concentrated hydrochloric acid (3.5 mL) under ice-cooling, and the solution was stirred at room temperature for one hour. The reaction solution was washed with chloroform five times, and then the aqueous layer was adjusted to pH 12 with a saturated sodium hydroxide solution. The basic solution was adjusted to pH 7.4 with hydrochloric acid, followed by extraction with chloroform. The organic layer was dried over anhydrous sodium sulfate and filtered, and then the solvent was evaporated under reduced pressure. The resulting residue was purified by PTLC (developed with the lower layer of chloroform:methanol:water=7:3:1). The resulting residue was solidified with isopropanol to give 7.1 mg of the title compound as a pale yellow solid.

$^1$H-NMR (400 MHz, 0.1N NaOD) δ: 8.50 (1H, s), 7.77 (1H, d, J=13.73 Hz), 5.80-4.80 (1H, m), 4.22-4.10 (1H, m), 3.99-3.85 (1H, m), 3.68-3.47 (2H, m), 3.43-3.34 (1H, m), 2.68 (3H, s), 2.21-1.98 (3H, m), 1.97-1.56 (4H, m), 1.42-1.23 (1H, m).

MS (FAB); m/z: 422 (M+H)$^+$.

Anal. Calcd $C_{21}H_{22}F_3N_3O_3 \cdot 0.5H_2O \cdot 0.25$IPA: C, 58.65; H, 5.66; F, 12.80; N, 9.43. Found: C, 58.63; H, 5.35; F, 12.35; N, 9.22.

IR (ATR) ν: 2971, 2856, 1722, 1614, 1450, 1432, 1322, 1132, 1097, 987, 954, 929, 887, 856, 804 cm$^{-1}$.

Example 18

7-[(1R,5S)-1-Amino-5-fluoro-3-azabicyclo[3.3.0]octan-3-yl]-1-(6-amino-3,5-difluoropyridin-2-yl)-1,4-dihydro-8-chloro-6-fluoro-4-oxoquinoline-3-carboxylic acid

[Formula 164]

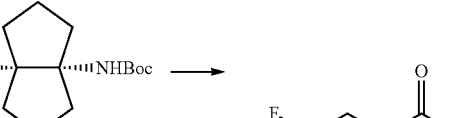

N-methylpyrrolidine (0.246 mL, 2.37 mmol) and 1-(6-amino-3,5-difluoropyridin-2-yl)-8-chloro-6,7-difluoro-1,4-dihydro-4-oxoquinoline-3-carboxylic acid (306 mg, 0.79 mmol) were added to a solution of (1R,5S)-1-(tert-butoxy-carbonylamino)-5-fluoro-3-azabicyclo[3.3.0]octane (193 mg, 0.79 mmol) in acetonitrile (10.0 mL), and the mixture was heated to reflux for 10 hours. 1-(6-Amino-3,5-difluoropyridin-2-yl)-8-chloro-6,7-difluoro-1,4-dihydro-4-oxo-quinoline-3-carboxylic acid (92 mg, 0.24 mmol) was added again to the reaction solution, and the mixture was further heated to reflux for 4.5 hours. The solvent was evaporated under reduced pressure, and then the residue was extracted with a 10% citric acid solution and ethyl acetate. Then, the organic layer was washed with water twice and brine, dried over anhydrous sodium sulfate, and filtered. Thereafter, the solvent was evaporated under reduced pressure. The resulting residue was subjected to silica gel column chromatography (dichloromethane:methanol=99:1). The resulting oil (409 mg) was dissolved in concentrated hydrochloric acid (3.0 mL) under ice-cooling, and the solution was stirred at room temperature for 2.5 hours. The reaction solution was washed with chloroform twice, and then the aqueous layer was adjusted to pH 12 with a saturated sodium hydroxide solution. The basic solution was adjusted to pH 7.4 with hydrochloric acid, followed by extraction with chloroform. The organic layer was dried over anhydrous sodium sulfate and filtered, and then the solvent was evaporated under reduced pressure. Chloroform was added to the residue, and the insoluble material was removed by filtration. Then, the filtrate was evaporated under reduced pressure, and the resulting residue was purified by recrystallization from ethanol to give 47 mg of the title compound as a pale yellow solid.

$^1$H-NMR (400 MHz, DMSO-$d_6$) δ: 8.79 (1H, s), 8.07-7.90 (2H, m), 6.75 (2H, d, J=8.58 Hz), 3.87-3.65 (2H, m), 3.50-3.25 (2H, m), 2.09-1.96 (2H, m), 1.88-1.53 (4H, m).

MS (FAB); m/z: 512 (M+H)$^+$.

Anal. Calcd $C_{22}H_{18}ClF_4N_5O_3 \cdot 0.5H_2O$: C, 50.73; H, 3.68; Cl, 6.81; F, 14.59; N, 13.45. Found: C, 50.75; H, 3.58; Cl, 6.52; F, 14.31; N, 13.09.

IR (ATR) ν: 3480, 3345, 3070, 2954, 2865, 1724, 1606, 1484, 1438, 1386, 1307, 1112 cm$^{-1}$.

Reference Example 79

3-(Oxiran-2-ylmethyl)-5-oxo-1-[(1R)-1-phenylethyl]pyrrolidine-3-carboxylic acid tert-butyl ester

[Formula 165]

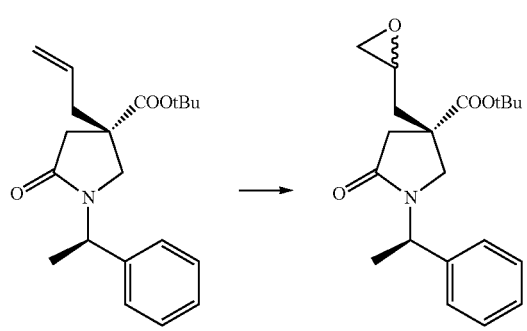

(3S)-3-Allyl-5-oxo-1-[(1R)-1-phenylethyl]pyrrolidine-3-carboxylic acid tert-butyl ester (4.9 g, 14.9 mmol) was dissolved in methylene chloride, and mCPBA (10.3 g, 59.5 mmol) was added. The mixture was stirred at room temperature for 15 hours and then heated to reflux for three hours. The solvent was evaporated under reduced pressure, and then the residue was blended with a mixture of ethyl acetate and a saturated sodium thiosulfate solution. The organic layer was washed with saturated sodium bicarbonate water, dried over magnesium sulfate, and filtered, and then the solvent was evaporated under reduced pressure. The residue was purified by silica gel chromatography (hexane/ethyl acetate=4:1→1:1) to give 4.33 g (84%) of the colorless oil title compound as a diastereomer mixture. The diastereomers were used for the next step without separation and purification.

Reference Example 80

(1S,5S)-7-Hydroxy-4-oxo-3-[(1R)-1-phenylethyl]-3-azabicyclo[3.3.0]octan-1-ylcarboxylic acid tert-butyl ester

[Formula 166]

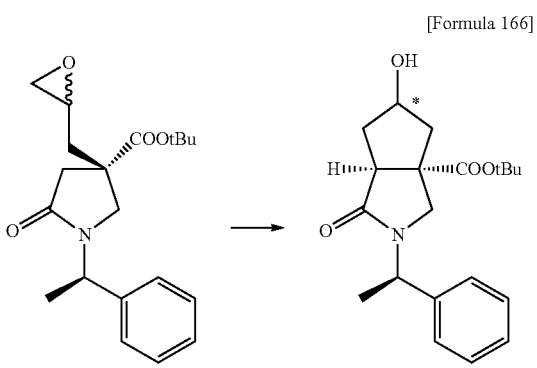

3-(Oxiran-2-ylmethyl)-5-oxo-1-[(1R)-1-phenylethyl]pyrrolidine-3-carboxylic acid tert-butyl ester (4.2 g, 12.16 mmol) was dissolved in tetrahydrofuran (50 mL). A 1 M solution of lithium hexamethyldisilazide in tetrahydrofuran (18 mL, 1.5 equivalents) was added in an argon atmosphere at −78° C., and the mixture was gradually heated. When the reaction temperature reached about room temperature, the reaction was quenched with an ammonium chloride solution, followed by extraction with ethyl acetate. The extract was dried over magnesium sulfate. After filtration, the solvent was evaporated under reduced pressure. The resulting residue was purified by silica gel chromatography (hexane:ethyl acetate=4:1→2:1→1:1→1:2) to give 1.07 g (26%) of the title compound having a single isomer as a colorless oil. 1.0 g (24%) of the raw material was collected. 1.20 g (29%) of a four-membered ring-closed compound as a by-product was obtained as a diastereomer mixture.

$^1$H-NMR (400 MHz, CDCl$_3$) δ: 7.36-7.26 (5H, m), 5.48 (1H, q, J=7.08 Hz), 4.36-4.30 (1H, m), 3.35-3.30 (2H, m), 3.12 (1H, d, J=10.25 Hz), 2.44-2.38 (2H, m), 2.29 (1H, dt,

J=13.83, 4.94 Hz), 2.16-2.09 (1H, m), 1.84 (1H, dd, J=13.79, 5.25 Hz), 1.50 (3H, d, J=7.08 Hz), 1.37 (9H, s).

Reference Example 81

(1R,5R)-7-Fluoro-4-oxo-3-[(1R)-1-phenylethyl]-3-azabicyclo[3.3.0]octan-1-ylcarboxylic acid tert-butyl ester

[Formula 167]

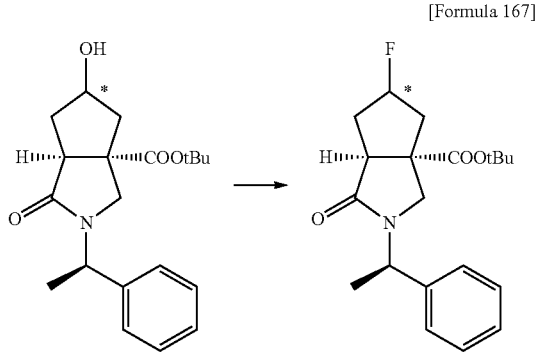

(1S,5S)-7-Hydroxy-4-oxo-3-[(1R)-1-phenylethyl]-3-azabicyclo[3.3.0]octan-1-ylcarboxylic acid tert-butyl ester (1.0 g, 2.89 mmol) was dissolved in methylene chloride (15 mL). Bis(2-methoxyethyl)aminosulfur trifluoride (BAST) (0.59 mL) was added under ice-cooling, and the mixture was stirred at the same temperature for one hour. The reaction solution was washed with saturated sodium bicarbonate water, dried over magnesium sulfate, and filtered. Then, the solvent was evaporated under reduced pressure. The residue was purified by silica gel chromatography (hexane:ethyl acetate=10:1→4:1→1:1) to give 711 mg (71%) of the title compound as a colorless oil.

$^1$H-NMR (400 MHz, CDCl$_3$) δ: 7.36-7.25 (5H, m), 5.50 (1H, q, J=7.1 Hz), 5.24 (1H, dt, J=52.2, 3.2 Hz), 3.48 (1H, d, J=10.0 Hz), 3.26-3.21 (2H, m), 2.61-2.37 (2H, m), 2.21-2.04 (2H, m), 1.48 (3H, d, J=7.1 Hz), 1.36 (9H, s).

Reference Example 82

(1R,5R)-7-Fluoro-4-oxo-3-[(1R)-1-phenylethyl]-3-azabicyclo[3.3.0]octan-1-ylcarboxylic acid

[Formula 168]

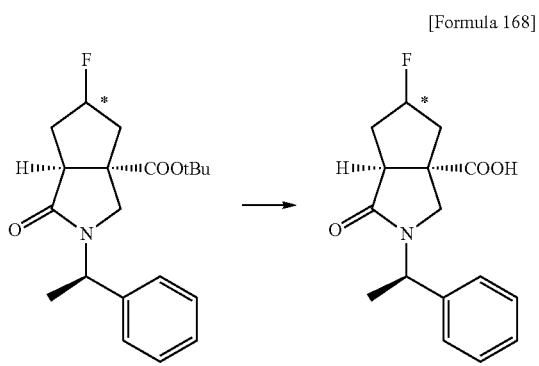

(1R,5R)-7-Fluoro-4-oxo-3-[(1R)-1-phenylethyl]-3-azabicyclo[3.3.0]octan-1-ylcarboxylic acid tert-butyl ester (705 mg, 2.03 mmol) was dissolved in methylene chloride (4 mL). Trifluoroacetic acid (4 mL) was added under ice-cooling, and then the mixture was stirred at room temperature for one hour. The reaction solution was concentrated under reduced pressure. Toluene was added to the residue, and the mixture was concentrated under reduced pressure again to give 595 mg (quantitative) of the title compound as a white solid.

$^1$H-NMR (400 MHz, CDCl$_3$) δ: 7.36-7.14 (5H, m), 5.48 (1H, q, J=7.08 Hz), 5.32-5.19 (1H, m), 3.61 (1H, d, J=10.74 Hz), 3.43 (1H, d, J=10.01 Hz), 3.33 (1H, d, J=10.50 Hz), 2.64-2.05 (4H, m), 1.49 (3H, d, J=7.08 Hz).

Reference Example 83

(1R,5S)-1-Amino-7-fluoro-4-oxo-3-[(1R)-1-phenylethyl]-3-azabicyclo[3.3.0]octane

[Formula 169]

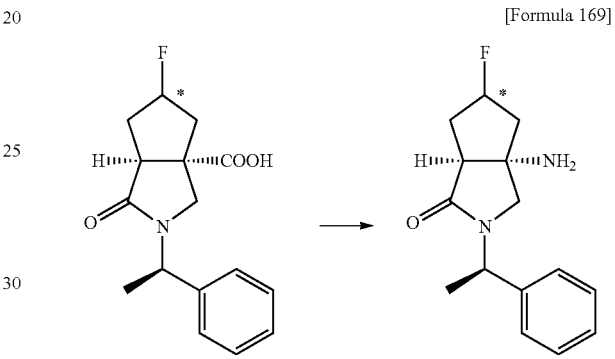

Toluene (10 mL) and triethylamine (565 μL, 4.05 mmol) were added to (1R,5R)-7-fluoro-4-oxo-3-[(1R)-1-phenylethyl]-3-azabicyclo[3.3.0]octan-1-ylcarboxylic acid (590 mg, 2.03 mmol). Then, diphenylphosphoryl azide (567 μL) was added, and the mixture was stirred at room temperature for 30 minutes. Thereafter, the reaction solution was heated to reflux for one hour and blended with a mixture of ethyl acetate-saturated sodium bicarbonate water. The organic layer was dried over magnesium sulfate and filtered. Then, the solvent was evaporated under reduced pressure. The residue was dissolved in dioxane (10 mL). 6N hydrochloric acid (10 mL) was added, and the mixture was heated with stirring at 70° C. for two hours. After washing with ether, the aqueous layer was made basic with a 10 M sodium hydroxide solution, followed by extraction with toluene five times. The extract was dried over magnesium sulfate and filtered, and then the solvent was evaporated under reduced pressure to give 476 mg (90%) of the title compound as a colorless oil. The product was used for the next step without purification.

$^1$H-NMR (400 MHz, CDCl$_3$) δ: 7.37-7.16 (5H, m), 5.53 (1H, q, J=7.00 Hz), 5.20 (1H, dt, J=52.70, 4.40 Hz), 3.49 (1H, d, J=10.30 Hz), 2.86 (1H, d, J=10.30 Hz), 2.66 (1H, d, J=10.00 Hz), 2.52-2.19 (3H, m), 1.93 (1H, ddd, J=39.50, 15.00, 4.10 Hz), 1.52 (2H, brs), 1.47 (3H, d, J=7.10 Hz).

Reference Example 84

(1R,5S)-1-(tert-Butoxycarbonylamino)-7-fluoro-3-[(1R)-1-phenylethyl]-3-azabicyclo[3.3.0]octane

[Formula 170]

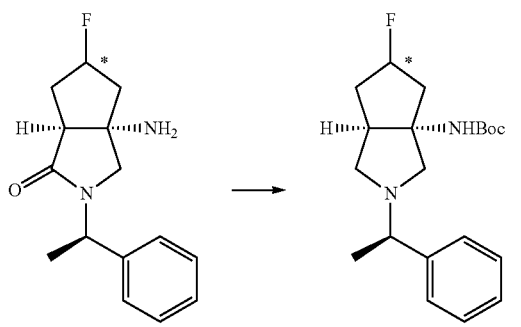

(1R,5S)-1-Amino-7-fluoro-4-oxo-3-[(1R)-1-phenylethyl]-3-azabicyclo[3.3.0]octane (537 mg, 2.05 mmol) was dissolved in toluene (20 mL). Red-Al™ (65% solution in toluene) (2.53 mL, 8.12 mmol) was added in an argon atmosphere, the mixture was stirred at 80° C. for one hour. A 5 M sodium hydroxide solution was added to the reaction solution, followed by extraction with toluene. The extract was dried over magnesium sulfate and filtered, and then the solvent was evaporated under reduced pressure. The residue was dissolved in toluene (20 mL). Di-tert-butyl dicarbonate (475 mg, 2.18 mmol) was added, and the mixture was stirred at 50° C. for one hour. The solvent was evaporated under reduced pressure, and then the residue was purified by silica gel chromatography (hexane:ethyl acetate=9:1→8:2→7:3) to give 450 mg (71%) of the title compound as a colorless oil.

$^1$H-NMR (400 MHz, CDCl$_3$) δ: 7.38-7.20 (5H, m), 5.20 (1H, d, J=54.00 Hz), 4.90 (1H, brs), 3.22 (1H, q, J=6.50 Hz), 2.92 (1H, d, J=7.60 Hz), 2.58 (1H, d, J=9.80 Hz), 2.48-2.20 (4H, m), 1.79 (1H, t, J=16.80 Hz), 1.43 (9H, s), 1.33 (3H, d, J=6.60 Hz).

Reference Example 85

(1R,5S)-1-(tert-Butoxycarbonylamino)-7-fluoro-3-bicyclo[3.3.0]octane

[Formula 171]

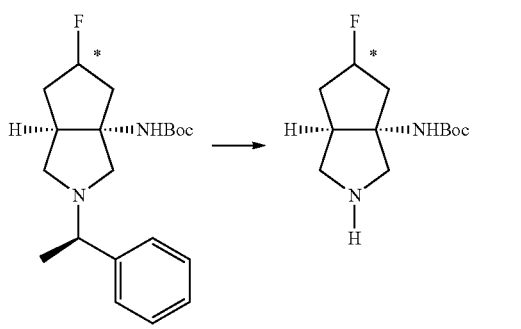

(1R,5S)-1-(tert-Butoxycarbonylamino)-7-fluoro-3-[(1R)-1-phenylethyl]-3-azabicyclo[3.3.0]octane (450 mg, 1.29 mmol) was dissolved in methanol (15 mL). A catalytic amount of a 10% palladium-carbon catalyst (50% wet) was added, and the mixture was stirred in a hydrogen atmosphere at 40° C. for 12 hours. After removing the catalyst by filtration, the filtrate was concentrated under reduced pressure to give 316 mg (quantitative) of the title compound as a colorless oil.

$^1$H-NMR (400 MHz, CDCl$_3$) δ: 5.24 (1H, d, J=53.71 Hz), 5.07 (1H, s), 3.48-3.42 (1H, m), 3.23 (2H, dd, J=14.77, 12.33 Hz), 2.93-2.87 (1H, m), 2.76 (1H, brs), 2.44-2.16 (3H, m), 1.95-1.86 (1H, m), 1.44 (9H, s).

Example 19

7-{(1R,5S)-1-Amino-7-fluoro-3-azabicyclo[3.3.0]octan-3-yl}-6-fluoro-1-[(1R,2S)-2-fluorocyclopropyl]-1,4-dihydro-8-methoxy-4-oxoquinoline-3-carboxylic acid

[Formula 172]

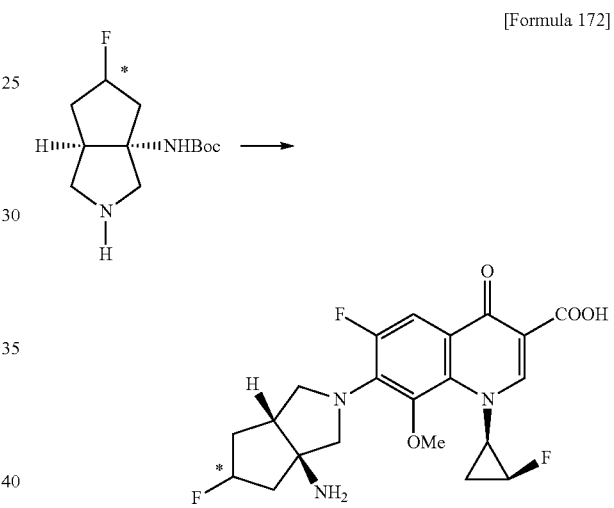

(1R,5S)-1-(tert-Butoxycarbonylamino)-7-fluoro-3-azabicyclo[3.3.0]octane (296 mg, 1.21 mmol) and 6,7-difluoro-1-[(1R,2S)-2-fluorocyclopropyl]-1,4-dihydro-8-methoxy-4-oxoquinoline-3-carboxylic acid-BF$_2$ chelate (437 mg, 1.21 mmol) were dissolved in dimethyl sulfoxide (6 mL). Triethylamine (203 μL, 1.45 mmol) was added, and the mixture was stirred at 40° C. for one day. Water was added to the reaction solution, and the precipitated crystals were collected by filtration, washed with water, and dried to give a yellow powder. This was dissolved in ethanol (35 mL)-water (9 mL). Triethylamine (202 μL) were added, and the mixture was heated to reflux for four hours. The solvent was evaporated under reduced pressure, and the residue was blended with a mixture of ethyl acetate and a 10% citric acid solution. The organic layer was dried over magnesium sulfate and filtered. The filtrate was evaporated under reduced pressure. Then, concentrated hydrochloric acid (9 mL) was added to the residue, and the mixture was stirred at room temperature for two hours. The reaction solution was diluted with concentrated hydrochloric acid, then transferred to a separatory funnel, and washed with chloroform three times. Thereafter, the hydrochloric acid layer was adjusted to pH 12 with a 12 M sodium hydroxide solution under ice-cooling. The layer was further adjusted to pH 7.4 with 1 M hydrochloric acid and 0.01 M hydrochloric acid, followed by extraction with chloroform-methanol (9:1). Then, the aqueous layer was adjusted to pH 7.4 again and an extraction operation was performed. After repeating this operation five times, the organic layer was dried over magnesium sulfate and filtered, and the filtrate was evaporated under reduced pressure. Ethanol was added to the residue, and the solvent was evaporated under reduced pressure. The residue was dried under reduced pressure to give 220 mg (42%) of the title compound as a pale yellow solid.

$^1$H-NMR (400 MHz, 0.1N NaOD) δ: 8.47 (1H, s), 7.66 (1H, d, J=13.70 Hz), 5.45-5.31 (1H, brm), 5.04-4.86 (1H, brm), 4.06-4.01 (1H, m), 3.87 (1H, t, J=8.90 Hz), 3.73-3.51 (6H, m), 2.52-2.25 (3H, m), 2.15-1.89 (2H, m), 1.64-1.47 (2H, m).

Anal; Calcd for $C_{21}H_{22}F_3N_3O_4 \cdot 1.0H_2O \cdot 0.4EtOH$: C, 55.26; H, 5.62; F, 12.03; N, 8.87. Found: C, 55.05; H, 5.35; F, 12.32; N, 8.76.

MS (ESI) m/z: 438 (M+H)$^+$.

Reference Example 86

(3S)-3-(2-Methoxycarbonyl-1-ethyl)-5-oxo-1-[(1R)-1-phenylethyl]pyrrolidine-3-carboxylic acid tert-butyl ester

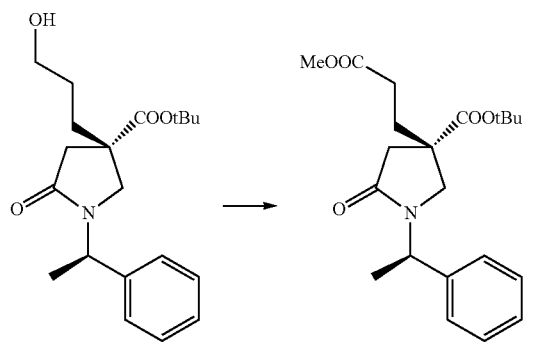

[Formula 173]

Carbon tetrachloride (550 mL), acetonitrile (550 mL), and water (550 mL) were dissolved in (3S)-3-(3-hydroxy-1-propyl)-5-oxo-1-[(1R)-1-phenylethyl]pyrrolidine-3-carboxylic acid tert-butyl ester (38.2 g, 0.110 mol), and ruthenium (III) chloride hydrate (456 mg, 2.20 mmol) and sodium periodide (94.1 g, 0.440 mol) were sequentially added. The mixture was stirred in a water bath with a thermostatic circulator at 15° C. for 2.5 hours while maintaining the internal temperature at 20 to 25° C. The reaction solution was cooled in an ice bath and a 1N hydrochloric acid solution (2.2 L) was added at an internal temperature of 10° C. or less, followed by extraction with 2 L of chloroform. The aqueous layer was extracted with chloroform (1 L×3). Then, the organic layers were combined, washed with brine (2 L×2), and dried over anhydrous sodium sulfate. After filtration, the solvent was concentrated under reduced pressure. The resulting crude was dissolved in N,N-dimethylformamide (370 mL). Sodium bicarbonate (37.9 g, 0.451 mol) and methyl iodide (70.7 g, 0.498 mol) were added with stirring at room temperature, and the mixture was stirred for three days. The reaction solution was poured into ice water (1.8 L), followed by extraction with ethyl acetate (1.8 L, 0.5 L). The organic layers were combined, washed with brine, and then dried over anhydrous sodium sulfate. After filtration, the filtrate was concentrated under reduced pressure, the residue was subjected to silica gel column chromatography (hexane:ethyl acetate=1:1), and the fraction containing the target substance was concentrated under reduced pressure. The resulting solid was dissolved in ethyl acetate, washed with a 10% sodium thiosulfate solution, and dried over anhydrous sodium sulfate. After filtration, the filtrate was concentrated under reduced pressure, and the resulting solid was dried to give 35.0 g of the title compound as a pale yellow brown solid.

$^1$H-NMR (400 MHz, CDCl$_3$) δ: 7.35-7.25 (5H, m), 5.48 (1H, q, J=7.1 Hz), 3.68 (3H, s), 3.33 (1H, d, J=10.3 Hz), 3.13 (1H, d, J=10.3 Hz), 2.93 (1H, d, J=16.8 Hz), 2.34-2.20 (3H, m), 2.13-1.94 (2H, m), 1.51 (3H, d, J=7.1 Hz), 1.32 (9H, s).

Reference Example 87

{(1S,5R)-4,6-Dioxo-3-[(1R)-1-phenylethyl]-3-azabicyclo[3,3,0]octan-1-yl}carboxylic acid tert-butyl ester

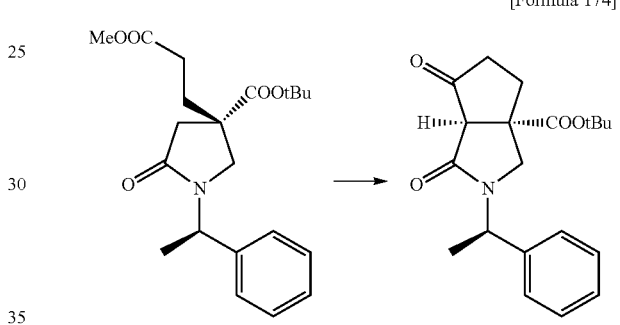

[Formula 174]

(3S)-3-(2-Methoxycarbonyl-1-ethyl)-5-oxo-1-[(1R)-1-phenylethyl]pyrrolidine-3-carboxylic acid tert-butyl ester (35.0 g, 93.2 mmol) was dissolved in tetrahydrofuran (1 L). A 2 M lithium diisopropylamide/heptane/tetrahydrofuran/ethylbenzene solution (100 mL, 200 mmol) was added dropwise in a nitrogen atmosphere at an internal temperature of −69° C. over 30 minutes. After stirring at the same temperature for one hour, the reaction solution was poured into a 1N hydrochloric acid solution (2 L) in an ice bath, followed by extraction with ethyl acetate (2 L, 1 L). The organic layers were combined, washed with brine, and dried over anhydrous sodium sulfate. After filtration, the filtrate was concentrated under reduced pressure, and the precipitated solid was collected by filtration to give 22.2 g of the title compound as pale red crystals. The filtrate was further concentrated to give 2.88 g of the title compound as pale red crystals. The filtrate was concentrated under reduced pressure, and the residue was subjected to silica gel column chromatography (hexane:ethyl acetate=1:1) to give 2.09 g of the title compound as colorless crystals.

$^1$H-NMR (400 MHz, CDCl$_3$) δ: 7.37-7.26 (5H, m), 5.50 (1H, q, J=7.1 Hz), 3.38 (1H, d, J=10.5 Hz), 3.23 (1H, d, J=10.5 Hz), 2.55-2.35 (3H, m), 2.05-1.94 (1H, m), 1.53 (3H, d, J=7.1 Hz), 1.38 (9H, s).

Reference Example 88

{(1S,5R,6R)-6-Fluoro-4-oxo-3-[(1R)-1-phenyl-ethyl]-3-azabicyclo[3,3,0]octan-1-yl}carboxylic acid tert-butyl ester {(1S,5R,6S)-6-Fluoro-4-oxo-3-[(1R)-1-phenylethyl]-3-azabicyclo[3,3,0]octan-1-yl}carboxylic acid tert-butyl ester

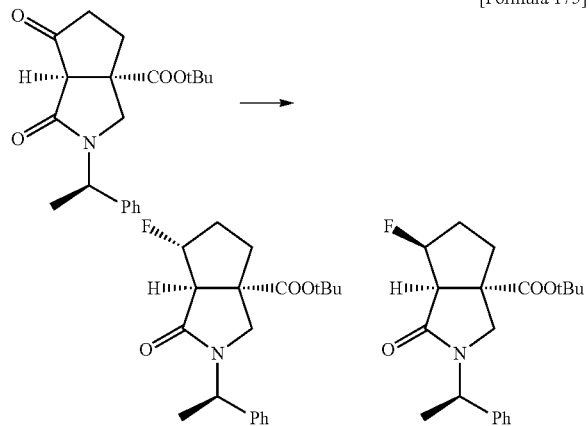

[Formula 175]

{(1S,5R)-4,6-Dioxo-3-[(1R)-1-phenylethyl]-3-azabicyclo[3,3,0]octan-1-yl}carboxylic acid tert-butyl ester (1.30 g, 3.88 mmol) was dissolved in tetrahydrofuran (40 mL). Sodium borohydride (185 mg, 4.92 mmol) was added at 0° C., and the mixture was stirred for one hour. A saturated ammonium chloride solution was added to the reaction solution, followed by extraction with ethyl acetate. The organic layer was washed with water and brine and then dried over anhydrous sodium sulfate. After filtration, the solvent was evaporated under reduced pressure, and the resulting residue was dissolved in dichloromethane (20 mL). [Bis(2-methoxyethyl)amino]sulfur trifluoride (1.73 g, 7.82 mmol) was added in a nitrogen atmosphere, and the mixture was stirred for two hours. The reaction solution was poured into saturated sodium bicarbonate water in an ice bath, followed by extraction with ethyl acetate. The organic layer was washed with a saturated sodium thiosulfate solution and brine and dried over anhydrous sodium sulfate. After filtration, the solvent was evaporated under reduced pressure, and the resulting residue was subjected to silica gel column chromatography (30% ethyl acetate/hexane) to give 797 mg of the title (6R)-fluoro isomer as a colorless oil and 170 mg of the title (6S)-fluoro isomer as a colorless oil.

(6R)-Fluoro Isomer:
$^1$H-NMR (400 MHz, CDCl$_3$) δ: 7.36-7.26 (5H, m), 5.46 (1H, q, J=7.08 Hz), 5.28 (1H, d, J=51.76 Hz), 3.48 (1H, d, J=22.71 Hz), 3.41 (1H, d, J=10.50 Hz), 3.08 (1H, d, J=10.50 Hz), 2.57-2.49 (1H, m), 2.21-2.12 (1H, m), 1.83-1.58 (2H, m), 1.50 (3H, d, J=7.08 Hz), 1.35 (9H, s).
MS (EI); m/z: 348 (M+H)$^+$.

(6S)-Fluoro Isomer:
$^1$H-NMR (400 MHz, CDCl$_3$) δ: 7.34-7.26 (5H, m), 5.49-5.40 (2H, m), 3.51 (1H, d, J=10.24 Hz), 3.41 (1H, d, J=29.76 Hz), 3.21 (1H, d, J=10.00 Hz), 2.46-2.44 (1H, m), 2.23-2.20 (1H, m), 2.03-1.93 (1H, m), 1.88-1.82 (1H, m), 1.52 (3H, d, J=6.83 Hz), 1.32 (9H, s).
MS (EI); m/z: 348 (M+H)$^+$.

Reference Example 89

{(1S,5S,6R)-3-Benzyloxycarbonyl-6-fluoro-3-azabicyclo[3,3,0]octan-1-yl}carboxylic acid tert-butyl ester

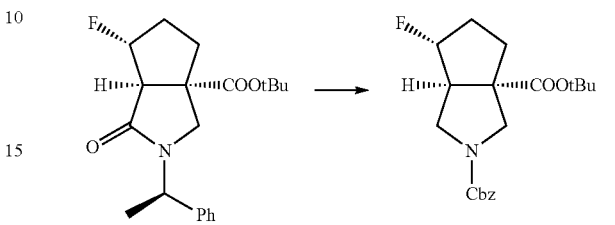

[Formula 176]

{(1S,5R,6R)-6-Fluoro-4-oxo-3-[(1R)-1-phenylethyl]-3-azabicyclo[3,3,0]octan-1-yl}carboxylic acid tert-butyl ester (420 mg, 1.21 mmol) was dissolved in tetrahydrofuran (20 mL), and a 1 M borane-tetrahydrofuran complex (3.63 mL, 3.63 mmol) was added dropwise in a nitrogen atmosphere. After five hours, a 1 M borane-tetrahydrofuran complex (3.63 mL, 3.63 mmol) was added; after 15 hours, a 1 M borane-tetrahydrofuran complex (3.63 mL, 3.63 mmol) was further added. After stirring for three hours, ethanol (18 mL), water (2 mL), and triethylamine (2 mL) were added, and the mixture was stirred at 80° C. for two hours. The reaction solution was evaporated under reduced pressure, and a saturated ammonium chloride solution was added to the resulting residue, followed by extraction with ethyl acetate. The organic layer was washed with water and brine and then dried over anhydrous sodium sulfate. After filtration, the solvent was evaporated under reduced pressure, and the resulting residue was dissolved in dichloromethane (3 mL). Benzyloxycarbonyl chloride (1.03 g, 6.04 mmol) was added, and the mixture was stirred for 16 hours. The reaction solution was concentrated under reduced pressure, and the residue was purified by silica gel column chromatography (30% ethyl acetate/hexane) to give 367 mg of the title compound as a colorless oil.
$^1$H-NMR (400 MHz, CDCl$_3$) δ: 7.38-7.26 (5H, m), 5.12 (2H, s), 4.85 (1H, d, J=52.44 Hz), 3.86 (1H, d, J=11.71 Hz), 3.77-3.73 (1H, m), 3.40-3.35 (2H, m), 3.16-3.10 (1H, m), 2.46-2.42 (1H, m), 2.03-1.82 (3H, m), 1.45 (9H, s).
MS (EI) m/z: 386 (M+Na)$^+$.

Reference Example 90

{(1S,5S,6S)-3-Benzyloxycarbonyl-6-fluoro-3-azabicyclo[3,3,0]octan-1-yl}carboxylic acid tert-butyl ester

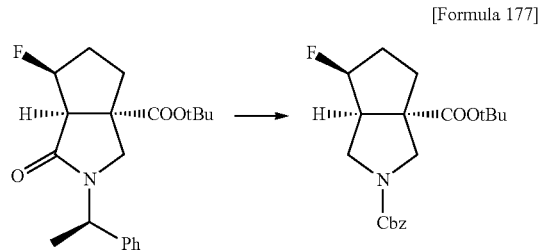

[Formula 177]

{(1S,5R,6S)-6-Fluoro-4-oxo-3-[(1R)-1-phenylethyl]-3-azabicyclo[3,3,0]octan-1-yl}carboxylic acid tert-butyl ester (402 mg, 1.16 mmol) was dissolved in tetrahydrofuran (20 mL), and a 1 M borane-tetrahydrofuran complex (5.79 mL, 5.79 mmol) was added dropwise in a nitrogen atmosphere. After two hours, a 1 M borane-tetrahydrofuran complex (3.47 mL, 3.47 mmol) was added; after 14 hours, a 1 M borane-tetrahydrofuran complex (3.47 mL, 3.47 mmol) was further added. After stirring for 2.5 hours, ethanol (18 mL), water (2 mL), and triethylamine (2 mL) were added, and the mixture was stirred at 80° C. for two hours. The reaction solution was evaporated under reduced pressure, and a saturated ammonium chloride solution was added to the resulting residue, followed by extraction with ethyl acetate. The organic layer was washed with water and brine and then dried over anhydrous sodium sulfate. After filtration, the solvent was evaporated under reduced pressure, and the resulting residue was dissolved in dichloromethane (2.8 mL). Benzyloxycarbonyl chloride (1.03 g, 6.04 mmol) was added, and the mixture was stirred at 40° C. for 14 hours. The reaction solution was concentrated under reduced pressure, and the residue was purified by silica gel column chromatography (25% ethyl acetate/hexane) to give 359 mg of the title compound as a colorless oil.

$^1$H-NMR (400 MHz, CDCl$_3$) δ: 7.34-7.29 (5H, m), 5.13 (2H, s), 5.06 (1H, d, J=49.84 Hz), 3.99 (1H, dd, J=20.12, 11.59 Hz), 3.79 (1H, d, J=11.95 Hz), 3.58-3.55 (1H, m), 3.38 (1H, dd, J=46.71, 11.34 Hz), 3.00 (1H, brd, J=25.37 Hz), 2.26-1.94 (4H, m), 1.43 (9.0H, s).

MS (EI) m/z: 386 (M+Na)$^+$.

Reference Example 91

{(1S,5R,6R)-1-tert-Butoxycarbonylamino-6-fluoro-3-azabicyclo[3,3,0]octan-3-yl}carboxylic acid benzyl ester

[Formula 178]

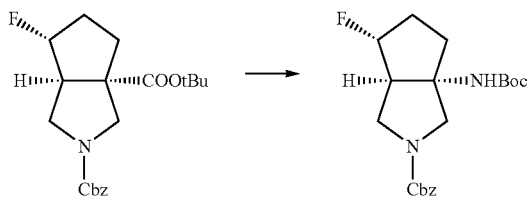

{(1S,5S,6R)-3-Benzyloxycarbonyl-6-fluoro-3-azabicyclo[3,3,0]octan-1-yl}carboxylic acid tert-butyl ester (362 mg, 1.00 mmol) was dissolved in dichloromethane (10 mL). Trifluoroacetic acid (2.5 mL) was added, and the mixture was stirred for 15 hours. The solvent was evaporated under reduced pressure. A 1N sodium hydroxide solution was added to the resulting residue, and the mixture was washed with chloroform. The aqueous layer was made acidic with a hydrochloric acid solution, followed by extraction with chloroform. The extract was dried over anhydrous sodium sulfate. After filtration, the solvent was evaporated under reduced pressure, and the resulting residue was dissolved in toluene (10 mL). Triethylamine (202 mg, 1.99 mmol) and diphenylphosphoryl azide (339 mg, 1.20 mmol) were added in a nitrogen atmosphere, and the mixture was stirred at 100° C. for two hours. The reaction solution was concentrated under reduced pressure. Then, dioxane (20 mL) and 6N hydrochloric acid (20 mL) were added, and the mixture was stirred at 40° C. for three hours. After concentration under reduced pressure and azeotropic distillation with ethanol, a 1N sodium hydroxide solution was added, followed by extraction with chloroform. After drying over anhydrous sodium sulfate and filtration, the solvent was evaporated under reduced pressure. Di-tert-butyl dicarbonate (1087 mg, 4.98 mmol) was added to the resulting residue, and the mixture was stirred at 50° C. for two hours. The reaction solution was purified by silica gel column chromatography (20% ethyl acetate/hexane) to give 125 mg of the title compound as a colorless oil.

$^1$H-NMR (400 MHz, CDCl$_3$) δ: 7.35-7.26 (5H, m), 5.11 (2H, s), 4.95-4.80 (2H, m), 3.88-3.63 (3H, m), 3.28-3.24 (1H, m), 2.83-2.75 (1H, m), 2.12-1.98 (4H, m), 1.44 (9H, s).

MS (EI) m/z: 401 (M+Na)$^+$.

Reference Example 92

{(1S,5R,6S)-1-tert-Butoxycarbonylamino-6-fluoro-3-azabicyclo[3,3,0]octan-3-yl}carboxylic acid benzyl ester

[Formula 179]

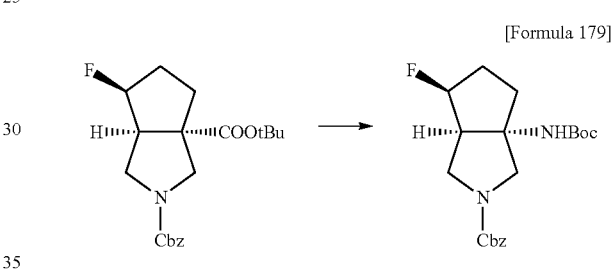

{(1S,5S,6S)-3-Benzyloxycarbonyl-6-fluoro-3-azabicyclo[3,3,0]octan-1-yl}carboxylic acid tert-butyl ester (354 mg, 0.97 mmol) was dissolved in dichloromethane (10 mL). Trifluoroacetic acid (3 mL) was added, and the mixture was stirred for 21 hours. The solvent was evaporated under reduced pressure. A 1N sodium hydroxide solution was added to the resulting residue, and the mixture was washed with chloroform. The aqueous layer was made acidic with a hydrochloric acid solution, followed by extraction with chloroform. The extract was dried over anhydrous sodium sulfate. After filtration, the solvent was evaporated under reduced pressure, and the resulting residue was dissolved in toluene (8 mL). Triethylamine (197 mg, 1.95 mmol) and diphenylphosphoryl azide (359 mg, 1.27 mmol) were added in a nitrogen atmosphere, and the mixture was stirred for one hour. Thereafter, tert-butanol (8 mL) was added, and the mixture was stirred at 100° C. for 19 hours. The reaction solution was concentrated under reduced pressure, and the residue was purified by silica gel column chromatography (25% ethyl acetate/hexane) to give 136 mg of the title compound as a colorless oil.

$^1$H-NMR (400 MHz, CDCl$_3$) δ: 7.35-7.26 (5H, m), 5.13 (2H, s), 5.05 (1H, d, J=58.77 Hz), 4.68 (1H, brs), 3.77 (1H, d, J=10.46 Hz), 3.71-3.60 (2H, m), 3.57-3.44 (1H, m), 3.11-2.86 (1H, m), 2.29-2.02 (4H, m), 1.43 (9H, s).

MS (EI); m/z: 401 (M+Na)$^+$.

Reference Example 93

(1S,5R,6R)-1-tert-Butoxycarbonylamino-6-fluoro-3-azabicyclo[3,3,0]octane

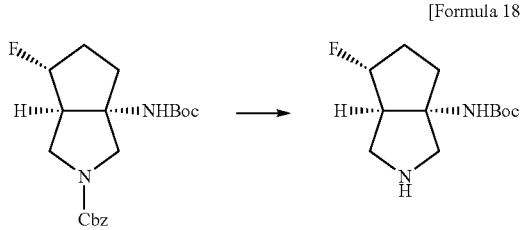

[Formula 180]

{(1S,5R,6R)-1-tert-Butoxycarbonylamino-6-fluoro-3-azabicyclo[3,3,0]octan-3-yl}carboxylic acid benzyl ester (120 mg, 0.32 mmol) was dissolved in methanol (10 mL). 10% palladium-carbon (M, wet) (50 mg) was added, and the mixture was stirred in a hydrogen atmosphere for three hours. The catalyst was removed by filtration, and then the filtrate was concentrated under reduced pressure. A 1N sodium hydroxide solution was added, followed by extraction with chloroform. After drying over anhydrous sodium sulfate and filtration, the filtrate was concentrated under reduced pressure to give 77.5 mg of the title compound as a colorless oil.

MS (EI); mhz: 245 (M+H)$^+$.

Reference Example 94

(1S,5R,6S)-1-tert-Butoxycarbonylamino-6-fluoro-3-azabicyclo[3,3,0]octane

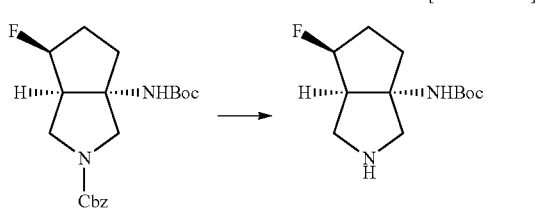

[Formula 181]

{(1S,5R,6S)-1-tert-Butoxycarbonylamino-6-fluoro-3-azabicyclo[3,3,0]octan-3-yl}carboxylic acid benzyl ester (132 mg, 0.35 mmol) was dissolved in methanol (10 mL). 10% palladium-carbon (M, wet) (50 mg) was added, and the mixture was stirred in a hydrogen atmosphere for three hours. The catalyst was removed by filtration, and then the filtrate was concentrated under reduced pressure. A 1N sodium hydroxide solution was added, followed by extraction with chloroform. After drying over anhydrous sodium sulfate and filtration, the filtrate was concentrated under reduced pressure to give 85 mg of the title compound as a colorless oil.

MS (EI); m/z: 245 (M+H)$^+$.

Example 20

7-{(1S,5R,6R)-1-Amino-6-fluoro-3-azabicyclo[3,3,0]octan-3-yl}-6-fluoro-1-[(1R,2S)-2-fluorocyclopropyl]-1,4-dihydro-8-methoxy-4-oxoquinoline-3-carboxylic acid

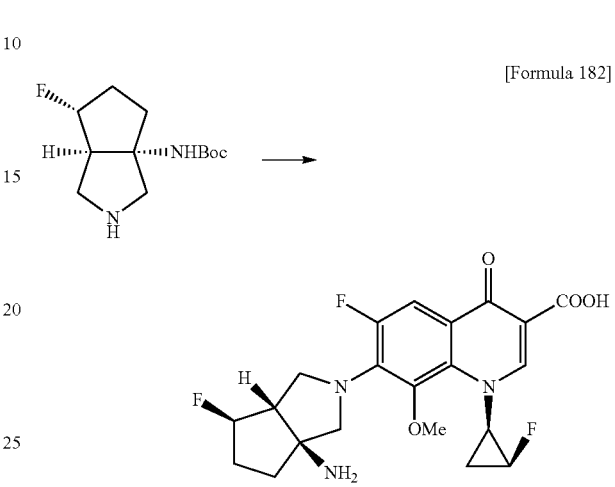

[Formula 182]

(1S,5R,6R)-1-tert-Butoxycarbonylamino-6-fluoro-3-azabicyclo[3,3,0]octane (77.5 mg, 0.32 mmol) was dissolved in dimethyl sulfoxide (2 mL). 6,7-Difluoro-1-[(1R,2S)-2-fluorocyclopropyl]-1,4-dihydro-8-methoxy-4-oxoquinoline-3-carboxylic acid-BF$_2$ chelate (120.2 mg, 0.33 mmol) and triethylamine (96.3 mg, 0.95 mmol) were added, and the mixture was stirred at 40° C. for 18 hours. Then, 90% aqueous ethanol (30 mL) and triethylamine (3 mL) were added to the reaction solution, and the mixture was stirred at 80° C. for three hours. The solvent was evaporated under reduced pressure, and a 10% citric acid solution was added to the residue, followed by extraction with ethyl acetate. The organic layer was washed with water and brine and dried over anhydrous sodium sulfate. After filtration, the solvent was evaporated under reduced pressure, and the resulting residue was subjected to short silica gel column chromatography (5% methanol/chloroform). The resulting crude was dissolved in concentrated hydrochloric acid and washed with chloroform. The aqueous layer was adjusted to pH 12 with aqueous sodium hydroxide at 0° C. and then adjusted to pH 7.5 with hydrochloric acid, followed by extraction with chloroform. The organic layer was dried over anhydrous sodium sulfate and filtered, and then the solvent was evaporated under reduced pressure. The resulting solid was washed with diethyl ether and dried under reduced pressure to give 96 mg of the title compound as a colorless solid.

mp: 179-181° C.

$^1$H-NMR (400 MHz, 0.1N NaOD) δ: 8.48 (1H, s), 7.71 (1H, d, J=13.67 Hz), 5.10-5.07 (1H, m), 5.09 (1H, d, J=52.00 Hz), 4.07-4.04 (1H, m), 3.88 (1H, t, J=9.64 Hz), 3.68-3.63 (4H, m), 3.57 (1H, dd, J=16.97, 10.62 Hz), 3.45 (1H, d, J=11.72 Hz), 2.63-2.56 (1H, m), 2.10-2.01 (4H, m), 1.61-1.51 (2H, m).

Anal; Calcd for C$_{21}$H$_{22}$F$_3$N$_3$O$_4$.0.5H$_2$O: C, 56.50; H, 5.19; N, 9.41; F, 12.77. Found: C, 56.28; H, 5.17; N, 9.03; F, 12.47.

MS (EI); m/z: 438 (M+H)$^+$.

IR (ATR) ν: 3390, 2943, 2872, 1720, 1618, 1512, 1452, 1360, 1321, 1277, 1213 cm$^{-1}$.

Example 21

7-[(1S,5R,6S)-1-Amino-6-fluoro-3-azabicyclo[3,3,0]octan-3-yl]-6-fluoro-1-[(1R,2S)-2-fluorocyclopropyl]-1,4-dihydro-8-methoxy-4-oxoquinoline-3-carboxylic acid

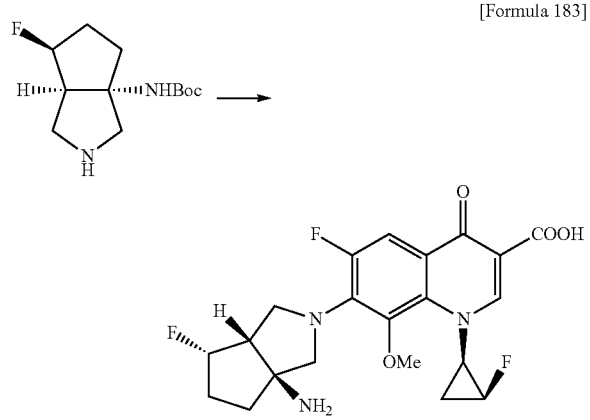

[Formula 183]

(1S,5R,6S)-1-tert-Butoxycarbonylamino-6-fluoro-3-azabicyclo[3,3,0]octane (85.2 mg, 0.35 mmol) was dissolved in dimethyl sulfoxide (2 mL). 6,7-Difluoro-1-[(1R,2S)-2-fluorocyclopropyl]-1,4-dihydro-8-methoxy-4-oxoquinoline-3-carboxylic acid-BF$_2$ chelate (132.2 mg, 0.37 mmol) and triethylamine (105.9 mg, 1.05 mmol) were added, and the mixture was stirred at 40° C. for 15 hours. Then, 90% aqueous ethanol (30 mL) and triethylamine (3 mL) were added to the reaction solution, and the mixture was stirred at 80° C. for three hours. The solvent was evaporated under reduced pressure, and a 10% citric acid solution was added to the residue, followed by extraction with ethyl acetate. The organic layer was washed with water and brine and dried over anhydrous sodium sulfate. After filtration, the solvent was evaporated under reduced pressure, and the resulting residue was subjected to short silica gel column chromatography (5% methanol/chloroform). The resulting crude was dissolved in concentrated hydrochloric acid and washed with chloroform. The aqueous layer was adjusted to pH 12 with aqueous sodium hydroxide at 0° C. and then adjusted to pH 7.5 with hydrochloric acid, followed by extraction with chloroform. The organic layer was dried over anhydrous sodium sulfate and filtered, and then the solvent was evaporated under reduced pressure. The resulting solid was washed with diethyl ether and dried under reduced pressure to give 101 mg of the title compound as a colorless solid.

mp: 117-119° C.

$^1$H-NMR (400 MHz, 0.1N NaOD) δ: 8.45 (1H, s), 7.70 (1H, d, J=14.15 Hz), 5.28 (1H, d, J=53.41 Hz), 5.07-4.73 (1H, m), 4.05-4.02 (1H, m), 3.84-3.64 (6H, m), 3.47 (1H, d, J=10.73 Hz), 2.59-2.53 (1H, m), 2.26-2.06 (3H, m), 1.79-1.78 (1H, m), 1.58-1.46 (2H, m).

Anal; Calcd for C$_{21}$H$_{22}$F$_3$N$_3$O$_4$·H$_2$O: C, 55.38; H, 5.31; N, 9.23; F, 12.51. Found: C, 55.43; H, 5.46; N, 9.00; F, 12.21.

MS (EI) m/z: 438 (M+H)$^+$.

IR (ATR) ν: 2966, 2839, 1720, 1614, 1576, 1537, 1508, 1446, 1362, 1319, 1271, 1207 cm$^{-1}$.

Reference Example 95

{(1S,5S)-6,6-Difluoro-3-[(1R)-1-phenylethyl]-3-azabicyclo[3,3,0]octan-1-yl}carboxylic acid tert-butyl ester

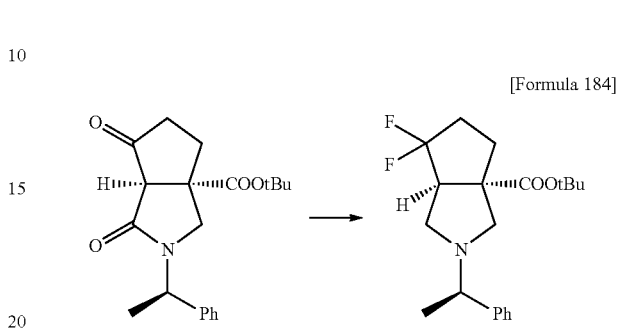

[Formula 184]

{(1S,5R)-4,6-Dioxo-3-[(1R)-1-phenylethyl]-3-azabicyclo[3,3,0]octan-1-yl}carboxylic acid tert-butyl ester (500 mg, 1.46 mmol) was dissolved in dichloromethane (20 mL). [Bis(2-methoxymethyl)amino]sulfur trifluoride (966.3 mg, 4.37 mmol) was added in a nitrogen atmosphere at 0° C., and the mixture was stirred at 20° C. for 17 hours. The reaction solution was poured into saturated sodium bicarbonate water in an ice bath, followed by extraction with ethyl acetate. The organic layer was washed with a saturated sodium thiosulfate solution and brine and dried over anhydrous sodium sulfate. After filtration, the filtrate was evaporated under reduced pressure, and the resulting residue was subjected to short silica gel column chromatography (25% ethyl acetate/hexane). The resulting crude was dissolved in tetrahydrofuran (15 mL). A 1 M borane-tetrahydrofuran complex (4.37 mL, 4.37 mmol) was added in a nitrogen atmosphere, and the mixture was stirred for 16 hours. A 1 M borane-tetrahydrofuran complex (4.37 mL, 4.37 mmol) was added, and the mixture was stirred for nine hours. A 1 M borane-tetrahydrofuran complex (4.37 mL, 4.37 mmol) was further added, and the mixture was stirred for 16 hours. Ethanol (45 mL), water (5 mL), and triethylamine (5 mL) were added to the reaction solution, and the mixture was stirred at 80° C. for four hours. Then, the solvent was evaporated under reduced pressure, and a saturated ammonium chloride solution was added to the residue. The organic layer was extracted with ethyl acetate, washed with water and brine, and dried over anhydrous sodium sulfate. After filtration, the solvent was evaporated under reduced pressure, and the resulting residue was subjected to silica gel column chromatography (15% ethyl acetate/hexane) to give 375.8 mg of the title compound as a colorless oil.

$^1$H-NMR (400 MHz, CDCl$_3$) δ: 7.32-7.22 (5H, m), 3.28 (1H, d, J=9.77 Hz), 3.13 (1H, q, J=6.51 Hz), 3.01 (1H, dd, J=19.04, 7.08 Hz), 2.60 (1H, d, J=9.28 Hz), 2.39-2.30 (3H, m), 2.15-2.09 (2H, m), 1.80-1.75 (1H, m), 1.41 (9H, s), 1.33 (3H, d, J=6.59 Hz).

MS (EI) m/z: 352 (M+H)$^+$.

Reference Example 96

{(1S,5S)-3-Benzyloxycarbonyl-6,6-difluoro-3-azabicyclo[3,3,0]octan-1-yl}carboxylic acid tert-butyl ester

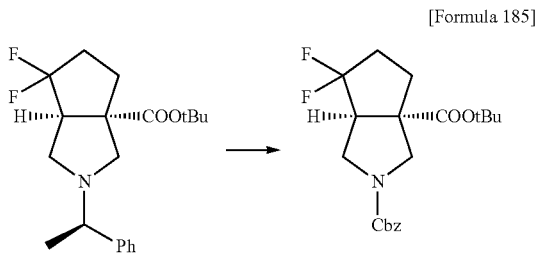

[Formula 185]

{(1S,5S)-6,6-Difluoro-3-[(1R)-1-phenylethyl]-3-azabicyclo[3,3,0]octan-1-yl}carboxylic acid tert-butyl ester (370.0 mg, 1.05 mmol) was dissolved in dichloromethane (3 mL). Benzyloxycarbonyl chloride (898 mg, 5.26 mmol) was added, and the mixture was stirred at 40° C. for 17 hours. The reaction solution was concentrated under reduced pressure, and the residue was purified by silica gel column chromatography (20% ethyl acetate/hexane) to give 338 mg of the title compound as a colorless oil.
$^1$H-NMR (400 MHz, CDCl$_3$) δ: 7.34-7.26 (5H, m), 5.13 (2H, s), 3.86 (2H, d, J=11.71 Hz), 3.54-3.42 (2H, m), 3.16-3.07 (1H, m), 2.37-2.11 (3H, m), 1.88-1.82 (1H, m), 1.45 (9H, s).
MS (EI) m/z: 404 (M+Na)$^+$.

Reference Example 97

{(1S,5R)-1-tert-Butoxycarbonylamino-6,6-difluoro-3-azabicyclo[3,3,0]octan-3-yl}carboxylic acid benzyl ester

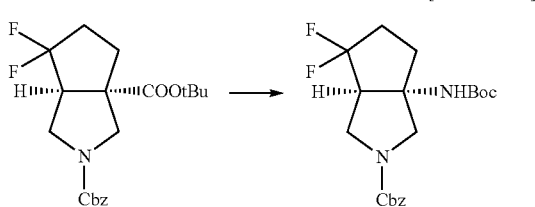

[Formula 186]

{(1S,5S)-3-Benzyloxycarbonyl-6,6-difluoro-3-azabicyclo[3,3,0]octan-1-yl}carboxylic acid tert-butyl ester (332.0 mg, 0.87 mmol) was dissolved in dichloromethane (10 mL). Trifluoroacetic acid (2 mL) was added, and the mixture was stirred for 23 hours. The reaction solution was concentrated under reduced pressure. A 1N sodium hydroxide solution was added, and the mixture was washed with chloroform. The aqueous layer was made acidic with a hydrochloric acid solution, followed by extraction with chloroform. After drying over anhydrous sodium sulfate and filtration, the solvent was evaporated under reduced pressure, and the resulting residue was dissolved in toluene (10 mL). Triethylamine (176.2 mg, 1.74 mmol) and diphenylphosphoryl azide (370.4 mg, 1.31 mmol) were added in a nitrogen atmosphere, and the mixture was stirred at 100° C. for 20 hours. The reaction solution was concentrated under reduced pressure. Then, dioxane (10 mL) and 6N hydrochloric acid (10 mL) were added, and the mixture was stirred at 40° C. for 1.5 hours. After concentration under reduced pressure and azeotropic distillation with ethanol, a 1N sodium hydroxide solution was added, followed by extraction with chloroform. After drying over anhydrous sodium sulfate and filtration, the solvent was evaporated under reduced pressure. Di-tert-butyl dicarbonate (949.9 mg, 4.35 mmol) was added to the resulting residue, and the mixture was stirred at 50° C. for 16 hours. The reaction solution was purified by silica gel column chromatography (25% ethyl acetate/hexane) to give 67.0 mg of the title compound as a colorless oil.
$^1$H-NMR (400 MHz, CDCl$_3$) δ: 7.36-7.17 (5H, m), 5.13 (2H, s), 4.80 (1H, s), 3.84-3.80 (1H, m), 3.71-3.65 (3H, m), 3.06-2.96 (1H, m), 2.39-2.31 (1H, m), 2.16-2.08 (3H, m), 1.44 (9H, s).
MS (EI) m/z: 397 (M+H)$^+$.

Reference Example 98

(1S,5R)-1-tert-Butoxycarbonylamino-6,6-difluoro-3-azabicyclo[3,3,0]octane

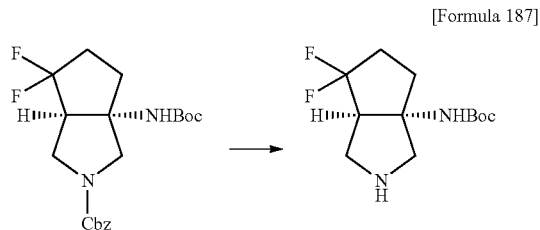 [SMILES: CC(C)(C)OC(=O)N[C@@]12CCC(F)(F)[C@@H]1CN(C(=O)OCc1ccccc1)C2 ; CC(C)(C)OC(=O)N[C@@]12CCC(F)(F)[C@@H]1CNC2]

[Formula 187]

[(1S,5R)-1-tert-Butoxycarbonylamino-6,6-difluoro-3-azabicyclo[3,3,0]octan-3-yl]carboxylic acid benzyl ester (65.0 mg, 0.16 mmol) was dissolved in methanol (10 mL). 10% palladium-carbon (50% wet) (20 mg) was added, and the mixture was stirred in a hydrogen atmosphere for one hour. The catalyst was removed by filtration, and then the filtrate was concentrated under reduced pressure. A 1N sodium hydroxide solution was added, followed by extraction with chloroform. After drying over anhydrous sodium sulfate and filtration, the filtrate was concentrated under reduced pressure to give 43 mg of the title compound as a colorless solid.
MS (EI); m/z: 263 (M+H)$^+$.

Example 22

7-[(1S,5R)-1-Amino-6,6-difluoro-3-azabicyclo[3,3,0]octan-3-yl]-6-fluoro-1-[(1R,2S)-2-fluorocyclopropyl]-1,4-dihydro-8-methoxy-4-oxoquinoline-3-carboxylic acid

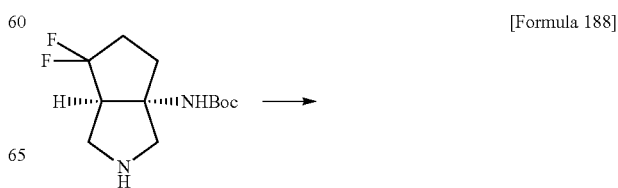

[Formula 188]

-continued

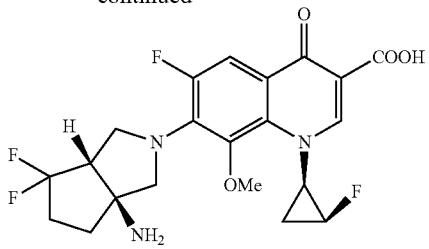

(1S,5R)-1-tert-Butoxycarbonylamino-6,6-difluoro-3-azabicyclo[3,3,0]octane (43.0 mg, 0.16 mmol) was dissolved in dimethyl sulfoxide (1.8 mL). 6,7-Difluoro-1-[(1R,2S)-2-fluorocyclopropyl]-1,4-dihydro-8-methoxy-4-oxoquinoline-3-carboxylic acid-BF$_2$ chelate (62.2 mg, 0.17 mmol) and triethylamine (49.8 mg, 0.49 mmol) were added, and the mixture was stirred at 40° C. for 16 hours. Then, 90% aqueous ethanol (20 mL) and triethylamine (2 mL) were added to the reaction solution, and the mixture was stirred at 80° C. for 2.5 hours. The solvent was evaporated under reduced pressure, and a 10% citric acid solution was added to the residue, followed by extraction with ethyl acetate. The organic layer was washed with water and brine and dried over anhydrous sodium sulfate. After filtration, the solvent was evaporated under reduced pressure, and the resulting residue was subjected to short silica gel column chromatography (3% methanol/chloroform). The resulting crude was dissolved in concentrated hydrochloric acid and washed with chloroform. The aqueous layer was adjusted to pH 12 with aqueous sodium hydroxide at 0° C. and then adjusted to pH 7.4 with hydrochloric acid, followed by extraction with chloroform. The organic layer was dried over anhydrous sodium sulfate and filtered, and then the solvent was evaporated under reduced pressure. The resulting solid was dissolved in ethanol-aqueous ammonia, and the solution was heated and stirred. After vaporization of ammonia, the precipitated crystals were collected by filtration and dried under reduced pressure to give 15.2 mg of the title compound as a pale yellow solid.

mp: 239-241° C.

$^1$H-NMR (400 MHz, 0.1N NaOD) δ: 8.47 (1H, s), 7.73 (1H, d, J=13.67 Hz), 5.07-4.91 (1H, m), 4.08-4.05 (1H, m), 3.91-3.88 (1H, m), 3.79-3.77 (1H, m), 3.72-3.70 (1H, m), 3.68 (3H, s), 3.55 (1H, d, J=10.74 Hz), 2.67-2.62 (1H, m), 2.36-2.33 (2H, m), 2.16-2.12 (1H, m), 1.96-1.89 (1H, m), 1.64-1.51 (2H, m).

Anal; Calcd for C$_{21}$H$_{21}$F$_4$N$_3$O$_4$.0.25H$_2$O: C, 54.84; H, 4.71; N, 9.14; F, 16.52. Found: C, 54.97; H, 4.53; N, 9.09; F, 16.53.

MS (EI); m/z: 456 (M+H)$^+$.

IR (ATR) v: 3392, 3031, 2883, 1718, 1618, 1510, 1450, 1360, 1333, 1306, 1250 cm$^{-1}$.

Reference Example 99

(1S,5R)-5-Methyl-4,6-dioxo-3-[(1R)-1-phenylethyl]-3-azabicyclo[3.3.0]octan-1-ylcarboxylic acid tert-butyl ester

[Formula 189]

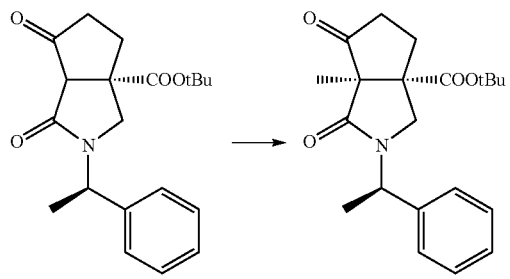

N,N-Dimethylformamide (2.0 mL) was added to sodium hydride (152 mg, 3.48 mmol) in an argon atmosphere. A solution of (1S,5R)-4,6-dioxo-3-[(1R)-1-phenylethyl]-3-azabicyclo[3.3.0]octan-1-ylcarboxylic acid tert-butyl ester (1.00 g, 2.91 mmol) in N,N-dimethylformamide (8.0 mL) was added dropwise to this suspension under ice-cooling, and the mixture was stirred at 0° C. for 30 minutes. Subsequently, methyl iodide (0.217 mL, 3.49 mmol) was added dropwise under ice-cooling, and the mixture was stirred at room temperature for 2.5 hours. The reaction solution was ice-cooled and then the reaction was quenched with water, followed by extraction with ethyl acetate. Then, the organic layer was washed with water and brine, dried over anhydrous sodium sulfate, and filtered. Thereafter, the solvent was evaporated under reduced pressure. The residue was subjected to silica gel column chromatography (hexane:ethyl acetate=2:1→1:1) to give 0.79 g of the title compound as a pale yellow solid.

$^1$H-NMR (400 MHz, CDCl$_3$) δ: 7.41-7.23 (5H, m), 5.48 (1H, q, J=6.62 Hz), 3.40 (1H, d, J=10.54 Hz), 3.13 (1H, d, J=10.54 Hz), 2.63-2.40 (3H, m), 1.96-1.83 (1H, m), 1.54 (3H, d, J=7.11 Hz), 1.39 (9H, s), 1.22 (3H, s).

Reference Example 100

(1S,5R)-6,6-Ethanediyldimercapto-5-methyl-4-oxo-3-[(1R)-1-phenylethyl]-3-azabicyclo[3.3.0]octan-1-ylcarboxylic acid methyl ester

[Formula 190]

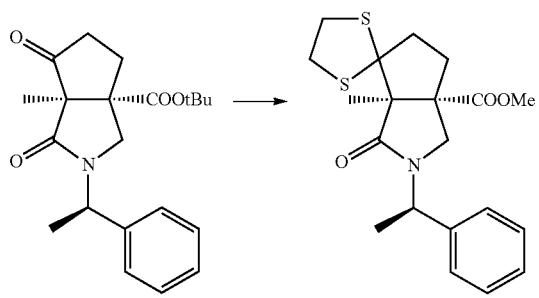

(1S,5R)-5-Methyl-4,6-dioxo-3-[(1R)-1-phenylethyl]-3-azabicyclo[3.3.0]octan-1-ylcarboxylic acid tert-butyl ester (0.28 g, 0.78 mmol) was dissolved in toluene (14 mL). Toluenesulfonic acid monohydrate (155 mg, 0.81 mmol) and ethanedithiol (0.14 mL, 1.7 mmol) were added, and the mixture was heated to reflux for nine hours. The solvent was evaporated under reduced pressure, and the resulting residue was subjected to silica gel column chromatography (dichloromethane:methanol=98:2) to give the target 1-position carboxylic acid (289 mg) as a pale yellow solid. The carboxylic acid (289 mg) was dissolved in tetrahydrofuran (10 mL) and methanol (3.0 mL). Trimethylsilyldiazomethane (1.7 mL) was added under ice-cooling, and the mixture was stirred at room temperature for two hours. The solvent was evaporated under reduced pressure, and the resulting residue was subjected to silica gel column chromatography (hexane:ethyl acetate=3:2) to give 267 mg of the title compound as a pale yellow solid.

$^1$H-NMR (400 MHz, CDCl$_3$) δ: 7.39-7.23 (5H, m), 5.52 (1H, q, J=6.86 Hz), 3.60 (3H, s), 3.55 (1H, d, J=10.05 Hz), 3.44-3.31 (1H, m), 3.28-3.19 (1H, m), 3.16 (1H, d, J=10.05 Hz), 2.79-2.70 (1H, m), 2.54-2.44 (1H, m), 2.26-2.15 (1H, m), 1.81-1.70 (1H, m), 1.59-1.52 (2H, m), 1.56 (3H, d, J=7.11 Hz), 1.33 (3H, s).

Reference Example 101

(1S,5R)-5-Methyl-4-oxo-3-[(1R)-1-phenylethyl]-3-azabicyclo[3.3.0]octan-1-ylcarboxylic acid methyl ester

[Formula 191]

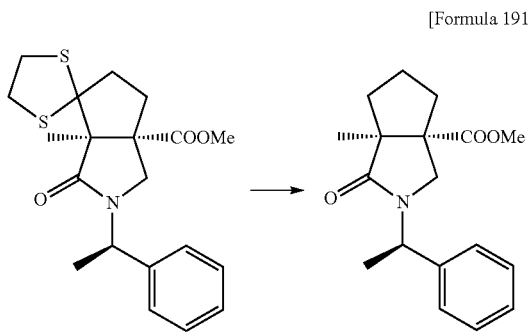

(1S,5R)-6,6-Ethanediyldimercapto-5-methyl-4-oxo-3-[(1R)-1-phenylethyl]-3-azabicyclo[3.3.0]octan-1-ylcarboxylic acid methyl ester (266 mg, 0.68 mmol) was dissolved in ethanol (10 mL). Raney nickel (2.0 mL) was added dropwise, and the mixture was heated to reflux for 5.5 hours. The catalyst was removed by filtration, and then the filtrate was concentrated under reduced pressure. The resulting residue was subjected to silica gel column chromatography (hexane:ethyl acetate=7:3→1:1) to give 133 mg of the title compound as a pale yellow solid.

$^1$H-NMR (400 MHz, CDCl$_3$) δ: 7.39-7.24 (5H, m), 5.56-5.44 (1H, m), 3.64 (3H, s), 3.51 (1H, d, J=10.05 Hz), 3.02-2.96 (1H, m), 2.49-2.26 (2H, m), 1.91-1.44 (4H, m), 1.52 (3H, d, J=7.35 Hz), 1.12 (3H, s).

Reference Example 102

(1S,5S)-1-(tert-Butoxycarbonylamino)-5-methyl-4-oxo-3-[(1R)-1-phenylethyl]-3-azabicyclo[3.3.0]octane

[Formula 192]

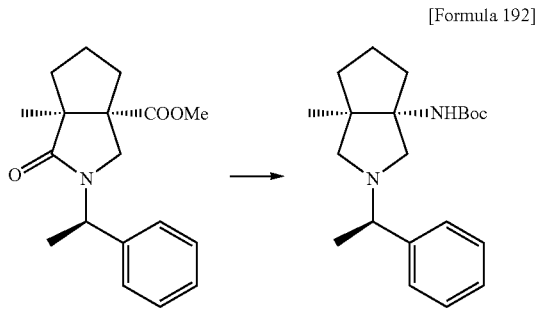 [SMILES: COC(=O)[C@@]12CCC[C@]1(C)C(=O)N([C@H](C)c1ccccc1)C2 ; C[C@H](c1ccccc1)N1C[C@@]2(C)CCC[C@@]2(NC(=O)OC(C)(C)C)C1]

(1S,5R)-5-Methyl-4-oxo-3-[(1R)-1-phenylethyl]-3-azabicyclo[3.3.0]octan-1-ylcarboxylic acid methyl ester (130 mg, 0.43 mmol) was dissolved in methanol (5.0 mL). A 1N sodium hydroxide solution (1.5 mL) was added dropwise under ice-cooling, and the mixture was stirred at room temperature for four hours. Then, a 1N sodium hydroxide solution (1.5 mL) was added dropwise, and the mixture was stirred at room temperature for 15 hours. Sodium hydroxide (93 mg) was further added, and the mixture was stirred at room temperature for six hours. Sodium hydroxide (90 mg) was added again, and the mixture was stirred at room temperature for four hours and then at 50° C. for one hour. The reaction solution was made weakly acidic with hydrochloric acid, and the solvent was evaporated under reduced pressure. The resulting residue was extracted with dichloromethane and dilute hydrochloric acid. The organic layer was dried over anhydrous sodium sulfate and filtered, and then the solvent was evaporated under reduced pressure. The resulting residue was dissolved in toluene (5.0 mL). Triethylamine (0.132 mL, 0.95 mmol) and diphenylphosphoryl azide (0.111 ml, 0.52 mmol) were added, and the mixture was heated to reflux for three hours. The reaction solution was extracted with ethyl acetate and saturated sodium bicarbonate water. Then, the organic layer was washed with brine, dried over anhydrous sodium sulfate, and filtered. Thereafter, the solvent was evaporated under reduced pressure. 1,4-Dioxane (2.0 mL) and 6N hydrochloric acid (2.0 mL) were added to the resulting residue, and the mixture was stirred at 50° C. for 15 hours. After extraction with water and ethyl acetate, the aqueous layer was made alkaline with a saturated sodium hydroxide solution and extracted with chloroform twice. The organic layers were combined, dried over anhydrous sodium sulfate, and filtered, and then the solvent was evaporated under reduced pressure. Toluene (3.0 mL) and Red-Al™ (65% solution in toluene) (0.50 mL) were sequentially added to the resulting residue, and the mixture was stirred at 80° C. for 2.5 hours. A 3N sodium hydroxide solution was added to the reaction solution under ice-cooling, and the layers were separated with toluene. The organic layer was dried over anhydrous sodium sulfate and filtered, and then the solvent was evaporated under reduced pressure. The resulting residue was dissolved in dichloromethane (10 mL) and methanol (5.0 mL). Di-tert-butyl dicarbonate (560 mg, 2.57 mmol) was added, and the mixture was stirred at room temperature for 16 hours. The reaction solution was subjected to silica gel column chromatography (dichloromethane:methanol=98:2) to give 77 mg of the title compound as a pale yellow solid.

$^1$H-NMR (400 MHz, CDCl$_3$) δ: 7.33-7.16 (5H, m), 4.79 (1H, brs), 3.17-3.00 (1H, m), 2.74-2.58 (2H, m), 2.53-2.44 (1H, m), 2.27-2.13 (1H, m), 2.08-1.89 (2H, m), 1.74-1.62 (2H, m), 1.60-1.24 (2H, m), 1.41 (9H, s), 1.28 (3H, d, J=6.59 Hz), 1.07 (3H, s).

Reference Example 103

(1S,5S)-1-(tert-Butoxycarbonylamino)-5-methyl-4-oxo-3-azabicyclo[3.3.0]octane

[Formula 193]

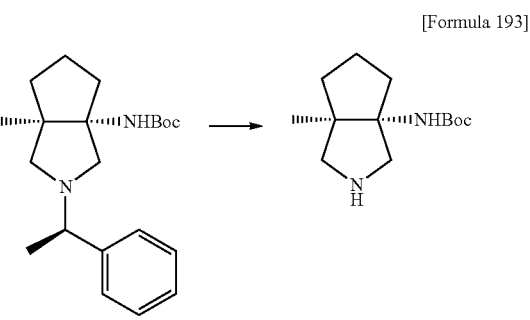 [SMILES: C[C@H](c1ccccc1)N1C[C@@]2(C)CCC[C@@]2(NC(=O)OC(C)(C)C)C1 ; CC(C)(C)OC(=O)N[C@@]12CCC[C@]1(C)CNC2]

(1S,5S)-1-(tert-Butoxycarbonylamino)-5-methyl-4-oxo-3-[(1R)-1-phenylethyl]-3-azabicyclo[3.3.0]octane (77 mg, 0.22 mmol) was dissolved in ethanol (6.0 mL). 10% palladium-carbon (50% wet) (69 mg) was added, and the mixture was stirred in a hydrogen atmosphere at 45° C. for 19.5 hours. After removing the catalyst by filtration, the filtrate was concentrated under reduced pressure to give 50 mg of the title compound as a pale yellow oil.

$^1$H-NMR (400 MHz, CDCl$_3$) δ: 4.68 (1H, brs), 3.36-3.19 (1H, m), 3.00-2.58 (4H, m), 2.40-1.89 (4H, m), 1.81-1.26 (2H, m), 1.44 (9H, s), 1.07 (3H, s).

Example 23

7-[(1R,5R)-1-Amino-3-aza-5-methylbicyclo[3.3.0]octan-3-yl]-6-fluoro-1-[(1R,2S)-2-fluorocyclopropane]-1,4-dihydro-8-methoxy-4-oxoquinoline-3-carboxylic acid

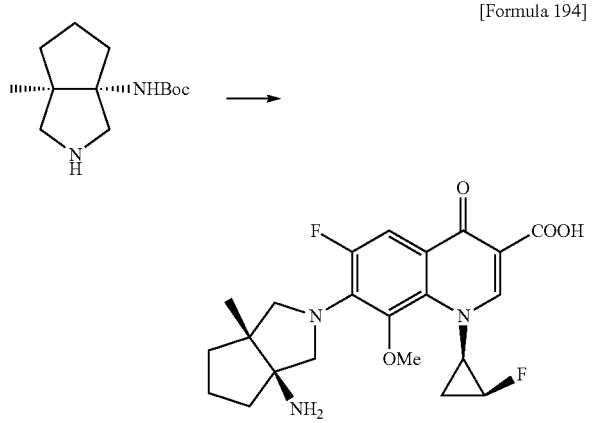

[Formula 194]

Triethylamine (0.092 mL, 0.66 mmol) and 6,7-difluoro-1-[(1R,2S)-2-fluorocyclopropane]-1,4-dihydro-8-methoxy-4-oxoquinoline-3-carboxylic acid-BF$_2$ chelate (79.1 mg, 0.22 mmol) were added to a solution of (1R,5R)-1-(tert-butoxycarbonylamino)-5-methyl-3-azabicyclo[3.3.0]octane (50.1 mg, 0.21 mmol) in dimethyl sulfoxide (2.0 mL). The mixture was stirred at 45° C. for 24 hours. Ethanol (3.0 mL), water (1.0 mL), and triethylamine (1.0 mL) were added to the reaction solution, and the mixture was heated to reflux for 2.5 hours. The solvent was evaporated under reduced pressure, and the resulting residue was extracted with a 10% citric acid solution and ethyl acetate. Then, the organic layer was washed with water twice and brine, dried over anhydrous sodium sulfate, and filtered. Thereafter, the solvent was evaporated under reduced pressure. The resulting residue was subjected to silica gel column chromatography (dichloromethane:methanol=99:1). The resulting oil (92.5 mg) was dissolved in concentrated hydrochloric acid (1.0 mL) under ice-cooling, and the solution was stirred at room temperature for 0.5 hour. The reaction solution was washed with chloroform twice, and then the aqueous layer was adjusted to pH 12 with a saturated sodium hydroxide solution. The basic solution was adjusted to pH 7.4 with hydrochloric acid, followed by extraction with chloroform. The organic layer was dried over anhydrous sodium sulfate and filtered, and then the solvent was evaporated under reduced pressure. The resulting residue was purified by recrystallization from ethanol to give 47 mg of the title compound as a pale yellow solid.

mp: 109-113° C. (dec.).

$[α]_D^{24}$+78° (c=0.135, 0.1N NaOH).

$^1$H-NMR (400 MHz, 0.1N NaOD) δ: 8.45 (1H, s), 7.66 (1H, d, J=14.5 Hz), 4.79-4.85 (1H, m), 4.00-4.10 (1H, m), 3.61 (3H, s), 3.51-3.75 (3H, m), 3.34-3.44 (1H, m), 1.94-2.07 (1H, m), 1.43-1.93 (7H, m), 1.10 (3H, s).

MS (FAB); m/z: 434 (M+H)$^+$.

Anal. Calcd for $C_{22}H_{25}F_2N_3O_4$·2H$_2$O: C, 56.28; H, 6.23; F, 8.09; N, 8.95. Found: C, 56.57; H, 6.24; F, 8.19; N, 9.01.

IR (ATR) ν: 2942, 2877, 1612, 1573, 1448, 1434, 1392, 1349, 1342, 1311, 1301, 1290, 1272, 821, 804 cm$^{-1}$.

Reference Example 104

(3S)-3-Hydroxymethyl-5-oxo-1-[(1R)-1-phenylethyl]pyrrolidine-3-carboxylic acid tert-butyl ester

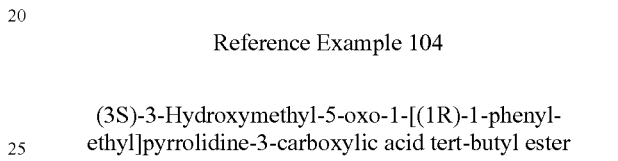

[Formula 195]

5-Oxo-1-[(1R)-1-phenylethyl]pyrrolidine-3-carboxylic acid tert-butyl ester (4 g, 13.82 mol) was dissolved in N,N-dimethylformamide (40 mL), and paraformaldehyde (0.83 g, 27.65 mmol) was suspended in the solution. Sodium hydride (0.60 g, 13.82 mmol) was added at room temperature, and the mixture was stirred for 30 minutes. Then, the reaction solution was poured into a 10% citric acid solution (150 mL) at 0° C. The mixture was extracted with ethyl acetate (300 mL). The organic layer was washed with water (100 mL×2) and brine (100 mL), dried over anhydrous sodium sulfate, and filtered. The solvent was evaporated under reduced pressure, and the resulting residue was purified by silica gel column chromatography (30% ethyl acetate/hexane→80% ethyl acetate/hexane) to give 1.03 g of the title compound as a colorless solid.

$^1$H-NMR (400 MHz, CDCl$_3$) δ: 7.34-7.28 (5H, m), 5.51 (1H, q, J=7.16 Hz), 3.77 (1H, dd, J=11.23, 5.37 Hz), 3.61 (1H, dd, J=11.23, 7.81 Hz), 3.39 (1H, d, J=10.50 Hz), 3.21 (1H, d, J=10.25 Hz), 2.78 (1H, d, J=17.09 Hz), 2.51 (1H, dd, J=7.81, 5.37 Hz), 2.40 (1H, d, J=17.33 Hz), 1.53 (3H, d, J=7.33 Hz), 1.35 (9H, s).

MS (EI); m/z: 320 (M+H)$^+$.

Reference Example 105

(3S)-3-Formyl-5-oxo-1-[(1R)-1-phenylethyl]pyrrolidine-3-carboxylic acid tert-butyl ester

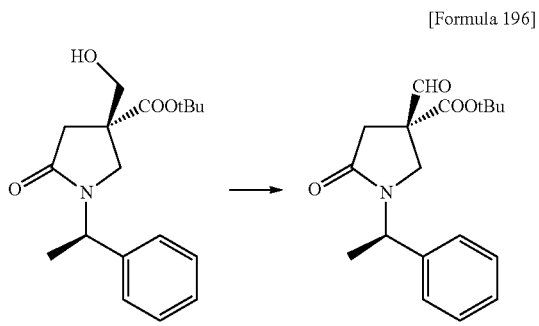

[Formula 196]

(3S)-3-Hydroxymethyl-5-oxo-1-[(1R)-1-phenylethyl]pyrrolidine-3-carboxylic acid tert-butyl ester (4.0 g, 12.52 mmol) was dissolved in dichloromethane. Triethylamine (6.34 g, 62.62 mmol), dimethyl sulfoxide (3.91 g, 50.09 mmol), and a $SO_3$-pyridine complex (3.99 g, 25.05 mmol) were sequentially added at 0° C., and the mixture was stirred for 17 hours. The reaction solution was concentrated under reduced pressure, and water was added to the residue, followed by extraction with ethyl acetate. The organic layer was washed with water and brine, dried over anhydrous sodium sulfate, and filtered. The solvent was evaporated under reduced pressure, and the resulting residue was subjected to silica gel column chromatography (60% ethyl acetate/hexane) to give 2.85 g of the title compound as a colorless solid.

$^1$H-NMR (400 MHz, $CDCl_3$) δ: 9.62 (1H, s), 7.35-7.28 (5H, m), 5.47 (1H, q, J=7.00 Hz), 3.79 (1H, t, J=9.52 Hz), 3.24 (1H, d, J=10.50 Hz), 2.93 (1H, d, J=17.33 Hz), 2.85 (1H, d, J=17.33 Hz), 1.53 (3H, d, J=7.08 Hz), 1.38 (9H, s).

MS (EI); m/z: 318 (M+H)$^+$.

Reference Example 106

(3R)-5-Oxo-1-[(1R)-1-phenylethyl]-3-vinylpyrrolidine-3-carboxylic acid tert-butyl ester

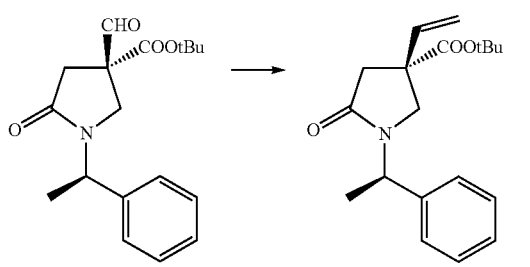

[Formula 197]

Methyltriphenylphosphonium bromide (187.4 mg, 0.52 mmol) was dissolved in tetrahydrofuran. A 2.62 M solution of n-butyllithium in hexane (0.16 mL, 0.42 mmol) was added dropwise in a nitrogen atmosphere at −78° C., and the mixture was stirred for one hour. After heating to 0° C., a solution of (3S)-3-formyl-5-oxo-1-[(1R)-1-phenylethyl]pyrrolidine-3-carboxylic acid tert-butyl ester (111 mg, 0.35 mmol) in tetrahydrofuran was added dropwise, and the mixture was stirred for one hour. A saturated ammonium chloride solution was added to the reaction solution, followed by extraction with ethyl acetate. The organic layer was washed with water and brine, dried over anhydrous sodium sulfate, and filtered. The solvent was evaporated under reduced pressure, and the resulting residue was subjected to silica gel column chromatography (25% ethyl acetate/hexane) to give 54 mg of the title compound as a yellow oil.

$^1$H-NMR (400 MHz, $CDCl_3$) δ: 7.33-7.26 (5H, m), 5.96 (1H, dd, J=17.33, 10.74 Hz), 5.52-5.45 (1H, m), 5.21-5.17 (2H, m), 3.45 (1H, d, J=10.25 Hz), 3.26 (1H, d, J=10.01 Hz), 3.01 (1H, d, J=16.60 Hz), 2.54 (1H, d, J=16.60 Hz), 1.50 (3H, d, J=7.08 Hz), 1.33 (9H, s).

MS (EI) m/z: 318 (M+H)$^+$.

Reference Example 107

(3S,4S)-4-Allyl-5-oxo-1-[(1R)-1-phenylethyl]-3-vinylpyrrolidine-3-carboxylic acid tert-butyl ester

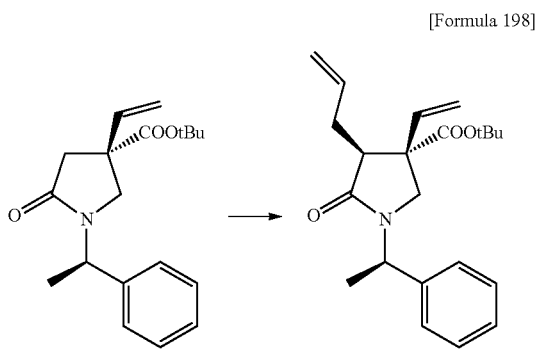

[Formula 198]

(3R)-5-oxo-1-[(1R)-1-phenylethyl]-3-vinylpyrrolidine-3-carboxylic acid tert-butyl ester (236.0 mg, 0.75 mmol) and allyl bromide (271.6 mg, 2.24 mmol) were dissolved in tetrahydrofuran. A 1 M solution of lithium hexamethyldisilazide in tetrahydrofuran (1.12 mL, 1.12 mmol) was added dropwise in a nitrogen atmosphere at 0° C. After stirring for 1.5 hours, a saturated ammonium chloride solution was added, followed by extraction with ethyl acetate. The organic layer was washed with water and brine, dried over anhydrous sodium sulfate, and filtered. The solvent was evaporated under reduced pressure, and the resulting residue was subjected to silica gel column chromatography (10% ethyl acetate/hexane) to give 135 mg of the title compound as a colorless oil.

$^1$H-NMR (400 MHz, $CDCl_3$) δ: 7.33-7.26 (5H, m), 5.98-5.82 (2H, m), 5.47 (1H, q, J=7.00 Hz), 5.24-4.97 (4H, m), 3.35-3.25 (2H, m), 3.03 (1H, t, J=6.82 Hz), 2.48-2.41 (1H, m), 2.39-2.32 (1H, m), 1.54 (3H, d, J=7.08 Hz), 1.33 (9H, s).

MS (EI); m/z: 356 (M+H)$^+$.

Reference Example 108

[(1S,5S)-4-Oxo-3-[(1R)-1-phenylethyl]-3-azabicyclo[3.3.0]oct-7-en-1-yl]carboxylic acid tert-butyl ester

[Formula 199]

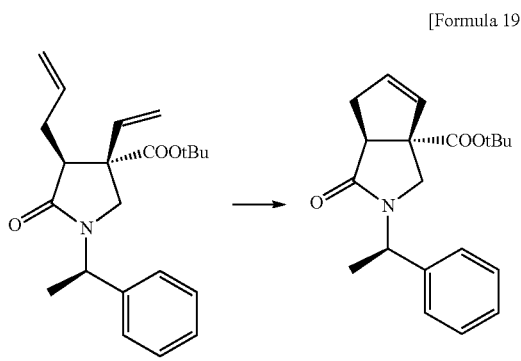

(3S,4S)-4-Allyl-5-oxo-1-[(1R)-1-phenylethyl]-3-vinylpyrrolidine-3-carboxylic acid tert-butyl ester (130.0 mg, 0.37 mmol) was dissolved in benzene (8 mL). The second generation Grubbs' catalyst (31.0 mg, 0.04 mmol) was added, and the mixture was stirred at room temperature for two hours. The reaction solution was concentrated under reduced pressure, and the resulting residue was subjected to silica gel column chromatography (15% ethyl acetate/hexane) to give 93.2 mg of the title compound as a yellow oil.

$^1$H-NMR (400 MHz, CDCl$_3$) δ: 7.34-7.28 (5H, m), 5.94-5.91 (1H, m), 5.60-5.59 (1H, m), 5.51 (1H, q, J=7.16 Hz), 3.34-3.24 (3H, m), 2.81-2.79 (2H, m), 1.45 (3H, d, J=7.32 Hz), 1.38 (9H, s).

MS (EI) m/z: 328 (M+H)$^+$.

Reference Example 109

[(1S,5S)-3-[(1R)-1-Phenylethyl]-4-thioxo-3-azabicyclo[3.3.0]oct-7-en-1-yl]carboxylic acid tert-butyl ester

[Formula 200]

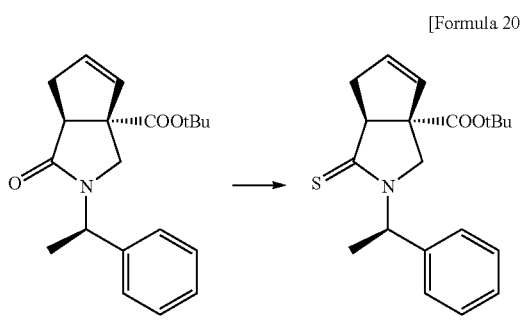

[(1S,5S)-4-Oxo-3-[(1R)-1-phenylethyl]-3-azabicyclo[3.3.0]oct-7-en-1-yl]carboxylic acid tert-butyl ester (88.0 mg, 0.27 mmol) was dissolved in toluene (8 mL). Lawesson's reagent (81.5 mg, 0.20 mmol) was added, and the mixture was stirred at 80° C. for four hours. The reaction solution was concentrated under reduced pressure, and the resulting residue was subjected to silica gel column chromatography (10% ethyl acetate/hexane) to give 91.6 mg of the title compound as a yellow oil.

$^1$H-NMR (400 MHz, CDCl$_3$) δ: 7.37-7.26 (5H, m), 6.41 (1H, q, J=7.08 Hz), 5.95-5.94 (1H, m), 5.55-5.54 (1H, m), 3.74 (1H, d, J=8.30 Hz), 3.60 (1H, d, J=11.96 Hz), 3.49 (1H, d, J=12.21 Hz), 3.15 (1H, d, J=17.09 Hz), 3.02-2.98 (1H, m), 1.51 (3H, d, J=7.08 Hz), 1.36 (9H, s).

MS (EI) m/z: 344 (M+H)$^+$.

Reference Example 110

[(1S,5S)-3-[(1R)-1-Phenylethyl]-3-azabicyclo[3.3.0]oct-7-en-1-yl]carboxylic acid tert-butyl ester

[Formula 201]

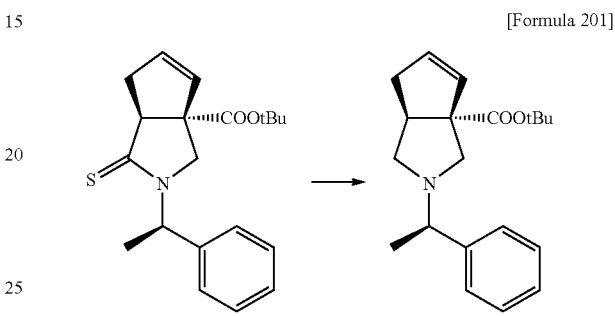

[(1S,5S)-3-[(1R)-1-Phenylethyl]-4-thioxo-3-azabicyclo[3.3.0]oct-7-en-1-yl]carboxylic acid tert-butyl ester (88.2 mg, 0.27 mmol) was dissolved in ethanol. Raney nickel was added, and the mixture was stirred for one hour. The catalyst was removed by filtration, and then the filtrate was concentrated under reduced pressure. The resulting residue was subjected to silica gel column chromatography (10% ethyl acetate/hexane) to give 55.4 mg of the title compound as a colorless oil.

$^1$H-NMR (400 MHz, CDCl$_3$) δ: 7.36-7.21 (5H, m), 5.74 (1H, brs), 5.54 (1H, brs), 3.15 (1H, q, J=6.75 Hz), 3.04 (1H, brs), 2.72-2.70 (2H, m), 2.61 (1H, t, J=7.81 Hz), 2.53-2.51 (2H, m), 2.18 (1H, d, J=16.85 Hz), 1.41 (9H, s), 1.32 (3H, d, J=6.59 Hz).

MS (EI) m/z: 314 (M+H)$^+$.

Reference Example 111

[(1S,5S)-3-Benzyloxycarbonyl-3-azabicyclo[3.3.0]oct-7-en-1-yl]carboxylic acid tert-butyl ester

[Formula 202]

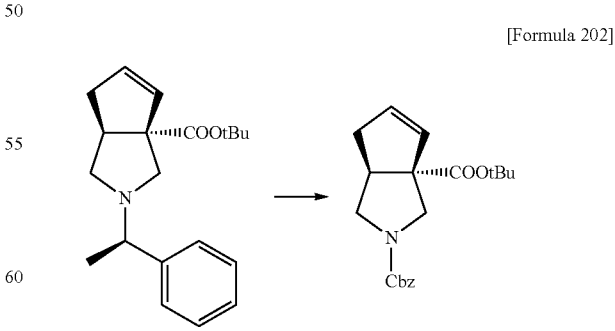

[(1S,5S)-3-[(1R)-1-Phenylethyl]-3-azabicyclo[3.3.0]oct-7-en-1-yl]carboxylic acid tert-butyl ester (370 mg, 1.18 mmol) was dissolved in dichloroethane (3 mL). Benzyloxycarbonyl chloride (1.01 g, 5.90 mmol) was added, and the mixture was stirred at 40° C. for three hours. The reaction solution was concentrated under reduced pressure, and the resulting residue was subjected to silica gel column chromatography (10% ethyl acetate/hexane) to give 385 mg of the title compound as a colorless oil.

$^1$H-NMR (400 MHz, CDCl$_3$) S: 7.35-7.29 (5H, m), 5.79 (1H, brs), 5.64 (1H, brs), 5.12 (2H, s), 3.79-3.68 (3H, m), 3.21-3.12 (2H, m), 2.74 (1H, dd, J=17.44, 6.22 Hz), 2.19 (1H, t, J=18.54 Hz), 1.43 (9H, s).

MS; (EI) m/z: 366 (M+Na)$^+$.

Reference Example 112

[(1S,5R)-1-tert-Butoxycarbonylamino-3-azabicyclo [3.3.0]oct-7-en-3-yl]carboxylic acid benzyl ester

[Formula 203]

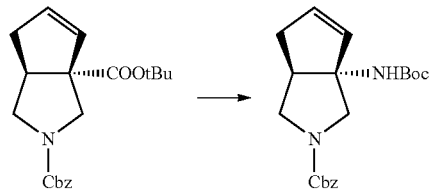

[(1S,5S)-3-Benzyloxycarbonyl-3-azabicyclo[3.3.0]oct-7-en-1-yl]carboxylic acid tert-butyl ester (380 mg, 1.11 mmol) was dissolved in dichloromethane (8 mL). Trifluoroacetic acid (1.5 mL) was added, and the mixture was stirred for one day. The reaction solution was concentrated under reduced pressure, and a 1N sodium hydroxide solution (100 mL) was added, and the mixture was washed with chloroform. The aqueous layer was made acidic with a hydrochloric acid solution, followed by extraction with chloroform (200 mL×2). After drying over anhydrous sodium sulfate and filtration, the solvent was evaporated under reduced pressure, and the resulting residue was dissolved in toluene (10 mL). Triethylamine (223.3 mg, 2.21 mmol) and diphenylphosphoryl azide (469.5 mg, 1.66 mmol) were added in a nitrogen atmosphere, and the mixture was stirred at 80° C. for 20 hours. The reaction solution was concentrated under reduced pressure. Then, 1,4-dioxane (10 mL) and 6N hydrochloric acid (10 mL) were added, and the mixture was stirred for three days. After concentration under reduced pressure and azeotropic distillation with ethanol, a 1N sodium hydroxide solution was added, followed by extraction with chloroform. After drying over anhydrous sodium sulfate and filtration, the solvent was evaporated under reduced pressure. Di-tert-butyl dicarbonate (1204 mg, 5.52 mmol) was added to the resulting residue, and the mixture was stirred at 50° C. for 16 hours. The reaction solution was purified by silica gel column chromatography (20% ethyl acetate/hexane) to give 92.1 mg of the title compound as a colorless oil.

$^1$H-NMR (400 MHz, CDCl$_3$) δ: 7.32-7.25 (5H, m), 5.84 (1H, s), 5.78 (1H, s), 5.10 (2H, s), 4.70 (1H, s), 3.87 (1H, dd, J=11.23, 8.79 Hz), 3.79-3.76 (2H, m), 3.24-3.21 (1H, m), 2.87-2.72 (2H, m), 2.21-2.18 (1H, m), 1.43 (9H, s).

MS (EI); m/z: 359 (M+H)$^+$.

Reference Example 113

(1S,5R)-1-tert-Butoxycarbonylamino-3-azabicyclo [3.3.0]oct-7-ene

[Formula 204]

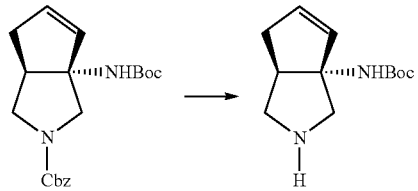

[(1S,5R)-1-tert-Butoxycarbonylamino-3-azabicyclo [3.3.0]oct-7-en-3-yl]carboxylic acid benzyl ester (85.0 mg, 0.24 mmol) was dissolved in tetrahydrofuran (20 mL). After bubbling with liquid ammonia (20 mL) at −78° C., sodium (17.1 mg, 0.71 mmol) was added, and the mixture was stirred for one hour. A saturated ammonium chloride solution (6 drops) were added, and then ammonia was vaporized in an ice water bath. A 1N sodium hydroxide solution was added, followed by extraction with chloroform twice. The organic layers were combined, dried over anhydrous sodium sulfate, and filtered. Then, the filtrate was concentrated under reduced pressure to give 52.9 mg of the title compound as a colorless solid.

MS (EI) m/z: 225 (M+H)$^+$.

Example 24

7-[(1S,5R)-1-Amino-3-azabicyclo[3.3.0]oct-7-en-3-yl]-6-fluoro-1-[(1R,2S)-2-fluorocyclopropyl]-8-methoxy-1,4-dihydro-4-oxoquinoline-3-carboxylic acid

[Formula 205]

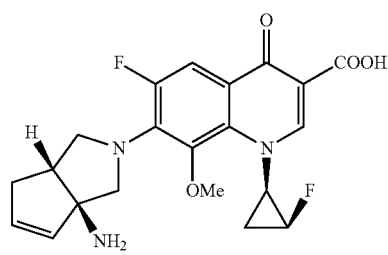

(1S,5R)-1-tert-Butoxycarbonylamino-3-azabicyclo[3.3.0] oct-7-ene (52.9 mg, 0.24 mmol) was dissolved in dimethyl sulfoxide (2 mL). 6,7-Difluoro-1-[(1R,2S)-2-fluorocyclopropyl]-8-methoxy-1,4-dihydro-4-oxoquinoline-3-carboxylic acid-BF$_2$ chelate (89.4 mg, 0.25 mmol) and triethylamine (71.6 mg, 0.71 mmol) were added, and the mixture was stirred at 40° C. for 20 hours. Then, 90% aqueous ethanol (20 mL) and triethylamine (2 mL) were added to the reaction solution, and the mixture was stirred at 80° C. for two hours. The solvent was evaporated under reduced pressure and a 10% citric acid solution was added, followed by extraction with ethyl acetate. The organic layer was washed with water and brine, dried over anhydrous sodium sulfate, and filtered. The solvent was evaporated under reduced pressure, and the resulting residue was subjected to short silica gel column chromatography (3% methanol/chloroform). The resulting crude was dissolved in concentrated hydrochloric acid and washed with chloroform. The aqueous layer was adjusted to pH 12 with aqueous sodium hydroxide at 0° C. and then adjusted to pH 8 with hydrochloric acid, followed by extraction with chloroform. The organic layer was dried over anhydrous sodium sulfate and filtered, and then the solvent was evaporated under reduced pressure. The resulting residue was washed with ethanol-diethyl ether and dried under reduced pressure to give 57.8 mg of the title compound as a pale yellow solid.

mp: 206-208° C.

$^1$H-NMR (400 MHz, 0.1N NaOD) δ: 8.47 (1H, s), 7.69 (1H, d, J=13.67 Hz), 5.90 (1H, brs), 5.69 (1H, brs), 4.96 (1H, d, J=60.79 Hz), 4.08-4.04 (1H, m), 3.77 (1H, t, J=8.91 Hz), 3.70 (3H, d, J=10.25 Hz), 3.64 (1H, s), 3.59-3.57 (1H, m), 3.54-3.51 (1H, m), 2.91-2.87 (1H, m), 2.55-2.53 (1H, m), 2.30 (1H, d, J=17.09 Hz), 1.63-1.55 (2H, m).

Anal; Calcd for $C_{21}H_{21}F_2N_3O_4 \cdot 0.25H_2O \cdot 0.5EtOH$: C, 59.39; H, 5.55; N, 9.44; F, 8.54. Found: C, 59.32; H, 5.44; N, 9.50; F, 8.28.

MS (EI); m/z: 418 (M+H)$^+$.

IR (ATR) ν: 2929, 2848, 2758, 1726, 1614, 1577, 1537, 1504, 1435, 1392, 1352, 1315, 1269 cm$^{-1}$.

Reference Example 114

(1R*,5S*)-7-Benzyl-3-oxa-7-azabicyclo[3.3.0]octan-2-one

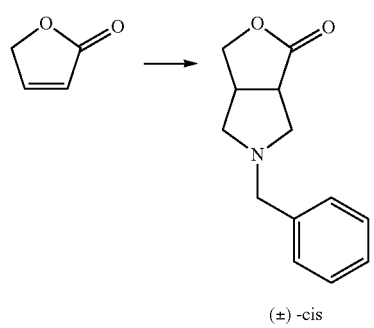

(±)-cis

[Formula 206]

Trifluoroacetic acid (0.136 mL) was added to a solution of N-benzyl-N-(methoxymethyl)-N-trimethylsilylamine (43.9 g, 185 mmol) and γ-crotonolactone (12.5 g, 176 mmol) in 1,2-dichloromethane (176 mL), and the mixture was stirred in a nitrogen atmosphere at room temperature for four hours. A saturated sodium bicarbonate solution (250 mL) was added to the reaction solution, followed by extraction with chloroform (200 mL×2). The organic layer was washed with brine (400 mL) and dried over anhydrous sodium sulfate. After filtration, the filtrate was concentrated under reduced pressure. The resulting residue was purified by silica gel column chromatography (hexane:ethyl acetate=100:0→90:10→84:16→80:20→75:25→66:34→50:50) to give 37.1 g of the title compound.

$^1$H-NMR (400 MHz, CDCl$_3$) δ: 7.30-7.26 (5H, m), 4.48 (1H, t, J=8.58 Hz), 4.08 (1H, dd, J=9.19, 3.55 Hz), 3.69 (1H, d, J=13.24 Hz), 3.54 (1H, d, J=13.24 Hz), 3.26 (1H, d, J=9.31 Hz), 3.08-2.98 (2H, m), 2.80 (1H, d, J=9.56 Hz), 2.49-2.38 (2H, m).

MS (ESI) m/z: 218 (M+H)$^+$.

Reference Example 115

1-Allyl-7-benzyl-3-oxa-7-azabicyclo[3.3.0]octan-2-one

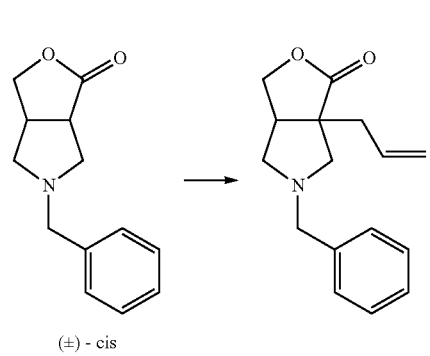

(±) - cis

[Formula 207]

Allyl bromide (2.48 mL, 29.3 mmol) was added to a solution of (1R*,5S*)-7-benzyl-3-oxa-7-azabicyclo[3.3.0]octan-2-one (4.25 g, 19.6 mmol) in tetrahydrofuran (98 mL) with stirring under salt-ice cooling. A 1 M solution of lithium hexamethyldisilazide in tetrahydrofuran (23.5 mL, 23.5 mmol) was added dropwise under cooling with ice-acetone. The mixture was stirred for two hours while gradually heating to room temperature. A saturated ammonium chloride solution (200 mL) was added to the reaction solution, followed by extraction with ethyl acetate (100 mL×2). The organic layer was washed with water (250 mL) and brine (250 mL) and dried over anhydrous sodium sulfate. After filtration, the filtrate was concentrated under reduced pressure. The resulting residue was purified by silica gel column chromatography (hexane:ethyl acetate=100:0→95:5→90:10→84:16→80:20→75:25→66:34→50:50) to give 1.51 g of the title compound.

$^1$H-NMR (400 MHz, CDCl$_3$) δ: 7.32-7.21 (5H, m), 5.80-5.70 (1H, m), 5.20-5.14 (2H, m), 4.35 (1H, t, J=8.95 Hz), 4.03 (1H, dd, J=9.19, 3.55 Hz), 3.63 (1H, d, J=13.24 Hz), 3.51 (1H, d, J=13.24 Hz), 3.26 (1H, d, J=9.07 Hz), 2.81 (1H, d, J=9.56 Hz), 2.73-2.71 (1H, m), 2.57 (1H, dd, J=13.73, 6.62 Hz), 2.49 (1H, dd, J=9.44, 6.74 Hz), 2.30 (1H, d, J=13.85, 8.21 Hz), 2.23 (1H, d, J=9.07 Hz).

MS (ESI); m/z: 258 (M+H)$^+$.

Reference Example 116

7-Benzyl-1-(3-hydroxypropyl)-3-oxa-7-azabicyclo[3.3.0]octan-2-one

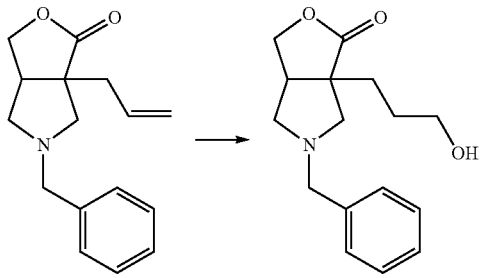

[Formula 208]

A solution of 1-allyl-7-benzyl-3-oxa-7-azabicyclo[3.3.0]octan-2-one (11.0 g, 42.7 mmol) in tetrahydrofuran (142 mL) was cooled with ice-acetone. A 0.5 mol/L solution of 9-borabicyclo[3.3.1]nonane in tetrahydrofuran (264 mL, 132 mmol) was added in a nitrogen atmosphere, and the mixture was stirred at room temperature for two hours. After cooling with ice-acetone, A 1 mol/L solution of sodium hydroxide (142 mL) and a 30% hydrogen peroxide solution were added in a nitrogen atmosphere, and the mixture was stirred at room temperature for one hour. The organic layer of the reaction solution was concentrated under reduced pressure and extracted with chloroform (300 mL×1, 250 mL×1). The organic layer was washed with brine (600 mL) and dried over anhydrous sodium sulfate. After filtration, the filtrate was concentrated under reduced pressure. The resulting residue was purified by silica gel column chromatography (hexane:ethyl acetate=100:0→66:34→50:50→34:66→20:80) to give 12.9 g of a residue containing the title compound which was directly used for the next reaction.

$^1$H-NMR (400 MHz, CDCl$_3$) δ: 7.32-7.22 (5H, m), 4.41 (1H, t, J=8.82 Hz), 4.05 (1H, dd, J=9.19, 3.55 Hz), 3.81 (1H, t, J=8.95 Hz), 3.68-3.63 (3H, m), 3.51 (1H, d, J=13.24 Hz), 3.29 (1H, d, J=9.31 Hz), 2.83 (1H, d, J=9.56 Hz), 2.69 (1H, s), 2.49 (1H, t, J=7.84 Hz), 2.19 (1H, t, J=8.58 Hz), 1.93-1.82 (3H, m).

MS (ESI); m/z: 276 (M+H)$^+$.

Reference Example 117

7-Benzyl-3-oxa-1-(3-oxopropyl)-7-azabicyclo[3.3.0]octan-2-one

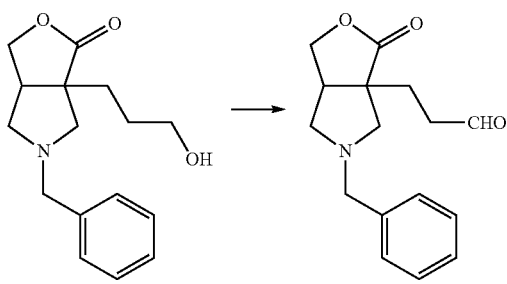

[Formula 209]

A dichloromethane (113 mL) solution was cooled with dry ice-methanol in a nitrogen atmosphere. Oxalyl chloride (11.2 mL, 128 mmol) and dimethyl sulfoxide (15.2 mL, 214 mmol) were added, and the mixture was stirred under cooling for 30 minutes. A solution of the residue containing 7-benzyl-1-(3-hydroxypropyl)-3-oxa-7-azabicyclo[3.3.0]octan-2-one (12.9 g, 42.7 mmol) in dichloromethane (100 mL) was added, and the mixture was stirred under ice-cooling for one hour. Triethylamine (35.8 mL, 256 mmol) was added under ice-cooling, and the mixture was stirred under cooling for one hour and then at room temperature for one hour. A saturated ammonium chloride solution (200 mL) was added to the reaction solution, followed by extraction with chloroform (150 mL×2). The organic layer was washed with brine (450 ml) and then dried over anhydrous sodium sulfate. After filtration, the filtrate was concentrated under reduced pressure. The resulting residue was purified by silica gel column chromatography (hexane:ethyl acetate=100:0→90:10→66:34→50:50) to give 8.91 g of a residue containing the title compound which was directly used for the next reaction.

$^1$H-NMR (400 MHz, CDCl$_3$) δ: 9.77 (1H, s), 7.32-7.22 (5H, m), 4.42 (1H, t, J=8.95 Hz), 4.06 (1H, dd, J=9.31, 3.68 Hz), 3.62 (1H, d, J=12.99 Hz), 3.53 (1H, d, J=13.24 Hz), 3.30 (1H, d, J=9.31 Hz), 2.84 (1.0H, d, J=9.31 Hz), 2.73-2.62 (2.0H, m), 2.55-2.51 (2.0H, m), 2.04-2.00 (2H, m).

MS (ESI); m/z: 274 (M+H)$^+$.

Reference Example 118

7-Benzyl-1-(3-buten-1-yl)-3-oxa-7-azabicyclo[3.3.0]octan-2-one

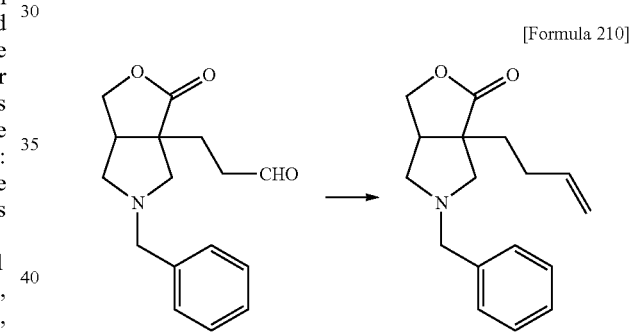

[Formula 210]

Tetrahydrofuran (45.7 mL) was added to methyltriphenylphosphonium iodide (6.16 g, 15.2 mmol) in a nitrogen atmosphere. A 1.57 mol/L solution of butyllithium in hexane (14.0 mL, 22.0 mmol) was added under ice-cooling, and then the reaction solution was stirred for 15 minutes. A solution of the residue containing 7-benzyl-3-oxa-1-(3-oxopropyl)-7-azabicyclo[3.3.0]octan-2-one (5.00 g, 18.3 mmol) in tetrahydrofuran (45.7 mL) was added dropwise thereto under ice-cooling, and the mixture was stirred at room temperature for one hour. Water (150 mL) was added to the reaction solution, followed by extraction with ethyl acetate (150 mL). The organic layer was washed with brine and dried over anhydrous sodium sulfate. After filtration, the filtrate was concentrated under reduced pressure. The resulting residue was purified by silica gel column chromatography (hexane:ethyl acetate=100:0→95:5→90:10→84:16→80:20→75:25) to give 1.09 g of the title compound.

$^1$H-NMR (400 MHz, CDCl$_3$) δ: 7.32-7.22 (10.8H, m), 5.83-5.73 (1H, m), 5.07-4.96 (2.1H, m), 4.40 (1H, t, J=8.95 Hz), 4.04 (1H, dd, J=9.19, 3.55 Hz), 3.63 (1H, d, J=12.99 Hz), 3.50 (1H, d, J=13.24 Hz), 3.29 (1H, d, J=9.31 Hz), 2.83 (1H, d, J=9.56 Hz), 2.71-2.69 (1H, m), 2.47 (1H, d, J=9.56, 6.62 Hz), 2.23-2.02 (3H, m), 1.92-1.88 (1H, m), 1.69-1.65 (1H, m).

MS (ESI); m/z: 272 (M+H)$^+$.

Reference Example 119

7-Benzyloxycarbonyl-1-(3-buten-1-yl)-3-oxa-7-azabicyclo[3.3.0]octan-2-one

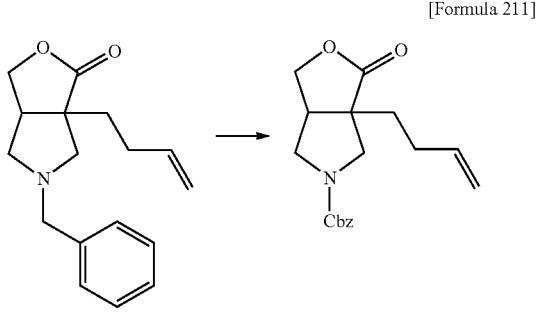 [SMILES: C=CCCC12CN(Cc3ccccc3)CC1COC2=O ; C=CCCC12CN(C(=O)OCc3ccccc3)CC1COC2=O]

[Formula 211]

Benzyl chloroformate (1.72 mL, 12.0 mmol) was added to a solution of 7-benzyl-1-(3-buten-1-yl)-3-oxa-7-azabicyclo[3.3.0]octan-2-one (1.09 g, 4.02 mmol) in dichloromethane (13.4 mL) in a nitrogen atmosphere, and the mixture was stirred at room temperature for five days. The reaction solution was concentrated under reduced pressure. The residue was purified by silica gel column chromatography (hexane:ethyl acetate=100:0→90:10→84:16→80:20→75:25→66:34→50:50) to give 1.13 g of the title compound.

$^1$H-NMR (400 MHz, CDCl$_3$) δ: 7.39-7.28 (5H, m), 5.82-5.72 (1H, m), 5.12-5.00 (4H, m), 4.42 (1H, t, J=8.33 Hz), 4.12 (1H, brs), 4.00 (1H, d, J=11.77 Hz), 3.83 (1H, dd, J=11.77, 8.33 Hz), 3.44 (2H, d, J=37.75 Hz), 2.95-2.89 (1H, m), 2.26-2.17 (1H, m), 2.10-2.06, (1H, m), 1.90-1.76 (2H, m).

MS (ESI); m/z: 316 (M+H)$^+$.

Reference Example 120

1-Benzyloxycarbonyl-3-(3-buten-1-yl)-4-phenylselenylmethyl-3-carboxylic acid methyl ester

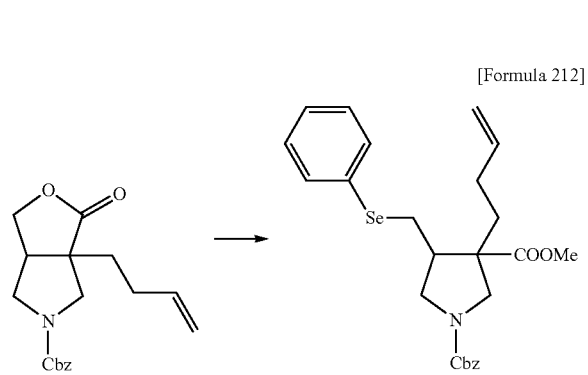 [SMILES: C=CCCC12CN(C(=O)OCc3ccccc3)CC1COC2=O ; C=CCCC1(C(=O)OC)CN(C(=O)OCc2ccccc2)CC1C[Se]c1ccccc1]

[Formula 212]

N,N-Dimethylformamide (16.3 mL) was added to diphenyl diselenide (946 mg, 3.03 mmol) in a nitrogen atmosphere. Then, the mixture was depressurized to vacuum and freeze-degassed (×3) while cooling with liquid nitrogen. Sodium borohydride (229 mg, 6.05 mmol) was added thereto at room temperature. The mixture was stirred at room temperature until gas generation was completed, and then depressurized to vacuum and freeze-degassed (×3) to prepare a reaction solution A.

Separately, a solution of 7-benzyl-1-(3-buten-1-yl)-3-oxa-7-azabicyclo[3.3.0]octan-2-one (955 mg, 3.03 mmol) in N,N-dimethylformamide (14.0 mL) was depressurized to vacuum and freeze-degassed (three times) while cooling with liquid nitrogen to prepare a reaction solution B.

The reaction solution B was added to the reaction solution A, and the mixture was stirred at 100° C. for one hour. The reaction solution was cooled to room temperature and then 1N hydrochloric acid (10 to 20 mL) was added, followed by extraction with ethyl acetate (100 mL×2). The organic layer was washed with brine and dried over anhydrous sodium sulfate. After filtration, the filtrate was concentrated under reduced pressure. The resulting residue was purified by silica gel column chromatography (chloroform:methanol=100:0→99:1→98:2→97:3→96:4) to give 2.08 g of the title compound which was directly used for the esterification step. Trimethylsilyldiazomethane (9.09 mL) was added to a solution of 2.08 g of the residue in methanol (30.3 mL) under ice-cooling, and the mixture was stirred at room temperature for 20 minutes. The reaction solution was concentrated under reduced pressure. Then, the residue was purified by silica gel column chromatography (hexane:ethyl acetate=100:0→95:5→90:10→84:16→80:20→75:25) to give 485 mg of the title compound.

$^1$H-NMR (400 MHz, CDCl$_3$) δ: 7.49-7.23 (5H, m), 5.73-5.69 (1H, m), 5.16-5.09 (2H, m), 4.98-4.95 (2H, m), 3.98 (1H, dd, J=21.33, 11.28 Hz), 3.80 (1H, ddd, J=24.08, 10.97, 7.05 Hz), 3.70 (3H, s), 3.32-3.21 (2H, m), 3.12 (1H, dd, J=12.38, 3.06 Hz), 2.49 (1H, t, J=12.01 Hz), 2.34-2.29 (1H, m), 2.10-2.05 (1H, m), 1.96-1.92 (2H, m), 1.38-1.35 (1H, m).

MS (ESI); m/z: 378 (M+H)$^+$.

Reference Example 121

1-Benzyloxycarbonyl-3-(3-buten-1-yl)-4-methylenepyrrolidine-3-carboxylic acid methyl ester

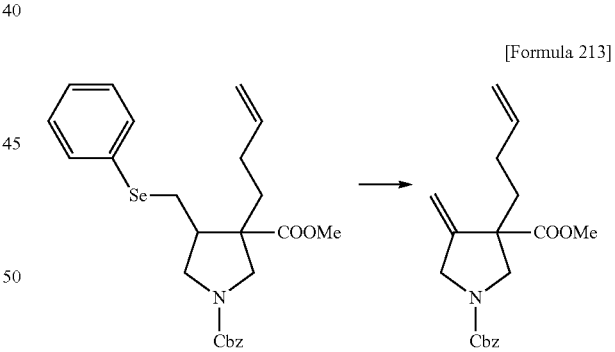

[Formula 213]

A 0.5N sodium periodide solution (4.99 mL, 2.50 mmol) was added to a solution of 1-benzyloxycarbonyl-3-(3-buten-1-yl)-4-phenylselenylmethyl-3-carboxylic acid methyl ester (485 mg, 0.997 mmol) in tetrahydrofuran (9.97 mL). The mixture was stirred at room temperature for five hours and then at 40° C. to 50° C. for 24 hours. Water (50 mL) was added to the reaction solution, followed by extraction with ethyl acetate (50 mL×2). The organic layer was dried over anhydrous sodium sulfate. After filtration, the filtrate was concentrated under reduced pressure. The resulting residue was purified by silica gel column chromatography (hexane:ethyl acetate=100:0→95:5→90:10→84:16→80:20→75:25) to give 285 mg of the title compound.

¹H-NMR (400 MHz, CDCl₃) δ: 7.42-7.28 (5H, m), 5.79-5.75 (1H, m), 5.20-5.15 (4H, m), 5.03-4.98 (2H, m), 4.21-4.13 (3H, m), 3.69 (3H, s), 3.41 (1H, dd, J=19.49, 11.40 Hz), 2.17-2.10 (1H, m), 2.04-2.02 (2H, m), 1.68-1.64 (1H, m).
MS (ESI) m/z: 330 (M+H)⁺.

Reference Example 122

{3-Benzyloxycarbonyl-3-azabicyclo[3.3.0]oct-5-en-1-yl}carboxylic acid methyl ester

[Formula 214]

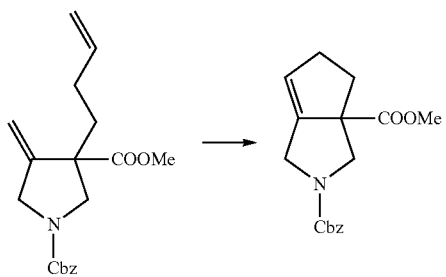

The Second Generation Grubbs' catalyst (29.6 mg, 0.871 mmol) was added to a solution of 1-benzyloxycarbonyl-3-(3-buten-1-yl)-4-methylenepyrrolidine-3-carboxylic acid methyl ester (286 mg, 0.871 mmol) in dichloromethane (8.71 mL) in a nitrogen atmosphere. The mixture was stirred at room temperature for 19 hours, and the dichloromethane (17.4 mL) was added. After stirring at 45° C. for six hours, the reaction solution was concentrated under reduced pressure. The resulting residue was purified by silica gel column chromatography (hexane:ethyl acetate=100:0→95:5→87:13→85:15→83:17→80:20→75:25→66:34) to give 187 mg of the title compound.
¹H-NMR (400 MHz, CDCl₃) δ: 7.37-7.29 (5H, m), 5.72 (1H, d, J=13.73 Hz), 5.17-5.12 (2H, m), 4.20 (1H, dd, J=10.79, 2.70 Hz), 4.04-3.94 (2H, m), 3.68 (3H, d, J=1.47 Hz), 3.07 (1H, dd, J=10.79, 7.11 Hz), 2.95-2.87 (1H, m), 2.63-2.48 (2H, m), 1.88-1.83 (1H, m).
MS (ESI) m/z: 302 (M+H)⁺.

Reference Example 123

{3-Benzyloxycarbonyl-3-azabicyclo[3.3.0]oct-5-en-1-yl}carboxylic acid

[Formula 215]

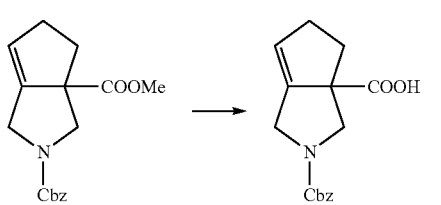

A 1N sodium hydroxide solution (1.86 mL) was added to a solution of {3-benzyloxycarbonyl-3-azabicyclo[3.3.0]oct-5-en-1-yl}carboxylic acid methyl ester (187 mg, 0.620 mmol) in methanol (6.20 mL) in a nitrogen atmosphere, and the mixture was stirred at room temperature for 16 hours. The reaction solution was concentrated under reduced pressure and then washed with diethyl ether (50 mL×2). The aqueous layer was made acidic with 1N hydrochloric acid under ice-cooling, followed by extraction with ethyl acetate (100 mL×1, 80 mL×1). The organic layer was washed with water (80 mL) and brine (80 mL) and dried over anhydrous sodium sulfate. After filtration, the filtrate was concentrated under reduced pressure to give 186 mg (quantitative) of the title compound.
¹H-NMR (400 MHz, CDCl₃) δ: 7.36-7.30 (5H, m), 5.77 (1H, d, J=17.16 Hz), 5.21-5.10 (2H, m), 4.25 (1H, dd, J=10.91, 5.02 Hz), 4.02 (2H, t, J=17.53 Hz), 3.09 (1H, dd, J=10.91, 7.72 Hz), 2.93 (1H, brs), 2.60-2.54 (2H, m), 1.93-1.83 (1H, m).
MS (ESI); m/z: 288 (M+H)⁺.

Reference Example 124

3-Benzyloxycarbonyl-1-tert-butoxycarbonylamino-3-azabicyclo[3.3.0]oct-5-ene (Optical Isomer A, Optical Isomer B)

[Formula 216]

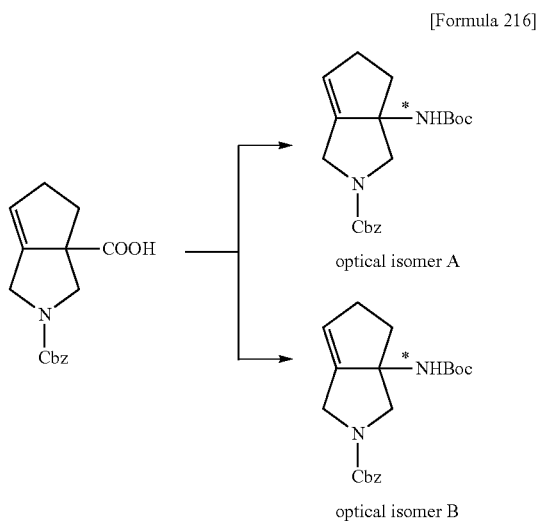 [SMILES: O=C(OCc1ccccc1)N1CC2=CCCC2(C(=O)O)C1 ; CC(C)(C)OC(=O)NC12CCC=C1CN(C(=O)OCc1ccccc1)C2 ; CC(C)(C)OC(=O)NC12CCC=C1CN(C(=O)OCc1ccccc1)C2]

Triethylamine (0.181 mL, 1.30 mmol) and diphenylphosphoryl azide (0.181 mL, 0.840 mmol) were added to a solution of {3-benzyloxycarbonyl-3-azabicyclo[3.3.0]oct-5-en-1-yl}carboxylic acid (186 mg, 0.647 mmol) in toluene (3.23 ml) in a nitrogen atmosphere. The mixture was stirred at room temperature for 30 minutes and then at 100° C. for 30 minutes. The reaction solution was concentrated under reduced pressure, and triethylamine was azeotropically distilled with toluene (×3). 1,4-Dioxane (1.62 mL) and 6N hydrochloric acid (1.62 mL) were added to the resulting residue, and the mixture was stirred at 50° C. for one hour. The reaction solution was diluted with water (6.5 mL), and the organic layer was evaporated off by concentration under reduced pressure. The residue was washed with diethyl ether (20 mL×2). The aqueous layer was made alkaline with a 1N sodium hydroxide solution under ice-cooling, followed by extraction with chloroform (40 mL×1, 30 mL×1). The organic layer was washed with water (40 mL) and brine (40 mL) and dried over anhydrous sodium sulfate. After filtration, the filtrate was concentrated under reduced pressure. Dichloromethane (3.23 ml) was added to the resulting residue, and di-tert-butyl dicarbonate (283 mg, 1.30 mmol) was added in a nitrogen atmosphere. After stirring at room temperature for 17 hours, the reaction solution was concentrated under reduced pressure. The resulting residue was purified by silica gel column chromatography (hexane:ethyl acetate=100:0→90:10→84:16→80:20→75:25) to give 120 mg of the title compound.

$^1$H-NMR (400 MHz, CDCl$_3$) δ: 7.37-7.31 (5H, m), 5.74 (1H, d, J=7.48 Hz), 5.17-5.11 (2H, m), 4.58 (1H, s), 4.26 (1H, dd, J=25.37, 11.40 Hz), 4.02-4.01 (2H, m), 3.14 (1H, dd, J=11.28, 8.82 Hz), 2.80 (1H, brs), 2.55-2.52 (1H, m), 2.37 (1H, brs), 1.94-1.91 (1H, m), 1.43 (9H, s).

The racemate 3-benzyloxycarbonyl-1-tert-butoxycarbonylamino-3-azabicyclo[3.3.0]oct-5-ene (108 mg, 0.301 mmol) obtained as described above was optically resolved by an optically active column (CHIRALCEL OJ, 20 mm diameter×250 mm, hexane:isopropyl alcohol=90:10, flow rate=20 mL/min, resolving 20 mg each time) to give 3-benzyloxycarbonyl-1-tert-butoxycarbonylamino-3-azabicyclo[3.3.0]oct-5-ene (optical isomer A) (50.5 mg, 1.41 mmol, retention time=8.0 min) and its enantiomer 3-benzyloxycarbonyl-1-tert-butoxycarbonylamino-3-azabicyclo[3.3.0]oct-5-ene (optical isomer B) (55.6 mg, 0.155 mmol, retention time=11.5 min).

Reference Example 125

1-tert-Butoxycarbonylamino-3-azabicyclo[3.3.0]oct-5-ene (Derived from Optical Isomer A)

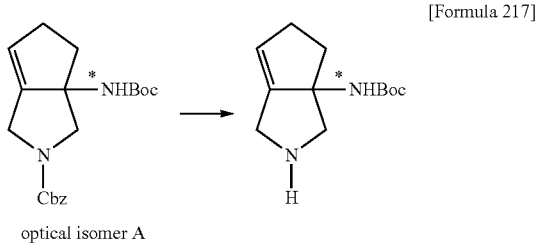 [SMILES: CC(C)(C)OC(=O)NC12CCC=C1CN(C(=O)OCc1ccccc1)C2 ; CC(C)(C)OC(=O)NC12CCC=C1CNC2]

[Formula 217]

optical isomer A

A solution of 3-benzyloxycarbonyl-1-tert-butoxycarbonylamino-3-azabicyclo[3.3.0]oct-5-ene (optical isomer A) (50.5 mg, 0.141 mmol) in tetrahydrofuran (1.41 mL) was bubbled with ammonia gas under cooling with dry ice-acetone to add 30 to 40 mL of liquid ammonia to the solution. Sodium (17.0 mg, 0.709 mmol) was added in a nitrogen atmosphere, and the mixture was stirred for 10 minutes. A saturated ammonium chloride solution (3 drops) was added at room temperature, and the mixture was stirred at room temperature to evaporate ammonia. A 1N sodium hydroxide solution (12.0 mL) was added, followed by extraction with chloroform (40 mL×1, 20 mL×1) and the lower layer of chloroform/methanol/water=7/3/1 (40 mL×1, 20 mL×1). The organic layers were combined, dried over anhydrous sodium sulfate, and filtered. Then, the filtrate was concentrated under reduced pressure to give 33 mg (quantitative) of the title compound.

$^1$H-NMR (400 MHz, CDCl$_3$) δ: 5.58 (1H, brs), 4.62 (1H, brs), 3.47 (3H, tt, J=14.34, 9.68 Hz), 2.96-2.87 (1H, m), 2.61-2.57 (2H, m), 2.28-2.25 (1H, m), 1.85 (1H, dt, J=16.42, 6.62 Hz), 1.45 (9H, s).

MS (ESI) m/z: 225 (M+H)$^+$.

Example 25

7-[1-Amino-3-azabicyclo[3.3.0]oct-5-en-3-yl]-6-fluoro-1-[(1R,2S)-2-fluorocyclopropyl]-1,4-dihydro-8-methoxy-4-oxoquinoline-3-carboxylic acid (7-Position Substituent: Derived from Optical Isomer A)

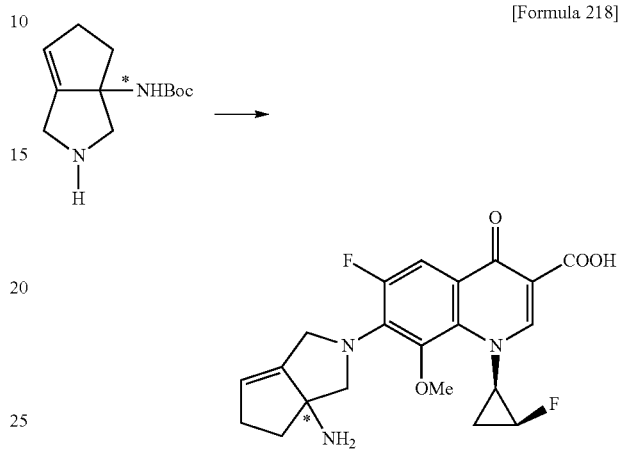

[Formula 218]

Triethylamine (0.0595 mL, 0.426 mmol) and 6,7-difluoro-1-[(1R,2S)-2-fluorocyclopropyl]-6,7-difluoro-1,4-dihydro-8-methoxy-4-oxoquinoline-3-carboxylic acid-BF$_2$ chelate (51.2 mg, 0.142 mmol) were added to a solution of 1-tert-butoxycarbonylamino-3-azabicyclo[3.3.0]oct-5-ene (derived from optical isomer A) (33.0 mg, 0.135 mmol) in dimethyl sulfoxide (0.284 mL). The mixture was stirred at room temperature for two hours and at 40° C. for 14 hours. A mixed solution of ethanol:water=4:1 (5 mL) and triethylamine (0.5 mL) were added to the reaction solution, and the mixture was heated to reflux for one hour. The reaction solution was concentrated under reduced pressure. The residue was dissolved in ethyl acetate (30 mL) and washed with a 10% citric acid solution (15 mL), water (15 mL), and brine (15 mL). The organic layer was dried over anhydrous sodium sulfate and filtered, and then the filtrate was concentrated under reduced pressure. The resulting residue was purified by silica gel column chromatography (chloroform:methanol=100:0→99:1→98:2). 61.4 mg of the resulting residue was dissolved in concentrated hydrochloric acid (1 mL) under ice-cooling, and the solution was stirred at room temperature for 15 minutes. After washing with chloroform (15 mL×3), the aqueous layer was adjusted to pH 12 with a saturated sodium hydroxide solution. The basic solution was adjusted to pH 7.4 with hydrochloric acid, followed by extraction with chloroform (80 mL), chloroform/methanol=10/1 (80 mL), and the lower layer of chloroform/methanol/water=7/3/1 (80 mL×3). The organic layer was dried over anhydrous sodium sulfate and filtered, and then the filtrate was concentrated under reduced pressure. The resulting residue was dissolved in hot ethanol (5 mL) and a 28% ammonia solution (1 to 2 mL), and the insoluble material was removed by filtration. The solvent was gradually evaporated under reduced pressure while heating with stirring. Further, ammonia was azeotropically distilled with ethanol (3 to 5 mL) (×10). Ethanol was concentrated until crystals were precipitated, followed by stirring at room temperature overnight. The precipitated crystals were collected by filtration, washed with ethanol and diethyl ether, and then dried under reduced pressure at 60° C. to give 9.65 mg of the title compound.

¹H-NMR (400 MHz, 0.1N NaOD) δ: 8.40 (1H, d, J=3.19 Hz), 7.69 (1H, d, J=14.46 Hz), 5.62 (1H, s), 5.12-4.96 (1H, m), 4.50 (1H, d, J=12.50 Hz), 4.04-4.01 (2H, m), 3.60 (5H, dd, J=16.67, 9.31 Hz), 2.91 (1H, s), 2.62-2.59 (1H, m), 2.15-2.07 (1H, m), 1.99-1.92 (1H, m), 1.58-1.54 (1H, m), 1.48-1.37 (1H, m).

Anal; Calcd for $C_{21}H_{21}F_2N_3O_4 \cdot 1.5H_2O$: C, 56.75; H, 5.44; N, 99.45. Found: C, 56.53; H, 4.96; N, 9.01.

MS (ESI); m/z: 418 (M+H)⁺.

IR (ATR) ν: 2935, 2852, 2755, 2657, 2572, 2103, 1716, 1614, 1569, 1531, 1498, 1463, 1455, 1361, 1324, 1116, 1043, 943, 919, 808 cm⁻¹.

Reference Example 126

1-tert-Butoxycarbonylamino-3-azabicyclo[3.3.0]oct-5-ene (derived from optical isomer B)

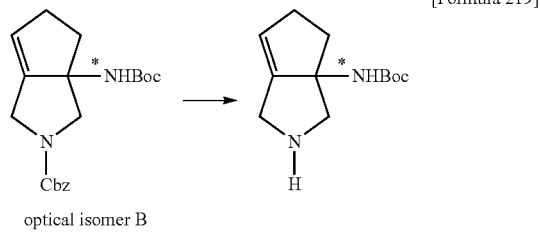

[Formula 219]

optical isomer B

A solution of 3-benzyloxycarbonyl-1-tert-butoxycarbonylamino-3-azabicyclo[3.3.0]oct-5-ene (optical isomer B) (54.7 mg, 0.153 mmol) in tetrahydrofuran (1.53 mL) was bubbled with ammonia gas under cooling with dry ice-acetone to add 30 to 40 mL of liquid ammonia to the solution. Sodium (18.4 mg, 0.767 mmol) was added in a nitrogen atmosphere, and the mixture was stirred for 10 minutes. A saturated ammonium chloride solution (10 drops) was added at room temperature, and the mixture was stirred at room temperature to evaporate ammonia. A 1N sodium hydroxide solution (3 to 4 mL) was added, and the mixture was concentrated under reduced pressure. Chloroform/methanol=10/1 (10 to 20 mL) was added. After ultrasonic treatment, the insoluble material was removed by filtration. The filtrate was concentrated under reduced pressure to give 150 mg of a residue containing the title compound, which was directly used for the next reaction.

MS (ESI) m/z: 225 (M+H)⁺.

Example 26

7-[1-Amino-3-azabicyclo[3.3.0]oct-5-en-3-yl]-6-fluoro-1-[(1R,2S)-2-fluorocyclopropyl]-1,4-dihydro-8-methoxy-4-oxoquinoline-3-carboxylic acid (7-Position Substituent: Derived from Optical Isomer B)

[Formula 220]

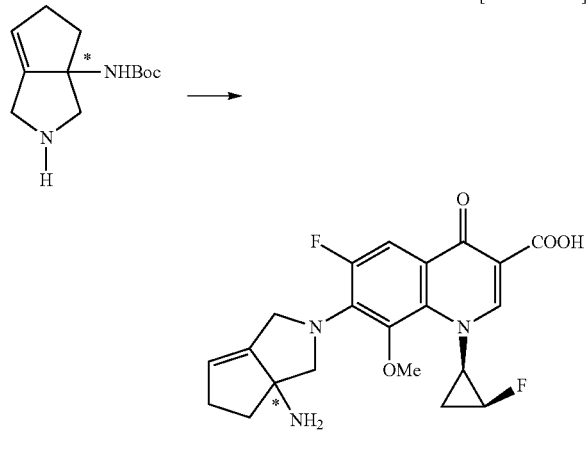

Triethylamine (0.0641 mL, 0.460 mmol) and 6,7-difluoro-1-[(1R,2S)-2-fluorocyclopropyl]-1,4-dihydro-8-methoxy-4-oxoquinoline-3-carboxylic acid-BF₂ chelate (58.0 mg, 0.161 mmol) were added to a solution of the residue containing 1-tert-butoxycarbonylamino-3-azabicyclo[3.3.0]oct-5-ene (derived from optical isomer B) (150 mg, 0.153 mmol) in dimethyl sulfoxide (0.306 mL). The mixture was stirred at room temperature for 1.5 hours. Dimethyl sulfoxide (0.306 mL) and triethylamine (0.0641 mL, 0.460 mmol) were added, and the mixture was stirred at 40° C. for one day. 6,7-Difluoro-1-[(1R,2S)-2-fluorocyclopropyl]-1,4-dihydro-8-methoxy-4-oxoquinoline-3-carboxylic acid-BF₂ chelate (174 mg, 0.483 mmol) was added to the reaction solution, and the mixture was stirred at 40° C. for 15 hours. A mixed solution of ethanol:water=4:1 (5 mL) and triethylamine (0.5 mL) were added to the reaction solution, and the mixture was heated to reflux for one hour. The reaction solution was concentrated under reduced pressure. The residue was dissolved in ethyl acetate (30 mL) and washed with a 10% citric acid solution (20 mL), water (20 mL), and brine (20 mL). The organic layer was dried over anhydrous sodium sulfate and filtered, and then the filtrate was concentrated under reduced pressure. The resulting residue was purified by silica gel column chromatography (chloroform:methanol=100:0→99:1→98:2). 194 mg of the resulting residue was dissolved in concentrated hydrochloric acid (1 mL) under ice-cooling, and the solution was stirred at room temperature for 15 minutes. After washing with chloroform (30 mL×5), the aqueous layer was adjusted to pH 12 with a saturated sodium hydroxide solution. The basic solution was adjusted to pH 7.4 with hydrochloric acid, followed by extraction with chloroform (80 mL), chloroform/methanol=10/1 (80 mL), and the lower layer of chloroform/methanol/water=7/3/1 (50 mL). The organic layer was dried over anhydrous sodium sulfate and filtered, and then the filtrate was concentrated under reduced pressure. The resulting residue was purified by PTLC (lower layer of chloroform/methanol/water=7/3/1). Chloroform/methanol (10/1) was added to the resulting residue, and the insoluble material was removed by filtration. The filtrate was concentrated under reduced pressure. Ethanol (1 mL) was added to the resulting residue, and the mixture was stirred at room temperature overnight. Diethyl ether (2 mL) was added, and the precipitated crystals were collected by filtration, washed with ethanol and diethyl ether, and then dried under reduced pressure at 50° C. to give 2.38 mg of the title compound.

¹H-NMR (400 MHz, 0.1N NaOD) δ: 8.50 (1H, s), 7.70 (1H, d, J=14.46 Hz), 5.62 (1H, s), 5.05-4.90 (1H, m), 4.65-4.59 (1H, m), 4.11 (1H, s), 3.93 (1H, d, J=14.95 Hz), 3.70 (1H, d, J=10.05 Hz), 3.62 (3H, s), 3.53 (1H, d, J=10.79 Hz), 3.00-2.82 (1H, m), 2.67-2.56 (1H, m), 2.15-2.12 (1H, m), 2.00-1.95 (1H, m), 1.72-1.58 (2H, m).

MS (ESI); m/z: 418 (M+H)⁺.

Reference Example 127

6-tert-Butoxycarbonylamino-8-benzyloxycarbonyl-8-azatricyclo[4.3.0.0¹,³]nonane (Derived from Optical Isomer A)

[Formula 221]

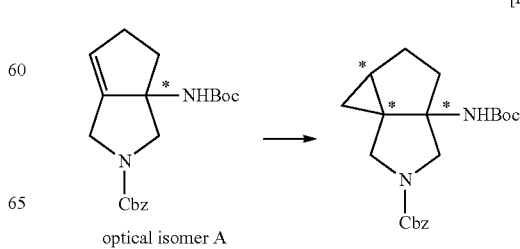

optical isomer A

A dichloromethane (3.52 mL) solution was cooled with ice-acetone. A 1.0 M solution of diethylzinc in n-hexane (0.88 mL, 0.88 mmol) and diiodomethane (0.071 mL, 0.881 mmol) were slowly added in a nitrogen atmosphere, and the mixture was stirred for 20 minutes under cooling. A solution of 3-benzyloxycarbonyl-1-tert-butoxycarbonylamino-3-azabicyclo[3.2.0]oct-5-ene (optical isomer A) (126 mg, 0.352 mmol) in dichloromethane (3.52 mL) was slowly added under cooling, the mixture was stirred at room temperature for 24 hours. A saturated sodium bicarbonate aqueous solution (10 mL) and a 10% sodium thiosulfate solution (10 mL) were added under cooling with ice-acetone, and the mixture was stirred until the vermillion color disappeared. The organic layer was extracted with chloroform (50 mL×1, 40 mL×1). The organic layer was washed with brine (80 mL), dried over anhydrous sodium sulfate, and filtered. The filtrate was then concentrated under reduced pressure. Acetonitrile (7.04 mL) and di-tert-butyl dicarbonate (384 mg, 1.76 mmol) were sequentially added to 212 mg of the resulting residue in a nitrogen atmosphere. After stirring at room temperature for 19 hours, the reaction solution was concentrated under reduced pressure. The resulting residue was purified by silica gel column chromatography (hexane:ethyl acetate=100:0→95:5→90:10→84:16→80:20→75:25) to give 95.2 mg of the title compound.

$^1$H-NMR (400 MHz, CDCl$_3$) δ: 7.35-7.31 (5H, m), 5.17-5.11 (2H, m), 4.93 (1H, brs), 4.21-4.11 (1H, m), 3.75 (1H, dd, J=10.91, 6.74 Hz), 3.32-3.12 (2H, m), 2.47-2.31 (1H, m), 1.97-1.88 (1H, m), 1.81-1.78 (1H, m), 1.43 (9H, s), 1.35-1.31 (1H, m), 1.19-1.16 (1H, m), 0.82-0.76 (2H, m).

MS (ESI); m/z: 395 (M+Na)$^+$.

Reference Example 128

6-tert-Butoxycarbonylamino-8-benzyloxycarbonyl-8-azatricyclo[4.3.0.0$^{1,3}$]nonane (Derived from Optical Isomer B)

[Formula 222]

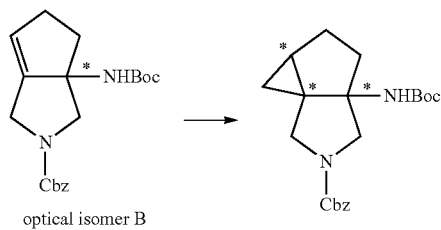

optical isomer B

A dichloromethane (4.18 mL) solution was cooled with ice-acetone. A 1.0 M solution of diethylzinc in n-hexane (1.05 mL, 1.05 mmol) and diiodomethane (0.0842 mL, 1.05 mmol) were slowly added in a nitrogen atmosphere, and the mixture was stirred for 20 minutes under cooling. A solution of 3-benzyloxycarbonyl-1-tert-butoxycarbonylamino-3-azabicyclo[3.2.0]oct-5-ene (optical isomer B) (150 mg, 0.418 mmol) in dichloromethane (4.18 mL) was slowly added under cooling, the mixture was stirred at room temperature for 22 hours. A saturated sodium bicarbonate aqueous solution (10 mL) and a 10% sodium thiosulfate solution (10 mL) were added under cooling with ice-acetone, and the mixture was stirred until the vermillion color disappeared. The organic layer was extracted with chloroform (60 mL×1, 50 mL×1). The organic layer was washed with brine (60 mL), dried over anhydrous sodium sulfate, and filtered. The filtrate was then concentrated under reduced pressure. Acetonitrile (8.36 mL) and di-tert-butyl dicarbonate (274 mg, 1.25 mmol) were sequentially added to 256 mg of the resulting residue in a nitrogen atmosphere. After stirring at room temperature for 13 hours, the reaction solution was concentrated under reduced pressure. The resulting residue was purified by silica gel column chromatography (hexane:ethyl acetate=100:0→95:5→90:10→84:16→80:20→75:25) to give 113 mg of the title compound.

$^1$H-NMR (400 MHz, CDCl$_3$) δ: 7.40-7.29 (5H, m), 5.13 (2H, t, J=6.74 Hz), 4.93 (1H, d, J=16.18 Hz), 4.23-4.09 (1H, m), 3.75 (1H, dd, J=11.03, 6.62 Hz), 3.27-3.19 (2H, m), 2.43 (1H, brs), 1.98-1.88 (1H, m), 1.82-1.74 (2H, m), 1.43 (9H, s), 1.37-1.22 (1H, m), 1.22-1.14 (1H, m), 0.81-0.77 (2H, m).

MS (ESI); m/z: 395 (M+Na)$^+$.

Reference Example 129

6-tert-Butoxycarbonylamino-8-azatricyclo[4.3.0.0$^{1,3}$]nonane (Derived from Optical Isomer A)

[Formula 223]

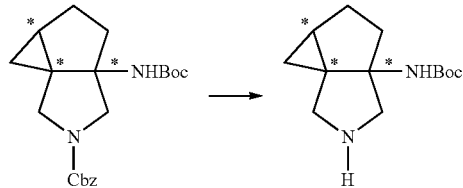

A 10% palladium-carbon catalyst (47.6 mg, 50 wt %) was added to a solution of 6-tert-butoxycarbonylamino-8-benzyloxycarbonyl-8-azatricyclo[4.3.0.0$^{1,3}$]nonane (derived from optical isomer A) (95.2 mg, 0.255 mmol) in methanol (2.55 mL) in a nitrogen atmosphere. After the atmosphere was replaced with hydrogen, the mixture was stirred at room temperature for one hour. A 10% palladium-carbon catalyst (28.6 mg, 30 wt %) was added. After the atmosphere was replaced with hydrogen, the mixture was stirred at room temperature for one hour. After the atmosphere was replaced with nitrogen, the reaction solution was filtered through Celite and concentrated under reduced pressure to give 56.0 mg of the title compound as a black oil.

$^1$H-NMR (400 MHz, CDCl$_3$) δ: 4.98 (1H, brs), 3.63 (1H, s), 3.46-3.44 (1H, m), 2.92 (2H, dd, J=30.52, 11.15 Hz), 2.37 (1H, brs), 2.00-1.96 (1H, m), 1.76-1.70 (1H, m), 1.44 (9H, s), 1.35-1.25 (1H, m), 1.21-1.15 (1H, m), 0.86-0.69 (2H, m).

MS (ESI); m/z: 239 (M+H)$^+$.

Example 27

7-[6-Amino-8-azatricyclo[4.3.0.0$^{1,3}$]nonan-8-yl]-6-fluoro-1-[(1R,2S)-2-fluorocyclopropyl]-1,4-dihydro-8-methoxy-4-oxoquinoline-3-carboxylic acid (7-Position Substituent: Derived from Optical Isomer A)

[Formula 224]

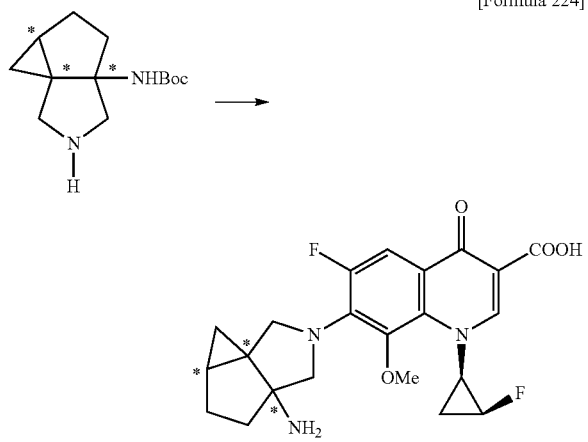

Triethylamine (0.0984 mL, 0.705 mmol) and 6,7-difluoro-1-[(1R,2S)-2-fluorocyclopropyl]-1,4-dihydro-8-methoxy-4-oxoquinoline-3-carboxylic acid-BF$_2$ chelate (89.1 mg, 0.247 mmol) were added to a solution of 6-tert-butoxycarbonylamino-8-azatricyclo[4.3.0.0$^{1,3}$]nonane (derived from optical isomer A) 56.0 mg (0.235 mmol) in dimethyl sulfoxide (0.470 mL). The mixture was stirred at 35° C. for 19 hours. A mixed solution of ethanol:water=4:1 (5.0 mL) and triethylamine (0.5 mL) were added to the reaction solution, and the mixture was heated to reflux for one hour. The reaction solution was concentrated under reduced pressure. The residue was dissolved in ethyl acetate (35 mL) and washed with a 10% citric acid solution (25 mL), water (25 mL), and brine (25 mL). The organic layer was dried over anhydrous sodium sulfate and filtered, and then the filtrate was concentrated under reduced pressure. The resulting residue was purified by silica gel column chromatography (chloroform:methanol=100:0→99:1). 80.5 mg of the resulting residue was dissolved in concentrated hydrochloric acid (1 mL) under ice-cooling, and the solution was stirred at room temperature for 15 minutes. After washing with chloroform (30 mL×4), the aqueous layer was adjusted to pH 12 with a saturated sodium hydroxide solution. The basic solution was adjusted to pH 7.4 with hydrochloric acid, followed by extraction with chloroform (60 mL×2) and chloroform/methanol=10/1 (60 mL×3). The organic layer was dried over anhydrous sodium sulfate and filtered, and then the filtrate was concentrated under reduced pressure. The residue was purified by PTLC (lower layer of chloroform/methanol/water=7/3/1). The resulting residue was dissolved in chloroform/methanol=10/1 (10 mL). The insoluble material was removed by filtration, and then the filtrate was concentrated under reduced pressure. The resulting residue was dissolved in hot ethanol (20 to 30 ml), and then concentrated under reduced pressure and dried. Ethanol (0.5 mL) and diethyl ether (5 mL) were added to the resulting residue, and the mixture was ultrasonically treated and ice-cooled. Then, the precipitated crystals were collected by filtration and washed with diethyl ether. The crystals were dried under reduced pressure at 45° C. to give 21.0 mg of the title compound.

$^1$H-NMR (400 MHz, 0.1N NaOD) δ: 8.38 (1H, d, J=2.94 Hz), 7.67 (1H, d, J=14.22 Hz), 5.12-4.96 (1H, m), 4.32-4.29 (1H, m), 4.04-3.99 (1H, m), 3.80 (1H, d, J=10.30 Hz), 3.61 (3H, s), 3.44 (1H, d, J=10.54 Hz), 3.31 (1H, d, J=10.30 Hz), 2.02-1.89 (2H, m), 1.77 (1H, dd, J=12.62, 8.46 Hz), 1.58-1.24 (4H, m), 0.82 (2H, dt, J=23.78, 5.82 Hz).

Anal; Calcd for C$_{22}$H$_{23}$F$_2$N$_3$O$_4$: C, 57.64; H, 5.72; F, 8.29; N, 9.17. Found: C, 57.70; H, 5.77; F, 8.57; N, 9.09.

MS (ESI); m/z: 432 (M+H)$^+$.

IR (ATR) ν: 2935, 2869, 1725, 1616, 1432, 1363, 1319, 1182, 1137, 1045, 943, 923, 806 cm$^{-1}$.

Reference Example 130

6-tert-Butoxycarbonylamino-8-azatricyclo[4.3.0.0$^{1,3}$]nonane (Derived from Optical Isomer B)

[Formula 225]

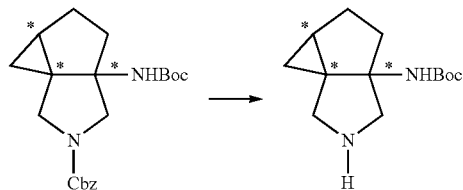

A 10% palladium-carbon catalyst (27.7 mg, 30 wt %) was added to a solution of 6-tert-butoxycarbonylamino-8-benzyloxycarbonyl-8-azatricyclo[4.3.0.0$^{1,3}$]nonane (derived from optical isomer B) (92.3 mg, 0.248 mmol) in methanol (2.48 mL) in a nitrogen atmosphere. The mixture was stirred in a hydrogen atmosphere at room temperature for one hour. A 10% palladium-carbon catalyst (18.5 mg, 20 wt %) was added, and the mixture was stirred in a hydrogen atmosphere at room temperature for 2.5 hours. After the atmosphere was replaced with nitrogen, the reaction solution was filtered through Celite and concentrated under reduced pressure to give 64.4 mg of a residue containing the title compound.

$^1$H-NMR (400 MHz, CDCl$_3$) δ: 4.87 (1H, brs), 3.50 (1H, brs), 3.29 (1H, d, J=11.03 Hz), 3.14-3.12 (1H, m), 2.76 (2H, dd, J=19.12, 11.28 Hz), 2.47-1.66 (3H, m), 1.43 (9H, s), 1.32 (1H, dd, J=24.14, 10.17 Hz), 1.08-1.04 (1H, m), 0.82-0.67 (2H, m).

MS (ESI); m/z: 239 (M+H)$^+$.

Example 28

7-[6-Amino-8-azatricyclo[4.3.0.0$^{1,3}$]nonan-8-yl]-6-fluoro-1-[(1R,2S)-2-fluorocyclopropyl]-1,4-dihydro-8-methoxy-4-oxoquinoline-3-carboxylic acid (7-Position Substituent: Derived from Optical Isomer B)

[Formula 224]

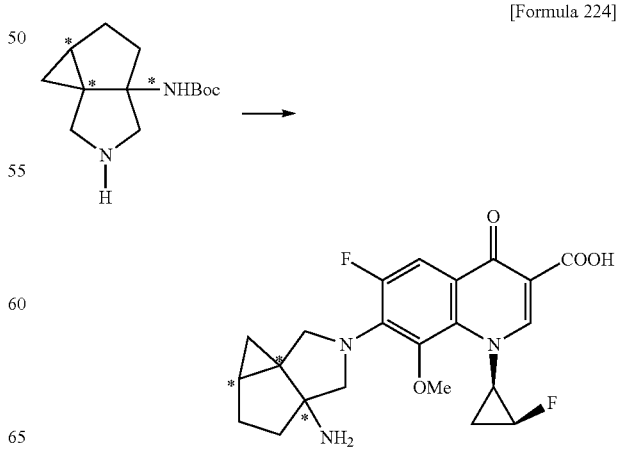

Triethylamine (0.104 mL, 0.745 mmol) and 1-[(1R,2S)-2-fluorocyclopropan-1-yl]-6,7-difluoro-8-methoxy-1,4-dihydro-4-oxoquinoline-3-carboxylic acid-$BF_2$ chelate (89.5 mg, 0.248 mmol) were added to a solution of 64.4 mg of the residue containing 6-tert-butoxycarbonylamino-8-azatricyclo[4.3.0.0$^{1,3}$]nonane (0.248 mmol equivalent) in dimethyl sulfoxide (0.496 mL), and the mixture was stirred at 35° C. for 17 hours. A mixed solution of ethanol:water=4:1 (5.0 mL) and triethylamine (0.5 mL) were added to the reaction solution, and the mixture was heated to reflux for 1.5 hours. The reaction solution was concentrated under reduced pressure. The residue was dissolved in ethyl acetate (35 mL) and washed with a 10% citric acid solution (25 mL), water (25 mL), and brine (25 mL). The organic layer was dried over anhydrous sodium sulfate and filtered, and then the filtrate was concentrated under reduced pressure. The resulting residue was purified by silica gel column chromatography (chloroform:methanol=100:0→99:1). 75.5 mg of the resulting residue was dissolved in concentrated hydrochloric acid (1 mL) under ice-cooling, and the solution was stirred at room temperature for 15 minutes. After washing with chloroform (30 mL×3), the aqueous layer was adjusted to pH 12 with a saturated sodium hydroxide solution. The basic solution was adjusted to pH 7.4 with hydrochloric acid, followed by extraction with chloroform (80 mL×1, 70 mL×1, 50 mL×1). The organic layer was dried over anhydrous sodium sulfate and filtered, and then the filtrate was concentrated under reduced pressure. The residue was dissolved in hot ethanol (10 mL), and the insoluble material was removed by filtration. The solvent was gradually evaporated under reduced pressure while heating with stirring. Then, the solution was concentrated until ethanol was about 0.5 mL, and then returned to room temperature. Diethyl ether (5 mL) was added and the mixture was ice-cooled. Then, the precipitated crystals were collected by filtration and then washed with diethyl ether. The crystals were dried under reduced pressure at 50° C. to give 25.9 mg of the title compound.

$^1$H-NMR (400 MHz, 0.1N NaOD) δ: 8.50 (1H, s), 7.67 (1H, d, J=14.71 Hz), 4.99-4.93 (1H, m), 4.39 (1H, dd, J=10.30, 3.43 Hz), 4.09 (1H, q, J=6.21 Hz), 3.87 (1H, dd, J=10.54, 2.94 Hz), 3.63 (3H, s), 3.37 (1H, d, J=10.54 Hz), 3.23 (1H, d, J=10.30 Hz), 2.01-1.95 (2H, m), 1.79-1.58 (3H, m), 1.34-1.17 (2H, m), 0.82 (2H, dt, J=22.22, 5.94 Hz).

Anal; Calcd for $C_{22}H_{23}F_2N_3O_4 \cdot 0.5H_2O$: C, 59.99; H, 5.49; F, 8.63; N, 9.54. Found: C, 60.28; H, 5.34; F, 8.57; N, 9.52.

MS (ESI); m/z: 432 (M+H)$^+$.

IR (ATR) ν: 2937, 2863, 1716, 1616, 1508, 1434, 1321, 1187, 1120, 1054, 939, 889, 804 cm$^{-1}$.

Reference Example 131

[(1R*,6R*)-8-Benzyl-8-azabicyclo[4.3.0]nonan-1-yl]carboxylic acid methyl ester

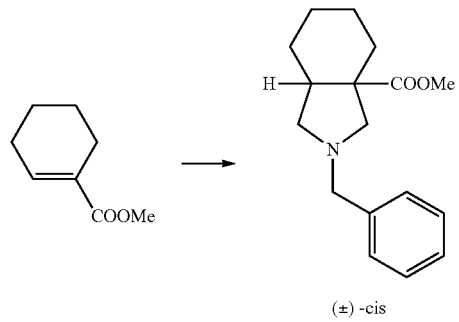

[Formula 227]

(±)-cis

A catalytic amount of trifluoroacetic acid was added to a solution of 1-cyclohexene-1-carboxylic acid methyl ester (25.0 g, 178 mmol) and N-benzyl-N-(methoxymethyl)-N-trimethylsilylmethylamine (46.6 g, 196 mmol) in 1,2-dichloroethane (178 mL) at room temperature, and the mixture was stirred at room temperature for two hours. A saturated sodium bicarbonate solution (200 mL) was added to the reaction solution, followed by extraction with chloroform (150 mL×1, 100 mL×1). The organic layer was washed with brine (450 ml) and dried over anhydrous sodium sulfate. After filtration, the filtrate was concentrated under reduced pressure. The resulting residue was purified by silica gel column chromatography (hexane:ethyl acetate=100:0→90:10→85:15→75:25) to give 21.3 g of the title compound.

$^1$H-NMR (400 MHz, CDCl$_3$) δ: 7.32-7.24 (5H, m), 3.70-3.65 (5H, m), 2.92 (1H, d, J=9.31 Hz), 2.73-2.68 (3H, m), 1.93 (1H, td, J=9.01, 4.82 Hz), 1.79-1.65 (2H, m), 1.53-1.21 (6H, m).

MS (ESI); m/z: 274 (M+H)$^+$.

Reference Example 132

[(1R*,6R*)-8-Benzyloxycarbonyl-8-azabicyclo[4.3.0]nonan-1-yl]carboxylic acid methyl ester

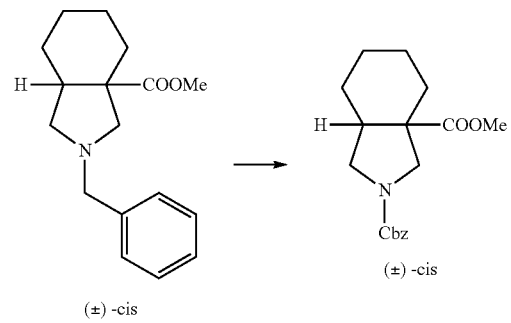

[Formula 228]

Benzyl chloroformate (33.4 mL, 234 mmol) was added to a solution of [(1R*,6R*)-8-benzyl-8-azabicyclo[4.3.0]nonan-1-yl]carboxylic acid methyl ester (21.3 g, 77.9 mmol) in dichloromethane (259 mL) in a nitrogen atmosphere, and the mixture was stirred at room temperature for 15 hours. The reaction solution was concentrated under reduced pressure. Then, the residue (58.0 g) was purified by silica gel column chromatography (hexane:ethyl acetate=100:0→95:5→90:10→80:20→75:25) to give 17.5 g of the title compound.

$^1$H-NMR (400 MHz, CDCl$_3$) δ: 7.37-7.29 (5H, m), 5.13 (2H, m), 3.71 (3H, d, J=3.19 Hz), 3.63 (1H, dd, J=10.91, 8.21 Hz), 3.52-3.28 (3H, m), 2.72-2.64 (1H, m), 1.93 (1H, m), 1.75 (1H, dq, J=20.41, 5.23 Hz), 1.63-1.38 (6H, m).

MS (ESI); m/z: 318 (M+H)$^+$.

Reference Example 133

[(1R*,6R*)-8-Benzyloxycarbonyl-8-azabicyclo[4.3.0]nonan-1-yl]carboxylic acid

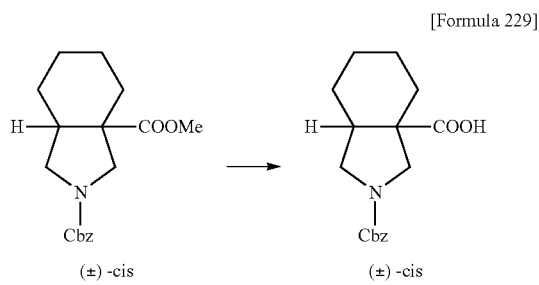 [SMILES: COC(=O)C12CCCCC1CN(C(=O)OCc1ccccc1)C2 ; O=C(OCc1ccccc1)N1CC2CCCCC2(C(=O)O)C1]

[Formula 229]

A 1 mol/L sodium hydroxide solution (70.8 mL) and tetrahydrofuran (78.8 mL) were added to a solution of [(1R*,6R*)-8-benzyloxycarbonyl-8-azabicyclo[4.3.0]nonan-1-yl] carboxylic acid methyl ester (7.50 g, 23.6 mmol) in methanol (78.8 mL) in a nitrogen atmosphere, and the mixture was stirred at room temperature for three days. The reaction solution was concentrated under reduced pressure and then washed with diethyl ether (50 mL×2). The aqueous layer was made acidic with 3 mol/L hydrochloric acid (28 mL) under ice-cooling, followed by extraction with ethyl acetate (100 mL×2). The organic layer was washed with brine (250 mL) and dried over anhydrous sodium sulfate. After filtration, the filtrate was concentrated under reduced pressure to give 6.70 g of the title compound.

$^1$H-NMR (400 MHz, CDCl$_3$) δ: 7.37-7.29 (5, m), 5.13 (2H, m), 3.70 (1H, dd, J=10.91, 4.78 Hz), 3.51 (2H, m), 3.40-3.30 (1H, m), 2.68 (1H, m), 2.00-1.96 (1H, m), 1.78-1.76 (1H, m), 1.65-1.60 (1H, m), 1.51-1.45 (5H, m).

MS (ESI); m/z: 304 (M+H)$^+$.

Reference Example 134

(1R*,6S*)-8-Benzyloxycarbonyl-1-tert-butoxycarbonylamino-8-azabicyclo[4.3.0]nonane

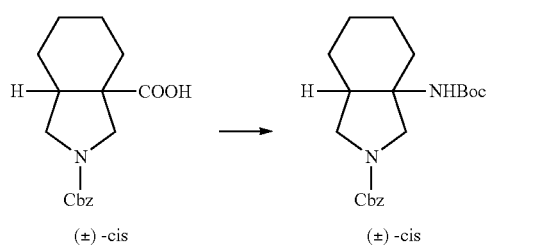

[Formula 230]

Triethylamine (6.17 mL, 44.2 mmol) and diphenylphosphoryl azide (6.19 mL, 28.7 mmol) were added to a solution of [(1R*,6R*)-8-benzyloxycarbonyl-8-azabicyclo[4.3.0]nonan-1-yl]carboxylic acid (6.70 g, 22.1 mmol) in toluene (110 mL) while stirring under ice-cooling in a nitrogen atmosphere. The mixture was stirred at room temperature for 40 minutes and then at 90° C. for one hour. The reaction solution was diluted with ethyl acetate (150 mL) at room temperature, washed with a saturated sodium bicarbonate solution (200 mL), water (200 mL), and brine (200 mL), and dried over anhydrous sodium sulfate. After filtration, the filtrate was concentrated under reduced pressure. 1,4-Dioxane (55.0 mL) and 6 mol/L hydrochloric acid (55.0 mL) were added to the resulting residue, and the mixture was stirred at 50° C. for two hours. The reaction solution was diluted with water (55.0 mL) and concentrated under reduced pressure. Then, the residue was azeotropically dried with ethanol (×5). Dichloromethane (110 mL) was added to the precipitated white solid (7.41 g). Triethylamine (15.4 mL, 110 mmol) and di-tert-butoxycarbonyl (9.65 g, 44.2 mol) were added in a nitrogen atmosphere, and the mixture was stirred at room temperature for 15 hours. The reaction solution was concentrated under reduced pressure, and ethyl acetate (150 mL) was added. The mixture was washed with water (200 mL) and brine (200 mL) and dried over anhydrous sodium sulfate. After filtration, the filtrate was concentrated under reduced pressure. The resulting residue was purified by silica gel column chromatography (hexane:ethyl acetate=100:0→90:10→83:17→66:34) to give 6.65 g of the title compound.

$^1$H-NMR (400 MHz, CDCl$_3$) δ: 7.37-7.29 (5H, m), 5.13 (2H, s), 4.55 (1H, d, J=13.97 Hz), 3.69 (1H, d, J=11.28 Hz), 3.58-3.45 (2H, m), 3.30 (1H, ddd, J=21.33, 10.66, 6.74 Hz), 2.03-1.99 (1H, m), 1.66-1.43 (17H, m).

MS (ESI); m/z: 374 (M+H)$^+$.

Reference Example 135

(1R,6S)-/(1S,6R)-8-Benzyloxycarbonyl-1-tert-butoxycarbonylamino-8-azabicyclo[4.3.0]nonane (Optical Isomer A, Optical Isomer B)

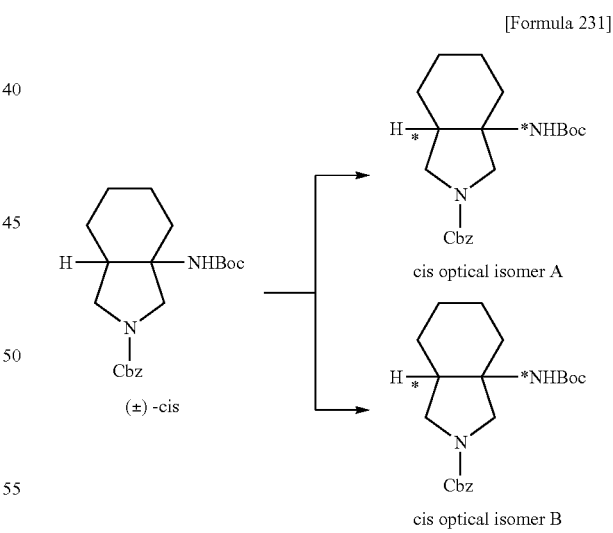

[Formula 231]

The racemate (1R*,6S*)-8-benzyloxycarbonyl-1-tert-butoxycarbonylamino-8-azabicyclo[4.3.0]nonane (6.65 g, 17.8 mmol) was optically resolved by an optically active column (CHIRALPAK AD, 20 mm diameter×250 mm, hexane:isopropyl alcohol=95:5, flow rate=20 ml/min) to give optically active 8-benzyloxycarbonyl-1-tert-butoxycarbonylamino-8-azabicyclo[4.3.0]nonane (optical isomer A) (427 mg, 1.14 mmol, retention time=14.2 min) and its optically active enantiomer 8-benzyloxycarbonyl-1-tert-butoxycarbonylamino-8- azabicyclo[4.3.0]nonane (optical isomer B) (415 mg, 1.11 mmol, retention time=19.4 min).

Reference Example 136

1-tert-Butoxycarbonylamino-8-azabicyclo[4.3.0]nonane (Derived from Optical Isomer A)

[Formula 232]

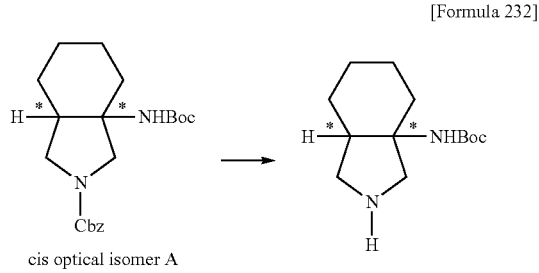 [SMILES: CC(C)(C)OC(=O)NC12CCCCC1CN(C(=O)OCc1ccccc1)C2 ; CC(C)(C)OC(=O)NC12CCCCC1CNC2]

cis optical isomer A

A 10% palladium-carbon catalyst (80.0 mg, 20 wt %) was added to a solution of 8-benzyloxycarbonyl-1-tert-butoxycarbonylamino-8-azabicyclo[4.3.0]nonane (optical isomer A) (400 mg, 1.07 mmol) in methanol (10.7 mL) in a nitrogen atmosphere. After the atmosphere was replaced with hydrogen, the mixture was stirred in a hydrogen atmosphere at room temperature for one hour. After the atmosphere was replaced with nitrogen, the reaction solution was filtered through Celite and concentrated under reduced pressure to give the title compound quantitatively.

$^1$H-NMR (400 MHz, CDCl$_3$) δ: 4.61 (1H, brs), 3.18-3.12 (2H, m), 3.02 (1H, d, J=11.28 Hz), 2.81 (1H, dd, J=10.66, 6.74 Hz), 2.16 (1H, brs), 2.01 (1H, brs), 1.57-1.43 (8H, m), 1.43 (9H, s).

MS (ESI); m/z: 241 (M+H)$^+$.

Example 29

7-[1-Amino-8-azabicyclo[4.3.0]nonan-8-yl]-6-fluoro-1-[(1R,2S)-2-fluorocyclopropan-1-yl]-1,4-dihydro-8-methoxy-4-oxoquinoline-3-carboxylic acid (7-Position Substituent: Derived from Optical Isomer A)

[Formula 233]

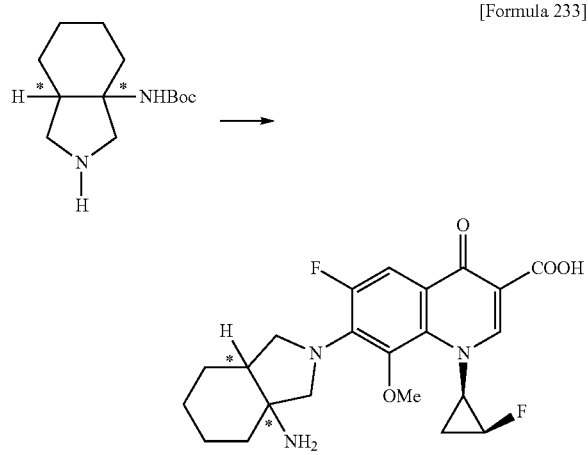

Triethylamine (0.407 mL, 2.92 mmol) and 6,7-difluoro-1-[(1R,2S)-2-fluorocyclopropan-1-yl]-1,4-dihydro-8-methoxy-4-oxoquinoline-3-carboxylic acid-BF$_2$ chelate (351 mg, 0.972 mmol) were added to a solution of 1-tert-butoxycarbonylamino-8-azabicyclo[4.3.0]nonane (derived from optical isomer A) (277 mg, 1.07 mmol) in dimethyl sulfoxide (1.94 mL), and the mixture was stirred at 35° C. for 17 hours. A mixed solution of ethanol:water=4:1 (20 mL) and triethylamine (2 mL) were added to the reaction solution, and the mixture was heated to reflux for one hour. The reaction solution was concentrated under reduced pressure. The residue was dissolved in ethyl acetate (40 mL) and washed with a 10% citric acid solution (50 mL), water (50 mL), and brine (50 mL). The organic layer was dried over anhydrous sodium sulfate and filtered, and then the filtrate was concentrated under reduced pressure. The resulting residue was purified by silica gel column chromatography (chloroform:methanol=100:0→99:1→98:2). 456 mg of the resulting residue was dissolved in concentrated hydrochloric acid (3.0 mL) under ice-cooling, and the solution was stirred at room temperature for 15 minutes. The reaction solution was adjusted to pH 13.6 with a saturated sodium hydroxide solution, and the basic solution was adjusted to pH 7.4 with hydrochloric acid, followed by extraction with chloroform (100 mL), chloroform/methanol=10/1 (150 mL×1, 100 mL×2), and the lower layer of chloroform/methanol/water=7/3/1 (150 mL). The organic layer was dried over anhydrous sodium sulfate and filtered, and then the filtrate was concentrated under reduced pressure. The residue was dissolved in hot ethanol (67.5 mL), and the insoluble material was removed by filtration. The solvent was gradually evaporated while heating with stirring. The solution was concentrated until ethanol was 10 mL, and then stirred at room temperature overnight. The precipitated crystals were collected by filtration and then washed with ethanol and diethyl ether. The crystals were dried under reduced pressure at 50° C. to give 271 mg of the title compound.

$^1$H-NMR (400 MHz, 0.1N NaOD) δ: 8.42 (1H, d, J=1.96 Hz), 7.65 (1H, d, J=14.71 Hz), 4.97 (1H, dt, J=49.76, 17.89 Hz), 4.05-4.00 (1H, m), 3.84 (1H, t, J=7.48 Hz), 3.71 (1H, d, J=10.30 Hz), 3.60 (4H, t, J=12.01 Hz), 3.36 (1H, d, J=8.33 Hz), 2.01 (1H, m), 1.77 (2H, m), 1.60-1.41 (8H, m).

Anal; Calcd for C$_{22}$H$_{25}$F$_2$N$_3$O$_4$.0.5H$_2$O: C, 59.72; H, 5.92; F, 8.59; N, 9.50. Found: C, 59.91; H, 5.97; F, 8.68; N, 9.39.

MS (ESI); m/z: 434 (M+H)$^+$.

IR (ATR) ν: 2927, 2856, 1724, 1616, 1508, 1430, 1324, 1268, 1186, 1120, 1049, 925, 877, 806 cm$^{-1}$.

Reference Example 137

1-tert-Butoxycarbonylamino-3-azabicyclo[4.3.0]nonane (Derived from Optical Isomer B)

[Formula 234]

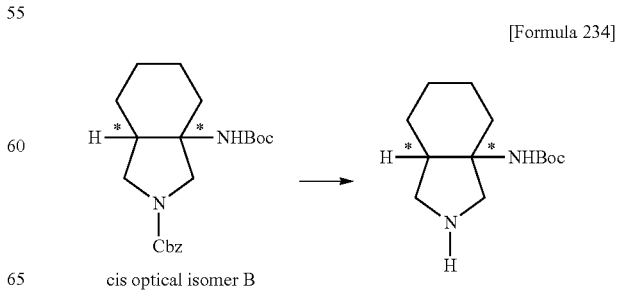

cis optical isomer B

A 10% palladium-carbon catalyst (83.0 mg, 20 wt %) was added to a solution of 8-benzyloxycarbonyl-1-tert-butoxycarbonylamino-8-azabicyclo[4.3.0]nonane (optical isomer B) (415 mg, 1.11 mmol) in methanol (11.1 mL) in a nitrogen atmosphere. After the atmosphere was replaced with hydrogen, the mixture was stirred in a hydrogen atmosphere at room temperature for one hour. After the atmosphere was replaced with nitrogen, the reaction solution was filtered through Celite and concentrated under reduced pressure to give the title compound quantitatively.

$^1$H-NMR (CDCl$_3$) δ: 4.60 (1H, brs), 3.17-3.12 (2H, m), 3.02 (1H, d, J=11.52 Hz), 2.81 (1H, brs), 2.15 (1H, brs), 2.00 (1H, s), 1.63-1.36 (8H, m), 1.43 (9H, s).

MS (ESI); m/z: 241 (M+H)$^+$.

Example 30

7-[1-Amino-8-azabicyclo[4.3.0]nonan-8-yl]-6-fluoro-1-[(1R,2S)-2-fluorocyclopropan-1-yl]-1,4-dihydro-8-methoxy-4-oxoquinoline-3-carboxylic acid (7-Position Substituent: Derived from Optical Isomer B)

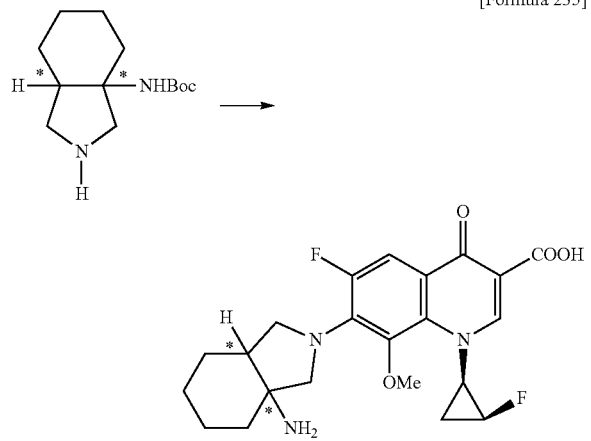

[Formula 235]

Triethylamine (0.422 mL, 3.03 mmol) and 6,7-difluoro-1-[(1R,2S)-2-fluorocyclopropan-1-yl]-1,4-dihydro-8-methoxy-4-oxoquinoline-3-carboxylic acid-BF$_2$ chelate (364 mg, 1.01 mmol) were added to a solution of 1-tert-butoxycarbonylamino-8-azabicyclo[4.3.0]nonane (derived from optical isomer B) (273 mg, 1.11 mmol) in dimethyl sulfoxide (1.94 mL), and the mixture was stirred at 35° C. for 17 hours. A mixed solution of ethanol:water=4:1 (20 mL) and triethylamine (2 mL) were added to the reaction solution, and the mixture was heated to reflux for one hour. The reaction solution was concentrated under reduced pressure. The residue was dissolved in ethyl acetate (40 mL) and washed with a 10% citric acid solution (50 mL), water (50 mL), and brine (50 mL). The organic layer was dried over anhydrous sodium sulfate and filtered, and then the filtrate was concentrated under reduced pressure. The resulting residue was purified by silica gel column chromatography (chloroform:methanol=100:0→99:1→98:2). 536 mg of the resulting residue was dissolved in concentrated hydrochloric acid (3.0 mL) under ice-cooling, and the solution was stirred at room temperature for 15 minutes. After washing with chloroform (20 mL×3), the aqueous layer was adjusted to pH 12 with a saturated sodium hydroxide solution. The basic solution was adjusted to pH 7 with hydrochloric acid, followed by extraction with chloroform/methanol=10/1 (150 mL×1, 100 mL×2). The organic layer was dried over anhydrous sodium sulfate and filtered, and then the filtrate was concentrated under reduced pressure. The residue was dissolved in hot ethanol (67.5 mL), and the insoluble material was removed by filtration. The solvent was gradually evaporated while heating with stirring. The solution was concentrated until ethanol was 10 mL, and then stirred at room temperature overnight. The precipitated crystals were collected by filtration and washed with ethanol and diethyl ether. The crystals were dried under reduced pressure at 50° C. to give 315 mg of the title compound.

$^1$H-NMR (400 MHz, 0.1N NaOD) δ: 8.45 (1H, d, J=1.47 Hz), 7.64 (1H, d, J=14.95 Hz), 5.04-4.84 (1H, m), 4.06-3.99 (2H, m), 3.88 (1H, dd, J=10.54, 2.21 Hz), 3.57 (3H, s), 3.42 (1H, d, J=10.54 Hz), 3.20 (1H, d, J=8.82 Hz), 1.94 (1H, m), 1.83 (1H, m), 1.73 (1H, m), 1.67-1.46 (6H, m), 1.33 (2H, m).

Anal; Calcd for $C_{22}H_{25}F_2N_3O_4 \cdot 0.75H_2O$: C, 59.12; H, 5.98; F, 8.50; N, 9.40. Found: C, 59.05; H, 6.12; F, 8.36; N, 9.20.

MS (ESI); m/z: 434 (M+H)$^+$.

IR (ATR) ν: 2927, 2859, 1724, 1616, 1573, 1509, 1432, 1369, 1355, 1319, 1267, 1118, 1049, 933, 879, 804 cm$^{-1}$.

Reference Example 138

(3S,4R)-3,4-Diallyl-5-oxo-1-[(1R)-1-phenylethyl]pyrrolidine-3-carboxylic acid tert-butyl ester

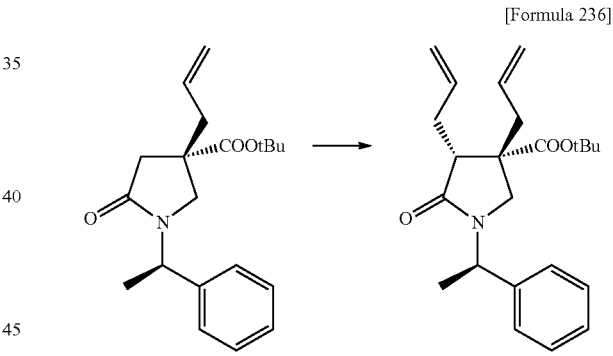

[Formula 236]

Allyl bromide (1.36 mL, 16.1 mmol) was added to a solution of (3S)-3-allyl-5-oxo-1-[(1R)-1-phenylethyl]pyrrolidine-3-carboxylic acid tert-butyl ester (4.05 g, 12.3 mmol) in tetrahydrofuran (41.0 mL) with stirring under salt ice cooling. A 1 M solution of lithium hexamethyldisilazide in tetrahydrofuran (16.0 mL, 16.0 mmol) was added dropwise with stirring under salt ice cooling, and the mixture was stirred under salt ice cooling for 15 minutes. A saturated ammonium chloride solution (40 mL) and water (20 mL) were added to the reaction solution, followed by extraction with ethyl acetate (40 mL×1, 20 mL×1). The organic layer was washed with brine (140 mL) and dried over anhydrous sodium sulfate. After filtration, the filtrate was concentrated under reduced pressure. The resulting residue was purified by silica gel column chromatography (hexane:ethyl acetate=100:0→90:10→89:11→88:12→87:13→83:17→80:20→75:25) to give 2.02 g of the title compound.

$^1$H-NMR (400 MHz, CDCl$_3$) δ: 7.32 (5H, m), 5.77-5.62 (2H, m), 5.48 (1H, q, J=7.11 Hz), 5.13 (2H, dd, J=13.36, 11.89 Hz), 5.02 (1H, t, J=9.07 Hz), 4.91 (1H, dd, J=5.52, 2.76

Hz), 3.21 (1H, d, J=10.54 Hz), 3.09 (1H, d, J=10.79 Hz), 2.56 (1H, dd, J=14.34, 6.01 Hz), 2.40 (3H, d, J=4.41 Hz), 2.27 (1H, dd, J=13.73, 8.33 Hz), 1.50 (3H, d, J=7.11 Hz), 1.40 (9H, s).
MS (ESI); m/z: 370 (M+H)$^+$.

Reference Example 139

[(1S,6R)-7-Oxo-8-[(1R)-1-phenylethyl]-8-azabicyclo [4.3.0]non-3-en-1-yl]carboxylic acid tert-butyl ester

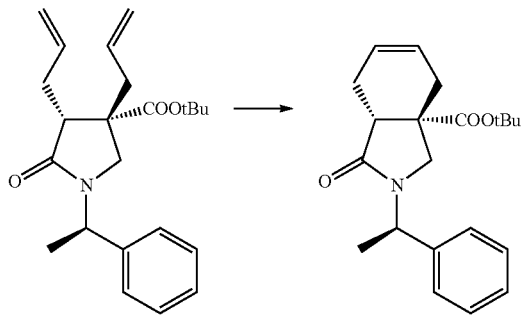

[Formula 237]

The Second Generation Grubbs' catalyst (91.9 mg, 0.108 mmol) was added to a solution of (3S,4R)-3,4-diallyl-5-oxo-1-[(1R)-1-phenylethyl]pyrrolidine-3-carboxylic acid tert-butyl ester (2.00 g, 5.41 mmol) in dichloromethane (54.1 mL) in a nitrogen atmosphere, and the mixture was stirred at room temperature for one hour. The reaction solution was concentrated under reduced pressure. The resulting residue was purified by silica gel column chromatography (hexane:ethyl acetate=100:0→90:10→80:20→75:25→66:34→50:50) to give 1.61 g of the title compound.
$^1$H-NMR (400 MHz, CDCl$_3$) δ: 7.34-7.21 (5H, m), 5.75 (1H, m), 5.67-5.62 (1H, m), 5.49 (1H, q, J=7.19 Hz), 3.22 (2H, dd, J=13.97, 10.05 Hz), 2.74 (1H, dd, J=16.42, 5.15 Hz), 2.62-2.54 (1H, m), 2.49 (1H, d, J=5.39 Hz), 2.42 (1H, m), 2.15-2.08 (1H, m), 1.48 (3H, d, J=7.11 Hz), 1.18 (9H, s).
MS (ESI); m/z: 342 (M+H)$^+$.

Reference Example 140

[(1S,6R)-7-Oxo-8-[(1R)-1-phenylethyl]-8-azabicyclo [4.3.0]non-3-en-1-yl]carboxylic acid

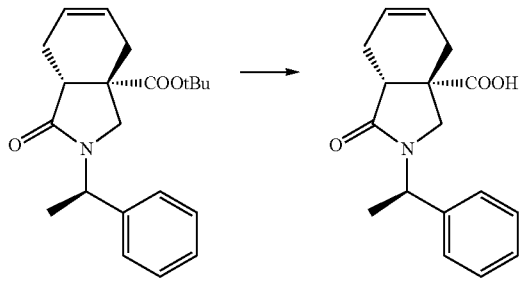

[Formula 238]

Trifluoroacetic acid (18.0 mL) was added to a solution of [(1S,6R)-7-oxo-8-[(1R)-1-phenylethyl]-8-azabicyclo[4.3.0] non-3-en-1-yl]carboxylic acid tert-butyl ester (2.04 g, 5.99 mmol) in dichloromethane (18.0 mL) with stirring under ice-cooling, and the mixture was stirred at room temperature for 1.5 hours. The reaction solution was concentrated under reduced pressure, and trifluoroacetic acid was azeotropically distilled with toluene (×3). A 1 mol/L sodium hydroxide solution (15.0 mL) was added to the resulting residue under ice-cooling, and the mixture was washed with diethyl ether (40 mL×2). The aqueous layer was made acidic with 1 mol/L hydrochloric acid (20 mL) under ice-cooling. Then, the precipitated crystals were collected by filtration and washed with 0.5 mol/L hydrochloric acid, ethyl acetate, and diethyl ether. The resulting crystals were dried under reduced pressure at 50° C. overnight to give 1.40 g of the title compound as white crystals. The aqueous layer of the filtrate was extracted with ethyl acetate (50 mL). The organic layers were combined, washed with water (150 mL) and brine (150 mL), and dried over anhydrous sodium sulfate. After filtration, the filtrate was concentrated under reduced pressure to give 250 mg of the title compound as white crystals.
$^1$H-NMR (400 MHz, CDCl$_3$) δ: 7.23 (5H, m), 5.81 (1H, m), 5.69 (1H, m), 5.51 (1H, q, J=7.11 Hz), 3.27 (1H, d, J=10.05 Hz), 3.18 (1H, d, J=10.05 Hz), 2.74 (1H, dd, J=16.67, 4.90 Hz), 2.59 (1H, m), 2.47 (1H, m), 2.22 (1H, d, J=16.67 Hz), 2.14 (1H, brs), 1.49 (3H, d, J=7.11 Hz).
MS (ESI); m/z: 286 (M+H)$^+$.

Reference Example 141

(1S,6R)-1-Amino-7-oxo-8-[(1R)-1-phenylethyl]-8-azabicyclo[4.3.0]non-3-ene

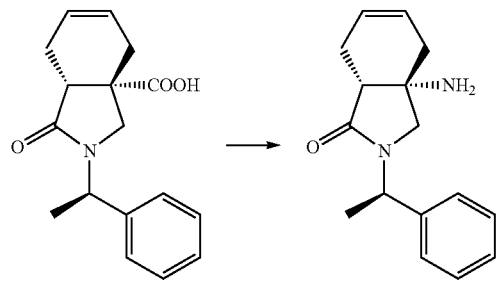

[Formula 239]

Triethylamine (1.61 mL, 11.5 mmol) and diphenylphosphoryl azide (1.62 mL, 7.52 mmol) were added to a solution of [(1S,6R)-7-oxo-8-[(1R)-1-phenylethyl]-8-azabicyclo [4.3.0]non-3-en-1-yl]carboxylic acid (1.65 g, 5.78 mmol) in toluene (28.9 mL) in a nitrogen atmosphere with stirring under ice-cooling, and the mixture was stirred at 100° C. for 30 minutes. The reaction solution was concentrated under reduced pressure, and triethylamine was azeotropically distilled with toluene (×3). 1,4-Dioxane (14.4 mL) and 4 mol/L hydrochloric acid (14.4 mL) were added to the resulting residue, and the mixture was stirred at 50° C. for six hours. The reaction solution was diluted with water (30.0 mL) and washed with ethyl acetate (50 mL×2). A 1 mol/L sodium hydroxide solution (55.0 mL) was added to the aqueous layer, followed by extraction with chloroform (100 mL×1, 80 mL×1). The organic layer was washed with brine (150 mL) and dried over anhydrous sodium sulfate. After filtration, the filtrate was concentrated under reduced pressure to give 1.24 g of the title compound as an amorphous.

¹H-NMR (400 MHz, CDCl₃) δ: 7.39-7.23 (5H, m), 5.81-5.77 (1H, m), 5.67-5.62 (1H, m), 5.53 (1H, q, J=7.11 Hz), 3.70 (2H, s), 3.23 (1H, d, J=9.80 Hz), 2.96 (1H, d, J=9.80 Hz), 2.45 (2H, m), 2.33 (1H, m), 2.27-2.16 (1H, m), 2.10 (1H, dd, J=16.79, 5.02 Hz), 1.50 (3H, d, J=7.11 Hz).

MS (ESI); m/z: 257 (M+H)⁺.

Reference Example 142

(1S,6S)-1-Amino-8-[(1R)-1-phenylethyl]-8-azabicyclo[4.3.0]non-3-ene

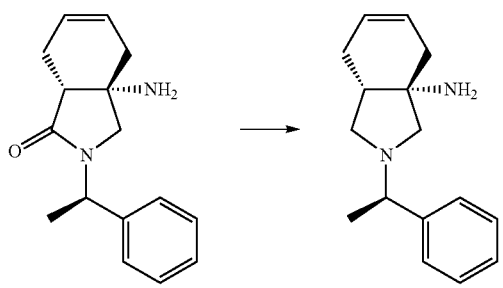

[Formula 240]

A 65% solution of sodium bis(2-methoxyethoxy)aluminum hydride in toluene (2.87 mL, 9.56 mmol) was added to a solution of (1S,6R)-1-amino-7-oxo-8-[(1R)-1-phenylethyl]-8-azabicyclo[4.3.0]non-3-ene (612 mg, 2.39 mmol) in toluene (11.9 mL), and the mixture was stirred at 80° C. for one hour. A 5 mol/L sodium hydroxide solution (15.0 mL) was added to the reaction solution with stirring under ice-cooling, followed by extraction with toluene (30 mL×2). The organic layer was washed with brine (90 ml) and dried over anhydrous sodium sulfate. After filtration, the filtrate was concentrated under reduced pressure to give 450 mg of the title compound.

¹H-NMR (400 MHz, CDCl₃) δ: 7.38-7.19 (5H, m), 5.72-5.59 (2H, m), 3.58 (1H, q, J=6.54 Hz), 2.86 (1H, d, J=9.07 Hz), 2.70 (1H, dd, J=9.56, 8.09 Hz), 2.54-2.48 (2H, m), 2.22-1.73 (5H, m), 1.33 (3H, d, J=6.62 Hz).

MS (ESI); m/z: 243 (M+H)⁺.

Reference Example 143

(1S,6S)-1-tert-Butoxycarbonylamino-8-[(1R)-1-phenylethyl]-8-azabicyclo[4.3.0]non-3-ene

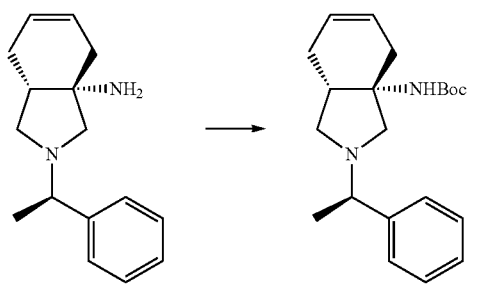

[Formula 241]

Di-tert-butyl dicarbonate (689 mg, 3.16 mmol) was added to a solution of (1S,6S)-1-amino-8-[(1R)-1-phenylethyl]-8-azabicyclo[4.3.0]non-3-ene (450 mg, 1.86 mmol) in dichloromethane (9.3 mL) in a nitrogen atmosphere, and the mixture was stirred at room temperature for 16 hours. The reaction solution was concentrated under reduced pressure. The resulting residue was purified by silica gel column chromatography (hexane:ethyl acetate=100:0→90:10→80:20→66:34→50:50→25:75→16:84) to give 456 mg of the title compound.

¹H-NMR (400 MHz, CDCl₃) δ: 7.29-7.18 (5H, m), 5.69-5.59 (2H, m), 4.43 (1H, s), 3.62 (1H, q, J=6.54 Hz), 3.53 (1H, d, J=10.54 Hz), 3.04 (1H, dd, J=8.95, 7.23 Hz), 2.89 (1H, d, J=18.38 Hz), 2.60 (1H, d, J=11.03 Hz), 2.52 (1H, dd, J=11.28, 9.31 Hz), 2.26-2.08 (2H, m), 1.99-1.83 (2H, m), 1.44 (9H, s), 1.32 (3H, d, J=6.62 Hz).

MS (ESI); m/z: 343 (M+H)⁺.

Reference Example 144

(1S,6S)-1-tert-Butoxycarbonylamino-8-azabicyclo[4.3.0]nonane

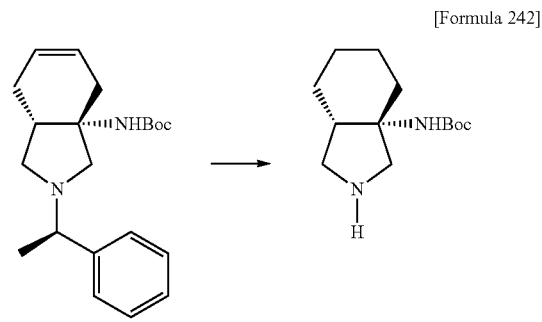 [SMILES: C[C@H](c1ccccc1)N1C[C@@H]2CC=CC[C@@]2(NC(=O)OC(C)(C)C)C1 ; CC(C)(C)OC(=O)N[C@@]12CCCC[C@H]1CNC2]

[Formula 242]

A 10% palladium-carbon catalyst (406 mg, 100 wt %) was added to a solution of (1S,6S)-1-tert-butoxycarbonylamino-8-[(1R)-1-phenylethyl]-8-azabicyclo[4.3.0]non-3-ene (406 mg, 1.18 mmol) in ethanol (11.8 mL) in a nitrogen atmosphere. After the atmosphere was replaced with hydrogen, the mixture was stirred in a hydrogen atmosphere at 40° C. to 50° C. for seven hours. After the atmosphere was replaced with nitrogen, the reaction solution was filtered through Celite and concentrated under reduced pressure to give the title compound quantitatively.

¹H-NMR (400 MHz, CDCl₃) δ: 4.24 (1H, brs), 3.59 (1H, brs), 3.01 (1H, dd, J=9.80, 7.60 Hz), 2.67-2.62 (2H, m), 2.52 (1H, d, J=11.28 Hz), 1.79-1.53 (9H, m), 1.44 (9H, s).

MS (ESI); m/z: 241 (M+H)⁺.

Example 31

7-[(1S,6S)-1-Amino-8-azabicyclo[4.3.0]nonan-8-yl]-6-fluoro-1-[(1R,2S)-2-fluorocyclopropyl]-8-methoxy-1,4-dihydro-4-oxoquinoline-3-carboxylic acid

[Formula 243]

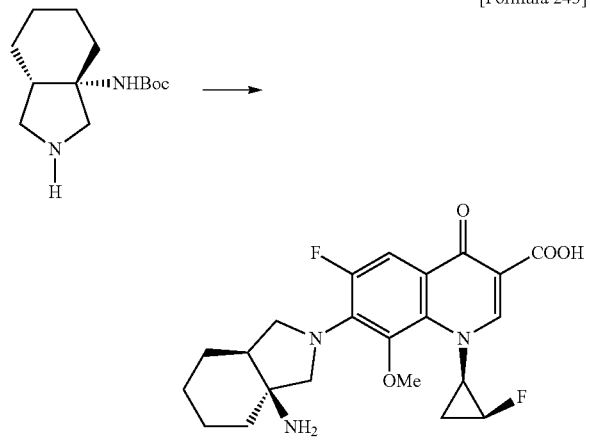

Triethylamine (0.449 mL, 3.22 mmol) and 1-[(1R,2S)-2-fluorocyclopropan-1-yl]-6,7-difluoro-1,4-dihydro-8-methoxy-4-oxoquinoline-3-carboxylic acid-$BF_2$ chelate (387 mg, 1.07 mmol) were added to a solution of (1S,6S)-1-tert-butoxycarbonylamino-8-azabicyclo[4.3.0]nonane (301 mg, 1.18 mmol) in dimethyl sulfoxide (2.14 mL), and the mixture was stirred at 35° C. for 15 hours. A mixed solution of ethanol:water=4:1 (20 mL) and triethylamine (2 mL) were added to the reaction solution, and the mixture was heated to reflux for 1.5 hours. The reaction solution was concentrated under reduced pressure. The residue was dissolved in ethyl acetate (30 mL) and washed with a 10% citric acid solution (40 mL), water (40 mL), and brine (40 mL). The organic layer was dried over anhydrous sodium sulfate and filtered, and then the filtrate was concentrated under reduced pressure. The resulting residue was purified by silica gel column chromatography (chloroform:methanol=100:0→99:1→98:2). 506 mg of the resulting residue was dissolved in concentrated hydrochloric acid (3.0 mL) under ice-cooling, and the solution was stirred at room temperature for 15 minutes. After washing with chloroform (20 mL×3), the aqueous layer was adjusted to pH 12 with a saturated sodium hydroxide solution. The basic solution was adjusted to pH 7.4 with hydrochloric acid, followed by extraction with chloroform (150 mL) and chloroform/methanol=10/1 (100 mL×2). The organic layer was dried over anhydrous sodium sulfate and filtered, and then the filtrate was concentrated under reduced pressure. The residue was dissolved in hot ethanol (45 mL), and the insoluble material was removed by filtration. The solvent was gradually evaporated while heating with stirring. The solution was concentrated until ethanol was 10 mL, and then stirred at room temperature overnight. The precipitated crystals were collected by filtration and then washed with ethanol and diethyl ether. The crystals were dried under reduced pressure at 50° C. to 60° C. to give 126 mg of the title compound.

$^1$H-NMR (400 MHz, 0.1N NaOD) δ: 8.35 (1H, d, J=3.92 Hz), 7.65 (1H, d, J=14.71 Hz), 5.15-4.96 (1H, m), 3.99 (1H, dt, J=10.21, 4.47 Hz), 3.62 (3H, m), 3.54 (3H, s), 3.44 (1H, t, J=8.46 Hz), 3.27 (1H, d, J=9.56 Hz), 1.87-1.28 (11H, m).

Anal; Calcd for $C_{22}H_{25}F_2N_3O_4 \cdot 0.25H_2O$: C, 60.33; H, 5.87; F, 8.68; N, 9.59. Found: C, 60.27; H, 5.84; F, 8.60; N, 9.58.

MS (ESI); m/z: 434 (M+H)$^+$.

IR (ATR) ν: 2929, 2859, 1722, 1617, 1508, 1432, 1363, 1319, 1045, 925, 804 cm$^{-1}$.

Example 32

7-[(1S,6S)-1-Amino-8-azabicyclo[4.3.0]nonan-8-yl]-8-cyano-6-fluoro-1-[(1R,2S)-2-fluorocyclopropyl]-1,4-dihydro-4-oxoquinoline-3-carboxylic acid

[Formula 244]

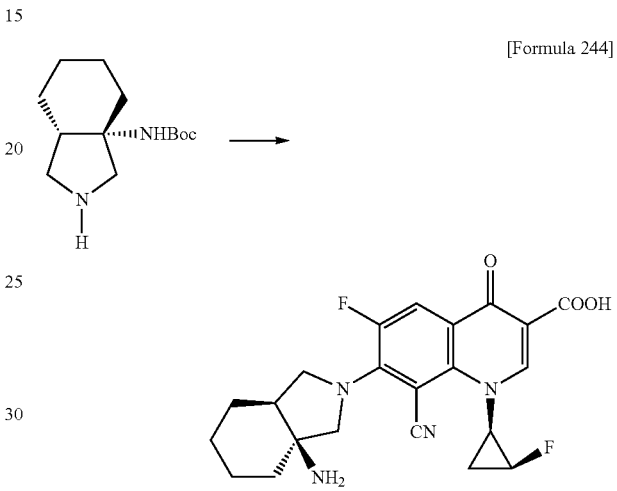

Triethylamine (478 μL, 3.42 mmol) and 8-cyano-6,7-difluoro-1-[(1R,2S)-2-fluorocyclopropan-1-yl]-1,4-dihydro-4-oxoquinoline-3-carboxylic acid ethyl ester (384 mg, 1.14 mmol) were added to a solution of (1S,6S)-1-tert-butoxycarbonylamino-8-azabicyclo[4.3.0]nonane (302 mg, 1.26 mmol) in acetonitrile (2.28 mL) in a nitrogen atmosphere. The mixture was stirred at room temperature for one hour and then at 45° C. for one hour. The reaction solution was concentrated under reduced pressure. Then, the residue was purified by silica gel column chromatography (hexane:ethyl acetate=100:0→90:10→66:34→50:50→40:60→30:70) to give a pale yellow amorphous. A 1 mol/L sodium hydroxide solution (4.64 mL) was added to a solution of 644 mg of the amorphous in ethanol (5.80 mL) under ice-cooling, and the mixture was stirred at room temperature for one hour. Then, tetrahydrofuran (8.70 mL) was added, and the mixture was stirred at room temperature for one hour. A 10% citric acid solution (15 mL) was added to the reaction solution, followed by extraction with ethyl acetate (50 mL×1, 40 mL×1). The organic layer was washed with brine (80 mL), dried over anhydrous sodium sulfate, and then filtered. The filtrate was concentrated under reduced pressure. The resulting residue was purified by silica gel column chromatography (chloroform:methanol=100:0→99:1→98:2). 554 mg of the resulting residue was dissolved in concentrated hydrochloric acid (2 mL) under ice-cooling, and the solution was stirred at room temperature for 10 minutes. The solution was washed with chloroform (25 mL×2). The reaction solution was adjusted to pH 12.5 with a saturated sodium hydroxide solution. The basic solution was adjusted to pH 7.4 with hydrochloric acid, followed by extraction with the lower layer of chloroform/methanol/water=7/3/1 (200 mL×3). The organic layer was dried over anhydrous sodium sulfate and filtered, and then the filtrate was concentrated under reduced pressure. Hot ethanol (80 mL) and 28% aqueous ammonia (5 mL) were added to the residue, and the insoluble material was removed by filtration. The solvent was gradually evaporated while heating with stirring. Ammonia was azeotropically removed with ethanol several times. The solution was concentrated to about 20 mL and then stirred at room temperature. The precipitated crystals were collected by filtration and then washed with ethanol and diethyl ether. The crystals were dried under reduced pressure at 50° C. overnight to give 341 mg of the title compound as pale yellow crystals.

$^1$H-NMR (400 MHz, 0.1N NaOD) δ: 8.29 (1H, d, J=3.92 Hz), 7.85 (1H, d, J=15.44 Hz), 5.18 (1H, ddd, J=66.61, 6.92, 4.47 Hz), 4.01-3.88 (3H, m), 3.70-3.65 (1H, m), 3.46 (1H, t, J=5.27 Hz), 1.95-1.32 (11H, m).

Anal; Calcd for $C_{22}H_{22}F_2N_4O_3 \cdot 1.25H_2O \cdot 0.25EtOH$: C, 58.91; H, 5.71; F, 8.28; N, 12.21. Found: C, 58.71; H, 5.66; N, 11.96.

MS (ESI); m/z: 429 (M+H)$^+$.

IR (ATR) ν: 3623, 2938, 2886, 2202, 1641, 1610, 1556, 1535, 1515, 1490, 1461, 1353, 1342, 1301, 1261 cm$^{-1}$.

Example 33

7-[(1S,6S)-1-Amino-8-azabicyclo[4.3.0]nonan-8-yl]-1-[(1R,2S)-2-fluorocyclopropyl]-1,4-dihydro-8-methyl-4-oxoquinoline-3-carboxylic acid

[Formula 245]

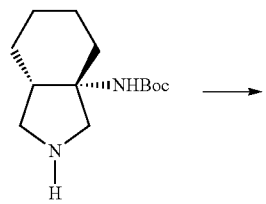

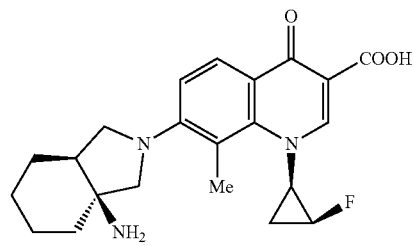

Triethylamine (0.277 mL, 1.98 mmol) and 7-fluoro-1-[(1R,2S)-2-fluorocyclopropyl]-1,4-dihydro-8-methyl-4-oxoquinoline-3-carboxylic acid (185 mg, 0.663 mmol) were added to a solution of (1S,6S)-1-tert-butoxycarbonylamino-8-azabicyclo[4.3.0]nonane (175 mg, 0.728 mmol) in dimethyl sulfoxide (1.33 mL) in a nitrogen atmosphere, and the mixture was stirred at 75° C. for 12 days. The reaction solution was diluted with ethyl acetate (45 mL) and then washed with a 10% citric acid solution (40 mL), water (40 mL), and a saturated sodium hydroxide solution (40 mL). The organic layer was dried over anhydrous sodium sulfate and filtered, and then the filtrate was concentrated under reduced pressure. The resulting residue was purified by silica gel column chromatography (chloroform:methanol=100:0→99:1→98:2). 260 mg (0.578 mmol) of the resulting residue was dissolved in concentrated hydrochloric acid (2.5 mL) under ice-cooling, and the solution was stirred at room temperature for 10 minutes. After washing with chloroform (50 mL×2), the aqueous layer was adjusted to pH 12 with a saturated sodium hydroxide solution. The basic solution was adjusted to pH 7.4 with hydrochloric acid, followed by extraction with chloroform (100 mL×2) and chloroform/methanol=10/1 (100 mL). The organic layer was dried over anhydrous sodium sulfate and filtered, and then the filtrate was concentrated under reduced pressure. The resulting residue was purified by PTLC (developed with the lower layer of chloroform/methanol/water=7/3/1). After the fluorescent part was collected, the lower layer of chloroform/methanol/water=7/3/1 (70 mL) was added. After ultrasonic treatment, the silica gel was filtered off. The filtrate was concentrated under reduced pressure and then vacuum dried. Ethanol (1 mL), diethyl ether, and 2-propanol were added to the residue. Diethyl ether was added. After repeating ultrasonic treatment and ice-cooling several times, the mixture was stirred at 40° C. for 30 minutes. After stirring at room temperature for two hours, the crystals were collected by filtration and dried under reduced pressure to give 88.7 mg of the title compound as pale yellow crystals.

$^1$H-NMR (400 MHz, 0.1N NaOD) δ: 8.40 (1H, d, J=3.68 Hz), 7.98 (1H, d, J=8.82 Hz), 7.07 (1H, d, J=9.31 Hz), 5.17-4.94 (1H, m), 4.06 (1H, dd, J=13.97, 5.64 Hz), 3.55 (2H, dd, J=19.36, 10.30 Hz), 3.22 (1H, t, J=8.09 Hz), 3.13 (1H, d, J=9.56 Hz), 2.43 (3H, s), 1.92-1.19 (11H, m).

Anal; Calcd for $C_{22}H_{26}FN_3O_3 \cdot 0.25H_2O$: C, 65.41; H, 6.61; F, 4.70; N, 10.40. Found: C, 65.18; H, 6.60; N, 10.48.

MS (ESI); m/z: 400 (M+H)$^+$.

IR (ATR) ν: 3380, 2927, 2863, 1712, 1614, 1509, 1428, 1396, 1359, 1348, 1340, 1315, 1301, 1035, 927 cm$^{-1}$.

Example 34

10-[(1S,6S)-1-Amino-8-azabicyclo[4.3.0]nonan-8-yl]-9-fluoro-2,3-dihydro-3-(S)-methyl-7-oxo-7H-pyrido[1,2,3-de][1,4]benzoxazine-6-carboxylic acid

[Formula 246]

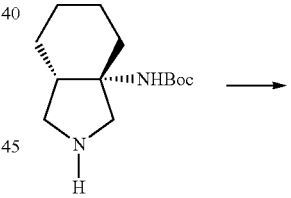

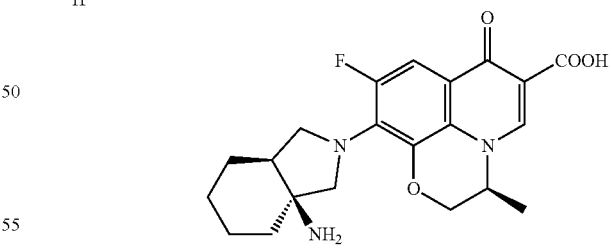

Triethylamine (0.208 mL, 1.49 mmol) and 9,10-difluoro-2,3-dihydro-3-(S)-methyl-7-oxo-7H-pyrido[1,2,3-de][1,4]benzoxazine-6-carboxylic acid-BF$_2$ chelate (164 mg, 0.498 mmol) were added to a solution of (1S,6S)-1-tert-butoxycarbonylamino-8-azabicyclo[4.3.0]nonane (126 mg, 0.524 mmol) in dimethyl sulfoxide (0.996 mL), and the mixture was stirred at 35° C. for 15 hours. A mixed solution of ethanol:water=4:1 (10 mL) and triethylamine (1 mL) were added to the reaction solution, and the mixture was heated to reflux for three hours. The reaction solution was concentrated under reduced pressure, and then a 10% citric acid solution (30 mL) was added to the residue, followed by extraction with ethyl acetate (30 mL). The interface part was extracted with chloroform. The organic layer was washed with water (30 mL) and brine (30 mL), respectively, dried over anhydrous sodium sulfate, and filtered. The filtrate was concentrated under reduced pressure. The resulting residue was purified by silica gel column chromatography (chloroform:methanol=100:0→99:1→98:2). 169 mg the resulting residue was dissolved in concentrated hydrochloric acid (1 mL) under ice-cooling, and the solution was stirred at room temperature for 15 minutes. After washing with chloroform (20 mL×3), the aqueous layer was adjusted to pH 12 with a saturated sodium hydroxide solution. The basic solution was adjusted to pH 7.4 with hydrochloric acid, followed by extraction with chloroform (100 mL×2) and chloroform/methanol=10/1 (100 mL×3). The organic layer was dried over anhydrous sodium sulfate and filtered, and then the filtrate was concentrated under reduced pressure. The residue (130 mg) was dissolved in ethanol/28% aqueous ammonia=7/1 (60 mL), and the insoluble material was removed by filtration. The filtrate was heated with stirring to gradually evaporate the solvent. Ammonia was azeotropically removed with ethanol several times. The solution was concentrated to 10 mL and then returned to room temperature. The precipitated crystals were collected by filtration, washed with ethanol and diethyl ether, and then dried under reduced pressure to give 109 mg of the title compound as pale yellow crystals.

$^1$H-NMR (400 MHz, 0.1N NaOD) δ: 8.30 (1H, s), 7.51 (1H, d, J=14.46 Hz), 4.62-4.54 (1H, m), 4.45 (1H, dd, J=11.40, 2.08 Hz), 4.26 (1H, dd, J=11.28, 2.21 Hz), 3.74 (1H, dd, J=10.05, 3.43 Hz), 3.70-3.64 (1H, m), 3.43 (1H, t, J=8.33 Hz), 3.34 (1H, d, J=8.33 Hz), 1.87-1.63 (5H, m), 1.56-1.22 (4H, m), 1.52 (3H, d, J=6.86 Hz).

Anal; Calcd for $C_{21}H_{24}FN_3O_4 \cdot 0.25H_2O$: C, 62.13; H, 6.08; F, 4.68; N, 10.35. Found: C, 62.03; H, 6.10; N, 10.31.

MS (ESI); m/z: 402 (M+H)$^+$.

IR (ATR) ν: 3590, 3295, 3222, 2929, 2883, 1614, 1554, 1471, 1344, 1311, 1259, 1234, 1110, 1041, 985, 815 cm$^{-1}$.

Reference Example 145

(1S,6S)-8-Benzyloxycarbonyl-1-tert-butoxycarbonylamino-8-azabicyclo[4.3.0]non-3-ene

[Formula 247]

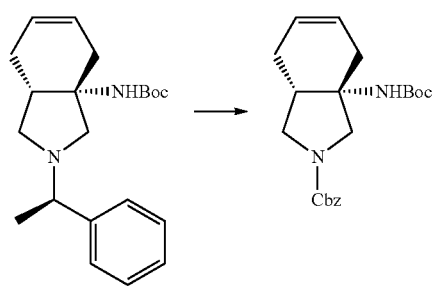

Benzyl chloroformate (0.600 mL, 4.20 mmol) was added to a solution of (1S,6S)-1-tert-butoxycarbonylamino-8-[(1R)-1-phenylethyl]-8-azabicyclo[4.3.0]non-3-ene (479 mg, 1.40 mmol) in dichloromethane (4.66 mL) in a nitrogen atmosphere, and the mixture was stirred at room temperature for 17 hours. The reaction solution was concentrated under reduced pressure. Then, the residue was purified by silica gel column chromatography (hexane:ethyl acetate=100:0→95:5→90:10→75:25→66:34) to give 401 mg of the title compound.

$^1$H-NMR (400 MHz, CDCl$_3$) δ: 7.43-7.18 (5H, m), 5.76-5.58 (2H, m), 5.19-5.09 (2H, m), 4.54-4.32 (2H, m), 3.70 (1H, dd, J=18.02, 7.97 Hz), 3.17-2.97 (3H, m), 2.39-1.47 (4H, m), 1.41 (9H, s).

MS (ESI); m/z: 395 (M+Na)$^+$.

Reference Example 146

(1S,6S)-1-tert-Butoxycarbonylamino-8-azabicyclo[4.3.0]non-3-ene

[Formula 248]

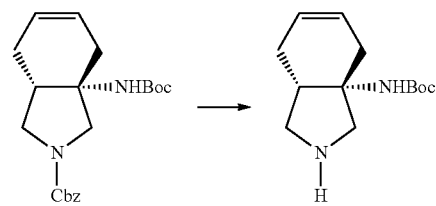

A solution of (1S,6S)-1-tert-butoxycarbonylamino-8-benzyloxycarbonyl-8-azabicyclo[4.3.0]non-3-ene (400 mg, 1.07 mmol) in tetrahydrofuran (5.35 mL) was bubbled with ammonia gas under cooling with dry ice-methanol for 10 minutes to add 30 to 40 mL of liquid ammonia to the solution. Sodium (128 mg, 5.34 mmol) was added, and the mixture was stirred for 10 minutes. A saturated ammonium chloride solution (15 drops) was added at room temperature, and the mixture was stirred at room temperature to evaporate ammonia. A 1 mol/L sodium hydroxide solution (15.0 mL) was added, followed by extraction with chloroform (30 mL×2). The aqueous layer was concentrated under reduced pressure. A 1 mol/L sodium hydroxide solution (5.0 mL) was added, followed by extraction with the lower layer of chloroform/methanol/water=7/3/1 (35 mL×2). The organic layers were combined, dried over anhydrous sodium sulfate, and filtered. Then, the filtrate was concentrated under reduced pressure to give 136 mg of the title compound as a white amorphous.

$^1$H-NMR (400 MHz, CDCl$_3$) δ: 5.74-5.63 (2H, m), 4.44-4.36 (1H, m), 3.12 (1H, dd, J=9.93, 7.72 Hz), 3.02-2.88 (2H, m), 2.72 (1H, t, J=10.79 Hz), 2.60 (2H, d, J=11.52 Hz), 2.30 (1H, t, J=11.52 Hz), 2.18-1.82 (4H, m), 1.39 (9H, s).

MS (ESI); m/z: 239 (M+H)$^+$.

Example 35

7-[(1S,6S)-1-Amino-8-azabicyclo[4.3.0]non-3-en-8-yl]-6-fluoro-1-[(1R,2S)-2-fluorocyclopropyl]-1,4-dihydro-8-methoxy-4-oxoquinoline-3-carboxylic acid

[Formula 249]

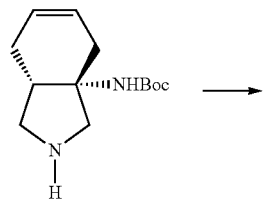

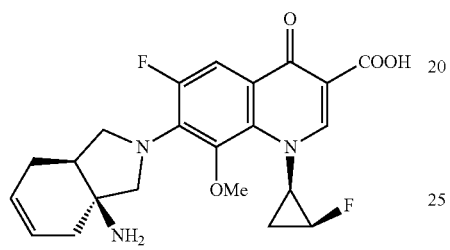

Triethylamine (0.217 mL, 1.55 mmol) and 1-[(1R,2S)-2-fluorocyclopropan-1-yl]-6,7-difluoro-1,4-dihydro-8-methoxy-4-oxoquinoline-3-carboxylic acid-BF$_2$ chelate (187 mg, 0.518 mmol) were added to a solution of (1S,6S)-1-tert-butoxycarbonylamino-8-azabicyclo[4.3.0]non-3-ene (136 mg, 0.571 mmol) in dimethyl sulfoxide (2.04 mL), and the mixture was stirred at 35° C. for 16 hours. A mixed solution of ethanol:water=4:1 (10 mL) and triethylamine (1 mL) were added to the reaction solution, and the mixture was heated to reflux for one hour. The reaction solution was concentrated under reduced pressure. The residue was dissolved in ethyl acetate (30 mL) and washed with a 10% citric acid solution (30 mL), water (30 mL), and brine (30 mL). The organic layer was dried over anhydrous sodium sulfate and filtered, and then the filtrate was concentrated under reduced pressure. The resulting residue was purified by silica gel column chromatography (chloroform:methanol=100:0→99:1→98:2). 242 mg of the resulting residue was dissolved in concentrated hydrochloric acid (2.0 mL) under ice-cooling, and the solution was stirred at room temperature for 10 minutes. After washing with chloroform (25 mL×3), the aqueous layer was adjusted to pH 12 with a saturated sodium hydroxide solution. The basic solution was adjusted to pH 7.4 with hydrochloric acid, followed by extraction with chloroform/methanol=10/1 (150 mL×1, 75 mL×1, 50 mL×1). The organic layer was dried over anhydrous sodium sulfate and filtered, and then the filtrate was concentrated under reduced pressure. The residue was dissolved in hot 2-propanol (40 ml), and the insoluble material was removed by filtration. The solvent was gradually evaporated while heating with stirring. The solution was concentrated to 10 ml and then stirred at room temperature overnight. The precipitated crystals were collected by filtration, washed with 2-propanol and diethyl ether, and then dried under reduced pressure to give 129 mg of the title compound.

$^1$H-NMR (400 MHz, 0.1N NaOD) δ: 8.36 (1H, d, J=3.68 Hz), 7.66 (1H, d, J=14.46 Hz), 5.88-5.72 (2H, m), 5.15-4.94 (1H, m), 4.05-3.98 (1H, m), 3.80-3.61 (3H, m), 3.57 (3H, s), 3.45 (1H, d, J=9.31 Hz), 2.48-1.97 (5H, m), 1.55-1.48 (1H, m), 1.45-1.29 (1H, m).

Anal; Calcd for C$_{22}$H$_{23}$F$_2$N$_3$O$_4$.0.5H$_2$O.iPrOH: C, 59.99; H, 6.44; F, 7.59; N, 8.39. Found: C, 59.95; H, 6.30; F, 7.61; N, 8.25.

MS (ESI); m/z: 432 (M+H)$^+$.

IR (ATR) ν: 2962, 1725, 1612, 1450, 1436, 1386, 1351, 1309, 1035, 819 cm$^{-1}$.

Reference Example 147

(3S,4R)-3-Allyl-4-benzyloxymethyl-5-oxo-1-[(1R)-1-phenylethyl]pyrrolidine-3-carboxylic acid tert-butyl ester; (3S,4S)-3-Allyl-4-benzyloxymethyl-5-oxo-1-[(1R)-1-phenylethyl]pyrrolidine-3-carboxylic acid tert-butyl ester

[Formula 250]

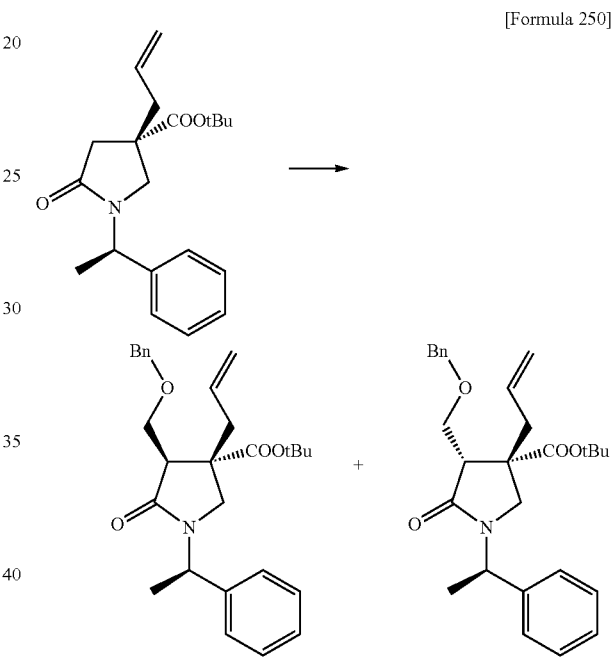

Benzyl chloromethyl ether (11.0 ml, 79.1 mmol) was added to a solution of (3S)-3-allyl-5-oxo-1-[(1R)-1-phenylethyl]pyrrolidine-3-carboxylic acid tert-butyl ester (20.0 g, 60.7 mmol) in tetrahydrofuran (303 mL) with stirring under salt ice cooling. A 1 M solution of lithium hexamethyldisilazide in tetrahydrofuran (78.9 mL, 78.9 mmol) was added dropwise with stirring under salt ice cooling, and the mixture was stirred under ice-cooling for 10 minutes. A saturated ammonium chloride solution (300 mL) was added to the reaction solution, followed by extraction with ethyl acetate (200 mL). The organic layer was washed with brine (600 mL) and dried over anhydrous sodium sulfate. After filtration, the filtrate was concentrated under reduced pressure. The resulting residue was purified by silica gel column chromatography (hexane:ethyl acetate=100:0→84:16→75:25→66:34) to give 9.81 g of the title compound (3S,4R)-isomer and 6.76 g of the title compound (3R,4S)-isomer.

(3S,4R)-Isomer:

$^1$H-NMR (400 MHz, CDCl$_3$) δ: 7.39-7.21 (10H, m), 5.75-5.59 (1H, m), 5.51-5.41 (1H, m), 5.17-5.08 (1H, m), 5.06-4.97 (1H, m), 4.71 (1H, s), 4.50 (1H, dd, J=22.31, 11.77 Hz), 3.97-3.95 (1H, m), 3.85-3.83 (1H, m), 3.35-3.04 (2H, m), 2.64-2.61 (1H, m), 2.45-2.37 (1H, m), 1.49 (1H, dd, J=7.11, 4.66 Hz), 1.42 (3H, d, J=7.35 Hz), 1.28 (9.H, s).

MS (ESI); m/z: 450 (M+H)⁺.

(3R,4S)-Isomer:

¹H-NMR (400 MHz, CDCl₃) δ: 7.27-6.96 (10H, m), 5.76-5.65 (1H, m), 5.52 (1H, q, J=7.03 Hz), 5.17-5.12 (2H, m), 4.42-4.35 (2H, m), 3.50 (1H, d, J=10.05 Hz), 3.04 (1H, d, J=10.05 Hz), 2.52 (1H, dd, J=13.73, 6.37 Hz), 2.45 (1H, t, J=2.82 Hz), 2.36 (1H, dd, J=13.73, 8.09 Hz), 1.51 (3H, d, J=7.11 Hz), 1.38 (9H, s).

MS (ESI); m/z: 450 (M+H)⁺.

Reference Example 148

(3S,4R)-4-Benzyloxymethyl-3-hydroxyethyl-5-oxo-1-[(1R)-1-phenylethyl]pyrrolidine-3-carboxylic acid tert-butyl ester

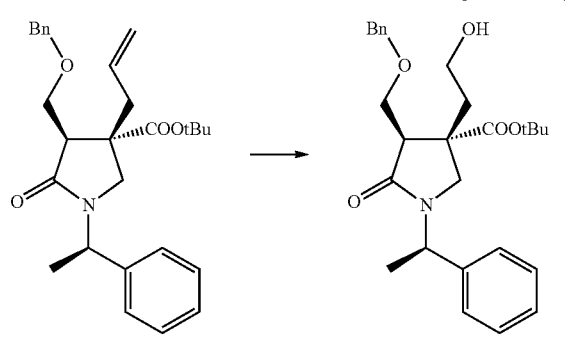

[Formula 251]

A solution of (3S,4R)-3-allyl-4-benzyloxymethyl-5-oxo-1-[(1R)-1-phenylethyl]pyrrolidine-3-carboxylic acid tert-butyl ester (8.00 g, 17.8 mmol) in methanol (177 mL) was bubbled with oxygen for 10 minutes. After bubbling with ozone for 30 minutes with stirring under cooling with dry ice-methanol, ozone was removed by bubbling with nitrogen. Sodium borohydride (1.68 g, 44.4 mmol) was added under cooling with ice-acetone, and the mixture was stirred under cooling for 1.5 hours. A saturated ammonium chloride solution (150 mL) was added to the reaction solution, and methanol was evaporated by concentration under reduced pressure. The mixture was extracted with ethyl acetate (200 mL×1, 150 mL×1). The organic layer was washed with brine (300 mL) and dried over anhydrous sodium sulfate. After filtration, the filtrate was concentrated under reduced pressure. The resulting residue was purified by silica gel column chromatography (hexane:ethyl acetate=100:0→90:10→66:34→50:50) to give 3.79 g of the title compound as a pale yellow oil.

¹H-NMR (400 MHz, CDCl₃) δ: 7.38-7.22 (5H, m), 5.46 (1H, q, J=7.03 Hz), 4.50 (2H, dd, J=17.28, 11.64 Hz), 3.97 (1H, dd, J=9.80, 4.41 Hz), 3.84 (1H, dd, J=9.80, 2.45 Hz), 3.60 (2H, t, J=6.37 Hz), 3.42 (1H, d, J=9.31 Hz), 3.26 (1H, d, J=9.31 Hz), 3.10 (1H, dd, J=4.41, 2.45 Hz), 2.11 (1H, dt, J=15.52, 5.58 Hz), 1.99-1.93 (1H, m), 1.41 (3H, d, J=7.35 Hz), 1.28 (9H, s).

MS (ESI); m/z: 454 (M+H)⁺.

Reference Example 149

(3S,4R)-3-Benzyloxymethyl-3-methanesulfonyloxyethyl-5-oxo-1-[(1R)-1-phenylethyl]pyrrolidine-3-carboxylic acid tert-butyl ester

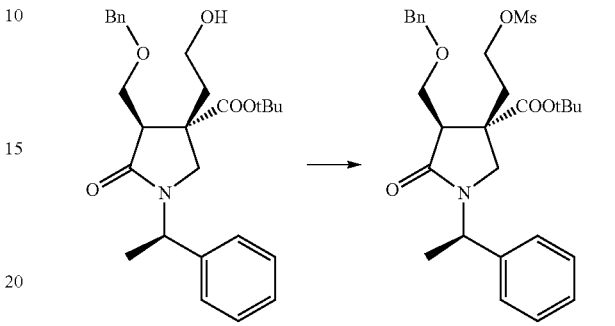

[Formula 252]

Triethylamine (2.79 mL, 19.9 mmol) was added to a solution of (3S,4R)-4-benzyloxymethyl-3-hydroxyethyl-5-oxo-1-[(1R)-1-phenylethyl]pyrrolidine-3-carboxylic acid tert-butyl ester (4.57 g, 10.0 mmol) in dichloromethane (50.0 mL) in a nitrogen atmosphere. Methanesulfonyl chloride (1.17 mL, 15.1 mmol) was added under cooling with ice-acetone, and the mixture was stirred at room temperature for 15 minutes. Water (150 mL) was added to the reaction solution, followed by extraction with chloroform (150 mL×1, 80 mL×1). The organic layer was washed with brine (200 mL) and dried over anhydrous sodium sulfate. After filtration, the filtrate was concentrated under reduced pressure to give 7.09 g of a residue containing the title compound, which was directly used for the next step without further purification.

¹H-NMR (400 MHz, CDCl₃) δ: 7.36-7.25 (10H, m), 5.45 (1H, q, J=7.11 Hz), 4.50 (2H, dd, J=17.16, 11.52 Hz), 4.23-4.20 (1H, m), 4.14-4.11 (1H, m), 3.99 (1H, dd, J=9.93, 4.29 Hz), 3.81 (1H, dd, J=9.93, 2.57 Hz), 3.37 (1H, d, J=9.56 Hz), 3.25 (1H, d, J=9.56 Hz), 3.08 (1H, dd, J=4.41, 2.45 Hz), 2.90 (3H, s), 2.33-2.26 (1H, m), 2.21-2.17 (1H, m), 1.42 (3H, d, J=7.11 Hz), 1.28 (9H, s).

MS (ESI); m/z: 532 (M+H)⁺.

Reference Example 150

(3S,4R)-4-Hydroxymethyl-3-methanesulfonyloxyethyl-5-oxo-1-[(1R)-1-phenylethyl]pyrrolidine-3-carboxylic acid tert-butyl ester

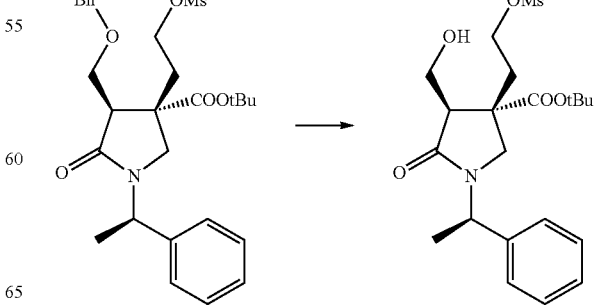

[Formula 253]

A 20% palladium hydroxide-carbon catalyst (7.09 g, 100 wt %) was added to a solution of (3S,4R)-3-benzyloxymethyl-3-methanesulfonyloxyethyl-5-oxo-1-[(1R)-1-phenylethyl]pyrrolidine-3-carboxylic acid tert-butyl ester (7.09 g) in ethanol (100 mL) in a nitrogen atmosphere. After the atmosphere was replaced with hydrogen, the mixture was stirred in a hydrogen atmosphere at room temperature for one hour and at 50° C. for one hour. After the atmosphere was replaced with nitrogen, the reaction solution was filtered through Celite, concentrated under reduced pressure, and dried under reduced pressure to give 4.49 g of a residue containing the title compound, which was directly used for the next step without further purification.

$^1$H-NMR (400 MHz, CDCl$_3$) δ: 7.39-7.25 (5H, m), 5.48 (1H, q, J=7.03 Hz), 4.30-4.19 (2H, m), 4.11-3.96 (2H, m), 3.34 (2H, dd, J=26.72, 10.54 Hz), 2.99 (3H, s), 2.98-2.95 (1H, m), 2.31-2.24 (1H, m), 2.17-2.10 (1H, m), 1.56 (3H, d, J=7.11 Hz), 1.37 (9H, s).

MS (ESI); m/z: 442 (M+H)$^+$.

Reference Example 151

(1S,6R)-{4-Oxa-7-oxo-8-[(1R)-1-phenylethyl]-8-azabicyclo[4.3.0]nonan-1-yl}carboxylic acid tert-butyl ester

[Formula 254]

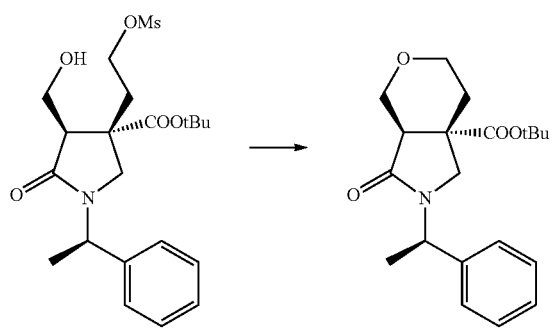

A solution of (3S,4R)-4-hydroxymethyl-3-methanesulfonyloxyethyl-5-oxo-1-[(1R)-1-phenylethyl]pyrrolidine-3-carboxylic acid tert-butyl ester (4.49 g) in pyridine (100 mL) was stirred in a nitrogen atmosphere at 50° C. for 15 hours. The reaction solution was concentrated under reduced pressure. The resulting residue was purified by silica gel column chromatography (hexane:ethyl acetate=100:0→90:10→66:34→50:50→10:90) to give 1.75 g of the title compound as white crystals.

$^1$H-NMR (400 MHz, CDCl$_3$) δ: 7.36-7.23 (5H, m), 5.58 (1H, q, J=7.11 Hz), 4.38 (1H, d, J=11.77 Hz), 3.83-3.79 (1H, m), 3.71 (1H, dd, J=12.01, 3.92 Hz), 3.42 (1H, td, J=12.01, 2.21 Hz), 3.04 (1H, d, J=10.05 Hz), 2.96 (1H, d, J=9.80 Hz), 2.62 (1H, d, J=3.43 Hz), 1.97 (1H, d, J=14.22 Hz), 1.75 (1H, ddd, J=15.44, 10.79, 3.19 Hz), 1.54 (3H, d, J=7.11 Hz), 1.44 (9H, s).

MS (ESI); m/z: 346 (M+H)$^+$.

Reference Example 152

(1S,6R)-{4-Oxa-7-oxo-8-[(1R)-1-phenylethyl]-8-azabicyclo[4.3.0]nonan-1-yl}carboxylic acid

[Formula 255]

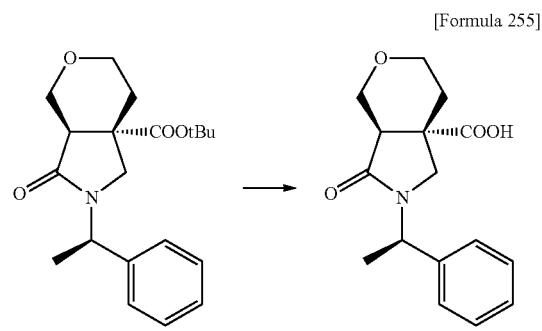

Trifluoroacetic acid (6.63 mL) was added to a solution of (1S,6R)-{4-oxa-7-oxo-8-[(1R)-1-phenylethyl]-8-azabicyclo[4.3.0]nonan-1-yl}carboxylic acid tert-butyl ester (763 mg, 2.21 mmol) in dichloromethane (6.63 mL) with stirring under ice-cooling, and the mixture was stirred at room temperature for 1.5 hours. The reaction solution was concentrated under reduced pressure, and trifluoroacetic acid was azeotropically distilled with toluene (three times). A 1 mol/L sodium hydroxide solution (20 mL) was added to the resulting residue under ice-cooling, and the mixture was washed with diethyl ether (50 mL×2). The aqueous layer was made acidic with 1 mol/L hydrochloric acid (20 mL) under ice-cooling, followed by extraction with ethyl acetate (60 mL×1, 50 mL×1). The organic layers were combined, washed with brine (90 mL), and dried over anhydrous sodium sulfate. After filtration, the filtrate was concentrated under reduced pressure to give 637 mg of the title compound as white crystals.

$^1$H-NMR (400 MHz, CDCl$_3$) δ: 7.43-7.24 (5H, m), 5.58 (1H, q, J=7.11 Hz), 4.41 (1H, d, J=12.26 Hz), 3.83 (1H, dd, J=12.13, 2.82 Hz), 3.70 (1H, dd, J=12.01, 3.68 Hz), 3.44 (1H, td, J=12.13, 1.88 Hz), 3.11 (1H, d, J=10.05 Hz), 3.02 (1H, d, J=10.05 Hz), 2.69 (1H, d, J=3.43 Hz), 2.09-2.05 (1H, m), 1.84-1.76 (1H, m), 1.55 (3H, d, J=7.11 Hz).

MS (ESI); m/z: 290 (M+H)$^+$.

Reference Example 153

(1S,6R)-1-tert-Butoxycarbonylamino-4-oxa-7-oxo-8-[(1R)-1-phenylethyl]-8-azabicyclo[4.3.0]nonane

[Formula 256]

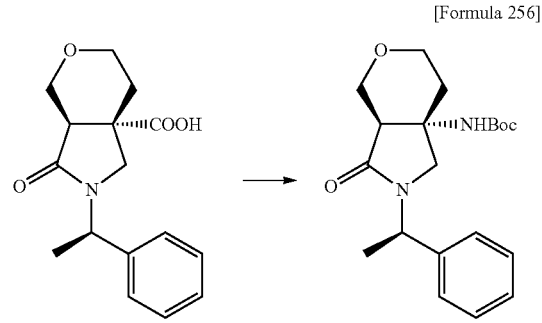 [SMILES: C[C@H](c1ccccc1)N1C[C@]2(C(=O)O)CCOC[C@@H]2C1=O ; C[C@H](c1ccccc1)N1C[C@]2(NC(=O)OC(C)(C)C)CCOC[C@@H]2C1=O]

Triethylamine (0.720 mL, 5.16 mmol) and diphenylphosphoryl azide (0.723 mL, 3.35 mmol) were added to a solution of (1S,6R)-{4-oxa-7-oxo-8-[(1R)-1-phenylethyl]-8-azabicyclo[4.3.0]nonan-1-yl}carboxylic acid (747 mg, 2.58 mmol) in toluene (12.9 mL) in a nitrogen atmosphere with stirring under ice-cooling. The mixture was stirred at room temperature for 30 minutes and then at 100° C. for 30 minutes. The reaction solution was concentrated under reduced pressure, and triethylamine was azeotropically distilled with toluene (×3). 1,4-Dioxane (6.45 mL) and 6 mol/L hydrochloric acid (6.45 mL) were added to the resulting residue, and the mixture was stirred at 50° C. for one hour. The reaction solution was diluted with water (15 mL) and washed with ethyl acetate (50 mL×2). The aqueous layer was made alkaline with a 1 mol/L sodium hydroxide solution under ice-cooling, followed by extraction with chloroform (50 mL×2). The organic layer was washed with brine (80 mL) and dried over anhydrous sodium sulfate. After filtration, the filtrate was concentrated under reduced pressure. Dichloromethane (14.9 mL) was added to the resulting residue, di-tert-butyl dicarbonate (813 mg, 3.73 mmol) was added in a nitrogen atmosphere, and the mixture was stirred at room temperature for four days. The reaction solution was concentrated under reduced pressure. The resulting residue was purified by silica gel column chromatography (hexane:ethyl acetate=100:0→95:5→90:10→75:25→60:40→50:50) to give 470 mg (51%) of the title compound.

$^1$H-NMR (400 MHz, CDCl$_3$) δ: 7.36-7.25 (5H, m), 5.58 (1H, q, J=7.19 Hz), 4.81 (1H, brs), 4.31 (1H, dd, J=12.26, 1.72 Hz), 3.77 (1H, td, J=7.54, 4.09 Hz), 3.61 (1H, dd, J=12.26, 3.92 Hz), 3.48 (2H, m), 3.09 (1H, d, J=10.05 Hz), 2.39 (1H, brs), 2.16-2.05 (1H, m), 1.81 (1H, ddd, J=15.26, 10.85, 3.62 Hz), 1.53 (3H, d, J=7.11 Hz), 1.39 (9H, s).

MS (ESI); m/z: 361 (M+H)$^+$.

Reference Example 154

(1S,6R)-1-tert-Butoxycarbonylamino-4-oxa-8-[(1R)-1-phenylethyl]-7-thioxo-8-azabicyclo[4.3.0]nonane

[Formula 257]

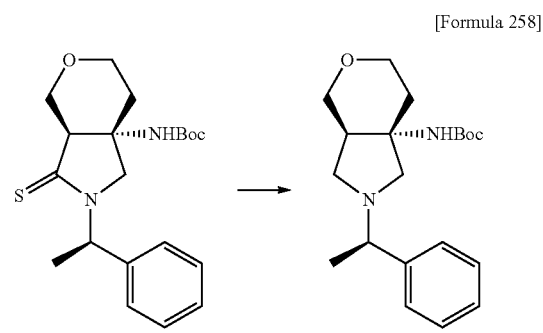 [SMILES: C[C@H](c1ccccc1)N1C[C@]2(NC(=O)OC(C)(C)C)CCOC[C@@H]2C1=S ; C[C@H](c1ccccc1)N1C[C@H]2COCC[C@@]2(NC(=O)OC(C)(C)C)C1]

Lawesson's reagent was added to a solution of (1S,6R)-1-tert-butoxycarbonylamino-4-oxa-8-[(1R)-1-phenylethyl]-7-oxo-8-azabicyclo[4.3.0]nonane (470 mg, 1.30 mmol) in tetrahydrofuran (13.0 mL), and the mixture was stirred at 60° C. for 2.5 hours. The reaction solution was concentrated under reduced pressure. The resulting residue was purified by silica gel column chromatography (hexane:ethyl acetate=100:0→95:5→90:10→80:20→75:25→66:34) to give a residue containing the title compound, which was directly used for the next step.

$^1$H-NMR (400 MHz, CDCl$_3$) δ: 7.34-7.29 (5H, m), 6.97 (1H, dt, J=12.83, 4.60 Hz), 6.44 (1H, q, J=7.03 Hz), 4.39 (1H, d, J=9.31 Hz), 3.87-3.82 (3H, m), 3.72-3.57 (2H, m), 2.70 (1H, brs), 2.03-1.94 (1H, m), 1.90-1.79 (1H, m), 1.60 (3H, d, J=7.11 Hz), 1.36 (9H, s).

MS (ESI); m/z: 377 (M+H)$^+$.

Reference Example 155

(1S,6R)-1-tert-Butoxycarbonylamino-4-oxa-8-[(1R)-1-phenylethyl]-8-azabicyclo[4.3.0]nonane

[Formula 258]

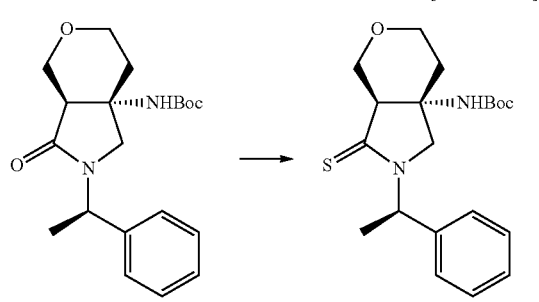

Raney nickel (14.2 mL) was added to a solution of (1S,6R)-1-tert-Butoxycarbonylamino-4-oxa-8-[(1R)-1-phenylethyl]-7-thioxo-8-azabicyclo[4.3.0]nonane (700 mg) in ethanol (28.4 mL) in a nitrogen atmosphere. The mixture was vigorously stirred at room temperature for one hour. The reaction solution was filtered through Celite and concentrated under reduced pressure to give 423 mg of the title compound quantitatively.

$^1$H-NMR (400 MHz, CDCl$_3$) δ: 7.36-7.20 (5H, m), 4.66 (1H, brs), 3.75-3.40 (4H, m), 2.90 (2H, s), 2.78-2.69 (2H, m), 2.20-1.96 (3H, m), 1.41 (9H, s), 1.34 (3H, d, J=6.59 Hz).

MS (ESI); m/z: 347 (M+H)$^+$.

Reference Example 156

(1S,6S)-1-tert-Butoxycarbonylamino-4-oxabicyclo[4.3.0]nonane

[Formula 259]

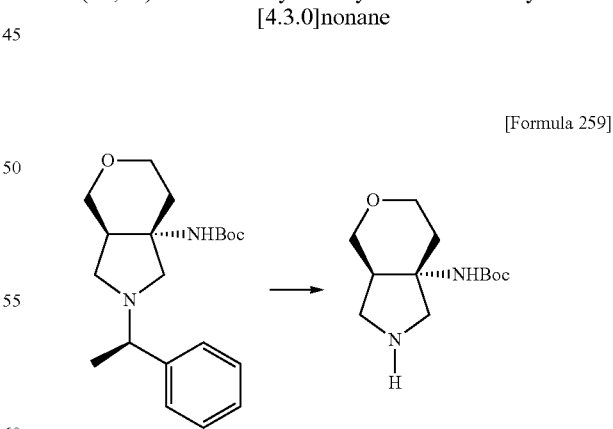

A 10% palladium-carbon catalyst (205 mg) was added to a solution of (1S,6R)-1-tert-butoxycarbonylamino-4-oxa-8-[(1R)-1-phenylethyl]-8-azabicyclo[4.3.0]nonane (205 mg, 0.592 mmol) in ethanol (5.92 mL) in a nitrogen atmosphere. After the atmosphere was replaced with hydrogen, the mixture was stirred in a hydrogen atmosphere at room temperature for 45 minutes and at 50° C. for one hour. After the atmosphere was replaced with nitrogen, the reaction solution was filtered through Celite and concentrated under reduced pressure. A 10% palladium-carbon catalyst (205 mg) was added to a solution of the resulting residue in ethanol (5.92 mL) in a nitrogen atmosphere. After the atmosphere was replaced with hydrogen, the mixture was stirred at 50° C. for 16 hours. After the atmosphere was replaced with nitrogen, the reaction solution was filtered through Celite and concentrated under reduced pressure. A 20% palladium hydroxide-carbon catalyst (205 mg) was added to a solution of the resulting residue in ethanol (5.92 mL) in a nitrogen atmosphere. After the atmosphere was replaced with hydrogen, the mixture was stirred in a hydrogen atmosphere at 50° C. for one hour. After the atmosphere was replaced with nitrogen, the reaction solution was filtered through Celite, concentrated under reduced pressure, and dried under reduced pressure to give 128 mg of the title compound as a pale vermillion oil.

$^1$H-NMR (400 MHz, CDCl$_3$) δ: 4.83 (1H, brs), 3.68-3.57 (4H, m), 3.30-3.19 (3H, m), 3.00-2.98 (1H, m), 2.14-1.96 (3H, m), 1.44 (9H, s).

MS (ESI); m/z: 243 (M+H)$^+$.

Example 36

7-[(1S,6R)-1-Amino-4-oxa-8-azabicyclo[4.3.0]nonan-8-yl]-6-fluoro-1-[(1R,2S)-2-fluorocyclopropyl]-1,4-dihydro-8-methoxy-4-oxoquinoline-3-carboxylic acid

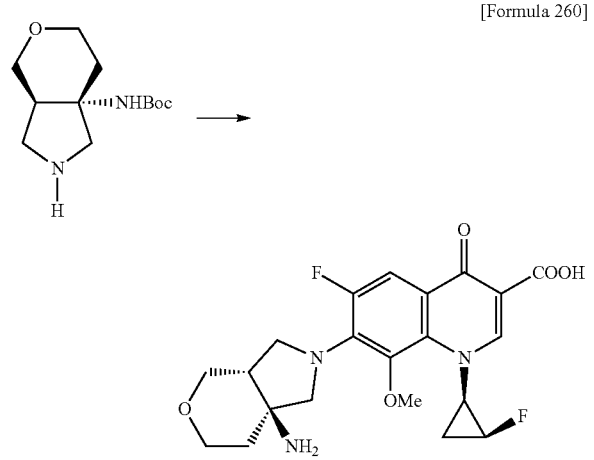

[Formula 260]

Triethylamine (0.198 mL, 1.42 mmol) and 6,7-difluoro-1-[(1R,2S)-2-fluorocyclopropyl]-1,4-dihydro-8-methoxy-4-oxoquinoline-3-carboxylic acid-BF$_2$ chelate (171 mg, 0.474 mmol) were added to a solution of (1S,6R)-8-aza-1-tert-butoxycarbonylamino-4-oxabicyclo[4.3.0]nonane (126 mg, 0.520 mmol) in dimethyl sulfoxide (0.948 mL), and the mixture was stirred at 35° C. for 16 hours. A mixed solution of ethanol:water=4:1 (10 mL) and triethylamine (1 mL) were added to the reaction solution, and the mixture was heated to reflux for one hour. The reaction solution was concentrated under reduced pressure. The residue was dissolved in ethyl acetate (30 mL) and washed with a 10% citric acid solution (30 mL), water (30 mL), and brine (30 mL). The organic layer was dried over anhydrous sodium sulfate and filtered, and then the filtrate was concentrated under reduced pressure. The resulting residue was purified by silica gel column chromatography (chloroform:methanol=100:0→99:1→98:2). Trifluoroacetic acid (0.694 mL, 3 v/w) was added to a solution of 125 mg of the resulting residue in dichloromethane (2.31 mL) with stirring under ice-cooling, and the mixture was stirred at room temperature for one hour. The reaction solution was concentrated under reduced pressure, and trifluoroacetic acid was azeotropically distilled with toluene (×3). Hydrochloric acid at pH 1 (20.0 mL) was added to the resulting residue under ice-cooling, and the mixture was washed with diethyl ether (40 mL×4). The aqueous layer was adjusted to pH 12 with a 1 mol/L sodium hydroxide solution under ice-cooling. The basic solution was adjusted to pH 7.4 with 1 mol/L hydrochloric acid, followed by extraction with chloroform (100 mL×2) and chloroform/methanol=10/1 (100 mL). The organic layer was dried over anhydrous sodium sulfate and filtered, and then the filtrate was concentrated under reduced pressure. The residue was dissolved in hot ethanol (10 mL), and the insoluble material was removed by filtration. The solvent was gradually evaporated while heating with stirring. The residue was concentrated until ethanol was 3 to 4 ml, and then stirred at room temperature overnight. The precipitated crystals were collected by filtration, washed with ethanol and diethyl ether, and then dried under reduced pressure at 60° C. to give 20.5 mg of the title compound.

$^1$H-NMR (400 MHz, 0.1N NaOD) δ: 8.45 (1H, s), 7.68 (1H, d, J=14.71 Hz), 5.08-4.92 (1H, m), 4.07 (1H, dd, J=13.73, 6.13 Hz), 3.92 (1H, dd, J=12.50, 3.68 Hz), 3.83 (4H, dd, J=13.85, 8.95 Hz), 3.73-3.58 (6H, m), 2.20-2.13 (1H, m), 2.06-1.99 (1H, m), 1.68-1.49 (3H, m).

Anal; Calcd for $C_{21}H_{23}F_2N_3O_5 \cdot 0.75H_2O$: C, 56.18; H, 5.50; N, 9.36. Found: C, 56.15; H, 5.46; N, 9.65.

MS (ESI); m/z: 436 (M+H)$^+$.

IR (ATR) ν: 2937, 2892, 2856, 1724, 1625, 1515, 1454, 1324, 1137, 1099, 1054, 985, 927, 887, 802 cm$^{-1}$.

Reference Example 157

(3S,4S)-4-Benzyloxymethyl-5-oxo-3-(2-oxoethyl)-1-[(1R)-1-phenylethyl]pyrrolidine-3-carboxylic acid tert-butyl ester

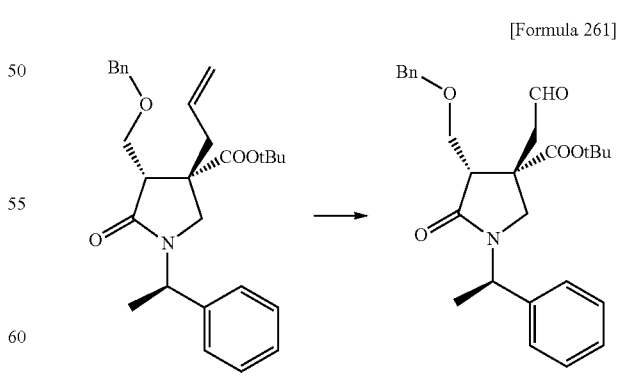

[Formula 261]

A solution of (3S,4S)-3-allyl-4-benzyloxymethyl-5-oxo-1-[(1R)-1-phenylethyl]pyrrolidine-3-carboxylic acid tert-butyl ester (6.76 g, 15.0 mmol) in methanol (150 mL) was bubbled with oxygen for five minutes. After bubbling with ozone for 1.5 hours with stirring under cooling with dry ice-methanol, ozone was removed by bubbling with nitrogen. Dimethyl sulfide (5.64 mL, 76.8 mmol) was added under cooling, and the mixture was stirred for 19 hours. The reaction solution was concentrated under reduced pressure. The resulting residue was purified by silica gel column chromatography (hexane:ethyl acetate=100:0→90:10→80:20→75:25→66:34→50:50) to give 4.58 g of the title compound as a transparent oil.

$^1$H-NMR (400 MHz, CDCl$_3$) δ: 9.74 (1H, s), 7.37-7.15 (5H, m), 5.47 (1H, q, J=7.19 Hz), 4.42 (2H, s), 3.92 (1H, dd, J=9.80, 3.68 Hz), 3.81 (1H, dd, J=9.56, 6.62 Hz), 3.68 (1H, d, J=10.54 Hz), 3.21 (1H, t, J=8.58 Hz), 3.13 (1H, d, J=10.54 Hz), 2.70 (1H, dd, J=6.37, 3.68 Hz), 2.61 (1H, d, J=17.16 Hz), 1.50 (3H, d, J=7.11 Hz), 1.27 (9H, s).

MS (ESI); m/z: 452 (M+H)$^+$.

Reference Example 158

(3S,4S)-4-Benzyloxymethyl-3-carboxymethyl-5-oxo-1-[(1R)-1-phenylethyl]pyrrolidine-3-carboxylic acid tert-butyl ester

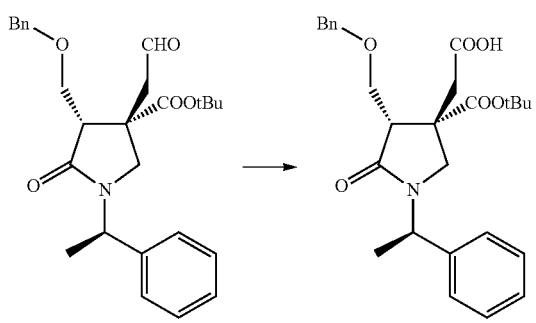

[Formula 262]

2-Methyl-2-butene was added to a solution of (3S,4S)-4-benzyloxymethyl-5-oxo-3-(2-oxoethyl)-1-[(1R)-1-phenylethyl]pyrrolidine-3-carboxylic acid tert-butyl ester (4.58 g, 10.1 mmol) in tert-butyl alcohol (25.2 mL) under ice-cooling, and the mixture was stirred. Sodium chlorite (2.29 g, 25.3 mmol) was added to a solution of sodium dihydrogenphosphate dihydrate (4.10 g, 26.3 mmol) in water (20.2 mL) to separately prepare a solution. This solution was added to the above solution under ice-cooling, and the mixture was stirred at room temperature for one hour. The precipitated solid was collected by filtration, washed with water and hexane, and then dried under reduced pressure at 40° C. to give 3.93 g of the title compound as white powder crystals.

$^1$H-NMR (400 MHz, CDCl$_3$) δ: 7.30-7.14 (5H, m), 5.48 (1H, q, J=7.03 Hz), 4.42 (2H, s), 3.90 (1H, dd, J=9.68, 3.55 Hz), 3.82 (1H, dd, J=9.56, 6.13 Hz), 3.69 (1H, d, J=10.54 Hz), 3.27 (1H, d, J=10.79 Hz), 3.10 (1H, d, J=16.18 Hz), 2.70 (1H, dd, J=6.13, 3.68 Hz), 2.58 (1H, d, J=16.18 Hz), 1.79 (1H, brs), 1.52 (3H, d, J=7.11 Hz), 1.29 (9H, s).

MS (ESI); m/z: 468 (M+H)$^+$.

Reference Example 159

(3S,4S)-3-Carboxymethyl-4-hydroxymethyl-5-oxo-1-[(1R)-1-phenylethyl]pyrrolidine-3-carboxylic acid tert-butyl ester

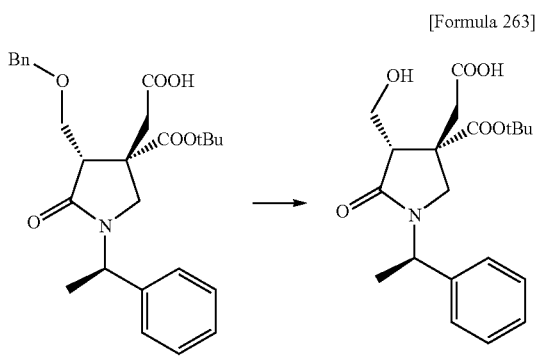

[Formula 263]

A 10% palladium-carbon catalyst (3.93 g) was added to a solution of (3S,4S)-4-benzyloxymethyl-3-carboxymethyl-5-oxo-1-[(1R)-1-phenylethyl]pyrrolidine-3-carboxylic acid tert-butyl ester (3.93 g, 8.41 mmol) in methanol (84.0 mL) in a nitrogen atmosphere. After the atmosphere was replaced with hydrogen, the mixture was stirred in a hydrogen atmosphere at room temperature for three days. After the atmosphere was replaced with nitrogen, the reaction solution was filtered through Celite and concentrated under reduced pressure to give 2.54 g of the title compound.

$^1$H-NMR (400 MHz, CDCl$_3$) δ: 7.39-7.27 (5H, m), 5.44 (1H, q, J=7.11 Hz), 3.88 (1H, dd, J=11.28, 7.60 Hz), 3.80 (1H, dd, J=11.28, 5.39 Hz), 3.69 (1H, d, J=10.79 Hz), 3.26 (1H, d, J=10.79 Hz), 3.05 (1H, d, J=16.91 Hz), 2.68 (1H, dd, J=7.35, 5.39 Hz), 2.59 (1H, d, J=16.91 Hz), 1.53 (3H, d, J=7.11 Hz), 1.28 (9H, s).

MS (ESI); m/z: 378 (M+H)$^+$.

Reference Example 160

{(1S,6S)-4-Oxa-3,7-dioxo-8-[(1R)-1-phenylethyl]-8-azabicyclo[4.3.0]nonan-1-yl}carboxylic acid tert-butyl ester

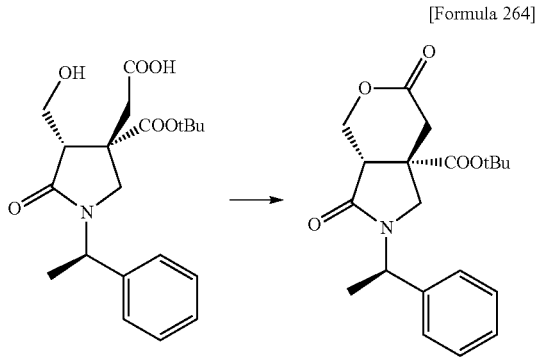

[Formula 264]

Triethylamine (1.32 mL, 9.46 mmol) and 2,4,6-trichlorobenzoyl chloride (1.16 mL, 7.45 mmol) were added to a solution of (3S,4S)-3-carboxymethyl-4-hydroxymethyl-5-oxo-1-[(1R)-1-phenylethyl]pyrrolidine-3-carboxylic acid tert-butyl ester (2.54 g, 6.73 mmol) in tetrahydrofuran (44.8 mL) in a nitrogen atmosphere. After stirring at room temperature for 30 minutes, and then toluene (179 mL) and 4-dimethylamino pyridine (1.23 g, 10.1 mmol) were added. After stirring at room temperature for 18 hours, the reaction solution was diluted with ethyl acetate (100 ml) and washed with 1 mol/L hydrochloric acid (150 mL), water (150 mL), a saturated sodium bicarbonate solution (150 mL), water (150 mL), and brine (150 mL). The organic layer was dried over anhydrous sodium sulfate and filtered, and then the filtrate was concentrated under reduced pressure. The resulting residue was purified by silica gel column chromatography (hexane:ethyl acetate=100:0→90:10→80:20→66:34→50:50→34:66→25:75) to give 2.06 g of the title compound.

$^1$H-NMR (400 MHz, CDCl$_3$) δ: 7.37-7.27 (5H, m), 5.43 (1H, q, J=7.19 Hz), 4.76-4.72 (2H, m), 3.34-3.20 (3H, m), 2.90 (1H, dd, J=10.42, 7.97 Hz), 2.56 (1H, d, J=16.91 Hz), 1.52 (3H, d, J=7.35 Hz), 1.24 (9H, s).

MS (ESI); m/z: 360 (M+H)$^+$.

Reference Example 161

{(1S,6S)-3-Acetoxy-4-oxa-7-oxo-8-[(1R)-1-phenylethyl]-8-azabicyclo[4.3.0]nonan-1-yl}carboxylic acid tert-butyl ester

[Formula 265]

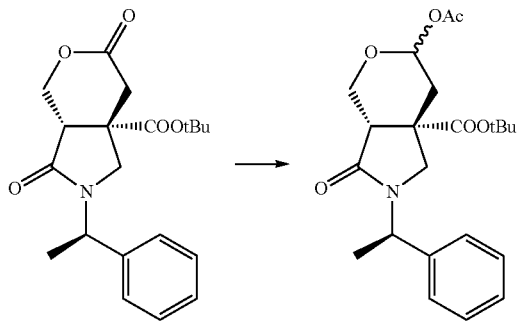

A 0.97 mol/L solution of diisobutylaluminum hydride in hexane (1.65 mL, 1.60 mmol) was added to a solution of {(1S,6S)-4-oxa-3,7-dioxo-8-[(1R)-1-phenylethyl]-8-azabicyclo[4.3.0]nonan-1-yl}carboxylic acid tert-butyl ester (500 mg, 1.39 mmol) in dichloromethane (6.95 mL) with stirring under cooling with dry ice-methanol. After stirring under cooling for one hour, a 0.97 mol/L solution of diisobutylaluminum hydride in hexane (0.716 mL, 0.695 mmol) was added. After stirring under cooling for two hours, a solution of pyridine (0.338 mL, 4.18 mmol) and 4-dimethylaminopyridine (204 mg, 1.67 mmol) in dichloromethane (3.5 mL) and a solution of acetic anhydride (0.526 mL, 5.56 mmol) in dichloromethane (1.8 mL) were added. The mixture was stirred under cooling for one hour and then ice-cooled, and a saturated tetraammonium chloride solution (20 mL) was added.

After stirring under ice-cooling for 30 minutes, the reaction solution was extracted with ethyl acetate (50 mL×1, 40 mL×1). The organic layer was washed with 10% citric acid (60 mL), water (60 mL), a saturated sodium bicarbonate solution (60 mL), and brine (60 mL). The organic layer was dried over anhydrous sodium sulfate and filtered, and then the filtrate was concentrated under reduced pressure. The resulting residue was purified by silica gel column chromatography (hexane:ethyl acetate=100:0→90:10→66:34→60:40→50:50) to give 350 mg of the title compound as a white solid.

$^1$H-NMR (400 MHz, CDCl$_3$) δ: 7.35-7.23 (5H, m), 5.74 (1H, dd, J=7.35, 4.17 Hz), 5.45 (1H, dd, J=20.84, 10.42 Hz), 4.29-4.14 (2H, m), 2.70-2.60 (2H, m), 2.09 (3H, s), 1.67 (1H, dd, J=12.62, 7.23 Hz), 1.48 (3H, d, J=7.11 Hz), 1.23 (9H, s).

MS (ESI); m/z: 404 (M+H)$^+$.

Reference Example 162

(1S,5S)-3-Aza-4,10-dioxo-3-[(1R)-1-phenylethyl]-7,9-dioxatricyclo[6.2.1.0$^{1,5}$]undecane

[Formula 266]

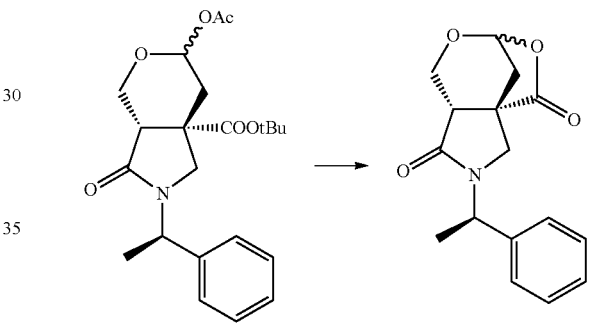

A solution of {(1S,6S)-3-acetoxy-7-oxa-8-[(1R)-1-phenylethyl]-8-azabicyclo[4.3.0]nonan-1-yl}carboxylic acid tert-butyl ester (663 mg, 1.64 mmol) in acetonitrile (8.20 mL) was cooled with ice-acetone. Triethylsilane (0.787 ml, 4.93 mmol) and trimethylsilyl triflate (0.595 mL, 3.29 mmol) were added in a nitrogen atmosphere, and the mixture was stirred under cooling for 15 minutes. A saturated sodium bicarbonate solution (50 mL) was added to the reaction solution, followed by extraction with ethyl acetate (100 mL×1, 60 mL×1). The organic layer was washed with water (50 mL) and brine (100 mL). The organic layer was dried over anhydrous sodium sulfate and filtered, and then the filtrate was concentrated under reduced pressure. The resulting residue was purified by silica gel column chromatography (hexane:ethyl acetate=100:0→90:10→80:20→75:25→66:34→50:50→34:66) to give 413 mg of the title compound as a transparent oil.

$^1$H-NMR (400 MHz, CDCl$_3$) δ: 7.34-7.17 (5H, m), 5.45 (1H, q, J=7.03 Hz), 4.25 (1H, dd, J=11.28, 4.17 Hz), 4.18-4.10 (1H, m), 3.97-3.92 (2H, m), 3.31-3.25 (2H, m), 2.61 (1H, dd, J=10.66, 4.29 Hz), 2.19 (1H, d, J=13.24 Hz), 1.80 (1H, td, J=12.62, 4.66 Hz), 1.48 (3H, d, J=7.11 Hz).

Reference Example 163

{(1S,6S)-4-Oxa-7-oxo-8-[(1R)-1-phenylethyl]-8-azabicyclo[4.3.0]nonan-1-yl}carboxylic acid

[Formula 267]

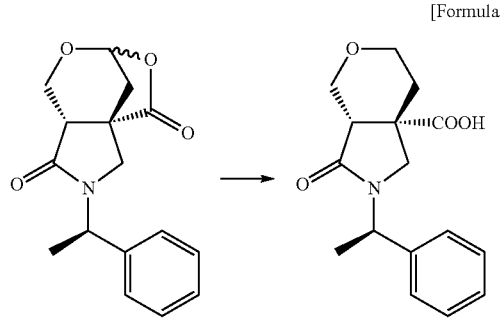

A solution of (1S,5S)-3-aza-4,10-dioxo-3-[(1R)-1-phenylethyl]-7,9-dioxatricyclo[6.2.1.0$^{1,5}$]undecane (413 mg, 1.44 mmol) in dichloromethane (7.20 mL) was cooled with dry ice-methanol. Triethylsilane (0.690 mL, 4.32 mmol) and a 1.0 mol/L solution of tetrachlorotitanium in dichloromethane (2.88 mL, 2.88 mmol) were added in a nitrogen atmosphere, and the mixture was stirred under cooling for 30 minutes. A saturated sodium bicarbonate solution (50 mL) was added to the reaction solution, and the mixture was washed with ethyl acetate (100 mL×2). The aqueous layer was made acidic with 6 mol/L hydrochloric acid and 1 mol/L hydrochloric acid, followed by extraction with chloroform (100 mL×1, 60 mL×1). The organic layer was washed with water (100 mL) and brine (150 mL), and then dried over anhydrous sodium sulfate and filtered. The filtrate was then concentrated under reduced pressure and dried under reduced pressure to give 235 mg of the title compound as white crystals.

$^1$H-NMR (400 MHz, CDCl$_3$) δ: 7.33-7.23 (5H, m), 5.46 (1H, d, J=7.35 Hz), 4.26 (1H, dd, J=11.03, 4.41 Hz), 3.97-3.91 (2H, m), 3.33-3.24 (3H, m), 2.60 (1H, dd, J=10.66, 4.29 Hz), 2.19 (1H, d, J=12.50 Hz), 1.85-1.67 (2H, m), 1.49 (3H, d, J=7.11 Hz).

MS (ESI); m/z: 290 (M+H)$^+$.

Reference Example 164

(1S,6S)-1-tert-Butoxycarbonylamino-4-oxa-7-oxo-8-[(1R)-1-phenylethyl]-8-azabicyclo[4.3.0]nonane Triethylamine (0.330 mL, 2.36 mmol) and diphenylphosphoryl azide (0.330 mL, 1.53 mmol) were added to a solution of [(1S,6S)-4-oxa-7-oxo-8-[(1R)-1-phenylethyl]-8-azabicyclo[4.3.0]nonan-1-yl]carboxylic acid (340 mg, 1.18 mmol) in toluene (5.90 mL) in a nitrogen atmosphere with stirring under ice-cooling. The mixture was stirred at room temperature for 30 minutes and then at 100° C. for one hour. The reaction solution was concentrated under reduced pressure, and triethylamine was azeotropically distilled with toluene (×3). 1,4-Dioxane (2.95 mL) and 6 mol/L hydrochloric acid (2.95 mL) were added to the resulting residue, and the mixture was stirred at 50° C. for one hour. The reaction solution was diluted with water (9.0 mL) and washed with diethyl ether (40 mL×2). The aqueous layer was made alkaline with a 1 mol/L sodium hydroxide solution under ice-cooling, followed by extraction with chloroform (80 mL×1, 60 mL×1). The organic layer was washed with water (80 mL) and brine (80 mL) and dried over anhydrous sodium sulfate. After filtration, the filtrate was concentrated under reduced pressure. Dichloromethane (5.90 mL) was added to the resulting residue, and di-tert-butyl dicarbonate (773 mg, 3.54 mmol) was added in a nitrogen atmosphere. The mixture was stirred at room temperature for 14 hours and at 50° C. for seven hours, di-tert-butyl dicarbonate (515 mg, 2.36 mmol) was added. After stirring at 50° C. for 17 hours, the reaction solution was concentrated under reduced pressure. The resulting residue was purified by silica gel column chromatography (hexane: ethyl acetate=100:0→90:10→80:20→66:34→60:40) to give 320 mg of the title compound.

$^1$H-NMR (400 MHz, CDCl$_3$) δ: 7.34-7.23 (5H, m), 5.44 (1H, q, J=6.95 Hz), 4.53 (1H, brs), 4.16-4.11 (1H, m), 3.81 (1H, dd, J=12.13, 3.80 Hz), 3.62 (3H, tt, J=14.83, 6.37 Hz), 3.15 (1H, d, J=10.30 Hz), 2.69 (1H, dd, J=11.52, 4.41 Hz), 1.71 (1H, td, J=12.68, 4.98 Hz), 1.49 (3H, d, J=7.11 Hz), 1.26 (9H, s).

MS (ESI); m/z: 361 (M+H)$^+$.

Reference Example 165

(1S,6S)-1-tert-Butoxycarbonylamino-4-oxa-8-[(1R)-1-phenylethyl]-8-azabicyclo[4.3.0]nonane

[Formula 268]

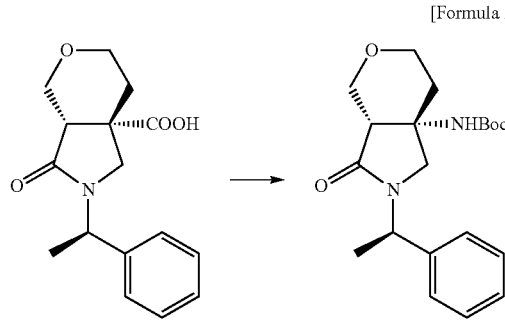

[Formula 269]

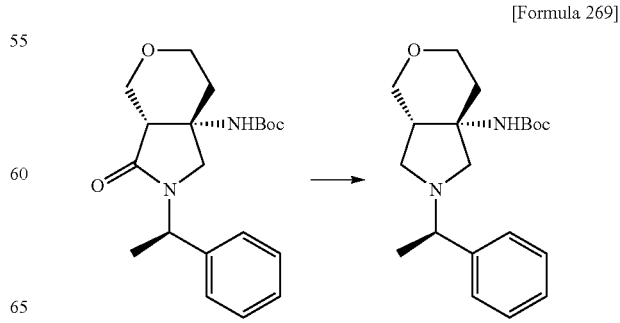

A solution of (1S,6S)-1-tert-butoxycarbonylamino-4-oxa-7-oxo-8-[(1R)-1-phenylethyl]-8-azabicyclo[4.3.0]nonane (331 mg, 0.918 mmol) in tetrahydrofuran (3.0 mL) was cooled with ice-acetone. A 1.2 mol/L solution of borane in tetrahydrofuran (3.83 mL, 4.59 mmol) was added in a nitrogen atmosphere, and the mixture was stirred at room temperature for 19 hours. After cooling with ice-acetone again, a 1.2 mol/L solution of borane in tetrahydrofuran (3.83 mL, 4.59 mmol) was added in a nitrogen atmosphere, and the mixture was stirred at room temperature for one hour. The reaction solution was concentrated under reduced pressure. Then, a mixed solution of ethanol:water=4:1 (10 mL) and triethylamine (1 mL) were added, and the mixture was heated to reflux for 1.5 hours. The reaction solution was concentrated under reduced pressure and a saturated sodium bicarbonate solution (50 mL) was added to the residue, followed by extraction with chloroform (50 mL×1, 40 mL×1). The organic layer was washed with brine and dried over anhydrous sodium sulfate. After filtration, the filtrate was concentrated under reduced pressure. The resulting residue was purified by silica gel column chromatography (hexane:ethyl acetate=100:0→→90:10→60:40→50:50→34:66→25:75→16:84→10:90→5:95→2:98→0:100) to give 255 mg of the title compound.

¹H-NMR (400 MHz, CDCl₃) δ: 7.31-7.21 (5H, m), 4.35 (1H, s), 3.81 (2H, ddd, J=22.43, 11.64, 4.04 Hz), 3.62 (2H, td, J=11.95, 2.37 Hz), 3.49 (1H, t, J=11.52 Hz), 3.37 (1H, d, J=10.05 Hz), 2.91 (1H, t, J=8.33 Hz), 2.55-2.42 (2H, m), 2.17 (1H, t, J=5.88 Hz), 1.56-1.50 (1H, m), 1.47 (9H, s), 1.32 (3H, d, J=6.37 Hz).

MS (ESI); m/z: 347 (M+H)⁺.

Reference Example 166

(1S,6S)-1-tert-Butoxycarbonylamino-4-oxa-8-bicyclo[4.3.0]nonane

[Formula 270]

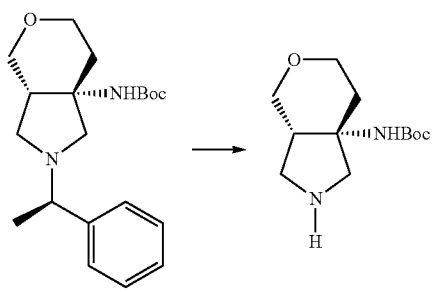

A 20% palladium hydroxide-carbon catalyst (262 mg) was added to a solution of (1S,6S)-1-tert-butoxycarbonylamino-4-oxa-8-[(1R)-1-phenylethyl]-8-azabicyclo[4.3.0]nonane (262 mg, 0.756 mmol) in ethanol (7.56 mL) in a nitrogen atmosphere. After the atmosphere was replaced with hydrogen, the mixture was stirred in a hydrogen atmosphere at 45° C. for 2.5 hours. After the atmosphere was replaced with nitrogen, the reaction solution was filtered through Celite, concentrated under reduced pressure, and dried under reduced pressure to give 183 mg of the title compound.

¹H-NMR (400 MHz, CDCl₃) δ: 4.33 (1H, brs), 3.95 (1H, dd, J=11.64, 4.29 Hz), 3.84 (1H, dd, J=12.50, 4.66 Hz), 3.72 (1H, q, J=7.03 Hz), 3.62-3.55 (2H, m), 3.49 (1H, t, J=11.64 Hz), 3.06 (1H, dd, J=9.93, 7.97 Hz), 2.68-2.57 (3H, m), 2.13-2.04 (1H, m), 1.57 (1H, td, J=12.93, 4.74 Hz), 1.45 (9H, s).

MS (ESI); m/z: 243 (M+H)⁺.

Example 37

7-[(1S,6S)-1-Amino-4-oxa-8-azabicyclo[4.3.0]nonan-8-yl]-6-fluoro-1-[(1R,2S)-2-fluorocyclopropyl]-1,4-dihydro-8-methoxy-4-oxoquinoline-3-carboxylic acid

[Formula 271]

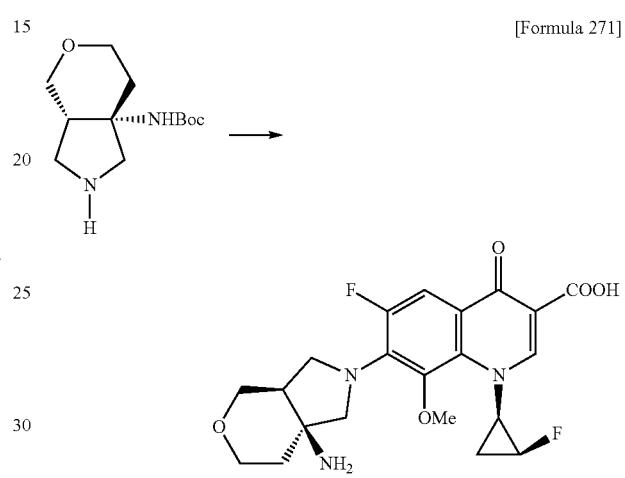

Triethylamine (0.165 mL, 1.18 mmol) and 6,7-difluoro-1-[(1R,2S)-2-fluorocyclopropyl]-1,4-dihydro-8-methoxy-4-oxoquinoline-3-carboxylic acid-BF₂ chelate (142 mg, 0.393 mmol) were added to a solution of (1S,6S)-1-tert-butoxycarbonylamino-4-oxa-8-bicyclo[4.3.0]nonane (142 mg, 0.421 mmol) in dimethyl sulfoxide (0.787 mL), and the mixture was stirred at room temperature for 14 hours. A mixed solution of ethanol:water=4:1 (10 mL) and triethylamine (1 mL) were added to the reaction solution, and the mixture was heated to reflux for one hour. The reaction solution was concentrated under reduced pressure. The residue was dissolved in ethyl acetate (30 mL) and washed with a 10% citric acid solution (30 mL), water (30 mL), and brine (30 mL). The organic layer was dried over anhydrous sodium sulfate and filtered, and then the filtrate was concentrated under reduced pressure. The resulting residue was purified by silica gel column chromatography (chloroform:methanol=100:0→99:1→98:2). Trifluoroacetic acid (0.975 mL, 3 v/w) was added to a solution of 174 mg of the resulting residue in dichloromethane (3.25 mL) with stirring under ice-cooling, and the mixture was stirred at room temperature for two hours. The reaction solution was concentrated under reduced pressure, and trifluoroacetic acid was azeotropically distilled with toluene (×3). 1N hydrochloric acid (25.0 mL) was added to the resulting residue under ice-cooling, and the mixture was washed with diethyl ether (50 mL×5). The aqueous layer was adjusted to pH 12 with a 1 mol/L sodium hydroxide solution under ice-cooling. The basic solution was adjusted to pH 7.4 with 1 mol/L hydrochloric acid, followed by extraction with chloroform (100 mL×2, 50 mL×2). The organic layer was dried over anhydrous sodium sulfate and filtered, and then the filtrate was concentrated under reduced pressure. The residue was dissolved in chloroform/methanol=10/1, and the insoluble material was removed by filtration. The filtrate was concentrated under reduced pressure and dissolved in hot ethanol. The solvent was gradually evaporated while heating with stirring. Then, the solution was concentrated until ethanol was about 10 ml, and stirred at room temperature for three hours. The precipitated crystals were collected by filtration and then washed with ethanol and diethyl ether. The crystals were dried under reduced pressure at 50° C. overnight to give 55.3 mg of the title compound.

$^1$H-NMR (400 MHz, 0.1N NaOD) δ: 8.36 (1H, d, J=3.68 Hz), 7.67 (1H, d, J=14.46 Hz), 5.15-4.96 (1H, m), 4.00 (3H, ddd, J=20.71, 11.03, 4.53 Hz), 3.84-3.63 (4H, m), 3.58 (3H, s), 3.53 (1H, t, J=8.58 Hz), 3.39 (1H, d, J=9.31 Hz), 2.32-2.20 (1H, m), 1.99-1.85 (2H, m), 1.58-1.43 (1H, m), 1.43-1.27 (1H, m).

Anal; Calcd for $C_{21}H_{23}F_2N_3O_5 \cdot 0.25H_2O$: C, 57.33; H, 5.38; N, 9.55. Found: C, 57.55; H, 5.40; N, 9.47.

MS (ESI); m/z: 436 (M+H)$^+$.

IR (ATR) ν: 3052, 2927, 2869, 1727, 1614, 1594, 1508, 1446, 1428, 1363, 1322, 1110, 1078, 1043, 989, 948, 910, 809 cm$^{-1}$.

Example 38

7-[(1S,6S)-1-amino-4-oxa-8-azabicyclo[4.3.0]nonan-8-yl]-8-cyano-6-fluoro-1-[(1R,2S)-2-fluorocyclopropyl]-1,4-dihydro-4-oxoquinoline-3-carboxylic acid

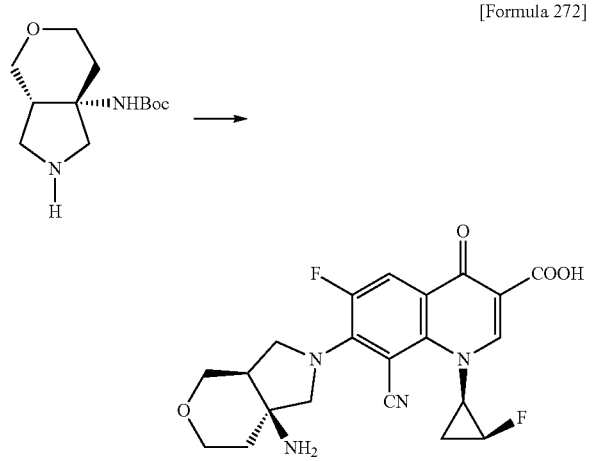

[Formula 272]

Triethylamine (0.263 mL, 1.88 mmol) and ethyl 8-cyano-6,7-difluoro-1-[(1R,2S)-2-fluorocyclopropan-1-yl]-1,4-dihydro-4-oxoquinoline-3-carboxylate (211 mg, 0.627 mmol) were added to a solution of (1S,6S)-1-tert-butoxycarbonylamino-4-oxa-8-azabicyclo[4.3.0]nonane (151 mg, 0.628 mmol) in acetonitrile (1.25 mL) in a nitrogen atmosphere. The mixture was stirred at room temperature for 18 hours. The reaction solution was concentrated under reduced pressure. Then, the resulting residue was purified by silica gel column chromatography (hexane:ethyl acetate=100:0→90:10→60:40→50:50→34:66→25:75→16:84). A 1 mol/L sodium hydroxide solution (1.94 mL) was added to a solution of the resulting residue in ethanol (2.42 mL) under ice-cooling, and the mixture was stirred at room temperature for one hour. A 10% citric acid solution (30 mL) was added to the reaction solution, followed by extraction with ethyl acetate (40 mL×1, 30 mL×1). The organic layer was washed with brine (45 mL) and then dried over anhydrous sodium sulfate and filtered. The filtrate was then concentrated under reduced pressure. The resulting residue was purified by silica gel column chromatography (chloroform:methanol=100:0→99:1→98:2). Trifluoroacetic acid (1.38 ml, 3 v/w) was added to a solution of 243 mg of the resulting residue in dichloromethane (4.58 mL) with stirring under ice-cooling, and the mixture was stirred at room temperature for 2.5 hours. The reaction solution was concentrated under reduced pressure. Then, hydrochloric acid at pH 1 was added to the resulting residue under ice-cooling, and the mixture was washed with chloroform (40 mL×3). The aqueous layer was adjusted to pH 12 with a 1 mol/L sodium hydroxide solution under ice-cooling. The basic solution was adjusted to pH 7.4 with 1 mol/L hydrochloric acid, followed by extraction with chloroform (100 mL×1, 70 mL×1, 50 mL×1). The organic layer was dried over anhydrous sodium sulfate and filtered, and then the filtrate was concentrated under reduced pressure. The aqueous layer was concentrated under reduced pressure. The resulting residue was dissolved in chloroform/methanol=10/1, and the insoluble material was removed by filtration (×2). The residues obtained from the organic layer and the aqueous layer were purified by PTLC (lower layer of chloroform/methanol/water=7/3/1), respectively. These were combined and dissolved in dichloromethane (20 mL), and dichloromethane was azeotropically removed with ethanol (three times). Ethanol (5 mL) was added to the resulting residue, and the mixture was ultrasonically treated and then cooled. The precipitated solid was collected by filtration, washed with ethanol and diethyl ether, and dried under reduced pressure at 60° C. to give 122 mg of the title compound.

$^1$H-NMR (400 MHz, 0.1N NaOD) δ: 8.30 (1H, d, J=3.92 Hz), 7.90 (1H, d, J=15.44 Hz), 5.19 (1H, dd, J=63.24, 3.43 Hz), 4.06-3.97 (5H, m), 3.81-3.74 (3H, m), 3.58 (1H, d, J=10.30 Hz), 2.33-2.31 (1H, m), 2.03-1.73 (3H, m), 1.61-1.49 (1H, m).

Anal; Calcd for $C_{21}H_{20}F_2N_4O_4 \cdot 0.25H_2O$: C, 58.00; H, 4.75; F, 8.74; N, 12.88. Found: C, 58.07; H, 4.60; F, 8.70; N, 12.74.

MS (ESI); m/z: 431 (M+H)$^+$.

IR (ATR) ν: 3081, 2960, 2873, 2211, 1725, 1629, 1446, 1400, 1307, 1261, 927, 912, 804 cm$^{-1}$.

Example 39

7-[(1S,6S)-1-Amino-4-oxa-8-azabicyclo[4.3.0]nonan-8-yl]-1-[(1R,2S)-2-fluorocyclopropyl]-1,4-dihydro-8-methyl-4-oxoquinoline-3-carboxylic acid

[Formula 273]

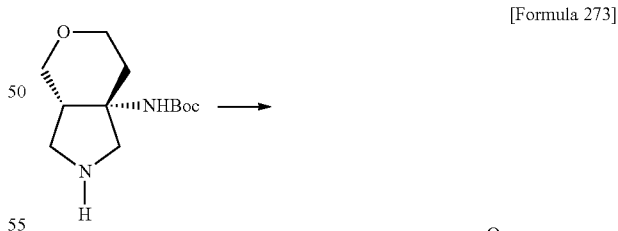

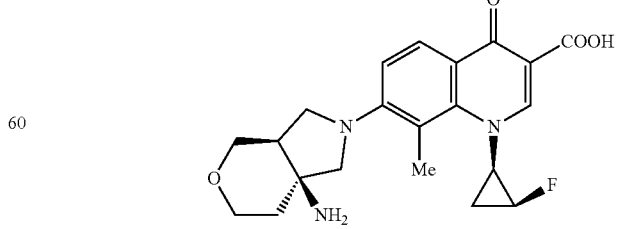

Triethylamine (0.0737 ml, 0.528 mmol) and 7-fluoro-1-[(1R,2S)-2-fluorocyclopropyl]-1,4-dihydro-8-methyl-4- oxoquinoline-3-carboxylic acid (49.0 mg, 0.175 mmol) were added to a (1S,6S)-1-tert-butoxycarbonylamino-4-oxa-8-azabicyclo[4.3.0]nonane (42.2 mg, 0.176 mmol) in dimethyl sulfoxide (0.352 mL) in a nitrogen atmosphere, and the mixture was stirred at 75° C. for two days. Dimethyl sulfoxide (0.352 mL) and triethylamine (0.147 mL, 1.06 mmol) were added to the reaction solution, and the mixture was stirred at 75° C. for four days. Dimethyl sulfoxide (0.352 mL) and triethylamine (0.147 ml, 1.06 mmol) were added to the reaction solution, and the mixture was stirred at 75° C. for two days. 7-Fluoro-1-[(1R,2S)-2-fluorocyclopropyl]-1,4-dihydro-8-methyl-4-oxoquinoline-3-carboxylic acid (24.6 mg, 0.0881 mmol) and triethylamine (0.147 mL, 1.06 mmol) were added to the reaction solution, and the mixture was stirred for five days. The reaction solution was diluted with ethyl acetate (30 mL) and then washed with a 10% citric acid solution (25 mL), water (25 mL), and a saturated sodium hydroxide solution (25 mL). Further, the organic layer was extracted again from the washing 10% citric acid solution and the washing water with ethyl acetate (40 mL). The organic layers were combined, dried over anhydrous sodium sulfate, and filtered, and then the filtrate was concentrated under reduced pressure. The resulting residue was purified by silica gel column chromatography (chloroform:methanol=100:0→99:1→98:2). Trifluoroacetic acid (0.402 mL, 3 v/w) was added to a solution of 67.5 mg of the resulting residue in dichloromethane (1.32 mL) with stirring under ice-cooling, and the mixture was stirred at room temperature for one hour. The reaction solution was concentrated under reduced pressure, and trifluoroacetic acid was azeotropically distilled with toluene (×3). 6 mol/L hydrochloric acid was added to the resulting residue under ice-cooling, and the mixture was washed with chloroform (30 mL×5). The aqueous layer was adjusted to pH 12 with a 1 mol/L sodium hydroxide solution under ice-cooling. The basic solution was adjusted to pH 7.4 with 1 mol/L hydrochloric acid, followed by extraction with chloroform (100 mL×2) and chloroform/methanol=10/1 (50 mL). The organic layer was dried over anhydrous sodium sulfate and filtered, and then the filtrate was concentrated under reduced pressure. The residue was purified by PTLC (lower layer of chloroform/methanol/water=7/3/1) and concentrated under reduced pressure. The resulting residue was dissolved in hot ethanol, and the insoluble material was removed by filtration. The filtrate was concentrated under reduced pressure, dissolved in hot ethanol (1 mL), ultrasonically treated, and cooled with ice water. Then, the slurry was washed with diethyl ether (10 mL). After stirring at room temperature overnight, the precipitated crystals were collected by filtration, washed with ethanol and diethyl ether, and then dried under reduced pressure at 60° C. to give 12.4 mg of the title compound.

$^1$H-NMR (400 MHz, 0.1N NaOD) δ: 8.41 (1H, d, J=3.68 Hz), 8.00 (1H, d, J=8.58 Hz), 7.09 (1H, d, J=8.82 Hz), 5.16-4.96 (1H, m), 4.10-3.95 (3H, m), 3.83-3.77 (2H, m), 3.66 (1H, d, J=9.80 Hz), 3.59 (1H, t, J=10.91 Hz), 3.26 (2H, dd, J=15.32, 8.70 Hz), 2.45 (3H, s), 2.33-2.23 (1H, m), 2.02-1.87 (3H, m), 1.68-1.57 (1H, m), 1.33-1.21 (1H, m).

Anal; Calcd for $C_{21}H_{24}FN_3O_4 \cdot 1.5H_2O$: C, 58.87; H, 6.35; N, 9.81.
Found: C, 58.97; H, 5.98; N, 9.40.

MS (ESI); m/z: 402 (M+H)$^+$.
IR (ATR) ν: 2937, 2865, 1710, 1608, 1508, 1428, 1388, 1349, 1315, 1257, 794 cm$^{-1}$.

Reference Example 167

(3S)-3-Ethoxycarbonylmethoxymethyl-5-oxo-1-[(1R)-1-phenylethyl]pyrrolidine-3-carboxylic acid tert-butyl ester

[Formula 274]

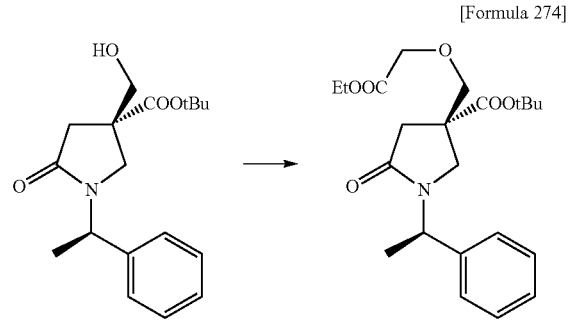

(3S)-3-Hydroxymethyl-5-oxo-1-[(1R)-1-phenylethyl]pyrrolidine-3-carboxylic acid tert-butyl ester (2.0 g, 6.26 mmol) and bromoethyl acetate (2.09 g, 12.52 mmol) were dissolved in tetrahydrofuran (40 mL). Sodium hydride (0.33 g, 7.51 mmol) was added at 0° C., and the mixture was stirred at room temperature for 18 hours. A saturated ammonium chloride solution (100 mL) was added to the reaction solution at 0° C., followed by extraction with ethyl acetate (300 mL). The organic layer was washed with water (100 mL) and brine (100 mL) and dried over anhydrous sodium sulfate. After filtration, the solvent was evaporated under reduced pressure. The resulting residue was purified by silica gel column chromatography (40% ethyl acetate/hexane) to give 1.74 g of the title compound as a colorless oil.

$^1$H-NMR (400 MHz, CDCl$_3$) δ: 7.30 (5H, m), 5.49 (1H, q, J=6.99 Hz), 4.21 (2H, q, J=7.15 Hz), 4.08 (2H, s), 3.68 (2H, brs), 3.46 (1H, d, J=10.24 Hz), 3.31 (1H, d, J=10.24 Hz), 2.80 (1H, d, J=17.07 Hz), 2.56 (1H, d, J=17.07 Hz), 1.53 (3H, d, J=7.32 Hz), 1.35 (9H, s), 1.28 (3H, t, J=7.19 Hz).
MS (EI) m/z: 406 (M+H)$^+$.

Reference Example 168

{(1S)-3-Oxa-7-oxo-8-[(1R)-1-phenylethyl]-8-azabicyclo[4,3,0]non-5-en-1-yl}carboxylic acid tert-butyl ester

[Formula 275]

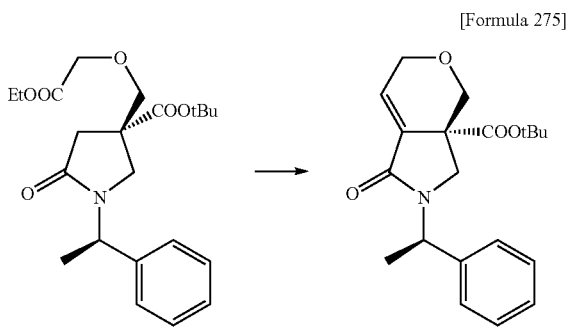

(3S)-3-Ethoxycarbonylmethoxymethyl-5-oxo-1-[(1R)-1-phenylethyl]pyrrolidine-3-carboxylic acid tert-butyl ester (9.31 g, 25.9 mmol) was dissolved in tetrahydrofuran (200 mL). A 1 M solution of lithium hexamethyldisilazide in tetrahydrofuran (64.7 mL) was added dropwise in a nitrogen atmosphere at 0° C., and the mixture was stirred for 1.5 hours. A saturated ammonium chloride solution (300 mL) was added, followed by extraction with ethyl acetate (900 mL). The organic layer was washed with water (300 mL) and brine (100 mL) and dried over anhydrous sodium sulfate. After filtration, the solvent was evaporated under reduced pressure, and the resulting residue was dissolved in tetrahydrofuran (200 mL). Sodium borohydride (1.27 g, 33.67 mmol) was added at 0° C., and the mixture was stirred for one hour. A saturated ammonium chloride solution (200 mL) was added to the reaction solution, followed by extraction with ethyl acetate (600 mL). The organic layer was washed with water (200 mL) and brine (200 mL) and dried over anhydrous sodium sulfate. After filtration, the solvent was evaporated under reduced pressure, and the resulting residue was subjected to short silica gel column chromatography (40% ethyl acetate/hexane). The concentrate was dissolved in dichloromethane (150 mL). Triethylamine (5.69 mL, 41.02 mmol) was added, and methanesulfonyl chloride (1.90 mL, 24.61 mmol) was added dropwise at −10° C. After stirring for one hour, a saturated ammonium chloride solution (200 mL) was added to the reaction solution, followed by extraction with ethyl acetate (600 mL). The organic layer was washed with water (200 mL) and brine (200 mL) and dried over anhydrous sodium sulfate. After filtration, the solvent was evaporated under reduced pressure, and the resulting residue was dissolved in toluene (150 mL). DBU (12.24 mL, 82.03 mmol) was added, and the mixture was stirred at 40° C. for 15 hours. The reaction solution was concentrated under reduced pressure and then a saturated ammonium chloride solution (150 mL) was added, followed by extraction with ethyl acetate (400 mL). The organic layer was washed with water (150 mL) and brine (150 mL) and dried over anhydrous sodium sulfate. After filtration, the solvent was evaporated under reduced pressure. The resulting residue was purified by silica gel column chromatography (75% ethyl acetate/hexane) to give 3.28 g of the title compound as a colorless solid.

$^1$H-NMR (400 MHz, CDCl$_3$) δ: 7.32-7.29 (5H, m), 6.60 (1H, t, J=2.32 Hz), 5.57 (1H, q, J=7.16 Hz), 4.50-4.45 (2H, m), 4.24 (1H, dd, J=18.55, 2.44 Hz), 3.26 (1H, d, J=10.25 Hz), 3.21 (1H, d, J=10.01 Hz), 3.13 (1H, d, J=10.01 Hz), 1.51 (3H, d, J=7.08 Hz), 1.27 (9H, s).

MS (EI) m/z: 344 (M+H)$^+$.

Reference Example 169

{(1S,6S)-3-Oxa-7-oxo-8-[(1R)-1-phenylethyl]-8-azabicyclo[4,3,0]nonan-1-yl}carboxylic acid tert-butyl ester {(1S,6R)-3-Oxa-7-oxo-8-[(1R)-1-phenylethyl]-8-azabicyclo[4,3,0]nonan-1-yl}carboxylic acid tert-butyl ester

[Formula 276]

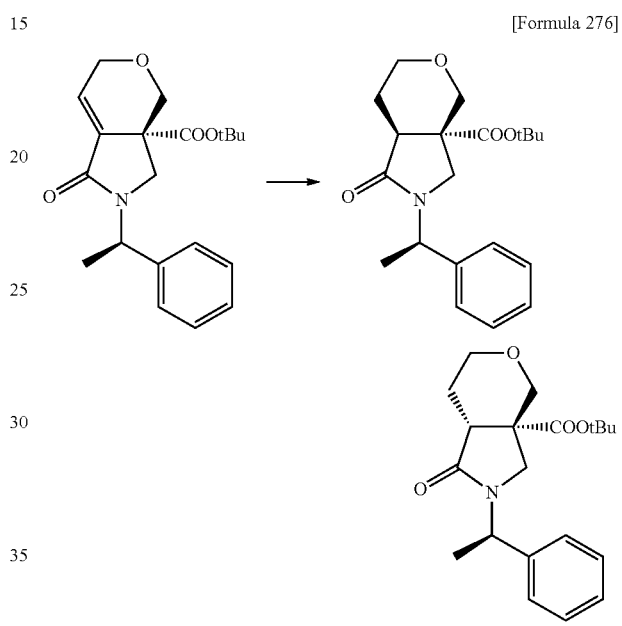

{(1S)-3-Oxa-7-oxo-8-[(1R)-1-phenylethyl]-8-azabicyclo[4,3,0]non-5-en-1-yl}carboxylic acid tert-butyl ester (231 mg, 0.67 mmol) was dissolved in tetrahydrofuran. 10% palladium-carbon (50% wet) (100 mg) was added, and the mixture was stirred in a hydrogen atmosphere for four hours. The catalyst was removed by filtration, the filtrate was concentrated under reduced pressure. The resulting residue was purified by silica gel column chromatography (20% ethyl acetate/hexane→50%) to give 187 mg of the title compound (1S,6S)-isomer as a colorless solid and 44 mg of the title compound (1S,6R)-isomer as a colorless solid.

(1S,6S)-Isomer:

$^1$H-NMR (400 MHz, CDCl$_3$) δ: 7.29-7.24 (5H, m), 5.48 (1H, q, J=7.24 Hz), 4.41 (1H, d, J=10.24 Hz), 4.10 (1H, dd, J=10.98, 4.39 Hz), 3.38-3.33 (2H, m), 3.17 (1H, d, J=9.76 Hz), 3.08 (1H, d, J=10.00 Hz), 2.28-2.19 (2H, m), 1.96-1.92 (1H, m), 1.46 (3H, d, J=7.32 Hz), 1.23 (9H, s).

MS (EI) m/z: 346 (M+H)$^+$.

(1S,6R)-Isomer:

$^1$H-NMR (400 MHz, CDCl$_3$) δ: 7.36-7.26 (5H, m), 5.54 (1H, q, J=7.07 Hz), 4.12 (1H, d, J=11.71 Hz), 3.82-3.77 (1H, m), 3.39 (1H, m), 3.29 (1H, d, J=11.71 Hz), 3.02 (1H, t, J=4.63 Hz), 2.91 (2H, dd, J=18.29, 10.24 Hz), 2.03-2.01 (2H, m), 1.53 (3H, d, J=7.07 Hz), 1.41 (9H, s).

MS (EI) m/z: 346 (M+H)$^+$.

Reference Example 170

[(1S,6S)-3-Oxa-8-benzyloxycarbonyl-8-azabicyclo[4,3,0]nonan-1-yl]carboxylic acid tert-butyl ester

[Formula 277]

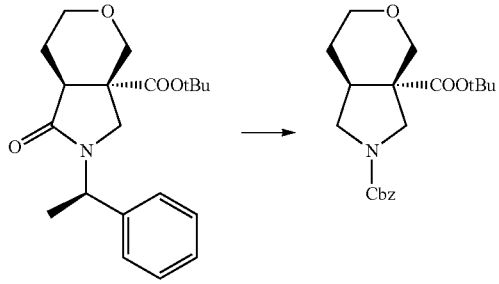

[(1S,6S)-3-Oxa-7-oxo-8-[(1R)-1-phenylethyl]-8-azabicyclo[4,3,0]nonan-1-yl]carboxylic acid tert-butyl ester (3.36 g, 9.73 mmol) was dissolved in tetrahydrofuran (50 mL), and a 1 M solution of a borane-tetrahydrofuran complex in tetrahydrofuran (48.63 mL) was added dropwise in a nitrogen atmosphere. After stirring for three days, 90% aqueous ethanol (30 mL) and triethylamine (3 mL) were added to the reaction solution, and the mixture was stirred at 80° C. for two hours. The reaction solution was concentrated under reduced pressure and then a saturated ammonium chloride solution (100 mL) was added, followed by extraction with ethyl acetate (300 mL). The organic layer was washed with water (100 mL) and brine (100 mL) and dried over anhydrous sodium sulfate. After filtration, the solvent was evaporated under reduced pressure, and the residue was subjected to short silica gel column chromatography (35% ethyl acetate/hexane). The resulting crude was dissolved in 1,2-dichloroethane (18 mL). Benzyloxycarbonyl chloride (3.40 g, 19.91 mmol) was added, and the mixture was stirred at 40° C. for one day. The reaction solution was concentrated under reduced pressure, and the residue was purified by silica gel column chromatography (35% ethyl acetate/hexane) to give 2.39 g of the title compound as a colorless oil.

$^1$H-NMR (400 MHz, CDCl$_3$) δ: 7.39-7.24 (5H, m), 5.14 (2H, s), 3.88 (1H, dd, J=20.63, 11.84 Hz), 3.77-3.54 (6H, m), 3.48 (1H, t, J=10.50 Hz), 3.41-3.33 (1H, m), 2.81-2.70 (1H, m), 1.93-1.80 (1H, m), 1.44 (9H, s).

MS (EI) m/z: 384 (M+Na)$^+$.

Reference Example 171

{(1S,6R)-8-Benzyloxycarbonyl-3-oxa-8-azabicyclo[4,3,0]nonan-1-yl}carboxylic acid tert-butyl ester

[Formula 278]

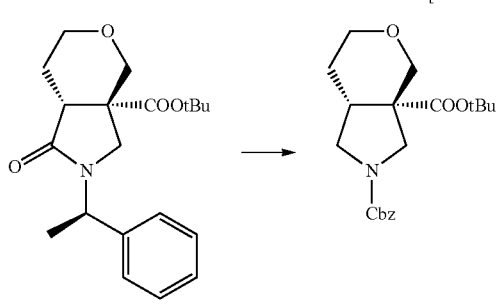

{(1S,6R)-3-Oxa-7-oxo-8-[(1R)-1-phenylethyl]-8-azabicyclo[4,3,0]nonan-1-yl}carboxylic acid tert-butyl ester (709 mg, 2.05 mmol) was dissolved in tetrahydrofuran (20 mL), and a 1 M solution of a borane-tetrahydrofuran complex in tetrahydrofuran (10.26 mL) was added dropwise in a nitrogen atmosphere. After stirring for three days, 90% aqueous ethanol (30 mL) and triethylamine (3 mL) were added to the reaction solution, and the mixture was stirred at 80° C. for two hours. The reaction solution was concentrated under reduced pressure and then a saturated ammonium chloride solution (80 mL) was added, followed by extraction with ethyl acetate (240 mL). The organic layer was washed with water (80 mL) and brine (80 mL) and dried over anhydrous sodium sulfate. After filtration, the solvent was evaporated under reduced pressure, and the resulting residue was subjected to short silica gel column chromatography (35% ethyl acetate/hexane). The resulting fraction was concentrated under reduced pressure, and the residue was dissolved in 1,2-dichloroethane (4 mL). Benzyloxycarbonyl chloride (788 mg, 4.62 mmol) was added, and the mixture was stirred at 40° C. for four days. The reaction solution was concentrated under reduced pressure, and the residue was purified by silica gel column chromatography (40% ethyl acetate/hexane) to give 435 mg of the title compound as a colorless oil.

$^1$H-NMR (400 MHz, CDCl$_3$) δ: 7.33-7.28 (5H, m), 5.13 (2H, d, J=3.42 Hz), 4.48 (1H, dd, J=20.75, 10.50 Hz), 4.10-4.07 (1H, m), 3.77 (1H, dd, J=24.05, 11.11 Hz), 3.62-3.52 (2H, m), 3.38 (1H, td, J=11.66, 2.77 Hz), 3.22 (1H, dd, J=10.50, 6.84 Hz), 3.07 (1H, dd, J=10.99, 3.42 Hz), 2.24-2.21 (1H, m), 1.98-1.96 (1H, m), 1.63-1.60 (1H, m), 1.44 (9H, s).

MS (EI); m/z: 384 (M+Na)$^+$.

Reference Example 172

[(1S,6R)-1-tert-Butoxycarbonylamino-3-oxa-8-azabicyclo[4,3,0]nonan-8-yl]carboxylic acid benzyl ester

[Formula 279]

{(1S,6S)-8-Benzyloxycarbonyl-3-oxa-8-azabicyclo[4,3,0]nonan-1-yl}carboxylic acid tert-butyl ester (2.30 g, 6.94 mmol) was dissolved in dichloromethane (20 mL). Trifluoroacetic acid (10 mL) was added, and the mixture was stirred for one day. The reaction solution was concentrated under reduced pressure, and a 1N sodium hydroxide solution (100 mL) was added, and the mixture was washed with chloroform. The aqueous layer was made acidic with a hydrochloric acid solution, followed by extraction with chloroform (200 mL×2). After drying over anhydrous sodium sulfate and filtration, the solvent was evaporated under reduced pressure, and the resulting residue was dissolved in acetonitrile (40 mL). 1,1-Carbonylbis-1H-imidazole (1.55 g, 9.53 mmol) was added in a nitrogen atmosphere at 0° C., and the mixture was stirred for one hour and then bubbled with ammonia gas at room temperature. Ethyl acetate and water were added, and the mixture was washed with brine. The organic layer was dried over anhydrous sodium sulfate and then filtered. The solvent was evaporated under reduced pressure, and the resulting residue was subjected to short silica gel column chromatography (ethyl acetate). The resulting crude was dissolved in tert-butanol (50 mL). Lead tetraacetate (3.98 g, 8.97 mmol) was added, and the mixture was stirred in a nitrogen atmosphere at 80° C. for one hour. Sodium bicarbonate (3.52 g, 41.86 mmol) and ethyl acetate were added to the reaction solution, and the mixture was filtered through Celite. Then, the filtrate was washed with saturated sodium bicarbonate water and brine and dried over anhydrous sodium sulfate. After filtration, the solvent was evaporated under reduced pressure. The resulting residue was purified by silica gel column chromatography (30% ethyl acetate/hexane) to give 1.70 g of the title compound as a colorless oil.

¹H-NMR (400 MHz, CDCl₃) δ: 7.36-7.31 (5H, m), 5.13 (2H, s), 4.66 (1H, d, J=7.57 Hz), 3.86-3.57 (7H, m), 3.36 (1H, dq, J=23.01, 5.45 Hz), 2.63-2.55 (1H, m), 1.87-1.79 (1H, m), 1.54-1.50 (1H, m), 1.43 (9H, s).
MS (EI) m/z: 399 (M+Na)⁺.

Reference Example 173

{(1S,6S)-1-tert-Butoxycarbonylamino-3-oxa-8-bicyclo[4,3,0]nonan-8-yl}carboxylic acid benzyl ester

[Formula 280]

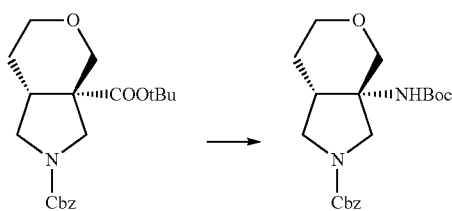

{(1S,6R)-8-Benzyloxycarbonyl-3-oxa-8-bicyclo[4,3,0]nonan-1-yl}carboxylic acid tert-butyl ester (725 mg, 2.01 mmol) was dissolved in dichloromethane (20 mL). Trifluoroacetic acid (4 mL) was added, and the mixture was stirred for 15 hours. The reaction solution was concentrated under reduced pressure, and a 1N sodium hydroxide solution (50 mL) was added, and the mixture was washed with chloroform. The aqueous layer was made acidic with a hydrochloric acid solution, followed by extraction with chloroform (50 mL×2). After drying over anhydrous sodium sulfate and filtration, the solvent was evaporated under reduced pressure, and the resulting residue was dissolved in toluene (20 mL). Triethylamine (406 mg, 4.01 mmol) and diphenylphosphoryl azide (740 mg, 2.61 mmol) were added in a nitrogen atmosphere, and the mixture was stirred at 110° C. for 1.5 hours. The reaction solution was concentrated under reduced pressure. Then, dioxane (20 mL) and 6N hydrochloric acid (20 mL) were added, and the mixture was stirred at 50° C. for two hours. After concentration under reduced pressure and azeotropic distillation with ethanol, a 1N sodium hydroxide solution (50 mL) was added, followed by extraction with chloroform (100 mL×2). After drying over anhydrous sodium sulfate and filtration, the solvent was evaporated under reduced pressure. Di-tert-butyl dicarbonate (2189 mg, 10.03 mmol) was added to the resulting residue, and the mixture was stirred at 50° C. for 1.5 hours. The reaction solution was purified by silica gel column chromatography (60% ethyl acetate/hexane) to give 623 mg of the title compound as a colorless oil.

¹H-NMR (400 MHz, CDCl₃) δ: 7.52-7.26 (5H, m), 5.13 (2H, s), 4.55 (1H, dd, J=19.51, 11.22 Hz), 4.45 (1H, d, J=10.73 Hz), 4.25 (1H, t, J=12.44 Hz), 4.13-4.08 (1H, m), 3.70-3.62 (1H, m), 3.36-3.34 (1H, m), 3.16-3.09 (3H, m), 2.02-1.97 (1H, m), 1.69-1.62 (2H, m), 1.43 (9H, s).
MS (EI) m/z: 399 (M+Na)⁺.

Reference Example 174

(1S,6R)-1-tert-Butoxycarbonylamino-3-oxa-8-azabicyclo[4,3,0]nonane

[Formula 281]

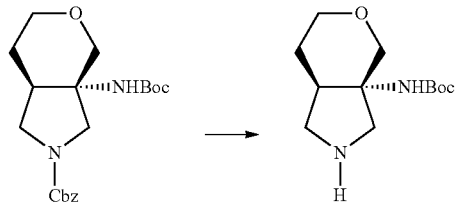

[(1S,6R)-1-tert-Butoxycarbonylamino-3-oxa-8-azabicyclo[4,3,0]nonan-8-yl]carboxylic acid benzyl ester (401 mg, 1.07 mmol) was dissolved in methanol (20 mL). 10% palladium-carbon (50% wet) (200 mg) was added, and the mixture was stirred in a hydrogen atmosphere for 2.5 hours. The catalyst was removed by filtration, and then the filtrate was concentrated under reduced pressure. A 1N sodium hydroxide solution was added, followed by extraction with chloroform. After drying over anhydrous sodium sulfate and filtration, the solvent was evaporated under reduced pressure to give 256 mg of the title compound as a colorless solid.
MS (EI) m/z: 243 (M+H)⁺.

Example 40

7-[(1S,6R)-1-Amino-3-oxa-8-azabicyclo[4,3,0]nonan-8-yl]-6-fluoro-1-[(1R,2S)-2-fluorocyclopropyl]-1,4-dihydro-8-methoxy-4-oxoquinoline-3-carboxylic acid

[Formula 282]

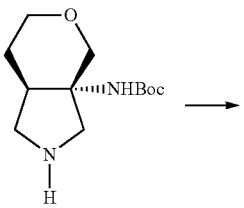

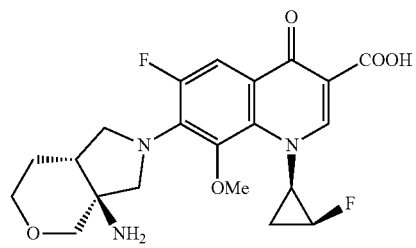

(1S,6R)-8-Aza-1-tert-butoxycarbonylamino-3-oxabicyclo[4,3,0]nonane (252 mg, 1.04 mmol) was dissolved in dimethyl sulfoxide (8 mL). 6,7-Difluoro-1-[(1R,2S)-2-fluorocyclopropyl]-1,4-dihydro-8-methoxy-4-oxoquinoline-3-carboxylic acid-BF₂ chelate (450.6 mg, 1.25 mmol) and triethylamine (315.7 mg, 3.12 mmol) were added, and the mixture was stirred at 40° C. for 17 hours. Then, 90% aqueous ethanol (30 mL) and triethylamine (3 mL) were added to the reaction solution, and the mixture was stirred at 80° C. for five hours. The solvent was evaporated under reduced pressure, and then a 10% citric acid solution was added to the residue, followed by extraction with ethyl acetate. The organic layer was washed with water and brine and dried over anhydrous sodium sulfate. After filtration, the solvent was evaporated under reduced pressure, and the resulting residue was subjected to short silica gel column chromatography (3% methanol/chloroform). The resulting fraction was dissolved in concentrated hydrochloric acid and washed with chloroform. The aqueous layer was adjusted to pH 12 with aqueous sodium hydroxide at 0° C. and then adjusted to pH 8 with hydrochloric acid, followed by extraction with chloroform. The organic layer was dried over anhydrous sodium sulfate and filtered, and then the solvent was evaporated under reduced pressure. The resulting residue was washed with ethanol and diethyl ether and dried under reduced pressure to give 302 mg of the title compound as pale yellow crystals.

mp: 132-134° C.

$^1$H-NMR (400 MHz, 0.1N NaOD) δ: 8.41 (1H, s), 7.66 (1H, d, J=14.63 Hz), 4.99 (1H, d, J=63.90 Hz), 4.04-4.03 (2H, m), 3.91-3.88 (1H, m), 3.82 (2H, t, J=11.22 Hz), 3.68-3.62 (2H, m), 3.59 (3H, s), 3.51 (1H, d, J=11.95 Hz), 3.37 (1H, d, J=10.98 Hz), 2.23-2.20 (1H, m), 1.93-1.91 (1H, m), 1.57-1.47 (3H, m).

Anal; Calcd for $C_{21}H_{23}F_2N_3O_5 \cdot 0.5H_2O \cdot 0.4CHCl_3$: C, 55.42; H, 5.30; N, 9.06; F, 8.19. Found: C, 55.19; H, 5.19; N, 9.09; F, 8.32.

MS (EI) m/z: 436 (M+H)$^+$.

IR (ATR) ν: 2943, 2887, 2845, 1720, 1622, 1516, 1452, 1346, 1323, 1275 cm$^{-1}$.

Example 41

7-[(1S,6R)-1-Amino-3-oxa-8-azabicyclo[4,3,0]nonan-8-yl]-6-fluoro-1-[(1R,2S)-2-fluorocyclopropyl]-1,4-dihydro-8-methyl-4-oxoquinoline-3-carboxylic acid triethylamine (93.6 mg, 0.92 mmol) were added, and the mixture was stirred for 14 days. Then, 90% aqueous ethanol (18 mL) and triethylamine (2 mL) were added to the reaction solution, and the mixture was stirred at 80° C. for two hours. The solvent was evaporated under reduced pressure, and a 10% citric acid solution was added to the resulting residue, followed by extraction with ethyl acetate. The organic layer was washed with water and brine and dried over anhydrous sodium sulfate. After filtration, the solvent was evaporated under reduced pressure. Then, the residue was purified by PTLC (5% methanol/chloroform), and the resulting fraction was dissolved in concentrated hydrochloric acid and washed with chloroform twice. The aqueous layer was adjusted to pH 12 with aqueous sodium hydroxide at 0° C. and then adjusted to pH 7.9 with hydrochloric acid, followed by extraction with 5% methanol/chloroform twice. The organic layer was dried over anhydrous sodium sulfate and filtered, and then the solvent was evaporated under reduced pressure. The precipitated crystals were collected by filtration and dried under reduced pressure to give 51 mg of the title compound as colorless crystals.

mp: 158-160° C.

$^1$H-NMR (400 MHz, 0.1N NaOD) δ: 8.44 (1H, d, J=3.17 Hz), 7.67 (1H, d, J=14.16 Hz), 5.01 (1H, d, J=64.94 Hz), 4.16 (1H, t, J=6.71 Hz), 4.07 (1H, dt, J=9.93, 4.46 Hz), 4.01 (1H, d, J=10.01 Hz), 3.95-3.92 (1H, m), 3.85 (1H, d, J=11.96 Hz), 3.62-3.54 (1H, m), 3.47 (1H, d, J=11.72 Hz), 3.17 (1H, d, J=9.77 Hz), 3.06 (1H, d, J=10.01 Hz), 2.48 (3H, s), 2.20-2.15 (1H, m), 1.89-1.82 (1H, m), 1.65-1.60 (2H, m), 1.26-1.19 (1H, m).

Anal; Calcd for $C_{21}H_{23}F_2N_3O_4 \cdot 0.75H_2O \cdot 0.25EtOH$: C, 58.10; H, 5.90; N, 9.45; F, 8.55. Found: C, 58.35; H, 5.86; N, 9.19; F, 8.53.

MS (EI) m/z: 420 (M+H)$^+$.

IR (ATR) ν: 3365, 2945, 2839, 1716, 1616, 1510, 1466, 1454, 1431, 1342, 1311, 1265, 1215 cm$^{-1}$.

Reference Example 175

(1S,6S)-1-tert-Butoxycarbonylamino-3-oxa-8-azabicyclo[4,3,0]nonane

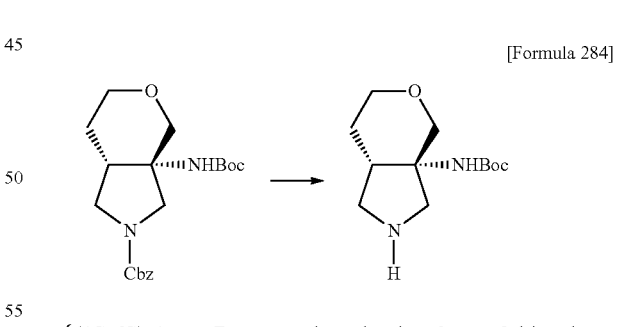

[Formula 284]

{(1S,6S)-1-tert-Butoxycarbonylamino-3-oxa-8-bicyclo[4,3,0]nonan-8-yl}carboxylic acid benzyl ester (610 mg, 1.62 mmol) was dissolved in methanol (20 mL). 10% palladium-carbon (50% wet) (200 mg) was added, and the mixture was stirred in a hydrogen atmosphere for three hours. The catalyst was removed by filtration, and then the filtrate was concentrated under reduced pressure. A 1N sodium hydroxide solution was added, followed by extraction with chloroform. After drying over anhydrous sodium sulfate and filtration, the solvent was evaporated under reduced pressure to give 362 mg of the title compound as a colorless solid.

MS (EI) m/z: 243 (M+H)$^+$.

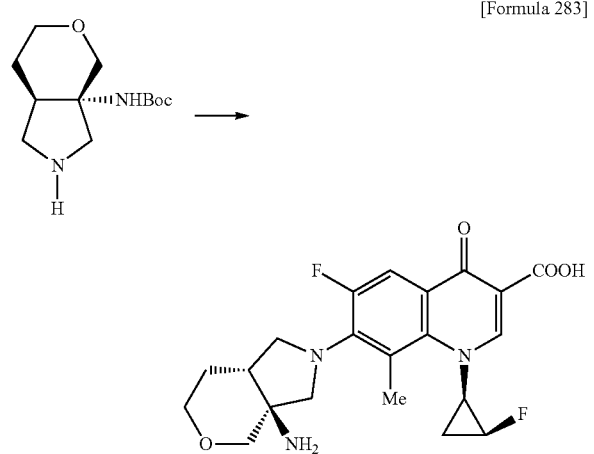

[Formula 283]

(1S,6R)-1-tert-Butoxycarbonylamino-3-oxa-8-azabicyclo[4,3,0]nonane (187 mg, 0.77 mmol) was dissolved in dimethyl sulfoxide (4 mL). 6,7-Difluoro-1-[(1R,2S)-2-fluorocyclopropyl]-1,4-dihydro-8-methyl-4-oxoquinoline-3-carboxylic acid-BF$_2$ chelate (316.5 mg, 0.92 mmol) and

Example 42

10-[(1S,6S)-1-Amino-3-oxa-8-azabicyclo[4,3,0]nonan-8-yl]-9-fluoro-2,3-dihydro-3-methyl-(S)-7-oxo-7H-pyrido[1,2,3-de][1,4]benzoxazine-6-carboxylic acid

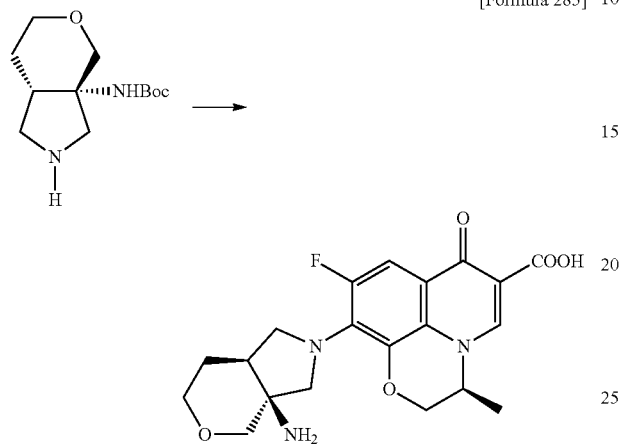

[Formula 285]

(1S,6S)-1-tert-Butoxycarbonylamino-3-oxa-8-azabicyclo[4,3,0]nonane (147.7 mg, 0.61 mmol) was dissolved in dimethyl sulfoxide (2.5 mL). 9,10-Difluoro-2,3-dihydro-3-(S)-methyl-7-oxo-7H-pyrido[1,2,3-de][1,4]benzoxazine-6-carboxylic acid-$BF_2$ chelate (211.3 mg, 0.64 mmol) and triethylamine (185.7 mg, 1.83 mmol) were added, and the mixture was stirred at 40° C. for 18 hours. Then, 90% aqueous ethanol (33 mL) and triethylamine (3 mL) were added to the reaction mixture, which was stirred at 80° C. for four hours. The solvent was evaporated under reduced pressure and a 10% citric acid solution was added, followed by extraction with ethyl acetate. The organic layer was washed with water and brine and dried over anhydrous sodium sulfate. After filtration, the solvent was evaporated under reduced pressure, and the resulting residue was subjected to short silica gel column chromatography (3% methanol/chloroform). The resulting fraction was dissolved in concentrated hydrochloric acid and washed with chloroform. The aqueous layer was adjusted to pH 12 with aqueous sodium hydroxide at 0° C. and then adjusted to pH 7.4 with hydrochloric acid, followed by extraction with chloroform. The organic layer was dried over anhydrous sodium sulfate and filtered, and then the solvent was evaporated under reduced pressure. The resulting residue was dissolved in ethanol-aqueous ammonia, and the solution was heated and stirred. After vaporization of ammonia, the precipitated crystals were collected by filtration and dried under reduced pressure to give 180 mg of the title compound as colorless crystals.

mp: >300° C.
$^1$H-NMR (400 MHz, 0.1N NaOD) δ: 8.31 (1H, s), 7.51 (1H, d, J=14.63 Hz), 4.58 (1H, d, J=7.07 Hz), 4.45 (1H, dd, J=11.34, 1.83 Hz), 4.27 (1H, d, J=11.22 Hz), 4.08 (1H, dd, J=11.22, 3.66 Hz), 3.93 (1H, d, J=10.49 Hz), 3.78 (1H, dd, J=10.37, 3.05 Hz), 3.75-3.68 (1H, m), 3.55 (1H, d, J=10.98 Hz), 3.49-3.43 (2H, m), 3.29 (1H, d, J=10.00 Hz), 2.04-2.01 (1H, m), 1.81-1.72 (2H, m), 1.52 (3H, d, J=6.59 Hz).
Anal; Calcd for $C_{20}H_{22}FN_3O_5 \cdot 1.5H_2O$: C, 55.81; H, 5.85; N, 9.76; F, 4.41. Found: C, 55.80; H, 5.89; N, 9.74; F, 4.34.
MS (EI) m/z: 404 (M+H)$^+$.
IR (ATR) ν: 3498, 3407, 3224, 3045, 2956, 2877, 1616, 1573, 1523, 1473, 1379, 1352, 1306, 1261 cm$^{-1}$.

Example 43

7-[(1S,6S)-1-Amino-8-aza-3-oxabicyclo[4,3,0]nonan-8-yl]-6-fluoro-1-[(1R,2S)-2-fluorocyclopropyl]-1,4-dihydro-8-methoxy-4-oxoquinoline-3-carboxylic acid

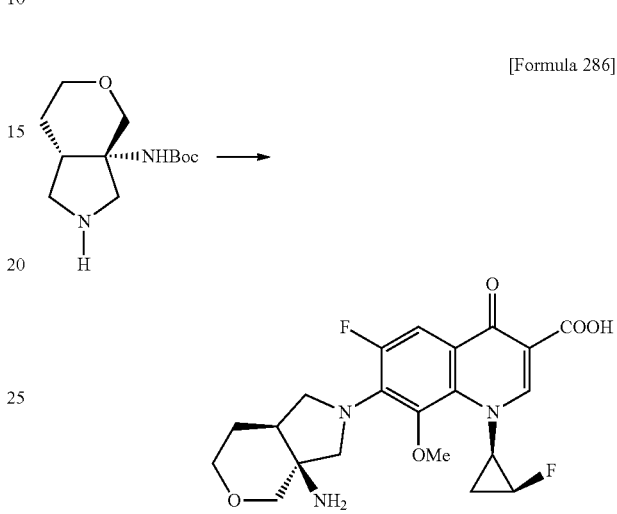

[Formula 286]

(1S,6S)-8-Aza-1-tert-butoxycarbonylamino-3-oxabicyclo[4,3,0]nonane (108.8 mg, 0.45 mmol) was dissolved in dimethyl sulfoxide (4 mL). 6,7-Difluoro-1-[(1R,2S)-2-fluorocyclopropyl]-1,4-dihydro-8-methoxy-4-oxoquinoline-3-carboxylic acid-$BF_2$ chelate (210.7 mg, 0.58 mmol) and triethylamine (136.3 mg, 1.35 mmol) were added, and the mixture was stirred at 40° C. for 18 hours. Then, 90% aqueous ethanol (30 mL) and triethylamine (3 mL) were added to the reaction solution, and the mixture was stirred at 80° C. for five hours. The solvent was evaporated under reduced pressure, and a 10% citric acid solution was added to the residue, followed by extraction with ethyl acetate. The organic layer was washed with water and brine and dried over anhydrous sodium sulfate. After filtration, the solvent was evaporated under reduced pressure, and the resulting residue was subjected to short silica gel column chromatography (3% methanol/chloroform). The resulting crude was dissolved in concentrated hydrochloric acid and washed with chloroform. The aqueous layer was adjusted to pH 12 with aqueous sodium hydroxide at 0° C. and then adjusted to pH 7.4 with hydrochloric acid, followed by extraction with chloroform. The organic layer was dried over anhydrous sodium sulfate and filtered, and then the solvent was evaporated under reduced pressure. The resulting residue was purified by recrystallization from ethanol and dried under reduced pressure to give 121 mg of the title compound as pale yellow crystals.

mp: 190-192° C.
$^1$H-NMR (400 MHz, 0.1N NaOD) δ: 8.36 (1H, d, J=3.66 Hz), 7.65 (1H, d, J=14.40 Hz), 5.06 (1H, dd, J=64.09, 3.54 Hz), 4.09 (1H, dd, J=11.35, 4.03 Hz), 4.02-3.95 (2H, m), 3.67-3.51 (8H, m), 3.24 (1H, d, J=10.25 Hz), 2.14-2.11 (1H, m), 1.88-1.71 (2H, m), 1.54-1.48 (1H, m), 1.36-1.32 (1H, m).
Anal; Calcd for $C_{21}H_{23}F_2N_3O_5 \cdot 0.25H_2O$: C, 57.33; H, 5.38; N, 9.55; F, 8.64. Found: C, 57.28; H, 5.39; N, 9.27; F, 8.48.
MS (EI) m/z: 436 (M+H)$^+$.
IR (ATR) ν: 3502, 3374, 3091, 2948, 2881, 2850, 1716, 1617, 1513, 1450, 1365, 1321, 1309, 1268, 1223 cm$^{-1}$.

Example 44

7-[(1S,6S)-1-Amino-3-oxa-8-azabicyclo[4,3,0]nonan-8-yl]-6-fluoro-1-[(1R,2S)-2-fluorocyclopropyl]-1,4-dihydro-8-methyl-4-oxoquinoline-3-carboxylic acid

[Formula 287]

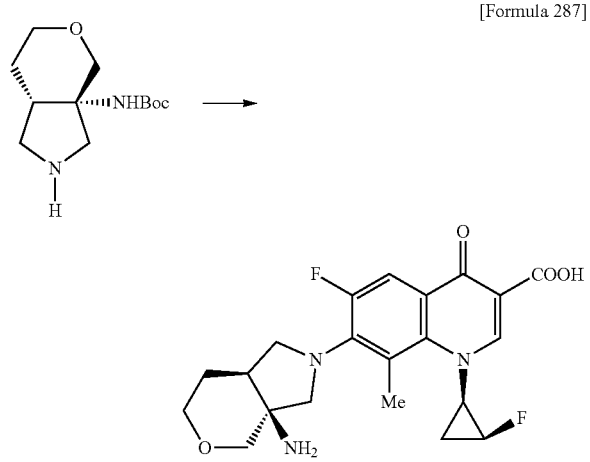

(1S,6S)-1-tert-Butoxycarbonylamino-3-oxa-8-azabicyclo[4,3,0]nonane (184.7 mg, 0.76 mmol) was dissolved in dimethyl sulfoxide (4 mL). 6,7-Difluoro-1-[(1R,2S)-2-fluorocyclopropyl]-8-methyl-1,4-dihydro-4-oxoquinoline-3-carboxylic acid-$BF_2$ chelate (289.4 mg, 0.84 mmol) and triethylamine (115.7 mg, 1.14 mmol) were added, and the mixture was stirred for seven days. Then, 90% aqueous ethanol (22 mL) and triethylamine (2 mL) were added to the reaction solution, and the mixture was stirred at 75° C. for two hours. The solvent was evaporated under reduced pressure and a 10% citric acid solution was added, followed by extraction with ethyl acetate. The organic layer was washed with water and brine and dried over anhydrous sodium sulfate. After filtration, the solvent was evaporated under reduced pressure, and the resulting residue was subjected to short silica gel column chromatography (3% methanol/chloroform). The resulting fraction was dissolved in concentrated hydrochloric acid and washed with chloroform. The aqueous layer was adjusted to pH 12 with aqueous sodium hydroxide at 0° C. and then adjusted to pH 7.5 with hydrochloric acid, followed by extraction with chloroform. The organic layer was dried over anhydrous sodium sulfate and filtered, and then the solvent was evaporated under reduced pressure. The resulting residue was dissolved in ethanol-aqueous ammonia, and the solution was heated and stirred. After vaporization of ammonia, the precipitated crystals were collected by filtration and dried under reduced pressure to give 94.7 mg of the title compound as colorless crystals.

mp: 159-161° C.

$^1$H-NMR (400 MHz, 0.1N NaOD) δ: 8.42 (1H, s), 7.67 (1H, d, J=14.15 Hz), 5.03 (1H, d, J=60.24 Hz), 4.10-4.08 (2H, m), 3.96 (1H, d, J=10.49 Hz), 3.82 (1H, d, J=9.27 Hz), 3.68 (1H, t, J=10.49 Hz), 3.61 (1H, d, J=10.49 Hz), 3.49 (1H, t, J=11.10 Hz), 3.26 (1H, t, J=8.17 Hz), 3.08 (1H, d, J=9.51 Hz), 2.45 (3H, s), 2.21-2.18 (1H, m), 1.84-1.57 (3H, m), 1.23 (1H, d, J=26.10 Hz).

Anal; Calcd for $C_{21}H_{23}F_2N_3O_4 \cdot 1.25H_2O$: C, 57.07; H, 5.82; N, 9.51; F, 8.60. Found: C, 56.87; H, 5.99; N, 9.49; F, 8.43.

MS (EI) m/z: 420 (M+H)$^+$.

IR (ATR) ν: 3518, 3251, 3059, 2935, 2885, 1720, 1614, 1540, 1508, 1441, 1387, 1358, 1325, 1306, 1273 cm$^{-1}$.

Reference Example 176

(5,6-Dihydro-4H-pyran-2-yl)methyl methanesulfonate

[Formula 288]

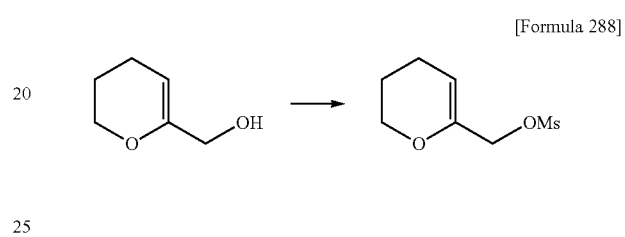

Methanesulfonyl chloride (17.9 mL, 232 mmol) was added dropwise to a solution of (5,6-dihydro-4H-pyran-2-yl)methanol (25.51 g, 193 mmol) [see Synlett, Vol. 5, p. 533 (1997)] and triethylamine (40.4 mL, 290 mmol) in dichloromethane (600 mL) under salt ice cooling over 15 minutes. After stirring at the same temperature for two hours, triethylamine (18.8 mL, 135 mmol) and methanesulfonyl chloride (7.5 mL, 97 mmol) were added, and the mixture was further stirred for 30 minutes. Water (300 mL) was added to the reaction solution, followed by extraction with ethyl acetate (1.5 L). The resulting organic layer was washed with water (300 mL) and brine (300 mL). The organic layer was dried over anhydrous sodium sulfate and then filtered, and the solvent was evaporated under reduced pressure. The resulting crude title compound was used for the next reaction without purification.

Reference Example 177

2-Azidomethyl-5,6-dihydro-4H-pyran

[Formula 289]

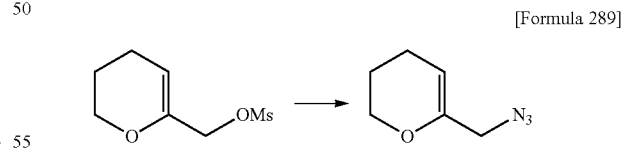

Water (35 mL) and sodium azide (15.1 g, 232 mmol) were added to a solution of the crude (5,6-dihydro-4H-pyran-2-yl)methyl methanesulfonate (about 193 mmol) in N,N-dimethylformamide (350 mL), and the mixture was stirred at room temperature for 20 hours. Water (300 mL) was added to the reaction solution, followed by extraction with ethyl acetate (1.5 L). The resulting organic layer was washed with water (3×200 mL) and brine (200 mL). The organic layer was dried over anhydrous sodium sulfate and then filtered, and the solvent was evaporated under reduced pressure to about 300 mL. The resulting crude title compound solution was used for the next reaction without purification.

Reference Example 178

2-Aminomethyl-5,6-dihydro-4H-pyran

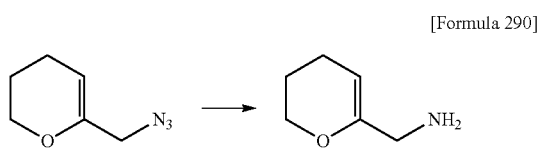 [SMILES: [N-]=[N+]=NCC1=CCCCO1 ; NCC1=CCCCO1]

[Formula 290]

Tetrahydrofuran (500 mL), water (50 mL), and triphenylphosphine (35.4 g, 135 mmol) were sequentially added to the crude 2-azidomethyl-5,6-dihydro-4H-pyran (about 193 mmol), and the mixture was heated with stirring on an oil bath at 60° C. for two hours. Ethyl acetate (1 L) was added to the reaction solution, and the aqueous layer was removed. Then, the organic layer was dried over anhydrous sodium sulfate and filtered, and the solvent was evaporated under reduced pressure. The resulting crude title compound was used for the next reaction without further purification.

Reference Example 179

2-(Tritylamino)methyl-5,6-dihydro-4H-pyran

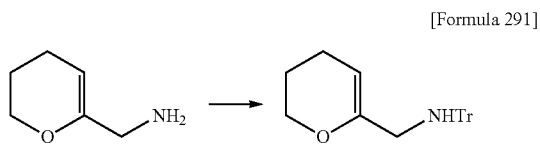

[Formula 291]

Triethylamine (37.7 mL, 270 mmol) and trityl chloride (41.4 g, 149 mmol) were sequentially added to a solution of the crude 2-aminomethyl-5,6-dihydro-4H-pyran (about 193 mmol) in dichloromethane (500 mL), and the mixture was stirred at room temperature for 11 hours. The reaction solution was diluted with dichloromethane (500 mL), washed with water (2×500 mL) and brine (500 mL), and then dried over anhydrous sodium sulfate and filtered. The solvent was evaporated under reduced pressure. Then, the residue was purified by silica gel column chromatography (ethyl acetate: hexane=5:95→10:90) to give 22.2 g (four steps, 32%) of the title compound as a colorless transparent gummy solid.

$^1$H-NMR (400 MHz, CDCl$_3$) δ: 7.16-7.49 (15H, m), 4.81 (1H, brs), 3.97 (2H, t, J=5.1 Hz), 2.66 (2H, brs), 2.02-2.04 (2H, m), 1.76-1.82 (2H, m).

Reference Example 180

2-(Tritylamino)methyl-3,4,5,6-tetrahydro-2H-pyran-3-ol

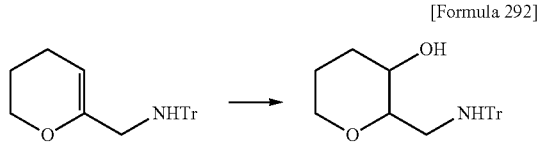

[Formula 292]

A solution of a borane-tetrahydrofuran complex in tetrahydrofuran (1 M, 187 mL, 187 mmol) was added dropwise to a solution of 2-(tritylamino)methyl-5,6-dihydro-4H-pyran (22.2 g, 62.4 mmol) in tetrahydrofuran (180 mL) at room temperature over 20 minutes. After stirring at room temperature for 2.5 hours, the reaction solution was ice-cooled, and a 3N sodium hydroxide solution (208 mL, 624 mmol) was added dropwise over 10 minutes. Subsequently a 31% hydrogen peroxide solution (69 mL, 629 mmol) was added dropwise at the same temperature over 10 minutes, and then the mixture was stirred at room temperature for one hour. The reaction solution was extracted with diethyl ether (2×300 mL). The combined organic layers were washed with water (300 mL) and brine (300 mL), and then dried over anhydrous sodium sulfate and filtered. The solvent was evaporated under reduced pressure, and then the residue was suspended in a mixed solvent of dichloromethane/hexane (1:1, 80 mL). The insoluble material was removed by filtration, and then the filtrate was evaporated under reduced pressure to give 18.54 g (80%) of the title compound as a pale yellow gummy solid.

$^1$H-NMR (400 MHz, CDCl$_3$) δ: 7.41-7.46 (6H, m), 7.26-7.33 (6H, m), 7.18-7.23 (3H, m), 3.81-3.84 (1H, m), 3.73-3.76 (1H, m), 3.60-3.66 (1H, m), 3.25-3.32 (1H, m), 3.05-3.10 (1H, m), 2.64 (1H, dd, J=11.6, 7.7 Hz), 2.35 (1H, dd, J=11.7, 4.9 Hz), 2.13-2.21 (1H, m), 1.83-1.86 (1H, m), 1.62-1.68 (1H, m), 1.38-1.48 (1H, m).

Reference Example 181

2-(Tritylamino)methyl-5,6-dihydro-2H-pyran-3(4H)-one

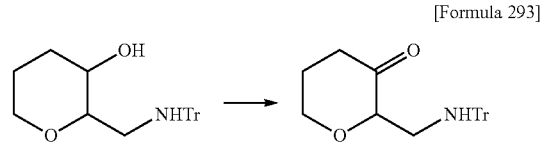

[Formula 293]

A solution of a sulfur trioxide-pyridine complex (23.7 g, 149 mmol) in dimethyl sulfoxide (150 mL) was added to a solution of 2-(tritylamino)methyl-3,4,5,6-tetrahydro-2H-pyran-3-ol (18.54 g, 49.6 mmol) and triethylamine (45 mL, 323 mmol) in dimethyl sulfoxide (150 mL) in a nitrogen atmosphere at room temperature. The mixture was stirred at the same temperature for 10 hours. The reaction solution was poured into ice water (1 L), followed by extraction with ethyl acetate (2×1 L). Then, the organic layers were combined and washed with water (2×1 L) and brine (1 L). The resulting organic layer was dried over anhydrous sodium sulfate and filtered. Then, the solvent was evaporated under reduced pressure. The residue was purified by silica gel column chromatography (ethyl acetate:hexane=5:95→10:90→20:80) to give 9.56 g (52%) of the title compound as a colorless transparent gummy solid.

$^1$H-NMR (400 MHz, CDCl$_3$) δ: 7.44-7.47 (6H, m), 7.15-7.28 (9H, m), 3.93-4.00 (2H, m), 3.65-3.72 (1H, m), 2.41-2.61 (4H, m), 1.99-2.20 (2H, m).

Reference Example 182

6-(Tritylamino)methyl-7-oxa-1,3-diazaspiro[4.5]decane-2,4-dione

[Formula 294]

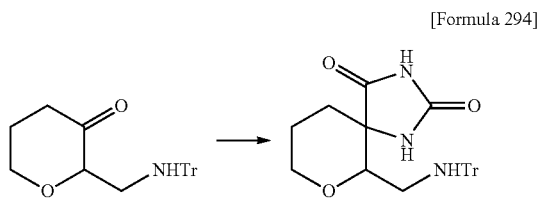

A mixture of 2-(tritylamino)methyl-5,6-dihydro-2H-pyran-3(4H)-one (9.56 g, 25.7 mmol), sodium cyanide (2.52 g, 51.4 mmol), ammonium chloride (2.75 g, 51.4 mmol), ammonium carbonate (10.18 g, 128.7 mmol), concentrated aqueous ammonia (50 mL), and ethanol (50 mL) was stirred in a nitrogen atmosphere on an oil bath at 60° C. for 4.5 hours. Ammonium carbonate (10.18 g, 128.7 mmol) was added, and the mixture was stirred at the same temperature for further 19.5 hours. The resulting reaction solution was concentrated under reduced pressure, and the residue was extracted with ethyl acetate (300 mL, 100 mL). Then, the organic layers were combined and washed with water (2×100 mL) and brine (100 mL). The resulting organic layer was dried over anhydrous magnesium sulfate and filtered. Then, the solvent was evaporated under reduced pressure to give 11.35 g (quantitative) of the title compound as a colorless amorphous.

$^1$H-NMR (400 MHz, CDCl$_3$) δ: 7.65 (1H, s), 7.38-7.49 (6H, m), 7.15-7.30 (9H, m), 5.79 (1H, s), 3.97 (1H, dm, J=13.2 Hz), 3.68 (1H, dd, J=7.1, 5.1 Hz), 3.51 (1H, dt, J=11.2, 4.4 Hz), 2.34 (1H, dd, J=12.1, 5.0 Hz), 2.18-2.23 (1H, m), 2.05-2.14 (1H, m), 1.81 (1H, brd, J=13.4 Hz), 1.55-1.70 (2H, m).

Reference Example 183

(2R*,3R*)-3-Amino-2-(tert-butoxycarbonylamino)methyl-3,4,5,6-tetrahydro-2H-pyrane-3-carboxylic acid

[Formula 295]

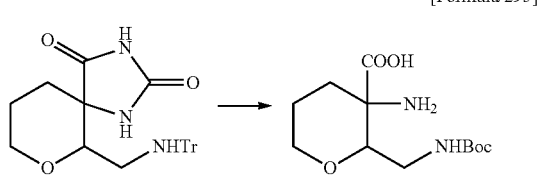

6-(Tritylamino)methyl-7-oxa-1,3-diazaspiro[4.5]decane-2,4-dione (10.69 g, 24.2 mmol) was dissolved in trifluoroacetic acid (50 mL) at room temperature, and the mixture was stirred for 15 minutes. Water (50 mL) was added to the reaction solution, and the solvent was evaporated under reduced pressure. Then, water (200 mL) was added to the residue, and the mixture was washed with diethyl ether (2×100 mL).

Sodium hydroxide (40 g, 1.0 mol) was added to the resulting solution (about 250 mL), and the mixture was heated to reflux on an oil bath at 130° C. for 16 hours. The reaction solution was ice-cooled and then adjusted to pH 7.0 by gradually adding concentrated hydrochloric acid, and the solvent was evaporated under reduced pressure.

The resulting residue was suspended in a 1N sodium hydroxide solution (75 mL) and 1,4-dioxane (150 mL). Di-tert-butyl dicarbonate (52.8 g, 242 mmol) was added at room temperature, and the mixture was stirred at the same temperature for five days. The solvent was concentrated under reduced pressure. Then, the residue was suspended in a 1N sodium hydroxide solution (300 mL), and the mixture was washed with diisopropyl ether (3×300 mL). Concentrated hydrochloric acid was gradually added to the resulting aqueous layer under ice-cooling to adjust the aqueous layer to pH 7.0. The solvent was evaporated under reduced pressure. The residue was suspended in methanol (100 mL), and then most of sodium chloride was removed by filtration (twice). Thereafter, the residue was purified by an ion exchange resin HP-20 (eluted with methanol) to give 1.21 g (three steps, 18%) of the title compound as a pale brown solid.

$^1$H-NMR (400 MHz, 0.1N NaOD) δ: 3.99-4.03 (1H, m), 3.69-3.73 (1H, m), 3.53 (1H, t, J=12.0 Hz), 3.00-3.12 (2H, m), 2.00-2.06 (1H, m), 1.70-1.87 (2H, m), 1.52-1.56 (1H, m), 1.43 (9H, s).

Reference Example 184

(2R*,3R*)-3-(Benzyloxycarbonylamino)-2-(tert-butoxycarbonylamino)methyl-3,4,5,6-tetrahydro-2H-pyrane-3-carboxylic acid

[Formula 296]

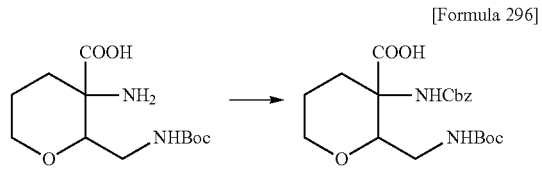 [SMILES: CC(C)(C)OC(=O)NCC1OCCCC1(N)C(=O)O ; CC(C)(C)OC(=O)NCC1OCCCC1(NC(=O)OCc1ccccc1)C(=O)O]

N-(Benzyloxycarbonyloxy)succinimide (1.49 g, 5.98 mmol) was added to a solution of (2R*,3R*)-3-amino-2-(tert-butoxycarbonylamino)methyl-3,4,5,6-tetrahydro-2H-pyrane-3-carboxylic acid (1.09 g, 3.99 mmol) and triethylamine (1.11 mL, 7.96 mmol) in tetrahydrofuran (10 mL)/water (10 mL) under ice-cooling, and the mixture was stirred at room temperature for 15 hours. The reaction solution was diluted with ethyl acetate (150 mL) and washed with 1N hydrochloric acid (50 mL). The resulting organic layer was dried over anhydrous sodium sulfate and filtered. Then, the solvent was evaporated under reduced pressure. The residue was purified by silica gel column chromatography (methanol:chloroform=2:98→5:95) and then dissolved in a 1N sodium hydroxide solution (50 mL) and washed with diethyl ether (2×20 mL) to remove the remaining benzyl alcohol. The resulting aqueous layer was adjusted to pH 1 to 2 with concentrated hydrochloric acid, followed by extraction with dichloromethane (2×80 mL). The organic layers were combined, dried over anhydrous sodium sulfate, and filtered. Then, the solvent was evaporated under reduced pressure to obtain 1.08 g (66%) of the title compound as a white solid.

$^1$H-NMR (400 MHz, CDCl$_3$) δ: 7.37-7.28 (5H, m), 5.53 (1H, brs), 5.20-5.07 (2H, m), 4.94 (1H, brs), 3.99 (1H, dd, J=11.1, 4.5 Hz), 3.65 (1H, m), 3.55-3.30 (2H, m), 3.17 (1H, m), 2.59 (1H, m), 2.06 (1H, m), 1.73 (1H, m), 1.57-1.51 (1H, m), 1.43 (9H, m).

MS (ESI); m/z: 309 (M-Boc+2H)$^+$.

Reference Example 185

(1R*,6R*)-6-(Benzyloxycarbonylamino)-2-oxa-7-oxo-8-azabicyclo[4.3.0]nonane

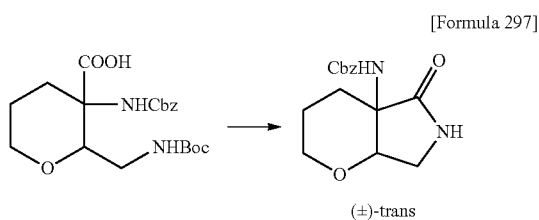 [SMILES: CC(C)(C)OC(=O)NCC1OCCCC1(NC(=O)OCc1ccccc1)C(=O)O ; O=C(NC12CCCOC1CNC2=O)OCc1ccccc1]

[Formula 297]

(2R*,3R*)-3-(Benzyloxycarbonylamino)-2-(tert-butoxycarbonylamino)methyl-3,4,5,6-tetrahydro-2H-pyrane-3-carboxylic acid (1.08 g, 2.64 mmol) was dissolved in a solution of 4N hydrogen chloride in 1,4-dioxane at room temperature. The mixture was stirred at the same temperature for 20 minutes, and then the solvent was evaporated under reduced pressure. The resulting residue was azeotropically distilled with dioxane (twice) to give 921 mg (quantitative) of a residue.

691 mg (2.00 mmol) of the resulting residue and N,N-diisopropylethylamine (1.75 mL, 10.0 mmol) were dissolved in dichloromethane (25 mL). Bis(2-oxo-3-oxazolidinyl)phosphinyl chloride (1.02 g, 4.01 mmol) was added at room temperature, and the mixture was stirred at the same temperature for 18 hours. The reaction solution was diluted with chloroform (50 mL) and sequentially washed with 1N hydrochloric acid (30 mL), water (30 mL), a saturated sodium bicarbonate solution (30 mL), and brine (30 mL). The resulting organic layer was dried over anhydrous sodium sulfate and filtered. Then, the solvent was evaporated under reduced pressure at room temperature. The residue was purified by silica gel column chromatography (methanol:chloroform=2:98→5:95) to give 834 mg (quantitative) of the title compound as a pale brown gummy solid.

$^1$H-NMR (400 MHz, CDCl$_3$) S: 7.38-7.23 (5H, m), 5.60 (1H, brs), 5.42 (1H, brs), 5.12 (2H, s), 4.06 (1H, dd, J=11.7, 5.4 Hz), 3.67-3.55 (2H, m), 3.43-3.38 (1H, m), 3.33 (1H, t, J=4.2 Hz), 2.76-2.68 (1H, m), 1.94-1.82 (1H, m), 1.65-1.55 (2H, m).

MS (ESI); m/z: 291 (M+H)$^+$.

Reference Example 186

(1R*,6R*)-8-Benzyl-6-(benzyloxycarbonylamino)-2-oxa-7-oxo-8-azabicyclo[4.3.0]nonane

[Formula 298]

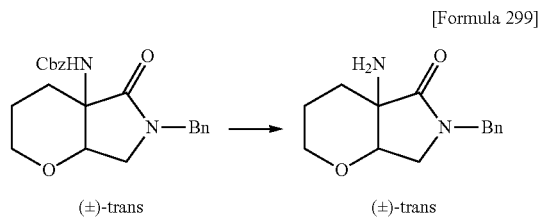 [SMILES: O=C(NC12CCCOC1CN(Cc1ccccc1)C2=O)OCc1ccccc1 ; NC12CCCOC1CN(Cc1ccccc1)C2=O]

Sodium hydride (55% mineral oil dispersion, 111 mg, 2.54 mmol) was added to a solution of (1R*,6R*)-6-(benzyloxycarbonylamino)-2-oxa-7-oxo-8-azabicyclo[4.3.0]nonane (818 mg, about 1.96 mmol) in N,N-dimethylformamide under ice-cooling, and the mixture was stirred at the same temperature for 20 minutes. Then, benzyl bromide (0.304 mL, 2.56 mmol) was added, and the mixture was stirred at room temperature for 20 minutes. The reaction solution was poured into a 10% citric acid solution (30 mL), followed by extraction with ethyl acetate (100 mL). The resulting organic layer was washed with water (2×30 mL) and brine (30 mL). This was dried over anhydrous sodium sulfate and filtered, and then the solvent was evaporated under reduced pressure. The residue was purified by silica gel column chromatography (ethyl acetate:chloroform=50:50→methanol:chloroform=1:99→2:98) to give 224 mg (0.59 mmol, three steps, 30%) of the title compound as a colorless transparent gummy solid.

$^1$H-NMR (400 MHz, CDCl$_3$) δ: 7.39-7.16 (5H, m), 5.38 (1H, brs), 5.20-5.09 (2H, m), 4.46 (2H, s), 4.02 (1H, dd, J=11.5, 5.7 Hz), 3.57-3.50 (2H, m), 3.23 (1H, t, J=9.2 Hz), 3.13 (1H, dd, J=9.2, 6.7 Hz), 2.75 (1H, m), 1.94-1.84 (1H, m), 1.68-1.61 (1H, m), 1.56-1.53 (1H, m), MS (ESI); m/z: 381 (M+H)$^+$.

Reference Example 187

(1R*,6R*)-6-Amino-8-benzyl-2-oxa-7-oxo-8-azabicyclo[4.3.0]nonane

[Formula 299]

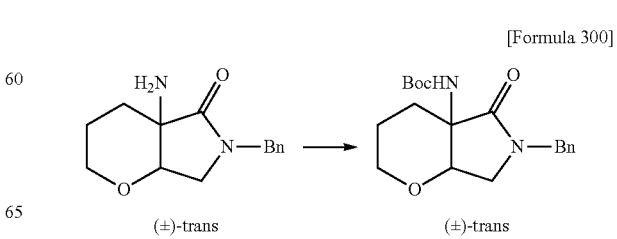

A 10% palladium-carbon catalyst (50% wet, 80 mg) was added to a solution of (1R*,6R*)-8-benzyl-6-(benzyloxycarbonylamino)-2-oxa-7-oxo-8-azabicyclo[4.3.0]nonane (220 mg, 0.58 mmol) in methanol (10 ml), and the mixture was stirred in a hydrogen atmosphere at room temperature for 1.5 hours. The reaction solution was filtered, and the filtrate was concentrated under reduced pressure to give 143 mg (quantitative) of the title compound as a colorless transparent gummy solid.

$^1$H-NMR (400 MHz, CDCl$_3$) δ: 7.38-7.24 (5H, m), 4.58 (1H, d, J=15.1 Hz), 4.38 (1H, d, J=14.9 Hz), 4.09 (1H, dd, J=11.6, 5.5 Hz), 3.58-3.40 (3H, m), 3.17 (1H, dd, J=8.1, 6.1 Hz), 2.53 (2H, brs), 2.15-2.04 (2H, m), 1.79-1.72 (1H, m), 1.60-1.55 (1H, m).

MS (ESI); m/z: 247 (M+H)$^+$.

Reference Example 188

(1R*,6S*)-8-Benzyl-6-(tert-butoxycarbonylamino)-2-oxa-8-azabicyclo[4.3.0]nonane

[Formula 300]

Lithium aluminum hydride (65 mg, 1.71 mmol) was added to a solution of (1R*,6R*)-6-amino-8-benzyl-2-oxa-7-oxo-8-azabicyclo[4.3.0]nonane (140 mg, 0.57 mmol) in tetrahydrofuran (6 mL) under ice-cooling, and the mixture was stirred at room temperature for 30 minutes. The reaction solution was ice-cooled. Water (0.06 mL), a 15% sodium hydroxide solution (0.06 mL), and water (0.18 mL) were sequentially added carefully, and the mixture was stirred at room temperature for overnight. Thereafter, anhydrous magnesium sulfate was added, and the mixture was stirred for 10 minutes. The resulting mixture was filtered through Celite, and then the filtrate was concentrated under reduced pressure.

The resulting residue was dissolved in dichloromethane (3 mL). Di-tert-butyl dicarbonate (252 mg, 1.15 mmol) was added, and the mixture was stirred at room temperature for four hours. The solvent was evaporated under reduced pressure, and then the resulting residue was purified by PTLC (methanol:chloroform=2:98) to give 50 mg (0.152 mmol, two steps, 26%) of the title compound as a colorless transparent gummy solid.

$^1$H-NMR (400 MHz, CDCl$_3$) δ: 7.30-7.20 (5H, m), 4.93 (1H, brs), 4.02 (1H, dd, J=11.6, 5.2 Hz), 3.81 (2H, s), 3.61-3.48 (3H, m), 3.07 (1H, t, J=8.0 Hz), 2.71-2.67 (2H, m), 2.52 (1H, m), 1.90-1.55 (3H, m), 1.47 (9H, s).

MS (ESI); m/z: 333 (M+H)$^+$.

Example 45

7-[(1R*,6S*)-6-Amino-2-oxa-8-azabicyclo[4.3.0]nonan-3-yl]-1-cyclopropyl-6-fluoro-1,4-dihydro-8-methoxy-4-oxoquinoline-3-carboxylic acid

[Formula 301]

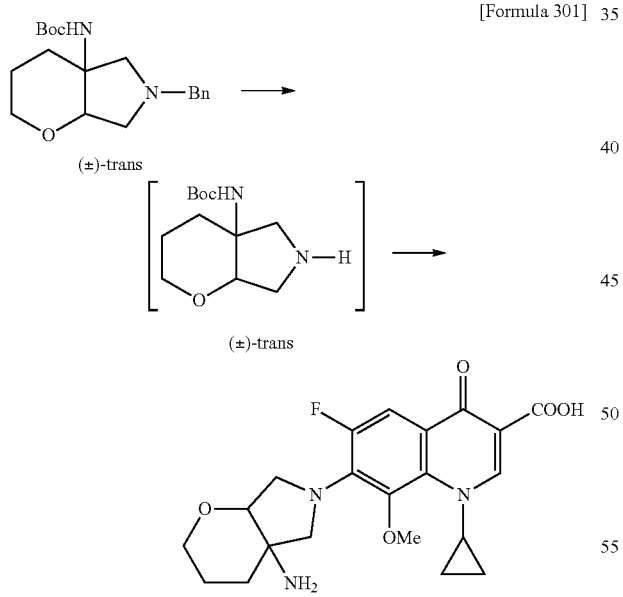

A 10% palladium-carbon catalyst (50% wet, 50 mg) was added to a solution of (1R*,6S*)-8-benzyl-6-(tert-butoxycarbonylamino)-2-oxa-8-azabicyclo[4.3.0]nonane (50 mg, 0.152 mmol) in methanol (10 mL), and the mixture was stirred in a hydrogen atmosphere at room temperature for 1.5 hours. The catalyst was removed by filtration, and then the solvent was evaporated under reduced pressure to give 45 mg of (1R*,6S*)-6-(tert-butoxycarbonylamino)-2-oxa-8-azabicyclo[4.3.0]nonane.

A mixture of the resulting (1R*,6S*)-6-(tert-butoxycarbonylamino)-2-oxa-8-azabicyclo[4.3.0]nonane (45 mg), 1-cyclopropyl-6,7-difluoro-8-methoxy-1,4-dihydro-4-oxoquinoline-3-carboxylic acid-BF$_2$ chelate (572 mg, 1.67 mmol), triethylamine (0.128 mL, 0.92 mmol) and dimethyl sulfoxide (0.5 mL) was stirred on an oil bath at 40° C. for 19 hours. Next, ethanol (16 mL), water (4 mL), and triethylamine (2 mL) were added to the reaction solution, and the mixture was heated to reflux on an oil bath at 110° C. for 2.5 hours. The solvent was evaporated under reduced pressure, and then a 10% citric acid solution (20 mL) was added to the resulting residue, followed by extraction with ethyl acetate (60 mL). The organic layer was washed with water (20 mL×2) and brine (20 mL), dried over anhydrous sodium sulfate, and filtered. Then, the solvent was evaporated under reduced pressure. The resulting residue was dissolved in concentrated hydrochloric acid (10 mL) at room temperature. The resulting acidic solution was transferred to a separatory funnel and then washed with chloroform (5×30 mL, 3×50 mL). The aqueous layer was adjusted to pH 12.0 with a 10 mol/L sodium hydroxide solution under ice-cooling and then adjusted to pH 7.4 with hydrochloric acid. Thereafter, the solvent was evaporated under reduced pressure. The residue was suspended in methanol and filtered, and the filtrate was evaporated under reduced pressure. Then, the residue was again suspended in methanol and filtered, and the filtrate was evaporated under reduced pressure. The resulting residue was purified by PTLC (lower layer solvent of chloroform:methanol:water=7:3:1) and further crystallized using diethyl ether and purified to give 10 mg (16%) of the title compound as a pale yellow powder.

$^1$H-NMR (400 MHz, CDCl$_3$) δ: 8.78 (1H, s), 7.79 (1H, d, J=12.9 Hz), 4.20-3.60 (5H, m), 3.58 (3H, s), 3.50-3.40 (3H, m), 2.02 (2H, m), 1.80-1.60 (2H, m), 1.35-1.05 (3H, m), 0.81 (1H, m).

Anal. Calcd for C$_{21}$H$_{24}$FN$_3$O$_5$.0.25H$_2$O.0.25Et$_2$O: C, 59.99; H, 6.18; N, 9.54. Found: C, 59.94; H, 5.94; N, 9.12.

MS (EI) m/z: 417 (M$^+$).

HRMS (FAB) Calcd for C$_{21}$H$_{24}$FN$_3$O$_5$: 417.1700. Found: 417.1695.

Example 46

(3S)-10-[6-Amino-8-azatricyclo[4.3.0.0$^{1,3}$]nonan-8-yl]-9-fluoro-2,3-dihydro-3-(S)-methyl-7-oxo-7H-pyrido[1,2,3-de][1,4]benzoxazine-6-carboxylic acid

[Formula 302]

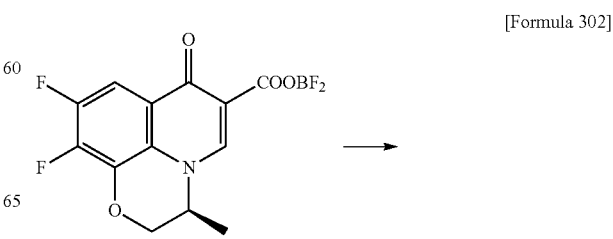

-continued

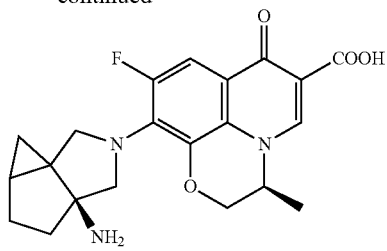

Triethylamine (0.266 ml, 1.91 mmol) and (3S)-9,10-difluoro-2,3-dihydro-3-methyl-7-oxo-7H-pyrido[1,2,3-de][1,4]benzoxazine-6-carboxylic acid-$BF_2$ chelate (209 mg, 0.635 mmol) were added to a solution of 6-tert-butoxycarbonylamino-8-azatricyclo[4.3.0.0$^{1,3}$]nonane (160 mg, 0.666 mmol) in dimethyl sulfoxide (1.27 ml), and the mixture was stirred at 35° C. for 16 hours. A mixed solution of ethanol:water=4:1 (10 ml) and triethylamine (1 ml) were added to the reaction solution, and the mixture was heated to reflux for 2.5 hours. The reaction solution was concentrated under reduced pressure, and then a 10% citric acid solution (40 ml) was added to the residue, followed by extraction with ethyl acetate (50 ml). The interface part was extracted with chloroform. The organic layer was washed with water (40 ml) and brine (40 ml), respectively, dried over anhydrous sodium sulfate, and filtered. The filtrate was concentrated under reduced pressure. The resulting residue was purified by silica gel column chromatography (chloroform:methanol=100:0→99.5:0.5→99:1→98:2→96:4→92:8). The resulting residue (224 mg) was dissolved in concentrated hydrochloric acid (1.5 ml) under ice-cooling, and the solution was stirred at room temperature for 15 minutes. After washing with chloroform (25 ml×3), the aqueous layer was adjusted to pH 12 with a saturated sodium hydroxide solution. The basic solution was adjusted to pH 7.4 with hydrochloric acid, followed by extraction with chloroform (80 ml×3, 60 ml×1). The organic layer was dried over anhydrous sodium sulfate and filtered, and then the filtrate was concentrated under reduced pressure. The residue (190 mg) was dissolved in hot ethanol (about 100 ml), and the insoluble material was removed by filtration through a fluted filter paper. The solvent was gradually evaporated by heating the filtrate with stirring. The solution was concentrated to about 10 to 20 ml and then stirred at room temperature overnight. The precipitated crystals were collected by filtration and washed with ethanol and diethyl ether. The crystals were dried under reduced pressure at 60° C. overnight to give 120 mg of the title compound as pale yellow crystals.

$^1$H-NMR (0.1NNaOD) δ: 8.32 (1H, s), 7.53 (1H, d, J=14.46 Hz), 4.61-4.59 (1H, m), 4.48 (1H, dd, J=11.52, 1.96 Hz), 4.32-4.30 (2H, m), 3.85 (1H, dd, J=10.54, 2.70 Hz), 3.49 (1H, d, J=9.80 Hz), 3.29 (1H, d, J=10.30 Hz), 1.95-1.91 (2H, m), 1.75 (1H, dd, J=12.50, 8.58 Hz), 1.52 (3H, d, J=6.86 Hz), 1.31-1.17 (3H, m), 0.82-0.76 (2H, m).

Anal. Calcd for $C_{21}H_{22}FN_3O_4$: C, 63.15; H, 5.55; F, 4.76; N, 10.52.

Found: C, 62.94; H, 5.53; F, 4.62; N, 10.40.

MS (ESI) m/z: 400 (M+H)$^+$.

IR (ATR): 3370, 2933, 2877, 1708, 1618, 1523, 1463, 1444, 1396, 1353, 1311, 1274, 1228, 1145, 1085, 1045, 985, 970, 956, 860, 831, 800 cm$^{-1}$.

Reference Example 189

(3S)-3-(3-Oxo-1-propyl)-5-oxo-1-[(1R)-1-phenylethyl]pyrrolidine-3-carboxylic acid tert-butyl ester

[Formula 303]

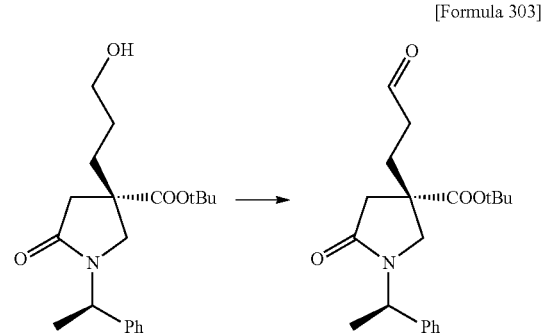

Dichloromethane (35 ml) was cooled with dry ice-methanol in a nitrogen atmosphere. Oxalyl chloride (3.45 ml, 39.5 mmol) and dimethyl sulfoxide (4.68 ml, 66.0 mmol) were added, and the mixture was stirred under cooling for 15 minutes. A solution of (3S)-3-(3-hydroxy-1-propyl)-5-oxo-1-[(1R)-1-phenylethyl]pyrrolidine-3-carboxylic acid tert-butyl ester (4.58 g, 13.2 mmol) in dichloromethane (31 mL) was added, and the mixture was stirred under cooling for one hour. Triethylamine (11.1 ml, 79.5 mmol) was added under cooling, and the mixture was stirred under cooling for one hour and then at room temperature for one hour. A saturated ammonium chloride solution (100 ml) was added to the reaction solution, followed by extraction with chloroform (100 ml×1, 80 ml×1). The organic layer was washed with brine (120 ml) and then dried over anhydrous sodium sulfate. After filtration, the filtrate was concentrated under reduced pressure. The resulting residue was purified by silica gel column chromatography (hexane:ethyl acetate=100:0→90:10→66:34→60:40→50:50→40:60→34:66→25:75) to give 4.59 g of the title compound as white crystals.

$^1$H-NMR (CDCl$_3$) δ: 9.76 (1H, s), 7.35-7.24 (5H, m), 5.49 (1H, q, J=7.19 Hz), 3.34 (1H, d, J=10.05 Hz), 3.13 (1H, d, J=10.05 Hz), 2.94 (1H, d, J=16.91 Hz), 2.44 (2H, dt, J=11.52, 4.72 Hz), 2.29 (1H, d, J=16.91 Hz), 2.12-2.05 (1H, m), 1.99-1.91 (1H, m), 1.52 (3H, d, J=7.11 Hz), 1.32 (9H, s).

MS (ESI) m/z: 346 (M+H)$^+$.

Reference Example 190

(3S)-3-(3-Oxo-2-methylene-1-propyl)-5-oxo-1-[(1R)-1-phenylethyl]pyrrolidine-3-carboxylic acid tert-butyl ester

[Formula 304]

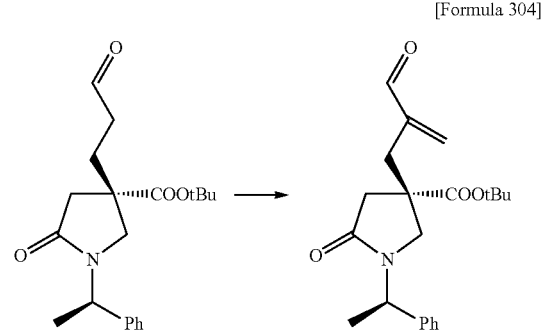

1,8-Diazabicyclo[5.4.0]-7-undecene (2.17 ml, 14.5 mmol) and Eschenmoser salt (3.66 g, 19.8 mmol) were added to a solution of (3S)-3-(3-oxo-1-propyl)-5-oxo-1-[(1R)-1-phenylethyl]pyrrolidine-3-carboxylic acid tert-butyl ester in dichloromethane (88.0 ml) in a nitrogen atmosphere, and the mixture was stirred at room temperature for 16 hours. Thereafter, Eschenmoser salt (1.22 g, 6.59 mmol) was added, and the mixture was stirred at room temperature for three hours. A saturated ammonium chloride solution (150 ml) was added to the reaction solution, followed by extraction with chloroform (100 ml×1, 150 ml×1). The organic layer was washed with brine (200 ml) and then dried over anhydrous sodium sulfate. After filtration, the filtrate was concentrated under reduced pressure. The resulting residue was purified by silica gel column chromatography (hexane:ethyl acetate=100:0→90: 10→66:34→60:40→50:50→34:66) to give 3.14 g of the title compound as white crystals.

$^1$H-NMR (CDCl$_3$) δ: 9.51 (1H, s), 7.34-7.24 (5H, m), 6.31 (1H, s), 6.12 (1H, s), 5.47 (1H, q, J=7.08 Hz), 3.31 (1H, d, J=10.50 Hz), 3.22 (1H, d, J=10.25 Hz), 2.89 (1H, d, J=17.09 Hz), 2.75-2.64 (2H, m), 2.41 (1H, d, J=17.09 Hz), 1.51 (3H, d, J=7.08 Hz), 1.30 (9H, s).

MS (ESI) m/z: 358 (M+H)$^+$.

Reference Example 191

(3S)-3-(3-Hydroxy-2-methylene-1-propyl)-5-oxo-1-[(1R)-1-phenylethyl]pyrrolidine-3-carboxylic acid tert-butyl ester

[Formula 305]

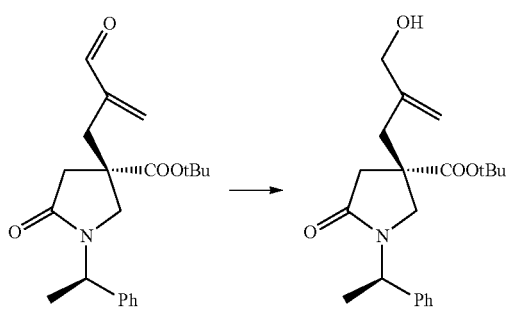

Ethanol (43.9 ml) was added to sodium borohydride (644 mg, 17.0 mmol) in a nitrogen atmosphere, and the mixture was cooled with ice-acetone. Cerium chloride heptahydrate (6.55 g, 17.6 mmol) and (3S)-3-(3-oxo-2-methylene-1-propyl)-5-oxo-1-[(1R)-1-phenylethyl]pyrrolidine-3-carboxylic acid tert-butyl ester (3.14 g, 6.55 mmol) were added under cooling. The mixture was stirred under cooling for one hour, and then cerium chloride heptahydrate (1.64 g, 4.40 mmol) and sodium borohydride (166 mg, 4.39 mmol) were added. The mixture was stirred under cooling for 30 minutes and then ice-cooled. A saturated ammonium chloride solution (150 ml) was added to the reaction solution. The mixture was concentrated under reduced pressure and ethanol was removed. The mixture was extracted with ethyl acetate (150 ml×1, 100 ml×1). The organic layer was washed with brine (200 ml) and then dried over anhydrous sodium sulfate. After filtration, the filtrate was concentrated under reduced pressure. The resulting residue was purified by silica gel column chromatography (hexane:ethyl acetate=100:0→90:10→66: 34→50:50→34:66→25:75→17:83→5:95) to give 2.83 g of the title compound.

$^1$H-NMR (CDCl$_3$) δ: 7.35-7.23 (5H, m), 5.49 (1H, q, J=7.11 Hz), 5.15 (1H, d, J=1.23 Hz), 4.87 (1H, d, J=1.23 Hz), 3.98 (2H, d, J=6.37 Hz), 3.33 (1H, d, J=10.30 Hz), 3.22 (1H, d, J=10.30 Hz), 2.94 (1H, d, J=17.16 Hz), 2.62 (1H, d, J=14.95 Hz), 2.46 (1H, d, J=15.44 Hz), 2.44 (1H, d, J=17.16 Hz), 1.72 (1H, t, J=6.25 Hz), 1.52 (3H, d, J=7.11 Hz), 1.32 (9H, s).

MS (ESI) m/z: 360 (M+H)$^+$.

Reference Example 192

(3S)-3-(3-Bromo-2-methylene-1-propyl)-5-oxo-1-[(1R)-1-phenylethyl]pyrrolidine-3-carboxylic acid tert-butyl ester

[Formula 306]

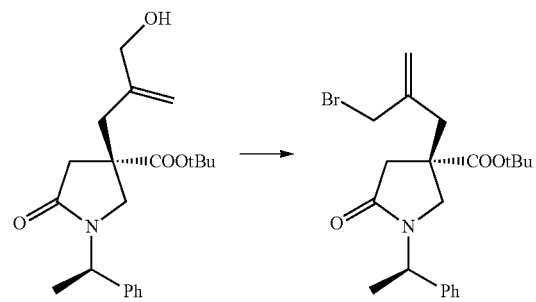

Carbon tetrabromide (3.24 g, 9.77 mmol) and triphenylphosphine (2.57 g, 9.80 mmol) were added to a solution of (3S)-3-(3-hydroxy-2-methylene-1-propyl)-5-oxo-1-[(1R)-1-phenylethyl]pyrrolidine-3-carboxylic acid tert-butyl ester in dichloromethane (113 ml) under ice water-cooling in a nitrogen atmosphere. The mixture was stirred under ice water-cooling for 15 minutes and then concentrated under reduced pressure to remove the solvent. The resulting residue was purified by silica gel column chromatography (hexane: ethyl acetate=100:0→95:5→90:10→80:20→75:25→66:34) to give 3.22 g of the title compound as white crystals.

$^1$H-NMR (CDCl$_3$) δ: 7.34-7.22 (5H, m), 5.48 (1H, q, J=7.19 Hz), 5.26 (1H, s), 4.89 (1H, s), 3.88 (2H, s), 3.36 (1H, d, J=10.05 Hz), 3.21 (1H, d, J=10.30 Hz), 2.99 (1H, d, J=16.91 Hz), 2.72 (1H, d, J=15.44 Hz), 2.57 (1H, d, J=15.44 Hz), 2.44 (1H, d, J=16.91 Hz), 1.51 (3H, d, J=7.35 Hz), 1.30 (9H, s).

MS (ESI) m/z: 422 (M$^+$).

Reference Example 193

[(1S,5S)-7-Methylene-4-oxo-3-[(1R)-1-phenylethyl]-3-aza-bicyclo[3.3.0]octan-1-yl]carboxylic acid tert-butyl ester

[Formula 307]

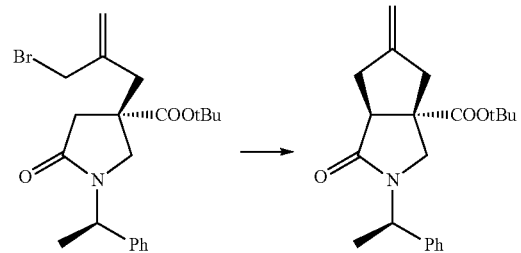

A 1 M solution of lithium hexamethyldisilazide in THF (9.15 ml, 9.15 mmol) was added to a solution of (3S)-3-(3-bromo-2-methylene-1-propyl)-5-oxo-1-[(1R)-1-phenylethyl]pyrrolidine-3-carboxylic acid tert-butyl ester (3.22 g, 7.62 mmol) in tetrahydrofuran (76.2 ml) under cooling with ice-acetone in a nitrogen atmosphere, and the mixture was stirred for 10 minutes. A 10% citric acid solution (120 ml) was added to the reaction solution, followed by extraction with ethyl acetate (100 ml×2). The organic layer was washed with brine (200 ml) and dried over anhydrous sodium sulfate. After filtration, the filtrate was concentrated under reduced pressure. The resulting residue was purified by silica gel column chromatography (hexane:ethyl acetate=100:0→95:5→90:10→83:17→80:20→75:25) to give 2.47 g of the title compound as white crystals.

¹H-NMR (CDCl₃) δ: 7.34-7.23 (5H, m), 5.46 (1H, q, J=7.11 Hz), 4.88 (2H, d, J=1.72 Hz), 3.31 (1H, d, J=10.30 Hz), 3.13 (2H, t, J=6.37 Hz), 3.08 (2H, d, J=10.30 Hz), 2.89 (1H, d, J=15.69 Hz), 2.72 (2H, d, J=6.13 Hz), 2.30 (1H, d, J=15.93 Hz), 1.47 (3H, d, J=7.11 Hz), 1.35 (9H, s).

MS (ESI) m/z: 342 (M+H)⁺.

Reference Example 194

[(1S,5S)-7-Methylene-4-oxo-3-[(1R)-1-phenylethyl]-3-azabicyclo[3.3.0]octan-1-yl]carboxylic acid

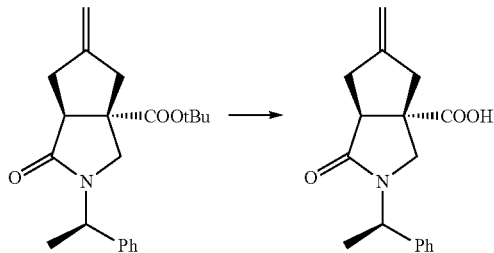

[Formula 308]

Trifluoroacetic acid (26.0 ml) was added to a solution of [(1S,5S)-7-methylene-4-oxo-3-[(1R)-1-phenylethyl]-3-azabicyclo[3.3.0]octan-1-yl]carboxylic acid tert-butyl ester (2.47 g, 8.66 mmol) in dichloromethane (26.0 ml) with stirring under ice-cooling, and the mixture was stirred at room temperature for one hour. The reaction solution was concentrated under reduced pressure, and trifluoroacetic acid was azeotropically distilled with toluene (×3). A 1 mol/l sodium hydroxide solution (15.0 ml) was added to the resulting residue under ice-cooling, and the mixture was washed with diethyl ether (60 ml×2). The aqueous layer was made acidic with 6 mol/l hydrochloric acid (4 ml) under ice-cooling, followed by extraction with ethyl acetate (100 ml×2). The organic layers were combined, washed with water (100 mL) and brine (100 ml), and dried over anhydrous sodium sulfate. After filtration, the filtrate was concentrated under reduced pressure to give 2.15 g of the title compound as white crystals.

¹H-NMR (CDCl₃) δ: 7.36-7.24 (5H, m), 5.48 (1H, q, J=7.03 Hz), 4.93 (2H, s), 3.40 (1H, d, J=10.30 Hz), 3.27 (1H, dd, J=7.48, 4.78 Hz), 3.16 (1H, d, J=10.54 Hz), 3.02 (1H, d, J=15.93 Hz), 2.77 (2H, d, J=5.39 Hz), 2.38 (1H, d, J=15.93 Hz), 1.50 (3H, d, J=7.11 Hz).

MS (ESI) m/z: 342 (M+H)⁺.

Reference Example 195

(1S,5S)-1-Amino-7-methylene-4-oxo-3-[(1R)-1-phenylethyl]-3-azabicyclo[3.3.0]octane

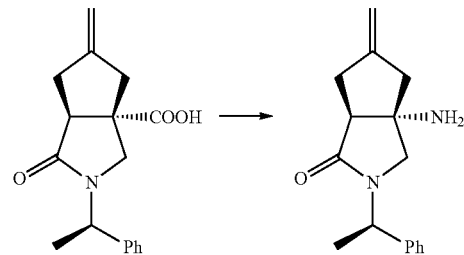

[Formula 309]

Triethylamine (0.489 ml, 3.50 mmol) and diphenylphosphoryl azide (0.491 ml, 2.28 mmol) were added to a solution of [(1S,5S)-7-methylene-4-oxo-3-[(1R)-1-phenylethyl]-3-azabicyclo[3.3.0]octan-1-yl]carboxylic acid (500 mg, 1.75 mmol) in toluene (8.75 ml) in a nitrogen atmosphere with stirring under ice-cooling. The mixture was stirred at room temperature for 30 minutes and then at 100° C. for 30 minutes. The reaction solution was concentrated under reduced pressure, and triethylamine was azeotropically removed with toluene (×3). 1,4-Dioxane (4.37 ml) and 6 mol/L hydrochloric acid (4.37 ml) were added to the resulting residue, and the mixture was stirred at 50° C. for one hour. The reaction solution was diluted with water (18.0 ml) and washed with diethyl ether (60 ml×2). The aqueous layer was made alkaline with a 1 mol/l sodium hydroxide solution, followed by extraction with chloroform (80 ml×1, 70 ml×1). The organic layer was washed with water (80 ml) and brine (80 ml) and dried over anhydrous sodium sulfate. After filtration, the filtrate was concentrated under reduced pressure to give 238 mg of the title compound.

¹H-NMR (CDCl₃) δ: 7.38-7.24 (5H, m), 5.53 (1H, q, J=7.11 Hz), 4.92 (2H, brs), 3.25 (1H, d, J=10.05 Hz), 2.79-2.73 (3H, m), 2.58 (1H, dd, J=9.44, 4.04 Hz), 2.40 (2H, dd, J=35.17, 15.57 Hz), 1.48 (3H, d, J=7.11 Hz).

MS (ESI) m/z: 257 (M+H)⁺.

Reference Example 196

(1S,5R)-1-Amino-7-methylene-3-[(1R)-1-phenylethyl]-3-azabicyclo[3.3.0]octane

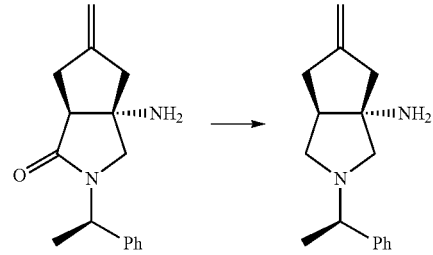

[Formula 310]

A 65% solution of sodium bis(2-methoxyethoxy)aluminum hydride in toluene (0.539 ml, 1.79 mmol) was added to a solution of (1S,5S)-1-amino-7-methylene-4-oxo-3-[(1R)-1-phenylethyl]-3-azabicyclo[3.3.0]octane (115 mg, 0.449 mmol) in toluene (2.24 ml), and the mixture was stirred at room temperature for 30 minutes and at 80° C. for 30 minutes. A 5 mol/l sodium hydroxide solution (15.0 ml) was added to the reaction solution with stirring under ice-cooling, followed by extraction with toluene (30 ml×1, 20 ml×1). The organic layer was washed with brine and dried over anhydrous sodium sulfate. After filtration, the filtrate was concentrated under reduced pressure to give 106 mg of the title compound.

$^1$H-NMR (CDCl$_3$) δ: 7.38-7.19 (5H, m), 4.80-4.78 (2H, m), 3.14 (1H, q, J=6.45 Hz), 2.78 (1H, t, J=8.21 Hz), 2.65-2.56 (2H, m), 2.47 (1H, d, J=14.71 Hz), 2.33 (1H, d, J=9.07 Hz), 2.22 (1H, d, J=14.95 Hz), 2.13-2.06 (3H, m), 1.31 (3H, d, J=6.62 Hz).

MS (ESI) m/z: 243 (M+H)$^+$.

Reference Example 197

(1S,5R)-1-tert-Butoxycarbonylamino-7-methylene-3-[(1R)-1-phenylethyl]-3-azabicyclo[3.3.0]octane

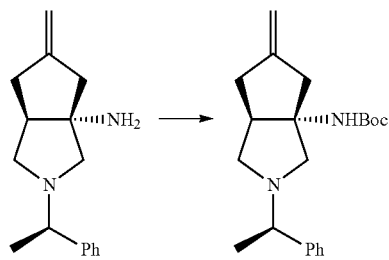

[Formula 311]

Di-tert-butyl dicarbonate (191 mg, 0.875 mmol) was added to a solution of (1S,5R)-1-amino-7-methylene-3-[(1R)-1-phenylethyl]-3-azabicyclo[3.3.0]octane (106 mg, 0.437 mmol) in dichloromethane (2.18 ml) in a nitrogen atmosphere, and the mixture was stirred at room temperature for 22 hours. The reaction solution was concentrated under reduced pressure. The resulting residue was purified by silica gel column chromatography (hexane:ethyl acetate=100:0→95:5→90:10→88:12→84:16→80:20→75:25) to give 203 mg of the title compound as a transparent oil.

$^1$H-NMR (CDCl$_3$) δ: 7.29-7.22 (5H, m), 4.86 (1H, brs), 4.79 (2H, d, J=7.84 Hz), 3.16 (1H, q, J=6.45 Hz), 2.92 (1H, d, J=9.07 Hz), 2.76 (4H, t, J=8.58 Hz), 2.67-2.57 (4H, m), 2.40 (2H, d, J=9.56 Hz), 2.08-1.99 (2H, m), 1.43 (9H, s), 1.31 (3H, d, J=6.62 Hz).

MS (ESI) m/z: 343 (M+H)$^+$.

Reference Example 198

(1S,5R)-3-Benzyloxycarbonyl-1-tert-butoxycarbonylamino-7-methylene-3-azabicyclo[3.3.0]octane

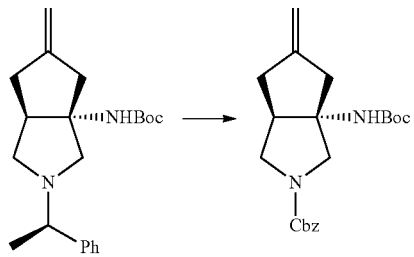

[Formula 312]

Benzyl chloroformate (0.250 ml, 1.75 mmol) was added to a solution of the residue containing (1S,5R)-1-tert-butoxycarbonylamino-7-methylene-3-[(1R)-1-phenylethyl]-3-azabicyclo[3.3.0]octane (200 mg, equivalent to 0.437 mmol) in dichloromethane (1.94 ml) in a nitrogen atmosphere, and the mixture was stirred at room temperature for 15 hours and at 40° C. for four hours. The reaction solution was concentrated under reduced pressure. The residue was purified by silica gel column chromatography (hexane:ethyl acetate=100:0→95:5→90:10→87:13→86:14→83:17→80:20→75:25) to give 95.1 mg of the title compound as a transparent oil.

$^1$H-NMR (CDCl$_3$) δ: 7.36-7.30 (7H, m), 5.12 (2H, s), 4.92 (2H, d, J=8.82 Hz), 4.67 (1H, brs), 3.74-3.72 (2H, m), 3.56 (1H, d, J=11.77 Hz), 3.27-3.24 (1H, m), 2.72-2.68 (4H, m), 2.19-2.17 (1H, m), 1.43 (9H, s).

MS (ESI) m/z: 373 (M+H)$^+$.

Reference Example 199

(1S,5R)-3-Benzyloxycarbonyl-1-tert-butoxycarbonylaminospiro(3-azabicyclo[3.3.0]octane-7,1'-cyclopropane)

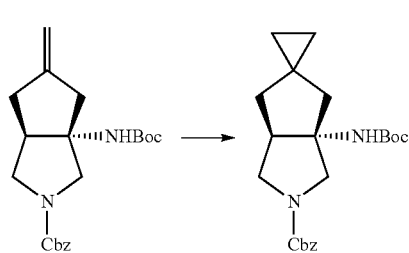

[Formula 313]

N-Methyl-N'-nitro-N-nitrosoguanidine (50% mixture with water, 6 g) was added to a two-layer solution of a 40% potassium hydroxide solution (18 ml) and diethyl ether (60 ml) in an open system under ice water-cooling to prepare a solution of diazomethane in diethyl ether.

Palladium acetate (5.26 mg, 0.0234 mmol) was added to (1S,5R)-3-benzyloxycarbonyl-1-tert-butoxycarbonylamino-7-methylene-3-azabicyclo[3.3.0]octane (175 mg, 0.469 mmol) in diethyl ether (4.69 ml) in an open system under ice-cooling. The previously prepared solution of diazomethane in diethyl ether (20 ml) was slowly added to this solution under ice-cooling, and the mixture was stirred at room temperature for 16 hours. After filtration through Celite, the filtrate was concentrated under reduced pressure. The residue was purified by silica gel column chromatography (hexane:ethyl acetate=100:0→95:5→90:10→88:12→87:13→86:14→85:15→83:17→80:20→75:25) to give 138 mg of the title compound as a transparent oil.

$^1$H-NMR (CDCl$_3$) δ: 7.38-7.28 (5H, m), 5.13 (2H, s), 4.80 (1H, d, J=9.31 Hz), 3.77-3.72 (3H, m), 3.37-3.35 (1H, m), 2.66 (1H, s), 2.05-1.97 (3H, m), 1.60 (1H, s), 1.43 (10H, s), 0.47-0.46 (4H, m).

MS (ESI) m/z: 387 (M+H)$^+$.

Reference Example 200

(1S,5R)-1-tert-Butoxycarbonylaminospiro(3-azabicyclo[3.3.0]octane-7,1'-cyclopropane)

[Formula 314]

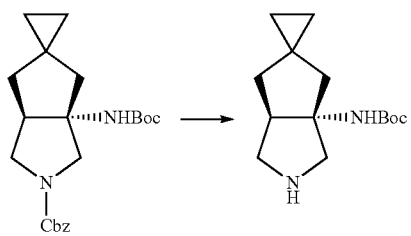

A 10% palladium-carbon catalyst (45.6 mg, 30 wt %) was added to a solution of (1S,5R)-3-benzyloxycarbonyl-1-tert-butoxycarbonylaminospiro(3-azabicyclo[3.3.0]octane-7,1'-cyclopropane) (152 mg, 0.393 mmol) in methanol (3.93 ml) in a nitrogen atmosphere. After the atmosphere was replaced with hydrogen, the mixture was stirred at room temperature for 30 minutes. After the atmosphere was replaced with nitrogen, the reaction solution was filtered through Celite and concentrated under reduced pressure to give 97.9 mg of the title compound as a transparent oil.

MS (ESI) m/z: 253 (M+H)$^+$.

Example 47

7-[(1S,5R)-1-Aminospiro(3-azabicyclo[3.3.0]octane-7,1'-cyclopropane)-3-yl]-6-fluoro-1-[(1R,2S)-2-fluorocyclopropan-1-yl]-8-methoxy-4-oxo-1,4-dihydroquinoline-3-carboxylic acid

[Formula 315]

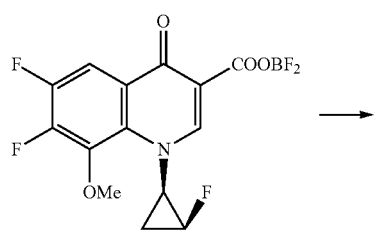

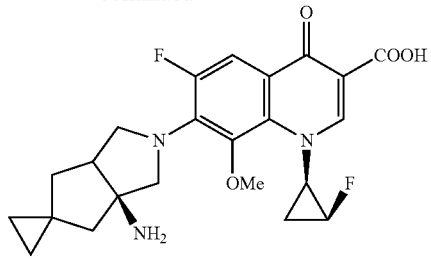

Triethylamine (0.162 ml, 0.388 mmol) and 1-[(1R,2S)-2-fluorocyclopropan-1-yl]-6,7-difluoro-8-methoxy-1,4-dihydro-4-oxoquinoline-3-carboxylic acid-BF$_2$ chelate (140 mg, 0.388 mmol) were added to a solution of (1S,5R)-1-tert-butoxycarbonylaminospiro(3-azabicyclo[3.3.0]octane-7,1'-cyclopropane) (97.9 mg, 0.388 mmol) in dimethyl sulfoxide (0.776 ml), and the mixture was stirred at 35° C. for 14 hours. A mixed solution of ethanol:water=4:1 (10.0 ml) and triethylamine (1.0 ml) were added to the reaction solution, and the mixture was heated to reflux for one hour. The reaction solution was concentrated under reduced pressure. The residue was dissolved in ethyl acetate (30 ml) and washed with a 10% citric acid solution (30 ml), water (30 ml), and brine (30 ml). The organic layer was dried over anhydrous sodium sulfate and then filtered, and the filtrate was concentrated under reduced pressure. The resulting residue was purified by silica gel column chromatography (chloroform:methanol=100:0→99:1→98:2). The resulting residue (165 mg) was dissolved in concentrated hydrochloric acid (1.0 ml) under ice-cooling, and the solution was stirred at room temperature for 15 minutes. After washing with chloroform (25 ml×3), the aqueous layer was adjusted to pH 12 with a saturated sodium hydroxide solution. The basic solution was adjusted to pH 7.4 with hydrochloric acid, followed by extraction with chloroform (80 ml×5) and chloroform/methanol=10/1 (60 ml×1). The organic layer was dried over anhydrous sodium sulfate and filtered, and then the filtrate was concentrated under reduced pressure. The resulting residue was dissolved in hot ethanol (20 ml), and the insoluble material was removed by filtration through a fluted filter paper. The solvent was gradually evaporated by heating the filtrate with stirring. The solution was concentrated to about 5 ml and then stirred at room temperature overnight. The precipitated crystals were collected by filtration and washed with ethanol and diethyl ether. The crystals were dried under reduced pressure at 50° C. overnight to give 86.0 mg of the title compound as pale yellow crystals.

$^1$H-NMR (0.1NNaOD) δ: 8.46 (1H, s), 7.70 (1H, d, J=14.15 Hz), 5.06-5.04 (1H, m), 4.09-4.04 (1H, m), 3.92-3.86 (1H, m), 3.70-3.68 (4H, m), 3.58 (1H, d, J=10.73 Hz), 3.53-3.49 (1H, m), 2.54-2.46 (1H, m), 2.15-2.09 (1H, m), 1.86-1.76 (2H, m), 1.67-1.46 (3H, m), 0.57-0.45 (4H, m).

Anal. Calcd for C$_{23}$H$_{25}$F$_2$N$_3$O$_4$0.5H$_2$O: C, 60.79; H, 5.77; F, 8.36; N, 9.25.

Found: C, 60.82; H, 5.73; F, 8.17; N, 9.23.

MS (ESI) m/z: 446 (M+H)$^+$.

IR (ATR): 2931, 2850, 1725, 1616, 1508, 1434, 1342, 1315, 1270, 1209, 1186, 1120, 1052, 1014, 987, 927, 881, 850, 806, 746 cm$^{-1}$.

Example 48

7-[(1S,5R)-1-Amino-3-azabicyclo[3.3.0]octan-3-yl]-1-cyclopropyl-6,8-difluoro-1,4-dihydro-4-oxoquinoline-3-carboxylic acid

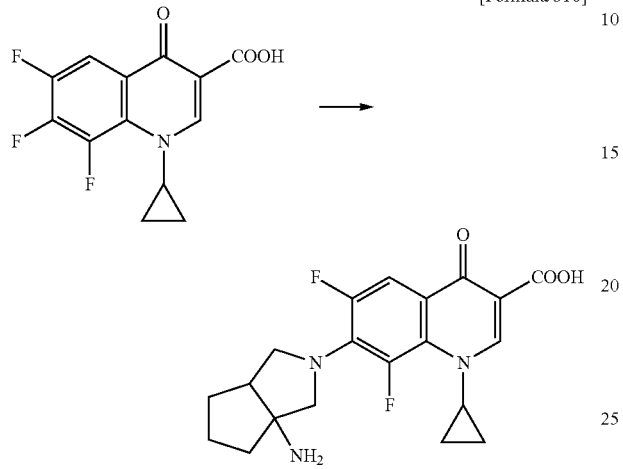

[Formula 316]

A 10% palladium-carbon catalyst (M, about 50% wet, 72.6 mg) was added to a solution of (+)-(1S,5R)-3-benzyloxycarbonyl-1-tert-butoxycarbonylamino-3-azabicyclo[3.3.0]octane (363 mg, 1.01 mmol) in methanol (10.1 ml), and the mixture was stirred in a hydrogen atmosphere in a rubber balloon at room temperature for 45 minutes. The catalyst was removed by filtration, and then the solvent was evaporated under reduced pressure to give 229 mg of a residue containing (1S,5R)-1-(tert-butoxycarbonylamino)-3-azabicyclo[3.3.0]octane as a colorless transparent gummy solid.

Triethylamine (0.423 ml, 3.03 mmol) and 1-cyclopropyl-6,7,8-trifluoro-8-methoxy-1,4-dihydro-4-oxoquinoline-3-carboxylic acid (272 mg, 0.960 mmol) were added to a solution of the residue containing (1S,5R)-1-tert-butoxycarbonylamino-3-azabicyclo[3.3.0]octane obtained above (229 mg) in acetonitrile (3.84 ml) in a nitrogen atmosphere, and the mixture was heated to reflux for six hours. The reaction solution was ice-cooled, and then the precipitated crystals were collected by filtration and washed with acetonitrile and diethyl ether. The crystals were dried under reduced pressure at 50° C. overnight. The resulting residue (410 mg) was dissolved in concentrated hydrochloric acid (3 ml) under ice-cooling, and then the solution was stirred at room temperature for 15 minutes. After washing with chloroform (40 ml×3), the aqueous layer was adjusted to pH 12 with a saturated sodium hydroxide solution. The basic solution was adjusted to pH 7.4 with hydrochloric acid, followed by extraction with chloroform (80 ml×2) and chloroform/methanol=10/1 (100 ml×6). The organic layer was dried over anhydrous sodium sulfate and filtered, and then the filtrate was concentrated under reduced pressure. Hot ethanol (150 ml) and 28% aqueous ammonia (3 to 5 ml) were added to the residue, and the insoluble material was removed by filtration through a fluted filter paper. The solvent was gradually evaporated while heating with stirring. Ammonia was azeotropically removed with ethanol several times. The solution was concentrated to about 10 ml and then stirred at room temperature for four hours. The precipitated crystals were collected by filtration and washed with ethanol and diethyl ether. The crystals were dried under reduced pressure at 45° C. overnight to give 289 mg of the title compound as pale yellow crystals.

$^1$H-NMR (0.1NNaOD) δ: 8.44 (1H, s), 7.62 (1H, d, J=13.73 Hz), 3.97-3.86 (2H, m), 3.59 (1H, d, J=10.30 Hz), 3.49 (1H, d, J=10.30 Hz), 3.32 (1H, d, J=5.64 Hz), 2.31-2.26 (1H, m), 2.02 (1H, dt, J=20.43, 7.48 Hz), 1.90-1.84 (1H, m), 1.81-1.74 (2H, m), 1.70-1.63 (1H, m), 1.51-1.48 (1H, m), 1.19 (2H, t, J=7.11 Hz), 1.07 (2H, s).

Anal. Calcd for $C_{20}H_{21}F_2N_3O_3 \cdot 0.75H_2O$: C, 59.62; H, 5.63; F, 9.43; N, 10.43.

Found: C, 59.69; H, 5.58; F, 9.31; N, 10.35.

MS (ESI) m/z: 390 (M+H)$^+$.

IR (ATR): 2956, 1612, 1573, 1542, 1508, 1459, 1402, 1351, 1317, 1274, 1201, 1166, 1106, 1031, 979, 817, 732 cm$^{-1}$.

Reference Example 201

(3S,4S)-3-Allyl-4-(tert-butyldimethylsilyloxy)methyl-2-oxo-1-[(1R)-1-phenylethyl]pyrrolidine

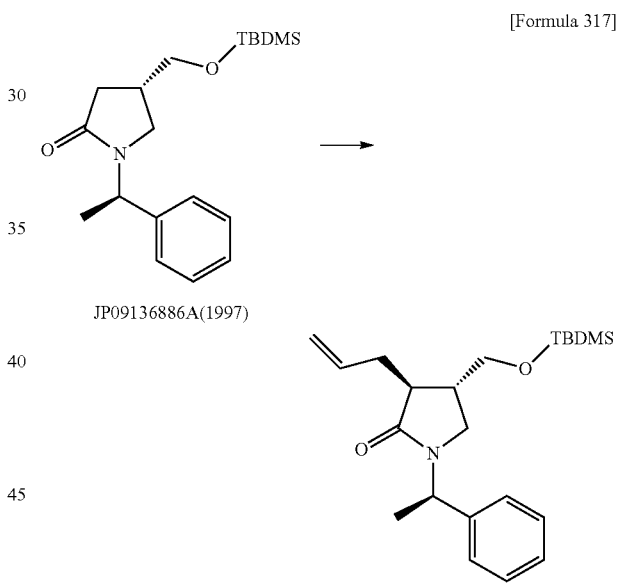

[Formula 317]

JP09136886A(1997)

(4S)-4-(tert-Butyldimethylsilyloxy)methyl-2-oxo-1-[(1R)-1-phenylethyl]pyrrolidine (333.5 g, 1.00 mol) and allyl bromide (90.9 mL, 1.05 mol) were dissolved in tetrahydrofuran (1.10 L). Lithium hexamethyldisilazide (1.0 M solution in tetrahydrofuran) (1.10 L, 1.10 mol) was added dropwise at −15° C., and the mixture was stirred at −5° C. for one hour. The reaction solution was extracted with a saturated ammonium chloride solution and ethyl acetate. Then, the organic layer was washed with brine and dried over anhydrous sodium sulfate. Thereafter, the solvent was evaporated under reduced pressure. The residue was subjected to silica gel column chromatography (hexane:ethyl acetate=4:1→2:1) to give 327 g of the title compound as a colorless syrup.

$^1$H-NMR (400 MHz, CDCl$_3$) δ: 7.42-7.32 (5H, m), 5.93-5.80 (1H, m), 5.57 (1H, q, J=7.1 Hz), 5.22-5.12 (2H, m), 3.56 (1H, dd, J=10.0, 4.9 Hz), 3.48-3.43 (1H, m), 3.34 (1H, dd, J=10.3, 8.1 Hz), 2.82 (1H, dd, J=9.8, 5.9 Hz), 2.65-2.57 (1H, m), 2.48-2.40 (2H, m), 2.32-2.24 (1H, m), 1.59 (3H, d, J=7.6 Hz), 0.86 (9H, s), 0.00 (6H, s).

Reference Example 202

(3S,4S)-3-Allyl-4-(tert-butyldimethylsilyloxy)methyl-1-[(1R)-1-phenylethyl]pyrrolidine

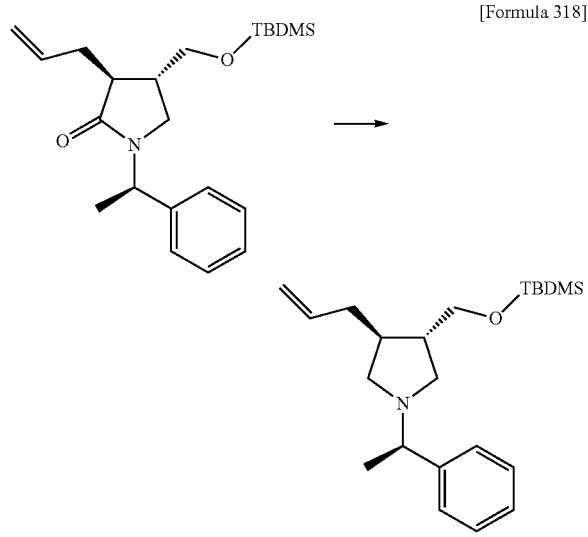

[Formula 318]

A 65% solution of Red-Al™ in toluene (788 mL, 2.63 mol) was added dropwise to a solution of (3S,4S)-3-allyl-4-(tert-butyldimethylsilyloxy)methyl-2-oxo-1-[(1R)-1-phenylethyl]pyrrolidine (327 g, 875 mmol) in toluene (1500 mL) in a nitrogen atmosphere over one hour. The reaction solution was stirred at 45° C. for five hours and then cooled to 0° C., and a 20% (+)-potassium sodium tartrate tetrahydrate solution (2.00 L) was added. The reaction solution was poured into a mixture of ethyl acetate and brine, followed by extraction with ethyl acetate. The organic layer was washed with brine, dried over anhydrous sodium sulfate, and then concentrated under reduced pressure. The resulting residue was purified by silica gel column chromatography (hexane:ethyl acetate=20:1→4:1) to give 213 g of the title compound as a colorless syrup.

$^1$H-NMR (400 MHz, CDCl$_3$) δ: 7.29-7.10 (5H, m), 5.73-5.63 (1H, m), 4.97-4.87 (2H, m), 3.49 (2H, d, J=6.8 Hz), 3.09 (1H, q, J=6.6 Hz), 2.57-2.49 (2H, m), 2.39 (1H, t, J=8.5 Hz), 2.20-2.13 (1H, m), 2.09-2.00 (2H, m), 1.91-1.83 (1H, m), 1.78-1.68 (1H, m), 1.28 (3H, d, J=6.6 Hz), 0.85 (9H, s), 0.27 (6H, d, J=1.0 Hz).

Reference Example 203

(3S,4S)-3-Allyl-1-benzyloxycarbonyl-4-hydroxymethylpyrrolidine

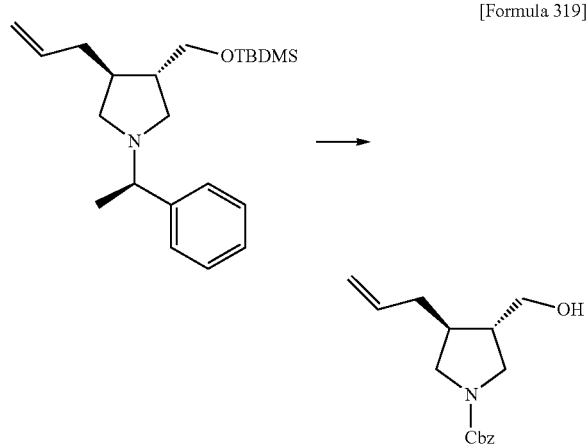

[Formula 319]

(3S,4S)-3-Allyl-4-(tert-butyldimethylsilyloxy)methyl-1-[(1R)-1-phenylethyl]pyrrolidine (213 g, 592 mmol) was dissolved in dichloromethane (420 mL). Benzyl chloroformate (169.2 mL, 1.19 mol) was added dropwise, and the mixture was stirred at 55° C. for 10 hours and then at room temperature for 14 hours. A 1 M solution of hydrochloric acid in ethanol (250 mL, 250 mmol) was further added to the reaction solution, and the mixture was stirred at room temperature for 24 hours. The reaction solution was extracted with a saturated sodium bicarbonate solution and ethyl acetate. Then, the organic layer was washed with brine, dried over anhydrous sodium sulfate, and then concentrated under reduced pressure. The resulting residue was purified by silica gel column chromatography (hexane:ethyl acetate=10:1→1:1) to give 140 g of the title compound as a pale yellow oil.

$^1$H-NMR (400 MHz, CDCl$_3$) δ: 7.38-7.25 (5H, m), 5.75 (1H, brs), 5.13-5.02 (4H, m), 3.76-3.54 (4H, m), 3.31-3.23 (1H, m), 3.15-3.07 (1H, m), 2.32-2.26 (1H, m), 2.14-2.03 (3H, m).

Reference Example 204

(3S,4S)-4-Allyl-1-benzyloxycarbonylpyrrolidine-3-carboxylic acid tert-butyl ester

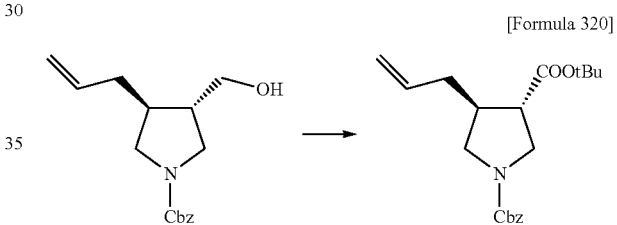

[Formula 320]

Oxalyl dichloride (48.0 mL, 559 mmol) was dissolved in dichloromethane (1000 mL). Dimethyl sulfoxide (39.7 mL, 559 mmol) was added dropwise at −70° C., and the mixture was stirred for 15 hours. A solution of (3S,4S)-3-allyl-1-benzyloxycarbonyl-4-hydroxymethylpyrrolidine (140 g, 508 mmol) in dichloromethane (400 mL) was added dropwise to the reaction solution, and the mixture was stirred for 50 minutes. Triethylamine (354 mL, 2.54 mol) was added dropwise to the reaction solution, and then the mixture was stirred at −10° C. for 10 minutes. The reaction solution was extracted with water and dichloromethane. Then, the organic layer was washed with brine, dried over anhydrous magnesium sulfate, and concentrated under reduced pressure.

The resulting residue was dissolved in a mixed solution of tert-butyl alcohol (250 mL) and tetrahydrofuran (750 mL). 2-Methyl-2-butene (538 mL, 5.08 mol) was added and then a suspension of sodium chlorite (60.3 g, 533 mmol) and sodium dihydrogenphosphate dihydrate (238 g, 1.52 mol) in water (250 ml) was added at 0° C., and the mixture was stirred at room temperature for 20 hours. The reaction solution was concentrated under reduced pressure, and then a 1N hydrochloric acid solution was added, followed by extraction with diethyl ether. The organic layer was washed with a 5% sodium thiosulfate solution and brine, and then dried over anhydrous magnesium sulfate and concentrated under reduced pressure.

The resulting residue was dissolved in dichloromethane (1000 mL). N,N'-Diisopropyl-O-tert-butylisourea (509 g, 2.54 mol) was added dropwise, and the mixture was stirred at 50° C. for four hours and then at room temperature for 15 hours. The precipitated solid was filtered off, and then the filtrate was concentrated under reduced pressure. The resulting residue was purified by silica gel column chromatography (hexane:ethyl acetate=10:1→4:1) to give 126 g of the title compound as a colorless oil.

$^1$H-NMR (400 MHz, CDCl$_3$) δ: 7.36-7.31 (5H, m), 5.81-5.65 (1H, m), 5.14-5.07 (2H, m), 5.06-5.00 (2H, m), 3.77-3.63 (2H, m), 3.58-3.49 (1H, m), 3.13-3.01 (1H, m), 2.71-2.59 (1H, m), 2.48 (1H, brs), 2.36-2.26 (1H, m), 2.16-2.04 (1H, m), 1.45 (9H, s).

Reference Example 205

(3S,4R)-1-Benzyloxycarbonyl-4-(1-formylvinyl)pyrrolidine-3-carboxylic acid tert-butyl ester

[Formula 321]

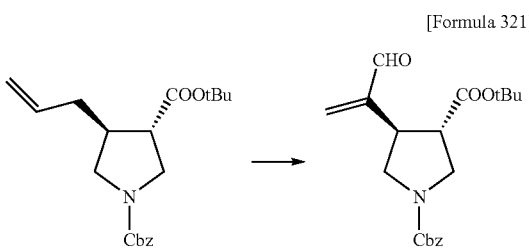

(3S,4S)-4-Allyl-1-benzyloxycarbonylpyrrolidine-3-carboxylic acid tert-butyl ester (70.0 g, 203 mmol) was dissolved in a mixed solution of tetrahydrofuran (350 mL) and water (350 mL). Sodium metaperiodate (86.7 g, 406 mmol) and osmium tetroxide (a catalytic amount) were sequentially added, and the mixture was stirred at room temperature for 20 hours. A 10% sodium bisulfite solution was added to the reaction solution, followed by extraction with dichloromethane. The organic layer was washed with water and brine, and then dried over anhydrous magnesium sulfate and concentrated under reduced pressure.

The resulting residue was dissolved in dichloromethane (700 mL). N,N-Dimethylmethyleneammonium iodide (56.3 g, 305 mmol) and 1,8-diazabicyclo[5.4.0]undecene (33.4 mL, 223 mmol) were added dropwise, and the mixture was stirred at room temperature for 59 hours. A saturated ammonium chloride solution was added to the reaction solution, followed by extraction with ethyl acetate. The organic layer was washed with brine, and then dried over anhydrous sodium sulfate and concentrated under reduced pressure. The resulting residue was purified by silica gel column chromatography (hexane:ethyl acetate=24:1→4:1) to give 56.7 g of the title compound as a colorless oil.

$^1$H-NMR (400 MHz, CDCl$_3$) δ: 9.55 (1H, d, J=5.1 Hz), 7.40-7.28 (5H, m), 6.38 (1H, d, J=2.0 Hz), 6.15 (1H, d, J=3.2 Hz), 5.13 (2H, d, J=4.1 Hz), 3.89-3.74 (2H, m), 3.60 (1H, t, J=9.6 Hz), 3.49-3.41 (1H, m), 3.29 (1H, dt, J=30.0, 9.7 Hz), 3.15-3.07 (1H, m), 1.41 (9H, s).

Reference Example 206

(3S,4R)-1-Benzyloxycarbonyl-4-[1-(hydroxymethyl)vinyl]pyrrolidine-3-carboxylic acid tert-butyl ester

[Formula 322]

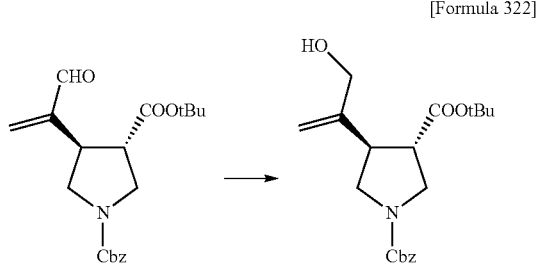

Cerium (III) chloride heptahydrate (57.0 g, 153 mmol) was dissolved in ethanol (700 mL). Sodium borohydride (5.79 g, 153 mmol) was added at 0° C., and the mixture was stirred for 10 minutes. A solution of (3S,4R)-1-benzyloxycarbonyl-4-(1-formylvinyl)pyrrolidine-3-carboxylic acid tert-butyl ester (55.0 g, 153 mmol) in ethanol (700 mL) was added dropwise to the reaction solution at 0° C., and the mixture was stirred at room temperature for three hours. The reaction solution was extracted with a 10% citric acid solution, water, and ethyl acetate. Then, the organic layer was washed with brine, dried over anhydrous sodium sulfate, and concentrated under reduced pressure. The resulting residue was purified by silica gel column chromatography (hexane:ethyl acetate=24:1→2:1) to give 42.2 g of the title compound as a colorless oil.

$^1$H-NMR (400 MHz, CDCl$_3$) δ: 7.39-7.28 (5H, m), 5.20 (1H, brs), 5.17-5.10 (2H, m), 5.04 (1H, d, J=5.4 Hz), 4.16-4.09 (3H, m), 3.87-3.77 (2H, m), 3.52 (1H, dd, J=17.2, 8.9 Hz), 3.29 (1H, q, J=10.9 Hz), 3.18-2.98 (2H, m), 1.43 (9H, s).

Reference Example 207

(3S,4R)-1-Benzyloxycarbonyl-4-[1-(bromomethyl)vinyl]pyrrolidine-3-carboxylic acid tert-butyl ester

[Formula 323]

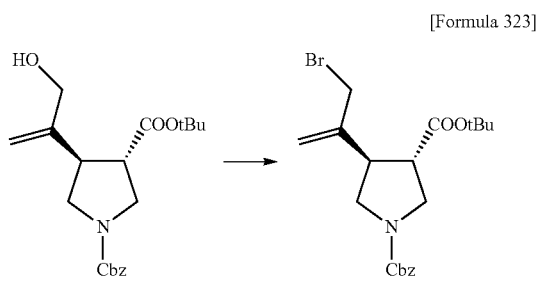

(3S,4R)-1-Benzyloxycarbonyl-4-[1-(hydroxymethyl)vinyl]pyrrolidine-3-carboxylic acid tert-butyl ester (30.0 g, 83.0 mmol) was dissolved in dichloromethane (300 mL). Triphenylphosphine (23.2 g, 87.2 mmol) and carbon tetrabromide (29.4 g, 87.2 mmol) were added, and the mixture was stirred at room temperature for 30 minutes. The reaction solution was concentrated under reduced pressure. Then, the resulting residue was purified by silica gel column chromatography (hexane:ethyl acetate=100:1→1:1) to give 26.9 g of the title compound as a colorless oil.

¹H-NMR (400 MHz, CDCl₃) δ: 7.39-7.30 (5H, m), 5.34 (1H, s), 5.16-5.12 (3H, m), 3.99 (2H, q, J=10.6 Hz), 3.91-3.78 (2H, m), 3.59-3.53 (1H, m), 3.34-3.22 (2H, m), 3.08-2.96 (1H, m), 1.44 (9H, s).

Reference Example 208

(1S,5S)-3-Benzyloxycarbonyl-6-methylene-3-azabicyclo[3.2.0]heptane-1-carboxylic acid tert-butyl ester

[Formula 324]

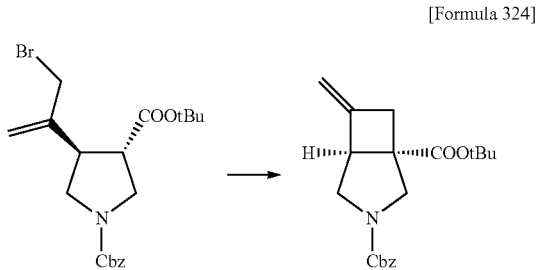

(3S,4R)-1-Benzyloxycarbonyl-4-[1-(bromomethyl)vinyl]pyrrolidine-3-carboxylic acid tert-butyl ester (22.8 g, 53.7 mmol) and 1,3-dimethyl-3,4,5,6-tetrahydro-2(1H)-pyrimidinone (19.5 mL, 161 mmol) were dissolved in a mixed solution of tetrahydrofuran (220 mL) and toluene (220 mL). Lithium hexamethyldisilazide (1.0 M solution in tetrahydrofuran) (80.6 mL, 80.6 mmol) was added dropwise at −78° C., and then the mixture was stirred at room temperature for five minutes. The reaction solution was extracted with a saturated ammonium chloride solution and ethyl acetate. Then, the organic layer was washed with brine, dried over anhydrous sodium sulfate, and concentrated under reduced pressure. The residue was subjected to silica gel column chromatography (hexane:ethyl acetate=24:1→2:1) to give 8.34 g of the title compound as a colorless syrup.

¹H-NMR (400 MHz, CDCl₃) δ: 7.37-7.24 (5H, m), 5.14 (2H, d, J=2.4 Hz), 4.98-4.88 (2H, m), 3.93-3.76 (2H, m), 3.66 (1H, d, J=11.7 Hz), 3.59-3.54 (1H, m), 3.45-3.38 (1H, m), 3.24 (1H, dt, J=16.4, 2.6 Hz), 2.67-2.57 (1H, m), 1.46 (9H, s).

Reference Example 209

(1S,5S,6R)-/(1S,5S,6S)-3-Benzyloxycarbonyl-6-hydroxymethyl-3-azabicyclo[3.2.0]heptane-1-carboxylic acid tert-butyl ester

[Formula 325]

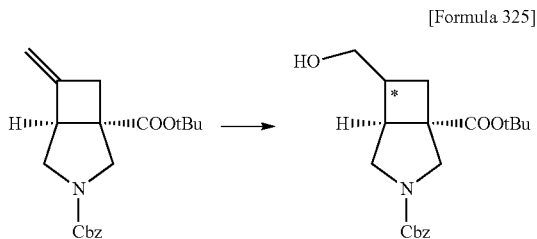

(1S,5S)-3-Benzyloxycarbonyl-6-methylene-3-azabicyclo[3.2.0]heptane-1-carboxylic acid tert-butyl ester (2.00 g, 5.82 mmol) was dissolved in tetrahydrofuran (40 mL). A 9-borabicyclo[3.3.1]nonane dimmer (0.5 M solution in tetrahydrofuran) (17.5 mL, 8.73 mmol) was added dropwise, and then the mixture was stirred for two hours. A 3 M sodium hydroxide solution (3.49 mL, 10.5 mmol) and 30% aqueous hydrogen peroxide (2.47 mL) were added dropwise to the reaction solution at 0° C., and then the mixture was stirred at room temperature for 16 hours. The reaction solution was extracted with water and ethyl acetate. Then, the organic layer was washed with brine, dried over anhydrous sodium sulfate, and concentrated under reduced pressure. The residue was subjected to silica gel column chromatography (hexane:ethyl acetate=100:1→1:2) to give 1.58 g of an isomer A (less polar isomer) of the title compound and 50.0 mg of an isomer B (more polar isomer) of the title compound as colorless syrups.

Isomer A; ¹H-NMR (400 MHz, CDCl₃) δ: 7.40-7.30 (5H, m), 5.17 (2H, s), 4.00 (1H, d, J=12.4 Hz), 3.75-3.54 (4H, m), 3.42 (1H, d, J=11.7 Hz), 3.29 (1H, dd, J=12.6, 7.9 Hz), 3.09 (1H, t, J=8.2 Hz), 2.74-2.64 (1H, m), 2.67-2.54 (1H, m), 1.47 (9H, s).

Isomer B; ¹H-NMR (400 MHz, CDCl₃) δ: 7.39-7.28 (5H, m), 5.17 (2H, s), 3.86-3.56 (6H, m), 3.38 (1H, dd, J=11.6, 6.0 Hz), 2.85-2.78 (1H, m), 2.32-2.22 (1H, m), 2.19-2.09 (1H, m), 1.45 (9H, s).

Reference Example 210

(1S,5S)-3-Benzyloxycarbonyl-6-fluoromethyl-3-azabicyclo[3.2.0]heptane-1-carboxylic acid tert-butyl ester (Derived from Isomer A)

[Formula 326]

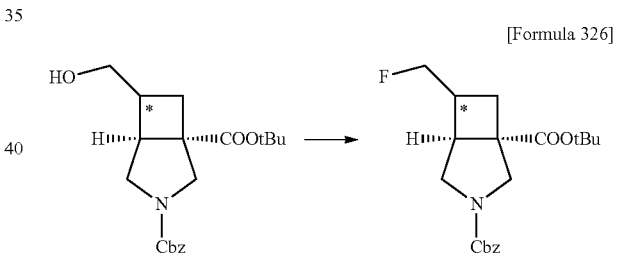

(1S,5S)-3-Benzyloxycarbonyl-6-hydroxymethyl-3-azabicyclo[3.2.0]heptane-1-carboxylic acid tert-butyl ester (isomer A) (1.51 g, 4.18 mmol) was dissolved in dichloromethane (30 mL). Triethylamine (1.28 mL, 9.20 mmol) and chloromethylsulfonyl chloride (746 µL, 8.36 mmol) were added dropwise at 0° C., and then the mixture was stirred for 15 minutes. The reaction solution was extracted with a saturated ammonium chloride solution and ethyl acetate at 0° C. Then, the organic layer was washed with brine, dried over anhydrous sodium sulfate, and concentrated under reduced pressure.

The resulting residue was dissolved in tetrahydrofuran (20 mL). Tetrabutylammonium fluoride (1.0 M solution in tetrahydrofuran) (16.7 mL, 16.7 mmol) was added dropwise at 0° C., and then the mixture was stirred for 16 hours. The reaction solution was concentrated under reduced pressure. The residue was subjected to silica gel column chromatography (hexane:ethyl acetate=100:1→1:1) to give 1.01 g of the title compound as a colorless syrup.

¹H-NMR (400 MHz, CDCl₃) δ: 7.40-7.31 (5H, m), 5.18 (2H, s), 4.48-4.26 (2H, m), 3.99 (1H, d, J=12.7 Hz), 3.72 (1H, brs), 3.43 (1H, d, J=12.6 Hz), 3.31 (1H, dd, J=13.2, 7.8 Hz), 3.11 (1H, t, J=8.0 Hz), 2.96-2.79 (1H, m), 2.62-2.53 (1H, m), 1.69-1.60 (1H, m), 1.48 (9H, s).

Reference Example 211

(1S,5S)-3-Benzyloxycarbonyl-6-fluoromethyl-3-azabicyclo[3.2.0]heptane-1-carboxylic acid tert-butyl ester (Derived from Isomer B)

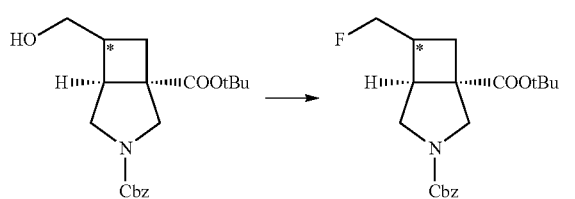

[Formula 327]

(1S,5S)-3-Benzyloxycarbonyl-6-hydroxymethyl-3-azabicyclo[3.2.0]heptane-1-carboxylic acid tert-butyl ester (isomer B) (180 mg, 498 μmol) was dissolved in dichloromethane (4 mL). Triethylamine (153 μL, 1.10 mmol) and chloromethylsulfonyl chloride (89.0 μL, 996 μmol) were added dropwise at 0° C., and then the mixture was stirred for 15 minutes. The reaction solution was extracted with a saturated ammonium chloride solution and ethyl acetate at 0° C. Then, the organic layer was washed with brine, dried over anhydrous sodium sulfate, and concentrated under reduced pressure.

The resulting residue was dissolved in tetrahydrofuran (4 mL). Tetrabutylammonium fluoride (1.0 M solution in tetrahydrofuran) (1.99 mL, 1.99 mmol) was added dropwise at 0° C., and then the mixture was stirred for two hours. The reaction solution was concentrated under reduced pressure. The residue was subjected to silica gel column chromatography (hexane:ethyl acetate=100:1→1:1) to give 80.6 mg of the title compound as a colorless syrup.

$^1$H-NMR (400 MHz, CDCl$_3$) δ: 7.40-7.31 (5H, m), 5.17 (2H, s), 4.52-4.31 (2H, m), 3.89-3.56 (3H, m), 3.38 (1H, dd, J=12.0, 6.6 Hz), 2.89 (1H, t, J=5.6 Hz), 2.40-2.25 (2H, m), 2.06-2.02 (1H, m), 1.46 (9H, s).

Reference Example 212

(1S,5R)-3-Benzyloxycarbonyl-1-(tert-butoxycarbonylamino)-6-fluoromethyl-3-azabicyclo[3.2.0]heptane (Derived from Isomer A)

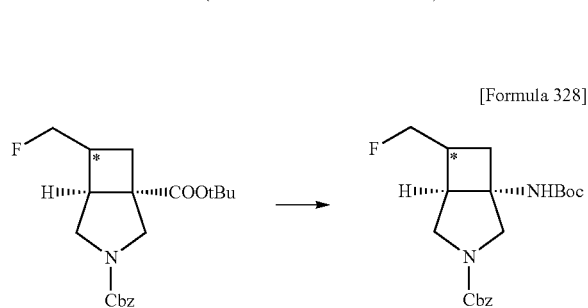

[Formula 328]

Trifluoroacetic acid (4 mL) was added dropwise to a solution of (1S,5S)-3-benzyloxycarbonyl-6-fluoromethyl-3-azabicyclo[3.2.0]heptane-1-carboxylic acid tert-butyl ester (derived from isomer A) (887 mg, 2.44 mmol) in dichloromethane (4 mL) under ice-cooling, and the mixture was stirred at room temperature for two hours. The reaction solution was concentrated under reduced pressure, and then a 1 M sodium hydroxide solution was added to the residue under ice-cooling. The solution was washed with diethyl ether, and then the aqueous layer was adjusted to pH 2 to 3 with concentrated hydrochloric acid under ice-cooling, followed by extraction with chloroform. The organic layer was dried over anhydrous sodium sulfate and concentrated under reduce pressure.

1,1'-Carbonylbis-1H-imidazole (594 mg, 3.66 mmol) was added to a solution of the resulting residue in acetonitrile (16 mL), and the mixture was stirred for one hour. The reaction solution was bubbled with ammonia gas for 1.5 hours. Then, water was added to the reaction solution, followed by extraction with chloroform. The organic layer was washed with brine, dried over anhydrous sodium sulfate, and concentrated under reduced pressure.

Lead tetraacetate (2.16 g, 4.88 mmol) was added to a solution of the resulting residue in tert-butyl alcohol (16 mL), and the mixture was heated with stirring at 80° C. for 15 minutes. After allowing to cool, sodium bicarbonate (2.50 g) and diethyl ether were added to the reaction solution, and the mixture was stirred under ice-cooling for 30 minutes. The insoluble material was removed by filtration through Celite, and then the filtrate was washed with a saturated sodium bicarbonate solution and brine. The organic layer was dried over anhydrous magnesium sulfate and concentrated under reduced pressure. The residue was purified by silica gel column chromatography (hexane:ethyl acetate=7:1→1:1) to give 754 mg of the title compound as a colorless syrup.

$^1$H-NMR (400 MHz, CDCl$_3$) δ: 7.40-7.29 (5H, m), 5.16 (2H, s), 4.89-4.79 (1H, m), 4.53-4.27 (2H, m), 3.91 (1H, d, J=12.5 Hz), 3.77 (1H, d, J=11.5 Hz), 3.51-3.40 (1H, m), 3.33-3.26 (1H, m), 3.00-2.86 (2H, m), 2.37-2.23 (1H, m), 1.87 (1H, dd, J=13.1, 6.7 Hz), 1.45 (9H, s).

Reference Example 213

(1S,5R)-3-Benzyloxycarbonyl-1-(tert-butoxycarbonylamino)-6-fluoromethyl-3-azabicyclo[3.2.0]heptane (Derived from Isomer B)

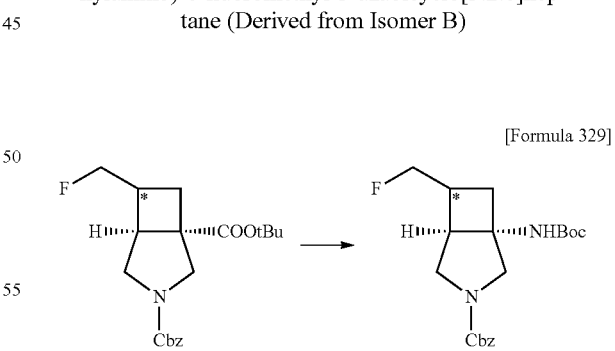

[Formula 329]

Trifluoroacetic acid (3 mL) was added dropwise to a solution of (1S,5S)-3-benzyloxycarbonyl-6-fluoromethyl-3-azabicyclo[3.2.0]heptane-1-carboxylic acid tert-butyl ester (derived from isomer B) (660 mg, 1.82 mmol) in dichloromethane (3 mL) under ice-cooling, and the mixture was stirred at room temperature for two hours. The reaction solution was concentrated under reduced pressure, and then a 1 M sodium hydroxide solution was added to the residue under ice-cooling. The solution was washed with diethyl ether, and then the aqueous layer was adjusted to pH 2 to 3 with concentrated hydrochloric acid under ice-cooling, followed by extraction with chloroform. The organic layer was dried over anhydrous sodium sulfate and concentrated under reduced pressure.

1,1'-Carbonylbis-1H-imidazole (443 mg, 2.73 mmol) was added to a solution of the resulting residue in acetonitrile (12 mL), and the mixture was stirred for one hour. The reaction solution was bubbled with ammonia gas for 1.5 hours. Then, water was added to the reaction solution, followed by extraction with chloroform. The organic layer was washed with brine, dried over anhydrous sodium sulfate, and concentrated under reduced pressure.

Lead tetraacetate (1.61 g, 3.64 mmol) was added to a solution of the resulting residue in tert-butyl alcohol (12 mL), and the mixture was heated with stirring at 80° C. for 15 minutes. After allowing to cool, sodium bicarbonate (2.00 g) and diethyl ether were added to the reaction solution, and the mixture was stirred under ice-cooling for 30 minutes. The insoluble material was filtered off through Celite, and then the filtrate was washed with a saturated sodium bicarbonate solution and brine. The organic layer was dried over anhydrous magnesium sulfate and concentrated under reduced pressure. The residue was purified by silica gel column chromatography (hexane:ethyl acetate=16:1→1:1) to give 590 mg of the title compound as a colorless syrup.

$^1$H-NMR (400 MHz, CDCl$_3$) δ: 7.39-7.30 (5H, m), 5.15 (2H, s), 4.89-4.74 (1H, m), 4.58-4.32 (2H, m), 3.91 (1H, d, J=11.7 Hz), 3.76-3.46 (3H, m), 2.83-2.66 (1H, m), 2.31 (1H, dd, J=10.7, 8.8 Hz), 2.19-2.05 (2H, m), 1.43 (9H, s).

Reference Example 214

(1S,5R)-1-(tert-Butoxycarbonylamino)-6-fluoromethyl-3-azabicyclo[3.2.0]heptane (Derived from Isomer A)

[Formula 330]

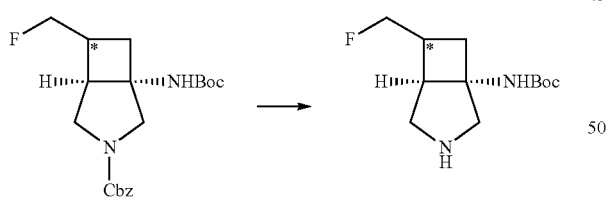

(1S,5R)-3-Benzyloxycarbonyl-1-(tert-butoxycarbonylamino)-6-fluoromethyl-3-azabicyclo[3.2.0]heptane (derived from isomer A) (625 mg, 1.65 mmol) was dissolved in tetrahydrofuran (12 mL). 20% palladium hydroxide-carbon (50% wet) (200 mg) was added, and the mixture was stirred in a hydrogen atmosphere for one hour. The catalyst was removed by filtration, and then the filtrate was concentrated under reduced pressure. A 1 M sodium hydroxide solution was added to the residue under ice-cooling, followed by extraction with chloroform. The organic layer was dried over anhydrous sodium sulfate and concentrated under reduced pressure to give 403 mg of the title compound as a colorless syrup.

$^1$H-NMR (400 MHz, CDCl$_3$) δ: 4.89-4.78 (1H, m), 4.66-4.39 (2H, m), 3.15 (1H, d, J=11.5 Hz), 3.07-2.78 (4H, m), 2.71 (1H, d, J=10.3 Hz), 2.34-2.26 (1H, m), 1.90 (1H, dd, J=12.7, 8.3 Hz), 1.46 (9H, s).

Reference Example 215

(1S,5R)-1-(tert-Butoxycarbonylamino)-6-fluoromethyl-3-azabicyclo[3.2.0]heptane (Derived from Isomer B)

[Formula 331]

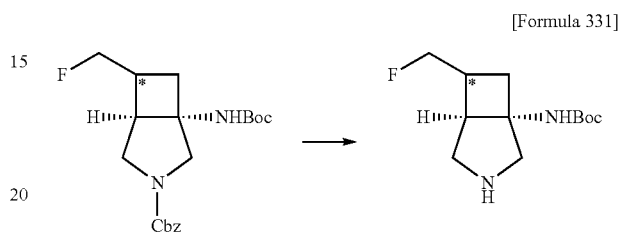

(1S,5R)-3-Benzyloxycarbonyl-1-(tert-butoxycarbonylamino)-6-fluoromethyl-3-azabicyclo[3.2.0]heptane (derived from isomer B) (305 mg, 806 μmol) was dissolved in tetrahydrofuran (6 mL). 20% palladium hydroxide-carbon (50% wet) (100 mg) was added, and the mixture was stirred in a hydrogen atmosphere for one hour. The catalyst was removed by filtration, and then the filtrate was concentrated under reduced pressure. A 1 M sodium hydroxide solution was added to the residue under ice-cooling, followed by extraction with chloroform. The organic layer was dried over anhydrous sodium sulfate and concentrated under reduced pressure to give 196 mg of the title compound as a colorless syrup.

$^1$H-NMR (400 MHz, CDCl$_3$) δ: 4.82 (1H, brs), 4.58-4.39 (2H, m), 3.16 (1H, d, J=11.2 Hz), 3.06 (1H, dd, J=11.1, 5.2 Hz), 2.85 (2H, dd, J=19.3, 11.7 Hz), 2.65-2.53 (1H, m), 2.27-1.86 (3H, m), 1.44 (9H, s).

Example 49

7-[(1S,5R)-1-Amino-6-fluoromethyl-3-azabicyclo[3.2.0]heptan-3-yl]-6-fluoro-1-[(1R,2S)-2-fluoro-1-cyclopropyl]-8-methoxy-1,4-dihydro-4-oxoquinoline-3-carboxylic acid (Derived from Isomer A)

[Formula 332]

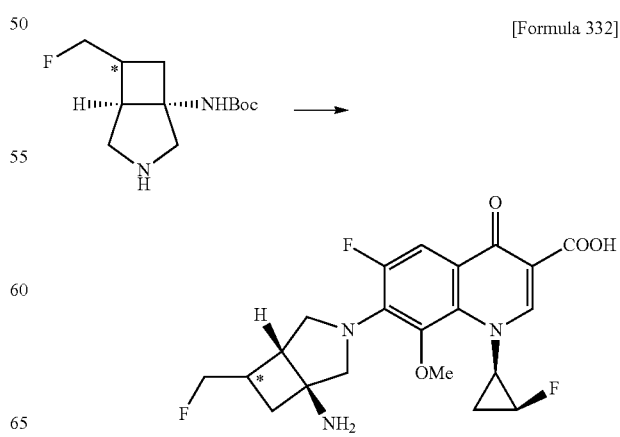

Triethylamine (143 μL, 1.03 mmol) and 6,7-difluoro-1-[(1R,2S)-2-fluoro-1-cyclopropyl]-8-methoxy-1,4-dihydro-4-oxoquinoline-3-carboxylic acid-BF$_2$ chelate (309 mg, 855 μmol) were added to a solution of (1S,5R)-1-(tert-butoxycarbonylamino)-6-fluoromethyl-3-azabicyclo[3.2.0]heptane (derived from isomer A) (209 mg, 855 μmol) in sulfolane (3 mL). The mixture was stirred at 40° C. for 87 hours. Ethanol (20 mL), water (2 mL), and triethylamine (0.5 mL) were added to the reaction solution, and the mixture was heated to reflux for two hours. The solvent was evaporated under reduced pressure, and then the resulting residue was extracted with a 10% citric acid solution and ethyl acetate. Then, the organic layer was washed with water three times and brine, dried over anhydrous sodium sulfate, and concentrated under reduced pressure. The residue was subjected to silica gel column chromatography (chloroform:methanol=99:1→9:1). The resulting oil (1.02 g) was dissolved in concentrated hydrochloric acid (5 ml) under ice-cooling, and the solution was stirred at room temperature for 15 minutes. The reaction solution was washed with chloroform five times, and then the aqueous layer was adjusted to pH 11 with a saturated sodium hydroxide solution. The basic solution was adjusted to pH 7.4 with hydrochloric acid, followed by extraction with chloroform. The organic layer was dried over anhydrous sodium sulfate and concentrated under reduced pressure. The residue was purified by PTLC (using the lower layer of chloroform:methanol:water=7:3:1 as a developing solvent), and then the resulting fraction was concentrated under reduced pressure. The resulting residue was recrystallized from ethanol to give 120 mg of the title compound as a white solid.

mp: 122-125° C.

$^1$H-NMR (400 MHz, 0.1N NaOD) δ: 8.47 (1H, brs), 7.74 (1H, d, J=13.4 Hz), 5.00 (1H, d, J=64.5 Hz), 4.70-4.49 (2H, m), 4.09-4.01 (1H, m), 3.75-3.54 (6H, m), 3.14 (1H, d, J=10.5 Hz), 3.02-2.89 (1H, m), 2.65 (1H, t, J=7.8 Hz), 2.16 (1H, t, J=11.8 Hz), 2.00 (1H, dd, J=12.7, 7.8 Hz), 1.67-1.41 (2H, m).

Anal. Calcd for C$_{21}$H$_{22}$F$_3$N$_3$O$_4$.2.5H$_2$O: C, 52.28; H, 5.64; N, 8.71. Found: C, 52.03; H, 5.50; N, 8.47.

IR (KBr) ν: 3404, 2963, 1731, 1619, 1579, 1541, 1452, 1392, 1360, 1320, 1293, 1270, 1053 cm$^{-1}$.

Example 50

7-[(1S,5R)-1-Amino-6-fluoromethyl-3-azabicyclo[3.2.0]heptan-3-yl]-6-fluoro-1-[(1R,2S)-2-fluoro-1-cyclopropyl]-8-methoxy-1,4-dihydro-4-oxoquinoline-3-carboxylic acid (Derived from Isomer B)

[Formula 333]

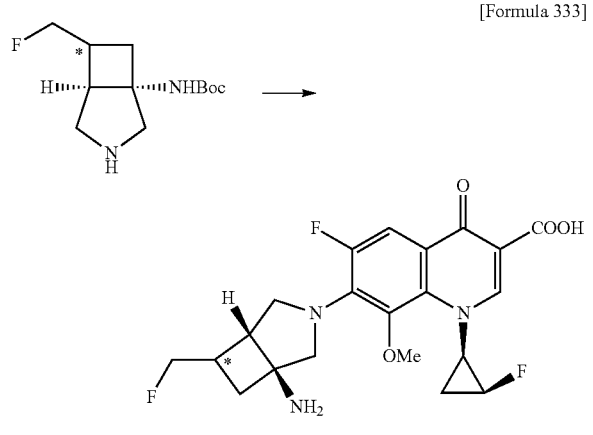

Triethylamine (135 μL, 967 μmol) and 6,7-difluoro-1-[(1R,2S)-2-fluoro-1-cyclopropyl]-8-methoxy-1,4-dihydro-4-oxoquinoline-3-carboxylic acid-BF$_2$ chelate (291 mg, 806 μmol) were added to a solution of (1S,5R)-1-(tert-butoxycarbonylamino)-6-fluoromethyl-3-azabicyclo[3.2.0]heptane (derived from isomer B) (196 mg, 806 μmol) in sulfolane (2 mL). The mixture was stirred at 40° C. for 111 hours. Ethanol (10 mL), water (1 mL), and triethylamine (0.5 mL) were added to the reaction solution, and the mixture was heated to reflux for one hour. The solvent was evaporated under reduced pressure, and then the resulting residue was extracted with a 10% citric acid solution and ethyl acetate. Then, the organic layer was washed with water three times and brine, dried over anhydrous sodium sulfate, and concentrated under reduced pressure. The residue was subjected to silica gel column chromatography (chloroform:methanol=99:1→9:1). The resulting oil (515 mg) was dissolved in concentrated hydrochloric acid (5 ml) under ice-cooling, and then the solution was stirred at room temperature for 15 minutes. The reaction solution was washed with chloroform five times, and then the aqueous layer was adjusted to pH 11 with a saturated sodium hydroxide solution. The basic solution was adjusted to pH 7.4 with hydrochloric acid, followed by extraction with chloroform. The organic layer was dried over anhydrous sodium sulfate and concentrated under reduced pressure. The residue was purified by PTLC (using the lower layer of chloroform:methanol:water=7:3:1 as a developing solvent), and then the resulting fraction was concentrated under reduced pressure. The resulting residue was recrystallized from ethanol to give 125 mg of the title compound as a white solid.

mp: 193-195° C.

$^1$H-NMR (400 MHz, 0.1N NaOD) δ: 8.48 (1H, brs), 7.73 (1H, d, J=13.7 Hz), 4.98 (1H, d, J=65.2 Hz), 4.68-4.48 (2H, m), 4.10-4.04 (1H, m), 3.76-3.67 (5H, m), 3.58-3.52 (1H, m), 3.22 (1H, d, J=10.5 Hz), 2.46-2.41 (1H, m), 2.40-2.22 (2H, m), 1.96-1.87 (1H, m), 1.69-1.44 (2H, m).

Anal. Calcd for C$_{21}$H$_{22}$F$_3$N$_3$O$_4$: C, 57.66; H, 5.07; F, 13.03; N, 9.61. Found: C, 57.42; H, 5.07; F, 12.98; N, 9.53.

IR (KBr) ν: 3393, 3086, 3063, 3034, 2954, 2930, 2897, 2872, 1720, 1621, 1514, 1452, 1395, 1365, 1344, 1318, 1288, 1273, 1186, 1123, 1108, 1060, 1038, 1020 cm$^{-1}$.

Example 51

7-[(1S,5R)-1-Amino-6-fluoromethyl-3-azabicyclo[3.2.0]heptan-3-yl]-6-fluoro-1-[(1R,2S)-2-fluoro-1-cyclopropyl]-8-methyl-1,4-dihydro-4-oxoquinoline-3-carboxylic acid (Derived from Isomer A)

[Formula 334]

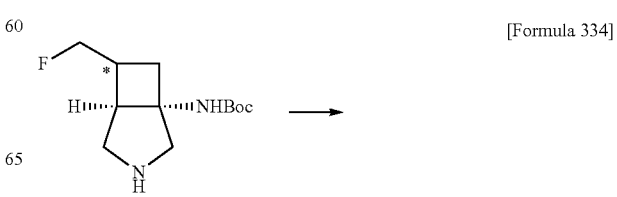

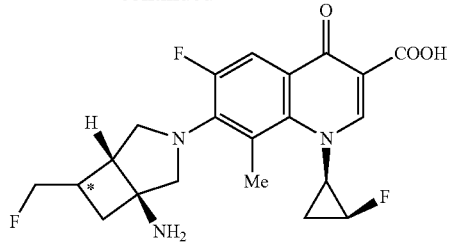

A solution of (1S,5R)-1-(tert-butoxycarbonylamino)-6-fluoromethyl-3-azabicyclo[3.2.0]heptane (derived from isomer A) (157 mg, 643 μmol), 7-bromo-6-fluoro-1-[(1R,2S)-2-fluoro-1-cyclopropyl]-8-methyl-1,4-dihydro-4-oxoquinoline-3-carboxylic acid ethyl ester (226 mg, 643 μmol), rac-2,2'-bis(diphenylphosphino)-1,1'-dinaphthyl (273 mg, 438 mol), tris(dibenzylideneacetone)dipalladium (0) (134 mg, 146 μmol), and cesium carbonate (381 mg, 1.17 mmol) in dioxane (5.00 mL) was stirred in an argon atmosphere at room temperature for 30 minutes and at 100° C. for 16 hours. Water was added to the reaction solution, followed by extraction with ethyl acetate and chloroform. Then, the organic layer was dried over anhydrous sodium sulfate. The solvent was evaporated under reduced pressure, and the resulting residue was subjected to silica gel column chromatography (hexane:ethyl acetate=7:1→ethyl acetate).

A 1N sodium hydroxide solution (1.21 mL) was added to a solution of the resulting pale yellow foam in ethanol (5 mL) at 0° C., and the mixture was stirred at room temperature for 30 hours. A 10% citric acid solution was added to the reaction solution at 0° C., followed by extraction with ethyl acetate. The organic layer was dried over anhydrous sodium sulfate and then concentrated under reduced pressure.

The resulting residue was dissolved in concentrated hydrochloric acid (5 mL) at 0° C. The mixture was stirred for 15 minutes and then washed with chloroform five times. The aqueous layer was adjusted to pH 12 with a saturated sodium hydroxide solution at 0° C. and then adjusted to pH 7.4 with hydrochloric acid, followed by extraction with chloroform. The organic layer was dried over anhydrous sodium sulfate and then concentrated under reduced pressure. The residue was purified by PTLC (using the lower layer of chloroform:methanol:water=7:3:1 as a developing solvent). Then, the resulting fraction was recrystallized from ethanol to give 28.5 mg of the title compound as a white solid.

mp: 130-133° C.

$^1$H-NMR (400 MHz, 0.1N NaOD) δ: 8.46 (1H, d, J=3.2 Hz), 7.73 (1H, d, J=13.8 Hz), 5.01 (1H, d, J=64.2 Hz), 4.78-4.46 (2H, m), 4.13-4.06 (1H, m), 3.91-3.84 (1H, m), 3.51 (1H, d, J=9.6 Hz), 3.34 (1H, d, J=11.0 Hz), 2.99-2.87 (2H, m), 2.71-2.64 (4H, m), 2.24-2.12 (2H, m), 1.66-1.55 (1H, m), 1.29-1.16 (1H, m).

Anal. Calcd for $C_{21}H_{22}F_3N_3O_3 \cdot 2.25H_2O \cdot 0.25IPA$: C, 54.77; H, 6.02; F, 11.95; N, 8.81. Found: C, 54.82; H, 5.71; F, 11.84; N, 8.85.

IR (KBr) ν: 3414, 2970, 1723, 1616, 1580, 1546, 1508, 1458, 1434, 1394, 1363, 1320, 1103, 1023 cm$^{-1}$.

Reference Example 216

Ethyl 2-(4-bromo-2,5-difluoro-3-methylbenzoyl)-3-dimethylaminoacrylate

[Formula 335]

2,5-Difluoro-4-bromo-3-methylbenzoic acid (10.7 g, 42.4 mmol) was dissolved in toluene (160 mL). Thionyl chloride (5.00 mL, 63.9 mmol) and dimethylformamide (5.0 mL) were added, and the mixture was heated to reflux for two hours. The solvent was evaporated under reduced pressure, and the residue was dissolved in tetrahydrofuran (300 mL). Ethyl 3-dimethylaminoacrylate (7.30 ml, 50.9 mmol) and triethylamine (7.60 mL, 54.5 mmol) were added, and the mixture was heated to reflux for three hours. The solvent was evaporated under reduced pressure, and dichloromethane and water were added to the residue to separate the layers. Then, the organic layer was dried over anhydrous sodium sulfate, and the solvent was evaporated under reduced pressure. The residue was subjected to flash column chromatography (hexane:ethyl acetate=2:1→1:1→1:2) to give the title compound (11.35 g) as a yellow oil.

$^1$H-NMR (CDCl$_3$) δ: 7.81-7.74 (1H, m), 7.27-7.16 (1H, m), 4.00 (2H, q, J=7.1 Hz), 3.31 (3H, br s), 2.89 (3H, br s), 2.35 (3H, d, J=2.9 Hz), 0.97 (3H, t, J=7.1 Hz).

Reference Example 217

Ethyl 7-bromo-6-fluoro-1-[(1R,2S)-2-fluorocyclopropyl]-8-methyl-4-oxo-1,4-dihydro-3-quinolinecarboxylate

[Formula 336]

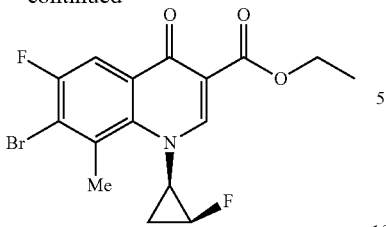

Ethyl 2-(4-bromo-2,5-difluoro-3-methylbenzoyl)-3-dimethylaminoacrylate (11.4 g, 30.2 mmol) was dissolved in dichloromethane (200 mL). (1R,2S)-2-Fluorocyclopropylamine tosylate (8.24 g, 33.3 mmol) was added, and the mixture was cooled to −25° C. Triethylamine (6.60 mL, 47.4 mmol) was added dropwise to the reaction solution at −25° C., and the mixture was stirred at −15° C. for one hour and at 0° C. for 2.5 hours. The solvent was evaporated under reduced pressure, and ethyl acetate and water were added to the residue to separate the layers. The organic layer was washed with brine and dried over anhydrous sodium sulfate. The solvent was evaporated under reduced pressure to give an aminoacrylate as a yellow oil. The resulting aminoacrylate was dissolved in N,N-dimethylformamide (350 mL). Cesium carbonate (19.8 g, 60.9 mmol) was added, and the mixture was stirred at room temperature for 12 hours. The solvent was evaporated under reduced pressure, and ethyl acetate and water were added to the residue to separate the layers. The organic layer was washed with brine and dried over anhydrous sodium sulfate, and the solvent was evaporated under reduced pressure. The residue was subjected to flash column chromatography (hexane:ethyl acetate=9:1→1:1→1:2) to give the title compound (2.98 g) as a colorless powder.

$^1$H-NMR (CDCl$_3$) δ: 8.56 (1H, d, J=3.2 Hz), 8.06 (1H, d, J=8.1 Hz), 4.98-4.73 (1H, m), 4.40 (2H, q, J=7.1 Hz), 3.91-3.82 (1H, m), 2.85 (3H, s), 1.61-1.22 (2H, m), 1.41 (3H, t, J=7.1 Hz).

Reference Example 218

Ethyl 7-[(1S,5R)-1-tert-butoxycarbonylamino-6,6-difluoro-3-azabicyclo[3.3.0]octan-3-yl]-6-fluoro-1-[(1R,2S)-2-fluorocyclopropyl]-1,4-dihydro-8-methyl-4-oxoquinoline-3-carboxylate

[Formula 337]

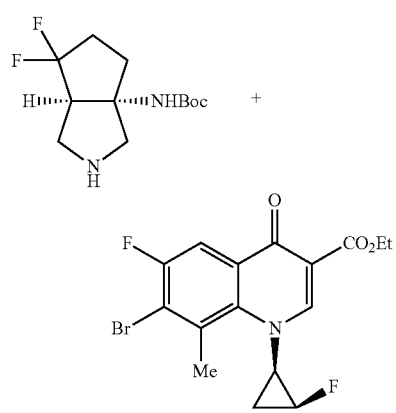

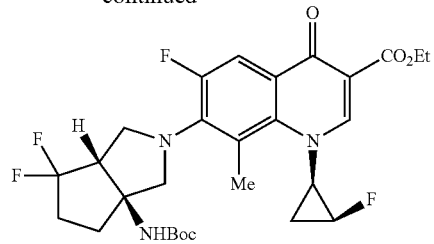

A mixture of (1S,5R)-1-tert-butoxycarbonylamino-6,6-difluoro-3-azabicyclo[3.3.0]octane (318 mg, 1.21 mmol), ethyl 7-bromo-6-fluoro-1-[(1R,2S)-2-fluorocyclopropyl]-1,4-dihydro-8-methyl-4-oxoquinoline-3-carboxylate (426 mg, 1.10 mmol), 1,1'-bis(diphenylphosphino)ferrocene (183 mg, 0.331 mmol), tris(dibenzylideneacetone)dipalladium(0) (101 mg, 0.110 mmol) and cesium carbonate (718 mg, 2.20 mmol) in dioxane (5.51 mL) was stirred at room temperature for 30 minutes, and at 100° C. for 11 hours under argon atmosphere. The mixture was diluted with water, and extracted with ethyl acetate and chloroform (3×). The combined organic layer was dried over anhydrous sodium sulfate, and the solvent was distilled off under reduced pressure. The residue was purified by silica gel flush column chromatography (ethyl acetate/hexane=10:90→50:50→67:33→ethyl acetate) to afford 436 mg of the title compound as a pale yellow foam.

$^1$H-NMR (400 MHz, CDCl$_3$) δ: 8.54 (1H, d, J=2.9 Hz), 7.96 (1H, d, J=12.9 Hz), 4.99 (1H, brs), 4.94-4.72 (1H, m), 4.39 (2H, q, J=7.1 Hz), 3.91-3.79 (2H, m), 3.62 (2H, s), 3.49-3.41 (1H, m), 2.91-2.76 (1H, m), 2.62 (3H, s), 2.42-2.12 (4H, m), 1.45 (9H, s), 1.61-1.43 (1H, m), 1.41 (3H, t, J=7.1 Hz), 1.34-1.21 (1H, m).

MS (ESI) m/z: 568 (M+H)$^+$.

Reference Example 219

7-[(1S,5R)-1-tert-Butoxycarbonylamino-6,6-difluoro-3-azabicyclo[3.3.0]octan-3-yl]-6-fluoro-1-[(1R,2S)-2-fluorocyclopropyl]-1,4-dihydro-8-methyl-4-oxoquinoline-3-carboxylic acid

[Formula 338]

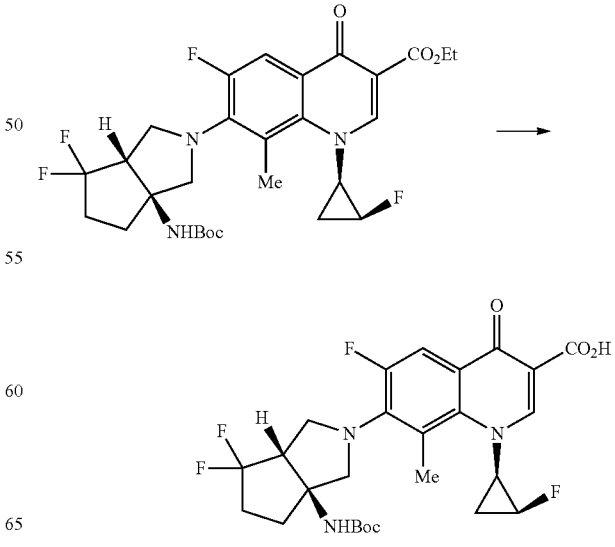

To a solution of ethyl 7-[(1S,5R)-1-tert-butoxycarbonylamino-6,6-difluoro-3-azabicyclo[3.3.0]octan-3-yl]-6-fluoro-1-[(1R,2S)-2-fluorocyclopropyl]-1,4-dihydro-8-methyl-4-oxoquinoline-3-carboxylate (436 mg, 0.769 mmol) in ethanol (5 mL) was added 1 mol/L aqueous solution of sodium hydroxide (0.845 mL) at 0° C., and the mixture was stirred at room temperature for 13 hours. To the mixture was further added 1 mol/L aqueous solution of sodium hydroxide (0.845 mL) at 0° C., and the mixture was stirred at room temperature for 4 hours. To the mixture was added 10% aqueous solution of citric acid, and ethanol was distilled off under reduced pressure. The residue was diluted with water and extracted with dichloromethane (3×). The combined organic layer was dried over anhydrous sodium sulfate, and the solvent was distilled off under reduced pressure. The residue was purified by silica gel flush column chromatography (ethyl acetate/hexane=1:3→1:1→2:1→ethyl acetate) to afford 342 mg of the title compound as a colorless foam.

$^1$H-NMR (CDCl$_3$) δ: 14.98 (1H, s), 8.78 (1H, d, J=2.9 Hz), 7.95 (1H, d, J=12.7 Hz), 5.03-4.77 (2H, m), 4.02-3.87 (2H, m), 3.77-3.64 (2H, m), 3.57-3.49 (1H, m), 2.98-2.83 (1H, m), 2.66 (3H, s), 2.43-2.12 (4H, m), 1.70-1.53 (1H, m), 1.46 (9H, s), 1.40-1.26 (1H, m).

MS (ESI) m/z: 540 (M+H)$^+$.

Example 52

7-[(1S,5R)-1-Amino-6,6-difluoro-3-azabicyclo[3.3.0]octan-3-yl]-6-fluoro-1-[(1R,2S)-2-(fluorocyclopropyl)]-1,4-dihydro-8-methyl-4-oxoquinoline-3-carboxylic acid

[Formula 339]

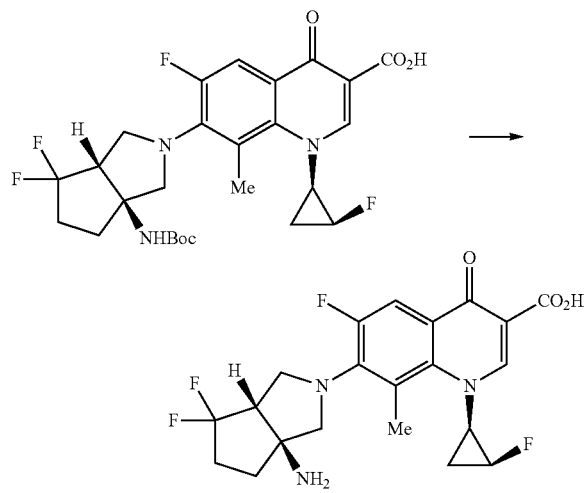

7-[(1S,5R)-1-tert-Butoxycarbonylamino-6,6-difluoro-3-azabicyclo[3.3.0]octan-3-yl]-6-fluoro-1-[(1R,2S)-2-fluorocyclopropyl]-1,4-dihydro-8-methyl-4-oxoquinoline-3-carboxylic acid (414 mg, 0.767 mmol) was dissolved in concentrated hydrochloric acid (4 mL) at 0° C., and the mixture was stirred at 0° C. for an hour. The aqueous solution was washed with chloroform (3×). The mixture was basified to pH 12 with saturated aqueous solution of sodium hydroxide, and then neutralized to pH 7.4 at 0° C. The solution was extracted with chloroform (5×). The combined organic layer was dried with anhydrous sodium sulfate, and the solvent was distilled off under reduced pressure. The residue was recrystallized from ethanol to afford 219 mg of the title compound as a white solid.

Melting point: 211-212° C.

$^1$H-NMR (400 MHz, 0.1N NaOD) δ: 8.52-8.46 (1H, m), 7.79-7.67 (1H, m), 5.12-4.88 (1H, m), 4.18-4.05 (1H, m), 3.91-3.79 (1H, m), 3.68-3.55 (1H, m), 3.52-3.40 (1H, m), 3.36-3.25 (1H, m), 2.71-2.58 (4H, m), 2.45-2.28 (2H, m), 2.24-2.12 (1H, m), 1.97-1.85 (1H, m), 1.69-1.54 (1H, m), 1.38-1.17 (1H, m).

Anal. Calcd for C$_{21}$H$_{21}$F$_4$N$_3$O$_3$·0.2H$_2$O: C, 56.93; H, 4.87; N, 9.49; F, 17.15. Found: C, 56.91; H, 4.83; N, 9.47; F, 17.55.

MS (ESI) m/z: 440 (M+H)$^+$.

IR (ATR) ν: 3391, 3061, 2962, 2871, 1714, 1615, 1510, 1460, 1434, 1356, 1336, 1301, 1235, 1207, 1177, 1157, 1140, 1075, 1061, 1045, 1015 cm$^{-1}$.

Reference Example 220 tert-Butyl (3S)-4-Chloro-3-(3-hydroxy-1-propyl)-5-oxo-1-[(1R)-1-phenylethyl]pyrrolidine-3-carboxylic acid

[Formula 340]

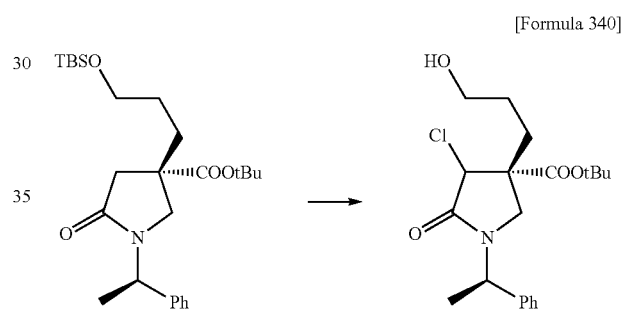

Under nitrogen atmosphere, to a solution of tert-butyl (3S)-3-[3-(tert-butyldimethylsilyloxy)propan-1-yl]-5-oxo-1-[(1R)-1-phenylethyl]pyrrolidine-3-carboxylic acid (960 mg, 2.08 mmol) in THF (15 mL) was added 1.0M lithium bis(trimethylsilyl)amide in THF solution (2.29 mL, 2.29 mmol) at −78° C., and the mixture was stirred for 30 minutes. Then, N-chlorosuccinimide (333 mg, 2.50 mmol) added and the mixture was stirred for 1 hour at −60° C., and further stirred for 10 minutes at 0° C. To the mixture were added saturated aqueous solution of ammonium chloride and ethyl acetate. The separated organic layer was washed with water and brine. The solution was dried over anhydrous sodium sulfate, and the solvent was distilled off under reduced pressure. At 0° C., to a solution of this residue in THF (20 mL) were added acetic acid (0.24 mL, 4.16 mmol) and 1.0M tetrabutylammonium fluoride in THF solution (4.16 mL, 4.16 mmol), the mixture was stirred for 16 hours at room temperature. To the mixture were added 10% aqueous solution of citric acid and ethyl acetate. The separated organic layer was washed with water and brine. The solution was dried over anhydrous sodium sulfate, and the solvent was distilled off under reduced pressure. The residue was purified by silica gel flush column chromatography (ethyl acetate/hexane=1:1→1:2) to afford 506 mg of the title compound as a pale yellow oil.

$^1$H-NMR (CDCl$_3$) δ: 7.34-7.26 (5H, m), 5.49-5.40 (1H, m), 4.75 (1H, s), 3.68-3.61 (2H, m), 3.39-3.34 (2H, m), 3.24

(0.75H, d, J=10.0 Hz), 3.14 (0.25H, d, J=10.9 Hz), 1.95-1.80 (2H, m), 1.68-1.40 (2H, m), 1.52 (3H, d, J=7.1 Hz), 1.28 (9H, s).

Reference Example 221 tert-Butyl (1S,5R)-5-chloro-4-oxo-3-[(1R)-1-phenylethyl]-3-azabicyclo[3.3.0]octan-1-ylcarboxylic acid

[Formula 341]

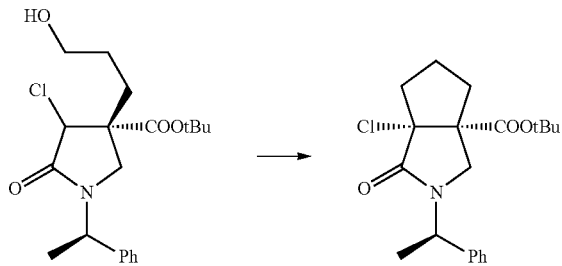

At 0° C., to a solution of tert-butyl (3S)-4-chloro-3-(3-hydroxypropan-1-yl)-5-oxo-1-[(1R)-1-phenylethyl]pyrrolidine-3-carboxylic acid (500 mg, 1.31 mmol) in dichloromethane (10 mL) were added carbon tetrabromide (434 mg, 1.31 mmol) and triphenylphosphine (344 mg, 1.31 mmol). After stirring the mixture for 2 hours at room temperature, carbon tetrabromide (143 mg, 0.431 mmol) and triphenylphosphine (114 mg, 0.434 mmol) were added to the mixture. After stirring for 2 hours, carbon tetrabromide (72 mg, 0.216 mmol) and triphenylphosphine (57 mg, 0.217 mmol) were added and the mixture was stirred for 16 hours. The solvent was distilled off under reduced pressure. The residue was purified by short silica gel flush column chromatography (15% ethyl acetate/hexane) to afford a colorless oil. Under nitrogen atmosphere, to a solution of this oil in THF (12 mL) was added 1.0M lithium bis(trimethylsilyl)amide in THF solution (1.46 mL, 1.46 mmol) at −78° C., and the reaction mixture was warmed to 0° C. over 2 hours. To the mixture were added saturated aqueous solution of ammonium chloride and ethyl acetate. The separated organic layer was washed with water and brine. The solution was dried over anhydrous sodium sulfate and the solvent was distilled off under reduced pressure. The residue was purified by silica gel flush column chromatography (15% ethyl acetate/hexane) to afford 337 mg of the title compound as a pale yellow solid.

$^1$H-NMR (CDCl$_3$) δ: 7.37-7.26 (5H, m), 5.54 (1H, q, J=7.1 Hz), 3.51 (1H, d, J=10.7 Hz), 3.02 (1H, d, J=10.7 Hz), 2.76-2.71 (1H, m), 2.52-2.45 (1H, m), 2.38-2.30 (1H, m), 2.02-1.96 (1H, m), 1.74-1.60 (2H, m), 1.53 (3H, d, J=7.1 Hz), 1.45 (9H, s).

Reference Example 222

(1S,5R)-5-Chloro-4-oxo-3-[(1R)-1-phenylethyl]-3-azabicyclo[3.3.0]octan-1-ylcarboxylic acid

[Formula 342]

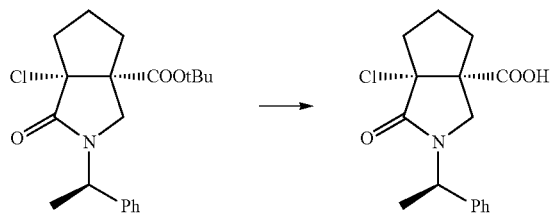

A mixture of tert-butyl (1S,5R)-5-chloro-4-oxo-3-[(1R)-1-phenylethyl]-3-azabicyclo[3.3.0]octan-1-ylcarboxylic acid (332 mg, 0.912 mmol) and trifluoroacetic acid (2 mL) in dichloromethane (4 mL) was stirred for 14.5 hours at room temperature. The solvent was distilled off under reduced pressure. To the residue was added diethyl ether (3 mL), and then the precipitate was collected by filtration to afford 245 mg of the title compound as a colorless solid.

$^1$H-NMR (CDCl$_3$) δ: 7.38-7.26 (5H, m), 5.50 (1H, q, J=7.1 Hz), 3.53 (1H, d, J=10.7 Hz), 3.07 (1H, d, J=10.8 Hz), 2.78-2.73 (1H, m), 2.63-2.56 (1H, m), 2.41-2.33 (1H, m), 2.05-2.01 (1H, m), 1.79-1.63 (2H, m), 1.54 (3H, d, J=7.1 Hz).

Reference Example 223

(1R,5R)-1-(tert-Butoxycarbonylamino)-5-chloro-4-oxo-3-[(1R)-1-phenylethyl]-3-azabicyclo[3.3.0]octane

[Formula 343]

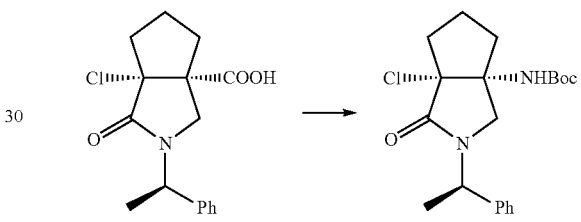

A solution of (1S,5R)-5-chloro-4-oxo-3-[(1R)-1-phenylethyl]-3-azabicyclo[3.3.0]octan-1-ylcarboxylic acid (239 mg, 0.777 mmol), triethylamine (0.215 mL, 1.55 mmol) and diphenylphosphoryl azide (0.184 mL, 0.855 mmol) in toluene (6 mL) was stirred for 30 minutes at 80° C. The solvent was distilled off under reduced pressure. To a solution of the residue in 1,4-dioxane (5 mL) was added 6N aqueous solution of hydrochloric acid (5 mL). The mixture was stirred for 5 hours at 50° C. The solvent was distilled off under reduced pressure. To the residue was added 1N aqueous solution of sodium hydroxide. The solution was extracted with CHCl$_3$ twice, and the combined organic layers were dried over anhydrous sodium sulfate and the solvent was distilled off under reduced pressure. A mixture of the residue and di-tert-butyl dicarbonate (847 mg, 3.89 mmol) was stirred for 3 hours at 50° C. and the mixture was purified by silica gel flush column chromatography (15% ethyl acetate/hexane) to afford 222 mg of the title compound as a colorless oil.

$^1$H-NMR (CDCl$_3$) δ: 7.37-7.26 (5H, m), 5.50 (1H, q, J=6.9 Hz), 5.25 (1H, brs), 3.66 (1H, brd, J=10.0 Hz), 2.96 (1H, d, J=6.8 Hz), 2.76-2.69 (1H, m), 2.55-2.51 (1H, m), 2.18-2.08 (1H, m), 1.98-1.84 (2H, m), 1.51 (3H, d, J=7.1 Hz), 1.65-1.50 (1H, m), 1.40 (9H, s).

Reference Example 224

(1R,5R)-1-(tert-Butoxycarbonylamino)-5-chloro-3-[(1R)-1-phenylethyl]-3-azabicyclo[3.3.0]octane

[Formula 344]

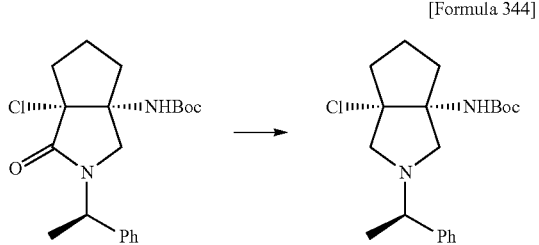 [SMILES: C[C@H](c1ccccc1)N1C[C@]2(NC(=O)OC(C)(C)C)CCC[C@]2(Cl)C1=O ; C[C@H](c1ccccc1)N1C[C@@]2(Cl)CCC[C@@]2(NC(=O)OC(C)(C)C)C1]

Under nitrogen atmosphere, to a solution of (1R,5R)-1-(tert-butoxycarbonylamino)-5-chloro-4-oxo-3-[(1R)-1-phenylethyl]-3-azabicyclo[3.3.0]octane (217 mg, 0.573 mmol) in THF (10 mL) was added 1.0M borane-THF complex in THF solution (1.72 mL, 1.72 mmol) at room temperature. After stirring for 14 hours, 1.0M borane-THF complex in THF solution (0.86 mL, 0.86 mmol) was added. The mixture was warmed to 50° C., and stirred for 18 hours. To the mixture was further added 1.0M borane-THF complex in THF solution (0.86 mL, 0.86 mmol) and the mixture was stirred for 24 hours at 50° C. After being cooled to 0° C., to the mixture were added water (1 mL), EtOH (9 mL) and triethylamine (1 mL). The mixture was warmed to 80° C., and stirred for 2 hours. The solvent was distilled off under reduced pressure. To the residue were added saturated aqueous solution of ammonium chloride and ethyl acetate. The separated organic layer was washed with water and brine. The solution was dried over anhydrous sodium sulfate and the solvent was distilled off under reduced pressure. The residue was purified by silica gel flush column chromatography (10% ethyl acetate/hexane) to afford 67.3 mg of the title compound as a colorless oil.

$^1$H-NMR (CDCl$_3$) δ: 7.29-7.19 (5H, m), 5.53 (1H, brs), 3.22 (1H, q, J=6.8 Hz), 3.07 (1H, brd, J=8.8 Hz), 2.93 (1H, brd, J=8.7 Hz), 2.82-2.71 (1H, m), 2.64-2.57 (1H, m), 2.27-2.15 (2H, m), 2.09-2.06 (2H, m), 1.74-1.67 (2H, m), 1.55 (9H, s), 1.31 (3H, d, J=6.6 Hz).

Reference Example 225

(1R,5R)-1-(tert-Butoxycarbonylamino)-5-chloro-3-azabicyclo[3.3.0]octane

[Formula 345]

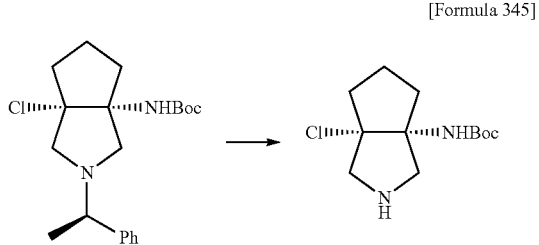 [SMILES: C[C@H](c1ccccc1)N1C[C@@]2(Cl)CCC[C@@]2(NC(=O)OC(C)(C)C)C1 ; CC(C)(C)OC(=O)N[C@@]12CCC[C@]1(Cl)CNC2]

Under hydrogen atmosphere, a mixture of (1R,5R)-1-(tert-butoxycarbonylamino)-5-chloro-3-[(1R)-1-phenylethyl]-3-azabicyclo[3.3.0]octane (63.0 mg, 0.173 mmol), 10% Pd—C (50 wt %, M, 32 mg) in methanol (6 mL) was stirred for 4 hours at room temperature and for 19 hours at 40° C. After removing catalyst by filtration, the filtrate was distilled off under reduced pressure.

MS (ESI) m/z: 261 (M+H)$^+$.

Example 53

7-[(1R,5R)-1-Amino-5-chloro-3-azabicyclo[3.3.0]octan-3-yl]-6-fluoro-1-[(1R,2S)-2-fluorocyclopropan-1-yl]-1,4-dihydro-8-methoxy-4-oxoquinoline-3-carboxylic acid

[Formula 346]

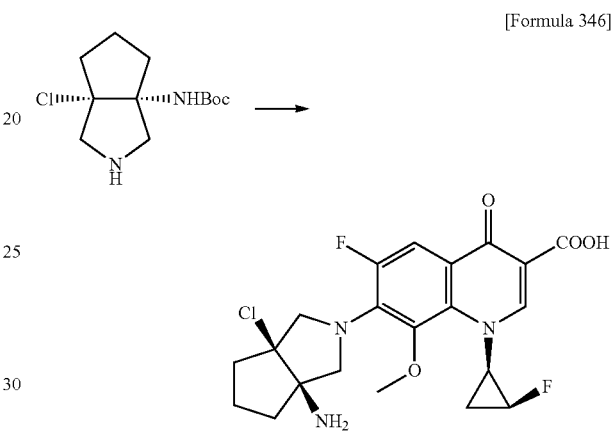

A mixture of (1R,5R)-1-(tert-butoxycarbonylamino)-5-chloro-3-azabicyclo[3.3.0]octane (45.0 mg, 0.173 mmol), 6,7-difluoro-1-[(1R,2S)-2-fluorocyclopropan]-1,4-dihydro-8-methoxy-4-oxoquinoline-3-carboxylic acid-difluoroboron complex (62.3 mg, 0.173 mmol) and triethylamine (0.0598 mL, 0.433 mmol) in dimethylsulfoxide (3 mL) was stirred for 45 hours at 45° C. To the mixture were added water (1 mL), EtOH (9 mL) and triethylamine (1 mL). The mixture was stirred for 1.5 hours at 80° C. After being cooled to room temperature, the solvent was distilled under reduced pressure. To the residue were added 10% aqueous solution of citric acid and ethyl acetate. The separated organic layer was washed with H$_2$O and brine. The solution was dried over anhydrous sodium sulfate and the solvent was distilled off under reduced pressure. The residue was purified by TLC (5% MeOH/CHCl$_3$) to afford 48.0 mg of the N-Boc protected compound as a yellow oil. To this oil was added hydrochloric acid and the mixture was stirred for 30 minutes at room temperature. The mixture was basified to pH 12 with aqueous solution of sodium hydroxide, and then neutralized to pH 7.8 at 0° C. The solution was extracted with chloroform twice. The combined organic layers were dried over anhydrous sodium sulfate, and the solvent was distilled off under reduced pressure. The residue was dried under reduced pressure to afford 33.9 mg of the title compound as a pale yellow solid.

Melting point: 161-163° C.

$^1$H-NMR (400 MHz, 0.1N NaOD) δ: 8.48 (1H, s), 7.70 (1H, d, J=14.2 Hz), 5.07-4.85 (1H, m), 4.19-4.08 (2H, m), 3.92 (1H, d, J=11.8 Hz), 3.76-3.63 (5H, m), 2.48-2.41 (1H, m), 2.30-2.25 (1H, m), 2.08-1.87 (4H, m), 1.70-1.51 (2H, m), 1.19 (1.8H, t, J=7.2 Hz).

Anal. Calcd for C$_{21}$H$_{22}$ClF$_4$N$_3$O$_3$0.6EtOH: C, 55.38; H, 5.36; N, 8.73; F, 7.89; Cl, 7.36. Found: C, 55.24; H, 4.91; N, 8.85; F, 8.27; Cl, 6.92.

MS (ESI) m/z: 454 (M+H)⁺.
IR (ATR) ν: 3384, 3075, 2880, 1728, 1621, 1513, 1453, 1360, 1318, 1188, 1136, 1120, 1103, 1056 cm⁻¹.

Example 54

7-[6-amino-8-azatricyclo[4.3.0.0$^{1,3}$]nonan-8-yl]-6-fluoro-1-[(1R,2S)-2-fluorocyclopropan-1-yl]-8-methyl-4-oxo-1,4-dihydroquinoline-3-carboxylic acid (7 Position: Derivative from Optical Isomer A)

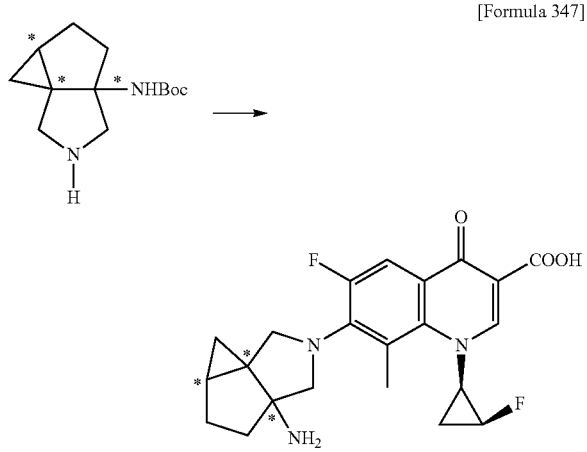

[Formula 347]

To a solution of tris(dibenzylideneacetone)dipalladium (0) (332 mg, 0.363 mmol) and 4,5-bis(diphenyl)phosphino-9,9-dimethylxanthene (462 mg, 0.798 mmol) in 1,4-dioxane (9.06 ml) were added ethyl 7-bromo-6-fluoro-1-[(1R,2S)-2-fluorocyclopropyl]-8-methyl-1,4-dihydro-4-oxoquinoline-3-carboxylate (350 mg, 0.906 mmol), 6-tert-butoxycarbonyl amino-8-azatricyclo[4.3.0.0$^{1,3}$]nonane (216 mg, 0.906 mmol) and cesium carbonate (355 mg, 1.09 mmol) and the mixture was stirred at 90° C. for 22 hours under nitrogen atmosphere. The reaction mixture was diluted with water (80 ml) and extracted with ethyl acetate (90 ml). The organic layer was washed with saturated aqueous solution of sodium chloride (80 ml) and dried with anhydrous sodium sulfate and concentrated under reduced pressure. The residue was purified by silica gel column chromatography (chloroform-methanol; 100:0→99:1→98:2) to afford a pale yellow solid. To a solution of this solid in ethanol (3.32 ml) was added 1 mol/l aqueous solution of sodium hydroxide (1.50 ml) in an ice bath and the mixture was stirred at room temperature for 14 hours. To this reaction solution was added 1 mol/l aqueous solution of hydrochloric acid (1.50 ml) in an ice bath and the organic layer was concentrated under reduced pressure. The aqueous solution was diluted with water (30 ml) and extracted with ethyl acetate (40 ml). The organic layer was dried with anhydrous sodium sulfate and concentrated under reduced pressure. The residue was purified by silica gel column chromatography (chloroform-methanol; 100:0→99:1→98:2) to afford a pale yellow solid. The solid was dissolved in concentrated hydrochloric acid (1.0 ml) in an ice bath and the aqueous solution was washed with chloroform (25 ml×3). To the aqueous layer was added saturated solution of sodium hydroxide to adjust pH to 12.0 and the basic aqueous solution was adjusted with hydrochloric acid to pH 7.4. The solution was extracted with chloroform (120 ml×1, 80 ml×2). The organic layer was dried with anhydrous sodium sulfate and concentrated under reduced pressure. The residue was purified by recrystallization from ethanol to afford the title compound 68.1 mg (18%) as pale yellow solid.

mp: 145-149° C.
¹H-NMR (400 MHz, 0.1N NaOD) δ: 8.43 (1H, d, J=3.2 Hz), 7.70 (1H, d, J=14.2 Hz), 5.12-4.92 (1H, m), 4.29 (1H, d, J=9.2 Hz), 4.12-4.07 (1H, m), 3.91-3.88 (1H, m), 3.24 (1H, d, J=9.6 Hz), 3.08 (1H, d, J=9.2 Hz), 2.54 (3H, s), 2.08-1.97 (1H, m), 1.92-1.87 (1H, m), 1.79-1.74 (1H, m), 1.65-1.55 (1H, m), 1.32-1.19 (3H, m), 0.84-0.76 (2H, m). Anal. Calcd for $C_{22}H_{23}F_2N_3O_3 \cdot 1.5H_2O$: C, 59.72; H, 5.92; F, 8.59; N, 9.50.
Found: C, 59.72; H, 5.65; F, 59.08; N, 9.47.
MS (ESI) m/z: 416 (M+H)⁺.
IR(ATR): 2939, 2867, 1719, 1612, 1542, 1507, 1460, 1428, 1354, 1314, 1284, 1184, 1136, 1024, 967, 921, 884, 806 cm⁻¹.

Example 55

7-[6-Amino-8-azatricyclo[4.3.0.0$^{1,3}$]nonan-8-yl]-1-[(1R,2S)-2-fluorocyclopropan-1-yl]-8-methyl-4-oxo-1,4-dihydroquinoline-3-carboxylic acid (7 Position: Derivative from Optical Isomer A)

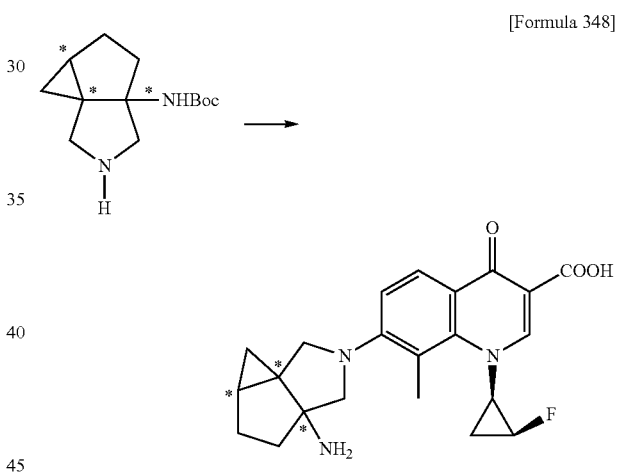

[Formula 348]

To a solution of 6-tert-butoxycarbonyl amino-8-azatricyclo[4.3.0.0$^{1,3}$]nonane (290 mg, 1.22 mmol) in dimethyl sulfoxide (2.42 ml) were added triethylamine (0.507 ml, 3.63 mmol) and 7-fluoro-1-[(1R,2S)-2-fluorocyclopropyl]-1,4-dihydro-8-methyl-4-oxoquinoline-3-carboxylic acid (337 mg, 1.21 mmol) and the mixture was stirred at 70° C. for 13 days under nitrogen atmosphere. The reaction solution was diluted with ethyl acetate and washed with 10% aqueous solution of citric acid (50 ml), water (60 ml), and saturated aqueous solution of sodium chloride (60 ml). The organic layer was dried with anhydrous sodium sulfate and concentrated under reduced pressure. The residue was purified by silica gel column chromatography (chloroform-methanol; 100:0→99:1→98:2→95:5) to afford a pale yellow solid. The solid was dissolved in concentrated hydrochloric acid (1.0 ml) in an ice bath and the aqueous solution was washed with chloroform (30 ml×5). To the aqueous layer was added saturated aqueous solution of sodium hydroxide to adjust pH to 12.0 and the basic aqueous solution was adjusted with hydrochloric acid to pH 7.4. The solution was extracted with chloroform (80 ml×4) and 10% methanol-chloroform (80 ml×1, 50 ml×1). The organic layer was dried with anhydrous sodium sulfate and concentrated under reduced pressure. The residue was purified by recrystallization from ethanol to afford the title compound 138 mg (29%) as a pale yellow solid.

mp: >254° C. (decomp.).

$^1$H-NMR (400 MHz, 0.1N NaOD) δ: 8.42 (1H, d, J=3.9 Hz), 8.00 (1H, d, J=9.3 Hz), 7.14 (1H, d, J=9.0 Hz), 5.13-4.94 (1H, m), 4.32 (1H, d, J=10.0 Hz), 4.10-4.04 (1H, m), 3.73 (1H, d, J=10.3 Hz), 3.23 (1H, d, J=10.0 Hz), 3.00 (1H, d, J=10.3 Hz), 2.46 (3H, s), 2.04-1.92 (2H, m), 1.79-1.73 (1H, m), 1.66-1.55 (1H, m), 1.35-1.17 (3H, m), 0.86-0.77 (2H, m).

Anal. Calcd for $C_{22}H_{24}FN_3O_3 \cdot 0.25H_2O$: C, 65.74; H, 6.14; F, 4.73; N, 10.45.

Found: C, 65.84; H, 6.28; F, 5.00; N, 10.41.

MS (ESI) m/z: 398 (M+H)$^+$.

IR(ATR): 3376, 3030, 2989, 2929, 2858, 1703, 1614, 1547, 1510, 1450, 1430, 1387, 1354, 1337, 1313, 1295, 1266, 1230, 1189, 1177, 1153, 1138, 1090, 1079, 1054, 1022, 998, 990, 923 cm$^{-1}$.

Example 56

7-{(1R,5S)-1-Amino-5-fluoro-3-azabicyclo[3.2.0]heptan-3-yl}-6-fluoro-1-[(1R,2S)-2-fluorocyclopropan-1-yl]-8-methyl-4-oxo-1,4-dihydroquinoline-3-carboxylic acid

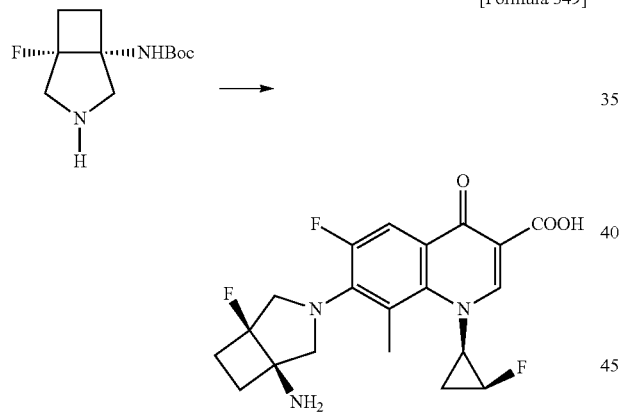

[Formula 349]

To a solution of tris(dibenzylideneacetone)dipalladium (0) (414 mg, 0.452 mmol) and 4,5-bis(diphenyl)phosphino-9,9-dimethylxanthene (522 mg, 0.902 mmol) in 1,4-dioxane (20.0 ml) were added ethyl 7-bromo-6-fluoro-1-[(1R,2S)-2-fluorocyclopropyl]-8-methyl-1,4-dihydro-4-oxoquinoline-3-carboxylate (1.28 g, 3.31 mmol), (1R,5S)-1-(tert-butoxycarbonyl amino)-5-fluoro-3-azabicyclo[3.2.0]heptane (693 mg, 3.01 mmol) and cesium carbonate (1.96 g, 6.02 mmol) and the mixture was stirred at 95° C. for 14 hours under nitrogen atmosphere. The reaction mixture was diluted with water (100 ml) and extracted with ethyl acetate (100 ml×2). The organic layer was dried with anhydrous sodium sulfate and concentrated under reduced pressure. The residue was purified by silica gel column chromatography (n-hexane-ethyl acetate; 100:0→95:5→90:10→75:25→5:95→0:100) to afford a pale yellow solid. To a solution of this solid in ethanol (15.9 ml) was added 1 mol/l aqueous solution of sodium hydroxide (5.98 ml) in an ice bath and the mixture was stirred at room temperature for 13 hours. To this reaction solution was added 1 mol/l aqueous solution of hydrochloric acid (5.98 ml) in an ice bath and the organic layer was concentrated under reduced pressure. The aqueous solution was diluted with water (80 ml) and extracted with ethyl acetate (100 ml×1, 80 ml×1). The organic layer was dried with anhydrous sodium sulfate and concentrated under reduced pressure. The residue was purified by silica gel column chromatography (chloroform-methanol; 100:0→99:1→98:2→97:3→96:4→95:5→94:6→93:7) to afford a pale yellow solid. The solid was dissolved in concentrated hydrochloric acid (3.0 ml) in an ice bath and the aqueous solution was washed with chloroform (40 ml×4). To the aqueous layer was added saturated solution of sodium hydroxide to adjust pH to 12.0 and the basic aqueous solution was adjusted with hydrochloric acid to pH 7.4. The solution was extracted with chloroform (250 ml×4). The organic layer was dried with anhydrous sodium sulfate and concentrated under reduced pressure. The residue was purified by recrystallization from ethanol to afford the title compound 690 mg (56%) as pale yellow solid.

mp: >272° C. (decomp.).

$^1$H-NMR (400 MHz, 0.1N NaOD) δ: 8.49 (1H, d, J=2.2 Hz), 7.70 (1H, dd, J=13.2, 4.2 Hz), 5.08-4.88 (1H, m), 4.12-4.06 (1H, m), 3.69-3.56 (2H, m), 3.42-3.39 (1H, m), 3.21-3.18 (1H, m), 2.64 (3H, d, J=5.1 Hz), 2.54-2.39 (1H, m), 2.31-2.20 (1H, m), 2.12-1.93 (2H, m), 1.66-1.56 (1H, m), 1.32-1.19 (1H, m).

Anal. Calcd for $C_{20}H_{20}F_3N_3O_3$: C, 58.96; H, 4.95; F, 13.99; N, 10.31.

Found: C, 58.76; H, 4.88; F, 14.11; N, 10.28.

MS (ESI) m/z: 408 (M+H)$^+$.

IR(ATR): 3089, 2980, 2936, 2862, 2837, 1719, 1614, 1544, 1506, 1474, 1454, 1432, 1350, 1318, 1268, 1231, 1213, 1181, 1159, 1140, 1093, 1058, 1047, 1021, 1009, 977, 962, 930, 898, 864, 837, 805 cm$^{-1}$.

Example 57

7-[6-amino-8-azatricyclo[4.3.0.0$^{1,3}$]nonan-8-yl]-6-fluoro-1-[(1R,2S)-2-fluorocyclopropan-1-yl]-8-methoxy-4-oxo-1,4-dihydroquinoline-3-carboxylic acid methanesulfonate

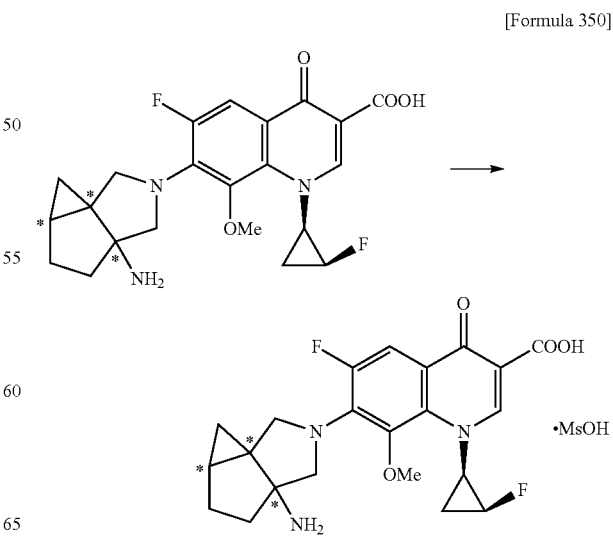

[Formula 350]

To a suspension of 7-[6-amino-8-azatricyclo[4.3.0.0$^{1,3}$]nonan-8-yl]-6-fluoro-1-[(1R,2S)-2-fluorocyclopropan-1-yl]-8-methoxy-4-oxo-1,4-dihydroquinoline-3-carboxylic acid (2.24 g, 4.82 mmol) in ethanol (48.2 ml) was added methanesulfonic acid (0.316 ml, 4.87 mmol) and the mixture was stirred at room temperature for 15 hours. To this reaction solution was added water (5 ml) and the mixture was concentrated under reduced pressure. To this residue was added 2-propanol (20 ml) and the mixture was stirred at room temperature for 15 hours. The precipitated solids were collected by filtration. The solids were washed with an excess amount of 2-propanol to afford the title compound 2.41 g (95%) as pale yellow solid.

mp: 202-204° C.

$^1$H-NMR (400 MHz, 0.1N NaOD) δ: 8.39 (1H, d, J=2.9 Hz), 7.64 (1H, d, J=14.4 Hz), 5.09-4.93 (1H, m), 4.21 (1H, dd, J=10.0, 2.7 Hz), 3.97 (1H, dt, J=10.0, 4.6 Hz), 3.72 (1H, dd, J=10.6, 2.7 Hz), 3.53 (3H, s), 3.39 (1H, d, J=10.3 Hz), 3.18 (1H, d, J=10.3 Hz), 2.83 (3H, s), 1.99-1.85 (2H, m), 1.73 (1H, dd, J=12.2, 8.5 Hz), 1.56-1.46 (1H, m), 1.39-1.23 (2H, m), 1.17-1.13 (1H, m), 0.79-0.74 (2H, m).

Anal. Calcd for $C_{22}H_{23}F_2N_3O_4CH_4O_3S$ 0.5H$_2$O: C, 51.49; H, 5.26; F, 7.08; N, 7.83; S, 5.98.

Found: C, 51.21; H, 5.20; F, 7.44; N, 7.82; S, 6.00.

MS (ESI) m/z: 432 (M+H)$^+$.

IR(ATR): 3412, 2944, 2878, 1694, 1617, 1597, 1536, 1513, 1437, 1361, 1330, 1315, 1297, 1273, 1219, 1167, 1135, 1109, 1040, 952, 925, 883, 805 cm$^{-1}$.

Example 58

7-[(1R,5S)-1-Amino-5-fluoro-3-azabicyclo[3.3.0]octan-3-yl]-6-fluoro-1-[(1R,2S)-2-fluorocyclopropane]-1,4-dihydro-8-methyl-4-oxoquinoline-3-carboxylic acid methanesulfonate

[Formula 351]

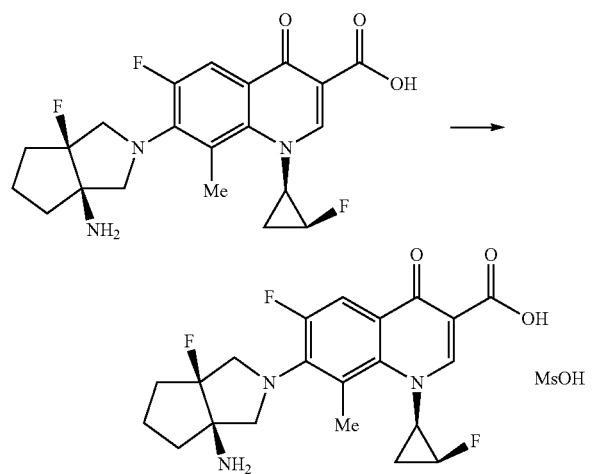

To a suspension of 7-[(1R,5S)-1-amino-5-fluoro-3-azabicyclo[3.3.0]octan-3-yl]-6-fluoro-1-[(1R,2S)-2-fluorocyclopropane]-1,4-dihydro-8-methyl-4-oxoquinoline-3-carboxylic acid (4.50 g, 10.7 mmol) in ethanol (90 ml) was added methanesulfonic acid (0.695 ml, 10.7 mmol), and the mixture was stirred at room temperature for 30 minutes. The mixture was diluted with water (20 ml), and distilled off under reduced pressure. The residue was purified by slurry in 2-propanol to afford 4.96 g of the title compound as a pale yellow powder.

$^1$H-NMR (400 MHz, 0.1N NaOD) δ: 8.48 (1H, d, J=2.9 Hz), 7.72 (1H, d, J=13.7 Hz), 5.11-4.86 (1H, m), 4.15-4.07 (1H, m), 3.93-3.81 (1H, m), 3.60-3.31 (3H, m), 2.82 (3H, s), 0.62 (3H, s), 2.16-1.98 (3H, m), 1.92-1.55 (4H, m), 1.33-1.19 (1H, m).

MS (FAB); m/z: 422 (M+H)$^+$.

Anal. Calcd $C_{21}H_{22}F_3N_3O_3 \cdot CH_3SO_3H \cdot 1.75H_2O$:C, 48.13; H, 5.42; F, 10.38; N, 7.65; S, 5.84. Found: C, 47.81; H, 5.09; F, 10.43; N, 7.63; S, 5.75.

IR(ATR) ν: 3442, 2871, 1709, 1615, 1509, 1432, 1370, 1319, 1265, 1161, 1038, 971, 929, 892, 853, 806 cm$^{-1}$.

Reference Example 226

(3aS)-1-Hydroxy-6-oxo-5-[(R)-1-phenylethyl]tetrahydrofuro[3,4-c]pyrrole-3a-carboxylic acid tert-butyl ester

[Formula 352]

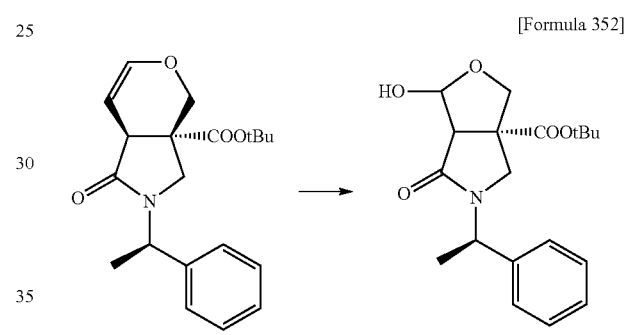

A mixture of (3aS,7aS)-1-oxo-2-[(R)-1-phenylethyl]-1,2,3,7a-tetrahydropyrano[3,4-c]pyrrole-3a-carboxylic acid tert-butyl ester (4.0 g, 11.6 mmol), N-methylmorpholine-N-oxide (2.95 g, 22.0 mmol) and osmium tetroxide (cat.) was dissolved in tert-butanol (20 mL) and water (10 mL), and stirred at room temperature for 3 days. The reaction mixture was diluted with AcOEt and 10% aq. sodium thiosulfate added. The layers were separated and the aqueous layer extracted with AcOEt. The combined extracts were washed with sat. aq. NaHCO$_3$, brine, dried (Na$_2$SO$_4$), and concentrated in vacuo, giving a dark brown oil (4.4 g). The crude product (2.6 g) was dissolved in tetrahydrofuran (60 mL) and water (30 mL), and sodium periodate (2.6 g) added. The reaction mixture was stirred at room temperature for 18 h, and diluted with AcOEt and water. The layers were separated and the aqueous layer extracted with AcOEt. The combined extracts were washed with sat. aq. NaHCO$_3$, brine, dried (Na$_2$SO$_4$), and concentrated in vacuo. The residue was dissolved in ethanol and tetrahydrofuran (20 mL; 17:3) and 1N aq. NaOH (5.2 mL) added dropwise at 0° C. The mixture was stirred at room temperature for 3 h, after which time additional 1N aq. NaOH (2.2 mL) was added and the reaction mixture was stirred for another 1 h. The solvent was removed in vacuo and the resulting residue was partitioned between AcOEt and water, and the aqueous layer extracted. The combined extracts were washed with sat. aq. NaHCO$_3$, brine, dried (Na$_2$SO$_4$), and concentrated in vacuo. The resulting residue was purified by silica gel chromatography eluting with 50% AcOEt in hexane to afford the title compound (1.10 g) as a white solid.

¹H-NMR (400 MHz, CDCl₃) δ: 7.39-7.25 (5H, m), 5.71 (1H, d, J=7.3 Hz), 5.66-5.44 (1.2H, m), 4.96 (0.2H, d, J=7.3 Hz), 4.49 (0.8H, d, J=9.6 Hz), 4.25 (0.2H, d, J=9.6 Hz), 4.00 (0.2H, d, J=9.2 Hz), 3.90 (0.8H, d, J=9.2 Hz), 3.64 (0.8H, d, J=7.3 Hz), 3.38-3.24 (3H, m), 1.54-1.38 (12H, m).
MS (ESI) m/z: 348 (M+H)⁺.

Reference Example 227

(3S)-3,4-Bis(hydroxymethyl)-5-oxo-1-[(R)-1-phenylethyl]pyrrolidine-3-carboxylic acid tert-butyl ester

[Formula 353]

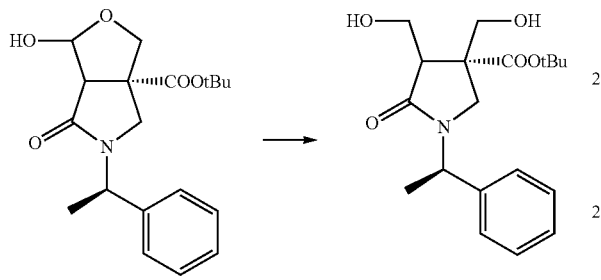

To a cooled solution (–20° C.) of (3aS)-1-hydroxy-6-oxo-5-[(R)-1-phenylethyl]tetrahydrofuro[3,4-c]pyrrole-3a-carboxylic acid tert-butyl ester (350 mg, 1.01 mmol) in tetrahydrofuran and ethanol (10 mL; 4:1), sodium borohydride (38.0 mg, 1.00 mmol) was added portionwise, and the mixture was stirred at the same temperature for 5.5 h. The reaction mixture was concentrated in vacuo and taken up in AcOEt and water. The layers were separated and the aqueous layer extracted with AcOEt. The combined extracts were washed with brine, dried (Na₂SO₄), and concentrated in vacuo. The residue was purified by silica gel chromatography eluting with 90% AcOEt in hexane to afford the title compound (153 mg) as a colorless oil.
¹H-NMR (400 MHz, CDCl₃) δ: 7.38-7.25 (5H, m), 5.50 (1H, q, J=7.0 Hz), 4.19-3.80 (4H, m), 3.40-3.05 (5H, m), 1.52 (3H, d, J=7.0 Hz), 1.40 (9H, s).
MS (ESI) m/z: 350 (M+H)⁺.

Reference Example 228

(3aS)-6-Oxo-5-[(R)-1-phenylethyl]tetrahydrofuro[3,4-c]pyrrole-3a-carboxylic acid tert-butyl ester

[Formula 354]

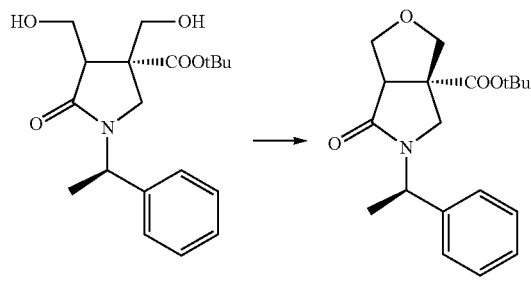

To a cooled (0° C.) solution of (3S)-3,4-bis(hydroxymethyl)-5-oxo-1-[(R)-1-phenylethyl]pyrrolidine-3-carboxylic acid tert-butyl ester (710 mg, 2.03 mmol) and triphenylphosphine (450 mg, 2.64 mmol) in tetrahydrofuran (10 mL) was added a solution of 40% diethyl azodicarboxylate in toluene (1.06 mL, 2.33 mmol) dropwise. The reaction mixture was allowed to warm to room temperature and stirred for 6 h. The mixture was concentrated in vacuo. The residue was purified by silica gel chromatography eluting with 40% AcOEt in hexane to afford the title compound (435 mg) as a white solid.
¹H-NMR (400 MHz, CDCl₃) δ: 7.39-7.25 (5H, m), 5.48 (1H, q, J=7.2 Hz), 4.32-4.26 (1H, m), 4.01 (1H, d, J=9.6 Hz), 3.97-3.91 (1H, m), 3.85 (1H, d, J=9.6 Hz), 3.43 (1H, d, J=10.1 Hz), 3.37-3.32 (1H, m), 3.26 (1H, d, J=10.1 Hz), 1.54 (3H, d, J=6.9 Hz), 1.38 (9H, br s).
MS (ESI) m/z: 332 (M+H)⁺.

Reference Example 229

[(3aS)-5-[(R)-1-Phenylethyl]tetrahydrofuro[3,4-c]pyrrol-3a-yl]carbamic acid tert-butyl ester

[Formula 355]

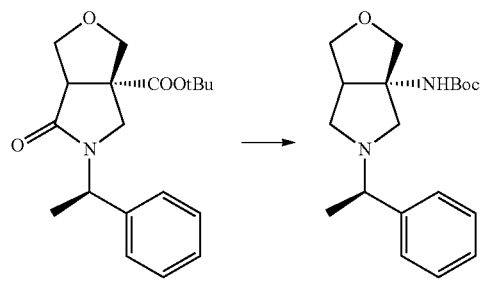

To a solution of [(3aS)-6-oxo-5-[(R)-1-phenylethyl]tetrahydrofuro[3,4-c]pyrrol-3a-yl]carbamic acid tert-butyl ester (820 mg, 2.47 mmol) in dichloromethane (8 mL) was added trifluoroacetic acid (8 mL), and the mixture was stirred at room temperature for 2 h. The solvent was removed in vacuo and pumped to dryness, giving a white solid (680 mg).
1,1'-carbonybis-1H-imidazole (480 mg, 2.94 mmol) was added to a solution of the crude product (540 mg) in acetonitrile (10 ml) at 0° C., and the mixture was stirred for 1 h at the same temperature and then warmed to room temperature. Ammonia gas was bubbled through the reaction mixture for 30 min and the solvent was concentrated in vacuo. The resulting residue was taken up in dichloromethane, washed with 1N HCl, sat. aq. NaHCO₃ and brine, dried (Na₂SO₄), and concentrated in vacuo to give a white solid (536 mg).
To a suspension of the white solid (536 mg) in tert-butanol (20 mL) was added lead tetraacetate (1.73 g, 3.90 mmol), and the mixture was heated to 100° C. for 5 h. The reaction mixture was allowed to cool to room temperature, diluted with diethyl ether (200 mL) and sodium hydrogen carbonate (3 g) added. After stirring for 30 min, the precipitate was filtered off. The filtrate was concentrated in vacuo, and the residue was taken up in dichloromethane, washed with sat. aq. NaHCO₃ and brine, dried (Na₂SO₄), and concentrated in vacuo. The crude product was obtained as a white solid (620 mg).
Trifluoroacetic acid (6 ml) was added to a solution of the crude product (200 mg) in dichloromethane (6 mL), and the reaction mixture was stirred for 1 h then the solvent removed in vacuo and pumped to dryness. This was taken forward to the next step.

To a solution of this material in toluene (6 mL) was slowly added sodium bis(2-methoxyethoxy)aluminum hydride (65% toluene solution, 690 μL, 2.3 mmol), and the mixture was heated to 60° C. for 1 h. The reaction mixture was cooled to room temperature then 5N aq. NaOH added, and stirred for 1 h. The layers were separated and the aqueous layer extracted with toluene. The combined extracts were washed with brine, dried ($Na_2SO_4$), and concentrated in vacuo. The crude product (540 mg) was carried forward without purification.

Di-tert-butyl dicarbonate (589 mg) was added to a solution of the crude product in dichloromethane (6 mL), and the mixture was stirred for 18 h and the solvent removed in vacuo. The residue was purified by silica gel chromatography eluting with 30% AcOEt in hexane to afford the title compound (150 mg) as a white solid.

$^1$H-NMR (400 MHz, $CDCl_3$) δ: 7.31-7.21 (5H, m), 5.00 (1H, s), 4.09-3.78 (3H, m), 3.53 (1H, dd, J=8.7, 4.6 Hz), 3.27 (1H, q, J=6.7 Hz), 2.78-2.65 (3H, m), 2.50-2.36 (2H, m), 1.42 (9H, s), 1.33 (3H, d, J=6.4 Hz).

MS (ESI) m/z: 333 (M+H)$^+$

Reference Example 230

(3aS)-(Tetrahydrofuro[3,4-c]pyrrol-3a-yl)carbamic acid tert-butyl ester

[Formula 356]

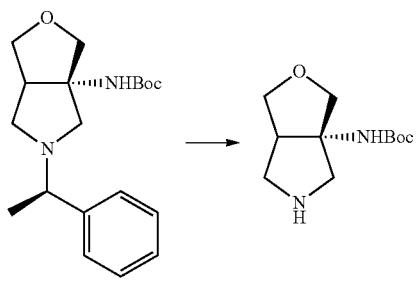

[(3aS)-5-[(R)-1-Phenylethyl]tetrahydrofuro[3,4-c]pyrrol-3a-yl]carbamic acid tert-butyl ester (355 mg, 1.06 mmol) was dissolved in dioxane (10 ml) and 20% palladium hydroxide catalyst (20 wt. % Pd on carbon, wet; cat.) was added. The mixture was vigorously stirred under a hydrogen atmosphere at 40° C. for 24 h. After removing the catalyst by filtration, the filtrate was concentrated under reduced pressure. The residue was taken up in dichloromethane, and washed with 1N aq. NaOH and brine. The organic layer was dried over anhydrous sodium sulfate and the solvent removed in vacuo to give the crude title compound (243 mg) as a colorless syrup.

MS (ESI) m/z: 229 (M+H)$^+$.

Example 59

7-[(3aS)-3a-Aminotetrahydrofuro[3,4-c]pyrrol-5-yl]-6-fluoro-1-[(1R,2S)-2-fluorocyclopropyl]-1,4-dihydro-8-methoxy-4-oxoquinoline-3-carboxylic acid

[Formula 357]

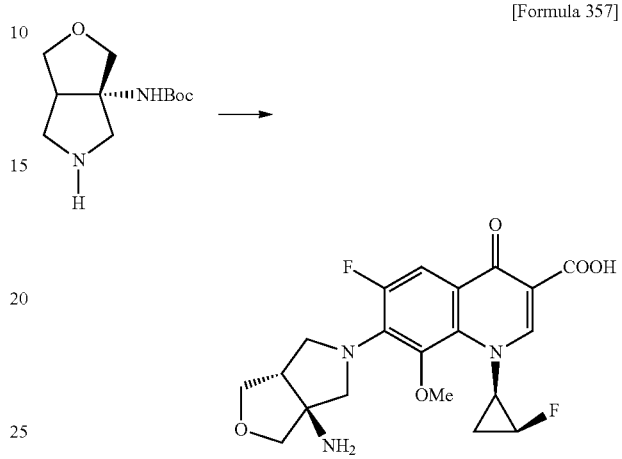

To a solution of 6,7-difluoro-1-[(2S,1R)-2-fluorocyclopropyl]-1,4-dihydro-8-methoxy-4-oxoquinoline-3-carboxylic acid-difluoroboron complex (426 mg, 1.18 mmol) in dimethyl sulfoxide (6 ml) were added (S)-(tetrahydro-2-oxa-5-azacyclopropa[c]pentalen-3a-yl)carbamic acid tert-butyl ester (270 mg, 1.18 mmol) and triethylamine (0.50 ml, 3.54 mmol), and the mixture was stirred at 40° C. for 17 h. The reaction solution was concentrated in vacuo, and the concentrate was dissolved in a mixed solution of ethanol and water (9:1) (150 ml). After adding triethylamine (5 ml), the mixture was heated under reflux for 5 h. The reaction mixture was concentrated under reduced pressure, and the concentrate was dissolved in AcOEt (100 ml×2), and washed with 10% aq. citric acid (100 ml) and brine (100 ml). The organic layer was dried over anhydrous sodium sulfate, and the solvent was distilled off under reduced pressure. After purification by silica gel column chromatography (3% MeOH in $CHCl_3$), the solid obtained was dissolved in concentrated hydrochloric acid (5 ml) in an ice bath, and the aqueous solution was washed with chloroform (50 ml×3). To the aqueous layer was added 10 mol/l aqueous solution of sodium hydroxide to adjust pH to 12.0, and the basic aqueous solution was adjusted with hydrochloric acid to pH 7.4. The solution was extracted with chloroform (100 ml×6) and the combined extracts were dried with anhydrous sodium sulfate, and the solvent was distilled off under reduced pressure. The residue was purified by preparative chromatography, and further purified by recrystallization from ethanol, and subsequently, dried under reduced pressure to give the title compound (220 mg) as pale yellow crystals.

mp: 201-202° C.

$^1$H-NMR (400 MHz, $CDCl_3$) δ: 8.76 (1H, d, J=1.4 Hz), 7.87 (1H, d, J=12.8 Hz), 4.92-4.71 (1H, m), 4.27 (1H, dd, J=9.2, 7.3 Hz), 3.93-3.57 (11H, m), 2.57-2.49 (1H, m), 1.68-1.47 (2H, m). Anal; Calcd for $C_{20}H_{21}F_2N_3O_5H_2O$:C, 54.67; H, 5.28; N, 9.56; F, 8.65. Found: C, 54.52; H, 5.18; N, 9.58; F, 8.73.

MS (ESI) m/z: 422 (M+H)$^+$.

IR(ATR) ν: 3301, 2974, 2847, 1722, 1614, 1580, 1516, 1447, 1403, 1378, 1365, 1355, 1340, 1316, 1289, 1265 cm⁻¹.

Example 60

7-[(1R,5S)-1-Amino-5-fluoro-3-azabicyclo[3.3.0]octan-3-yl]-6-fluoro-1-[(1R,2S)-2-fluorocyclopropane]-1,4-dihydro-8-methyl-4-oxoquinoline-3-carboxylic acid

[Formula 358]

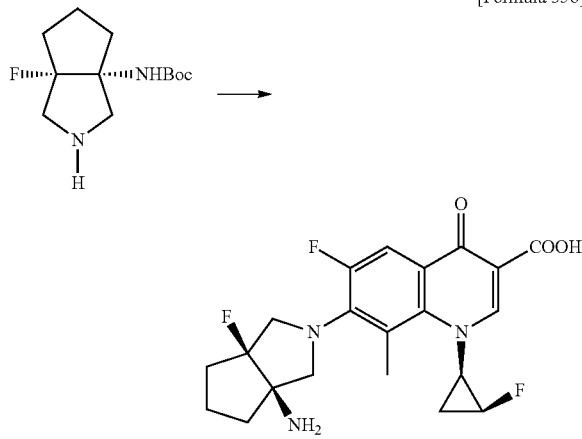

To a solution of tris(dibenzylideneacetone)dipalladium (0) (7.75 g, 8.46 mmol), 4,5-bis(diphenyl)phosphino-9,9-dimethylxanthene (14.7 g, 25.4 mmol), ethyl 7-bromo-6-fluoro-1-[(1R,2S)-2-fluorocyclopropyl]-8-methyl-1,4-dihydro-4-oxoquinoline-3-carboxylate (14.2 g, 36.8 mmol) and (1R,5S)-1-(tert-butoxycarbonyl amino)-5-fluoro-3-azabicyclo[3.3.0]octan (6.90 g, 28.2 mmol) in 1,4-dioxane (345 ml) were added cesium carbonate (18.4 g, 56.5 mmol) and the mixture was stirred at 110° C. for 23 hours under nitrogen atmosphere. The reaction mixture was diluted with water (400 ml) and extracted with ethyl acetate (600 ml×1, 250 ml×1). The organic layer was dried with anhydrous sodium sulfate and concentrated under reduced pressure. The residue was purified by silica gel column chromatography (chloroform-methanol; 100:0→99.5:0.5→99.25:0.75→99:1) to afford a solid. To a solution of this solid in ethanol (273 ml) was added 1 mol/l aqueous solution of sodium hydroxide (68.2 ml) in an ice bath and the mixture was stirred at room temperature for 1 hours. To this reaction solution was added ethanol (327 ml) and 1 mol/l aqueous solution of sodium hydroxide (27.3 ml) and the mixture was stirred at room temperature for 13 hours. To this reaction solution was added 1 mol/l aqueous solution of hydrochloric acid (95.5 ml) in an ice bath and the organic layer was concentrated under reduced pressure. The aqueous solution was diluted with water (150 ml) and extracted with chloroform (250 ml×1, 150 ml×1). The organic layer was dried with anhydrous sodium sulfate and concentrated under reduced pressure. The residue was purified by silica gel column chromatography (n-hexane-ethyl acetate; 100:0→2:1→1:1→1:1.5→1:1.7→1:1.85→1:2→1:5→1:9→0:100) to afford a pale yellow solid. The solid was dissolved in concentrated hydrochloric acid (30 ml) in an ice bath and the aqueous solution was washed with chloroform (100 ml×5). To the aqueous layer was added saturated solution of sodium hydroxide to adjust pH to 12.0. To the solution was added water (1.8 l) and the basic aqueous solution was adjusted with hydrochloric acid to pH 7.4. The solution was extracted with chloroform (1.5 1×1, 800 ml×1). The organic layer was dried with anhydrous sodium sulfate and concentrated under reduced pressure. The residue was purified by recrystallization from 2-propanol/methanol=10/1 to afford the title compound 6.14 g (52%) as pale yellow solid. And all spectroscopic data of this compound proved to be in good agreement with those of Example 17.

Reference Example 231

(3aS)-6-Oxo-5-[(R)-1-phenylethyl]-5,6-dihydro-4H-furo[3,4-c]pyrrole-3a-carboxylic acid tert-butyl ester

[Formula 359]

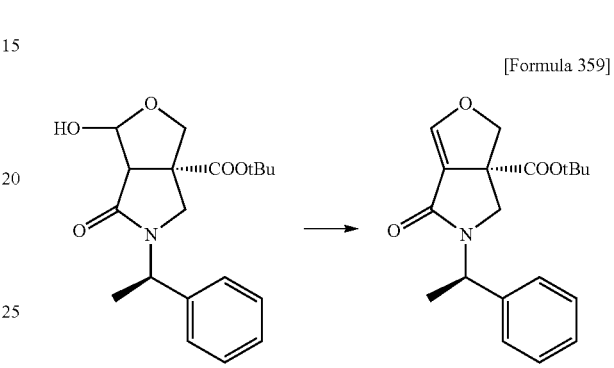

To a solution of (3aS)-(tetrahydrofuro[3,4-c]pyrrol-3a-yl) carboxylic acid tert-butyl ester (8.80 g, 25.0 mmol) and triethylamine (7.8 mL) in dichloromethane (75 mL) was added dropwise methanesulfonyl chloride (3.13 mL, 40.0 mmol) at −10° C. and the mixture was stirred for 1.5 h at the same temperature and then additional triethylamine (7.8 mL) added. The reaction mixture was heated to 40° C. and stirred for 5 days. After cooling to room temperature, the solvent was removed in vacuo and the residue was purified by silica gel chromatography eluting with a mixed solution of AcOEt, hexane and triethylamine (40:60:0.5) to afford the title compound as a white solid (2.56 g).
¹H-NMR (400 MHz, CDCl₃) δ: 7.38-7.25 (5H, m), 7.08 (1H, s), 5.48 (1H, q, J=6.9 Hz), 5.03 (1H, d, J=9.6 Hz), 4.25 (1H, d, J=9.6 Hz), 3.43 (1H, d, J=10.1 Hz), 3.26 (1H, d, J=10.1 Hz), 1.38 (3H, d, J=6.9 Hz), 1.30 (9H, s).
MS (ESI) m/z: 330 (M+H)⁺.

Reference Example 232

(S)-6-Oxo-5-[(R)-1-phenylethyl]tetrahydro-2-oxa-5-azacyclopropa[c]pentalene-3a-carboxylic acid tert-butyl ester

[Formula 360]

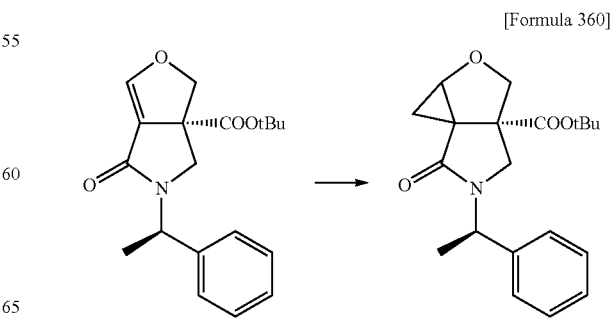

To a solution of diethyl zinc (1M hexane solution, 22.3 ml) in dichloromethane (75 mL) was added dropwise diiodomethane (1.79 mL, 22.3 mmol) at −10° C., and the mixture was stirred for 15 min at the same temperature. A solution of (S)-6-oxo-5-[(R)-1-phenylethyl]-5,6-dihydro-4H-furo[3,4-c]pyrrole-3a-carboxylic acid tert-butyl ester in dichloromethane was added at −10° C., and the resulting mixture was stirred for 8 h at room temperature. The reaction mixture was quenched with 10% aq. citric acid. The layers were separated and the aqueous layer was extracted with dichloromethane. The combined organic layers were washed with sat. aq. NaHCO₃ and brine, dried (Na₂SO₄) and concentrated in vacuo. The residue was purified by silica gel chromatography eluting with 30% AcOEt in hexane to afford the title compound (1.96 g) as a white solid.

¹H-NMR (400 MHz, CDCl₃) δ: 7.38-7.25 (5H, m), 5.54 (1H, q, J=7.0 Hz), 4.45 (1H, d, J=9.2 Hz), 4.24 (1H, dd, J=5.5, 2.8 Hz), 4.14 (1H, d, J=9.2 Hz), 3.51 (1H, d, J=10.1 Hz), 3.40 (1H, d, J=10.1 Hz), 1.73-1.67 (1H, m), 1.58-1.53 (4H, m), 1.33 (9H, s).

MS (ESI) m/z: 344 (M+H)⁺

Reference Example 233

[(S)-5-[(R)-1-Phenylethyl]tetrahydro-2-oxa-5-azacyclopropa[c]pentalen-3a-yl]carbamic acid tert-butyl ester

[Formula 361]

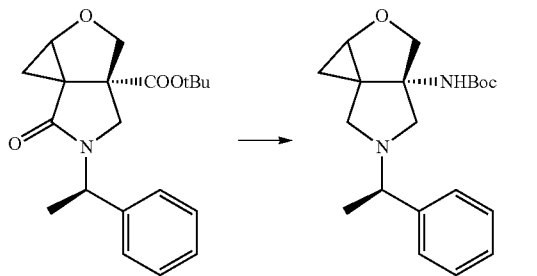

To a solution of (S)-6-oxo-5-[(R)-1-phenylethyl]tetrahydro-2-oxa-5-azacyclopropa[c]pentalene-3a-carboxylic acid tert-butyl ester (880 mg, 2.56 mmol) in dichloromethane (7 mL) was added trifluoroacetic acid (8 ml), and the mixture was stirred at room temperature for 2 h. The solvent was removed in vacuo to give a white solid (800 mg).

1,1'-carbonybis-1H-imidazole (677 mg, 4.18 mmol) was added to a solution of the white solid (800 mg) in acetonitrile (15 ml) at −0° C., and the mixture was stirred for 1 h at the same temperature and then allowed to warm to room temperature. Ammonia gas was bubbled through the reaction mixture for 30 min and the solvent was concentrated in vacuo. The resulting residue was taken up in dichloromethane, washed with 1N HCl, sat. aq. NaHCO₃ and brine, dried (Na₂SO₄), and concentrated in vacuo to give a white solid (750 mg).

To a suspension of the white solid (120 mg) in tert-butanol (5 mL) was added lead tetraacetate (558 mg, 1.26 mmol), and the mixture was heated to 100° C. for 5 h. The reaction mixture was allowed to cool to room temperature, diluted with diethyl ether (50 mL) and sodium hydrogen carbonate (1 g) added. After stirring for 30 min, the solids were filtered off. The filtrate was removed in vacuo, and the residue was taken up in dichloromethane, washed with sat. aq. NaHCO₃ and brine, dried (Na₂SO₄), and concentrated in vacuo. The crude product was taken on without further purification.

Trifluoroacetic acid (6 mL) was added to a solution of the crude product in dichloromethane (5 mL), and the reaction mixture was stirred for 1 h then the solvent removed in vacuo, and pumped to dryness. This was taken forward to the next step.

To a solution of this material in toluene (4 mL) was slowly added sodium bis(2-methoxyethoxy)aluminum hydride (65% toluene solution, 600 μL, 2.0 mmol), and the mixture was heated to 60° C. for 1 h. The reaction mixture was cooled to room temperature and 5N aq. NaOH added, and then stirred for 1 h. The layers were separated and the aqueous layer extracted with toluene. The combined extracts were washed with brine, dried (Na₂SO₄), and concentrated in vacuo. The crude product was carried forward without purification.

Di-tert-butyl dicarbonate (163 mg) was added to a solution of the crude product in dichloromethane (6 mL), and the mixture was stirred for 18 h and the solvent removed in vacuo. The residue was purified by silica gel chromatography eluting with 25% AcOEt in hexane to afford the title compound (140 mg) as a white solid.

¹H-NMR (400 MHz, CDCl₃) δ: 7.36-7.19 (5H, m), 4.92 (1H, s), 4.20 (1H, d, J=9.6 Hz), 3.98-3.85 (2H, m), 3.43 (1H, q, J=6.6 Hz), 2.99 (1H, d, J=8.7 Hz), 2.81-2.62 (3H, m), 1.40 (9H, s), 1.35 (3H, d, J=6.6 Hz), 1.19 (1H, d, J=6.4 Hz), 0.91 (1H, t, J=5.7 Hz).

MS (ESI) m/z: 345 (M+H)⁺.

Reference Example 234

(S)-(Tetrahydro-2-oxa-5-azacyclopropa[c]pentalen-3a-yl)carbamic acid tert-butyl ester

[Formula 362]

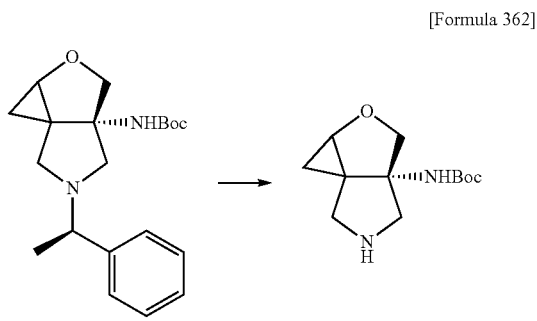

An [(S)-5-[(R)-1-Phenylethyl]tetrahydro-2-oxa-5-azacyclopropa[c]pentalen-3a-yl]carbamic acid tert-butyl ester (480 mg, 1.39 mmol) was dissolved in dioxane (10 ml) and 20% palladium hydroxide catalyst (20 wt. % Pd on carbon, wet; cat.) was added. The mixture was vigorously stirred under a hydrogen atmosphere at room temperature for 3 days. After removing the catalyst by filtration, the filtrate was concentrated under reduced pressure. The residue was taken up in dichloromethane, and washed with 1N aq. NaOH and brine. The organic layer was dried over anhydrous sodium sulfate and the solvent removed in vacuo to give the crude title compound as a white solid (280 mg).

MS (ESI) m/z: 241 (M+H)⁺.

Example 61

7-[(3aS)-3a-Amino-5-aza-oxatetrahydrocyclopentalen-5-yl]-6-fluoro-1-[(1R,2S)-2-fluorocyclopropyl]-1,4-dihydro-8-methoxy-4-oxoquinoline-3-carboxylic acid

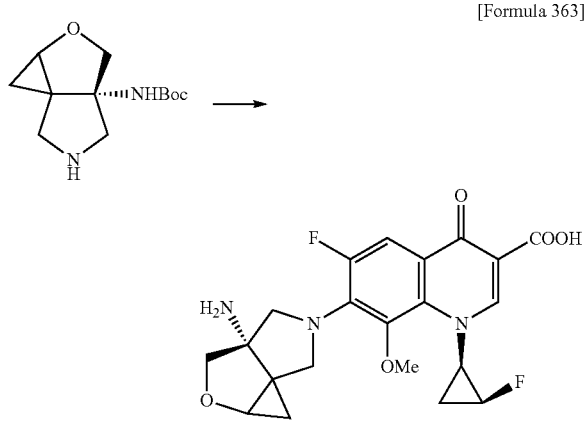

[Formula 363]

To a solution of 6,7-difluoro-1-[(2S,1R)-2-fluorocyclopropyl]-1,4-dihydro-8-methoxy-4-oxoquinoline-3-carboxylic acid-difluoroboron complex (361 mg, 1.00 mmol) in dimethyl sulfoxide (5 ml) were added (S)-(tetrahydro-2-oxa-5-azacyclopropa[c]pentalen-3a-yl)carbamic acid tert-butyl ester (250 mg, 1.08 mmol) and triethylamine (0.50 ml, 3.54 mmol), and the mixture was stirred at room temperature for 2 days. The reaction solution was concentrated in vacuo, and the concentrate was dissolved in a mixed solution of ethanol and water (9:1) (150 ml). After adding triethylamine (5 ml), the mixture was heated under reflux for 5 h. The reaction mixture was concentrated under reduced pressure, and the concentrate was dissolved in AcOEt (100 ml×2), and washed with 10% aq. citric acid (100 ml) and brine (100 ml). The organic layer was dried over anhydrous sodium sulfate, and the solvent was distilled off under reduced pressure. After purification by silica gel chromatography (5% MeOH in CHCl$_3$), the residue was dissolved in concentrated hydrochloric acid (5 ml) in an ice bath, and the aqueous solution was washed with chloroform (50 ml×3). To the aqueous layer was added 10 mol/l aqueous solution of sodium hydroxide to adjust pH to 12.0, and the basic aqueous solution was adjusted with hydrochloric acid to pH 7.4. The solution was extracted with chloroform (100 ml×6) and the combined extracts were dried with anhydrous sodium sulfate, and the solvent was distilled off under reduced pressure. The residue was purified by preparative chromatography, and further purified by recrystallization from ethanol, and subsequently, dried under reduced pressure to give the title compound (135 mg) as pale yellow needle crystals.

mp: 189-191° C.

$^1$H-NMR (400 MHz, 0.1N NaOD) δ: 8.42 (1H, d, J=2.8 Hz), 7.71 (1H, d, J=13.8 Hz), 5.13-4.89 (1H, m), 4.17-4.01 (4H, m), 3.94 (1H, dd, J=10.5, 2.3 Hz), 3.67 (3H, s), 3.64-3.47 (3H, m), 1.63-1.37 (3H, m), 1.02 (1H, dd, J=7.8, 5.5 Hz).

Anal; Calcd for C$_{21}$H$_{21}$F$_2$N$_3$O$_5$·1.25H$_2$O:C, 55.32; H, 5.20; N, 9.22; F, 8.33. Found: C, 55.48; H, 5.12; N, 9.00; F, 8.61.

MS (ESI) m/z: 434 (M+H)$^+$.

IR(ATR) ν: 3358, 3076, 2941, 2879, 1721, 1620, 1513, 1437, 1367, 1323, 1274 cm$^{-1}$.

Test Example 1

Antibacterial activity of the compounds of the present invention was measured in accordance with the standard method specified by the Japanese Society of Chemotherapy. The results are shown as MIC (μg/mL) (Table 2).

For comparison with the MIC values of the compounds of the present invention, Table 2 also shows MIC values of 7-[3-(R)-(1-aminocyclopropyl)pyrrolidin-1-yl]-8-cyano-1-[2-(S)-fluoro-1-(R)-cyclopropyl]-1,4-dihydro-4-oxoquinoline-3-carboxylic acid described in WO 02/40478 (control drug 1: the following formula), levofloxacin (LVFX), ciprofloxacin (CPFX), and moxifloxacin (MXFX).

The compound specifically exemplified in EP-A-343524 described in the section "Description of the Related Art", which is represented by the following formula:

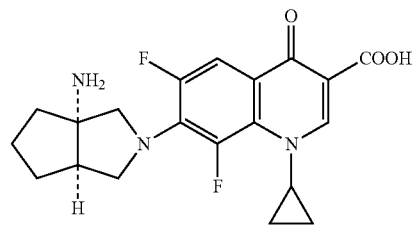

[Formula 364]

has one of two optical isomers as its 7-position substituent. The present inventors synthesized a compound represented by the following formula:

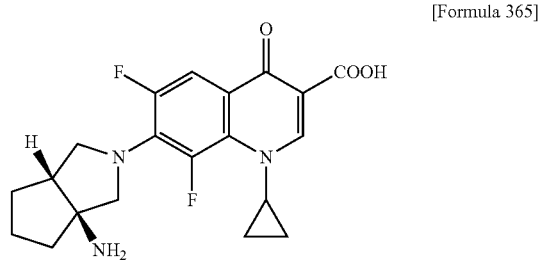 [SMILES: N[C@@]12CCC[C@@H]1CN(c1c(F)cc3c(=O)c(C(=O)O)cn(C4CC4)c3c1F)C2]

[Formula 365]

which has a (1S,5R)-1-amino-3-azabicyclo[3.3.0]octan-3-yl group that is a highly active isomer as its 7-position substituent. The compound represented by the formula 365 was confirmed to be positive for induction of micronuclei in a mouse bone marrow micronucleus test after intravenous administration. That is, the compound was suggested to be genotoxic. Further, the compound was found to be positive for phototoxicity in a mouse phototoxicity test after intravenous administration. On the other hand, the compound described in Example 11 which is a representative compound of the present invention was found to be negative in the above two tests. That is, the compound was suggested to be weakly genotoxic and not phototoxic and therefore highly safe as a human medicine.

TABLE 2

| | Table Antibacterial activity | | | | | | | | |
|---|---|---|---|---|---|---|---|---|---|
| | Compound (Example No.) | | | | | | | | |
| Bacteria | 2 | 5 | 10 | 11 | 15 | 17 | 24 | 25 | 27 |
| *E. coli* NIHJ | 0.025 | 0.025 | 0.025 | 0.025 | 0.006 | ≤0.003 | 0.025 | 0.012 | 0.012 |
| *K. pneumoniae* TYPE 1 | 0.1 | 0.1 | 0.2 | 0.1 | 0.05 | 0.012 | 0.1 | 0.05 | 0.1 |
| *P. mirabilis* 08103 | 0.012 | 0.025 | 0.05 | 0.05 | 0.025 | 0.006 | 0.025 | 0.025 | 0.05 |
| *E. cloacae* 03400 | 0.025 | 0.025 | 0.025 | 0.012 | 0.025 | 0.006 | 0.025 | 0.012 | 0.025 |
| *S. marcescens* 10100 | 0.2 | 0.2 | 0.2 | 0.1 | 0.2 | 0.05 | 0.2 | 0.1 | 0.2 |
| *P. aeruginosa* PAO1 | 0.78 | 0.78 | 0.78 | 0.78 | 0.78 | 0.2 | 0.39 | 0.39 | 0.78 |
| *H. influenzae* ATCC49247 | 0.006 | 0.012 | 0.012 | 0.006 | ≤0.003 | ≤0.003 | 0.006 | 0.006 | 0.006 |
| *M(B). Caterrhalis* ATCC25238 | 0.025 | 0.05 | 0.025 | 0.025 | 0.025 | 0.006 | 0.05 | 0.025 | 0.05 |
| *S. aureus* FDA 209-P | ≤0.003 | 0.006 | 0.006 | 0.012 | 0.012 | 0.006 | 0.025 | 0.025 | 0.012 |
| *S. epidermidis* 56500 | 0.012 | 0.025 | 0.025 | 0.05 | 0.05 | 0.025 | 0.1 | 0.1 | 0.05 |
| *S. pneumoniae* J24 | 0.012 | 0.025 | 0.025 | 0.05 | 0.05 | 0.025 | 0.05 | 0.05 | 0.025 |
| *S. pyogenes* JCM5674(ATCC12344) | 0.025 | 0.05 | 0.025 | 0.025 | 0.05 | 0.025 | 0.1 | 0.05 | 0.05 |
| *E. faecalis* 19433 | 0.05 | 0.1 | 0.1 | 0.1 | 0.2 | 0.05 | 0.1 | 0.2 | 0.1 |
| *S. aureus* 870307 | 0.1 | 0.2 | 0.1 | 0.78 | 0.39 | 0.2 | 0.78 | 0.39 | 0.2 |
| *S. pneumoniae* 104835 | 0.1 | 0.2 | 0.2 | 0.39 | 0.39 | 0.1 | 0.39 | 0.39 | 0.2 |
| | Compound (Example No.) | | | | | | | | |
| Bacteria | 31 | 34 | 35 | 37 | 43 | 44 | LVFX | CPFX | MXFX |
| *E. coli* NIHJ | 0.006 | 0.006 | 0.006 | 0.006 | 0.006 | ≤0.003 | 0.012 | ≤0.003 | 0.012 |
| *K. pneumoniae* TYPE 1 | 0.05 | 0.025 | 0.05 | 0.1 | 0.05 | 0.025 | 0.05 | 0.025 | 0.1 |
| *P. mirabilis* 08103 | 0.012 | 0.012 | 0.025 | 0.05 | 0.025 | 0.025 | 0.025 | 0.012 | 0.025 |
| *E. cloacae* 03400 | 0.012 | 0.006 | 0.012 | 0.025 | 0.012 | 0.006 | 0.012 | 0.006 | 0.012 |
| *S. marcescens* 10100 | 0.1 | 0.05 | 0.1 | 0.2 | 0.2 | 0.05 | 0.05 | 0.025 | 0.2 |
| *P. aeruginosa* PAO1 | 0.39 | 0.2 | 0.39 | 1.56 | 0.78 | 0.39 | 0.39 | 0.05 | 0.78 |
| *H. influenzae* ATCC25238 | 0.012 | 0.006 | 0.012 | ≤0.003 | 0.006 | ≤0.003 | 0.012 | 0.006 | 0.012 |
| *M(B). Caterrhalis* ATCC49247 | 0.025 | 0.012 | 0.025 | 0.025 | 0.025 | 0.006 | 0.025 | 0.025 | 0.05 |
| *S. aureus* FDA 209-P | 0.012 | 0.025 | 0.025 | 0.006 | 0.012 | 0.012 | 0.1 | 0.1 | 0.05 |
| *S. epidermidis* 56500 | 0.05 | 0.05 | 0.05 | 0.012 | 0.05 | 0.025 | 0.39 | 0.2 | 0.1 |
| *S. pneumoniae* J24 | 0.025 | 0.1 | 0.05 | 0.05 | 0.1 | 0.05 | 0.78 | 0.78 | 0.1 |
| *S. pyogenes* JCM5674(ATCC12344) | 0.025 | 0.05 | 0.05 | 0.05 | 0.05 | 0.05 | 0.39 | 0.39 | 0.2 |
| *E. faecalis* 19433 | 0.1 | 0.1 | 0.2 | 0.1 | 0.2 | 0.1 | 0.78 | 0.78 | 0.2 |
| *S. aureus* 870307 | 0.1 | 0.39 | 0.2 | 0.05 | 0.2 | 0.2 | 6.25 | >6.25 | 0.78 |
| *S. pneumoniae* 104835 | 0.2 | 0.39 | 0.39 | 0.39 | 0.78 | 0.39 | >6.25 | >6.25 | 3.13 |

The invention claimed is:

1. A compound of formula (I), or a salt thereof:

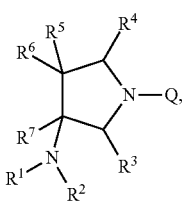

(I)

wherein $R^1$ is a hydrogen atom;

$R^2$ is a hydrogen atom;

$R^3$ and $R^4$ are hydrogen atoms;

$R^5$ is a hydrogen atom or a fluorine atom;

$R^6$ and $R^7$ taken together with the carbon atoms to which they are bonded form a five- to six-membered cyclic structure, the cyclic structure representing a partial structure that together with the pyrrolidine ring forms a fused cyclic structure, wherein the five- to six-membered cyclic structure does not contain a double bond and optionally contains an oxygen atom as a ring constituent atom, $R^5$ is optionally a methylene group taken together with $R^6$ to form a three-membered fused cyclic structure; and Q is a partial structure represented by formula (II):

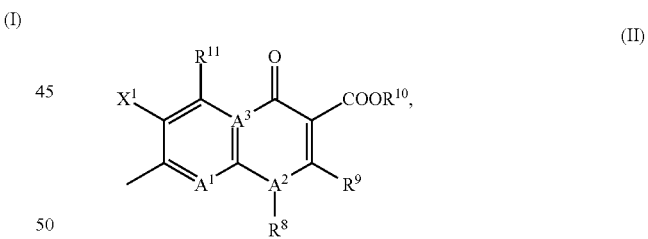

(II)

wherein $R^8$ is a 1,2-cis-2-halogenocyclopropyl group, a cyclopropyl group, or a 6-amino-3,5-difluorophenyl group;

$R^9$ is a hydrogen atom;

$R^{10}$ is a hydrogen atom;

$R^{11}$ is a hydrogen atom or an amino group;

$X^1$ is a fluorine atom or a hydrogen atom;

$A^1$ is a partial structure represented by formula (III):

(III)

wherein $X^2$ is a methyl group or a methoxy group,
or $X^2$ and $R^8$ taken together with the atoms of formula (II) through which they are connected form a cyclic structure such that Q represents a partial structure represented by the following formula:

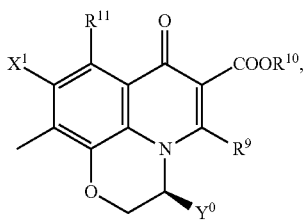

wherein $Y^0$ is a methyl group or a fluoromethyl group, and $X^1$, $R^9$, $R^{10}$ and $R^{11}$ are defined as above.

2. The compound or salt according to claim 1, wherein the compound of formula (I) is represented by the formula:

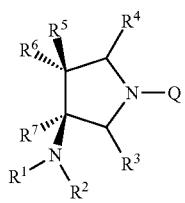

or the formula:

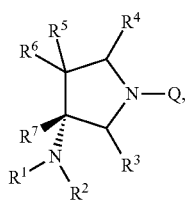

wherein $R^1$, $R^2$, $R^3$, $R^4$, $R^5$, $R^6$, $R^7$, and Q are as defined in claim 1.

3. The compound or salt according to claim 1, wherein the compound of formula (I) is represented by the formula:

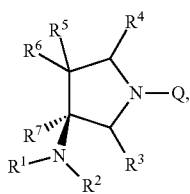

wherein $R^1$, $R^2$, $R^3$, $R^4$, $R^5$, $R^6$, $R^7$, and Q are as defined in claim 1.

4. The compound or salt according to claim 1, wherein $R^6$ and $R^7$ together with the carbon atoms to which they are bonded form a five- or six-membered cyclic structure, wherein said five- or six-membered cyclic structure optionally contains an oxygen atom as a ring constituent atom.

5. The compound or salt according to claim 1, wherein the cyclic structure which is formed by taking $R^6$ and $R^7$ together with the carbon atoms to which they are bonded is a five- or six-membered cyclic structure represented by the following formula:

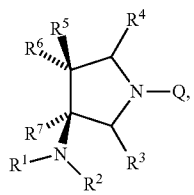

wherein $R^1$, $R^2$, $R^3$, $R^4$, $R^5$, $R^6$, $R^7$, and Q are as defined in claim 1.

6. The compound or salt according to claim 1, wherein the cyclic structure which is formed by taking $R^6$ and $R^7$ together with the carbon atoms to which they are bonded is a five- or six-membered cyclic structure represented by the following formula:

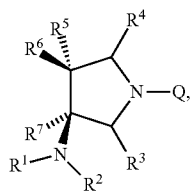

wherein $R^1$, $R^2$, $R^3$, $R^4$, $R^5$, $R^6$, $R^7$, and Q are as defined in claim 1.

7. The compound or salt according to claim 1, wherein $X^1$ in the formula (II) is a fluorine atom.

8. The compound or salt according to claim 1, wherein $R^8$ is a 1,2-cis-2-halogenocyclopropyl group in the partial structure Q, represented by the formula (II), in the formula (I).

9. The compound or salt according to claim 1, wherein $R^8$ is a stereochemically single 1,2-cis-2-halogenocyclopropyl group in the partial structure Q, represented by the formula (II), in the formula (I).

10. The compound or salt according to claim 9, wherein the stereochemically single 1,2-cis-2-halogenocyclopropyl group of $R^8$ is a (1R,2S)-2-halogenocyclopropyl group in the partial structure Q, represented by the formula (II), in the formula (I).

11. The compound or salt according to claim 10, wherein the stereochemically single (1R,2S)-2-halogenocyclopropyl group of $R^8$ is a (1R,2S)-2-fluorocyclopropyl group in the partial structure Q, represented by the formula (II), in the formula (I).

12. The compound or salt according to claim 1, wherein Q is represented by the formula:

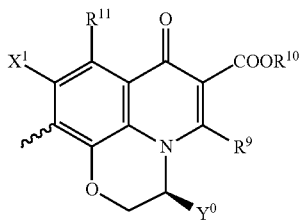

wherein R⁹, R¹⁰, R¹¹, and X¹ are as defined in claim 1 and Y⁰ is a methyl group or a fluoromethyl group.

13. The compound or salt according to claim 1, wherein Q is represented by formula (IV):

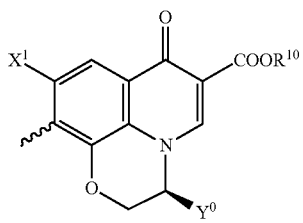

(IV)

wherein R¹⁰ and X¹ are as defined in claim 1 and Y⁰ is a methyl group.

14. The compound or salt according to claim 1, wherein the compound represented by formula (I) is a stereochemically single compound.

15. The compound or salt according to claim 1, wherein the partial structure substituted on Q is:
 a (1R,5S)-1-amino-5-fluoro-3-azabicyclo[3.3.0]octan-3-yl group;
 a 6-amino-8-azatricyclo[4.3.0.0¹,³]nonan-8-yl group;
 a (1S,6S)-1-amino-4-oxa-8-azabicyclo[4.3.0]nonan-8-yl group; or
 a (1S,6S)-1-amino-3-oxa-8-azabicyclo[4.3.0]nonan-8-yl group.

16. An antibacterial agent comprising the compound or salt according to claim 1, and a pharmaceutically acceptable additive.

17. A method of making an antibacterial agent or a therapeutic agent comprising combining the compound or salt according to claim 1 and a pharmaceutically acceptable additive.

18. A compound or salt according to claim 1, wherein the compound of formula (I) is 7-[(1R,5S)-1-amino-5-fluoro-3-azabicyclo[3.3.0]octan-3-yl]-6-fluoro-1-[(1R,2S)-2-fluorocyclopropan-1-yl]-1,4-dihydro-8-methoxy-4-oxoquinoline-3-carboxylic acid.

19. A compound or salt according to claim 1, wherein the compound of formula (I) is 7-[(1R,5S)-1-amino-5-fluoro-3-azabicyclo[3.3.0]octan-3-yl]-6-fluoro-1-[(1R,2S)-2-fluorocyclopropan-1-yl]-1,4-dihydro-8-methyl-4-oxoquinoline-3-carboxylic acid.

20. A compound or salt according to claim 1, wherein the compound of formula (I) is 7-[6-amino-8-azatricyclo[4.3.0.0¹,³]nonan-8-yl]-6-fluoro-1-[(1R,2S)-2-fluorocyclopropan-1-yl]-1,4-dihydro-8-methoxy-4-oxoquinoline-3-carboxylic acid.

21. A compound or salt according to claim 1, wherein the compound of formula (I) is 7-[(1S,6S)-1-amino-4-oxa-8-azabicyclo[4.3.0]nonan-8-yl]-6-fluoro-1-[(1R,2S)-2-fluorocyclopropan-1-yl]-1,4-dihydro-8-methoxy-4-oxoquinoline-3-carboxylic acid.

22. A compound or salt according to claim 1, wherein the compound of formula (I) is 7-[(1S,6S)-1-amino-8-aza-3-oxabicyclo[4.3.0]nonan-8-yl]-6-fluoro-1-[(1R,2S)-2-fluorocyclopropan-1-yl]-1,4-dihydro-8-methoxy-4-oxoquinoline-3-carboxylic acid.

23. A compound or salt according to claim 1, wherein the compound of formula (I) is 7-[(1S,6S)-1-amino-3-oxa-8-azabicyclo[4.3.0]nonan-8-yl]-6-fluoro-1-[(1R,2S)-2-fluorocyclopropan-1-yl]-1,4-dihydro-8-methyl-4-oxoquinoline-3-carboxylic acid.

24. A compound or salt according to claim 1, wherein the compound of formula (I) is 7-[6-amino-8-azatricyclo[4.3.0.0¹,³]nonan-8-yl]-6-fluoro-1-[(1R,2S)-2-fluorocyclopropan-1-yl]-1,4-dihydro-8-methyl-4-oxoquinoline-3-carboxylic acid.

25. A compound or salt according to claim 1, wherein the compound of formula (I) is selected from the following formulas:

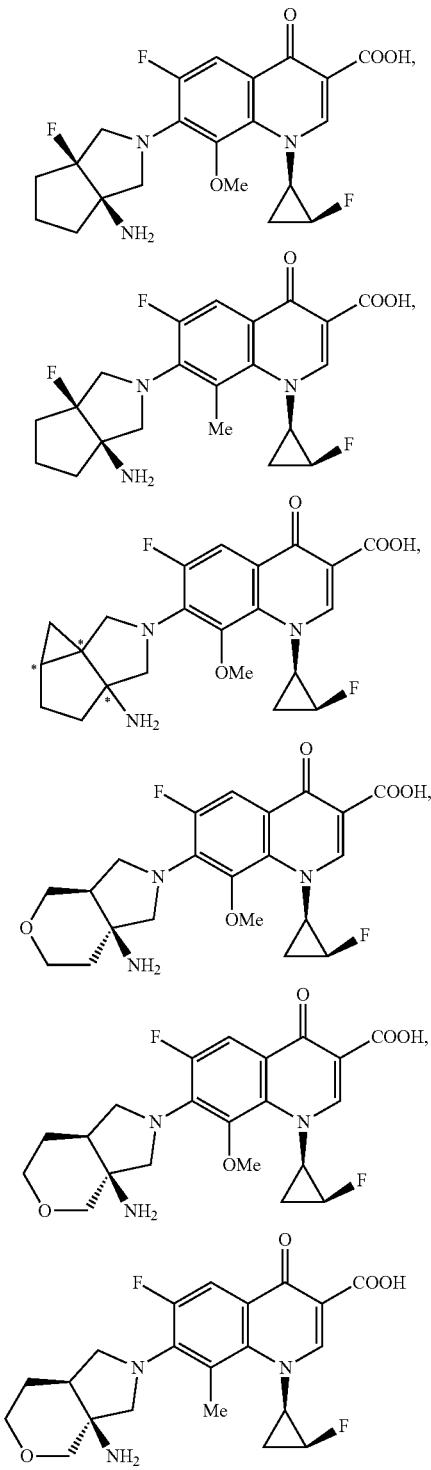

26. A compound or salt according to claim 1, wherein the compound of formula (I) is:

27. A compound or salt according to claim 1, wherein the compound of formula (I) is:

28. A compound or salt according to claim 1, wherein the compound of formula (I) is:

29. A compound or salt according to claim 1, wherein the compound of formula (I) is:

30. A compound or salt according to claim 1, wherein the compound of formula (I) is:

31. A compound or salt according to claim 1, wherein the compound of formula (I) is:

32. A compound or salt according to claim 1, wherein the compound of formula (I) is:

33. An antibacterial agent comprising the compound or salt according to claim 18, and a pharmaceutically acceptable additive.

34. A method of making an antibacterial agent or a therapeutic agent comprising combining the compound or salt according to claim 18, and a pharmaceutically acceptable additive.

35. An antibacterial agent comprising the compound or salt according to claim 19, and a pharmaceutically acceptable additive.

36. A method of making an antibacterial agent or a therapeutic agent comprising combining the compound or salt according to claim 19, and a pharmaceutically acceptable additive.

* * * * *

UNITED STATES PATENT AND TRADEMARK OFFICE
CERTIFICATE OF CORRECTION

PATENT NO. : 8,618,094 B2
APPLICATION NO. : 12/459612
DATED : December 31, 2013
INVENTOR(S) : Hisashi Takahashi et al.

Page 1 of 1

It is certified that error appears in the above-identified patent and that said Letters Patent is hereby corrected as shown below:

In the Claims:

In claim 1, at column 300, at lines 45-50, delete

"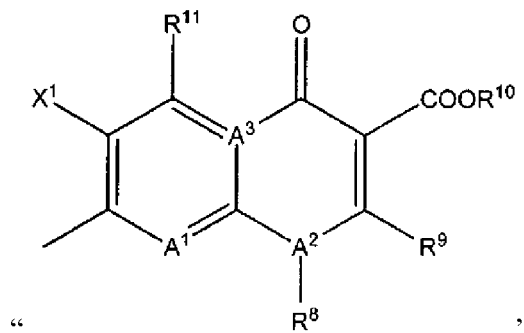 " and insert -- 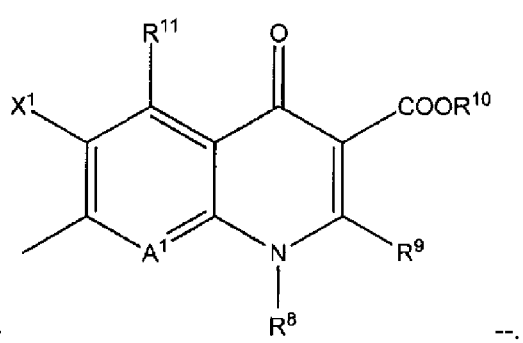 --.

In claim 2, at column 301, at lines 25-30, delete

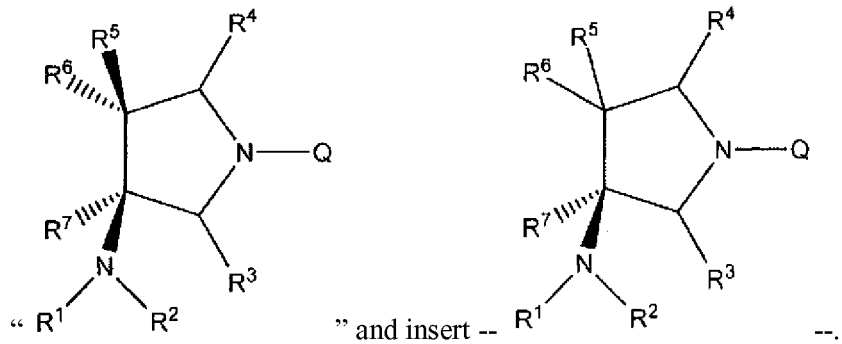

Signed and Sealed this
Twentieth Day of May, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,618,094 B2 | Page 1 of 1 |
| APPLICATION NO. | : 12/459612 | |
| DATED | : December 31, 2013 | |
| INVENTOR(S) | : Takakashi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1073 days.

Signed and Sealed this
Nineteenth Day of May, 2015

Michelle K. Lee
*Director of the United States Patent and Trademark Office*